United States Patent
Görgens et al.

(10) Patent No.: US 10,934,301 B2
(45) Date of Patent: *Mar. 2, 2021

(54) PYRAZOLOPYRIMIDINE DERIVATIVES

(71) Applicant: BAYER ANIMAL HEALTH GMBH, Leverkusen (DE)

(72) Inventors: Ulrich Görgens, Ratingen (DE); Claudia Welz, Düsseldorf (DE); Daniel Kulke, Leverkusen (DE); Claudia Böhm, Hannover (DE)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/776,377

(22) Filed: Jan. 29, 2020

(65) Prior Publication Data
US 2020/0239482 A1 Jul. 30, 2020

Related U.S. Application Data

(63) Continuation of application No. 16/093,565, filed as application No. PCT/EP2017/058519 on Apr. 10, 2017, now Pat. No. 10,604,525.

(30) Foreign Application Priority Data

Apr. 15, 2016 (EP) ..................... 16165572

(51) Int. Cl.
*C07D 487/04* (2006.01)
*C07D 487/02* (2006.01)
*A61P 33/10* (2006.01)

(52) U.S. Cl.
CPC ............ *C07D 487/04* (2013.01); *A61P 33/10* (2018.01); *C07D 487/02* (2013.01)

(58) Field of Classification Search
CPC .......................... C07D 487/04; A61K 31/519
USPC ........................................ 544/281; 514/259.1
See application file for complete search history.

(56) References Cited

U.S. PATENT DOCUMENTS

| 10,604,525 B2 * | 3/2020 | Kohler | C07D 487/02 |
| 2007/0037828 A1 | 2/2007 | Gebauer | |
| 2019/0071447 A1 | 3/2019 | Köhler | |

FOREIGN PATENT DOCUMENTS

| EA | 009517 B1 | 2/2008 |
| EP | 1505068 A1 | 2/2005 |
| EP | 1918291 A1 | 5/2008 |
| WO | WO2016012485 A1 | 1/2016 |

OTHER PUBLICATIONS

Azimioara, M. et al. (2014) "Novel tricyclic pyrazolopyrimidines as potent and selective GPR119 agonist," Bioorganic & Medicinal Chemistry Letters 24:5478-5483.
Berge, S. et al. (Jan. 1977) "Pharmaceutical Salts," Journal of Pharmaceutical Sciences, 66(1):1-19.
Blad C. et al. (2012) "Novel 3,6,7-Substituted Pyrazolopyrimidines as Positive Allosteric Modulators for the Hydroxycarboxylic Acid Receptor (GPR109A)," J. Med. Chem., 55:3563-3567.
Cross et al. (1976). "International Union of Pure and Applied Chemistry: Organic Chemistry Division Commission on Nomenclature of Organic Chemistry," Pure & Appl. Chem. 45:11-30.
Danagulyan, G. et al. (Jun. 2011) "C-C-Recyclizations of some 2,7-Disubstituted 6-Ethoxycarbonylpyrazolo[,5-α] Pyrimidines," Chemistry of Heterocyclic Compounds, 43(3):321-331.
El Tayar, N. et al. (1984) "The lipophilicity of deuterium atoms. A comparison of shake-flask and HPLC methods," Int J Pharm; 19(3), 271-281.
Greene, T. (1999) "Protective Group in Organic Synthesis," Third Editions, 799 pages.
Gregg B. et al. (2007) "Pyrazolo[1,5-α]pyrimidines. Identification of the Privileged Structure and Combinatorial Synthesis of 3-(Hetero)arylpyrazolo[1,5-α]pyrimidine-6-carboxamides," J. Comb. Chem., 9(3):507-512.
Lennox A. et al. (2014) "Selection of boron reagents for Suzuki-Miyaura coupling," Chem. Soc. Rev., 43:412-443.
MacBean, C. (2012) "The Pesticide Manual: A World Compendium," BCPC, 16th edition, 9 pages.
Maltais, F. et al. (2009) "In Vitro and in Vivo Isotope Effects with Hepatitis C Protease Inhibitors: Enhanced Plasma Exposure of Deuterated Telaprevir versus Telaprevir in Rats," J Med Chem; 52:7993-8001.

(Continued)

*Primary Examiner* — Deepak R Rao
(74) *Attorney, Agent, or Firm* — McBee Moore & Vanik IP, LLC

(57) ABSTRACT

The present invention covers Pyrazolopyrimidine compounds of general formula (I):

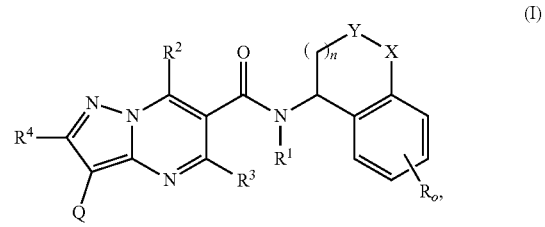

in which n, o, X, Y, R, Q, $R^1$, $R^2$, $R^3$ and $R^4$ are as defined herein, methods of preparing said compounds, intermediate compounds useful for preparing said compounds, pharmaceutical compositions and combinations comprising said compounds and the use of said compounds for manufacturing pharmaceutical compositions for the treatment, control and/or prevention of diseases, in particular of helminth infections, as a sole agent or in combination with other active ingredients.

12 Claims, No Drawings

(56) References Cited

OTHER PUBLICATIONS

Mutlib, A. et al. (2000) "The Species-Dependent Metabolism of Efavirenz Produces a Nephrotoxic Glutathione Conjugate in Rats," Toxicology and Applied Pharmacology; 169:102-113.
Perrin, C. et al (2007) "Secondary Deuterium Isotope Effects on the Acidity of Carboxylic Acids and Phenols," J Am Chem Soc; 129:4490-4497.
Perrin, C. et al. (2005) "Stereochemistry of β-Deuterium Isotope Effects on Amine Basicity," J Am Chem Soc, 127:9641-9647.
Poupaert J. (2007) "Drug Design: Basic Principles and Applications," 2 Encyclopedia of Pharmaceutical Technology, 3rd edition, 1362-1369.
Rosman, K., et al. (1998). "Isotopic Compositions of the Elements 1997," Technical Report, Pure & Appl. Chem., 70 (1):217-235.
Schneider, F. et al. (2006) "Enhanced Plasma Concentration by Selective Deuteration of Rofecoxib in Rats," Arzneim-Forsch/Drug Res; 56(4):295-300.
Sharma, A. et al. (2013) "Nevirapine Bioactivation and Covalent Binding in the Skin," Chem Res Toxicol; 26:410-421.
Sharpe, C. et al. (Dec. 19, 2017) "A sticky end for gastrointestinal Helminths; the role of the mucus barrier," Parasite Immunology, 40:e12517, 10 pages.
Sharpless, N. et al. (Aug. 18, 2006) "The mighty mouse: genetically engineered mouse models in cancer drug development," Nature Reviews Drug Discovery, pp. 1-14.
Shen, H. (2008). "Discovery of pyrazolopyrimidines as the first class of allosteric agonists for the high affinity nicotinic acid receptor GPR109A," Bioorg. Med. Chem., 18:4948-4951.
U.S. Appl. No. 16/776,374, filed Jan. 29, 2020, for Hans-Georg Schwarz (U.S. Patent Application is not submitted herewith pursuant to the waiver of 37 C.F.R. § 1.98(a)(2)(iii) issued by the Office on Sep. 21, 2004.).
Wenthur, C. et al. (2013) "Discovery of (R)-(2-Fluoro-4-((-4-methoxyphenyl)ethynyl)phenyl) (3-Hydroxypiperidin-1-yl) methanone (ML337), An mGlu3 Selective and CNS Penetrant Negative Allosteric Modulator (NAM)," J Med Chem, 56:5208-5212.
Zon, L. et al. (Jan. 2005) "In Vivo Drug Discovery in the Zebrafish," Nature Reviews, 4:35-44.
International Search Report dated May 30, 2018 for International Application No. PCT/EP2017/058519, filed Apr. 10, 2017, 3 pages.
Written Opinion dated May 30, 2018 for International Application No. PCT/EP2017/058519, filed Apr. 10, 2017, 5 pages.

* cited by examiner

PYRAZOLOPYRIMIDINE DERIVATIVES

CROSS REFERENCE TO RELATED APPLICATIONS

This application is a continuation of U.S. patent application Ser. No. 16/093,565, which adopts the international filing date of Apr. 10, 2017, which is the National Phase application under 35 U.S.C. § 371 of International Application No. PCT/EP2017/058519, filed Apr. 10, 2017, which claims priority benefit of European Application No. 16165572.5, filed Apr. 15, 2016.

The present invention covers new pyrazolopyrimidine derivatives of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the control, treatment and/or prevention of diseases, in particular for the control, treatment and/or prevention of infections with helminths, more particularly of infections with gastro-intestinal and extra-intestinal nematodes, in animals and humans, formulations containing such compounds and methods for the control, treatment and/or prevention of infections with helminths, more particularly of infections with gastro-intestinal and extra-intestinal nematodes, in animals and humans as a sole agent or in combination with other active ingredients.

BACKGROUND

The occurrence of resistances against all commercial anthelmintics seems to be a growing problem in the area of veterinary medicine. The extensive utilisation of anthelmintics to manage the control of nematodes resulted in significant selection of highly resistant worm populations. Therefore, the spread of resistance against all anthelmintic drug classes threatens effective worm control in cattle, goats, sheep and horses. Furthermore, successful prevention of heartworm disease in dogs, which currently solely relies on the utilisation of macrocyclic lactones, is in danger due to the unequivocal proof of macrocyclic lactone resistance in heartworm in some regions of the United States of America and Brazil.

Although resistance of human helminths against anthelmintics seems currently to be rare, the spread of anthelmintic resistance in the veterinary field as mentioned before needs to be considered in the treatment of human helminthosis as well. Persistent underdosed treatments against filariosis may lead to highly resistant genotypes and resistances have already been described for certain anthelminthics (e.g. praziquantel, benzimidazole and niclosamide).

Therefore, resistance-breaking anthelmintics with new molecular modes of action are urgently required.

It is an object of the present invention to provide compounds which can be used as anthelmintics in the medical, especially veterinary, field with a satisfactory or improved anthelmintic activity against a broad spectrum of helminths, particularly at relatively low dosages, for the control, treatment and/or prevention of infections with helminths in animals and humans, preferably without any adverse toxic effects to the treated organism.

Certain pyrazolopyrimidine carboxamides are related to their activity increasing the efficacy of the endogenous ligand 3-hydroxybutyrateas as described in Journal of Medicinal Chemistry, 55, (7), 3563-3567. Other pyrazolopyrimidine carboxamides are described as allosteric agonists for the high affinity nicotinic acid receptor GPR109A as in Bioorganic & Medicinal Chemistry Letters, 18, (18), 4948-4951. Furthermore, pyrazolopyrimidine carboxamides are known as protein kinase modulators (EP1918291), as active ingredients for treatment or prevention of skin diseases (WO 2009041663) or as NAD(P)H oxidase inhibitors (WO 2003091256). A certain method for a library synthesis process of said compounds is described in Journal of Combinatorial Chemistry, 9, (3), 507-512.

However, the state of the art does not describe the new pyrazolopyrimidine derivatives of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively interact with Slo-1 of nematodes. This interaction is characterized by achieving paralysis/inhibition in particular of gastro-intestinal nematodes, of free-living nematodes, and of filariae, for which data are given in the biological experimental section. Therefore the compounds of the present invention may be used as anthelmintics for the control, treatment and/or prevention of gastro-intestinal and extra-intestinal helminth infections, in particular gastro-intestinal and extra-intestinal infections with nematodes, including filariae.

DESCRIPTION OF THE INVENTION

In accordance with a first aspect, the present invention covers compounds of general formula (I):

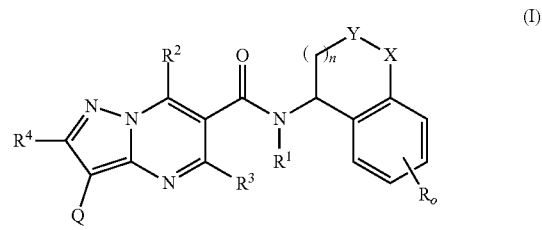

(I)

in which:

o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, n is 0 or 1, X, Y are independently selected from the group consisting of $CR^5R^6$, O, S, and N—$R^7$, wherein at least one of X and Y is $CR^5R^6$, $R^1$ is selected from the group consisting of hydrogen, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, amino-$C_1$-$C_4$-alkyl, $C_1$-$C_4$-alkylamino-$C_1$-$C_4$-alkyl, di- ($C_1$-$C_4$-alkyl)amino-$C_1$-$C_4$-alkyl, $C_1$-$C_4$-alkylcarbonyl, $C_1$-$C_4$-halogenoalkylcarbonyl having 1 to 5 halogen atoms, $C_1$-$C_4$-alkoxycarbonyl, benzyloxycarbonyl, $C_1$-$C_4$-alkoxy-$C_1$-$C_4$-alkylcarbonyl, —$SO_2$—$C_1$-$C_4$-alkyl, and —$SO_2$—$C_1$-$C_4$-halogenoalkyl having 1 to 5 halogen atoms, $R^2$ is selected from the group consisting of hydrogen, halogen, cyano, —CHO, $C_1$-$C_4$-alkyl, $C_2$-$C_4$-alkenyl, $C_2$-$C_4$-alkinyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, benzyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH(4- to 7-membered heterocycloalkyl), —N($C_1$-$C_4$-alkyl)(4- to 7-membered heterocycloalkyl), —NH($C_1$-$C_4$-alkoxy), —N($C_1$-$C_4$-alkyl)($C_1$-$C_4$-alkoxy), —NH—$SO_2$—($C_1$-$C_4$-alkyl), —N($SO_2$—[$C_1$-$C_4$-alkyl])($C_1$-$C_4$-alkyl), ($C_1$-$C_4$-alkyl)-NH—$C_1$-$C_4$-alkyl-, ($C_1$-$C_4$-alkyl)$_2$-N—$C_1$-$C_4$-alkyl-, —S—$C_1$-$C_4$-alkyl, —S(O)—$C_1$-$C_4$-alkyl, —$SO_2$—$C_1$-$C_4$-alkyl, ($C_1$-$C_4$-alkoxyimino)-$C_1$-$C_4$-alkyl, and a monocyclic heterocycle selected from the group of 4- to 7-membered heterocycloalkyl, 5-membered heteroaryl having at least one nitrogen atom via which the heteroaryl ring is connected to the rest of the molecule, and 6-membered heteroaryl having at least one nitrogen atom, each of which in $R^2$ is optionally substituted with 1, 2 or 3 substituents independently selected from the group consisting of hydrogen, halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, and wherein each $C_1$-$C_4$-alkyl, $C_3$-$C_6$-cycloalkyl and $C_1$-$C_4$-alkoxy in $R^2$ may be optionally substituted with halogen, OH, $NH_2$, —NH($C_1$-$C_4$-alkyl), —N($C_1$-$C_4$-alkyl)$_2$, cyano, carboxy, carbamoyl, alkoxycarbonyl, —C(O)—NH($C_1$-$C_4$-alkyl), —C(O)—N($C_1$-$C_4$-alkyl)$_2$, —C(O)—NH($C_3$-$C_6$-cycloalkyl), $C_1$-$C_4$-alkoxy, —S—$C_1$-$C_4$-alkyl, —S(O)—$C_1$-$C_4$-alkyl, —$SO_2$—$C_1$-$C_4$-alkyl, or optionally substituted by a monocyclic heterocycle selected from the group of 4- to 7-membered heterocycloalkyl or a 5-membered heteroaryl having at least one nitrogen atom via which the heteroaryl ring is connected to the $C_1$-$C_4$-alkyl or $C_3$-$C_6$-cycloalkyl, each of which is optionally substituted with 1, 2 or 3 substituents independently selected from the group consisting of hydrogen, halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R^3$ is selected from the group consisting of hydrogen, halogen, $C_1$-$C_4$-alkyl, $C_1$-$C_4$-halogenoalkyl having 1 to 5 halogen atoms, and $C_3$-$C_6$-cycloalkyl, $R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, and —$SO_2$—$C_1$-$C_4$-alkyl, $R^5$ is selected from the group consisting of hydrogen, fluorine and $C_1$-$C_4$-alkyl, $R^6$ is selected from the group consisting of hydrogen, fluorine and $C_1$-$C_4$-alkyl, $R^7$ is selected from the group consisting of hydrogen and $C_1$-$C_4$-alkyl, Q is selected from the group consisting of 6- or 10-membered aryl and 5- to 10-membered heteroaryl, each of which may be optionally substituted with 1, 2, 3, 4 or 5 substituents, and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group, or an isomer thereof. Particularly, said group has 1, 2 or 3 carbon atoms ("$C_1$-$C_3$-alkyl"), e.g. a methyl, ethyl, n-propyl or isopropyl group.

The term "$C_1$-$C_4$-hydroxyalkyl" means a linear or branched, saturated, monovalent hydrocarbon group in which the term "$C_1$-$C_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "—NH($C_1$-$C_4$-alkyl)" or "—N($C_1$-$C_4$-alkyl)$_2$" means a linear or branched, saturated, monovalent group in which the term "$C_1$-$C_4$-alkyl" is as defined supra, e.g. a methylamino, ethylamino, n-propylamino, isopropylamino, N,N-dimethylamino, N-methyl-N-ethylamino or N,N-diethylamino group.

The term "—S—$C_1$-$C_4$-alkyl", "—S(O)—$C_1$-$C_4$-alkyl" or "—SO$_2$—$C_1$-$C_4$-alkyl" means a linear or branched, saturated group in which the term "$C_1$-$C_4$-alkyl" is as defined supra, e.g. a methylsulfanyl, ethylsulfanyl, n-propylsulfanyl, isopropylsulfanyl, n-butylsulfanyl, sec-butylsulfanyl, isobutylsulfanyl or tert-butylsulfanyl group, a methylsulfinyl, ethylsulfinyl, n-propylsulfinyl, isopropylsulfinyl, n-butylsulfinyl, sec-butylsulfinyl, isobutylsulfinyl or tert-butylsulfinyl group, or a methylsulfonyl, ethylsulfonyl, n-propylsulfonyl, isopropylsulfonyl, n-butylsulfonyl, sec-butylsulfonyl, isobutylsulfonyl or tert-butylsulfonyl group.

The term "$C_1$-$C_4$-halogenoalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy or tert-butoxy group, or an isomer thereof.

The term "$C_1$-$C_4$-halogenoalkoxy" means a linear or branched, saturated, monovalent $C_1$-$C_4$-alkoxy group, as defined supra, in which one or more of the hydrogen atoms is replaced, identically or differently, with a halogen atom. Particularly, said halogen atom is a fluorine atom. Said $C_1$-$C_4$-halogenoalkoxy group is, for example, fluoromethoxy, difluoromethoxy, trifluoromethoxy, 2,2,2-trifluoroethoxy or pentafluoroethoxy.

The term "$C_2$-$C_4$-alkenyl" means a linear or branched, monovalent hydrocarbon group, which contains one double bond, and which has 2, 3 or 4 carbon atoms. Said $C_2$-$C_4$-alkenyl group is, for example, an ethenyl (or "vinyl"), a prop-2-en-1-yl (or "allyl"), prop-1-en-1-yl, but-3-enyl, but-2-enyl, but-1-enyl, prop-1-en-2-yl (or "isopropenyl"), 2-methylprop-2-enyl, 1-methylprop-2-enyl, 2-methylprop-1-enyl or a 1-methylprop-1-enyl, group. Particularly, said group is allyl.

The term "$C_2$-$C_4$-alkynyl" means a linear monovalent hydrocarbon group which contains one triple bond, and which contains 2, 3 or 4 carbon atoms. Said $C_2$-$C_4$-alkynyl group is, for example, an ethynyl, a prop-1-ynyl, prop-2-ynyl (or "propargyl"), but-1-ynyl, but-2-ynyl, but-3-ynyl or 1-methylprop-2-ynyl, group. Particularly, said alkynyl group is prop-1-ynyl or prop-2-ynyl.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_3$-$C_6$-halogenocycloalkyl" means a saturated, monovalent, monocyclic hydrocarbon ring in which the term "$C_3$-$C_6$-cycloalkyl" is as defined supra, and in which one or more of the hydrogen atoms are replaced, identically or differently, with a halogen atom. Particularly, said halogen atom is a fluorine or chlorine atom. Said $C_3$-$C_6$-halogenocycloalkyl group is for example, a monocyclic hydrocarbon ring substituted with one or two fluorine or chlorine atoms, e.g. a 1-fluoro-cyclopropyl, 2-fluorocyclopropyl, 2,2-difluorocyclopropyl, 2,3-difluorocyclopropyl, 1-chlorocyclopropyl, 2-chlorocyclopropyl, 2,2-dichlorocyclopropyl, 2,3-dichlorocyclopropyl, 2-fluoro-2-chlorocyclopropyl and 2-fluoro-3-chlorocyclopropyl group.

The terms "4- to 7-membered heterocycloalkyl" and "4- to 6-membered heterocycloalkyl" mean a monocyclic, saturated heterocycle with 4, 5, 6 or 7 or, respectively, 4, 5 or 6 ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

Particularly, "4- to 6-membered heterocycloalkyl" means a 4- to 6-membered heterocycloalkyl as defined supra containing one ring nitrogen atom and optionally one further ring heteroatom from the series: N, O, S. More particularly, "5- or 6-membered heterocycloalkyl" means a monocyclic, saturated heterocycle with 5 or 6 ring atoms in total, containing one ring nitrogen atom and optionally one further ring heteroatom from the series: N, O.

The term "6- or 10-membered aryl" means a monovalent, monocyclic or bicyclic aromatic ring having 6 or 10 carbon ring atoms, e.g. a phenyl or naphthyl group.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), particularly 5, 6, 9 or 10 ring atoms (a "5- to 10-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-halogenoalkyl", "$C_1$-$C_4$-hydroxyalkyl", "$C_1$-$C_4$-alkoxy" or "$C_1$-$C_4$-halogenoalkoxy" means an alkyl group having a finite number of carbon atoms of 1 to 4, i.e. 1, 2, 3 or 4 carbon atoms.

Further, as used herein, the term "$C_3$-$C_6$", as used in the present text, e.g. in the context of the definition of "$C_3$-$C_6$-cycloalkyl" or $C_3$-$C_6$-halogenocycloalkyl, means a cycloalkyl group having a finite number of carbon atoms of 3 to 6, i.e. 3, 4, 5 or 6 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_4$" encompasses $C_3$, $C_4$, and $C_3$-$C_4$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}O$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains a pyrazolopyrimidine moiety with $R^2$ as $NH(C_1$-$C_4$-alkyl) group can exist as an amino tautomer, or an imino tautomer, or even a mixture in any amount of the two tautomers, namely:

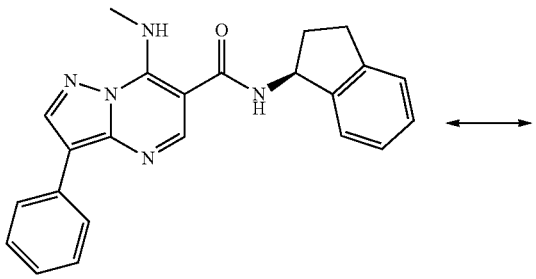 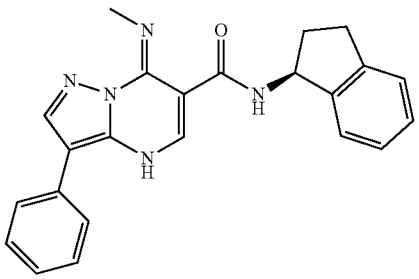

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods. The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na+", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

o is 0, 1, 2, 3 or 4

R is selected from the group consisting of hydrogen, halogen, $C_1$-$C_4$-alkyl and $C_1$-$C_4$-halogenoalkyl having 1 to 5 halogen atoms, n is 0 or 1, X, Y are independently selected from the group consisting of $CR^5R^6$, O, S, and N—$R^7$, wherein at least one of X and Y is $CR^5R^6$, $R^1$ is selected from the group consisting of hydrogen, $C_1$-$C_4$-alkyl, $C_3$-$C_6$-cycloalkyl, $C_1$-$C_4$-alkylcarbonyl, $C_1$-$C_4$-alkoxycarbonyl, $C_3$-$C_4$-alkenyl, $C_3$-$C_4$-alkynyl, $C_1$-$C_4$-alkoxy-$C_1$-$C_4$-alkyl, $R^2$ is selected from the group consisting of hydrogen, halogen, cyano, $C_1$-$C_4$-alkyl, $C_2$-$C_4$-alkenyl, $C_2$-$C_4$-alkinyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, benzyl having 1 to 5 halogen atoms, $C_1$-$C_4$-alkoxy, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH(4- to 7-membered heterocycloalkyl), —N($C_1$-$C_4$-alkyl)(4- to 7-membered heterocycloalkyl), —NH($C_1$-$C_4$-alkoxy), —N($C_1$-$C_4$-alkyl)($C_1$-$C_4$-alkoxy), —NH—SO$_2$—($C_1$-$C_4$-alkyl), —N(SO$_2$—[$C_1$-$C_4$-alkyl])($C_1$-$C_4$-alkyl), ($C_1$-$C_4$-alkyl)-NH—$C_1$-$C_4$-alkyl-, ($C_1$-$C_4$-alkyl)$_2$-N—$C_1$-$C_4$-alkyl-, —S—$C_1$-$C_4$-alkyl, —S(O)—$C_1$-$C_4$-alkyl, —SO$_2$—$C_1$-$C_4$-alkyl, ($C_1$-$C_4$-alkoxyimino)-$C_1$-$C_4$-alkyl, and a monocyclic heterocycle selected from the group of 4- to 7-membered heterocycloalkyl, 5-membered heteroaryl having at least one nitrogen atom via which the heteroaryl ring is connected to the rest of the molecule, and 6-membered heteroaryl having at least one nitrogen atom, each of which in $R^2$ is optionally substituted with 1, 2 or 3 substituents independently selected from the group consisting of hydrogen, halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl, —S(O)—$C_1$-$C_4$-halogenoalkyl and —SO$_2$—$C_1$-$C_4$-halogenoalkyl having 1 to 5 halogen atoms, wherein each $C_1$-$C_4$-alkyl, $C_3$-$C_6$-cycloalkyl and $C_1$-$C_4$-alkoxy in $R^2$ may be optionally substituted with halogen, OH, NH$_2$, —NH($C_1$-$C_4$-alkyl), —N($C_1$-$C_4$-alkyl)$_2$, cyano, carboxy, carbamoyl, alkoxycarbonyl, —C(O)—NH($C_1$-$C_4$-alkyl), —C(O)—N($C_1$-$C_4$-alkyl)$_2$, $C_1$-$C_4$-alkoxy, —S—$C_1$-$C_4$-alkyl, —S(O)—$C_1$-$C_4$-alkyl, —SO$_2$—$C_1$-$C_4$-alkyl, or optionally substituted by a monocyclic heterocycle selected from the group of azetidines, pyrrolidines, morpholines, piperidines, piperazines, pyrrolidinones, morpholinones, piperidinones, piperazinones, pyrazoles, triazoles, imidazoles and pyrroles, wherein a heteroaryl ring is connected to the $C_1$-$C_4$-alkyl or $C_3$-$C_6$-cycloalkyl via one of its nitrogen atoms, each of which as a substituent of $C_1$-$C_4$-alkyl, $C_3$-$C_6$-cycloalkyl and $C_1$-$C_4$-alkoxy in $R^2$ is optionally substituted with 1, 2 or 3 substituents independently selected from the group consisting of hydrogen, halogen, cyano, oxo, $C_1$-$C_4$-alkyl, $C_1$-$C_4$-halogenoalkyl having 1 to 5 halogen atoms, $R^3$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, $R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, —SO$_2$—$C_1$-$C_4$-alkyl, $R^5$ is selected from the group consisting of hydrogen, fluorine or $C_1$-$C_4$-alkyl, $R^6$ is selected from the group consisting of hydrogen, fluorine or $C_1$-$C_4$-alkyl, $R^7$ is selected from the group consisting of hydrogen or $C_1$-$C_4$-alkyl, Q is selected from the group consisting of 6- or 10-membered aryl and 5- to 10-membered heteroaryl, each of which may be optionally substituted with 1, 2, 3, 4 or 5 substituents, and stereoisomers, tautomers, N-oxides, hydrates, solvates, and salts thereof, and mixtures of same.

In accordance with a third embodiment of the first aspect, the present invention covers compounds of general formula (I), supra, in which:

o is 0, 1, 2, 3 or 4,

R is selected from the group consisting of hydrogen, fluorine, chlorine, $C_1$-$C_4$-alkyl, n is 0 or 1, X, Y are independently selected from the group consisting of $CR^5R^6$, O, S, and N—$R^7$, wherein at least one of X and Y is $CR^5R^6$, $R^1$ is selected from the group consisting of hydrogen and $C_1$-$C_4$-alkyl, $R^2$ is selected from the group consisting of hydrogen, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, benzyl having 1 to 5 halogen atoms, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —N($C_1$-$C_4$-alkyl)(6-membered heterocycloalkyl), —N($C_1$-$C_4$-alkyl)($C_1$-$C_4$-alkoxy), ($C_1$-$C_4$-alkyl)$_2$-N—$C_1$-$C_4$-alkyl-, and 4- to 6-membered heterocycloalkyl having at least one nitrogen atom via which the heterocycloalkyl ring is connected to the rest of the molecule wherein a heterocycloalkyl group in $R^2$ may be optionally substituted with 1 to 4 substituents selected from the group consisting of fluorine, chlorine, cyano, oxo, $C_1$-$C_4$-alkyl, $C_1$-$C_4$-alkoxy, —N($C_1$-$C_4$-alkyl)$_2$, and wherein each $C_1$-$C_4$-alkyl, $C_3$-$C_6$-cycloalkyl and $C_1$-$C_4$-alkoxy in $R^2$ may be optionally substituted with halogen, OH, NH$_2$, —NH($C_1$-$C_4$-alkyl), —N($C_1$-$C_4$-alkyl)$_2$, cyano, carboxy, carbamoyl, alkoxycarbonyl, —C(O)—NH($C_1$-$C_4$-alkyl), —C(O)—N ($C_1$-$C_4$-alkyl)$_2$, $C_1$-$C_4$-alkoxy, —S—$C_1$-$C_4$-alkyl, —S(O)—$C_1$-$C_4$-alkyl, —SO$_2$—$C_0$-$C_4$-alkyl, or optionally substituted with a monocyclic heterocycle selected from the group of azetidines, pyrrolidines, morpholines, piperidines and piperazines, each of which as a substituent of $C_1$-$C_4$-alkyl, $C_3$-$C_6$-cycloalkyl and $C_1$-$C_4$-alkoxy in $R^2$ is optionally substituted with 1, 2 or 3 substituents independently selected from the group consisting of hydrogen, halogen, cyano, oxo, $C_1$-$C_4$-alkyl, $C_1$-$C_4$-halogenoalkyl having 1 to 5 halogen atoms;

$R^3$ is selected from the group consisting of hydrogen and $C_1$-$C_4$-alkyl, $R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, —SO$_2$—$C_1$-$C_4$-alkyl, $R^5$ is hydrogen or methyl, $R^6$ is hydrogen or methyl, $R^7$ is hydrogen or methyl, and Q is a substituted phenyl ring of the formula (Q1)

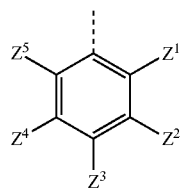

(Q1)

in which:

$Z^1, Z^2, Z^3, Z^4$, and $Z^5$ are independently selected from the group consisting of hydrogen, halogen, SF$_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, —O—($C_3$-$C_6$-cycloalkyl), cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl and cyano, or 5-membered heteroaryl having at least one nitrogen atom via which the heteroaryl ring is connected to the rest of the molecule, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with $C_1$-$C_4$-halogenoalkoxy having 1 to 5 halogen atoms, methyl substituted with $C_3$-$C_6$-cycloalkyl-$C_1$-$C_4$-alkoxy or methyl substituted with a 4- to 6-membered heterocycloalkyl which itself is optionally substituted with 1 or 2 substituents selected from the group consisting of fluorine, methyl and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl), —S(O)—($C_1$-$C_4$-halogenoalkyl), —SO$_2$—($C_1$-$C_4$-halogenoalkyl), —S—($C_1$-$C_4$-cycloalkyl), —S(O)—($C_1$-$C_4$-cycloalkyl), —SO$_2$—($C_1$-$C_4$-cycloalkyl), —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluoro and oxo, and $Z^3, Z^4$, and $Z^5$ are independently selected from the group consisting of hydrogen, halogen, SF$_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl), —S(O)—($C_1$-$C_4$-halogenoalkyl), —SO$_2$—($C_1$-$C_4$-halogenoalkyl), —CONH($C_1$-$C_4$-alkyl), —CONH ($C_3$-$C_6$-cycloalkyl), —NHCO($C_1$-$C_4$-alkyl), —NHCO ($C_3$-$C_6$-cycloalkyl), —NHCO($C_1$-$C_4$-halogenoalkyl) having 1 to 5 halogen atoms, or $Z^2$ and $Z^3$ form, together with the carbon atoms that they are connected to, a 5- or 6-membered cycloalkyl or heterocycloalkyl, a 5-membered heteroaryl, or a 6-membered heteroaryl, each of which may be optionally substituted with one or two substituents selected from the group consisting of methyl, fluoro and oxo, and $Z^1, Z^4$, and $Z^5$ are independently selected from the group consisting of hydrogen, halogen, SF$_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl), —S(O)—($C_1$-$C_4$-halogenoalkyl), —SO$_2$—($C_1$-$C_4$-halogenoalkyl), —CONH($C_1$-$C_4$-alkyl), —CONH ($C_3$-$C_6$-cycloalkyl), —NHCO($C_1$-$C_4$-alkyl), —NHCO ($C_3$-$C_6$-cycloalkyl), —NHCO($C_1$-$C_4$-halogenoalkyl) having 1 to 5 halogen atoms, or Q is a pyridine ring of the formula (Q2)

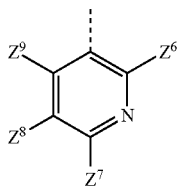

in which:
Z$^6$, Z$^7$, Z$^8$ and Z$^9$ are independently selected from the group consisting of hydrogen fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, or Q is a pyrimidine ring of the formula (Q3)

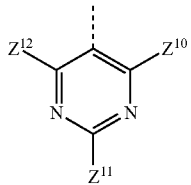

in which:
Z$^{10}$, Z$^1$ and Z$^{12}$ are independently selected from the group consisting of hydrogen, fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, or Q is a pyridine ring of the formula (Q4)

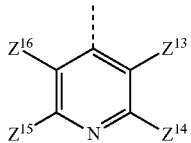

in which:
Z$^{13}$, Z$^{14}$, Z$^{15}$ and Z$^{16}$ are independently selected from the group consisting of hydrogen, fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, NH$_2$, —NH(C$_1$-C$_4$-alkyl), —N(C$_1$-C$_4$-alkyl)$_2$, —NH—CO—C$_1$-C$_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of hydrogen, halogen, cyano, nitro, —OH, oxo, thiono, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl, —S(O)—C$_1$-C$_4$-halogenoalkyl and —SO$_2$—C$_1$-C$_4$-halogenoalkyl having 1 to 5 halogen atoms, or Q is a pyridine ring of the formula (Q5)

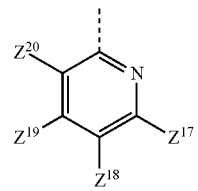

in which:
Z$^{17}$, Z$^{18}$, Z$^{19}$ and Z$^{20}$ are independently selected from the group consisting of hydrogen, fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, or Q a pyrazole ring of the formula (Q6)

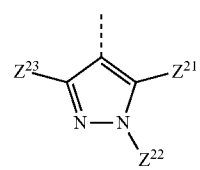

in which:
Z$^{21}$ and Z$^{23}$ are independently selected from the group consisting of hydrogen, C$_1$-C$_4$-alkyl, C$_1$-C$_4$-halogenoalkyl having 1 to 5 halogen atoms, and
Z$^{22}$ is selected from the group consisting of hydrogen, C$_1$-C$_4$-alkyl, C$_1$-C$_4$-halogenoalkyl having 1 to 5 halogen atoms, C$_1$-C$_4$-alkyl-C$_3$-C$_6$-cycloalkyl, C$_1$-C$_4$-alkoxy-C$_1$-C$_4$-alkyl, (C$_1$-C$_4$-alkyl)$_2$-N—C$_1$-C$_4$-alkyl-, morpholino-C$_1$-C$_4$-alkyl, (C$_1$-C$_4$-alkyl)-NH—C$_1$-C$_4$-alkyl-, or Q is a pyrazole ring of the formula (Q7)

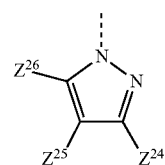

in which:
Z$^{24}$, Z$^{25}$ and Z$^{26}$ are independently selected from the group consisting of hydrogen, fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, and stereoisomers, tautomers, N-oxides, hydrates, solvates, and salts thereof, and mixtures of same.

In accordance with a fourth embodiment of the first aspect, the present invention covers compounds of general formula (I), supra, in which:

o is 0 or 1,
R is selected from the group consisting of hydrogen, fluorine, chlorine, $C_1$-$C_4$-alkyl,
n is 0 or 1,
X, Y are independently selected from the group consisting of $CH_2$ and O, wherein at least one of X and Y is $CH_2$,
$R^1$ is hydrogen,
$R^2$ is selected from the group consisting of hydrogen, $C_1$-$C_4$-alkyl, $C_3$-$C_6$-cycloalkyl, $C_1$-$C_4$-fluoroalkyl having 1 to 5 fluorine atoms, $C_1$-$C_4$-alkoxy-$C_1$-$C_4$-alkyl, benzyl having 1 to 5 halogen atoms, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —N($C_1$-$C_4$-alkyl) (6-membered heterocycloalkyl), —N($C_1$-$C_4$-alkyl)($C_1$-$C_4$-alkoxy), morpholino optionally substituted with 1 to 2 $C_1$-$C_4$-alkyl groups, $C_1$-$C_4$-alkyl-N($C_1$-$C_4$-alkyl)$_2$, wherein each $C_1$-$C_4$-alkyl in $R^2$ may be optionally substituted with halogen, —N($C_1$-$C_4$-alkyl)$_2$, $C_1$-$C_4$-alkoxy which itself may be substituted with $C_1$-$C_2$-alkoxy-substituted $C_1$-$C_2$-alkoxy, —S—$C_1$-$C_4$-alkyl, —S(O)—$C_1$-$C_4$-alkyl, —$SO_2$—$C_1$-$C_4$-alkyl, or optionally substituted by a monocyclic heterocycle selected from the group of 4- to 7-membered heterocycloalkyl, which itself may be substituted with methyl or oxo,
$R^3$ is selected from the group consisting of hydrogen and $C_1$-$C_4$-alkyl,
$R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, —$SO_2$—$C_1$-$C_4$-alkyl, and
Q is a substituted phenyl ring of the formula (Q1)

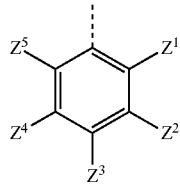

(Q1)

in which:
$Z^1$, $Z^2$, $Z^3$, $Z^4$, and $Z^5$ are independently selected from the group consisting of hydrogen, fluorine, chlorine, bromine, cyano, methyl, propyl, difluoromethyl, trifluoromethyl, hydroxy, methoxy, ethoxy, isopropoxy, —O-cyclopropyl, —$OCH_2$-cyclopropyl, —$OCH_2CN$, trifluoromethoxy, difluoromethoxy, trifluoroethoxy, methylamino, dimethylamino, methylethylamino, diethylamino, acetylamino, methylsulfonamide, trifluoroacetylamino, —$SO_2Me$, —$SO_2$-cyclopropyl, —$CH_2$—O— methyl, —$CH_2$—O-ethyl, —$CH_2$—O—$CH_2$-cyclopropyl, —$CH_2$—O-isopropyl, —$CH_2$—N ($CH_3$)$_2$, —$CH_2$—N($CH_2CH_3$)$_2$, —$CH_2$—N($CH_3$) ($CH_2CH_3$), —$CH_2$—$SCH_3$, —$CH_2$—S(O)$CH_3$, —$CH_2$—$SO_2$—$CH_3$, —C(O)NH-cyclopropyl, and

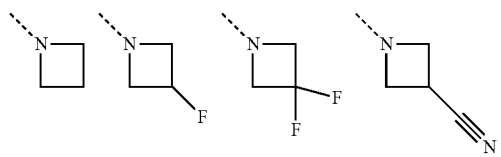

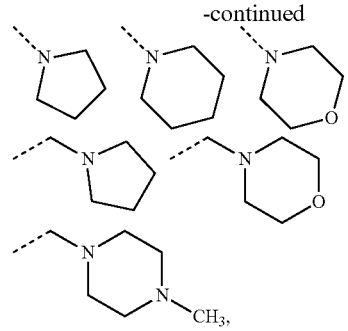

or
$Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, and
$Z^3$, $Z^4$, and $Z^5$ are independently selected from the group consisting of hydrogen, fluorine, chlorine, bromine, cyano, methyl, propyl, difluoromethyl, trifluoromethyl, hydroxy, methoxy, ethoxy, isopropoxy, —O-cyclopropyl, —$OCH_2$-cyclopropyl, —$OCH_2CN$, trifluoromethoxy, difluoromethoxy, trifluoroethoxy, methylamino, dimethylamino, methylethylamino, diethylamino, acetylamino, methylsulfonamide, trifluoroacetylamino, —$SO_2Me$, —$SO_2$-cyclopropyl, —$CH_2$—O— methyl, —$CH_2$—O-ethyl, —$CH_2$—O—$CH_2$-cyclopropyl, —$CH_2$—O-isopropyl, —$CH_2$—N ($CH_3$)$_2$, —$CH_2$—N($CH_2CH_3$)$_2$, —$CH_2$—N($CH_3$) ($CH_2CH_3$), —$CH_2$—$SCH_3$, —$CH_2$—S(O)$CH_3$, —$CH_2$—$SO_2$—$CH_3$, —C(O)NH-cyclopropyl, and

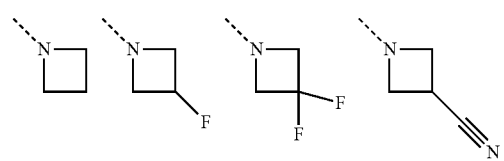

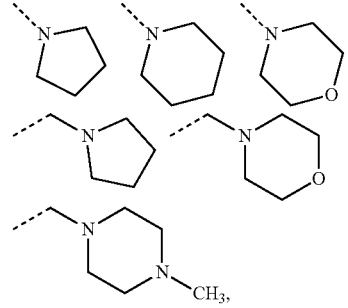

or
$Z^2$ and $Z^3$ form, together with the carbon atoms that they are connected to, a 5-membered cycloalkyl or heterocycloalkyl or a 5-membered heteroaryl, each of which may be optionally substituted with one or two substituents selected from the group consisting of methyl, fluorine and oxo, and
$Z^1$, $Z^4$, and $Z^5$ are independently selected from the group consisting of hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methylethylamino, diethylamino, acetylamino, methylsulfonamide, trifluoroacetylamino, —SO$_2$Me, —SO$_2$-cyclopropyl, —CH$_2$—O— methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl, and

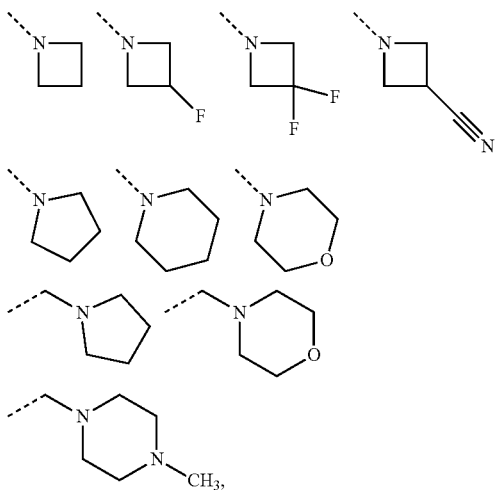

Q is a pyridine ring of the formula (Q2)

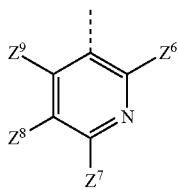

(Q2)

in which:

Z$^6$, Z$^7$, Z$^8$ and Z$^9$ are independently selected from the group consisting of hydrogen, fluorine or chlorine, or Q is a pyrimidine ring of the formula (Q3)

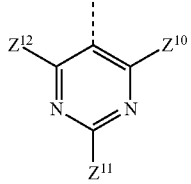

(Q3)

in which:

Z$^{10}$, Z$^{1'}$ and Z$^{12}$ are independently selected from the group consisting of hydrogen, fluorine, chlorine, C$_1$-C$_4$-alkyl, or Q is a pyridine ring of the formula (Q4)

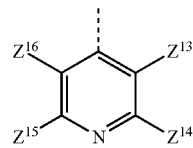

(Q4)

in which:

Z$^{13}$, Z$^{14}$, Z$^{15}$ and Z$^{16}$ are independently selected from the group consisting of hydrogen, fluorine, chlorine, C$_1$-C$_4$-alkyl, NH$_2$, —NH(C$_1$-C$_4$-alkyl), —N(C$_1$-C$_4$-alkyl)$_2$, —NH—CO—C$_1$-C$_4$-alkyl, and morpholino, pyrazoles, triazoles, imidazoles and pyrroles, wherein a heteroaryl ring is connected to the pyridine ring via one of its nitrogen atoms, each of which is optionally substituted with 1, 2 or 3 substituents independently selected from the group consisting of hydrogen, halogen, cyano, C$_1$-C$_4$-alkyl, C$_1$-C$_4$-halogenoalkyl having 1 to 5 halogen atoms, or Q is a pyridine ring of the formula (Q5)

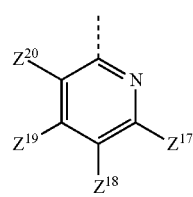

(Q5)

in which:

Z$^{17}$, Z$^{18}$, Z$^{19}$ and Z$^{20}$ are independently selected from the group consisting of hydrogen, fluorine, chlorine, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, or Q a pyrazole ring of the formula (Q6)

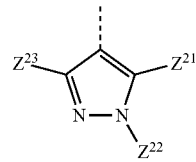

(Q6)

in which:

Z$^{21}$ and Z$^{23}$ are hydrogen, and

Z$^{22}$ is selected from the group consisting of hydrogen, C$_1$-C$_4$-alkyl, C$_1$-C$_4$-halogenoalkyl having 1 to 5 halogen atoms, C$_1$-C$_4$-alkyl-C$_3$-C$_6$-cycloalkyl, C$_1$-C$_4$-alkoxy-C$_1$-C$_4$-alkyl, C$_1$-C$_4$-alkyl-N(C$_1$-C$_4$-alkyl)$_2$, morpholino-C$_1$-C$_4$-alkyl, or Q is a pyrazole ring of the formula (Q7)

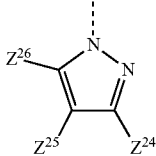

(Q7)

in which:
$Z^{24}$, $Z^{25}$ and $Z^{26}$ are independently selected from the group consisting of hydrogen, fluorine, chlorine, cyano, methyl, triflouromethyl,
and stereoisomers, tautomers, N-oxides, hydrates, solvates, and salts thereof, and mixtures of same.

In accordance with a fifth embodiment of the first aspect, the present invention covers compounds of general formula (I), supra, in which:
o is 0 or 1,
R is selected from the group consisting of hydrogen, fluorine, chlorine, methyl,
n is 0 or 1,
X is selected from the group consisting of $CH_2$ and O,
Y is $CH_2$,
$R^1$ is hydrogen,
$R^2$ is selected from the group consisting of hydrogen, methyl, ethyl, isopropyl, isobutyl, sec-butyl, cyclopropyl, methoxymethyl, difluoromethyl, trifluoromethyl, 4-fluorobenzyl, methoxy, methylamino, dimethylamino, cyclopropylamino, —N(CH$_3$)(cyclopropyl), —N(CH$_3$)(CH$_2$—N(CH$_3$)$_2$), —N(CH$_3$)(CH$_2$—CHF$_2$), —N(CH$_3$)((CH$_2$)$_2$O(CH$_2$)$_2$)O(CH$_2$)$_2$)OH$_2$)$_2$)CH$_3$), —N(CH$_3$)((CH$_2$)$_2$—S—CH$_3$), —N(CH$_3$)((CH$_2$)$_2$—S(O)—CH$_3$), —N(CH$_3$)((CH$_2$)$_2$—SO$_2$—CH$_3$), —N(CH$_3$)(1-methyl-piperidin-4-yl), —N(CH$_3$)((CH$_2$)$_2$-(oxopyrrolidin-1-yl)), morpholino, CH$_2$—N(CH$_3$)$_2$,
$R^3$ is selected from the group consisting of hydrogen and methyl,
$R^4$ is selected from the group consisting of hydrogen, chlorine, methyl, cyclopropyl, difluoromethyl, trifluoromethyl, —S-methyl, —S-ethyl, —S-isopropyl, —S(O)$_2$-methyl, —S(O)$_2$-ethyl, —S(O)$_2$-isopropyl, and
Q is a substituted phenyl ring of the formula (Q1)

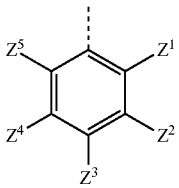

(Q1)

in which:
$Z^1$, $Z^2$, $Z^3$, $Z^4$, and $Z^5$ are independently selected from the group consisting of hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methylethylamino, diethylamino, acetylamino, methylsulfonamide, trifluoroacetylamino, —SO$_2$Me, —SO$_2$-cyclopropyl, —CH$_2$—O— methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl, and

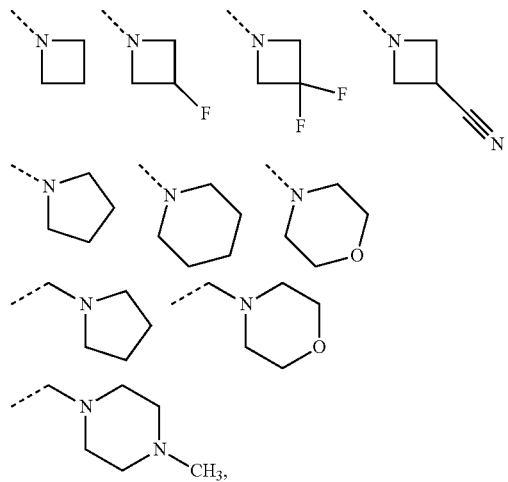

wherein at least two of $Z^1$, $Z^2$, $Z^3$, $Z^4$, and $Z^5$ are hydrogen, or

Q is a pyridine ring of the formula (Q2)

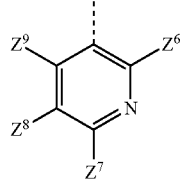

(Q2)

in which:
$Z^6$ is hydrogen,
$Z^7$, $Z^8$ are independently selected from the group consisting of hydrogen, fluorine, chlorine, and
$Z^9$ is selected from the group consisting of hydrogen and chlorine, or Q is a pyrimidine ring of the formula (Q3)

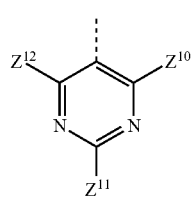

(Q3)

in which:
$Z^{10}$ and $Z^{12}$ are hydrogen, and
$Z^{11}$ is selected from the group consisting of hydrogen and chlorine, or Q is a pyridine ring of the formula (Q4)

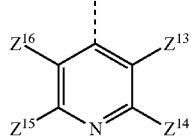

(Q4)

in which:
$Z^{13}$, $Z^{15}$, and $Z^{16}$ are hydrogen, and
$Z^{14}$ is selected from the group consisting of hydrogen, chlorine, $NH_2$, —NH—CO—$C_1$-$C_4$-alkyl, —NH($C_1$-$C_4$-alkyl), —N($C_1$-$C_4$-alkyl)$_2$, morpholino, or Q is a pyridine ring of the formula (Q5)

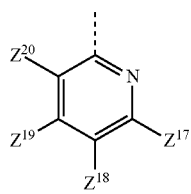

(Q5)

in which:
$Z^{17}$ is selected from the group consisting of fluorine, chlorine, methoxy, trifluoromethyl,
$Z^{18}$ and $Z^{20}$ are selected from the group consisting of hydrogen and chlorine,
$Z^{19}$ is selected from the group consisting of hydrogen and chlorine, preferably $Z^{19}$ is hydrogen, or Q a pyrazole ring of the formula (Q6)

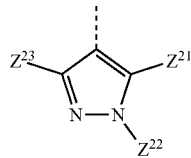

(Q6)

in which:
$Z^{21}$ and $Z^{23}$ are hydrogen, and
$Z^{22}$ is selected from the group consisting of hydrogen, methyl, ethyl, isopropyl, methoxyethyl, —$CH_2$-cyclopropyl, —$CH_2CF_3$, —$CH_2CHF_2$, —$CH_2$-morpholino, —$CH_2$—$CH_2$—$N(CH_3)_2$, and/or —$CH_2$—$CH_2$-morpholino, or Q is a pyrazole ring of the formula (Q7)

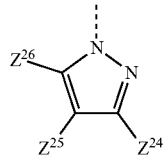

(Q7)

in which:
$Z^{24}$ and $Z^{26}$ are hydrogen, and
$Z^{25}$ is selected from the group consisting of hydrogen and chlorine, or Q is selected from the group consisting of

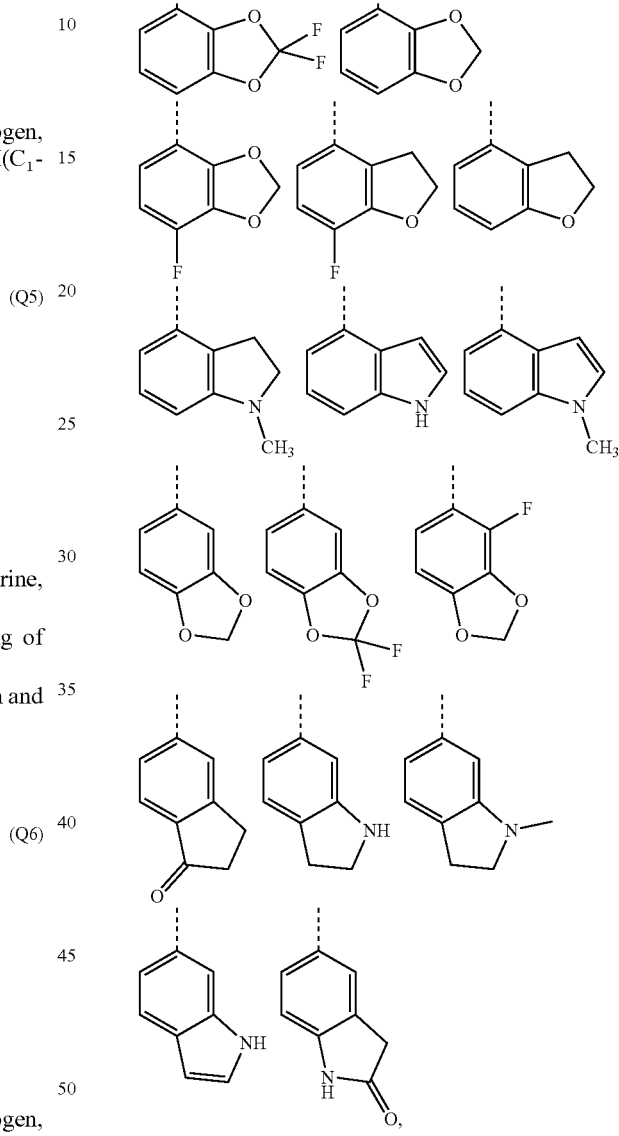

and stereoisomers, tautomers, N-oxides, hydrates, solvates, and salts thereof, and mixtures of same.

In accordance with a sixth embodiment of the first aspect, the present invention covers compounds of general formula (I), supra, in which:
o is 0 or 1,
R is selected from the group consisting of hydrogen, fluorine, chlorine, methyl,
n is 0 or 1,
X is selected from the group consisting of $CH_2$ and O,
Y is $CH_2$,
$R^1$ is hydrogen,
$R^2$ is selected from the group consisting of hydrogen, methyl, ethyl, isopropyl, isobutyl, sec-butyl, cyclopropyl, methoxymethyl, difluoromethyl, trifluoromethyl, 4-fluorobenzyl, methoxy, methylamino, dimethylamino, cyclopropylamino, —N(CH₃)(cyclopropyl), —N(CH₃)(CH₂—N(CH₃)₂), —N(CH₃)(CH₂—CHF₂), —N(CH₃)((CH₂)₂O(CH₂)₂)O(CH₂)₂)OCH₃), —N(CH₃)((CH₂)₂—S—CH₃), —N(CH₃)((CH₂)₂—S(O)—CH₃), —N(CH₃)((CH₂)₂—SO₂—CH₃), N(CH₃)(1-methyl-piperidin-4-yl), —N(CH₃)((CH₂)₂-(oxopyrrolidin-1-yl)), morpholino, CH₂—N(CH₃)₂, $R^3$ is selected from the group consisting of hydrogen and methyl, $R^4$ is selected from the group consisting of hydrogen, chlorine, methyl, cyclopropyl, difluoromethyl, trifluoromethyl, —S-methyl, —S-ethyl, —S-isopropyl, —S(O)₂-methyl, —S(O)₂-ethyl, —S(O)₂-isopropyl, and Q is a substituted phenyl ring of the formula (Q1)

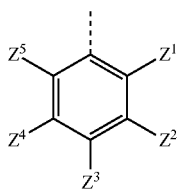

(Q1)

in which:

$Z^1$, $Z^2$, $Z^3$, $Z^4$, and $Z^5$ are independently selected from the group consisting of hydrogen, fluorine, chlorine, bromine, cyano, methyl, propyl, difluoromethyl, trifluoromethyl, hydroxy, methoxy, ethoxy, isopropoxy, —O-cyclopropyl, —OCH₂-cyclopropyl, —OCH₂CN, trifluoromethoxy, difluoromethoxy, trifluoroethoxy, methylamino, dimethylamino, methylethylamino, diethylamino, acetylamino, methylsulfonamide, trifluoroacetylamino, —SO₂Me, —SO₂-cyclopropyl, —CH₂—O—methyl, —CH₂—O-ethyl, —CH₂—O—CH₂-cyclopropyl, —CH₂—O-isopropyl, —CH₂—N(CH₃)₂, —CH₂—N(CH₂CH₃)₂, —CH₂—N(CH₃)(CH₂CH₃), —CH₂—SCH₃, —CH₂—S(O)CH₃, —CH₂—SO₂—CH₃, —C(O)NH-cyclopropyl, and

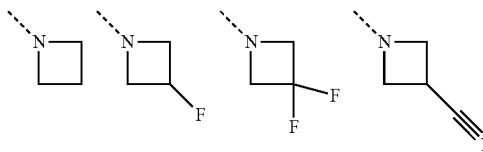

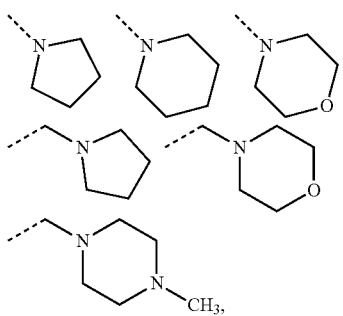

wherein at least two of $Z^1$, $Z^2$, $Z^3$, $Z^4$, and $Z^5$ are hydrogen, or

Q is selected from the group consisting of

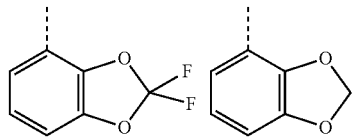

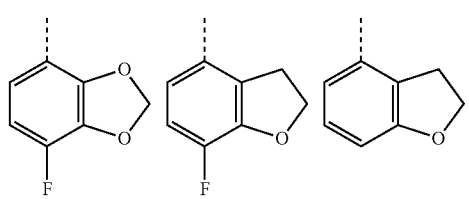

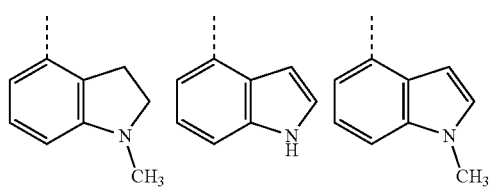

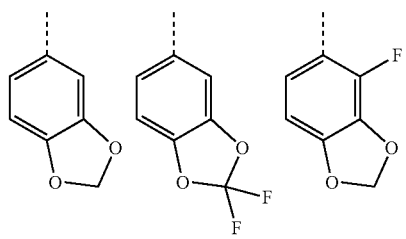

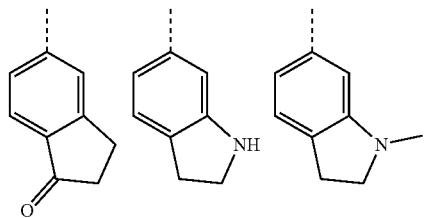

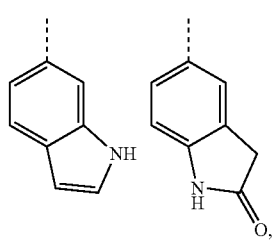

and stereoisomers, tautomers, N-oxides, hydrates, solvates, and salts thereof, and mixtures of same.

In accordance with a seventh embodiment of the first aspect, the present invention covers compounds of general formula (I), supra, in which the following compounds are excluded

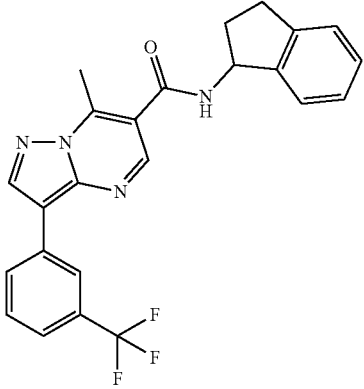

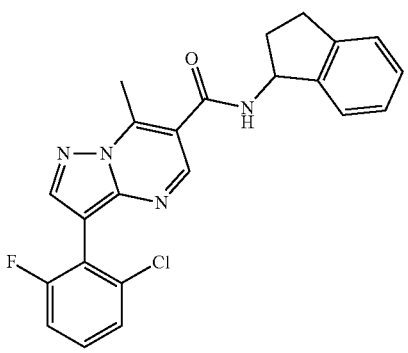

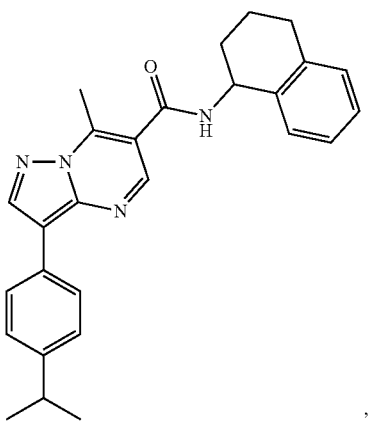

and stereoisomers, tautomers, N-oxides, hydrates, solvates, and salts thereof, and mixtures of same.

In accordance with a eighth embodiment of the first aspect, the present invention covers compounds of general formula (II):

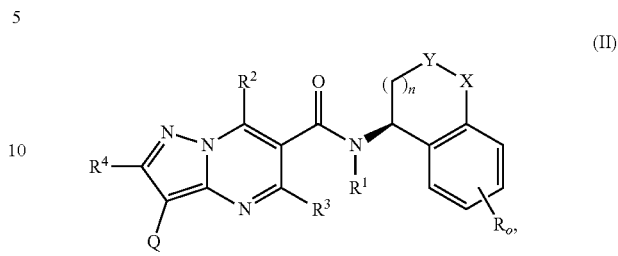

(II)

in which:
o is 0 or 1,
R is selected from the group consisting of hydrogen, fluorine, chlorine, methyl,
n is 0 or 1,
X is selected from the group consisting of $CH_2$ and O,
Y is $CH_2$,
$R^1$ is hydrogen,
$R^2$ is selected from the group consisting of hydrogen, methyl, ethyl, isopropyl, isobutyl, sec-butyl, cyclopropyl, methoxymethyl, difluoromethyl, trifluoromethyl, 4-fluorobenzyl, methoxy, methylamino, dimethylamino, cyclopropylamino, —$N(CH_3)$(cyclopropyl), —$N(CH_3)(CH_2$—$N(CH_3)_2)$, —$N(CH_3)(CH_2$—$CHF_2)$, —$N(CH_3)((CH_2)_2O(CH_2)_2)O(CH_2)_2)OH_2)_2)CH_3)$, —$N(CH_3)((CH_2)_2$—S—$CH_3)$, —$N(CH_3)((CH_2)_2$—S(O)—$CH_3)$, —$N(CH_3)((CH_2)_2$—$SO_2$—$CH_3)$, —$N(CH_3)$(1-methyl-piperidin-4-yl), —$N(CH_3)((CH_2)_2$-(oxopyrrolidin-1-yl)), morpholino, $CH_2$—$N(CH_3)_2$,
$R^3$ is selected from the group consisting of hydrogen and methyl,
$R^4$ is selected from the group consisting of hydrogen, chlorine, methyl, cyclopropyl, difluoromethyl, trifluoromethyl, —S-methyl, —S-ethyl, —S-isopropyl, —S(O)$_2$-methyl, —S(O)$_2$-ethyl, —S(O)$_2$-isopropyl, and
Q is a substituted phenyl ring of the formula (Q1)

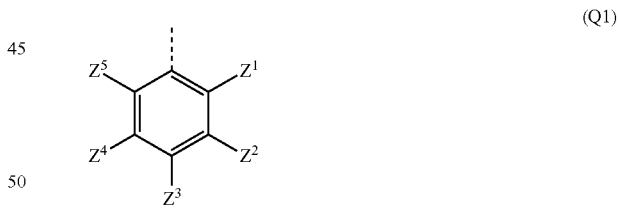

(Q1)

in which:
$Z^1$, $Z^2$, $Z^3$, $Z^4$, and $Z^5$ are independently selected from the group consisting of hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methylethylamino, diethylamino, acetylamino, methylsulfonamide, trifluoroacetylamino, —SO$_2$Me, —SO$_2$-cyclopropyl, —CH$_2$—O— methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl, and

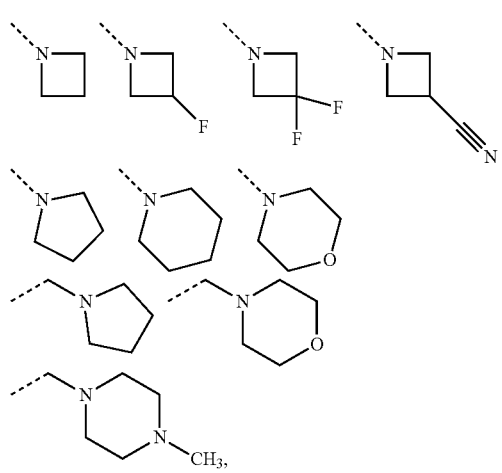

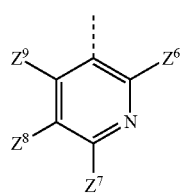

wherein at least two of $Z^1$, $Z^2$, $Z^3$, $Z^4$, and $Z^5$ are hydrogen, or

Q is a pyridine ring of the formula (Q2)

(Q2)

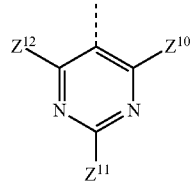

in which:
$Z^6$ is hydrogen,
$Z^7$, $Z^8$ are independently selected from the group consisting of hydrogen, fluorine, chlorine, and
$Z^9$ is selected from the group consisting of hydrogen and chlorine, or Q is a pyrimidine ring of the formula (Q3)

(Q3)

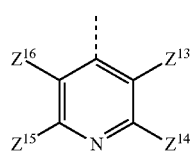

in which:
$Z^{10}$ and $Z^{12}$ are hydrogen, and
$Z^{11}$ is selected from the group consisting of hydrogen and chlorine, or Q is a pyridine ring of the formula (Q4)

(Q4)

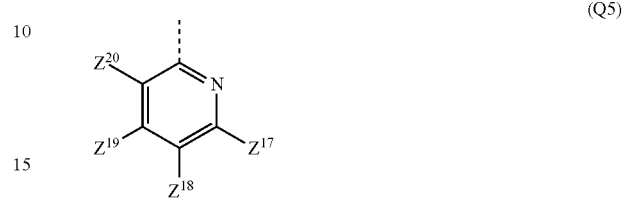

in which:
$Z^{13}$, $Z^{15}$, and $Z^{16}$ are hydrogen, and
$Z^{14}$ is selected from the group consisting of hydrogen and chlorine, $NH_2$, —NH—CO—$C_1$-$C_4$-alkyl, —NH($C_1$-$C_4$-alkyl), —N($C_1$-$C_4$-alkyl)$_2$, morpholino, or Q is a pyridine ring of the formula (Q5)

(Q5)

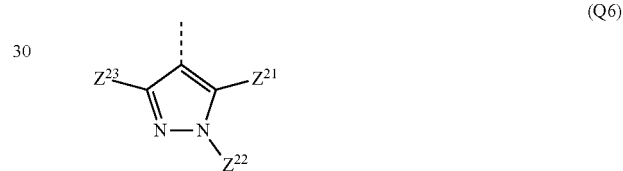

in which:
$Z^{17}$ is selected from the group consisting of fluorine, chlorine, methoxy, trifluoromethyl,
$Z^{18}$ and $Z^{20}$ are selected from the group consisting of hydrogen and chlorine,
$Z^{19}$ is selected from the group consisting of hydrogen and chlorine, preferably $Z^{19}$ is hydrogen, or Q a pyrazole ring of the formula (Q6)

(Q6)

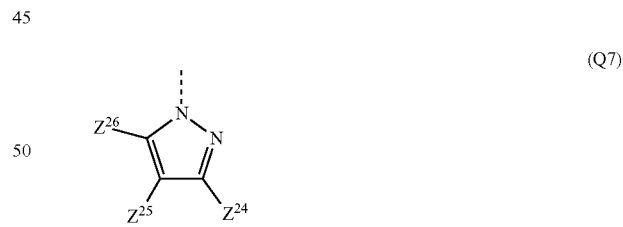

in which:
$Z^{21}$ and $Z^{23}$ are hydrogen, and
$Z^{22}$ is selected from the group consisting of hydrogen, methyl, ethyl, isopropyl, methoxyethyl, —$CH_2$-cyclopropyl, —$CH_2CF_3$, —$CH_2CHF_2$, —$CH_2$-morpholino, —$CH_2$—$CH_2$—$N(CH_3)_2$, and/or —$CH_2$—$CH_2$-morpholino, or Q is a pyrazole ring of the formula (Q7)

(Q7)

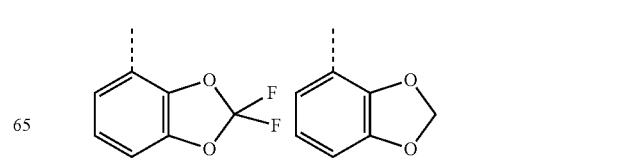

in which:
$Z^{24}$ and $Z^{26}$ are hydrogen, and
$Z^{25}$ is selected from the group consisting of hydrogen and chlorine, or Q is selected from the group consisting of -continued

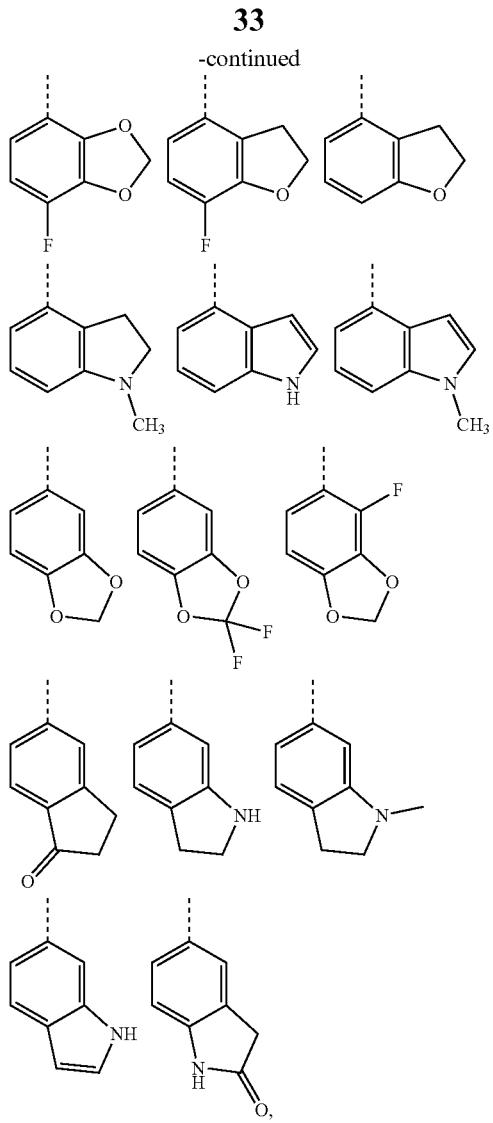

and stereoisomers, tautomers, N-oxides, hydrates, solvates, and salts thereof, and mixtures of same.

In accordance with a ninth embodiment of the first aspect, the present invention covers compounds of general formula (II), supra, in which:

the following compounds are excluded

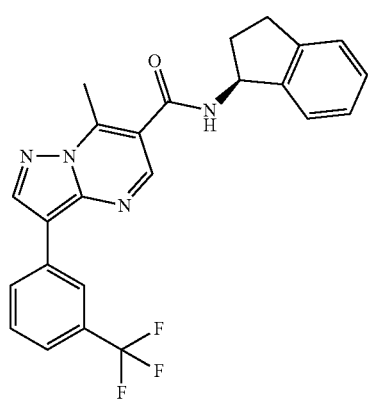

-continued

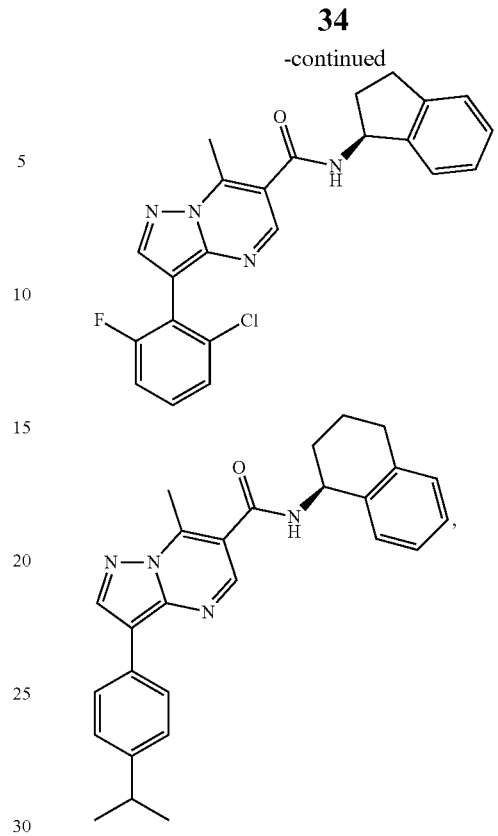

and stereoisomers, tautomers, N-oxides, hydrates, solvates, and salts thereof, and mixtures of same.

In a further embodiment of the first aspect, the present invention covers compounds of formula (I), supra, in which:
n is 0 or 1,
X is selected from the group consisting of $CH_2$ and O, and
Y is $CH_2$,
and stereoisomers, tautomers, N-oxides, hydrates, solvates, and salts thereof, and mixtures of same.

In a further embodiment of the first aspect, the present invention covers compounds of formula (I), supra, in which:
o is 0 or 1,
R is selected from the group consisting of hydrogen, fluorine, chlorine, methyl,
and stereoisomers, tautomers, N-oxides, hydrates, solvates, and salts thereof, and mixtures of same.

In a further embodiment of the first aspect, the present invention covers compounds of formula (I), supra, in which:
o is 0 or 1,
R is selected from the group consisting of hydrogen, fluorine, chlorine, methyl,
n is 0 or 1,
X is selected from the group consisting of $CH_2$ and O, and
Y is $CH_2$,
and stereoisomers, tautomers, N-oxides, hydrates, solvates, and salts thereof, and mixtures of same.

In a further embodiment of the first aspect, the present invention covers compounds of formula
(I), supra, in which:
n is 0,
o is 0 or 1,
R is hydrogen,
X is $CH_2$, and
Y is $CH_2$,
or
n is 1,
o is 0 or 1, R is selected from the group consisting of hydrogen, fluorine, chlorine, methyl, X is selected from the group consisting of $CH_2$ and O, and Y is $CH_2$, and stereoisomers, tautomers, N-oxides, hydrates, solvates, and salts thereof, and mixtures of same.

In a further embodiment of the first aspect, the present invention covers compounds of formula (I), supra, in which:
$R^1$ is hydrogen
and stereoisomers, tautomers, N-oxides, hydrates, solvates, and salts thereof, and mixtures of same.

In a further embodiment of the first aspect, the present invention covers compounds of formula (I), supra, in which:
$R^2$ is selected from the group consisting of hydrogen, methyl, ethyl, isopropyl, isobutyl, sec-butyl, cyclopropyl, methoxymethyl, difluoromethyl, trifluoromethyl, 4-fluorobenzyl, methoxy, methylamino, dimethylamino, cyclopropylamino, —N($CH_3$)(cyclopropyl), —N($CH_3$)($CH_2$—N($CH_3$)$_2$), —N($CH_3$)($CH_2$—$CHF_2$), —N($CH_3$)(($CH_2$)$_2$O($CH_2$)$_2$)O($CH_2$)$_2$)O$H_2$)$_2$)$CH_3$), —N($CH_3$)(($CH_2$)$_2$—S—$CH_3$), —N($CH_3$)(($CH_2$)$_2$—S(O)—$CH_3$), —N($CH_3$)(($CH_2$)$_2$—$SO_2$—$CH_3$), —N($CH_3$)(1-methyl-piperidin-4-yl), —N($CH_3$)(($CH_2$)$_2$-(oxopyrrolidin-1-yl)), morpholino, $CH_2$—N($CH_3$)$_2$,
and stereoisomers, tautomers, N-oxides, hydrates, solvates, and salts thereof, and mixtures of same.

In a further embodiment of the first aspect, the present invention covers compounds of formula (I), supra, in which:
$R^3$ is selected from the group consisting of hydrogen and methyl,
and stereoisomers, tautomers, N-oxides, hydrates, solvates, and salts thereof, and mixtures of same.

In a further embodiment of the first aspect, the present invention covers compounds of formula (I), supra, in which:
$R^4$ is selected from the group consisting of hydrogen, chlorine, methyl, cyclopropyl, difluoromethyl, trifluoromethyl, —S-methyl, —S-ethyl, —S-isopropyl, —S(O)$_2$-methyl, —S(O)$_2$-ethyl, —S(O)$_2$-isopropyl,
and stereoisomers, tautomers, N-oxides, hydrates, solvates, and salts thereof, and mixtures of same.

In a further embodiment of the first aspect, the present invention covers compounds of formula (I), supra, in which:
Q is a substituted phenyl ring of the formula (Q1)

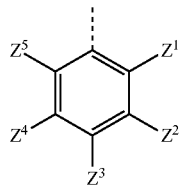

(Q1)

in which:
$Z^1$, $Z^2$, $Z^3$, $Z^4$, and $Z^5$ are independently selected from the group consisting of hydrogen, fluorine, chlorine, bromine, cyano, methyl, propyl, difluoromethyl, trifluoromethyl, hydroxy, methoxy, ethoxy, isopropoxy, —O-cyclopropyl, —O$CH_2$-cyclopropyl, —O$CH_2$CN, trifluoromethoxy, difluoromethoxy, trifluoroethoxy, methylamino, dimethylamino, methylethylamino, diethylamino, acetylamino, methylsulfonamide, trifluoroacetylamino, —$SO_2$Me, —$SO_2$-cyclopropyl, —$CH_2$—O— methyl, —$CH_2$—O-ethyl, —$CH_2$—O—$CH_2$-cyclopropyl, —$CH_2$—O-isopropyl, —$CH_2$—N($CH_3$)$_2$, —$CH_2$—N($CH_2$$CH_3$)$_2$, —$CH_2$—N($CH_3$)($CH_2$$CH_3$), —$CH_2$—$SCH_3$, —$CH_2$—S(O)$CH_3$, —$CH_2$—$SO_2$—$CH_3$, —C(O)NH-cyclopropyl, and

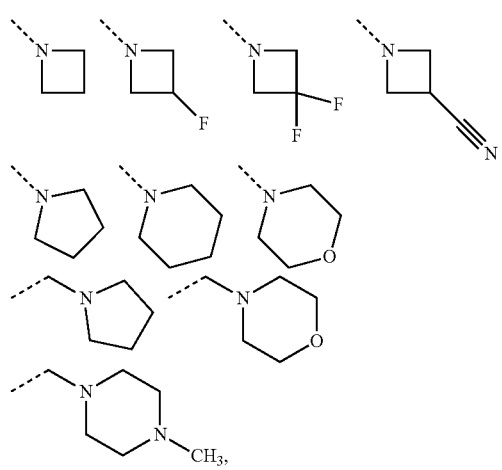

wherein at least two of $Z^1$, $Z^2$, $Z^3$, $Z^4$, and $Z^5$ are hydrogen,
and stereoisomers, tautomers, N-oxides, hydrates, solvates, and salts thereof, and mixtures of same.

In a further embodiment of the first aspect, the present invention covers compounds of formula (I), supra, in which:
Q is a pyridine ring of the formula (Q2)

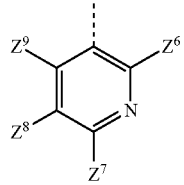

(Q2)

in which:
$Z^6$ is hydrogen,
$Z^7$, $Z^8$ are independently selected from the group consisting of hydrogen, fluorine, chlorine, and
$Z^9$ is selected from the group consisting of hydrogen and chlorine,
and stereoisomers, tautomers, N-oxides, hydrates, solvates, and salts thereof, and mixtures of same.

In a further embodiment of the first aspect, the present invention covers compounds of formula (I), supra, in which:
Q is a pyrimidine ring of the formula (Q3)

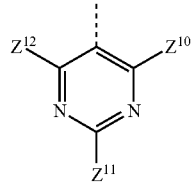

(Q3)

in which:
$Z^{10}$ and $Z^{12}$ are hydrogen, and
$Z^{11}$ is selected from the group consisting of hydrogen and chlorine,
and stereoisomers, tautomers, N-oxides, hydrates, solvates, and salts thereof, and mixtures of same.

In a further embodiment of the first aspect, the present invention covers compounds of formula (I), supra, in which:
Q is a pyridine ring of the formula (Q4)

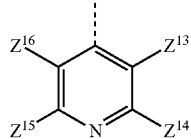

(Q4)

in which:
$Z^{13}$, $Z^{15}$, and $Z^{16}$ are hydrogen, and
$Z^{14}$ is selected from the group consisting of hydrogen, chlorine, $NH_2$, —NH—CO—$C_1$-$C_4$-alkyl, —NH($C_1$-$C_4$-alkyl), —N($C_1$-$C_4$-alkyl)$_2$, morpholino,
and stereoisomers, tautomers, N-oxides, hydrates, solvates, and salts thereof, and mixtures of same.

In a further embodiment of the first aspect, the present invention covers compounds of formula (I), supra, in which:
Q is a pyridine ring of the formula (Q5)

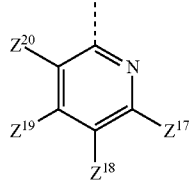

(Q5)

in which:
$Z^{17}$ is selected from the group consisting of fluorine, chlorine, methoxy, trifluoromethyl,
$Z^{18}$ and $Z^{20}$ are selected from the group consisting of hydrogen and chlorine,
$Z^{19}$ is selected from the group consisting of hydrogen and chlorine, preferably $Z^{19}$ is hydrogen,
and stereoisomers, tautomers, N-oxides, hydrates, solvates, and salts thereof, and mixtures of same.

In a further embodiment of the first aspect, the present invention covers compounds of formula (I), supra, in which:
Q a pyrazole ring of the formula (Q6)

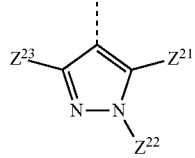

(Q6)

in which:
$Z^{21}$ and $Z^{23}$ are hydrogen, and
$Z^{22}$ is selected from the group consisting of hydrogen, methyl, ethyl, isopropyl, methoxyethyl, —$CH_2$-cyclopropyl, —$CH_2CF_3$, —$CH_2CHF_2$, —$CH_2$-morpholino, —$CH_2$—$CH_2$—$N(CH_3)_2$, and/or —$CH_2$—$CH_2$-morpholino,
and stereoisomers, tautomers, N-oxides, hydrates, solvates, and salts thereof, and mixtures of same.

In a further embodiment of the first aspect, the present invention covers compounds of formula (I), supra, in which:
Q is a pyrazole ring of the formula (Q7)

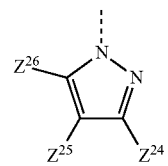

(Q7)

in which:
$Z^{24}$ and $Z^{26}$ are hydrogen, and
$Z^{25}$ is selected from the group consisting of hydrogen and chlorine,
and stereoisomers, tautomers, N-oxides, hydrates, solvates, and salts thereof, and mixtures of same.

In a further embodiment of the first aspect, the present invention covers compounds of formula (I), supra, in which:
Q is selected from the group consisting of

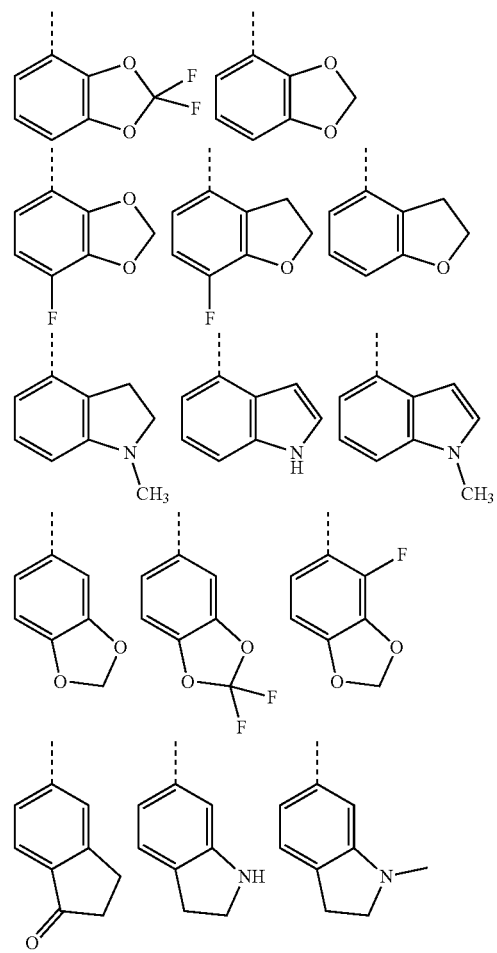

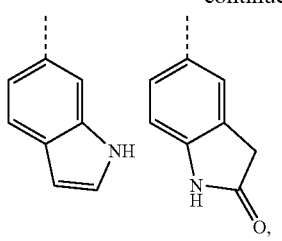

and stereoisomers, tautomers, N-oxides, hydrates, solvates, and salts thereof, and mixtures of same.

In a further embodiment of the first aspect, the present invention covers compounds of formula (I), supra, in which the following compounds are excluded:

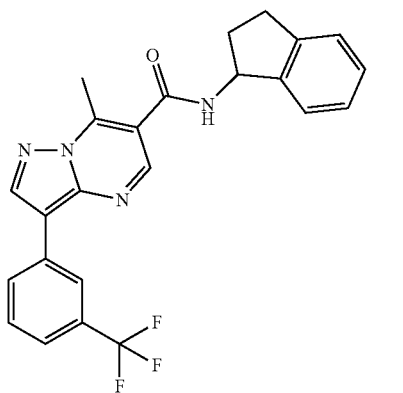

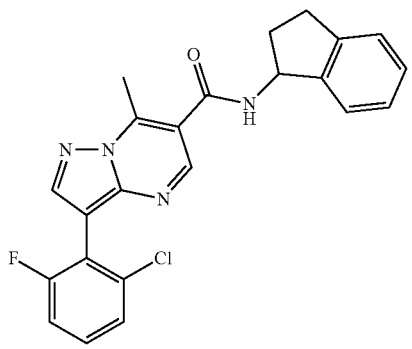

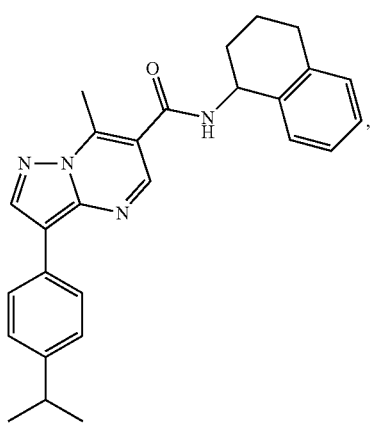

and stereoisomers, tautomers, N-oxides, hydrates, solvates, and salts thereof, and mixtures of same.

In a further embodiment of the first aspect, the present invention covers compounds of formula (I), supra, in which the stereochemistry is as represented by formula (II):

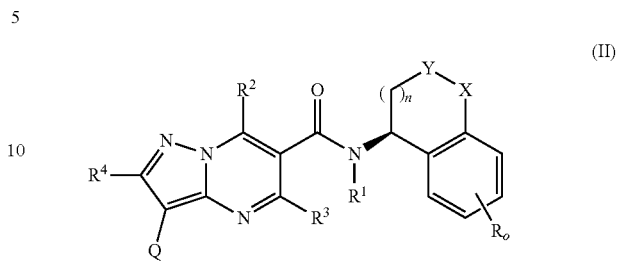

and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

In a particular further embodiment of the first aspect, the present invention covers any embodiment for compounds of general formula (I), supra, and any combination of two or more of the above mentioned embodiments under the heading "further embodiments of the first aspect of the present invention", for the compounds of general formula (II), supra.

The present invention covers any sub-combination within any embodiment or aspect of the present invention of compounds of general formula (I), supra.

The present invention covers the compounds of general formula (I) which are disclosed in the Example Section of this text, infra.

The compounds according to the invention of general formula (I) can be prepared according to the schemes 1 to 9 as shown in the Experimental Section to the present invention (General Procedures). The schemes and procedures described illustrate synthetic routes to the compounds of general formula (I) of the invention and are not intended to be limiting. It is clear to the person skilled in the art that the order of transformations as exemplified in schemes 1 to 9 can be modified in various ways. The order of transformations exemplified in these schemes is therefore not intended to be limiting. In addition, interconversion of any of the substituents, Q, R, $R^1$, $R^2$, $R^3$, $R^4$ or $R^5$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

Nine routes for the preparation of compounds of general formula (I) are described in schemes 1 to 9.

In accordance with a second aspect, the present invention covers methods of preparing compounds of general formula (I) as defined supra, said methods comprising the step of allowing an intermediate compound of general formula 1F:

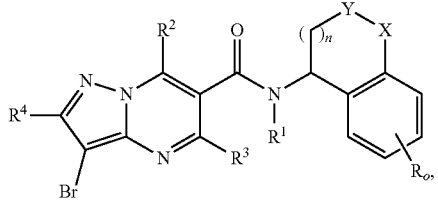

1F in which $R^0$, $R^1$, $R^2$, $R^3$, $R^4$, X, Y, o and n are as defined for the compound of general formula (I) as defined supra, to react with a compound of general formula 1H:

Q-B(OR)$_2$  1H, in which Q is as defined for the compound of general formula (I) as defined supra, and each R may be individually H or Me or both R are pinacolate, thereby giving a compound of general formula (I):

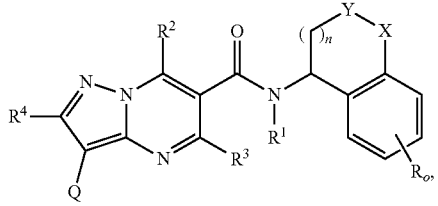

(I)

in which Q, $R^0$, $R^1$, $R^2$, $R^3$, $R^4$, X, Y, o and n are as defined supra.

In accordance with an alternative embodiment of the second aspect, the present invention covers methods of preparing compounds of general formula (I) as defined supra, said methods comprising the step of allowing an intermediate compound of general formula 2E:

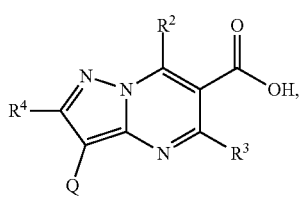

2E in which Q, $R^2$, $R^3$ and $R^4$ are as defined for the compound of general formula (I) as defined supra, to react with a compound of general formula 1G:

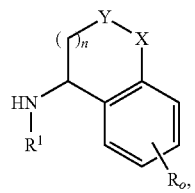

1G in which R, $R^1$, X, Y, o and n are as defined for the compound of general formula (I) as defined supra, thereby giving a compound of general formula (I):

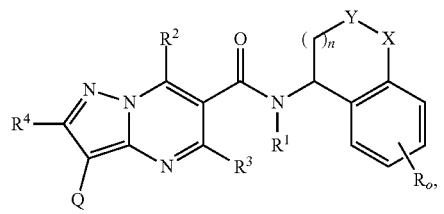

(I)

in which Q, $R^0$, $R^1$, $R^2$, $R^3$, $R^4$, X, Y, o and n are as defined supra.

In accordance with a third aspect, the present invention covers methods of preparing compounds of general formula (I) as defined supra, said methods comprising the step of allowing an intermediate compound of general formula 1F:

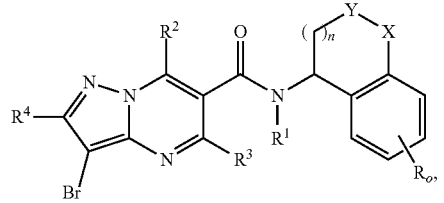

1F in which $R^0$, $R^1$, $R^2$, $R^3$, $R^4$, X, Y, o and n are as defined for the compound of general formula (I) as defined supra, to react with a compound of general formula 1H:

Q-B(OR)$_2$  1H, in which Q is as defined for the compound of general formula (I) as defined supra, and each R may be individually H or Me or both R are pinacolate, thereby giving a compound of general formula (I):

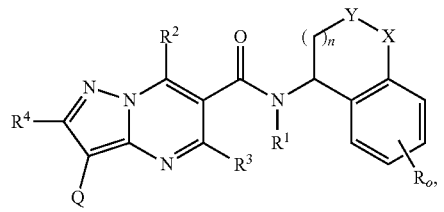

(I)

in which Q, $R^0$, $R^1$, $R^2$, $R^3$, $R^4$, X, Y, o and n are as defined supra,
then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 2E:

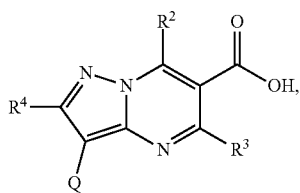

2E in which Q, $R^2$, $R^3$ and $R^4$ are as defined for the compound of general formula (I) as defined supra,
to react with a compound of general formula 1G:

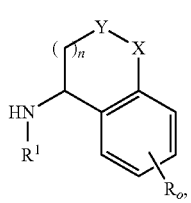

1G in which R, $R^1$, X, Y, o and n are as defined for the compound of general formula (I) as defined supra,
thereby giving a compound of general formula (I):

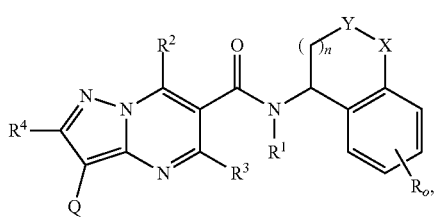

(I)

in which Q, $R^0$, $R^1$, $R^2$, $R^3$, $R^4$, X, Y, o and n are as defined supra,
then optionally converting said compound into solvates, salts and/or solvates of such salts using the corresponding (i) solvents and/or (ii) bases or acids.

The present invention covers methods of preparing compounds of the present invention of general formula (I), said methods comprising the steps as described in the Experimental Section herein.

The present invention covers the intermediate compounds which are disclosed in the Example Section of this text, infra.

The compounds of general formula (I) of the present invention can be converted to any salt, preferably pharmaceutically acceptable salts, as described herein, by any method which is known to the person skilled in the art.

Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively interact with Slo-1 and it is possible therefore that said compounds be used for the treatment or prevention of diseases, preferably helminthic infections, particularly of gastro-intestinal and extra-intestinal helminth infections, more particularly of gastro-intestinal and extra-intestinal infections with nematodes in humans and animals.

Compounds of the present invention can be utilized to control, treat and/or prevent helminth infections, in particular gastro-intestinal and extra-intestinal helminth infections. This method comprises administering to a mammal in need thereof an amount of a compound of this invention, or a pharmaceutically acceptable salt, isomer, polymorph, metabolite, hydrate, solvate or ester thereof; which is effective to treat the disorder.

In an alternative aspect, this method comprises administering to birds, namely cage birds or in particular poultry, in need thereof an amount of a compound of this invention, or a pharmaceutically acceptable salt, isomer, polymorph, metabolite, hydrate, solvate or ester thereof; which is effective to treat the disorder.

Specifically in the field of veterinary medicine, compounds of the present invention are suitable, with favourable toxicity in warm blooded animals, for controlling parasites, in particular helminths, which occur in animal breeding and animal husbandry in livestock, breeding, zoo, laboratory, experimental and domestic animals. They are active against all or specific stages of development of the parasites, in particular of the helminths.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture or, as the case may be, insects such as bees.

Domestic animals include, for example, mammals, such as hamsters, guinea pigs, rats, mice, chinchillas, ferrets or in particular dogs, cats; cage birds; reptiles; amphibians or aquarium fish.

The present invention also provides methods of treating helminth infections, particularly gastro-intestinal and extra-intestinal helminth infections, more particularly gastro-intestinal and extra-intestinal infections with nematodes.

These disorders have been well characterized in animals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a nematode infection. In particular, and particularly in the animal health or veterinary field, the term "treating" or "treatment" includes prophylactic, metaphylactic or therapeutical treatment Helminths pathogenic for humans or animals include, for example, acanthocephala, nematodes, pentastoma and platyhelmintha (e.g. monogenea, cestodes and trematodes).

Exemplary helminths include, without any limitation:
Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp. from the order of the Polymorphida, for example: *Filicollis* spp.; *from the order of the Echinorhynchida, for example: Acanthocephalus* spp., *Echinorhynchus* spp., *Leptorhynchoides* spp.

Pentastoma: from the order of the Porocephalida, for example: *Linguatula* spp.

The compounds of the present invention can be used in particular in therapy and prevention, i.e. prophylaxis, of helminth infections, particularly gastro-intestinal and extra-intestinal helminth infections, more particularly gastro-intestinal and extra-intestinal infections with nematodes.

By using the compounds of the present invention to control animal parasites, in particular helminths, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the present invention are effective in reducing the incidence of the respective parasite in an animal infected with such parasites to innocuous levels. More specifically, "controlling", as used herein, means that the compounds of the present invention are effective in killing the respective parasite, inhibiting its growth, or inhibiting its proliferation.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prevention of diseases, in particular of helminth infections, particularly of gastro-intestinal and extra-intestinal helminth infections, more particularly of gastro-intestinal and extra-intestinal infections with nematodes.

The pharmaceutical activity of the compounds according to the invention can be explained by their interaction with the Slo-1 ion channel.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prevention or treatment of diseases, in particular of helminth infections, particularly of gastro-intestinal and extra-intestinal helminth infections, more particularly of gastro-intestinal and extra-intestinal infections with nematodes.

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as an antiendoparasitical agent.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as a anthelmintic agent, in particular for use as a nematicidal agent, a platyhelminthicidal agent, an acanthocephalicidal agent, or a pentastomicidal agent.

In accordance with a further aspect, the present invention covers pharmaceutical compositions, in particular a veterinary formulation, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

In accordance with a further aspect, the present invention covers a method for preparing a pharmaceutical composition, in particular a veterinary formulation, comprising the step of mixing a compound of general formula (I), as described supra, or a stereoisomer, a tautomer, an N-oxide, a hydrate, a solvate, a salt thereof, particularly a pharmaceutically acceptable salt, or a mixture of same, with one or more excipients), in particular one or more pharmaceutically acceptable excipient(s).

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using a pharmaceutical composition, in particular a veterinary formulation, comprising an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers a method for controlling helminth infections in humans and/or animals, particularly of gastro-intestinal and extra-intestinal helminth infections, more particularly of gastro-intestinal and extra-intestinal infections with nematodes, by administering an anthelminthically effective amount of at least one compound of general formula (I), as described supra, or of general formula (II), as described supra, or of a pharmaceutical composition, in particular a veterinary formulation, comprising an effective amount of a compound of general formula (I), or of general formula (II), both as described supra.

The present invention furthermore covers pharmaceutical compositions, in particular veterinary formulations, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. Such administration can be carried out prophylactically, metaphylactically or therapeutically.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, chewables (for example soft chewables), powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, spot-ons, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prevention of an endo- and/or ectoparasiticidal infection.

The term "endoparasite" in the present invention is used as known to persons skilled in the art, and refers in particular to helminths. The term "ectoparasite" in the present invention is used as known to persons skilled in the art, and refers in particular to arthropods, particularly insects or acarids.

Particularly, the present invention covers a pharmaceutical combination, in particular a veterinary combination, which comprises:
one or more first active ingredients, in particular compounds of general formula (I) as defined supra, and
one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides). The classification is based on the current IRAC Mode of Action Classification Scheme at the time of filing of this patent application.

Examples of ectoparasiticides and/or endoparasiticides are insecticides, acaricides and nematicides, and include in particular:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCI) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(9) Modulators of Chordotonal Organs, such as for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide.

Further active ingredients such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metoflu-thrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on *Bacillus firmus* (I-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-

(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl) oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxom ethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7).

Active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite; Active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);

neonicotinoids, e.g. nithiazine;

dicloromezotiaz, triflumezopyrim;

macrocyclic lactones, e.g. nemadectin, ivermectin, latidectin, moxidectin, selamectin, eprinomectin, doramectin, emamectin benzoate; milbemycin oxime;

triprene, epofenonane, diofenolan;

Biologicals, hormones or pheromones, for example natural products, e.g. thuringiensin, codlemone or neem components;

dinitrophenols, e.g. dinocap, dinobuton, binapacryl;

benzoylureas, e.g. fluazuron, penfluron;

amidine derivatives, e.g. chlormebuform, cymiazole, demiditraz;

Bee hive varroa acaricides, for example organic acids, e.g. formic acid, oxalic acid.

Non-limiting examples of insecticides and acaricides of particular interest for use in animal health are and include in particular [i.e. Mehlhorn et al Encyclpaedic Reference of Parasitology $4^{th}$ edition (ISBN 978-3-662-43978-4)]:

Effectors at arthropod ligand gated chloride channels: chlordane, heptachlor, endoculfan. Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milbemycin, moxidectin, selamectin;

Modulators of arthropod octopaminergic receptors: amitraz, BTS27271, cymiazole, demiditraz;

Effectors at arthropod voltage-gated sodium channels: DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, tetramethrin;

Effectors at arthropod nicotinic cholinergic synapses (acetylcholine esterase, acetylcholine receptors): bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, spinetoram;

Effectors on arthropod development processes: cyromazine, dicyclanil, diflubenzuron, fluazuron, lufenuron, triflumuron, fenoxycarb, hydroprene, methoprene, pyriproxyfen, fenoxycarb, hydroprene, S-methoprene, pyriproxyfen.

Exemplary active ingredients from the group of endoparasiticides, as a further or other active ingredient in the present invention, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylanilides, for example: tribromsalan, bromoxanide, brotianide, clioxanide, closantel, niclosamide, oxyclozanide, rafoxanide;

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active ingredients in the present invention, including, without limitation, the following active ingredients:

from the class of triazines, for example: diclazuril, ponazuril, letrazuril, toltrazuril;

from the class of polyether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named other or further active ingredients in the present invention can, if their functional groups enable this, optionally form salts with suitable bases or acids.

Based upon standard laboratory techniques known to evaluate compounds useful for the treatment of helminth infections, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a subject is not dosed with a drug for a certain period of time, to be beneficial to the overall balance between pharmacological effect and tolerability. Furthermore, it is possible to have long-acting treatments, wherein the subject gets treated once for more than four weeks.

It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each subject will vary according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical and Chromatography Methods
Analytical and Preparative Liquid Chromatography Analytical (UP)LC-MS was performed by means of different equipments as described below. The masses (m/z) are reported from the positive mode electrospray ionisation unless the negative mode is indicated (ESI–).

Method L0:

Measurement of log P values was performed according to EEC directive 79/831 Annex V.A8 by HPLC (High Performance Liquid Chromatography) on reversed phase columns with the following methods:

[$^a$] log P value is determined by measurement of LC-UV, in an acidic range, with 0.1% formic acid in water and acetonitrile as eluent (linear gradient from 10% acetonitrile to 95% acetonitrile).

[$^b$] log P value is determined by measurement of LC-UV, in a neutral range, with 0.001 molar ammonium acetate solution in water and acetonitrile as eluent (linear gradient from 10% acetonitrile to 95% acetonitrile).

Calibration was done with straight-chain alkan-2-ones (with 3 to 16 carbon atoms) with known log P values (measurement of log P values using retention times with linear interpolation between successive alkanones). Lambda-max-values were determined using UV-spectra from 200 nm to 400 nm and the peak values of the chromatographic signals.

M+1 (or M+H) means the molecular ion peak, plus or minus 1 a.m.u. (atomic mass unit) respectively, as observed in mass spectroscopy by electrospray ionization (ESI+ or –).

Method L1:

MS instrument type: Agilent Technologies 6130 Quadrupole LC-MS; HPLC instrument type: Agilent Technologies 1260 Infinity; column: Waters XSelect (C18, 30×2.1 mm, 3.5µ); flow: 1 mL/min; column temp: 35° C.; eluent A: 0.1% formic acid in acetonitrile; eluent B: 0.1% formic acid in water; lin. gradient: t=0 min 5% A, t=1.6 min 98% A, t=3 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method L2:

MS instrument type: Agilent Technologies 6130 Quadrupole LC-MS; HPLC instrument type: Agilent Technologies 1260 Infinity; column: Waters XSelect (C18, 50×2.1 mm, 3.5µ); flow: 0.8 mL/min; column temp: 35° C.; eluent A: 0.1% formic acid in acetonitrile; eluent B: 0.1% formic acid in water; lin. gradient: t=0 min 5% A, t=3.5 min 98% A, t=6 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method L3:

MS instrument type: Agilent Technologies LC/MSD SL; HPLC instrument type: Agilent Technologies 1100 Series; column: Waters XSelect (C18, 30×2.1 mm, 3.5µ); flow: 1 mL/min; column temp: 25° C., eluent A: 95% acetonitrile+ 5% 10 mM ammoniumbicarbonate in water, eluent B: 10 mM ammoniumbicarbonate in water pH=9.0; lin. gradient: t=0 min 5% A, t=1.6 min 98% A, t=3 min 98% A; detection: DAD (220-320 nm); detection: MSD (ESI pos/neg) mass range: 100-800.

Method L4:

MS instrument type: Agilent Technologies LC/MSD SL; HPLC instrument type: Agilent Technologies 1100 Series; column: Waters XSelect (C18, 50×2.1 mm, 3.5µ; flow: 0.8 mL/min; column temp: 25° C.; eluent A: 95% acetonitrile+ 5% 10 mM ammoniumbicarbonate in water; eluent B: 10 mM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

Method L5:

Instrument type: Reveleris™ Flash Chromatography System; columns: Reveleris™ C18 Flash Cartridge; 4 g, flow 18 mL/min; 12 g, flow 30 mL/min; 40 g, flow 40 mL/min; 80 g, flow 60 mL/min; 120 g, flow 80 mL/min; eluent A: 0.1% formic acid in acetonitrile; eluent B: 0.1% formic acid in water; gradient: t=0 min 5% A, t=1 min 5% A, t=13 min 100% A, t=16 min 100% A; detection: UV (200-360 nm), ELSD.

Method L6:

Instrument type: Reveleris™ Flash Chromatography System; columns: GraceResolv™ Silica Cartridge; 4 g, flow 15 mL/min; 12 g, flow 28 mL/min; 24 g, flow 30 mL/min; 40 g, flow 40 mL/min; 80 g, flow 55 mL/min; 120 g, flow 80 mL/min and Davisil™ Chromatographic Silica Media (LC60A 20-45 micron); 300 g, flow 70 mL/min; 500 g, flow 70 mL/min; eluents: see experiment; detection: UV (200-360 nm), ELSD.

Method L7:

Instrument type: Büchi Pump Manager C-615, Büchi Pump Module C-601; columns: GraceResolv™ Silica Cartridge; 4 g, flow 15 mL/min; 12 g, flow 28 mL/min; 24 g, flow 30 mL/min; 40 g, flow 40 mL/min; 80 g, flow 55 mL/min; 120 g, flow 80 mL/min and Davisil™ Chromatographic Silica Media (LC60A 20-45 micron); 300 g, flow 70 mL/min; 500 g, flow 70 mL/min; eluents: see experiment; detection: TLC plates; TLC Silica gel 60 F254 (Merck).

Method L8:

MS instrument type: Agilent Technologies 6130 Quadrupole LC-MS; HPLC instrument type: Agilent Technologies 1260 Infinity; column: Waters XSelect (C18, 50×2.1 mm, 3.5µ); flow: 0.8 mL/min; column temp: 35° C.; eluent A: 0.1% formic acid in acetonitrile; eluent B: 0.1% formic acid in water; lin. gradient: t=0 min 5% A, t=3.5 min 98% A, t=8 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method L9:

MS instrument type: Agilent Technologies G1956B Quadrupole LC-MS; HPLC instrument type: Agilent Technologies 1200 preparative LC; column: Waters Sunfire (C18, 150×19 mm, 5µ); flow: 25 ml/min; column temp: RT; eluent A: 0.1% formic acid in acetonitrile; eluent B: 0.1% formic acid in water; detection: DAD (220-320 nm); detection: MSD (ESI pos/neg) mass range: 100-800; fraction collection based on MS and DAD, or MS instrument type: ACQ-SQD2; HPLC instrument type: Waters Modular Preparative HPLC System; column: Waters XSelect (C18, 150×19 mm, 10 µm); flow: 24 ml/min prep pump, 1 mL/min loading pump; column temp: RT; eluent A: 0.1% formic acid in acetonitrile; eluent B: 0.1% formic acid in water; detection: DAD (220-320 nm); detection: MSD (ESI pos/neg) mass range: 100-800; fraction collection based on MS and DAD.

Method L10:

MS instrument type: Agilent Technologies G1956B Quadrupole LC-MS; HPLC instrument type: Agilent Technologies 1200 preparative LC; column: Waters XSelect (C18, 150×19 mm, 5µ); flow: 25 ml/min; column temp: RT; eluent A: 99% acetonitrile+1% 10 mM ammonium bicarbonate in water pH=9.0, eluent B: 10 mM ammonium bicarbonate in water pH=9.0; detection: DAD (220-320 nm); detection: MSD (ESI pos/neg) mass range: 100-800; fraction collection based on MS and DAD, or MS instrument type: ACQ-SQD2; HPLC instrument type: Waters Modular Preparative HPLC System; column: Waters XSelect (C18, 150×19 mm, 10 µm); flow: 24 ml/min prep pump, 1 mL/min loading pump; column temp: RT; eluent A: 99% acetonitrile+1% 10 mM ammonium bicarbonate in water pH=9.5, eluent B: 10 mM ammonium bicarbonate in water pH=9.5; detection: DAD (220-320 nm); detection: MSD (ESI pos/neg) mass range: 100-800; fraction collection based on MS and DAD.

Method L11:

Instrument type: Reveleris Prep; detection: UV (220-360 nm), ELSD; column: XSelect™ CSH C18, 145×25 mm, 10p or GEMINI™ C18, 185×25 mm, 10p flow: 40 mL/min; eluent A: 10 mM ammoniumbicarbonate in water (pH=9.0), eluent B: 99% acetonitrile+1% 10 mM ammoniumbicarbonate in water in acetonitrile or eluent A: 250 mM ammonia in water, eluent B: 250 mM ammonia in acetonitrile.

Method L12:

MS instrument type: Agilent Technologies LC/MSD SL; HPLC instrument type: Agilent Technologies 1100 Series; column: Phenomenex Gemini NX (C18, 50×2.0 mm, 3.0p; flow: 0.8 mL/min; column temp: 25° C.; eluent A: 95% acetonitrile+5% 10 mM ammoniumbicarbonate in water pH=9.0; eluent B: 10 mM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

GC-MS Methods

Instrument: GC: Agilent 6890N, FID: Det. temp: 300° C. and MS: 5973 MSD, EI-positive, Det. temp.: 280° C. Mass range: 50-550; Column: RXi-5MS 20 m, ID 180 µm, df 0.18 µm; Average velocity: 50 cm/s; Injection vol: 1 µl; Injector temp: 250° C.; Split ratio: 20/1; Carrier gas: He.

Method S:

Initial temp: 60° C.; Initial time: 1.0 min; Solvent delay: 1.3 min; Rate 50° C./min; Final temp 250° C.; Final time 3.5 min.

Method A:

Initial temp: 100° C.; Initial time: 1.5 min; Solvent delay: 1.3 min; Rate 75° C./min; Final temp 250° C.; Final time 2.5 min.

Method C:

Initial temp: 100° C.; Initial time: 1.0 min; Solvent delay: 1.3 min; Rate 75° C./min; Final temp 280° C.; Final time 2.6 min.

Method U:

Initial temp: 100° C.; Initial time: 1.0 min; Solvent delay: 1.3 min; Rate 120° C./min; Final temp 280° C.; Final time 6.5 min.

$^1$H-NMR Data

Chemical shifts (δ) are displayed in parts per million [ppm]; the following abbreviations are used: s=singlet, d=doublet, t=triplet, q=quartet, m=multiplet, br.=broad; coupling constants are displayed in Hertz [Hz].

Method 1

$^1$H-NMR-data were determined with a Bruker Avance 400 (equipped with a flow cell (60 μl volume) or with a Bruker AVIII 400 equipped with 1.7 mm cryo CPTCI probe head or with a Bruker AVII 600 (600.13 MHz) equipped with a 5 mm cryo TCI probe head or with a Bruker AVIII 600 (601.6 MHz) equipped with a 5 mm cryo CPMNP probe head with tetramethylsilane as reference (0.0) and the solvents CD$_3$CN, CDCl$_3$ or D$_6$-DMSO.

Method 2

Alternatively $^1$H- and $^{13}$C-NMR instrument types: Bruker DMX300 ($^1$H NMR: 300 MHz; $^{13}$C NMR: 75 MHz), Bruker Avance III 400 ($^1$H NMR: 400 MHz; $^{13}$C NMR: 100 MHz) or Bruker 400 Ultrashield ($^1$H NMR: 400 MHz; $^{13}$C NMR: 100 MHz); internal standard: tetramethylsilane.

Experimental Section—General Procedures

The synthesis of the compounds of the formula (I) can be performed according to or in analogy to the following schemes (Scheme 1 to Scheme 9).

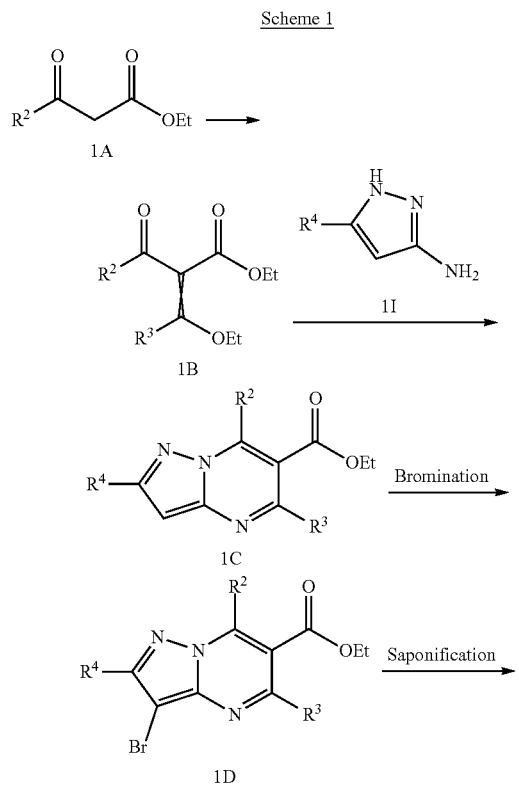

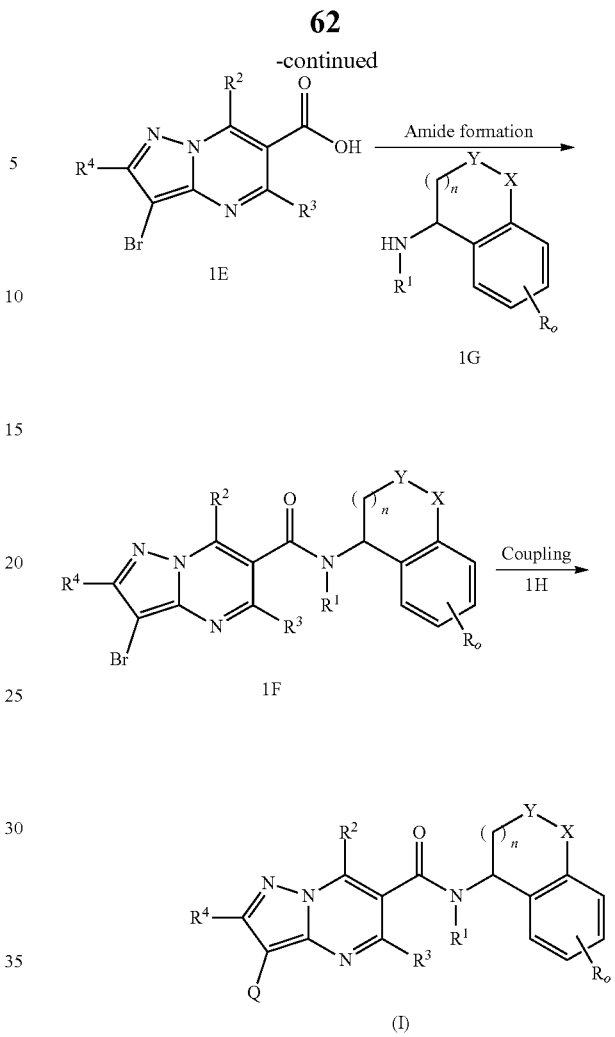

β-Ketoesters 1A can be easily transformed into the corresponding ethyl ethoxymethylene acetoacetates 1B by reaction with orthoformates. The pyrazolo[1,5-a]pyrimidines 1C can be synthesized by condensation of the ethyl ethoxymethyleneacetoacetates 1B with the 3-substituted 5-aminopyrazoles 1I as described in Chemistry of Heterocyclic Compounds 2011, 47, 321-331 for example.

The 3-position of the pyrazolo[1,5-a]pyrimidine 1C can be functionalized using N-bromosuccinimide to the versatile 3-bromo analogues 1D. Subsequent saponification of the ethyl esters 1D e.g. with lithium hydroxide smoothly results in the corresponding carboxylic acids 1E. The pyrazolo[1,5-a]pyrimidine carboxamides 1F are obtained by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example.

A Suzuki cross coupling reaction of intermediates 1F with boronic acids or boronic esters 1H Q-B(OR)$_2$ (R=H; R=Me or R,R=pinacolate) lead to final compounds (I) as described in Chem. Soc. Rev. 2014, 43, 412-443 or in WO2014070978.

Scheme 2

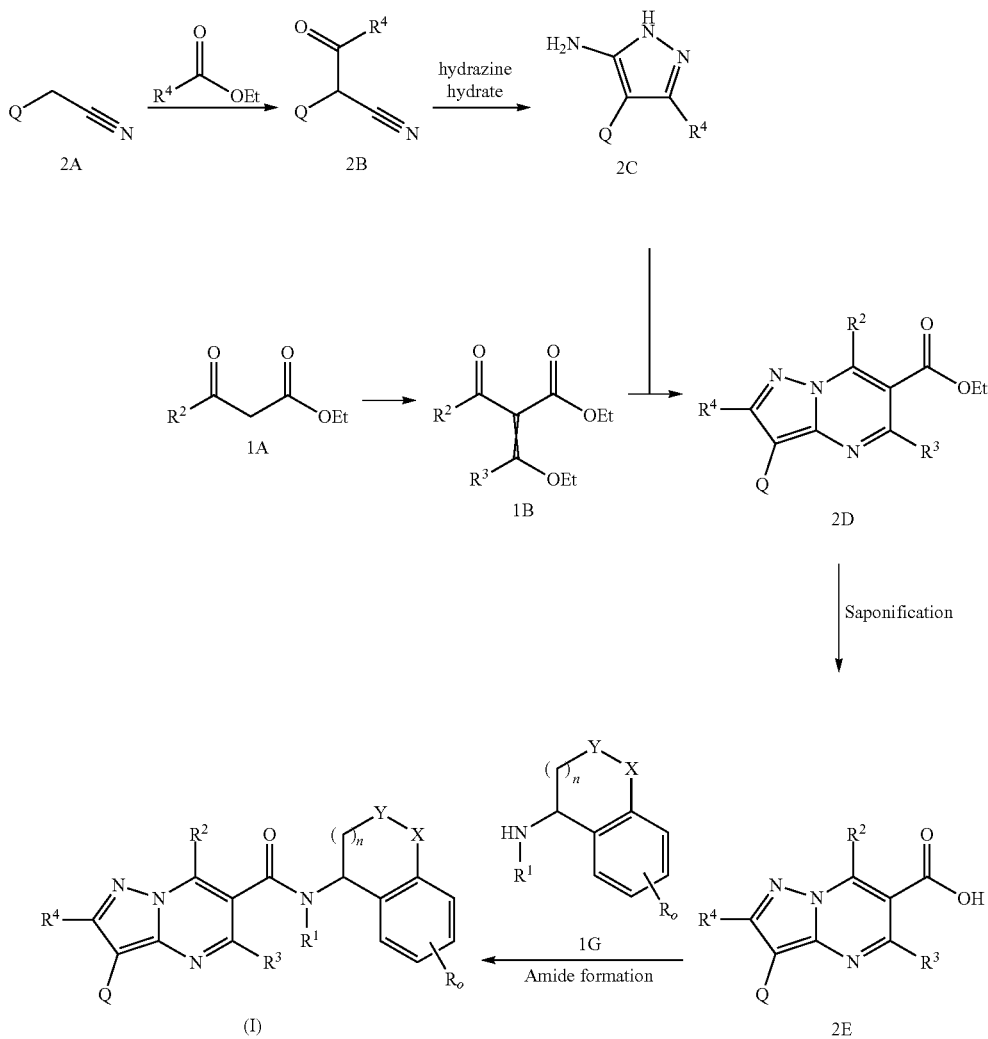

4-Aryl aminopyrazoles 2C are derived from the corresponding aryl acetonitriles 2A via condensation with ethyl carboxylates and subsequent cyclization with hydrazine as described in Bioorganic & Medicinal Chemistry Letters 2014, 24, 5478 for example.

Condensation of ethyl ethoxymethyleneacetoacetates 1B with the 4-aryl aminopyrazoles 2C gives the pyrazolo[1,5-a]pyrimidines 2D as described in Journal of Medicinal Chemistry 2012, 55, 3563-3567 for example.

Saponification of the ethyl esters 2D e.g. with lithium hydroxide resulted in the corresponding carboxylic acids 2E. The final pyrazolo[1,5-a]pyrimidine carboxamides (I) are obtained by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example.

Scheme 3

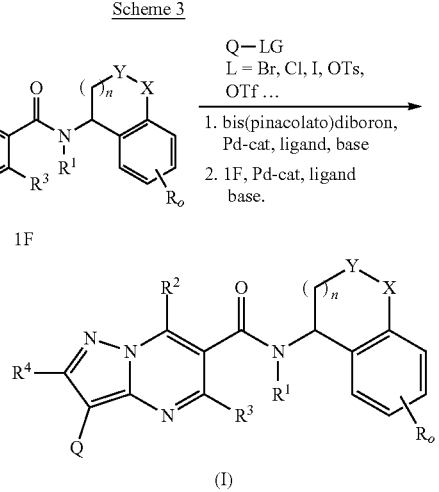

A Suzuki cross coupling reaction of intermediates 1F in situ formed boronic acids or boronic esters Q-B(OR)$_2$ (R=H; R=Me or R,R=pinacolate) lead to final compounds (I) as described in Chem. Soc. Rev. 2014, 43, 412-443 or in WO2014070978.

Scheme 4

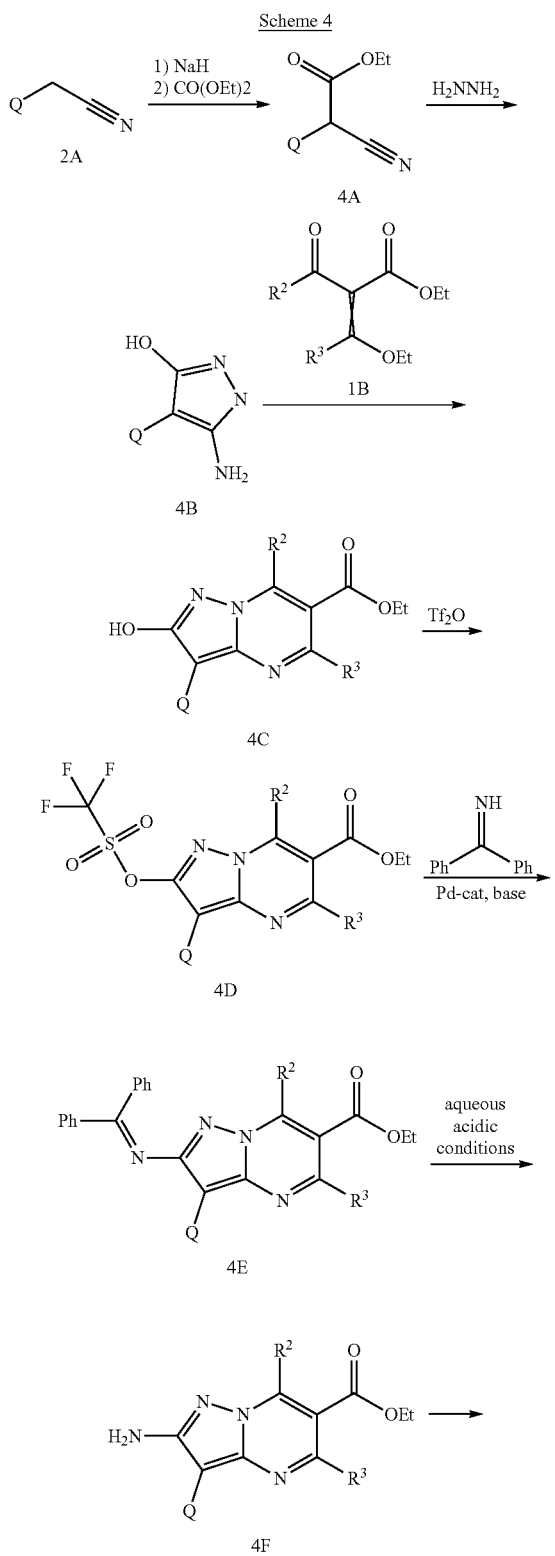

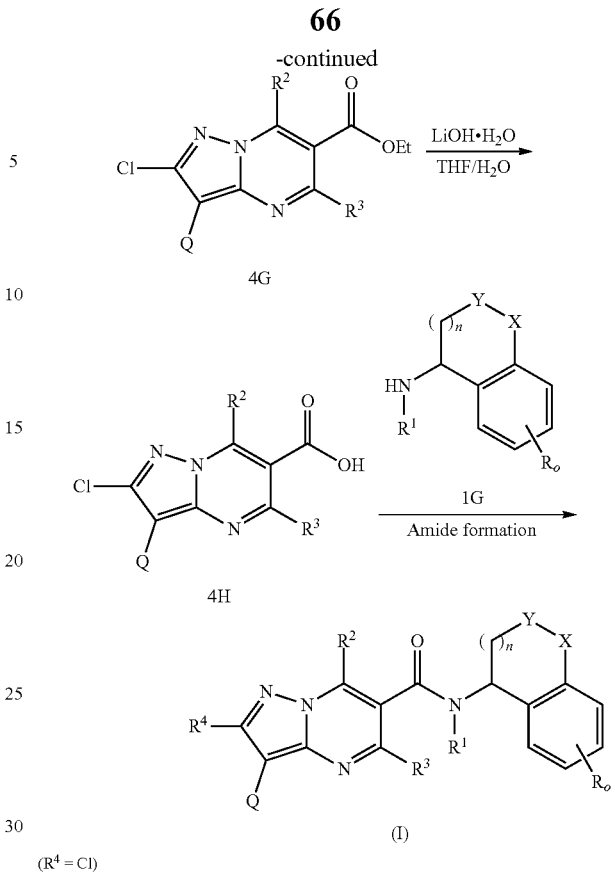

(R$^4$ = Cl)

4-Aryl hydroxyaminopyrazoles 4B are derived from the corresponding aryl acetonitriles 2A via condensation with diethyl carbonate and subsequent cyclization. Condensation of ethyl ethoxymethylene acetoacetates 1B with the 4-aryl hydroxyaminopyrazoles 4B give the pyrazolo[1,5-a]pyrimidines 4C as described in Journal of Medicinal Chemistry 2012, 55, 3563-3567 for example.

Hydroxypyrazolo[1,5-a]pyrimidines 4C can be converted into the corresponding triflate 4D. Buchwald-Hartwig coupling of 4D with benzophenone imine affords 4E, which can be converted into the amino pyrazolo[1,5-a]pyrimidines 4F. The Sandmeyer reaction of 4F affords the Chloropyrazolo[1,5-a]pyrimidines 4G.

Saponification of the ethyl esters 4G e.g. with lithium hydroxide smoothly resulted in the corresponding carboxylic acids 4H. The final pyrazolo[1,5-a]pyrimidine carboxamides (I-a) are obtained by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-di-methylaminoisopropyl)-N'-ethylcarbodiimide-hydrochloride (EDC). Similar syntheses are described in Journal of Medicinal Chemistry 2012, 55, 3563-3567 for example.

Scheme 5

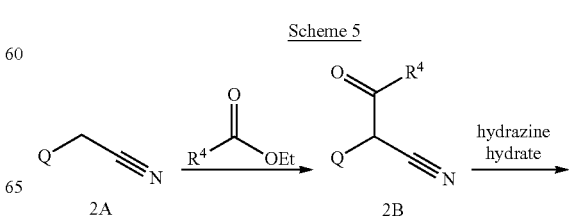

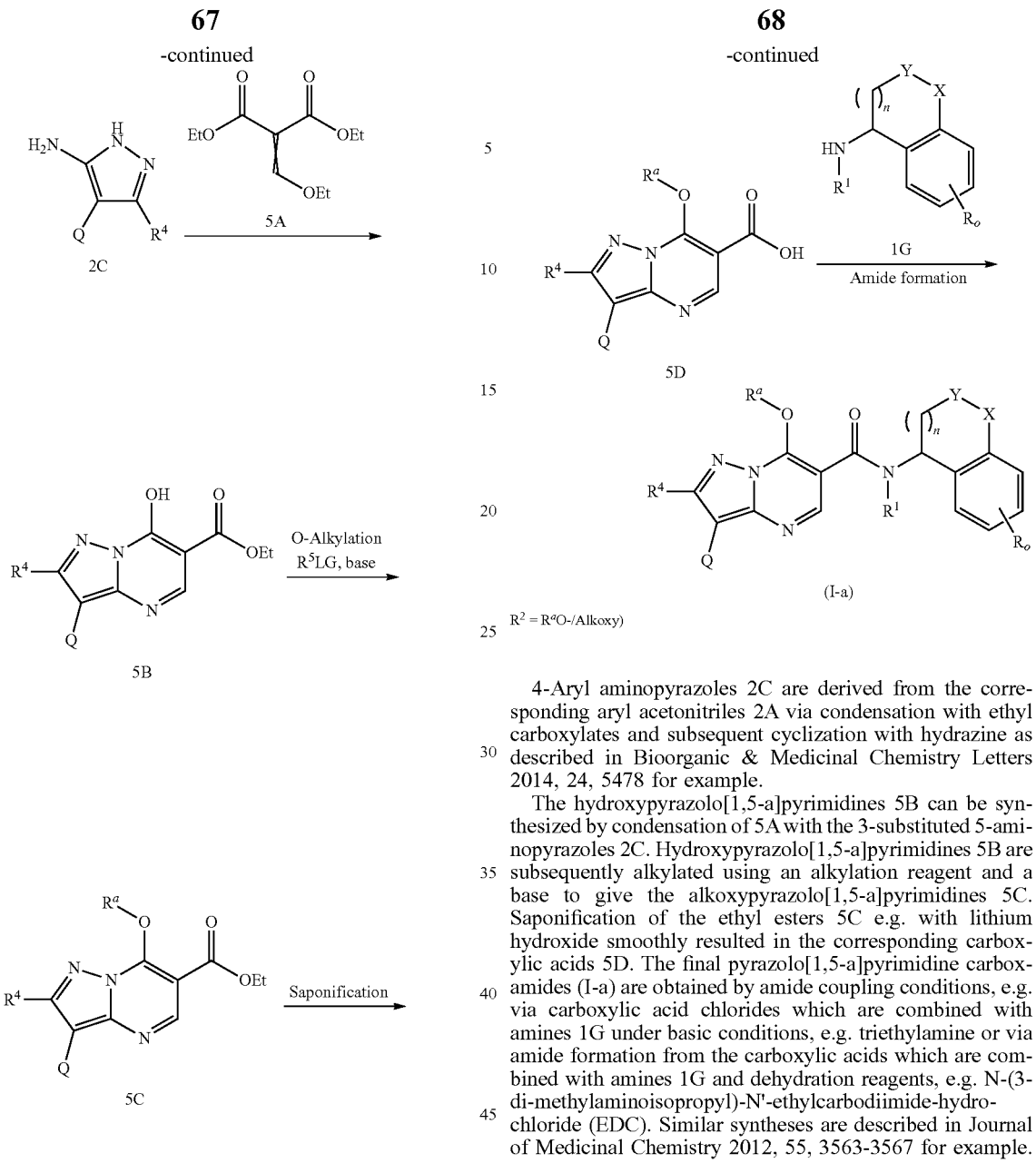

4-Aryl aminopyrazoles 2C are derived from the corresponding aryl acetonitriles 2A via condensation with ethyl carboxylates and subsequent cyclization with hydrazine as described in Bioorganic & Medicinal Chemistry Letters 2014, 24, 5478 for example.

The hydroxypyrazolo[1,5-a]pyrimidines 5B can be synthesized by condensation of 5A with the 3-substituted 5-aminopyrazoles 2C. Hydroxypyrazolo[1,5-a]pyrimidines 5B are subsequently alkylated using an alkylation reagent and a base to give the alkoxypyrazolo[1,5-a]pyrimidines 5C. Saponification of the ethyl esters 5C e.g. with lithium hydroxide smoothly resulted in the corresponding carboxylic acids 5D. The final pyrazolo[1,5-a]pyrimidine carboxamides (I-a) are obtained by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-di-methylaminoisopropyl)-N'-ethylcarbodiimide-hydrochloride (EDC). Similar syntheses are described in Journal of Medicinal Chemistry 2012, 55, 3563-3567 for example.

Scheme 6

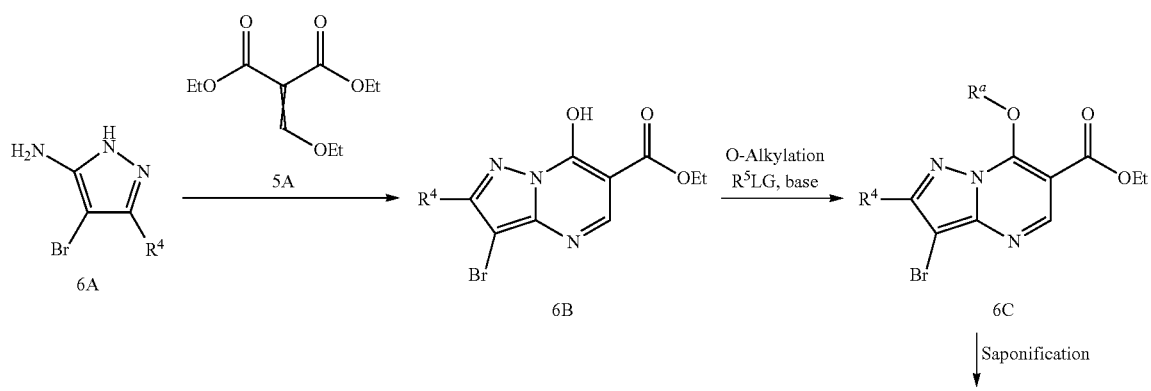

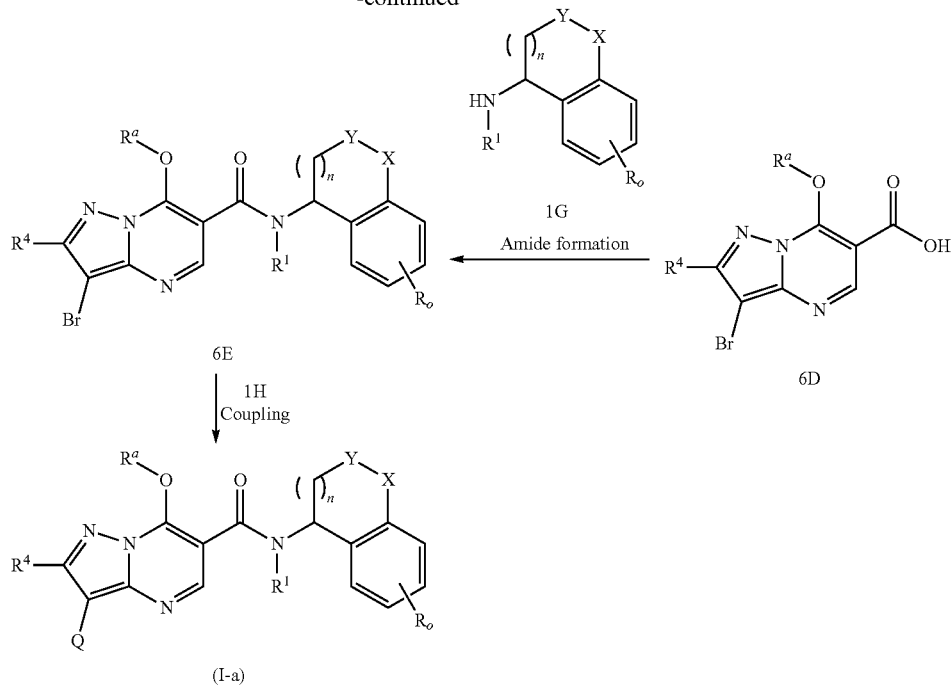

The hydroxypyrazolo[1,5-a]pyrimidines 6B can be synthesized by condensation of 5A with the 3-substituted 4-bromo-5-aminopyrazoles 6A. Hydroxypyrazolo[1,5-a]pyrimidines 6B are subsequently alkylated using an alkylation reagent and a base to give the alkoxypyrazolo[1,5-a]pyrimidines 6C. Saponification of the ethyl esters 6C e.g. with lithium hydroxide smoothly resulted in the corresponding carboxylic acids 6D. The carboxamide intermediate 6E are obtained from 6D by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example.

A Suzuki cross coupling reaction of intermediates 7E with boronic acids or boronic esters 1H Q-B(OR)₂ (R=H; R=Me or R,R=pinacolate) lead to final compounds (I-a) as described in Chem. Soc. Rev. 2014, 43, 412-443 or in WO2014070978.

Scheme 7

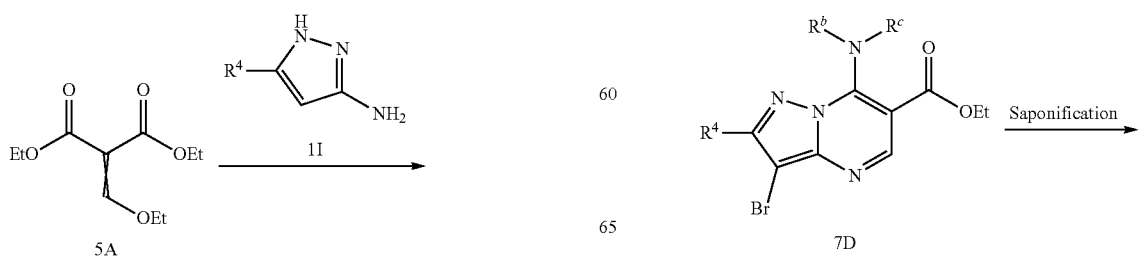

-continued

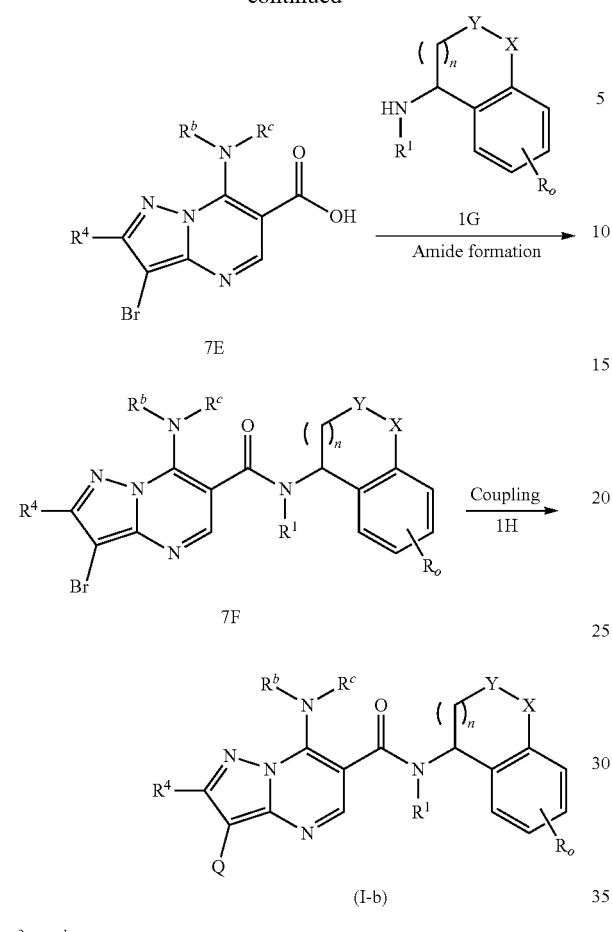

(I-b)

($R^2 = NR^bR^c$)

The pyrazolo[1,5-a]pyrimidines 7A can be synthesized by condensation of 5A with the 3-substituted 5-aminopyrazoles 1I. The hydroxyl group of 7A can be converted into the corresponding chloro derivative 7B by using a chlorination reagent like $POCl_3$ as it is described in WO02011/08689, for example. The 3-position of the pyrazolo[1,5-a]pyrimidine 7B can be functionalized using N-bromosuccinimide to the versatile 3-bromo analogues 7C.

The amination of 7C results in the corresponding 7-amino pyrazolo[1,5-a]pyrimidines 7D. Saponification of the ethyl esters 7D e.g. with boron tribromide smoothly resulted in the corresponding carboxylic acids 7E.

The pyrazolo[1,5-a]pyrimidine carboxamides 7F are obtained by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example.

A Suzuki cross coupling reaction of intermediates 7F with boronic acids or boronic esters 1H Q-B(OR)$_2$ (R=H; R=Me or R,R=pinacolate) lead to final compounds (I-b) as described in Chem. Soc. Rev. 2014, 43, 412-443 or in WO2014070978.

Scheme 8

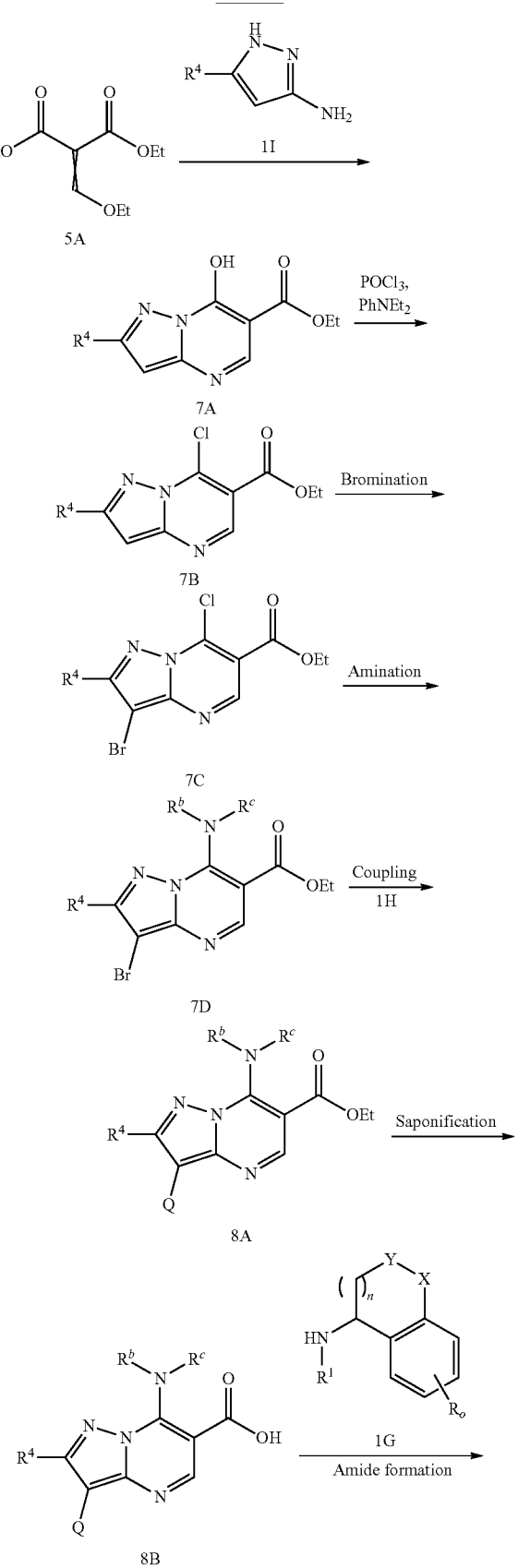

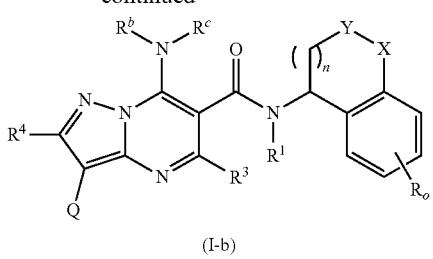

(I-b)

(R² = NR^b R^c)

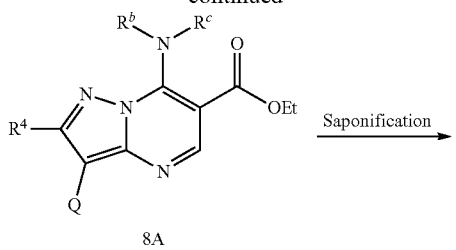

8A

A Suzuki cross coupling reaction of intermediates 7D with boronic acids or boronic esters 1H Q-B(OR)₂ (R=H; R=Me or R,R=pinacolate) lead to pyrazolo[1,5-a]pyrimidines 8A as described in Chem. Soc. Rev. 2014, 43, 412-443 or in WO2014070978. Saponification of the ethyl esters 8A e.g. with boron tribromide smoothly resulted in the corresponding carboxylic acids 8B.

The final pyrazolo[1,5-a]pyrimidine (I-b) are obtained from 8B by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example.

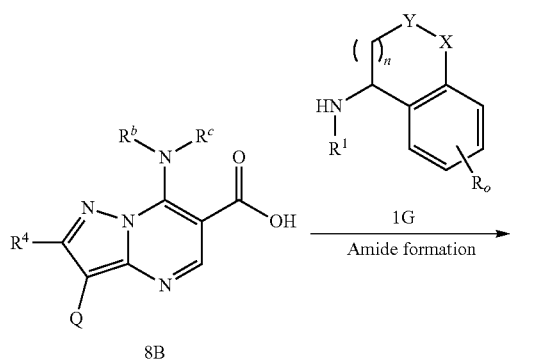

8B

Scheme 9

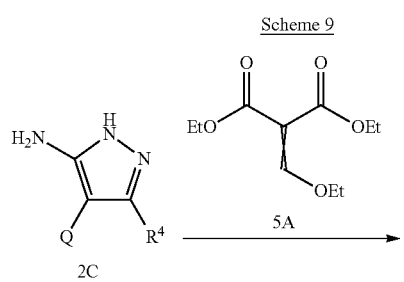

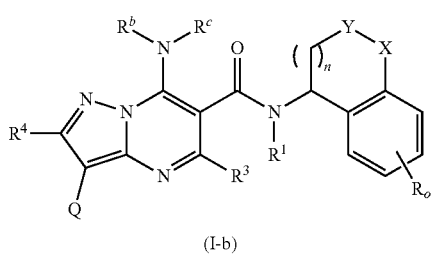

(I-b)

(R² = NR^b R^c)

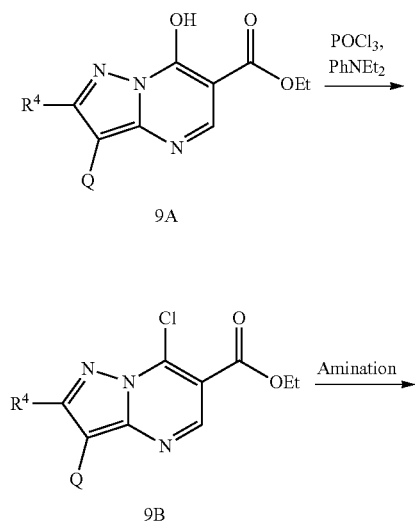

The pyrazolo[1,5-a]pyrimidines 9A can be synthesized by condensation of the malonic ester derivative 5A with the pre-Q-substituted 5-aminopyrazoles 2C. The hydroxyl group of 9A can be converted into the corresponding chloro derivative 9B by using a chlorination reagent like POCl₃ as it is described in WO2011/08689, for example. The amination of 9B results in the corresponding 7-amino pyrazolo[1,5-a]pyrimidines 8A. Saponification of the ethyl esters 8A e.g. with boron tribromide smoothly resulted in the corresponding carboxylic acids 8B. The final pyrazolo[1,5-a]pyrimidine (I-b) are obtained from 8B by amide coupling conditions, e.g. via carboxylic acid chlorides which are combined with amines 1G under basic conditions, e.g. triethylamine or via amide formation from the carboxylic acids which are combined with amines 1G and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example.

EXPERIMENTAL SECTION—EXAMPLES

Preparation Example 1: (S)—N-(2,3-Dihydro-1H-inden-1-yl)-3-(3-fluorophenyl)-7-isopropyl-2-methylpyrazolo[1,5-a]pyrimidine-6-carboxamide (Compound 290)

Step 1: Ethyl 2-(ethoxymethylene)-4-methyl-3-oxopentanoate (1B-1)

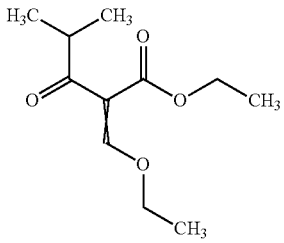

A mixture of ethyl isobutyrylacetate (24.8 g, 157 mmol, 25.3 mL), triethyl orthoformate (46.5 g, 314 mmol, 52.2 mL) and acetic anhydride (32.0 g, 314 mmol, 29.7 mL) was stirred at reflux for 19 h. The volatiles were removed in vacuo (100° C., 0.5 Torr) to afford 28.6 g (133 mmol; 85% of theory) of the title compound. Material was used as such.

Step 2: Ethyl 7-isopropyl-2-methylpyrazolo[1,5-a]pyrimidine-6-carboxylate (1C-1)

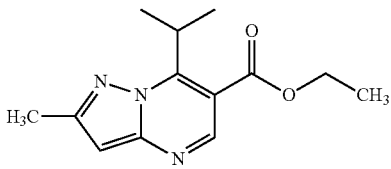 [SMILES: CCOC(=O)c1cnc2cc(C)nn2c1C(C)C]

A solution of 3-amino-5-methylpyrazole (12.95 g, 133 mmol) and ethyl 2-(ethoxymethylene)-4-methyl-3-oxopentanoate (28.56 g, 133 mmol) in absolute ethanol (400 mL) was stirred at reflux for 48 h. The reaction mixture was concentrated in vacuo to afford 32.38 g (128 mmol; 96% of theory) of the title compound.

LC-MS (Method L1): $R_t$=2.19 min; m/z=248 (M+H)$^+$ $^1$H NMR (300 MHz, Chloroform-d, Method M2) δ 8.71 (s, 1H), 6.46 (s, 1H), 4.55 (dq, J=14.1, 7.0 Hz, 1H), 4.40 (q, J=7.1 Hz, 2H), 2.51 (s, 3H), 1.58 (s, 6H), 1.41 (t, J=7.1 Hz, 3H).

Step 3: Ethyl 3-bromo-7-isopropyl-2-methylpyrazolo[1,5-a]pyrimidine-6-carboxylate (1D-1)

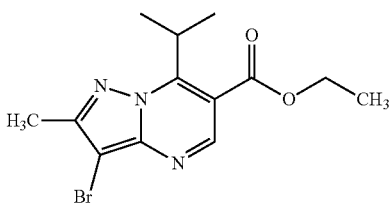 [SMILES: CCOC(=O)c1cnc2c(Br)c(C)nn2c1C(C)C]

To a stirring solution of ethyl 7-isopropyl-2-methylpyrazolo[1,5-a]pyrimidine-6-carboxylate (32.38 g, 131 mmol) in acetonitrile (1.3 L) was added N-bromosuccinimide (23.71 g, 133 mmol). After 20 minutes the reaction mixture was concentrated in vacuo, to afford 71.20 g of a solid, which was triturated in diethyl ether (0.4 L). The solids were filtered off and washed with diethyl ether.

The filtrate was concentrated in vacuo to yield 46.50 g of a solid. The material was triturated in diisopropyl ether (1.0 L). The solids were filtered off and the filtrate was treated with active charcoal (6.4 g). The charcoal was filtered off over kieselguhr and the filtrate was concentrated in vacuo to afford 42.06 g (126 mmol; 97% of theory) of the title compound.

LC-MS (Method L1): $R_t$=2.32 min; m/z=326/328 (M+H)$^+$ $^1$H NMR (300 MHz, Chloroform-d, Method M2) δ 8.79 (s, 1H), 4.54 (m, 1H), 4.41 (q, J=7.1 Hz, 2H), 2.52 (s, 3H), 1.59 (d, J=7.1 Hz, 6H), 1.42 (t, J=7.1 Hz, 3H).

Step 4: 3-Bromo-7-isopropyl-2-methylpyrazolo[1,5-a]pyrimidine-6-carboxylic Acid (1E-1)

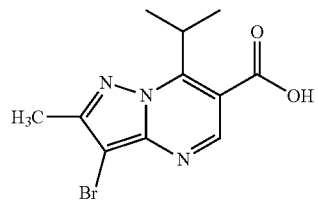 [SMILES: Cc1nn2c(C(C)C)c(C(=O)O)cnc2c1Br]

To a solution of ethyl 3-bromo-7-isopropyl-2-methylpyrazolo[1,5-a]pyrimidine-6-carboxylate (42.0 g, 129 mmol) in tetrahydrofuran (800 mL) was added a solution of lithium hydroxide monohydrate (42.0 g, 1001 mmol) in water (800 mL). The mixture was stirred at room temperature for 5 h. The organic solvent was removed in vacuo. The basic aqueous layer was washed with ethyl acetate (2×400 mL). The organic extracts were set aside. The aqueous layer was acidified with a solution of concentrated hydrochloric acid (50 mL) in water (500 mL) and was extracted with ethyl acetate (2×400 mL). The aqueous layer was further acidified with hydrochloric acid (4N; 200 mL) and was extracted with ethyl acetate (2×400 mL). The combined organic layers were washed with water (400 mL) and brine (400 mL) and were dried with sodium sulfate. Solvents were removed in vacuo and the residue was co-evaporated with toluene and ethyl acetate to afford 26.0 g (84 mmol) of the title compound.

The organic extracts that were obtained from washing the basic aqueous layer were concentrated and partitioned between hydrochloric acid (1N; 500 mL) and ethyl acetate (300 mL). The organic layer was separated and the aqueous layer was extracted with ethyl acetate (2×300 mL). The combined organic layers were washed with water and brine and were dried with sodium sulfate. Solvents were removed in vacuo to afford 8.9 g (27 mmol) of the title compound. In total 34.9 g (111 mmol; 86% of theory) of the title compound were obtained LC-MS (Method L1): $R_t$=2.12 min; m/z=298/300 (M+H)$^+$

Step 5: (S)-3-Bromo-N-(2,3-dihydro-1H-inden-1-yl)-7-isopropyl-2-methylpyrazolo[1,5-a]pyrimidine-6-carboxamide (1F-1)

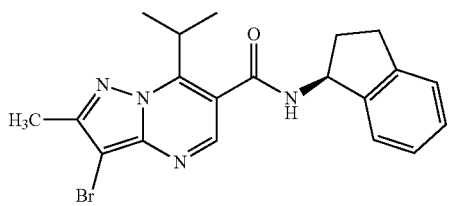 [SMILES: Cc1nn2c(C(C)C)c(C(=O)N[C@H]3CCc4ccccc43)cnc2c1Br]

To a solution of 3-bromo-7-isopropyl-2-methylpyrazolo[1,5-a]pyrimidine-6-carboxylic acid (15.6 g, 52.3 mmol) and (S)-2,3-dihydro-1H-inden-1-amine (6.9 g, 52.3 mmol, 6.7 mL) in dry N,N-dimethylformamide (500 m L) were added N-(3-dimethylaminopropyl)-N'-ethylcarbodiimide hydrochloride (11.0 g, 57.6 mmol) and 1-hydroxy-7-azabenzotriazole (0.7 g, 5.2 mmol) at 0° C. The mixture was stirred at 0° C. for 30 min and at room temperature for 5 h. Water (1.5 L) was added and a precipitate occurred. The suspension was stirred for 30 min after which the solid was filtered off and washed with water. The solid was dried at 40° C. for four days in vacuo to afford 20.2 g (49.0 mmol; 94% of theory) of the title compound.

LC-MS (Method L1): $R_t$=2.25 min; m/z=413/415 (M+H)$^+$ $^1$H NMR (300 MHz, DMSO-d6, Method M2) δ 9.06 (d, J=8.2 Hz, 1H), 8.52 (s, 1H), 7.43-7.33 (m, 1H), 7.33-7.19 (m, 3H), 5.51 (q, J=7.8 Hz, 1H), 4.05-3.83 (m, 1H), 3.06-2.78 (m, 2H), 2.61-2.51 (m, 1H), 2.46 (s, 3H), 2.02-1.83 (m, 1H), 1.52 (dd, J=7.0, 5.0 Hz, 6H).

Step 6: (S)—N-(2,3-Dihydro-1H-inden-1-yl)-3-(3-fluorophenyl)-7-isopropyl-2-methylpyrazolo[1,5-a]pyrimidine-6-carboxamide (Compound 290)

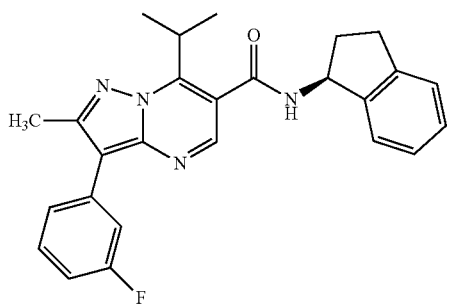 [SMILES: Cc1nn2c(C(C)C)c(C(=O)N[C@H]3CCc4ccccc43)cnc2c1-c1cccc(F)c1]

A solution of (S)-3-bromo-N-(2,3-dihydro-1H-inden-1-yl)-7-isopropyl-2-methylpyrazolo[1,5-a]pyrimidine-6-carboxamide (101 mg, 0.24 mmol), 3-fluorophenylboronic acid (38 mg, 0.27 mmol) and sodium carbonate (78 mg, 0.73 mmol) in a mixture of 1,2-dimethoxyethane (3.0 mL) and water (0.8 mL) was purged with argon for 5 minutes. Bis(triphenylphosphine)-palladium(II) chloride (9 mg, 0.01 mmol) was added and the resulting mixture was stirred at 100-C for 20 h. The reaction mixture was allowed to cool to room temperature and concentrated in vacuo. Purification by flash column chromatography (Method L7; heptane, 1%-15% ethyl acetate) afforded 76 mg (0.18 mmol; 73% of theory) of the title compound.

LC-MS (Method L2): $R_t$=3.78 min; m/z=429 (M+H)$^+$ $^1$H NMR (300 MHz, Chloroform-d, Method M2) δ 8.42 (s, 1H), 7.51-7.20 (m, 7H), 7.00 (m, 1H), 6.09 (d, J=8.4 Hz, 1H), 5.68 (q, J=7.6 Hz, 1H), 4.11 (p, J=7.0 Hz, 1H), 3.12-2.88 (m, 2H), 2.82-2.68 (m, 1H), 2.65 (s, 3H), 2.03-1.88 (m, 1H), 1.65 (dd, J=7.0, 4.1 Hz, 6H).

Preparation Example 2: (S)-7-(Difluoromethyl)-N-(2,3-dihydro-1H-inden-1-yl)-2-methyl-3-(3-(trifluoromethyl)phenyl)-pyrazolo[1,5-a]pyrimidine-6-carboxamide (Compound 311)

Step 1: 3-Oxo-2-(3-(trifluoromethyl)phenyl)butanenitrile (2B-1)

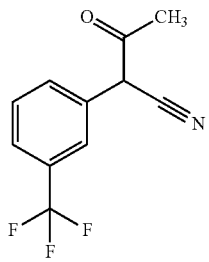 [SMILES: CC(=O)C(C#N)c1cccc(C(F)(F)F)c1]

Sodium hydride (60% (w/w) in mineral oil; 2.6 g, 65.9 mmol) was added portion wise to a solution of 3-(trifluoromethyl)phenylacetonitrile (9.4 g, 50.7 mmol, 8.0 mL) in dry tetrahydrofuran (100 mL) at 0° C. The mixture was stirred at 0° C. for 5 min and at room temperature for 1 h. Ethyl acetate (5.4 g, 60.9 mmol, 5.9 mL) was added and stirring was continued at 60° C. for 4 h. Water (100 mL) was added. The mixture was acidified to pH 3 and was extracted with ethyl acetate (2×200 mL). The combined organic layers were washed with brine and dried with sodium sulfate. Solvents were removed in vacuo. Purification by flash column chromatography (Method L7; heptane, 20%-60% ethyl acetate) afforded 8.8 g (38.5 mmol; 76% of theory) of the title compound.

LC-MS (Method L1): $R_t$=2.03 min; m/z=228 (M+H)$^+$

1H NMR (300 MHz, DMSO-d6, Method M2) δ=12.23 (s, 1H), 7.97 (s, 1H), 7.90-7.83 (m, 1H), 7.66-7.52 (m, 2H), 2.37 (s, 3H).

Step 2: 3-Methyl-4-(3-(trifluoromethyl)phenyl)-1H-pyrazol-5-amine (2C-1)

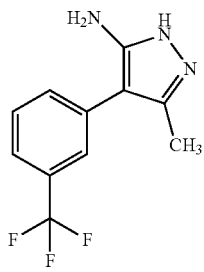 [SMILES: Cc1n[nH]c(N)c1-c1cccc(C(F)(F)F)c1]

To a solution of 3-oxo-2-(3-(trifluoromethyl)phenyl)butanenitrile (9.3 g, 40.7 mmol) in toluene (150 mL) were added acetic acid (8.3 g, 138 mmol, 8.0 mL) and hydrazine hydrate (4.5 g, 90 mmol, 4.4 mL). The mixture was stirred at reflux for 2.5 h and was allowed to cool to room temperature. Solvents were removed in vacuo. The residue was dissolved in hydrochloric acid (2M). The mixture was extracted with diethyl ether (2×100 mL). The layers were separated. The aqueous layer was basified to pH 11 and extracted with ethyl acetate (2×100 mL). The combined organic layers were washed with brine and dried with sodium sulfate. Solvents were removed in vacuo to afford 9.2 g (38 mmol; 93% of theory) of the title compound.

LC-MS (Method L1): $R_t$=1.66 min; m/z=242 (M+H)$^+$

1H NMR (300 MHz, DMSO-d6, Method 2) δ 11.56 (s, 1H), 7.68-7.46 (m, 4H), 4.48 (s, 2H), 2.19 (s, 3H).

Step 3: (E/Z)-Ethyl 2-(ethoxymethylene)-4,4-difluoro-3-oxobutanoate (1B-5)

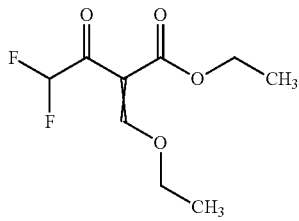

A mixture of ethyl 4,4-difluoroacetoacetate (9.7 g, 58.5 mmol), triethyl orthoformate (17.3 g, 117.0 mmol, 19.5 mL) and acetic anhydride (12.0 g, 117.0 mmol, 11.0 mL) was stirred at reflux for 18 h. The product was isolated after removal of the volatiles in vacuo (60° C., 0.003 bar). Material was used as such.

Step 4: Ethyl 7-(difluoromethyl)-2-methyl-3-(3-(trifluoromethyl)phenyl)pyrazolo[1,5-a]pyrimidine-6-carboxylate (2D-4)

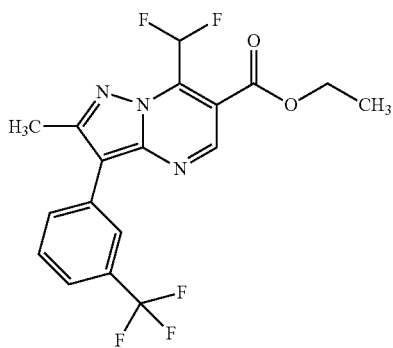 [SMILES: CCOC(=O)c1cnc2c(-c3cccc(C(F)(F)F)c3)c(C)nn2c1C(F)F]

A solution of (E/Z)-ethyl 2-(ethoxymethylene)-4,4-difluoro-3-oxobutanoate (453 mg, 2.0 mmol) and 3-methyl-4-(3-(trifluoromethyl)phenyl)-1H-pyrazol-5-amine (492 mg, 2.0 mmol) in ethanol (5 mL) was stirred at reflux for 3 h. Solvents were removed in vacuo. Purification by flash column chromatography (Method L7; 40 g; heptane, 0%-15% ethyl acetate) afforded 680 mg (1.7 mmol; 84% of theory) of the title compound.

LC-MS (Method L1): $R_t$=2.35 min; m/z=400 (M+H)$^+$

1H NMR (300 MHz, DMSO-d6, Method M2) δ=8.95 (s, 1H), 8.13-8.07 (m, 1H), 8.07-8.00 (m, 1H), 7.95 (s, 1H), 7.81-7.69 (m, 2H), 4.41 (q, J=7.1 Hz, 2H), 2.67 (s, 3H), 1.37 (t, J=7.1 Hz, 3H).

Step 5: 7-(Difluoromethyl)-2-methyl-3-(3-(trifluoromethyl)phenyl)pyrazolo[1,5-a]pyrimidine-6-carboxylic Acid (2E-4)

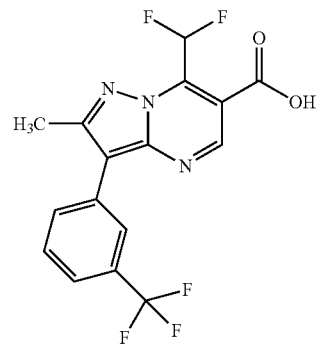 [SMILES: Cc1nn2c(C(F)F)c(C(=O)O)cnc2c1-c1cccc(C(F)(F)F)c1]

To a solution ethyl 7-(difluoromethyl)-2-methyl-3-(3-(trifluoromethyl)phenyl)pyrazolo[1,5-a]pyrimidine-6-carboxylate (680 mg, 1.7 mmol) in a mixture of tetrahydrofuran (2 mL) and water (2 mL) was added lithium hydroxide monohydrate (143 mg, 3.4 mmol). The mixture was stirred at room temperature for 2.5 h and was extracted with ethyl acetate (2×20 mL). The combined organic layers were washed with brine and dried with sodium sulfate. Solvents were removed in vacuo. Aqueous sodium hydroxide (1M; 50 mL) was added and the mixture was extracted with ethyl acetate (2×100 mL). The combined organic layers were washed with brine and dried with sodium sulfate. Solvents were removed in vacuo to afford 660 mg (1.5 mmol; 100% of theory) of the title compound with a purity of 56% according to LC-MS analysis. Material was used without further purification.

LC-MS (Method L1): $R_t$=2.07 min; m/z=372 (M+H)$^+$

Step 6: (S)-7-(Difluoromethyl)-N-(2,3-dihydro-1H-inden-1-yl)-2-methyl-3-(3-(trifluoromethyl)-phenyl)-pyrazolo[1,5-a]pyrimidine-6-carboxamide (Compound 311)

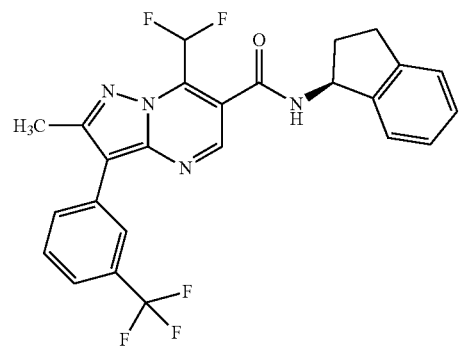 [SMILES: Cc1nn2c(C(F)F)c(C(=O)N[C@H]3CCc4ccccc43)cnc2c1-c1cccc(C(F)(F)F)c1]

N-(3-Dimethylaminopropyl)-N-ethylcarbodiimide hydrochloride (170 mg, 0.89 mmol) and 1-hydroxy-7-azabenzotriazole (11 mg, 0.08 mmol) were added to a solution of (S)-2,3-dihydro-1H-inden-1-amine (108 mg, 0.81 mmol, 0.104 mL) and 7-(difluoromethyl)-2-methyl-3-(3-(trifluoromethyl)phenyl)pyrazolo[1,5-a]pyrimidine-6-carboxylic acid (300 mg, 0.45 mmol; purity: 56%) in N,N-dimethylformamide (3 mL) at 0° C. The mixture was stirred at 0° C. for 10 min and at room temperature for 18 h. Water (10 mL) was added and the mixture was extracted with ethyl acetate (3×10 mL). The combined organic layers were washed with brine and dried with sodium sulfate. Solvents were removed in vacuo. Purification by flash column chromatography (Method L7; 12 g; heptane, 20% ethyl acetate) afforded 58 mg (0.12 mmol; 26% of theory) of the title compound.

LC-MS (Method L2): $R_t$=3.67 min; m/z=487 (M+H)$^+$

1H NMR (300 MHz, DMSO-d6, Method M2) δ=9.15 (d, J=8.1 Hz, 1H), 8.80 (s, 1H), 8.11 (s, 1H), 8.07-8.00 (m, 1H), 7.97-7.59 (m, 3H), 7.45-7.38 (m, 1H), 7.32-7.20 (m, 3H), 5.51 (q, J=7.7 Hz, 1H), 3.06-2.81 (m, 2H), 2.66 (s, 3H), 2.59-2.52 (m, 1H), 2.02-1.85 (m, 1H).

Preparation Example 3: (S)—N-(2,3-Dihydro-1H-inden-1-yl)-7-isopropyl-3-(6-methoxypyridin-2-yl)-2-methylpyrazolo[1,5-a]pyrimidine-6-carboxamide (Compound 177)

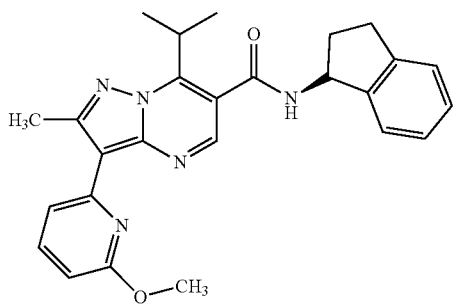

A stirred mixture of 2-chloro-6-methoxypyridine (144 mg, 1.00 mmol), bis(pinacolato)diboron (279 mg, 1.10 mmol) and potassium acetate (294 mg, 3.0 mmol) in 1,4-dioxane (2.0 mL) was sparged with nitrogen. [1,1'-Bis(diphenylphosphino)ferrocene]dichloropalladium(II) (37 mg, 0.05 mmol) was added. The resulting mixture was stirred at 90° C. under nitrogen atmosphere in a closed vessel for 1 h and was allowed to cool to room temperature.

To this mixture were added sodium carbonate (212 mg, 2.00 mmol), (S)-3-bromo-N-(2,3-dihydro-1H-inden-1-yl)-7-isopropyl-2-methylpyrazolo[1,5-a]pyrimidine-6-carboxamide (413 mg, 1.00 mmol) and water (0.3 mL). The mixture was sparged with nitrogen. Tri-tert-butylphosphine tetrafluoroborate (29 mg, 0.10 mmol) and tris(dibenzylidene-acetone)dipalladium(0) (23 mg, 0.03 mmol) were added. The reaction mixture was stirred at 90° C. under nitrogen atmosphere in a closed vessel overnight. The reaction mixture was cooled to room temperature, diluted with ethyl acetate (10 mL) and filtered over kieselguhr. The filtrate was concentrated in vacuo and purified by reversed phase flash column chromatography (Method L5; 40 g) to afford 98 mg (0.22 mmol; 22% of theory) of the title compound.

LC-MS (Method L2): $R_t$=4.14 min; m/z=442 (M+H)$^+$

1H NMR (300 MHz, DMSO-d6, Method M2) δ 9.10 (d, J=8.2 Hz, 1H), 8.60 (s, 1H), 8.07 (d, J=7.5 Hz, 1H), 7.77 (t, J=7.9 Hz, 1H), 7.45-7.35 (m, 1H), 7.34-7.19 (m, 3H), 6.66 (d, J=8.1 Hz, 1H), 5.53 (q, J=7.9 Hz, 1H), 4.06-3.88 (m, 4H), 3.08-2.79 (m, 5H), 2.62-2.44 (m, 1H), 2.04-1.83 (m, 1H), 1.57 (dd, J=6.9, 5.3 Hz, 6H).

Preparation Example 4: 2-Chloro-N—((S)-chroman-4-yl)-3-(2,3-difluorophenyl)-7-isopropylpyrazolo[1,5-a]pyrimidine-6-carboxamide (Compound 281)

Step 1: Ethyl 2-cyano-2-(2,3-difluorophenyl)acetate (4A-1)

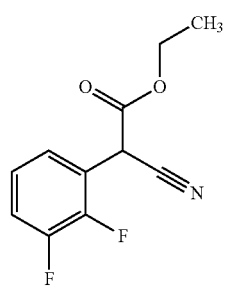 [SMILES: CCOC(=O)C(C#N)c1cccc(F)c1F]

To a solution of 2,3-difluorophenylacetonitrile (5.00 g, 32.7 mmol) in dry tetrahydrofuran (70 mL) sodium hydride (1.70 g, 42.4 mmol; 60% in mineral oil) was added portion wise at 0° C. Reaction mixture was allowed to warm to room temperature. After stirring for 1 h diethyl carbonate (4.63 g, 39.2 mmol, 4.8 mL) was slowly added. After stirring for 18 h. the reaction mixture was quenched by the addition of hydrochloric acid (1.0 M; 200 mL) and was extracted with ethyl acetate (2×150 mL). The combined organic layers were washed with brine, dried with sodium sulfate and concentrated in vacuo. Purification by flash column chromatography (Method L7; 120 g; heptane, 2%-15% ethyl acetate) afforded 6.96 g (30.2 mmol; 92% of theory) of the title compound.

LC-MS (Method L1): $R_t$=1.95 min; m/z=224 (M–H)$^-$

1H NMR (400 MHz, Chloroform-d, Method M2) δ 7.33-7.14 (m, 3H), 5.03 (s, 1H), 4.30 (m, 2H), 1.32 (t, J=7.1 Hz, 3H).

Step 2: 5-Amino-4-(2,3-difluorophenyl)-1H-pyrazol-3-ol (4B-1)

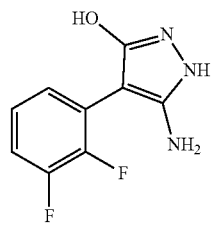 [SMILES: Nc1[nH]nc(O)c1-c1cccc(F)c1F]

A solution of ethyl 2-cyano-2-(2,3-difluorophenyl)acetate (6.96 g, 30.9 mmol) and hydrazine monohydrate (3.09 g, 61.8 mmol, 3.0 mL) in absolute ethanol (100 mL) was stirred at reflux for 1.5 h. The reaction mixture was concentrated in vacuo and co-evaporated with toluene and ethyl acetate. The residue was triturated in diethyl ether. The precipitate was filtered off and dried on air to afford 6.39 g (30.3 mmol; 98% of theory) of the title compound.

LC-MS (Method L1): $R_t$=0.66 min; m/z=212 (M+H)$^+$

1H NMR (400 MHz, DMSO-d6, Method M2) δ 8.26 (bs, 2H), 7.26 (m, 1H), 7.20-7.04 (m, 2H), 5.95 (s, 2H).

Step 3: Ethyl 3-(2,3-difluorophenyl)-2-hydroxy-7-isopropylpyrazolo[1,5-a]pyrimidine-6-carboxylate (4C-1)

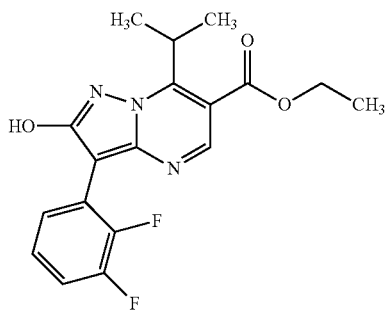 [SMILES: CCOC(=O)c1cnc2c(-c3cccc(F)c3F)c(O)nn2c1C(C)C]

A solution of 5-amino-4-(2,3-difluorophenyl)-1H-pyrazol-3-ol (4.58 g, 21.7 mmol) and ethyl 2-(ethoxymethylene)-4-methyl-3-oxopentanoate (5.58 g, 26.0 mmol) in absolute ethanol (150 mL) was stirred at reflux for 17 h. The reaction mixture was concentrated in vacuo and the residue was coated on hydromatrix. Purification by flash column chromatography (Method L6; 120 g; heptane, 2%-25% ethyl acetate) afforded 5.39 g (14.92 mmol; 69% of theory) of the title compound.

LC-MS (Method L1): $R_t$=2.30 min; m/z=362 (M+H)$^+$

1H NMR (400 MHz, Chloroform-d, Method M2) δ 8.82 (s, 1H), 7.93 (s, 1H), 7.48-7.40 (m, 1H), 7.21-7.09 (m, 2H), 4.55-4.46 (m, 1H), 4.42 (q, J=7.1 Hz, 2H), 1.59 (d, J=7.1 Hz, 6H), 1.42 (t, J=7.1 Hz, 3H).

Step 4: Ethyl 3-(2,3-difluorophenyl)-7-isopropyl-2-(((trifluoromethyl)sulfonyl)oxy)pyrazolo[1,5-a]pyrimidine-6-carboxylate (4D-1)

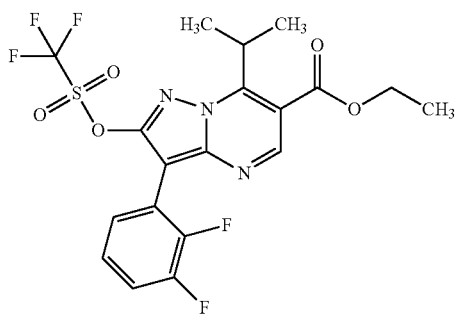 [SMILES: CCOC(=O)c1cnc2c(-c3cccc(F)c3F)c(OS(=O)(=O)C(F)(F)F)nn2c1C(C)C]

To a solution of ethyl 3-(2,3-difluorophenyl)-2-hydroxy-7-isopropylpyrazolo[1,5-a]pyrimidine-6-carboxylate (5.38 g, 14.89 mmol) in dichloromethane (250 mL) were added trifluoromethanesulfonic anhydride (5.78 g, 20.49 mmol, 3.4 mL) and pyridine (3.23 g, 40.8 mmol, 3.3 mL). After stirring for 1 h the reaction mixture was washed with hydrochloric acid (0.5 M; 2×200 mL) and brine, was dried with sodium sulfate and was concentrated in vacuo. The residue was combined with crude material that was obtained from a previous reaction towards the title compound starting from 0.63 g (1.60 mmol) of ethyl 3-(2,3-difluorophenyl)-2-hydroxy-7-isopropylpyrazolo[1,5-a]pyrimidine-6-carboxylate. Purification by flash column chromatography (Method L6; 120 g; heptane, 1%-12% ethyl acetate; two runs) afforded 7.09 g (14.11 mmol; 86% of theory, based on 16.49 mmol) of the title compound.

LC-MS (Method L1): $R_t$=2.56 min; m/z=494 (M+H)$^+$

1H NMR (400 MHz, Chloroform-d, Method M2) δ 8.93 (s, 1H), 7.44-7.35 (m, 1H), 7.31-7.18 (m, 2H), 4.55 (m, 1H), 4.46 (q, J=7.1 Hz, 2H), 1.63 (d, J=7.1 Hz, 6H), 1.44 (t, J=7.1 Hz, 3H).

Step 5: Ethyl 3-(2,3-difluorophenyl)-2-((diphenylmethylene)amino)-7-isopropylpyrazolo[1,5-a]pyrimidine-6-carboxylate (4E-1)

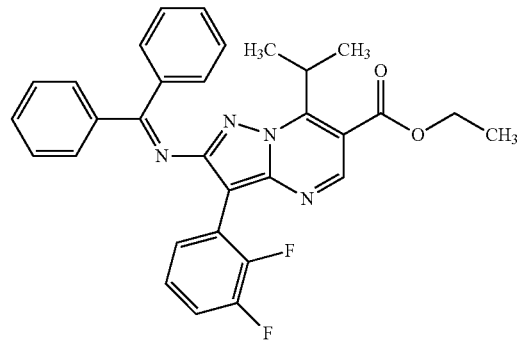 [SMILES: CCOC(=O)c1cnc2c(-c3cccc(F)c3F)c(N=C(c3ccccc3)c3ccccc3)nn2c1C(C)C]

A three-necked flask equipped with reflux setup and thermometer was loaded with cesium carbonate (9.36 g, 28.7 mmol). The flask was heated with a heat-gun at maximum capacity for approximately 15 minutes in vacuo. The flask was then allowed to cool to room temperature in vacuo and was flushed with nitrogen. Ethyl 3-(2,3-difluorophenyl)-7-isopropyl-2-(((trifluoromethyl)sulfonyl)oxy)pyrazolo[1,5-a]pyrimidine-6-carboxylate (7.09 g, 14.4 mmol), benzophenone imine (2.86 g, 15.8 mmol, 2.7 mL) and dry toluene (144 mL) were added. The resulting mixture was flushed with nitrogen. Tris(dibenzylideneacetone)dipalladium(0) (0.66 g, 0.72 mmol) and 9,9-dimethyl-4,5-bis(diphenylphosphino)xanthene (0.83 g, 1.44 mmol) were added and the resulting mixture was stirred at 100° C. overnight. The reaction mixture was allowed to cool to room temperature and was poured out into saturated aqueous ammonium chloride (500 mL). The mixture was extracted with ethyl acetate (3×100 mL). Combined organic extracts were dried with sodium sulfate and concentrated in vacuo. Purification by flash column chromatography (Method L6, 120 g, heptane, 5%-20% ethyl acetate) and (Method L6, 80 g, heptane, 5%-20% diisopropyl ether) afforded 1.62 g (2.75 mmol; 19% of theory) of the title compound.

LC-MS (Method L1): $R_t$=2.62 min; m/z=525 (M+1)$^+$

Step 6: Ethyl 2-amino-3-(2,3-difluorophenyl)-7-isopropylpyrazolo[1,5-a]pyrimidine-6-carboxylate (4F-1)

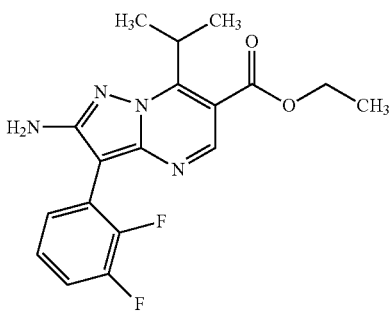

To a stirred solution of ethyl 3-(2,3-difluorophenyl)-2-((diphenylmethylene)amino)-7-isopropylpyrazolo[1,5-a]pyrimidine-6-carboxylate (1.62 g, 3.09 mmol) in tetrahydrofuran (31 mL) was added hydrochloric acid (2.0 M; 31 mL). The resulting mixture was stirred at room temperature for 30 min and was poured out into saturated aqueous sodium hydrogencarbonate (250 mL). The mixture was extracted with ethyl acetate (3×100 mL). The combined organic extracts were washed with brine, dried with sodium sulfate and concentrated in vacuo. Crystallization from diisopropyl ether (15 mL) afforded 650 mg (1.79 mmol; 58% of theory) of the title compound.

LC-MS (Method L1): $R_t$=2.31 min; m/z=361 (M+1)$^+$

1H NMR (400 MHz, DMSO-d6, Method M2) δ 8.56 (s, 1H), 7.43-7.32 (m, 2H), 7.31-7.23 (m, 1H), 6.12 (s, 2H), 4.45 (m, 1H), 4.32 (q, J=7.1 Hz, 2H), 1.54 (d, J=7.0 Hz, 6H), 1.33 (t, J=7.1 Hz, 3H).

Step 7: Ethyl 2-chloro-3-(2,3-difluorophenyl)-7-isopropylpyrazolo[1,5-a]pyrimidine-6-carboxylate (4G-1)

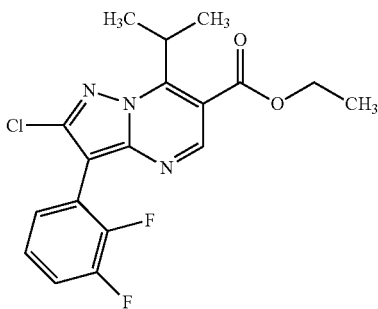 [SMILES: CCOC(=O)c1cnc2c(-c3cccc(F)c3F)c(Cl)nn2c1C(C)C]

At −15° C. to a vigorously stirred solution of ethyl 2-amino-3-(2,3-difluorophenyl)-7-isopropylpyrazolo[1,5-a]pyrimidine-6-carboxylate (650 mg, 1.80 mmol) in concentrated hydrochloric acid (9 mL) was added dropwise a solution of sodium nitrite (162 mg, 2.35 mmol) in water (1 mL). The resulting orange mixture was stirred for 1 h at −5° C. This mixture was added dropwise to a suspension of copper(I) chloride (286 mg, 2.89 mmol) in chloroform (6 mL) at room temperature. The resulting mixture was vigorously stirred overnight. The reaction mixture was poured out into aqueous sodium hydroxide (1.0 M; 120 mL). The resulting mixture was neutralized with saturated aqueous ammonium chloride (100 mL) and was extracted with dichloromethane (3×50 mL). The combined organic extract were dried with sodium sulfate and concentrated in vacuo. Purification by flash column chromatography (Method L6; 24 g; heptane, 5%-30% diisopropyl ether) afforded 397 mg (1.01 mmol; 56% of theory) of the title compound.

LC-MS (Method L1): $R_t$=2.52 min; m/z=380 (M+1)$^+$

1H NMR (400 MHz, DMSO-d6, Method M2) δ 8.86 (s, 1H), 7.61-7.51 (m, 1H), 7.45-7.34 (m, 2H), 4.47-4.32 (m, 3H), 1.56 (d, J=7.0 Hz, 6H), 1.36 (t, J=7.1 Hz, 3H).

Step 8: 2-Chloro-3-(2,3-difluorophenyl)-7-isopropylpyrazolo[1,5-a]pyrimidine-6-carboxylic Acid (4H-1)

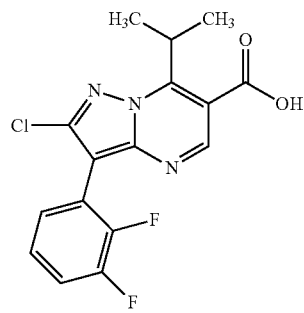 [SMILES: CC(C)c1c(C(=O)O)cnc2c(-c3cccc(F)c3F)c(Cl)nn12]

To a stirred solution of ethyl 2-chloro-3-(2,3-difluorophenyl)-7-isopropylpyrazolo[1,5-a]pyrimidine-6-carboxylate (397 mg, 1.05 mmol) in tetrahydrofuran (5 mL) was added aqueous sodium hydroxide (1.0 M; 1.25 mL). The resulting mixture was stirred overnight at room temperature and was poured out into saturated aqueous ammonium chloride (50 mL). The mixture was extracted with ethyl acetate (3×20 mL). Combined organic extracts were dried with sodium sulfate and concentrated in vacuo to afford 370 mg (0.95 mmol; 91% of theory) of the title compound.

LC-MS (Method L1): $R_t$=2.38 min; m/z=352 (M+1)$^+$

1H NMR (400 MHz, DMSO-d6, Method M2) δ 8.85 (s, 1H), 7.59-7.49 (m, 1H), 7.45-7.33 (m, 2H), 7.32-7.00 (m, 1H), 4.63 (m, 1H), 1.55 (d, J=7.1 Hz, 6H).

Step 9: 2-Chloro-N—((S)-chroman-4-yl)-3-(2,3-difluorophenyl)-7-isopropylpyrazolo[1,5-a]pyrimidine-6-carboxamide (Compound 281)

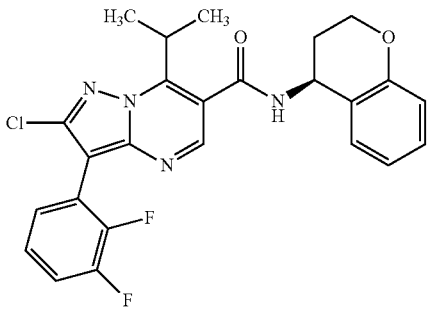 [SMILES: CC(C)c1c(C(=O)N[C@H]2CCOc3ccccc32)cnc2c(-c3cccc(F)c3F)c(Cl)nn12]

Under nitrogen atmosphere N-(3-dimethylaminopropyl)-3-ethylcarbodiimide hydrochloride (60 mg, 0.31 mmol) and ethyl cyanoglyoxylate-2-oxime (4 mg, 0.03 mmol) were added to a stirred mixture of 2-chloro-3-(2,3-difluorophenyl)-7-isopropylpyrazolo[1,5-a]pyrimidine-6-carboxylic acid (100 mg, 0.28 mmol), (S)-chroman-4-amine hydrochloride (55 mg, 0.30 mmol) and triethylamine (35 mg, 0.34 mmol, 0.05 mL) in dry N,N-dimethylformamide (2 mL) at 0° C. N-(3-dimethylaminopropyl)-3-ethylcarbodiimide hydrochloride (60 mg, 0.31 mmol) and ethyl cyanoglyoxylate-2-oxime (4 mg, 0.03 mmol). The resulting mixture was stirred overnight while warming to room temperature. The reaction mixture was poured out into water (20 mL) and was extracted with ethyl acetate (3×10 mL). The combined organic extracts were washed with brine (3×10 mL), dried with sodium sulfate and concentrated in vacuo. Purification by flash column chromatography (Method L6; 12 g; heptane, 5%-50% ethyl acetate) afforded 80 mg (0.17 mmol; 58% of theory) of the title compound.

LC-MS (Method L2): $R_t$=4.30 min; m/z=483 (M+1)$^+$

1H NMR (400 MHz, DMSO-d6, Method M2) δ 9.26 (d, J=8.0 Hz, 1H), 8.63 (s, 1H), 7.61-7.48 (m, 1H), 7.47-7.31 (m, 3H), 7.24-7.12 (m, 1H), 6.99-6.88 (m, 1H), 6.81 (d, J=8.2 Hz, 1H), 5.23 (q, J=5.6 Hz, 1H), 4.36-4.14 (m, 2H), 3.97-3.84 (m, 1H), 2.28-2.15 (m, 1H), 2.12-2.00 (m, 1H), 1.55 (m, 6H).

Experimental Section—Intermediates

Intermediates 1B (E/Z)-Ethyl 2-(ethoxymethylene)-3-oxopentanoate (1B-2)

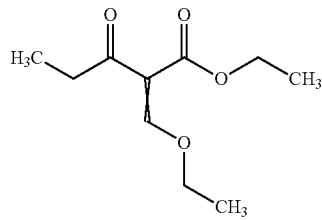

Ethyl propionylacetate (25.7 g, 178 mmol, 25.4 mL) was used as a starting material using the same procedure as for 1B-1. 35.5 g (177 mmol, 100% of theory) of the title compound were obtained.

GC-MS (Method A): $R_t$=3.53 and 3.56 min (E/Z isomers); m/z=200 M$^+$ (E/Z)-Ethyl 2-(cyclopropanecarbonyl)-3-ethoxyacrylate (1B-3)

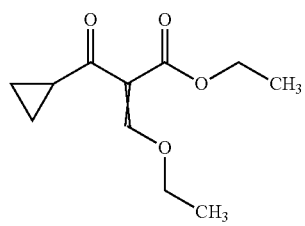

3-cyclopropyl-3-oxo-propionic acid ethyl ester (5.0 g, 31.9 mmol) was used as a starting material using the same procedure as for 1B-1. Material was used as such.

(E/Z)-Ethyl 2-(ethoxymethylene)-4-methoxy-3-oxobutanoate (1B-4)

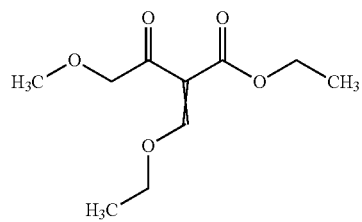

Methyl 4-methoxy-3-oxobutanoate (5.0 g, 34.2 mmol, 4.4 mL was used as a starting material using the same procedure as for 1B-1. Material was used as such.

(E/Z)-Ethyl 2-(ethoxymethylene)-4,4,4-trifluoro-3-oxobutanoate (1B-6)

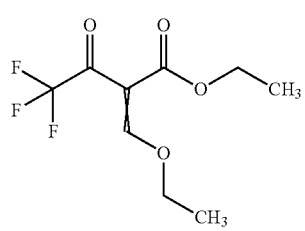 [SMILES: CCOC=C(C(=O)OCC)C(=O)C(F)(F)F]

Ethyl 4,4,4-trifluoro-3-oxobutanoate (12.5 g, 67.9 mmol, 10.0 mL was used as a starting material using the same procedure as for 1B-1. 13.4 g (55.8 mmol; 82% of theory) of the title compound were obtained. Material was used as such.

(E/Z)-Ethyl 4-(dimethylamino)-2-(ethoxymethylene)-3-oxobutanoate (1B-7)

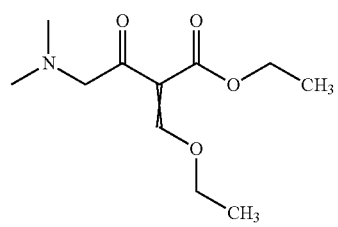 [SMILES: CCOC=C(C(=O)CN(C)C)C(=O)OCC]

Ethyl 4-(dimethylamino)-3-oxobutanoate (5.5 g, 31.8 mmol, 10.0 mL was used as a starting material using the same procedure as for 1B-1. 4.9 g (crude) of the title compound were obtained. Material was used as such.

Intermediates 1C

Ethyl 7-cyclopropyl-2-methylpyrazolo[1,5-a]pyrimidine-6-carboxylate (1C-2)

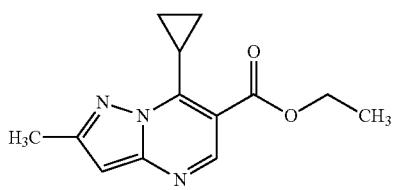 [SMILES: CCOC(=O)c1cnc2cc(C)nn2c1C1CC1]

A suspension of (E/Z)-ethyl 2-(cyclopropanecarbonyl)-3-ethoxyacrylate (20.38 g, 96 mmol) and 3-methyl-1H-pyrazol-5-amine (9.32 g, 96 mmol) in ethanol (150 mL) was stirred at reflux for 72 h. The suspension was allowed to cool to room temperature. Solvents were removed in vacuo. Solids were filtered off and washed with ethanol. The filtrate was concentrated in vacuo. Approximately 20 g of the title compound with a purity of 59% according to LC-MS were obtained. The material was used without further purification.
LC-MS (Method L1): $R_t$=2.00 min; m/z=246 (M+H)$^+$ Ethyl 2-methyl-7-(trifluoromethyl)pyrazolo[1,5-a]pyrimidine-6-carboxylate (1C-3)

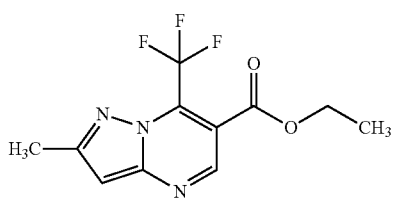 [SMILES: CCOC(=O)c1cnc2cc(C)nn2c1C(F)(F)F]

A solution of (E/Z)-ethyl 2-(ethoxymethylene)-4,4,4-trifluoro-3-oxobutanoate (13.4 g, 55.8 mmol) and 3-methyl-1H-pyrazol-5-amine (5.4 g, 55.8 mmol) in ethanol (100 mL) was stirred at reflux for 72 h. The reaction mixture was allowed to cool to room temperature. Solvent was removed in vacuo. Ethanol (50 mL) was added to the solid residue. The suspension was stirred at reflux for 72 h. The reaction mixture was allowed to cool to room temperature. Solvents were removed in vacuo. Material was used as such.
LC-MS (Method L1): $R_t$=1.97 min; m/z=274 (M+H)$^+$ Ethyl 2-cyclopropyl-7-isopropylpyrazolo[1,5-a]pyrimidine-6-carboxylate (1C-4)

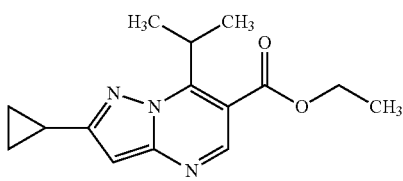 [SMILES: CCOC(=O)c1cnc2cc(C3CC3)nn2c1C(C)C]

A solution of 5-cyclopropyl-1H-pyrazol-3-amine (7.58 g, 61.5 mmol) and ethyl 2-(ethoxymethylene)-4-methyl-3-oxopentanoate (13.19 g, 61.5 mmol) in absolute ethanol (200 mL) was stirred at reflux for 18 h. The reaction mixture was allowed to cool to room temperature. Solvents were removed in vacuo. 16.81 g (58.4 mmol; 95% of theory) of the title compound were obtained.
LC-MS (Method L1): $R_t$=2.18 min; m/z=274 (M+H)$^+$
1H NMR (300 MHz, Chloroform-d, Method M2) δ 8.72 (s, 1H), 6.36 (s, 1H), 4.54 (p, J=7.0 Hz, 1H), 4.40 (q, J=7.1 Hz, 2H), 2.13 (m, 1H), 1.59 (d, J=7.0 Hz, 6H), 1.42 (t, J=7.1 Hz, 3H), 1.15-0.93 (m, 4H).

Ethyl 2-(difluoromethyl)-7-isopropylpyrazolo[1,5-a]pyrimidine-6-carboxylate (1C-5)

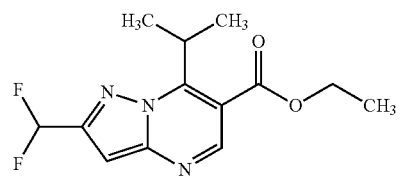 [SMILES: CCOC(=O)c1cnc2cc(C(F)F)nn2c1C(C)C]

A solution of 5-(difluoromethyl)-1H-pyrazol-3-amine (2.343 g, 17.60 mmol) and ethyl 2-(ethoxymethylene)-4-methyl-3-oxopentanoate (3.77 g, 17.60 mmol) in absolute ethanol (125 mL) was stirred at reflux for 21 h. The reaction mixture was concentrated in vacuo to afford 4.71 g (16.63 mmol; 93% of theory) of the title compound with a purity of 89% according to LC-MS.
LC-MS (Method L1): $R_t$=2.08 min; m/z=284 (M+H)$^+$ Ethyl 7-ethyl-2-methylpyrazolo[1,5-a]pyrimidine-6-carboxylate (10-6)

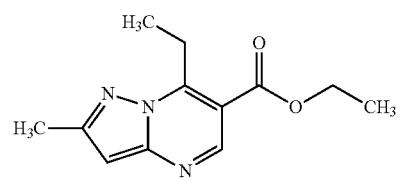 [SMILES: CCOC(=O)c1cnc2cc(C)nn2c1CC]

A solution of (E/Z)-ethyl 2-(ethoxymethylene)-3-oxopentanoate (35.5 g, 177 mmol) and 3-methyl-1H-pyrazol-5-amine (17.2 g, 177 mmol) in ethanol (350 mL) was stirred at reflux for 2 h.
The reaction mixture was cooled to room temperature. Solvents were removed in vacuo. The residue was coevaporated with toluene, ethyl acetate and diethyl ether to afford 41.3 g (177 mmol, 100% of theory) of the title compound.
LC-MS (Method L1): $R_t$=1.91 min, m/z=234 (M+H)$^+$ Ethyl 7-cyclopropyl-2-(difluoromethyl)pyrazolo[1,5-a]pyrimidine-6-carboxylate (1C-7)

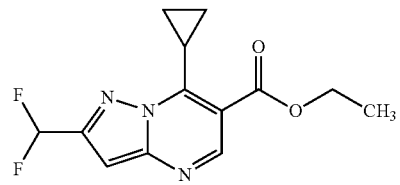 [SMILES: CCOC(=O)c1cnc2cc(C(F)F)nn2c1C1CC1]

A mixture of (E/Z)-ethyl 2-(cyclopropanecarbonyl)-3-ethoxyacrylate (3.0 g, 14.28 mmol) and 5-(difluoromethyl)-1H-pyrazol-3-amine (1.9 g, 14.28 mmol) in ethanol (95 mL) was stirred at reflux overnight. The reaction mixture was concentrated in vacuo to afford 4.0 g (14.22 mmol; 100% of theory) of the title compound with a purity of 89% according to LC-MS.

LC-MS (Method L1): $R_t$=2.03 min; m/z=282 (M+H)$^+$

Intermediates 1D

Ethyl 3-bromo-7-cyclopropyl-2-methylpyrazolo[1,5-a]pyrimidine-6-carboxylate (1 D-2)

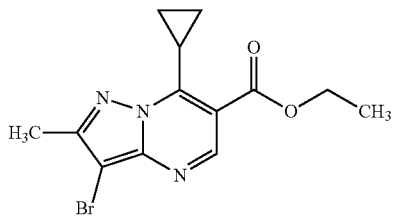 [SMILES: CCOC(=O)c1cnc2c(Br)c(C)nn2c1C1CC1]

Under nitrogen atmosphere at room temperature N-bromosuccinimide (8.21 g, 46.1 mmol) was added to a solution of ethyl 7-cyclopropyl-2-methylpyrazolo[1,5-a]pyrimidine-6-carboxylate (10.29 g, 42.0 mmol) in anhydrous acetonitrile (400 mL). The reaction mixture was stirred for 5 h. Solvents were removed in vacuo. Residue was triturated in methanol overnight. The solid was filtered off and triturated in methanol. Solid was filtered off and dried on air. 5.33 g of the title compound were obtained. The filtrate was concentrated in vacuo. The residue was triturated in methanol. The solid was filtered off and dried on air. 4.37 g of the title compound were obtained. Materials were combined. In total 9.70 g (29.9 mmol; 71% of theory) of the title compound were obtained.

LC-MS (Method L1): $R_t$=2.29 min; m/z=324/326 (M+H)$^+$

1H NMR (300 MHz, DMSO-d6, Method M2) δ 8.74 (s, 1H), 4.37 (q, J=7.1 Hz, 2H), 3.09-2.96 (m, 1H), 2.42 (s, 3H), 1.83 (dq, J=6.0, 3.4 Hz, 2H), 1.36 (t, J=7.1 Hz, 3H), 1.28-1.18 (m, 2H).

Ethyl 3-bromo-2-methyl-7-(trifluoromethyl)pyrazolo[1,5-a]pyrimidine-6-carboxylate (1D-3)

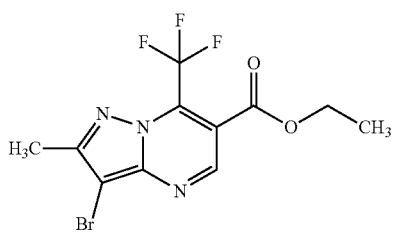 [SMILES: CCOC(=O)c1cnc2c(Br)c(C)nn2c1C(F)(F)F]

Under nitrogen atmosphere at room temperature N-bromosuccinimide (10.9 g, 61.4 mmol) was added to a suspension of ethyl 2-methyl-7-(trifluoromethyl)pyrazolo[1,5-a]pyrimidine-6-carboxylate (15.3 g, 55.8 mmol) in anhydrous acetonitrile (500 mL). The reaction mixture was stirred for 5 h. N-bromosuccinimide (0.99 g, 5.6 mmol) was added and stirring at room temperature was continued for 18 h. The solid was filtered off, washed with acetonitrile and dried on air. 5.36 g of the title compound were obtained. The filtrate was concentrated in vacuo. The solid residue was triturated in methanol. The solid was filtered off, washed with methanol and dried on air. 5.89 g of the title compound were obtained. Solids were combined. In total 11.25 g (32.0 mmol; 57% of theory) of the title compound were obtained.

LC-MS (Method L1): $R_t$=2.12 min; m/z=352/354 (M+H)$^+$

1H NMR (300 MHz, DMSO-d6, Method M2) δ 9.73 (s, 1H), 4.37 (q, J=7.1 Hz, 2H), 2.52 (s, 3H), 1.35 (t, J=7.1 Hz, 3H).

Ethyl 3-bromo-2-cyclopropyl-7-isopropylpyrazolo[1,5-a]pyrimidine-6-carboxylate (1D-4)

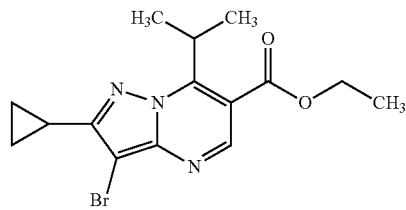 [SMILES: CCOC(=O)c1cnc2c(Br)c(C3CC3)nn2c1C(C)C]

N-bromosuccinimide (11.1 g, 62.4 mmol) was added to a solution of ethyl 2-cyclopropyl-7-isopropylpyrazolo[1,5-a]pyrimidine-6-carboxylate (16.8 g, 61.5 mmol) in acetonitrile (600 mL). The reaction mixture was stirred at room temperature for 15 min and was concentrated in vacuo. The residue was triturated in diethyl ether. The solids were filtered off and washed with diethyl ether. The filtrate was concentrated in vacuo and the residue was triturated in diisopropyl ether. The solids were filtered off. The filtrate was treated with active charcoal. The charcoal was filtered off over kieselguhr and the filtrate was concentrated in vacuo. 20.8 g (57.3 mmol; 93% of theory) of the title compound were obtained.

LC-MS (Method L1): $R_t$=2.35 min; m/z=352/354 (M+H)$^+$

1H NMR (300 MHz, Chloroform-d, Method M2) δ 8.79 (s, 1H), 4.51 (p, J=7.0 Hz, 1H), 4.41 (q, J=7.1 Hz, 2H), 2.20 (m, 1H), 1.54 (d, J=7.0 Hz, 6H), 1.42 (t, J=7.1 Hz, 3H), 1.13 (m, 4H).

Ethyl 3-bromo-2-(difluoromethyl)-7-isopropylpyrazolo[1,5-a]pyrimidine-6-carboxylate (1D-5)

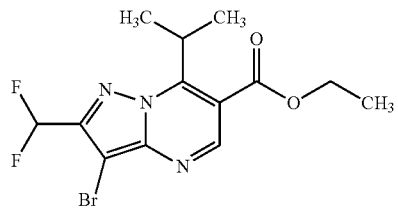 [SMILES: CCOC(=O)c1cnc2c(Br)c(C(F)F)nn2c1C(C)C]

To a solution of ethyl 2-(difluoromethyl)-7-isopropylpyrazolo[1,5-a]pyrimidine-6-carboxylate (4.71 g, 16.63 mmol) in acetonitrile (150 mL) was added N-bromosuccinimide (3.00 g, 16.88 mmol). After stirring for 1 h the reaction mixture was concentrated in vacuo and the residue was triturated in diethyl ether (150 mL). Solids were filtered off and the filtrate was concentrated in vacuo. The residue was triturated in diisopropyl ether (150 mL). The solids were filtered off and the filtrate was treated with active charcoal. The charcoal was filtered off over kieselguhr and the filtrate was concentrated in vacuo. The material was combined with an impure batch of the title compound that was obtained from a previous reaction starting with 5.72 mmol of ethyl 2-(difluoromethyl)-7-isopropylpyrazolo[1,5-a]pyrimidine-6-carboxylate. Purification by flash column chromatography (Method L7; 80 g; heptane, 1%-10% ethyl acetate) afforded 5.72 g (15.79 mmol; 70% of theory; based on 22.35 mmol) of the title compound.

LC-MS (Method L1): $R_t$=2.16 min; m/z=362/634 (M+H)$^+$

1H NMR (300 MHz, Chloroform-d. Method M2) δ 8.90 (s, 1H), 6.90 (t, J=53.3 Hz, 1H), 4.60-4.40 (m, 3H), 1.60 (d, J=7.1 Hz, 6H), 1.45 (t, J=7.1 Hz, 3H), 1.30-1.06 (m, 1H).

Ethyl 3-bromo-7-ethyl-2-methylpyrazolo[1,5-a]pyrimidine-6-carboxylate (1D-6)

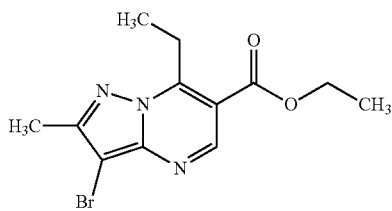 [SMILES: CCOC(=O)c1cnc2c(Br)c(C)nn2c1CC]

Under nitrogen atmosphere at room temperature N-bromosuccinimide (31.4 g, 176 mmol) was added to a solution of ethyl 7-ethyl-2-methylpyrazolo[1,5-a]pyrimidine-6-carboxylate (40.3 g, 173 mmol) in anhydrous acetonitrile (600 mL). The reaction mixture was stirred for 1 h at room temperature. Solvents were removed in vacuo. The residue was triturated in methanol. The solid was filtered off and dried on air. The filtrate was concentrated in vacuo. The residue was triturated in methanol. The solid was filtered off and dried on air. Solid materials were combined. In total 31.2 g (103 mmol, 60% of theory) of the title compound were obtained.

LC-MS (Method L1): $R_t$=2.12 min; m/z=312/314 (M+H)$^+$

Ethyl 3-bromo-2-(difluoromethyl)-7-isopropylpyrazolo[1,5-a]pyrimidine-6-carboxylate (1D-7)

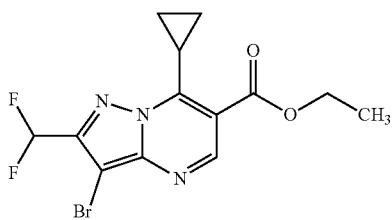 [SMILES: CCOC(=O)c1cnc2c(Br)c(C(F)F)nn2c1C1CC1]

To a stirred solution of ethyl 7-cyclopropyl-2-(difluoromethyl)pyrazolo[1,5-a]pyrimidine-6-carboxylate (4.0 g, 14.22 mmol) in acetonitrile (142 mL) was portionwise added bromosuccinimide (2.6 g, 14.44 mmol). The reaction mixture was stirred at room temperature for 15 minutes and was concentrated in vacuo. Purification by recrystallisation from ethanol (50 mL) afforded 3.26 g (9.05 mmol; 63% of theory) of the title compound.

LC-MS (Method L1): $R_t$=2.13 min; m/z=360/362 (M+1)$^+$

1H NMR (400 MHz, Chloroform-d, Method M2) δ 8.92 (s, 1H), 6.84 (t, J=53.3 Hz, 1H), 4.46 (q, J=7.1 Hz, 2H), 3.38-3.18 (m, 1H), 2.23-2.06 (m, 2H), 1.45 (t, J=7.1 Hz, 3H), 1.38-1.22 (m, 2H).

Ethyl 3-bromo-7-[(dimethylamino)methyl]-2-methylpyrazolo[1,5-a]pyrimidine-6-carboxylate (1D-8)

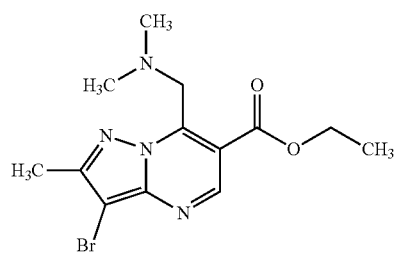 [SMILES: CCOC(=O)c1cnc2c(Br)c(C)nn2c1CN(C)C]

To a stirred solution of crude compound 1B-7 (4.9 g, 21.43 mmol) in ethanol (40 mL) was added 4-bromo-3-methyl-1H-pyrazol-5-amine (3.04 g, 17.1 mmol) at room temperature and the resulting mixture was refluxed for 2 h. Progress of reaction was monitored by TLC using (10% methanol in DCM). After complete consumption of starting material, the mixture was diluted with ethyl acetate (200 mL), washed with water (100 mL), brine (100 mL) and the separated organic layer was dried over sodium sulfate The solvent was removed on a rotary evaporator to give crude material as a brown liquid. The crude material was purified by combiflash chromatography using 30% ethyl acetate in hexane as an eluent to afford 1.5 g of the title compound 1D-8 as brown liquid.

1H NMR (400 MHz, Chloroform-d): δ 1.42 (t, J=7.16 Hz, 3H), 2.37 (s, 6H), 2.53 (s, 3H), 4.42 (q, J=7.16 Hz, 2H), 4.45 (s, 2H), 8.88 (s, 1H).

Intermediates 1E

3-Bromo-7-cyclopropyl-2-methylpyrazolo[1,5-a]pyrimidine-6-carboxylic Acid (1E-2)

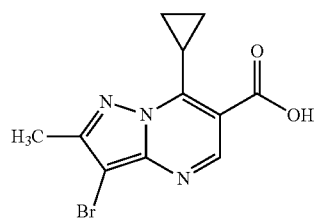 [SMILES: Cc1nn2c(C3CC3)c(C(=O)O)cnc2c1Br]

At room temperature to a solution of ethyl 3-bromo-7-cyclopropyl-2-methylpyrazolo[1,5-a]pyrimidine-6-carboxylate (11.16 g, 34.4 mmol) in tetrahydrofuran (200 mL) was added a solution of lithium hydroxide monohydrate (11.56 g, 275 mmol) in water (200 mL). The reaction mixture was stirred for 3 h. Organic solvents were removed in vacuo. Aqueous residue was acidified with hydrochloric acid (1M). The precipitate was filtered off, washed with water and dried on air. 9.47 g of the title compound were obtained. The aqueous filtrate was extracted with ethyl acetate (2×50 mL). The combined organic extracts were dried with sodium sulfate and solvents were removed in vacuo. 0.46 g of the title compound were obtained. Materials were combined and coevaporated with ethyl acetate. In total 9.93 g (15.8 mmol; 46% of theory) with a purity of 47% according to LC-MS were obtained. Material was used without further purification.

LC-MS (Method L1): $R_t$=1.90 min; m/z=296/298 (M+H)$^+$

3-Bromo-2-methyl-7-(trifluoromethyl)pyrazolo[1,5-a]pyrimidine-6-carboxylic Acid (1E-3)

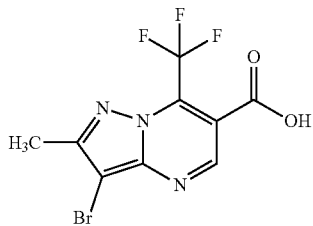 [SMILES: Cc1nn2c(C(F)(F)F)c(C(=O)O)cnc2c1Br]

At room temperature to a suspension of ethyl 3-bromo-2-methyl-7-(trifluoromethyl)-pyrazolo[1,5-a]pyrimidine-6-carboxylate (6.00 g, 17.0 mmol) in tetrahydrofuran (100 mL) was added a solution of lithium hydroxide monohydrate (5.72 g, 136 mmol) in water (100 mL). The suspension was stirred for 18 h. The solid was filtered off, washed with water and dried on air. The filtrate was acidified with hydrochloric acid (1M) and was extracted with ethyl acetate (3×100 mL). Combined organic extracts were dried with sodium sulfate. Solvents were removed in vacuo. The solid residue was combined with the previously obtained solid. In total 5.93 g (15.9 mmol; 93% of theory) of the title compound with a purity of 87% according to LC-MS were obtained. Material was used as such.

LC-MS (Method L1): $R_t$=2.24 min; m/z=324/326 (M+H)$^+$

1H NMR (300 MHz, DMSO-d6, Method M2) δ 10.15-10.06 (m, 1H), 2.30 (s, 3H). [acidic proton is not detected]

3-Bromo-2-cyclopropyl-7-isopropylpyrazolo[1,5-a]pyrimidine-6-carboxylic Acid (1E-4)

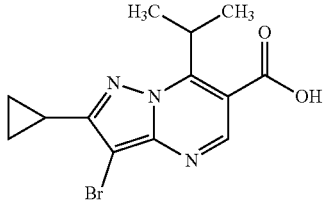 [SMILES: CC(C)c1c(C(=O)O)cnc2c(Br)c(C3CC3)nn12]

To a solution of ethyl 3-bromo-2-cyclopropyl-7-isopropylpyrazolo[1,5-a]pyrimidine-6-carboxylate (20.8 g, 59 mmol) in tetrahydrofuran (400 mL) was added a solution of lithium hydroxide monohydrate (19.8 g, 473 mmol) in water (400 mL). The mixture was stirred for 14 h at room temperature and the organic solvent was removed in vacuo. The aqueous residue was acidified with hydrochloric acid (1N; 500 mL). The resulting precipitate was filtered off, washed with water (100 mL) and heptane (2×100 mL) and was dried in vacuo at 50° C. 18.0 g (52 mmol; 88% of theory) of the title compound were obtained.

LC-MS (Method L1): $R_t$=2.20 min; m/z=324/326 (M+H)$^+$.

1H NMR (300 MHz, DMSO-d6, Method M2) δ 8.79 (s, 1H), 4.55 (p, J=7.0 Hz, 1H), 3.33 (s, 1H), 2.15 (m, 1H), 1.48 (d, J=7.0 Hz, 6H), 1.20-0.99 (m, 4H).

3-Bromo-2-(difluoromethyl)-7-isopropylpyrazolo[1,5-a]pyrimidine-6-carboxylic Acid (1E-5)

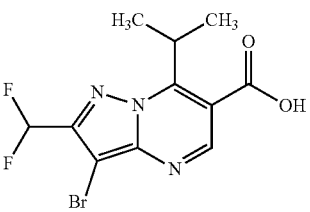 [SMILES: CC(C)c1c(C(=O)O)cnc2c(Br)c(C(F)F)nn12]

To a solution of ethyl 3-bromo-2-(difluoromethyl)-7-isopropylpyrazolo[1,5-a]pyrimidine-6-carboxylate (5.72 g, 15.79 mmol) in tetrahydrofuran (100 mL) was added a solution of lithium hydroxide monohydrate (5.30 g, 126 mmol) in water (100 mL). The mixture was stirred for 20 h. Organic solvents were removed in vacuo. The remaining aqueous layer was acidified with hydrochloric acid (2N; 200 mL). The resulting precipitate was filtered off, washed with water (100 mL) and heptane (2×100 mL) and was dried on air. 4.56 g (8.60 mmol; 54% of theory) of the title compound were obtained. The material was used without further purification.

LC-MS (Method L1): $R_t$=2.05 min; m/z=334/336 (M+H)$^+$.

3-Bromo-7-ethyl-2-methylpyrazolo[1,5-a]pyrimidine-6-carboxylic acid (1E-6)

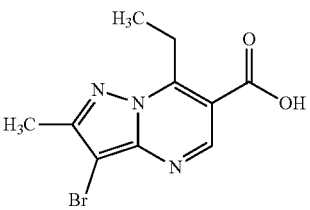 [SMILES: CCc1c(C(=O)O)cnc2c(Br)c(C)nn12]

At room temperature to a solution of ethyl 3-bromo-7-ethyl-2-methylpyrazolo[1,5-a]pyrimidine-6-carboxylate (32.1 g, 103 mmol) in tetrahydrofuran (400 mL) was added a solution of lithium hydroxide monohydrate (34.6 g, 823 mmol) in water (400 mL). The reaction mixture was stirred for 2 h at room temperature. Organic solvents were removed in vacuo. Aqueous residue was acidified with hydrochloric acid (1M). The resulting precipitate was filtered off, washed with water and dried on air for three days. The resulting sticky solid was coevaporated with toluene to afford 27.1 g (95 mmol, 93% of theory) of the title compound.

LC-MS (Method L1): $R_t$=1.92 min; m/z=284/286 (M+H)$^+$

3-Bromo-7-cyclopropyl-2-(difluoromethyl)pyrazolo[1,5-a]pyrimidine-6-carboxylic Acid (1E-7)

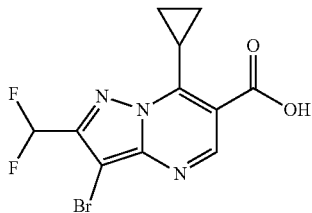 [SMILES: O=C(O)c1cnc2c(Br)c(C(F)F)nn2c1C1CC1]

To a stirred solution of ethyl 3-bromo-7-cyclopropyl-2-(difluoromethyl)pyrazolo[1,5-a]pyrimidine-6-carboxylate (3.26 g, 9.04 mmol) in tetrahydrofuran (50 mL) was added aqueous sodium hydroxide (2.0 M; 5.4 mL). The resulting mixture was stirred at room temperature overnight. The reaction mixture was acidified to pH 3 by the addition of hydrochloric acid (1.0 M), was diluted with brine (200 mL) and extracted with a mixture of dichloromethane and methanol (9:1; 3×100 mL). Combined organic extracts were dried with sodium sulfate and concentrated in vacuo to afford 2.90 g of the title compound with a purity of 36% according to LC-MS. The material was used without further purification.

LC-MS (Method L1): $R_t$=1.98 min; m/z=332/334 (M+1)

Intermediates 1F

(S)-3-Bromo-7-isopropyl-2-methyl-N-(1,2,3,4-tetrahydronaphthalen-1-yl)pyrazolo[1,5-a]pyrimidine-6-carboxamide (1F-2)

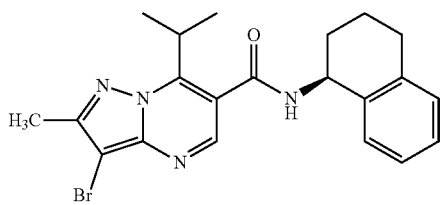 [SMILES: Cc1nn2c(C(C)C)c(C(=O)N[C@H]3CCCc4ccccc43)cnc2c1Br]

To a solution of 3-bromo-7-isopropyl-2-methylpyrazolo[1,5-a]pyrimidine-6-carboxylic acid (1.75 g, 5.87 mmol) and (S)-1,2,3,4-tetrahydro-1-naphtylamine (0.86 g, 5.87 mmol, 0.86 mL) in dry N,N-dimethylformamide (50 mL) at 0° C. were added N-(3-dimethylaminopropyl)-N-ethylcarbodiimide hydrochloride (1.24 g, 6.46 mmol) and 1-hydroxy-7-azabenzotriazole (0.08 g, 0.59 mmol). The mixture was stirred at 0° C. for 15 min and at room temperature for 2 h. Water (150 mL) was added and the resulting suspension was stirred for 20 min. The solid was filtered off, washed with water and dried at 40° C. in vacuo overnight. 2.30 g (5.22 mmol; 82% of theory) of the title compound were obtained.

LC-MS (Method L1): $R_t$=2.20 min; m/z=427/429 (M+H)$^+$

1H NMR (300 MHz, DMSO-d6, Method M2) δ 9.06 (d, J=8.4 Hz, 1H), 8.48 (s, 1H), 7.42-7.30 (m, 1H), 7.26-7.05 (m, 3H), 5.29-5.10 (m, 1H), 3.90 (p, J=7.0 Hz, 1H), 2.93-2.63 (m, 3H), 2.46 (s, 3H), 2.15-1.68 (m, 4H), 1.51 (t, J=7.3 Hz, 6H).

(S)-3-Bromo-N-(chroman-4-yl)-7-isopropyl-2-methylpyrazolo[1,5-a]pyrimidine-6-carboxamide (1F-3)

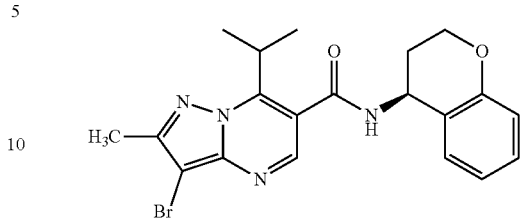

At 0° C. to a solution of 3-bromo-7-isopropyl-2-methylpyrazolo[1,5-a]pyrimidine-6-carboxylic acid (0.90 g, 2.78 mmol), (S)-chroman-4-ylamine hydrochloride (0.52 g, 2.78 mmol) and N,N-diisopropylethylamine (0.43 g, 3.33 mmol, 0.57 mL) in dry N,N-dimethylformamide (30 mL) and were added N-(3-Dimethylaminopropyl)-N-ethylcarbodiimide hydrochloride (0.59 g, 3.05 mmol) and 1-hydroxy-7-azabenzotriazole (0.04 g, 0.28 mmol). The mixture was stirred at 0° C. for 15 min and at room temperature for 2 h. Water (90 mL) was added and the resulting precipitate was filtered off and dried in vacuo at 500C overnight. 1.04 g (2.43 mmol; 88% of theory) of the title compound were obtained.

LC-MS (Method L1): $R_t$=2.11 min; m/z=429/431 (M+H)$^+$

1H NMR (300 MHz, Chloroform-d, Method M2) δ 8.39 (s, 1H), 7.27 (s, 1H), 7.26-7.17 (m, 1H), 6.94 (m, 1H), 6.90-6.83 (m, 1H), 6.16 (d, J=7.5 Hz, 1H), 5.39-5.29 (m, 1H), 4.35 (m, 1H), 4.19 (m, 1H), 4.05 (p, J=7.1 Hz, 1H), 2.52 (s, 3H), 2.47-2.32 (m, 1H), 2.22 (m, 1H), 1.60 (dd, J=7.0, 6.0 Hz, 6H).

(S)-3-Bromo-7-cyclopropyl-N-(2,3-dihydro-1H-inden-1-yl)-2-methylpyrazolo[1,5-a]pyrimidine-6-carboxamide (1F-4)

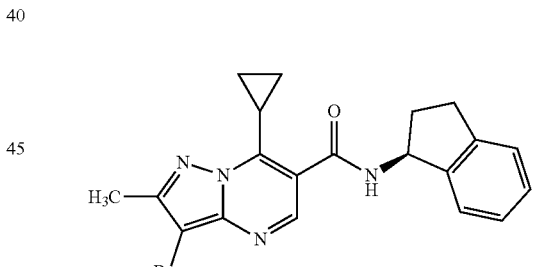

Under nitrogen atmosphere at room temperature diethyl cyanophosphonate (2.2 g, 13.2 mmol, 2.0 mL) was added to a solution of 3-bromo-7-cyclopropyl-2-methylpyrazolo[1,5-a]pyrimidine-6-carboxylic acid (3.0 g, 10.1 mmol; purity 47%), (S)-2,3-dihydro-1H-inden-1-amine (1.5 g, 11.1 mmol, 1.4 mL) and triethyl amine (2.6 g, 25.3 mmol, 3.5 mL) in dichloromethane (75 mL). The reaction mixture was stirred for 18 h. The precipitate was filtered off, washed with dichloromethane and dried on air. 0.4 g of the title compound were obtained. The filtrate was concentrated in vacuo. A precipitate formed. Solid was filtered off, washed with dichloromethane and methanol and was dried on air. 1.0 g were obtained. Materials were combined. In total 1.4 g (3.3 mmol; 69% of theory) of the title compound were obtained.

LC-MS (Method L1): $R_t$=2.02 min; m/z=411/413 (M+H)$^+$

(S)-3-Bromo-N-(2,3-dihydro-1H-inden-1-yl)-2-methyl-7-(trifluoromethyl)pyrazolo[1,5-a]pyrimidine-6-carboxamide (1F-5)

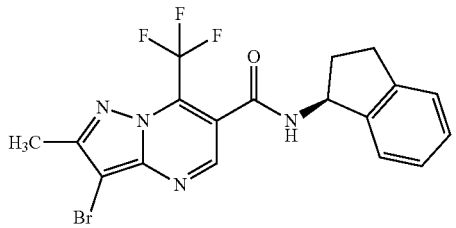 [SMILES: Cc1nn2c(C(F)(F)F)c(C(=O)N[C@H]3CCc4ccccc43)cnc2c1Br]

Under nitrogen atmosphere at room temperature diethyl cyanophosphonate (1.96 g, 12.04 mmol, 1.82 mL) was added to a solution of 3-bromo-2-methyl-7-(trifluoromethyl)pyrazolo[1,5-a]pyrimidine-6-carboxylic acid (3.00 g, 9.26 mmol), (S)-2,3-dihydro-1H-inden-1-amine (1.36 g, 10.18 mmol, 1.30 mL) and triethyl amine (2.34 g, 23.14 mmol, 3.21 mL) in dichloromethane (100 mL). Reaction mixture was stirred for 5 h. Water (30 mL) was added. Layers were separated. Organic layer was washed with water (30 mL). Combined aqueous layers were extracted with dichloromethane (2×100 mL). Combined organic layers were dried with sodium sulfate. Solvents were removed in vacuo. Flash column chromatography (Method L7; 500 g; heptane, 15%-55% ethyl acetate) afforded 2.95 g (6.72 mmol; 72%) of the title compound.

LC-MS (Method L1): $R_t$=2.15 min; m/z=439/441 (M+H)$^+$

1H NMR (300 MHz, DMSO-d6, Method M2) δ 11.84 (s, 1H), 8.52 (s, 1H), 7.34 (d, J=16.4 Hz, 4H), 5.62 (s, 1H), 3.13-2.83 (m, 2H), 2.73-2.58 (m, 1H), 2.35 (s, 3H), 2.28 (d, J=5.8 Hz, 1H).

(S)-3-Bromo-2-cyclopropyl-N-(2,3-dihydro-1H-inden-1-yl)-7-isopropylpyrazolo[1,5-a]pyrimidine-6-carboxamide (1F-6)

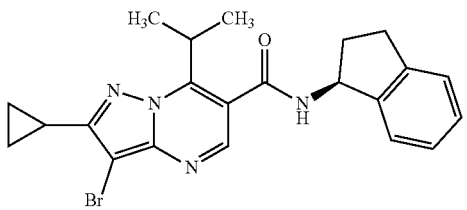 [SMILES: CC(C)c1c(C(=O)N[C@H]2CCc3ccccc32)cnc2c(Br)c(C3CC3)nn12]

To a solution of 3-bromo-2-cyclopropyl-7-isopropylpyrazolo[1,5-a]pyrimidine-6-carboxylic acid (5.06 g, 15.6 mmol) and (S)-2,3-dihydro-1H-inden-1-amine (2.08 g, 15.6 mmol, 2.0 mL) in dry N,N-dimethylformamide (150 mL) at 0° C. were added N-(3-dimethylaminopropyl)-N-ethylcarbodiimide hydrochloride (3.29 g, 17.2 mmol) and 1-hydroxy-7-azabenzotriazole (0.21 g, 1.6 mmol). Reaction mixture was stirred at 0° C. for 30 min and for 4 h at room temperature and was poured out into water (800 mL). The precipitate was filtered off, washed with water (5×100 mL) and was dried in vacuo at 30° C. for 60 h. 6.38 g (14.0 mmol; 90% of theory) of the title compound were obtained.

LC-MS (Method L1): $R_t$=2.25 min; m/z=439/441 (M+H)$^+$

1H NMR (300 MHz, Chloroform-d, Method M2) δ 8.39 (s, 1H), 7.38-7.20 (m, 4H), 6.09 (d, J=8.1 Hz, 1H), 5.66 (q, J=7.6 Hz, 1H), 3.97 (p, J=7.0 Hz, 1H), 2.99 (m, 2H), 2.81-2.67 (m, 1H), 2.19 (m, 1H), 1.94 (m, 1H), 1.55 (dd, J=7.0, 3.0 Hz, 6H), 1.19-1.05 (m, 4H).

(S)-3-Bromo-2-(difluoromethyl)-N-(2,3-dihydro-1H-inden-1-yl)-7-isopropylpyrazolo[1,5-a]pyrimidine-6-carboxamide (1F-7)

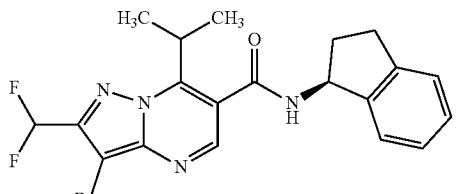

To a solution of 3-bromo-2-(difluoromethyl)-7-isopropylpyrazolo[1,5-a]pyrimidine-6-carboxylic acid (4.46 g, 8.41 mmol) and (S)-2,3-dihydro-1H-inden-1-amine (1.78 g, 13.35 mmol, 1.7 mL) in dry N,N-dimethylformamide (125 mL) at 0° C. were added N-(3-dimethylaminopropyl)-N-ethylcarbodiimide hydrochloride (2.81 g, 14.68 mmol) and 1-hydroxy-7-azabenzotriazole (0.182 g, 1.34 mmol). After stirring for 65 h the reaction mixture was poured out into water (1.5 L) and stirred for 15 min. The precipitate was filtered off, washed with water (3×75 mL) and dried on air. The material was dissolved in dichloromethane and the solvent was removed in vacuo. Purification by flash column chromatography (Method L7; 80 g; heptane, 3%-30% ethyl acetate) afforded 2.89 g (6.21 mmol; 74% of theory) of the title compound.

LC-MS (Method L1): $R_t$=2.13 min; m/z=449/451 (M+H)$^+$

1H NMR (300 MHz, Chloroform-d, Method M2) δ 8.52 (s, 1H), 7.37-7.20 (m, 4H), 6.89 (t, J=53.3 Hz, 1H), 6.16 (d, J=8.1 Hz, 1H), 5.66 (q, J=7.5 Hz, 1H), 4.04 (p, J=7.1 Hz, 1H), 3.13-2.89 (m, 2H), 2.74 (m, 1H), 2.04-1.88 (m, 1H), 1.60 (dd, J=7.1, 3.6 Hz, 6H).

(S)-3-Bromo-7-cyclopropyl-2-methyl-N-(1,2,3,4-tetrahydronaphthalen-1-yl)pyrazolo[1,5-a]pyrimidine-6-carboxamide (1F-8)

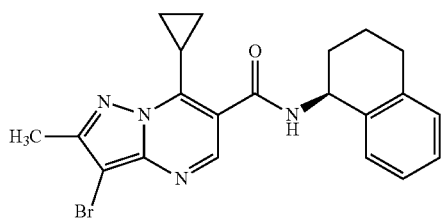 [SMILES: Cc1nn2c(C3CC3)c(C(=O)N[C@H]3CCCc4ccccc43)cnc2c1Br]

To a solution of 3-bromo-7-cyclopropyl-2-methylpyrazolo[1,5-a]pyrimidine-6-carboxylic acid (6.09 g, 20.57 mmol; purity 46%) and (S)-1,2,3,4-tetrahydro-1-naphtylamine (3.03 g, 20.57 mmol, 3.00 mL) in dry N,N-dimethylformamide (100 mL) at 0° C. were added N-(3-dimethylaminopropyl)-N'-ethylcarbodiimide hydrochloride (4.34 g, 22.62 mmol) and 1-hydroxy-7-azabenzotriazole (0.28 g, 2.06 mmol). The reaction mixture was allowed to warm to room temperature and stirring was continued for 72 h. The reaction mixture was poured out into water (800 mL). The resulting precipitate was filtered off, washed with water and dried on air. Crystallization from water and purification by reversed phase column chromatography (Method 5; 120 g) and column chromatography (Method L7; 120 g; dichloromethane, 0.2%-2.0% methanol) afforded 0.76 g (1.72 mmol; 8% of theory) of the title compound with a purity of 97% according to LC-MS and 0.70 g (1.32 mmol; 6% of theory) of the title compound with a purity of 80% according to LC-MS.

LC-MS (Method L1): $R_t$=2.04 min; m/z=425/427 (M+H)$^+$

1H NMR (300 MHz, Chloroform-d, Method M2) δ 8.48 (s, 1H), 7.38-7.33 (m, 1H), 7.23-7.19 (m, 2H), 7.16-7.11 (m, 1H), 6.16 (d, J=8.1 Hz, 1H), 5.46-5.36 (m, 1H), 2.84 (q, J=6.4, 6.0 Hz, 2H), 2.55-2.48 (m, 4H), 2.27-2.16 (m, 1H), 2.07-1.98 (m, 1H), 1.96-1.84 (m, 2H), 1.69-1.62 (m, 2H), 1.25 (dd, J=8.6, 2.4 Hz, 2H).

(S)-3-Bromo-N-(chroman-4-yl)-7-cyclopropyl-2-methylpyrazolo[1,5-a]pyrimidine-6-carboxamide (1F-9)

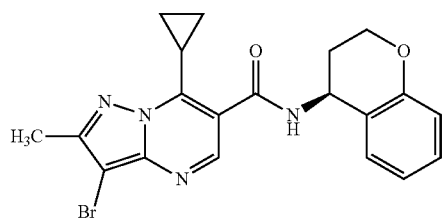 [SMILES: Cc1nn2c(C3CC3)c(C(=O)N[C@H]3CCOc4ccccc43)cnc2c1Br]

To a suspension of 3-bromo-7-cyclopropyl-2-methylpyrazolo[1,5-a]pyrimidine-6-carboxylic acid (750 mg, 2.53 mmol), (S)-chroman-4-amine hydrochloride (495 mg, 2.67 mmol) and triethyl amine (384 mg, 3.80 mmol, 0.53 mL) in dry N,N-dimethylformamide (25 mL) at 0° C. were added N-(3-dimethylaminopropyl)-N-ethylcarbodiimide hydrochloride (534 mg, 2.79 mmol) and 1-hydroxy-7-azabenzotriazole (35 mg, 0.25 mmol). The reaction mixture was allowed to warm to room temperature and stirring was continued for 18 h. N-(3-Dimethylaminopropyl)-N-ethylcarbodiimide hydrochloride (57 mg, 0.30 mmol) was added. The reaction mixture was stirred for 24 h and was poured out into water (300 mL). The mixture was stirred for 15 minutes. The resulting precipitate was filtered off, washed with water (2×40 mL) and diisopropyl ether (2×40 mL) and was dried on air to afford 857 mg (2.01 mmol; 79% of theory) of the title compound.

LC-MS (Method L1): $R_t$=1.98 min; m/z=427/429 (M+H)$^+$

1H NMR (400 MHz, DMSO-d6, Method M2) δ 9.14 (d, J=7.9 Hz, 1H), 8.49 (s, 1H), 7.40-7.10 (m, 2H), 7.03-6.67 (m, 2H), 5.22 (d, J=6.7 Hz, 1H), 4.38-4.08 (m, 2H), 2.54 (m, 1H), 2.44 (s, 3H), 2.31-1.95 (m, 2H), 1.49-1.09 (m, 4H).

(S)-3-Bromo-N-(chroman-4-yl)-7-ethyl-2-methylpyrazolo[1,5-a]pyrimidine-6-carboxamide (1F-10)

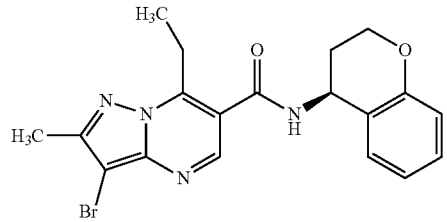 [SMILES: CCc1c(C(=O)N[C@H]2CCOc3ccccc32)cnc2c(Br)c(C)nn12]

To a suspension of 3-bromo-7-ethyl-2-methylpyrazolo[1,5-a]pyrimidine-6-carboxylic acid (1000 mg, 3.52 mmol), (S)-chroman-4-amine hydrochloride (653 mg, 3.52 mmol) and triethyl amine (534 mg, 5.28 mmol, 0.73 mL) in dry N,N-dimethylformamide (35 mL) at 0° C. were added N-(3-dimethylaminopropyl)-N-ethylcarbodiimide hydrochloride (810 mg, 4.22 mmol) and ethyl (hydroxyimino)cyanoacetate (50 mg, 0.352 mmol). The reaction mixture was allowed to warm to room temperature and stirring was continued for 18 h. The mixture was poured out into water (300 mL). The mixture was stirred for 15 minutes. The resulting white precipitate was filtered off, washed with water and dried on air. The solid was coevaporated with dichloromethane to afford 1312 mg (3.16 mmol, 90% of theory) of the title compound.

LC-MS (Method L1): $R_t$=2.03 min; m/z=415/417 (M+H)$^+$ (S)-3-Bromo-N-(chroman-4-yl)-2-(difluoromethyl)-7-isopropylpyrazolo[1,5-a]pyrimidine-6-carboxamide (1F-11)

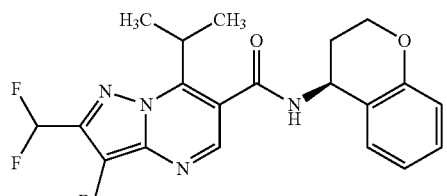

N-(3-Dimethylaminopropyl)-N-ethylcarbodiimide hydrochloride (1.43 g, 7.47 mmol) and ethyl cyano(hydroxyimino)acetate (0.10 g, 0.68 mmol) were added under nitrogen atmosphere to a stirred mixture of 3-bromo-2-(difluoromethyl)-7-isopropylpyrazolo[1,5-a]pyrimidine-6-carboxylic acid (2.27 g, 6.79 mmol), (S)-chroman-4-amine hydrochloride (1.26 g, 6.79 mmol) and triethylamine (0.83 g, 8.15 mmol, 1.13 mL) in dry N,N-dimethylformamide (50 mL) at 0° C. The resulting mixture was stirred while warming up to room temperature overnight. The reaction mixture was poured out into hydrochloric acid (1.0 M; 500 mL) and extracted with ethyl acetate (3×150 mL). Combined extracts were washed with brine (3×100 mL), dried with sodium sulfate and concentrated in vacuo. Purification by trituration in ethyl acetate (10 mL) and diisopropyl ether (5 mL)

afforded 1.95 g (4.20 mmol; 62% of theory) of the title compound.

LC-MS (Method L1): $R_t$=2.12 min; m/z=465/467 (M+1)$^+$

1H NMR (400 MHz, DMSO-d6, Method M2) δ 9.25 (d, J=8.0 Hz, 1H), 8.70 (s, 1H), 7.49-7.15 (m, 3H), 6.98-6.90 (m, 1H), 6.85-6.78 (m, 1H), 5.29-5.18 (m, 1H), 4.35-4.16 (m, 2H), 3.91 (hept, J=7.0 Hz, 1H), 2.29-2.16 (m, 1H), 2.13-2.00 (m, 1H), 1.51 (dd, J=9.2, 7.1 Hz, 6H).

(S)-3-Bromo-N-(chroman-4-yl)-7-cyclopropyl-2-(difluoromethyl)pyrazolo[1,5-a]pyrimidine-6-carboxamide (1F-12)

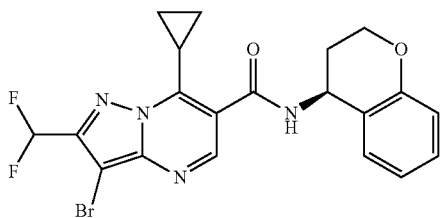 [SMILES: O=C(N[C@H]1CCOc2ccccc21)c1cnc2c(Br)c(C(F)F)nn2c1C1CC1]

N-(3-dimethylaminopropyl)-N-ethylcarbodiimide hydrochloride (1.84 g, 9.61 mmol) and ethyl cyano(hydroxyimino)acetate (0.12 g, 0.87 mmol) were added at 0° C. under nitrogen atmosphere to a stirred mixture of 3-bromo-7-cyclopropyl-2-(difluoromethyl)pyrazolo[1,5-a]pyrimidine-6-carboxylic acid (2.90 g, 8.73 mmol), (S)-chroman-4-amine hydrochloride (1.62 g, 8.73 mmol) and triethylamine (1.06 g, 10.48 mmol, 1.46 mL) in dry N,N-dimethylformamide (75 mL). The resulting mixture was stirred while warming up to room temperature overnight. The reaction mixture was poured into hydrochloric acid (1.0 M; 500 mL) and extracted with ethyl acetate (3×150 mL). Combined extracts were washed with brine (3×100 mL), dried with sodium sulfate and concentrated in vacuo. Purification by trituration in ethyl acetate (10 mL) and diisopropyl ether (5 mL) afforded 0.97 g (2.09 mmol; 23% of theory over two steps) of the title compound.

LC-MS (Method L1): $R_t$=2.12 min; m/z=463/465 (M+1)$^+$

1H NMR (400 MHz, DMSO-d6, Method M2) δ 9.18 (d, J=8.0 Hz, 1H), 7.49-7.14 (m, 3H), 6.97-6.90 (m, 1H), 6.81 (dd, J=8.2, 1.1 Hz, 1H), 5.28-5.19 (m, 1H), 4.35-4.26 (m, 1H), 4.26-4.17 (m, 1H), 2.60-2.51 (m, 2H), 2.28-2.17 (m, 1H), 2.13-2.01 (m, 1H), 1.38-1.30 (m, 2H), 1.27-1.18 (m, 2H).

Intermediates 1H 4-(4,4,5,5-Tetramethyl-1,3,2-dioxaborolan-2-yl)-1-(2,2,2-trifluoroethyl)-1H-pyrazole (1H-1)

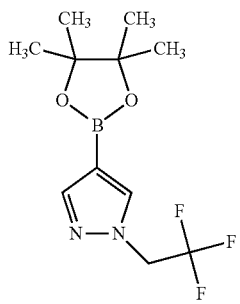 [SMILES: CC1(C)OB(c2cnn(CC(F)(F)F)c2)OC1(C)C]

2,2,2-Trifluoroethyl trifluoromethanesulfonate (0.66 g, 2.86 mmol, 0.4 mL) was added to a mixture of 4-(4,4,5,5-tetramethyl-1,3,2-dioxaborolan-2-yl)-1H-pyrazole (0.46 g, 2.37 mmol) and cesium carbonate (1.60 g, 4.92 mmol) in dry N,N-dimethylformamide (10.0 mL) at 0° C. After stirring for 30 min the reaction mixture was allowed to warm to room temperature. After stirring for 3 h the reaction mixture was poured out into water (200 mL) and the mixture was extracted with ethyl acetate (3×50 mL). The combined organic layers were washed with water (3×100 mL) and brine and were dried with sodium sulfate. Solvents were removed in vacuo to afford 0.42 g (1.51 mmol; 64% of theory) of the title compound.

GC-MS (Method L9): $R_t$=3.36 min; m/z=276 M$^+$ 3,3-Difluoro-1-(3-(4,4,5,5-tetramethyl-1,3,2-dioxaborolan-2-yl)phenyl)azetidine (1H-2)

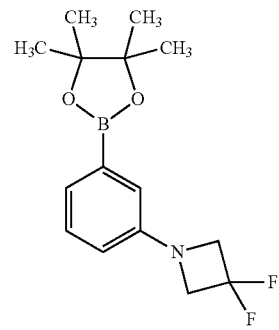 [SMILES: CC1(C)OB(c2cccc(N3CC(F)(F)C3)c2)OC1(C)C]

A mixture of 1,3-dibromobenzene (0.52 g, 2.22 mmol, 0.27 mL), 3,3-difluoroazetidine hydrochloride (0.19 g, 1.48 mmol), tris(dibenzylideneacetone)dipalladium(0) (0.68 g, 0.07 mmol), 9,9-dimethyl-4,5-bis(diphenylphosphino)xanthene (0.09 g, 0.15 mmol) and sodium tert-butoxide (0.57 g, 5.93 mmol) in dry 1,4-dioxane (12.0 mL) was purged with argon for 15 min and stirred at 100° C. for 3 h. Water was added to the reaction mixture (40 mL) and the resulting mixture was extracted with ethyl acetate (2×40 mL). The combined organic layers were washed with brine, dried with sodium sulfate and coated on hydromatrix. Purification by flash column chromatography (Method L7; 12 g; heptane, 0.5%-5% ethyl acetate) afforded 0.14 g (0.55 mmol; 37% of theory) of 1-(3-bromophenyl)-3,3-difluoroazetidine.

GC-MS (Method L9): $R_t$=3.54 min; m/z=247/249 M$^+$ $^1$H NMR (300 MHz, Chloroform-d, Method M2) δ 7.10 (t, J=8.0 Hz, 1H), 6.95 (m, 1H), 6.62 (t, J=2.1 Hz, 1H), 6.40 (m, 1H), 4.21 (t, J=11.8 Hz, 4H).

A mixture of 1-(3-bromophenyl)-3,3-difluoroazetidine (132 mg, 0.53 mmol), bis(pinacolato)diboron (203 mg, 0.80 mmol), 1,1'-bis(diphenylphosphino)ferrocene-palladium(II) dichloride (44 mg, 0.05 mmol) and potassium acetate (157 mg, 1.60 mmol) in dry 1,4-dioxane (5.0 mL) was purged with argon for 5 minutes and stirred at 90° C. for 1.5 h. The reaction mixture was allowed to cool to room temperature, diluted with ethyl acetate (30 mL) and washed with brine.

The organic layer was dried with sodium sulfate and coated on hydromatrix. Purification by flash column chromatography (Method L7; 12 g; heptane, 0.5%-5% ethyl acetate) afforded 58 mg (0.20 mmol; 37% of theory) of the title compound.

¹H NMR (300 MHz, Chloroform-d, Method M2) δ 7.41-7.21 (m, 2H), 6.94 (d, J=2.1 Hz, 1H), 6.66-6.53 (m, 1H), 4.21 (s, 4H), 1.34 (s, 12H).

N,N-Diethyl-3-(4,4,5,5-tetramethyl-1,3,2-dioxaborolan-2-yl)aniline (1H-3)

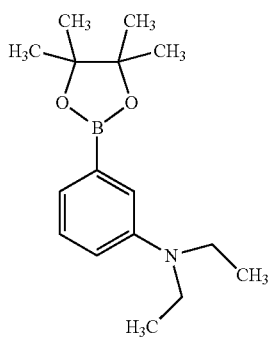 [SMILES: CCN(CC)c1cccc(B2OC(C)(C)C(C)(C)O2)c1]

A mixture of 1,3-dibromobenzene (590 mg, 2.48 mmol, 0.30 mL), tris(dibenzylideneacetone)-dipalladium(0) (80 mg, 0.08 mmol), 9,9-dimethyl-4,5-bis(diphenylphosphino)xanthene (100 mg, 0.17 mmol) and sodium tert-butoxide (640 mg, 6.62 mmol) in dry 1,4-dioxane (15.0 mL) was purged with argon for 10 min. Diethyl amine (120 mg, 1.66 mmol, 0.17 mL) was added and the resulting mixture was stirred at 100° C. for 3 h. Reaction mixture was allowed to cool to room temperature and water (40 mL) was added. The resulting mixture was extracted with ethyl acetate (2×40 mL). The combined organic layers were washed with brine, dried with sodium sulfate and coated on hydromatrix. Purification by flash column chromatography (Method L7; 12 g; heptane, 0.5%-5.0% diisopropyl ether) afforded 159 mg (0.49 mmol; 30% of theory) of 3-Bromo-N,N-diethylaniline.

GC-MS (Method L9): $R_t$=3.81 min; m/z=227/229 M⁺

A mixture of 3-bromo-N,N-diethylaniline (159 mg, 0.49 mmol, 70%), bis(pinacolato)diboron (186 mg, 0.73 mmol), 1,1'-bis(diphenylphosphino)ferrocenepalladium(II) dichloride (40 mg, 0.05 mmol) and potassium acetate (144 mg, 1.46 mmol) in dry 1,4-dioxane (7.0 mL) was purged with argon for 5 minutes and stirred at 90° C. for 1.5 h. The reaction mixture was allowed to cool to room temperature. Solvents were removed in vacuo and the residue was coated on hydromatrix. Purification by flash column chromatography (Method L7; 12 g; heptane, 0.5%-5% ethyl acetate) afforded 123 mg (0.40 mmol; 82% of theory) of the title compound.

GC-MS (Method L9): $R_t$=4.60 min; m/z=275 M⁺

1H NMR (300 MHz, Chloroform-d, Method M2) δ 7.25-7.07 (m, 3H), 6.80 (dd, J=8.2, 2.4 Hz, 1H), 3.37 (q, J=7.0 Hz, 4H), 1.33 (s, 12H), 1.15 (t, J=7.0 Hz, 6H).

N-Ethyl-N-methyl-3-(4,4,5,5-tetramethyl-1,3,2-dioxaborolan-2-yl)aniline (1H-4)

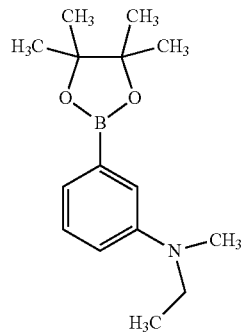

A mixture of 1,3-dibromobenzene (586 mg, 2.48 mmol, 0.30 mL), tris(dibenzylideneacetone)-dipalladium(0) (76 mg, 0.08 mmol), 9,9-dimethyl-4,5-bis(diphenylphosphino)xanthene (96 mg, 0.17 mmol) and sodium tert-butoxide (636 mg, 6.62 mmol) in dry 1,4-dioxane (15 mL) was purged with argon for 10 min. N-ethylmethylamine (136 mg, 2.30 mmol, 0.20 mL) was added and the reaction mixture was stirred at 100° C. for 3 h. Water (40 mL) was added and the resulting mixture was extracted with ethyl acetate (2×40 mL). The combined organic layers were washed with brine, dried with sodium sulfate and concentrated in vacuo. Purification by flash column chromatography (Method L7; 12 g; heptane, 0.5%-5% diisopropyl ether) afforded 253 mg (1.18 mmol; 71% of theory) of 3-bromo-N-ethyl-N-methylaniline.

GC-MS (Method L9): $R_t$=3.67 min; m/z=213/215 M⁺

A mixture of 3-bromo-N-ethyl-N-methylaniline (253 mg, 1.18 mmol), bis(pinacolato)diboron (450 mg, 1.77 mmol), 1,1'-bis(diphenylphosphino)ferrocenepalladium(II) dichloride (97 mg, 0.12 mmol) and potassium acetate (348 mg, 3.55 mmol) in dry 1,4-dioxane (10 mL) was purged with argon for 5 minutes and stirred at 90° C. for 1.5 h. The reaction mixture was allowed to cool to room temperature. Solvents were removed in vacuo and the residue was coated on hydromatrix. Purification by flash column chromatography (Method L7; 12 g; heptane, 0.5%-5% ethyl acetate) afforded 233 mg (0.88 mmol; 75% of theory) of the title compound.

GC-MS (Method L9): $R_t$=4.61 min; m/z=261 M⁺

1H NMR (300 MHz, Chloroform-d, Method M2) δ 7.28-7.10 (m, 3H), 6.88-6.79 (m, 1H), 3.42 (q, J=7.1 Hz, 2H), 2.92 (s, 3H), 1.33 (s, 12H), 1.11 (t, J=7.1 Hz, 3H).

1-(3-(4,4,5,5-Tetramethyl-1,3,2-dioxaborolan-2-yl)phenyl)azetidine (1H-5)

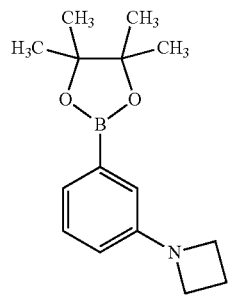 [SMILES: CC1(C)OB(c2cccc(N3CCC3)c2)OC1(C)C]

A mixture of 1,3-dibromobenzene (586 mg, 2.48 mmol, 0.30 mL), tris(dibenzylideneacetone)-dipalladium(0) (76 mg, 0.08 mmol), 9,9-dimethyl-4,5-bis(diphenylphosphino)xanthene (96 mg, 0.17 mmol) and sodium tert-butoxide (636 mg, 6.62 mmol) in dry 1,4-dioxane (15 mL) was purged with argon for 10 min. Azetidine (128 mg, 2.23 mmol, 0.15 mL) was added and the reaction mixture was stirred at 100° C. for 3 h. Water (40 mL) was added and the resulting mixture was extracted with ethyl acetate (2×40 mL). The combined organic layers were washed with brine, dried with sodium sulfate and concentrated in vacuo. The residue was coated on hydromatrix. Purification by flash column chromatography (Method L7; 12 g; heptane, 0.5%-5% diisopropyl ether) afforded 281 mg (1.33 mmol; 80% of theory) of 1-(3-bromophenyl)azetidine.

GC-MS (Method L9): $R_t$=3.94 min; m/z=211/213 $M^+$

A mixture of 1-(3-bromophenyl)azetidine (253 mg, 1.19 mmol), bis(pinacolato)diboron (454 mg, 1.79 mmol), 1,1'-bis(diphenylphosphino)ferrocenepalladium(II) dichloride (97 mg, 0.12 mmol) and potassium acetate (351 mg, 3.58 mmol) in dry 1,4-dioxane (10 mL) was purged with argon for 5 minutes and stirred at 90° C. for 1.5 h. The reaction mixture was concentrated in vacuo and coated on hydromatrix. Purification by flash column chromatography (Method L7; 12 g; heptane, 0.5%-5% ethyl acetate) afforded 282 mg (0.95 mmol; 79% of theory) of the title compound.

GC-MS (Method L9): $R_t$=4.85 min; m/z=259 $M^+$

1H NMR (300 MHz, Chloroform-d, Method M2) δ 7.28-7.15 (m, 2H), 6.88 (d, J=2.3 Hz, 1H), 6.56 (s, 1H), 3.89 (t, J=7.2 Hz, 4H), 2.41-2.28 (m, 2H), 1.34 (s, 12H).

2-(3-(Ethoxymethyl)phenyl)-4,4,5,5-tetramethyl-1,3,2-dioxaborolane (1H-6)

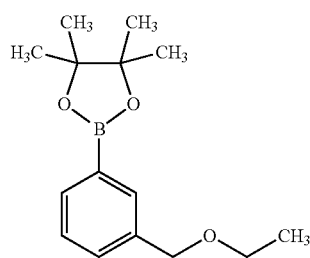

To a solution of ethanol (0.07 g, 1.52 mmol, 0.10 mL) in dry tetrahydrofuran (5 mL) was added sodium hydride 60% (w/w) in mineral oil (0.061 g, 1.52 mmol). After stirring for 5 min a solution of 2-(3-(bromomethyl)phenyl)-4,4,5,5-tetramethyl-1,3,2-dioxaborolane (0.45 g, 1.52 mmol) in dry tetrahydrofuran (5 mL) was added. After stirring for 2 h the reaction mixture was concentrated in vacuo and coated on hydromatrix. Purification by flash column chromatography (Method L7; 40 g; heptane, 1%-5% ethyl acetate) afforded 0.16 g (0.61 mmol; 40% of theory) of the title compound.

GC-MS (Method L9): $R_t$=4.27 min; m/z=262 $M^+$

1H NMR (300 MHz, Chloroform-d, Method M2) δ 7.80-7.69 (m, 2H), 7.52-7.43 (m, 1H), 7.36 (t, J=7.4 Hz, 1H), 4.51 (s, 2H), 3.53 (q, J=7.0 Hz, 2H), 1.34 (s, 12H), 1.24 (t, J=7.0 Hz, 3H).

2-(3-(Isopropoxymethyl)phenyl)-4,4,5,5-tetramethyl-1,3,2-dioxaborolane (1H-7)

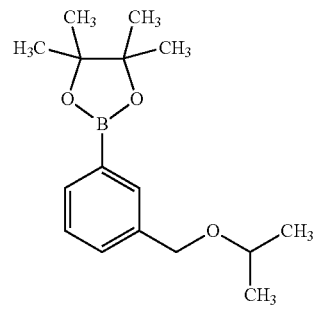 [SMILES: CC(C)OCc1cccc(B2OC(C)(C)C(C)(C)O2)c1]

To a solution of 2-(3-(bromomethyl)phenyl)-4,4,5,5-tetramethyl-1,3,2-dioxaborolane (400 mg, 1.35 mmol) and 2-propanol (405 mg, 6.73 mmol, 0.52 mL) in dry tetrahydrofuran (10 mL) was added sodium hydride 60% (w/w) in mineral oil (242 mg, 6.06 mmol). After stirring for 2 h the reaction mixture was coated on hydromatrix. Purification by flash column chromatography (Method L7; 12 g; heptane, 1%-5% ethyl acetate) afforded 100 mg (0.36 mmol; 25% of theory) of the title compound.

GC-MS (Method L9): $R_t$=4.01 min; m/z=276 $M^+$

1H NMR (300 MHz, Chloroform-d, Method M2) δ 7.79-7.68 (m, 2H), 7.53-7.44 (m, 1H), 7.35 (t, J=7.5 Hz, 1H), 4.51 (s, 2H), 3.75-3.60 (m, 1H), 1.34 (s, 12H), 1.21 (d, J=6.1 Hz, 6H).

4,4,5,5-Tetramethyl-2-(3-((2,2,2-trifluoroethoxy)methyl)phenyl)-1,3,2-dioxaborolane (1H-8)

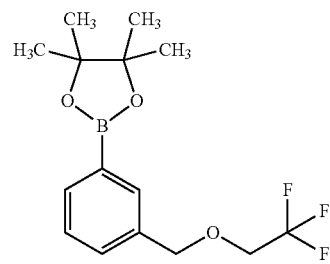 [SMILES: CC1(C)OB(c2cccc(COCC(F)(F)F)c2)OC1(C)C]

To a solution of 2-(3-(bromomethyl)phenyl)-4,4,5,5-tetramethyl-1,3,2-dioxaborolane (400 mg, 1.35 mmol) and 2,2,2-trifluoroethanol (674 mg, 6.73 mmol, 0.49 mL) in dry tetrahydrofuran (10 mL) was added sodium hydride 60% (w/w) in mineral oil (242 mg, 6.06 mmol). After stirring for 24 h the reaction mixture was filtered over kieselguhr and concentrated in vacuo. The crude material was used without further purification.

GC-MS (Method L9): $R_t$=4.01 min; m/z=316 M$^+$

N-Methyl-N-(3-(4,4,5,5-tetramethyl-1,3,2-dioxaborolan-2-yl)benzyl)ethanamine (1H-9)

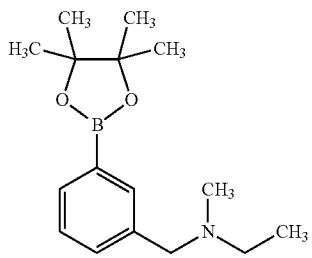 [SMILES: CCN(C)Cc1cccc(B2OC(C)(C)C(C)(C)O2)c1]

To a solution of 2-(3-(bromomethyl)phenyl)-4,4,5,5-tetramethyl-1,3,2-dioxaborolane (400 mg, 1.35 mmol) and N-ethylmethylamine (398 mg, 6.73 mmol, 0.59 mL) in dry tetrahydrofuran (10 mL) was added sodium hydride 60% (w/w) in mineral oil (242 mg, 6.06 mmol). After stirring for 2 h the reaction mixture was coated on hydromatrix. The hydromatrix was rinsed with a mixture of heptane and ethyl acetate. Solids were filtered off. The filtrate was concentrated in vacuo. The crude material was used without further purification.

GC-MS (Method L9): $R_t$=4.40 min; m/z=275 M$^+$ 4,4,5,5-Tetramethyl-2-(3-(propoxymethyl)phenyl)-1,3,2-dioxaborolane (1H-10)

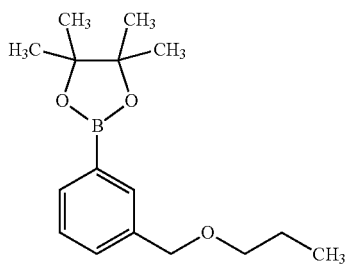 [SMILES: CCCOCc1cccc(B2OC(C)(C)C(C)(C)O2)c1]

To a solution of 2-(3-(bromomethyl)phenyl)-4,4,5,5-tetramethyl-1,3,2-dioxaborolane (400 mg, 1.35 mmol) and 1-propanol (405 mg, 6.73 mmol, 0.51 mL) in dry tetrahydrofuran (10 mL) was added sodium hydride 60% (w/w) in mineral oil (242 mg, 6.06 mmol). After stirring for 1.5 h the reaction mixture was filtered over kieselguhr and concentrated in vacuo to afford 503 mg of the title compound with a purity of 74% according to GC-MS. The material was used without further purification.

GC-MS (Method L9): $R_t$=4.46 min; m/z=276 M$^+$ 2-(3-(((Cyclopropylmethoxy)methyl)phenyl)-4,4,5,5-tetramethyl-1,3,2-dioxaborolane (1H-11)

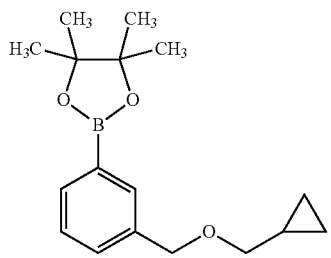 [SMILES: CC1(C)OB(c2cccc(COCC3CC3)c2)OC1(C)C]

To a solution of 2-(3-(bromomethyl)phenyl)-4,4,5,5-tetramethyl-1,3,2-dioxaborolane (400 mg, 1.35 mmol) and cyclopropanemethanol (486 mg, 6.73 mmol, 0.55 mL) in dry tetrahydrofuran (10 mL) was added sodium hydride 60% (w/w) in mineral oil (242 mg, 6.06 mmol). After stirring for 1.5 h the reaction mixture was filtered over kieselguhr and concentrated in vacuo to afford 573 mg (1.35 mmol; 100% of theory) of the title compound.

GC-MS (Method L9): $R_t$=4.86 min; m/z=288 M$^+$ 1-(2,2-Difluoroethyl)-4-(4,4,5,5-tetramethyl-1,3,2-dioxaborolan-2-yl)-1H-pyrazole (1H-12)

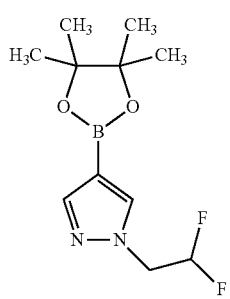 [SMILES: CC1(C)OB(c2cnn(CC(F)F)c2)OC1(C)C]

2,2-Difluoroethyl trifluoromethanesulfonate (1.00 g, 4.67 mmol) was added to a mixture of 4-(4,4,5,5-tetramethyl-1,3,2-dioxaborolan-2-yl)-1H-pyrazole (0.91 mg, 4.67 mmol) and caesium carbonate (3.04 g, 9.34 mmol) in dry N,N-dimethylformamide (18 mL). The resulting mixture was stirred at room temperature for 72 h. The reaction mixture was diluted with ethyl acetate (150 mL) and washed with brine (3×100 mL). The organic layer was dried with sodium sulfate and concentrated in vacuo. Purification by flash column chromatography (Method L7; 12 g; heptane, 10%-30% ethyl acetate) afforded 0.44 g (1.68 mmol; 36% of theory) of the title compound.

GC-MS (Method L9): $R_t$=3.58 min; m/z=258 M$^+$

1H NMR (300 MHz, Chloroform-d, Method M2) δ 7.83 (s, 1H), 7.76 (s, 1H), 6.09 (tt, J=55.5, 4.3 Hz, 1H), 4.47 (td, J=13.5, 4.3 Hz, 2H), 1.32 (s, 12H).

1-Isopropyl-4-(4,4,5,5-tetramethyl-1,3,2-dioxaborolan-2-yl)-1H-pyrazole (1H-13)

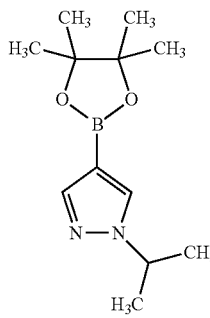

2-Iodopropane (1.14 g, 6.70 mmol, 0.67 mL) was added to a mixture of 4-(4,4,5,5-tetramethyl-1,3,2-dioxaborolan-2-yl)-1H-pyrazole (1.00 g, 5.15 mmol) and caesium carbonate (3.49 g, 10.72 mmol) in dry N,N-dimethylformamide (20 mL) at 0° C. After stirring for 30 min the ice-water bath was removed. The reaction mixture was stirred at room temperature overnight. The reaction mixture was diluted with ethyl acetate (150 mL) and washed with brine (3×100 mL). The organic layer was dried with sodium sulfate and concentrated in vacuo. Purification by flash column chromatography (Method L7; 12 g; heptane, 10%-30% ethyl acetate) afforded 0.69 g (2.32 mmol; 57% of theory) of the title compound.

GC-MS (Method L9): $R_t$=3.86 min; m/z=236 M$^+$

1H NMR (300 MHz, Chloroform-d, Method M2) δ 7.79 (s, 1H), 7.74 (s, 1H), 4.52 (p, J=6.7 Hz, 1H), 1.50 (d, J=6.7 Hz, 6H), 1.32 (s, 12H).

1-(Cyclopropylmethyl)-4-(4,4,5,5-tetramethyl-1,3,2-dioxaborolan-2-yl)-1H-pyrazole (1H-14)

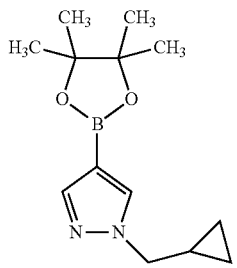 [SMILES: CC1(C)OB(c2cnn(CC3CC3)c2)OC1(C)C]

(Bromomethyl)cyclopropane (0.95 mg, 6.70 mmol, 0.70 mL, 95%) was added to a mixture of 4-(4,4,5,5-tetramethyl-1,3,2-dioxaborolan-2-yl)-1H-pyrazole (1.00 g, 5.15 mmol) and caesium carbonate (3.49 mg, 10.72 mmol) in dry N,N-dimethylformamide (20 mL) at 0° C. After stirring for 30 min the ice-water bath was removed. The reaction mixture was stirred at room temperature overnight. The reaction mixture was diluted with ethyl acetate (150 mL) and washed with brine (3×100 mL). The organic layer was dried with sodium sulfate and concentrated in vacuo to afforded 1.30 g (4.38 mmol, 85% of theory) of the title compound.

GC-MS (Method L9): $R_t$=4.35 min; m/z=247 M$^+$

1H NMR (300 MHz, Chloroform-d, Method M2) δ 7.81 (s, 1H), 7.79 (s, 1H), 3.99 (d, J=7.1 Hz, 2H), 1.32 (s, 12H), 1.27 (m, 1H), 0.71-0.58 (m, 2H), 0.41-0.33 (m, 2H).

1-(2-Methoxyethyl)-4-(4,4,5,5-tetramethyl-1,3,2-dioxaborolan-2-yl)-1H-pyrazole (1H-15)

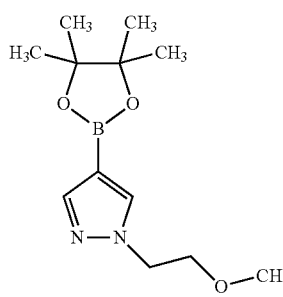

2-Bromoethyl methyl ether (0.93 g, 6.70 mmol, 0.64 mL) was added to a mixture of 4-(4,4,5,5-tetramethyl-1,3,2-dioxaborolan-2-yl)-1H-pyrazole (1.00 g, 5.15 mmol) and caesium carbonate (3.49 mg, 10.72 mmol) in dry N,N-dimethylformamide (20 mL) at 0° C. After stirring for 30 min the ice-water bath was removed. The reaction mixture was stirred at room temperature overnight. The reaction mixture was diluted with ethyl acetate (150 mL) and washed with brine (3×100 mL). The organic layer was dried with sodium sulfate and concentrated in vacuo. Purification by flash column chromatography (Method L7; 12 g; heptane, 10%-30% ethyl acetate) afforded 0.74 g (2.92 mmol; 57% of theory) of the title compound.

GC-MS (Method L9): $R_t$=4.21 min; m/z=251 M$^+$

1H NMR (300 MHz, Chloroform-d, Method M2) δ 7.79 (s, 1H), 7.76 (s, 1H), 4.29 (t, J=5.3 Hz, 2H), 3.75 (t, J=5.3 Hz, 2H), 3.32 (s, 3H), 1.31 (s, 12H).

1-Ethyl-4-(4,4,5,5-tetramethyl-1,3,2-dioxaborolan-2-yl)-1H-pyrazole (1H-16)

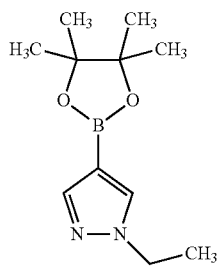 [SMILES: CCn1cc(B2OC(C)(C)C(C)(C)O2)cn1]

Ethyl trifluoromethanesulfonate (1.00 g, 5.61 mmol) was added to a mixture of 4-(4,4,5,5-tetramethyl-1,3,2-dioxaborolan-2-yl)-1H-pyrazole (0.99 g, 5.10 mmol) and caesium carbonate (3.46 g, 10.62 mmol) in dry N,N-dimethylformamide (20 mL) at 0° C. After stirring for 30 min the ice-water bath was removed. The reaction mixture was stirred at room temperature overnight. Iodoethane (0.80 g, 5.10 mmol, 0.41 ml) was added and the reaction mixture was stirred at room temperature overnight. The reaction mixture was diluted with ethyl acetate (150 mL) and washed with brine (3×100 mL). The organic layer was dried with sodium sulfate and concentrated in vacuo to afford 1.25 g (4.50 mmol, 68% of theory) of the title compound.

GC-MS (Method L9): R$_t$=3.78 min; m/z=222 M$^+$

1H NMR (300 MHz, Chloroform-d, Method M2) δ 7.80-7.76 (m, 1H), 7.70 (s, 1H), 4.19 (q, J=7.3 Hz, 2H), 1.47 (t, J=7.3 Hz, 3H), 1.32 (s, 12H).

4-(2-(4-(4,4,5,5-Tetramethyl-1,3,2-dioxaborolan-2-yl)-1H-pyrazol-1-yl)ethyl)morpholine (1H-17)

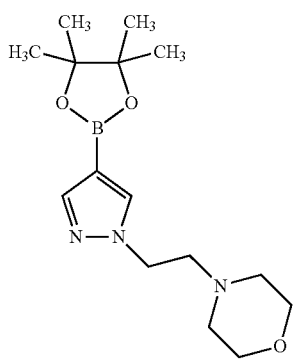 [SMILES: CC1(C)OB(c2cnn(CCN3CCOCC3)c2)OC1(C)C]

4-(2-Chloroethyl)morpholine hydrochloride (1.25 mg, 6.70 mmol) was added to a mixture of 4-(4,4,5,5-tetramethyl-1,3,2-dioxaborolan-2-yl)-1H-pyrazole (1.00 g, 5.15 mmol) and caesium carbonate (5.54 g, 17.01 mmol) in dry N,N-dimethylformamide (20 mL) at 0° C. After stirring for 30 min the ice-water bath was removed. The reaction mixture was stirred at room temperature for four days. The reaction mixture was diluted with ethyl acetate (150 mL) and washed with brine (3×100 mL). The organic layer was dried with sodium sulfate and concentrated in vacuo. Purification by flash column chromatography (Method L7; 12 g; ethyl acetate) afforded 0.75 g (2.44 mmol; 47% of theory) of the title compound.

GC-MS (Method L9): R$_t$=5.49 min; (no mass detected)

1H NMR (300 MHz, Chloroform-d, Method M2) δ 7.80-7.75 (m, 1H), 7.73 (s, 1H), 4.25 (t, J=6.8 Hz, 2H), 3.73-3.64 (m, 4H), 2.81 (t, J=6.8 Hz, 2H), 2.50-2.42 (m, 4H), 1.32 (s, 12H).

N,N-Dimethyl-2-(4-(4,4,5,5-tetramethyl-1,3,2-dioxaborolan-2-yl)-1H-pyrazol-1-yl)ethanamine (1H-18)

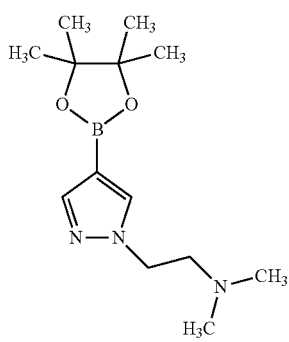

2-Dimethylaminoethyl chloride hydrochloride (0.97 g, 6.70 mmol) was added to a mixture of 4-(4,4,5,5-tetramethyl-1,3,2-dioxaborolan-2-yl)-1H-pyrazole (1.00 g, 5.15 mmol) and caesium carbonate (5.54 g, 17.01 mmol) in dry N,N-dimethylformamide (20 mL) at 0° C. After stirring for 30 min the ice-water bath was removed. The reaction mixture was stirred at room temperature for three days. The reaction mixture was diluted with ethyl acetate (150 mL) and washed with brine (3×100 mL). The organic layer was dried with sodium sulfate and concentrated in vacuo to afford 1.00 g (3.41 mmol; 66% of theory) of the title compound.

GC-MS (Method L9): R$_t$=4.48 min; (no mass detected)

1H NMR (300 MHz, Chloroform-d, Method M2) δ 7.78 (s, 1H), 7.74 (s, 1H), 4.23 (t, J=6.8 Hz, 2H), 2.76 (t, J=6.8 Hz, 2H), 2.26 (s, 6H), 1.31 (s, 12H).

1-Methyl-4-(4,4,5,5-tetramethyl-1,3,2-dioxaborolan-2-yl)indoline (1H-19)

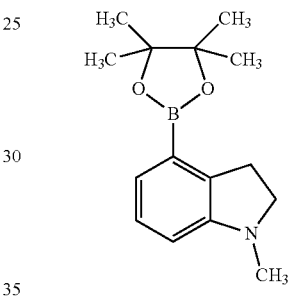

To a stirred solution of 4-bromoindoline (900 mg, 4.54 mmol) in tetrahydrofuran (10 mL) at 0° C. was portionwise added sodium hydride (60% in mineral oil, 254 mg, 6.36 mmol). After the addition the mixture was stirred for five minutes. Subsequently methyl iodide (838 mg, 5.91 mmol, 0.37 mL) was dropwise added at 0° C. The resulting suspension was stirred overnight while warming up to room temperature. The reaction mixture was poured out into water (100 mL) and extracted with diethyl ether (3×20 mL). Combined organic extracts were washed with brine and dried with sodium sulfate. Solvents were removed in vacuo. Purification by flash column chromatography (Method L7; 12 g; heptane, 0%-5% ethyl acetate) afforded 346 mg (0.16 mmol; 36% of theory) of 4-bromo-1-methylindoline.

LC-MS (Method L1): R$_t$=2.08 min; m/z=212/214 (M+H)$^+$

A stirred mixture of 4-bromo-1-methylindoline (346 mg, 1.63 mmol), bis(pinacolato)diboron (497 mg, 1.96 mmol) and potassium acetate (480 mg, 4.89 mmol) in dry 1,4-dioxane (5 mL) was degassed with argon for 10 minutes. 1,1'-bis(diphenylphosphino)ferrocenepalladium(II) dichloride (60 mg, 0.08 mmol) was added and the resulting mixture was stirred for 24 h under argon atmosphere in a closed vial at 90° C. at room temperature for 72 h. The reaction mixture was diluted with dichloromethane (100 mL) and filtered over kieselguhr. Water (30 mL) was added and the layers were separated. The aqueous layer was extracted with dichloromethane (2×20 mL). Combined organic layers were washed with brine (2×10 mL) and dried with sodium sulfate. Solvents were removed in vacuo.

Purification by flash column chromatography (Method L6; 40 g, heptane, 10%-35% ethyl acetate) afforded 289 mg (1.12 mmol; 68% of theory) of the title compound.

LC-MS (method L1): $R_t$=2.02 min; m/z=260 (M+H)$^+$

3-Fluoro-1-(3-(4,4,5,5-tetramethyl-1,3,2-dioxaborolan-2-yl)phenyl)azetidine (1H-20)

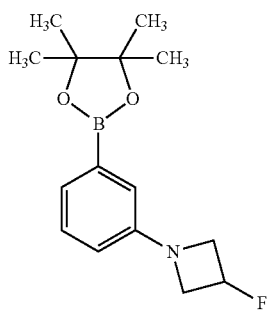 [SMILES: CC1(C)OB(c2cccc(N3CC(F)C3)c2)OC1(C)C]

To a degassed (argon, 10 min) suspension of 1,3-dibromobenzene (3.2 g, 13.45 mmol, 1.6 mL), 3-fluoroazetidine hydrochloride (1.0 g, 8.96 mmol), 9,9-dimethyl-4,5-bis(diphenylphosphino)xanthene (0.5 g, 0.89 mmol) and sodium tert-butoxide (3.5 g, 35.90 mmol) in dry 1,4-dioxane (70 mL) was added tris(dibenzylideneacetone)dipalladium(0) (0.4 g, 0.45 mmol). The reaction mixture was stirred at 95° C. for 18 h. Reaction mixture was allowed to cool to room temperature. Water (20 mL) and ethyl acetate (100 mL) were added. Layers were separated and aqueous layer was extracted with ethyl acetate (2×50 mL). Combined organic extracts were dried with sodium sulfate and solvents were removed in vacuo. Purification by flash column chromatography (Method L7; 500 g; heptane, 15%-40% ethyl acetate) afforded 1.1 g (4.10 mmol; 45% of theory) of 1-(3-bromophenyl)-3-fluoroazetidine with a purity of 89% according to GC-MS.

GC-MS (Method A) $R_t$=3.88 min; m/z=229/231 M$^+$

A mixture of 1-(3-bromophenyl)-3-fluoroazetidine (1.06 g, 4.61 mmol), bis(pinacolato)diboron (1.76 g, 6.91 mmol), potassium acetate (1.36 g, 13.82 mmol) and 1,1'-bis(diphenylphosphino)ferrocenepalladium(II) dichloride (0.38 g, 0.46 mmol) in dry 1,4-dioxane (60 mL) was purged with argon for 10 min. The reaction mixture was stirred at 90° C. for 1.5 h and at 60° C. for 72 h. Reaction mixture was allowed to cool to room temperature and was coated on hydromatrix. Purification by flash column chromatography (Method L7; 500 g; heptane, 10%-40% ethyl acetate) and (Method L7; 300 g; heptane, 10%-30% ethyl acetate) afforded 0.92 g (3.32 mmol; 72% of theory) of the title compound with a purity of 70% according to LC-MS. The material was used without further purification.

LC-MS (Method L1): $R_t$=2.10 min; m/z=278 (M+H)$^+$ 1-(3-(4,4,5,5-Tetramethyl-1,3,2-dioxaborolan-2-yl)phenyl)azetidine-3-carbonitrile (1H-21)

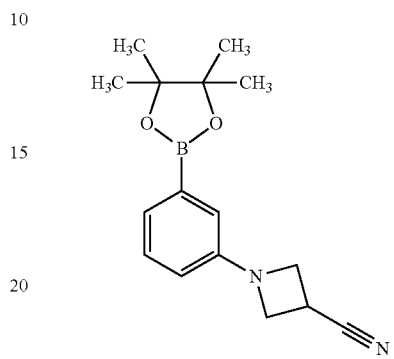

To a degassed (argon, 10 min) suspension of 1,3-dibromobenzene (2.98 g, 12.65 mmol, 1.5 mL), azetidine-3-carbonitrile hydrochloride (1.0 g, 8.43 mmol), 9,9-dimethyl-4,5-bis(diphenylphosphino)xanthene (0.49 g, 0.84 mmol) and sodium tert-butoxide (3.2 g, 33.70 mmol) in dry 1,4-dioxane (70 mL) was added tris(dibenzylideneacetone)dipalladium(0) (0.39 g, 0.42 mmol). The reaction mixture was stirred at 95° C. for 3 h and was allowed to cool to room temperature. Water (20 mL) and ethyl acetate (100 mL) were added. Layers were separated and aqueous layer was extracted with ethyl acetate (2×50 mL). Combined organic extracts were dried with sodium sulfate and solvents were removed in vacuo. Purification by flash column chromatography (Method L7; 500 g; heptane, 10%-30% ethyl acetate) afforded 1.25 g (5.28 mmol; 62% of theory) of 1-(3-bromophenyl)azetidine-3-carbonitrile.

GC-MS (Method A) $R_t$=4.87 min; m/z=236/238 M$^+$

1H NMR (300 MHz, DMSO-d6, Method M2) δ 7.14 (t, J=8.0 Hz, 1H), 6.97-6.82 (m, 1H), 6.66 (t, J=2.0 Hz, 1H), 6.51-6.42 (m, 1H), 4.10 (dd, J=8.4, 7.5 Hz, 2H), 3.99 (dd, J=7.5, 5.4 Hz, 2H), 3.90-3.77 (m, 1H).

A mixture of 1-(3-bromophenyl)azetidine-3-carbonitrile (1.25 g, 5.28 mmol), bis(pinacolato)diboron (2.01 g, 7.91 mmol), potassium acetate (1.55 g, 15.83 mmol) and 1,1'-bis(diphenylphosphino)ferrocenepalladium(II) dichloride (0.43 g, 0.53 mmol) in dry 1,4-dioxane (60 mL) was purged with argon for 5 min. The reaction mixture was stirred at 90° C. for 1.5 h. Reaction mixture was allowed to cool to room temperature and was coated on hydromatrix. Flash column chromatography (Method L7; 500 g; heptane, 10%-40% ethyl acetate) afforded 1.32 g (4.65 mmol; 88% of theory) of the title compound. According to 1H NMR analysis the material contained 20% (w/w) of bis(pinacolato)diboron. The material was used without further purification.

LC-MS (Method L1): $R_t$=2.04 min; m/z=285 (M+H)$^+$

1H NMR (300 MHz, DMSO-d6, Method M2) δ 7.22 (t, J=7.6 Hz, 1H), 7.09 (d, J=7.2 Hz, 1H), 6.72 (d, J=2.2 Hz, 1H), 6.61 (dd, J=7.5, 2.1 Hz, 1H), 4.13-4.04 (m, 2H), 4.03-3.93 (m, 2H), 3.87-3.77 (m, 1H), 1.28 (s, 12H).

2-(3-(Cyclopropylsulfonyl)phenyl)-4,4,5,5-tetramethyl-1,3,2-dioxaborolane (1H-22)

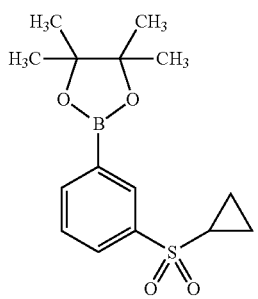 [SMILES: CC1(C)OB(c2cccc(S(=O)(=O)C3CC3)c2)OC1(C)C]

At 0° C. 3-chloroperbenzoic acid (3.23 g, 13.09 mmol, purity 70%) was added to a solution of (3-bromophenyl)(cyclopropyl)sulfane (1.00 g, 4.36 mmol) in dichloromethane (15 mL). The reaction mixture was allowed to warm to room temperature and was stirred for 2 h. Aqueous sodium thiosulfate (2M; 10 mL) and ethyl acetate (30 mL) were added to the reaction mixture. Layers were separated. Aqueous layer was extracted with ethyl acetate (2×30 mL). Combined organic extracts were washed with saturated aqueous sodium hydrogencarbonate (10 mL) and brine (10 mL) and were dried with sodium sulfate. Solvents were removed in vacuo. The solid residue was dissolved in ethyl acetate (20 mL) and the solution was washed with saturated aqueous sodium hydrogencarbonate (2×10 mL) and water (10 mL). The organic layer was dried with sodium sulfate and solvents were removed in vacuo. 1.08 g (4.14 mmol; 95% of theory) of 1-bromo-3-(cyclopropylsulfonyl)benzene were obtained.

GC-MS (Method A) $R_t$=4.69 min; m/z=260/262 M$^+$

1H NMR (300 MHz, DMSO-d6, Method M2) δ 8.06 (t, J=1.8 Hz, 1H), 8.00-7.88 (m, 2H), 7.63 (t, J=7.9 Hz, 1H), 3.03-2.93 (m, 1H), 1.20-1.11 (m, 2H), 1.11-1.03 (m, 2H).

A mixture of 1-bromo-3-(cyclopropylsulfonyl)benzene (1.08 g, 4.14 mmol), bis(pinacolato)diboron (1.58 g, 6.21 mmol), potassium acetate (1.22 g, 12.42 mmol) and 1,1'-bis(diphenylphosphino)ferrocenepalladium(II) dichloride (0.34 g, 0.41 mmol) in dry 1,4-dioxane (50 mL) was purged with argon for 5 min. The reaction mixture was stirred at 90° C. for 1.5 h. Reaction mixture was allowed to cool to room temperature and was coated on hydromatrix. Flash column chromatography (Method L7; 500 g; heptane, 10%-40% ethyl acetate) afforded 1.07 g (3.47 mmol; 84% of theory) of the title compound. According to 1H NMR analysis the material contained 4% (w/w) of bis(pinacolato)diboron. The material was used without further purification.

GC-MS (Method A): $R_t$=6.04 min; m/z=308 M$^+$

1H NMR (300 MHz, DMSO-d6, Method M2) δ 8.10 (s, 1H), 8.05-7.95 (m, 2H), 7.68 (t, J=7.6 Hz, 1H), 2.97-2.85 (m, 1H), 1.33 (s, 12H), 1.13-1.08 (m, 2H), 1.07-1.00 (m, 2H).

2,6-Difluoro-N,N-dimethyl-3-(4,4,5,5-tetramethyl-1,3,2-dioxaborolan-2-yl)aniline (1H-23)

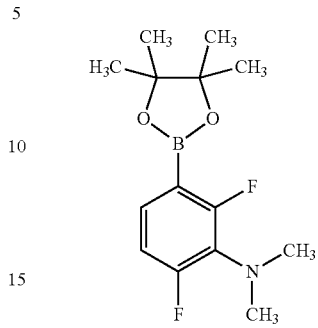

To a solution of 3-bromo-2,6-difluoroaniline (279 mg, 1.34 mmol) in dry N,N-dimethylformamide (10 mL) were added iodomethane (952 mg, 6.71 mmol, 0.4 mL) and sodium hydride (268 mg, 6.71 mmol; 60% in mineral oil). After stirring for 40 min, the reaction mixture was quenched with water (40 mL). The resulting mixture was extracted with diethyl ether (2×40 mL). The combined organic layers were washed with water (2×20 mL) and brine (2×20 mL), dried with sodium sulfate and concentrated in vacuo to afford 411 mg (>100% yield) of 3-Bromo-2,6-difluoro-N,N-dimethylaniline with a purity of 99% according to LC-MS. The material was used as such.

LC-MS (Method L1): $R_t$=2.21 min; m/z=236/238 (M+H)$^+$

To a degassed mixture (argon, 15 min) of 3-bromo-2,6-difluoro-N,N-dimethylaniline (317 mg, 1.34 mmol), bis(pinacolato)diboron (409 mg, 1.61 mmol) and potassium acetate (395 mg, 4.02 mmol) in dry 1,4-dioxane (11 mL) was added 1,1'-bis(diphenylphosphino)ferrocene-palladium(II) dichloride (51 mg, 0.07 mmol). The reaction mixture was stirred at 90° C. for 18 h. Bis(pinacolato)diboron (409 mg, 1.61 mmol) and potassium acetate (395 mg, 4.02 mmol) were added and the resulting mixture was purged with argon. 1,1'-bis(diphenyl-phosphino)ferrocenepalladium(II) dichloride (51 mg, 0.08 mmol) was added and the reaction mixture was stirred at 90° C. for 20 h. The reaction mixture was allowed to cool to room temperature and was coated on hydromatrix. Purification by flash column chromatography (Method L6; 12 g; heptane, 1%-10% ethyl acetate) afforded 442 mg (0.70 mmol; 52% of theory) of the title compound.

LC-MS (Method L1): $R_t$=2.21 min; m/z=284 (M+H)$^+$

1H NMR (400 MHz, Chloroform-d, Method M2) δ 7.35 (m, 1H), 6.83 (m, 1H), 2.90-2.83 (m, 6H), 1.35 (s, 12H).

Intermediates 1I

5-(Difluoromethyl)-1H-pyrazol-3-amine (1I-1)

At room temperature under nitrogen atmosphere to a suspension of 4,4-difluoro-3-oxobutanenitrile (28.3 g, 238 mmol) in absolute ethanol (750 mL) was added hydrazine hydrate (23.8 g, 476 mmol, 23 mL). The reaction mixture was stirred at reflux for 21 h and was allowed to cool to room temperature. Volatiles were removed in vacuo and the residue was coated on hydromatrix. Purification by flash column chromatography (Method L7; 80 g; heptane, 12%-85% ethyl acetate) afforded 2.0 g (15 mmol; 6% of theory over 2 steps) of the title compound with a purity of 67% according to LC-MS.

LC-MS (Method L3): $R_t$=0.33 min; m/z=134 (M+H)$^+$

Intermediates 2A 4,4-Difluoro-3-oxobutanenitrile (2A-1)

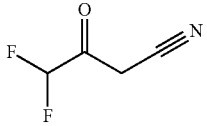

Under argon atmosphere to a refluxing suspension of sodium hydride (60% (w/w) in mineral oil; 11.41 g, 285 mmol) in dry tetrahydrofuran (500 ml) was added drop wise over a period of 40 min a mixture of acetonitrile (10.74 g, 262 mmol, 14 mL) and ethyl difluoroacetate (29.5 g, 238 mmol, 25 mL). The mixture was stirred at 80° C. overnight and was concentrated in vacuo. The residue was suspended in water (500 mL) and acidified to pH 1.0 by addition of hydrochloric acid (2N). The acidified solution was extracted with diethyl ether (2×400 mL). The combined organic layers were washed with brine, dried over sodium sulfate and concentrated under reduced pressure (500 mbar) at 40-C to afford an oil. The material was used as such in next step.

Intermediates 2D

Ethyl 7-ethyl-2-methyl-3-(3-(trifluoromethyl)phenyl)pyrazolo[1,5-a]pyrimidine-6-carboxylate (2D-1)

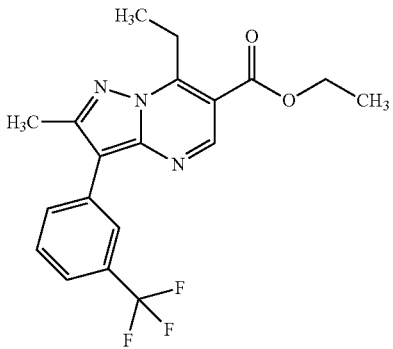 [SMILES: CCOC(=O)c1cnc2c(-c3cccc(C(F)(F)F)c3)c(C)nn2c1CC]

A solution of (E/Z)-ethyl 2-(ethoxymethylene)-3-oxopentanoate (462 mg, 2.2 mmol) and 3-methyl-4-(3-(trifluoromethyl)phenyl)-1H-pyrazol-5-amine (504 mg, 2.2 mmol) in ethanol (6 mL) was stirred at reflux for 2 h. Solvents were removed in vacuo. Purification by flash column chromatography (Method L7; 40 g; heptane, 0%-15% ethyl acetate) afforded 673 mg (1.8 mmol; 81% of theory) of the title compound.

LC-MS (Method L1): $R_t$=2.49 min; m/z=378 (M+H)$^+$
1H NMR (300 MHz, DMSO-d6, Method M2) δ=8.92 (s, 1H), 8.12 (s, 1H), 8.07-8.00 (m, 1H), 7.78-7.65 (m, 2H), 4.38 (q, J=7.1 Hz, 2H), 3.61 (q, J=7.4 Hz, 2H), 2.65 (s, 3H), 1.42-1.30 (m, 6H).

Ethyl 7-(methoxymethyl)-2-methyl-3-(3-(trifluoromethyl)phenyl)pyrazolo[1,5-a]pyrimidine-6-carboxylate (2D-2)

A solution of (E/Z)-ethyl 2-(ethoxymethylene)-4-methoxy-3-oxobutanoate (377 mg, 1.9 mmol) and 3-methyl-4-(3-(trifluoromethyl)phenyl)-1H-pyrazol-5-amine (450 mg, 1.9 mmol) in ethanol (3 ml) was stirred at reflux for 4.5 h. Solvents were removed in vacuo. Purification by flash column chromatography (Method L7; 40 g; heptane, 0%-15% ethyl acetate) afforded 610 mg (1.6 mmol; 83% of theory) of the title compound.

LC-MS (Method L1): $R_t$=2.33 min; m/z=394 (M+H)$^+$

Ethyl 7-cyclopropyl-2-methyl-3-(3-(trifluoromethyl)phenyl)pyrazolo[1,5-a]pyrimidine-6-carboxylate (2D-3)

A solution of (E/Z)-ethyl 2-(cyclopropanecarbonyl)-3-ethoxyacrylate (353 mg, 1.7 mmol) and 3-methyl-4-(3-(trifluoromethyl)phenyl)-1H-pyrazol-5-amine (401 mg, 1.7 mmol) in ethanol (3 mL) was stirred at reflux for 18 h. Solvents were removed in vacuo. Purification by flash column chromatography (Method L7; 40 g; heptane, 0%-15% ethyl acetate) afforded 525 mg (1.3 mmol; 81% of theory) of the title compound.

LC-MS (Method L1): $R_t$=2.50 min; m/z=390 (M+H)$^+$

1H NMR (300 MHz, DMSO-d6, Method M2) δ=8.80 (s, 1H), 8.12-7.97 (m, 2H), 7.77-7.64 (m, 2H), 4.38 (q, J=7.1 Hz, 2H), 3.20-3.05 (m, 1H), 2.60 (s, 3H), 2.01-1.90 (m, 2H), 1.37 (t, J=7.1 Hz, 3H), 1.31-1.21 (m, 2H).

Intermediates 2E

7-Ethyl-2-methyl-3-(3-(trifluoromethyl)phenyl)pyrazolo[1,5-a]pyrimidine-6-carboxylic acid (2E-1)

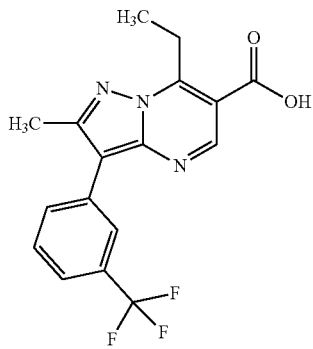 [SMILES: CCc1c(C(=O)O)cnc2c(-c3cccc(C(F)(F)F)c3)c(C)nn12]

To a solution of ethyl 7-ethyl-2-methyl-3-(3-(trifluoromethyl)phenyl)pyrazolo[1,5-a]pyrimidine-6-carboxylate (673 mg, 1.8 mmol) in a mixture of tetrahydrofuran (2 mL) and water (2 mL) was added lithium hydroxide monohydrate (150 mg, 3.6 mmol). The mixture was stirred at room temperature for 18 h; was acidified to pH 2 and extracted with ethyl acetate (2×10 mL). The combined organic layers were washed with brine and dried with sodium sulfate. Solvents were removed in vacuo to afford 631 mg (1.8 mmol; 100% of theory) of the title compound.

LC-MS (Method L1): $R_t$=2.34 min; m/z=350 (M+H)$^+$ 7-(Methoxymethyl)-2-methyl-3-(3-(trifluoromethyl)phenyl)pyrazolo[1,5-a]pyrimidine-6-carboxylic Acid (2E-2)

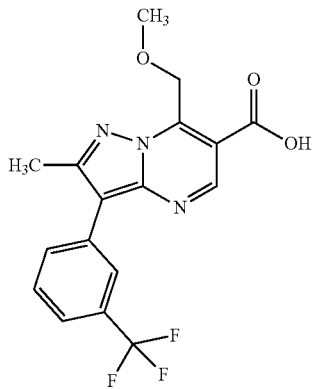 [SMILES: COCc1c(C(=O)O)cnc2c(-c3cccc(C(F)(F)F)c3)c(C)nn12]

To a solution of ethyl 7-(methoxymethyl)-2-methyl-3-(3-(trifluoromethyl)phenyl)pyrazolo[1,5-a]pyrimidine-6-carboxylate (610 mg, 1.6 mmol) in a mixture of tetrahydrofuran (2 mL) and water (2 mL) was added lithium hydroxide monohydrate (135 mg, 3.2 mmol). The mixture was stirred at room temperature for 2.5 h and was extracted with ethyl acetate (2×20 mL). The combined organic layers were washed with brine and dried with sodium sulfate. Solvents were removed in vacuo to afford 539 mg (1.5 mmol; 92% of theory) of the title compound.

LC-MS (Method L1): $R_t$=2.18 min; m/z=366 (M+H)$^+$

1H NMR (300 MHz, DMSO-d6, Method M2) δ=13.75 (s, 1H), 8.95 (s, 1H), 8.13-8.00 (m, 2H), 7.80-7.64 (m, 2H), 5.35 (s, 2H), 3.40 (s, 3H), 2.65 (s, 3H).

7-Cyclopropyl-2-methyl-3-(3-(trifluoromethyl)phenyl)pyrazolo[1,5-a]pyrimidine-6-carboxylic Acid (2E-3)

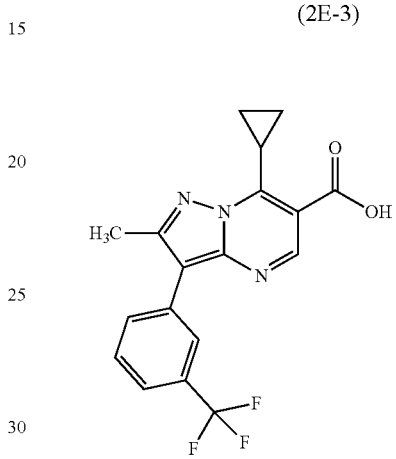

To a solution of ethyl 7-cyclopropyl-2-methyl-3-(3-(trifluoromethyl)phenyl)pyrazolo[1,5-a]pyrimidine-6-carboxylate (557 mg, 1.4 mmol) in a mixture of tetrahydrofuran (2 mL) and water (2 mL) was added lithium hydroxide monohydrate (120 mg, 2.9 mmol). The mixture was stirred at room temperature for 72 h; was acidified to pH 2 and extracted with ethyl acetate (2×10 mL). The combined organic layers were washed with brine and dried with sodium sulfate. Solvents were removed in vacuo to afford 368 mg (1.0 mmol; 71% of theory) of the title compound with a purity of 88% according to LC-MS analysis.

LC-MS (Method L1): $R_t$=2.36 min; m/z=362 (M+H)$^+$

Intermediates 4A

Ethyl 2-cyano-2-(3,4-difluorophenyl)acetate (4A-2)

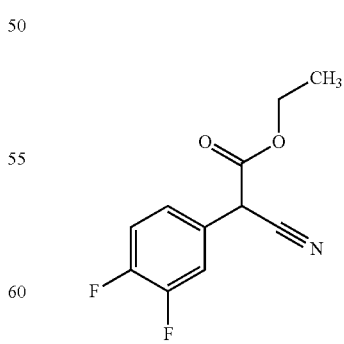

At 0° C. to a solution of 3,4-difluorophenylacetonitrile (5.00 g, 32.7 mmol, 4.0 mL) in dry tetrahydrofuran (70 mL) sodium hydride (1.70 g, 42.4 mmol; 60% in mineral oil) was added portion wise. Reaction mixture was allowed to warm to room temperature. After stirring for 1 h diethyl carbonate (4.63 g, 39.2 mmol, 4.8 mL) was slowly added. After stirring for 17 h the reaction mixture was quenched by the addition of hydrochloric acid (1.0 M; 200 mL) and was extracted with ethyl acetate (2×150 mL). The combined organic layers were washed with brine, dried with sodium sulfate and concentrated in vacuo. Purification by flash column chromatography (Method L7; 120 g; heptane, 2%-15% ethyl acetate) afforded 6.23 g (27.7 mmol; 85% of theory) of the title compound.

LC-MS (Method L1): $R_t$=1.96 min; m/z=224 (M−H)−

Ethyl 2-(3-chlorophenyl)-2-cyanoacetate (4A-3)

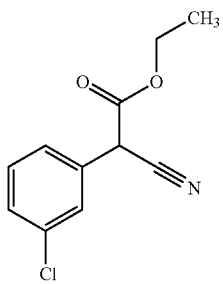

At 0° C. to a solution of 3-chlorobenzylcyanide (5.00 mL, 39.2 mmol) in dry tetrahydrofuran (100 mL) sodium hydride (2.04 g, 51.0 mmol; 60% in mineral oil) was added portion wise. Reaction mixture was allowed to warm to room temperature. After stirring for 1 h diethyl carbonate (5.56 g, 47.1 mmol, 5.7 mL) was slowly added. After stirring for 30 min the reaction mixture was quenched by the addition of hydrochloric acid (1.0 M; 200 mL) and was extracted with ethyl acetate (2×150 mL). The combined organic layers were washed with brine, dried with sodium sulfate and concentrated in vacuo. Purification by flash column chromatography (Method L7; 120 g; heptane, 2%-15% ethyl acetate) afforded 7.58 g (33.3 mmol; 85% of theory) of the title compound.

LC-MS (Method L1): $R_t$=2.01 min; m/z=222 (M−H)−

1H NMR (400 MHz, Chloroform-d, Method M2) δ 7.51-7.45 (m, 1H), 7.44-7.31 (m, 3H), 4.69 (s, 1H), 4.31-4.20 (m, 2H), 1.30 (t, J=7.2 Hz, 3H).

Intermediates 4B

5-Amino-4-(3,4-difluorophenyl)-1H-pyrazol-3-ol (4B-2)

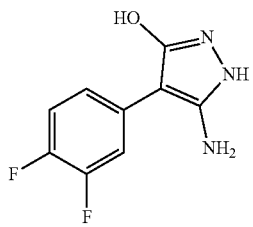

To a solution of ethyl 2-cyano-2-(3,4-difluorophenyl) acetate (6.23 g, 27.7 mmol) in absolute ethanol (100 mL) was added hydrazine monohydrate (2.77 g, 55.3 mmol, 2.7 mL). The reaction mixture was stirred at reflux for 30 min and was allowed to cool to room temperature. Volatiles were removed in vacuo. The residue was triturated in diethyl ether, filtered off and dried. 5.11 g (24.2 mmol; 87% of theory) of the title compound were obtained.

LC-MS (Method L1): $R_t$=1.10 min; m/z=212 (M+H)+

1H NMR (400 MHz, DMSO-d6, Method M2) δ 9.16 (s, 2H), 7.69 (m, 1H), 7.49-7.40 (m, 1H), 7.28 (m, 1H), 6.13 (s, 2H).

Ethyl 2-(3-chlorophenyl)-2-cyanoacetate (4B-3)

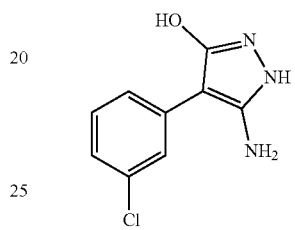

A solution of ethyl 2-(3-chlorophenyl)-2-cyanoacetate (7.58 g, 33.9 mmol) and hydrazine monohydrate (3.30 mL, 67.8 mmol) in absolute ethanol (100 mL) was stirred at reflux for 1.5 h. The precipitate was filtered off and washed with diethyl ether and dried. The filtrate was concentrated in vacuo and the residue was triturated in diisopropyl ether. The precipitate was filtered off and dried. The two solid batches were combined to afford 6.57 g (31.3 mmol; 93% of theory) of the title compound.

LC-MS (Method L1): $R_t$=1.44 min; m/z=210 (M+H)+

1H NMR (400 MHz, DMSO-d6, Method M2) δ 9.25 (bs, 2H), 7.78 (t, J=1.8 Hz, 1H), 7.58-7.49 (m, 1H), 7.27 (t, J=7.9 Hz, 1H), 7.04 (m, 1H), 6.12 (bs, 2H).

Intermediates 4C

Ethyl 3-(3,4-difluorophenyl)-2-hydroxy-7-isopropylpyrazlo[1,5-a]pyrimidine-6-carboxylate (4C-2)

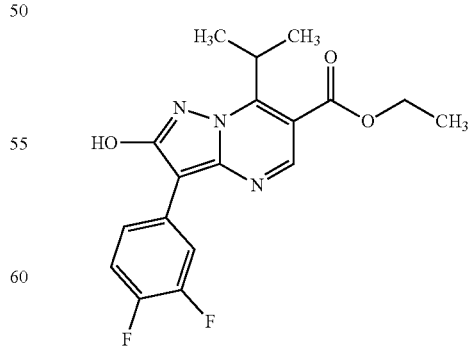

A mixture of 5-amino-4-(3,4-difluorophenyl)-1H-pyrazol-3-ol (1.00 g, 4.74 mmol) and ethyl 2-(ethoxymethylene)-4-methyl-3-oxopentanoate (1.02 g, 4.74 mmol) in absolute ethanol (50 mL) was stirred at reflux for 20 h. Ethyl 2-(ethoxymethylene)-4-methyl-3-oxopentanoate (0.21 g, 1.00 mmol) was added and the reaction mixture was stirred at reflux for 30 h. The reaction mixture was concentrated in vacuo and the residue was coated on hydromatrix. Purification by flash column chromatography (Method L6; 80 g; heptane, 2%-22% ethyl acetate) afforded 1.05 g (2.88 mmol; 61% of theory) of the title compound.

LC-MS (Method L1): $R_f$=2.42 min; m/z=362 (M+H)$^+$

1H NMR (400 MHz, Chloroform-d, Method M2) δ 8.83 (s, 1H), 8.66 (s, 1H), 8.13 (m, 1H), 7.98 (m, 1H), 7.22 (m, 1H), 4.46 (m, 3H), 1.59 (d, J=7.1 Hz, 6H), 1.44 (t, J=7.2 Hz, 3H).

Ethyl 3-(3-chlorophenyl)-2-hydroxy-7-isopropylpyrazolo[1,5-a]pyrimidine-6-carboxylate (4C-3)

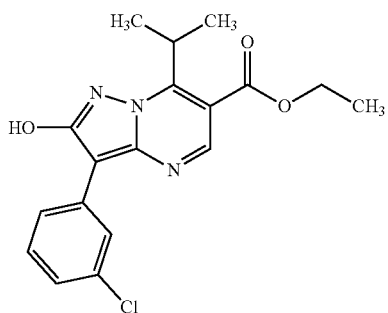 [SMILES: CCOC(=O)c1cnc2c(-c3cccc(Cl)c3)c(O)nn2c1C(C)C]

A mixture of 5-amino-4-(3-chlorophenyl)-1H-pyrazol-3-ol (1.96 g, 9.33 mmol) and ethyl 2-(ethoxymethylene)-4-methyl-3-oxopentanoate (2.00 g, 9.33 mmol) in absolute ethanol (50 mL) was stirred at reflux for 20 h. Ethyl 2-(ethoxymethylene)-4-methyl-3-oxopentanoate (0.30 g, 1.40 mmol) was added and the reaction mixture was stirred at reflux for 20 h. The reaction mixture was allowed to cool to room temperature. The solids were filtered off. The filtrate was concentrated in vacuo. The residue was triturated in ethyl acetate. The fine solid material was filtered off. The filtrate was concentrated in vacuo. The residue was coated on hydromatrix and purified by flash column chromatography (Method L6; 80 g; heptane, 2%-100% ethyl acetate). 2.49 g (6.92 mmol; 74% of theory) of the title compound were obtained.

LC-MS (Method L1): $R_f$=2.49 min; m/z=360 (M+H)$^+$

1H NMR (400 MHz, Chloroform-d, Method M2) δ 8.84 (s, 1H), 8.78 (d, J=34.1 Hz, 1H), 8.26 (t, J=1.8 Hz, 1H), 8.17-8.10 (m, 1H), 7.37 (t, J=7.9 Hz, 1H), 7.23 (m, 1H), 4.45 (m, 3H), 1.60 (d, J=7.1 Hz, 6H), 1.44 (t, J=7.1 Hz, 3H).

Intermediates 4D

Ethyl 3-(3,4-difluorophenyl)-7-isopropyl-2-(((trifluoromethyl)sulfonyl)oxy)pyrazolo[1,5-a]pyrimidine-6-carboxylate (4D-2)

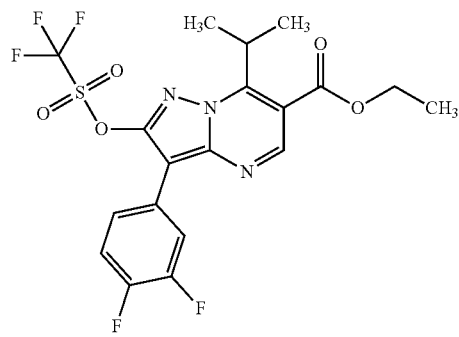 [SMILES: CCOC(=O)c1cnc2c(-c3ccc(F)c(F)c3)c(OS(=O)(=O)C(F)(F)F)nn2c1C(C)C]

To a suspension of ethyl 3-(3,4-difluorophenyl)-2-hydroxy-7-isopropylpyrazolo[1,5-a]pyrimidine-6-carboxylate (473 mg, 1.31 mmol) in dichloromethane (15 mL) were added trifluoromethanesulfonic anhydride (406 mg, 1.44 mmol, 0.24 mL) and pyridine (228 mg, 2.88 mmol, 0.23 mL). The resulting clear solution was stirred for 3.5 h. Trifluoromethanesulfonic anhydride (170 mg, 0.60 mmol, 0.10 mL) and pyridine (95 mg, 1.20 mmol, 0.10 mL) were added. After stirring for 17 h, water was added. The organic layer was collected via a phase separator and concentrated in vacuo to afford 616 mg (1.25 mmol; 93% of theory) of the title compound.

LC-MS (Method L1): $R_f$=2.49 min; m/z=494 (M+H)$^+$ 1H NMR (400 MHz, Chloroform-d, Method M2) δ 8.95 (s, 1H), 7.87 (m, 1H), 7.69-7.62 (m, 1H), 7.34-7.23 (m, 2H), 4.54 (m, 1H), 4.46 (q, J=7.1 Hz, 2H), 1.61 (d, J=7.1 Hz, 6H), 1.45 (t, J=7.2 Hz, 3H).

Ethyl 3-(3-chlorophenyl)-7-isopropyl-2-(((trifluoromethyl)sulfonyl)oxy)pyrazolo[1,5-a]pyrimidine-6-carboxylate (4D-3)

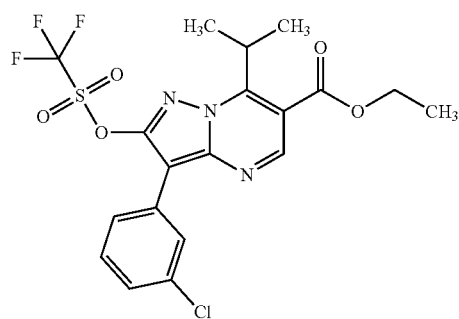 [SMILES: CCOC(=O)c1cnc2c(-c3cccc(Cl)c3)c(OS(=O)(=O)C(F)(F)F)nn2c1C(C)C]

To a solution of ethyl 3-(3-chlorophenyl)-2-hydroxy-7-isopropylpyrazolo[1,5-a]pyrimidine-6-carboxylate (2.49 g, 6.92 mmol) in dichloromethane (100 mL) were added trifluoromethanesulfonic anhydride (2.89 g, 10.24 mmol, 1.7 mL) and pyridine (1.66 g, 21.02 mmol, 1.7 mL). After stirring for 80 min, water (100 mL) was added. The layers were separated. The aqueous layer was extracted with dichloromethane (50 mL). The combined organic layers were concentrated in vacuo. The residue was dissolved in diethyl ether (100 mL) and washed with hydrochloric acid (0.5 M; 2×75 mL), water and brine. The organic layer was dried with sodium sulfate and concentrated in vacuo to afford 3.30 g (6.71 mmol; 97% of theory) of the title compound.

LC-MS (Method L1): $R_t$=2.62 min; m/z=492 (M+H)$^+$

1H NMR (400 MHz, Chloroform-d, Method M2) δ 8.96 (s, 1H), 8.00 (t, J=1.8 Hz, 1H), 7.83-7.76 (m, 1H), 7.43 (t, J=7.9 Hz, 1H), 7.34 (m, 1H), 4.50 (m, 3H), 1.61 (d, J=7.1 Hz, 6H), 1.45 (t, J=7.1 Hz, 3H).

Intermediates 4E

Ethyl 3-(3,4-difluorophenyl)-2-((diphenylmethylene)amino)-7-isopropylpyrazolo[1,5-a]pyrimidine-6-carboxylate (4E-2)

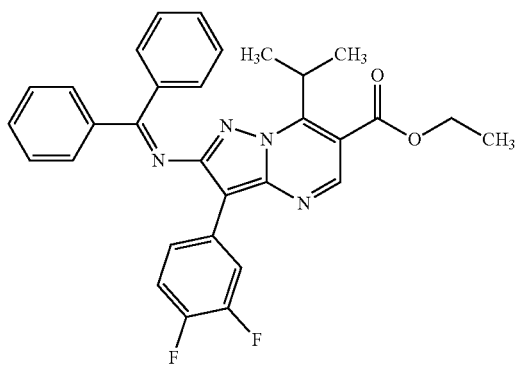 [SMILES: CCOC(=O)c1cnc2c(-c3ccc(F)c(F)c3)c(N=C(c3ccccc3)c3ccccc3)nn2c1C(C)C]

A mixture of ethyl 3-(3,4-difluorophenyl)-7-isopropyl-2-(((trifluoromethyl)sulfonyl)oxy)-pyrazolo[1,5-a]pyrimidine-6-carboxylate (370 mg, 0.75 mmol), benzophenone imine (149 mg, 0.83 mmol, 0.14 mL) and cesium carbonate (489 mg, 1.50 mmol) in dry toluene (8 mL) was purged with argon for 10 min. Tris(dibenzylideneacetone)dipalladium(0) (34 mg, 0.04 mmol) and 9,9-dimethyl-4,5-bis(diphenylphosphino)xanthene (43 mg, 0.08 mmol) were added. The reaction mixture was stirred at 100° C. for 20 h, was allowed to cool to room temperature and was combined with the crude reaction mixture of a previous reaction towards the title compound starting with 104 mg (0.21 mmol) of ethyl 3-(3,4-difluorophenyl)-7-isopropyl-2-(((trifluoromethyl)sulfonyl)oxy)-pyrazolo[1,5-a]pyrimidine-6-carboxylate. The mixture was partitioned between water and ethyl acetate. The aqueous layer was extracted with ethyl acetate. The combined organic layers were washed with brine, dried with sodium sulfate and concentrated in vacuo. Purification by flash column chromatography (Method L6; 40 g; heptane, 1%-22% ethyl acetate) afforded 258 mg (0.44 mmol; 46% of theory, based on 0.96 mmol) of the title compound with a purity of 89% according to LC-MS.

LC-MS (Method L1): $R_t$=2.66 min; m/z=525 (M+H)$^+$

Ethyl 3-(3-chlorophenyl)-2-((diphenylmethylene)amino)-7-isopropylpyrazolo[1,5-a]pyrimidine-6-carboxylate (4E-3)

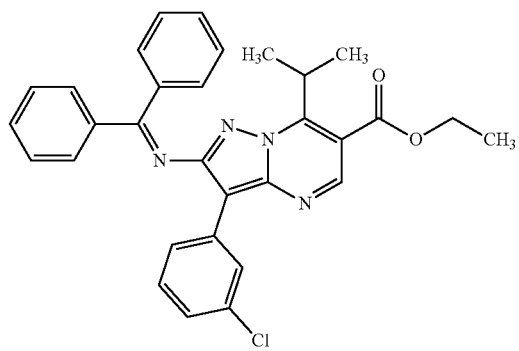 [SMILES: CCOC(=O)c1cnc2c(-c3cccc(Cl)c3)c(N=C(c3ccccc3)c3ccccc3)nn2c1C(C)C]

A mixture of ethyl 3-(3-chlorophenyl)-7-isopropyl-2-(((trifluoromethyl)sulfonyl)oxy)pyrazo-lo[1,5-a]pyrimidine-6-carboxylate (3.30 g, 6.71 mmol), benzophenone imine (1.34 g, 7.38 mmol, 1.2 ml) and cesium carbonate (4.37 g, 13.42 mmol) in dry toluene (80 mL) was purged with argon. Tris(dibenzylideneacetone)dipalladium(0) (0.31 g, 0.34 mmol) and 9,9-dimethyl-4,5-bis(diphenylphosphino)xanthene (0.39 g, 0.67 mmol) were added. The reaction mixture was stirred at 100° C. for 20 h and was partitioned between water and ethyl acetate. The aqueous layer was extracted with ethyl acetate. The combined organic layers were washed with water and brine, dried with sodium sulfate and concentrated in vacuo. Purification by flash column chromatography (Method L6; 80 g; heptane, 1%-20% ethyl acetate) afforded 1.18 g (1.28 mmol; 19% of theory) of the title compound with a purity of 57% according to LC-MS.

LC-MS (Method L1): $R_t$=2.78 min; m/z=523 (M+H)$^+$

Intermediates 4F

Ethyl 2-amino-3-(3,4-difluorophenyl)-7-isopropylpyrazolo[1,5-a]pyrimidine-6-carboxylate (4F-2)

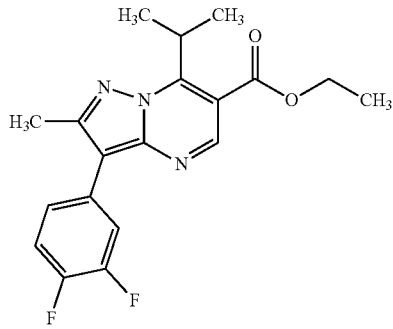 [SMILES: CCOC(=O)c1cnc2c(-c3ccc(F)c(F)c3)c(C)nn2c1C(C)C]

To a solution of ethyl 3-(3,4-difluorophenyl)-2-((diphenylmethylene)amino)-7-isopropylpyrazolo[1,5-a]pyrimidine-6-carboxylate (251 mg, 0.48 mmol) in tetrahydrofuran (40 mL) was added hydrochloric acid (2.0 M; 15 mL). After 40 min the reaction mixture was concentrated in vacuo. The aqueous residue was basified by the addition of saturated aqueous sodium hydrogencarbonate and was extracted with ethyl acetate (2×30 mL). The combined organic layers were washed with brine, dried with sodium sulfate and concentrated in vacuo. Purification by flash column chromatography (Method L6, 4 g, heptane, 1%-16% ethyl acetate) afforded 107 mg (0.29 mmol; 60% of theory) of the title compound.

LC-MS (Method L1): $R_t$=2.22 min; m/z=361 (M+H)$^+$

1H NMR (400 MHz, Chloroform-d, Method M2) δ 8.74 (s, 1H), 7.63 (m, 1H), 7.47 (m, 1H), 7.30-7.21 (m, 1H), 4.56 (m, 1H), 4.45 (s, 2H), 4.40 (q, J=7.1 Hz, 2H), 1.59 (d, J=7.1 Hz, 6H), 1.42 (t, J=7.1 Hz, 3H).

Ethyl 2-amino-3-(3-chlorophenyl)-7-isopropylpyrazolo[1,5-a]pyrimidine-6-carboxylate (4F-3)

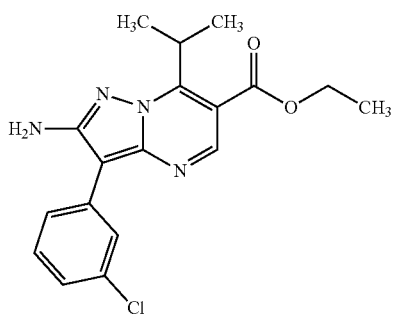 [SMILES: CCOC(=O)c1cnc2c(-c3cccc(Cl)c3)c(N)nn2c1C(C)C]

To a solution of ethyl 3-(3-chlorophenyl)-2-((diphenylmethylene)amino)-7-isopropylpyrazolo[1,5-a]pyrimidine-6-carboxylate (1.18 g, 1.28 mmol; purity 57%) in tetrahydrofuran (30 mL) was added hydrochloric acid (2.0 M; 15 mL). After stirring for 70 min the reaction mixture was neutralized by the addition of sodium hydrogencarbonate. Water (20 mL) was added and the resulting mixture was extracted with ethyl acetate (2×30 mL). The combined organic layers were washed with brine, dried with sodium sulfate and concentrated in vacuo. The residue was purified by flash column chromatography (Method L6; 40 g; heptane, 1%-15% ethyl acetate) to afford 0.36 g (1.01 mmol; 79% of theory) of the title compound.

LC-MS (Method L1): $R_t$=2.38 min; m/z=359 (M+H)$^+$

1H NMR (400 MHz, Chloroform-d, Method M2) δ 8.74 (s, 1H), 7.77 (t, J=1.8 Hz, 1H), 7.65 (m, 1H), 7.40 (t, J=7.9 Hz, 1H), 7.30-7.23 (m, 1H), 4.62-4.51 (m, 1H), 4.48 (s, 2H), 4.39 (q, J=7.1 Hz, 2H), 1.60 (d, J=7.1 Hz, 6H), 1.41 (t, J=7.1 Hz, 3H).

Intermediates 4G

Ethyl 2-chloro-3-(3,4-difluorophenyl)-7-isopropylpyrazolo[1,5-a]pyrimidine-6-carboxylate (4G-2)

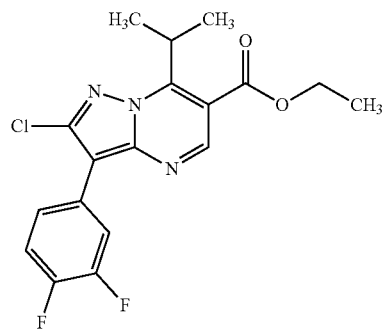 [SMILES: CCOC(=O)c1cnc2c(-c3ccc(F)c(F)c3)c(Cl)nn2c1C(C)C]

A solution of ethyl 2-amino-3-(3,4-difluorophenyl)-7-isopropylpyrazolo[1,5-a]pyrimidine-6-carboxylate (112 mg, 0.31 mmol) in concentrated hydrochloric acid (1.00 mL) was cooled in an ice-salt bath. A solution of sodium nitrite (28 mg, 0.40 mmol) in water (0.14 mL) was added dropwise. The resulting dark-orange mixture was stirred for 1 h while being cooled in the ice-salt bath. The cold mixture was then added dropwise to a suspension of copper(I) chloride (49 mg, 0.50 mmol) in chloroform (1.00 mL) at room temperature. Gas evolution was observed. The reaction mixture was stirred at room temperature for 1 h. Water (5 mL) and chloroform (5 mL) were added. The organic layer was collected via a phase separator. The aqueous layer was extracted with chloroform (2×5 mL). The combined organic layers were concentrated in vacuo. In addition the aqueous layer was extracted with ethyl acetate (50 mL). The organic layer was washed with brine, dried with sodium sulfate and concentrated in vacuo. The residual materials from the evaporation were combined. Purification by flash column chromatography (Method L7; 12 g; heptane, 1%-10% ethyl acetate) and preparative HPLC (Method L11) afforded 32 mg (0.08 mmol; 27% of theory) of the title compound.

LC-MS (Method L12): $R_t$=4.68 min; m/z=380 (M+H)$^+$

1H NMR (400 MHz, Chloroform-d, Method M2) δ 8.86 (s, 1H), 7.78 (m, 1H), 7.66 (m, 1H), 7.37-7.17 (m, 1H), 4.55 (m, 1H), 4.45 (q, J=7.1 Hz, 2H), 1.63 (d, J=7.1 Hz, 6H), 1.44 (t, J=7.1 Hz, 3H).

Ethyl 2-chloro-3-(3-chlorophenyl)-7-isopropylpyrazolo[1,5-a]pyrimidine-6-carboxylate (4G-3)

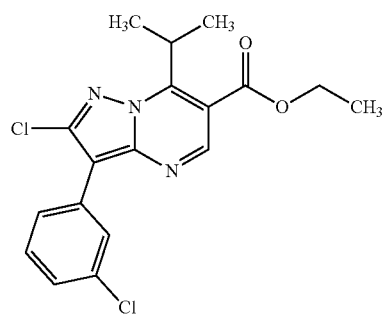 [SMILES: CCOC(=O)c1cnc2c(-c3cccc(Cl)c3)c(Cl)nn2c1C(C)C]

A mixture of ethyl 2-amino-3-(3-chlorophenyl)-7-isopropylpyrazolo[1,5-a]pyrimidine-6-carboxylate (364 mg, 1.014 mmol) in concentrated hydrochloric acid (5.0 mL) was cooled in an ice-salt bath. A solution of sodium nitrite (91 mg, 1.32 mmol) in water (0.5 mL) was added dropwise. The resulting dark-orange mixture was stirred for 1 h while being cooled in the ice-salt bath. The cold mixture was then added dropwise to a suspension of copper(I) chloride (161 mg, 1.62 mmol) in chloroform (3.0 mL) at room temperature. Gas evolution observed. The reaction mixture was stirred at room temperature for 1 h. Water (20 mL) was added and the mixture was extracted with ethyl acetate (2×40 mL) and dichloromethane (20 mL). The combined organic layers were washed with water (2×30 mL) and brine, dried with sodium sulfate and concentrated in vacuo. Purification by flash column chromatography (Method L6; 40 g; heptane, 1%-10% ethyl acetate) and preparative HPLC (Method 11) afforded 74 mg (0.20 mmol; 19% of theory) of the title compound.

LC-MS (Method L1): $R_t$=2.62 min; m/z=378/380 (M+H)$^+$

1H NMR (400 MHz, Chloroform-d, Method M2) δ 8.86 (s, 1H), 7.91 (t, J=1.8 Hz, 1H), 7.83-7.75 (m, 1H), 7.42 (t, J=7.8 Hz, 1H), 7.33 (m, 1H), 4.61-4.50 (m, 1H), 4.44 (q, J=7.1 Hz, 2H), 1.64 (d, J=7.1 Hz, 6H), 1.44 (t, J=7.1 Hz, 3H).

Intermediates 4H

2-Chloro-3-(3,4-difluorophenyl)-7-isopropylpyrazolo[1,5-a]pyrimidine-6-carboxylic acid (4H-2)

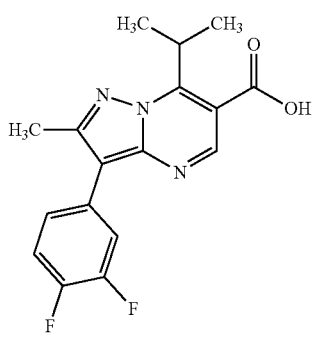 [SMILES: Cc1nn2c(C(C)C)c(C(=O)O)cnc2c1-c1ccc(F)c(F)c1]

To a solution of ethyl 2-chloro-3-(3,4-difluorophenyl)-7-isopropylpyrazolo[1,5-a]pyrimidine-6-carboxylate (32 mg, 0.08 mmol) in tetrahydrofuran (2 mL) was added a solution of lithium hydroxide monohydrate (54 mg, 1.29 mmol) in water (2 mL). After 75 min the reaction mixture was acidified with hydrochloric acid (1.0 M) and extracted with ethyl acetate (2×15 mL). The combined organic layers were washed with brine, dried with sodium sulfate and concentrated in vacuo to afford 30 mg (0.08 mmol; 92% of theory) of the title compound.

LC-MS (Method L1): $R_t$=2.37 min; m/z=352 (M+H)$^+$

2-Chloro-3-(3-chlorophenyl)-7-isoropylpyrazolo[1,5-a]pyrimidine-6-carboxylic acid (4H-3)

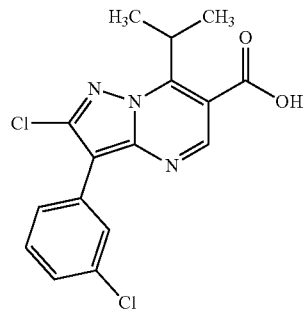 [SMILES: CC(C)c1c(C(=O)O)cnc2c(-c3cccc(Cl)c3)c(Cl)nn12]

To a solution of ethyl 2-chloro-3-(3-chlorophenyl)-7-isopropylpyrazolo[1,5-a]pyrimidine-6-carboxylate (74 mg, 0.20 mmol) in tetrahydrofuran (5 mL) was added a solution of lithium hydroxide monohydrate (123 mg, 2.93 mmol) in water (5 mL). After stirring for 95 min the reaction mixture was acidified by the addition of hydrochloric acid (1.0 M) and was extracted with ethyl acetate (2×15 mL). The combined organic layers were washed with brine, dried with sodium sulfate and concentrated in vacuo to afford 58 mg (0.15 mmol; 77% of theory) of the title compound.

LC-MS (Method L1): $R_t$=2.50 min; m/z=350/352 (M+H)$^+$

1H NMR (400 MHz, Chloroform-d. Method M2) δ 8.94 (s, 1H), 7.92-7.85 (m, 1H), 7.82-7.73 (m, 1H), 7.43 (t, J=7.9 Hz, 1H), 7.38-7.32 (m, 1H), 4.67 (m, 1H), 1.64 (d, J=6.9 Hz, 6H).

Intermediates 5B

Ethyl 3-(2-chloro-6-fluorophenyl)-7-hydroxy-2-methylpyrazolo[1,5-a]pyrimidine-6-carboxylate (5B-1)

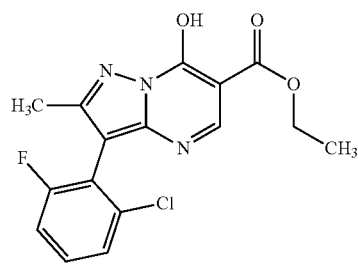 [SMILES: CCOC(=O)c1cnc2c(-c3c(F)cccc3Cl)c(C)nn2c1O]

4-(2-Chloro-6-fluorophenyl)-3-methyl-1H-pyrazol-5-amine (2.1 g, 9.3 mmol) was suspended in 21 mL glacial acetic acid. Then diethyl ethoxymethylenmalonate (2.21 g, 10.2 mmol) was added slowly at room temperature. The mixture was refluxed for 6 hours. After cooling, the precipitate was filtered off and washed with ethanol and diethyl ether to afford an off-white solid (2.0 g, 59.9%) which has been used in the next step without further purification.

1H NMR (400 MHz, DMSO-d6, Method M1): δ 13.11 (s, 1H, OH), 8.42 (s, 1H), 7.59-7.51 (m, 2H), 7.42-7.38 (dt, 1H), 4.27-4.22 (q, 2H), 2.17 (s, 3H), 1.29 (t, 3H).

Intermediates 5C

Ethyl 3-(2-chloro-6-fluorophenyl)-7-methoxy-2-methylpyrazolo[1,5-a]pyrimidine-6-carboxylate

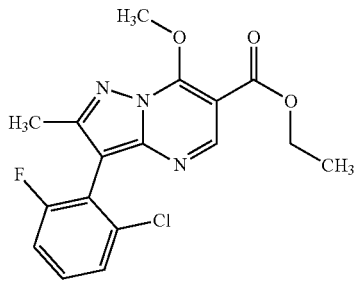 [SMILES: CCOC(=O)c1cnc2c(-c3c(F)cccc3Cl)c(C)nn2c1OC]

Ethyl 3-(2-chloro-6-fluorophenyl)-7-hydroxy-2-methylpyrazolo[1,5-a]pyrimidine-6-carboxylate (2.0 g, 5.71 mmol) was dissolved in 120 mL THF. Sodium hydroxide (0.23 g, 0.71 mmol) dissolved in 48 mL water was added at room temperature and heated at 60° C. for 20 hours. THF has been removed under reduced pressure, the remaining solution was dissolved with water and extracted with ethyl acetate. The organic layer was separated, dried over potassium sulfate and evaporated under reduced pressure. The remaining oil (1.67 g, 75.5%) was used in the next step without further purification.

1H NMR (400 MHz, DMSO-d6, Method M1): δ 8.60 (s, 1H), 7.63-7.54 (m, 2H), 7.46-7.41 (dt, 1H), 4.28-4.22 (q, 2H), 3.42 (s, 3H), 2.09 (s, 3H), 1.29 (t, 3H).

Ethyl 3-(3,5-dichlorophenyl)-7-methoxy-2-methylpyrazolo[1,5-a]pyrimidine-6-carboxylate (5C-2)

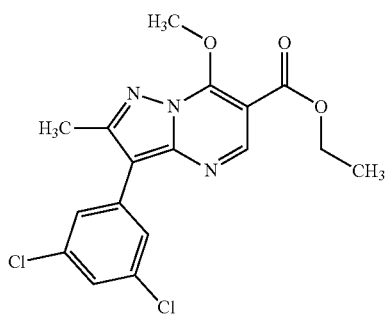 [SMILES: CCOC(=O)c1cnc2c(-c3cc(Cl)cc(Cl)c3)c(C)nn2c1OC]

1H NMR (400 MHz, DMSO-d6, Method M1): δ 8.60 (s, 1H), 7.70 (s, 1H), 7.57 (s, 2H), 4.25 (q, 2H), 3.45 (s, 3H), 2.14 (s, 3H), 1.28 (t, 3H).

Ethyl 3-(3,4-difluorophenyl)-7-methoxy-2-methylpyrazolo[1,5-a]pyrimidine-6-carboxylate (5C-3)

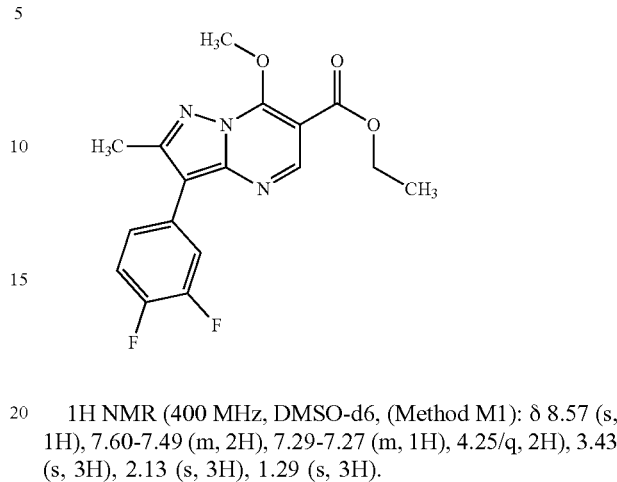

1H NMR (400 MHz, DMSO-d6, (Method M1): δ 8.57 (s, 1H), 7.60-7.49 (m, 2H), 7.29-7.27 (m, 1H), 4.25/q, 2H), 3.43 (s, 3H), 2.13 (s, 3H), 1.29 (s, 3H).

Intermediates 5D 3-(2-Chloro-6-fluorophenyl)-7-methoxy-2-methylpyrazolo[1,5-a]pyrimidine-6-carboxylic Acid (5D-1)

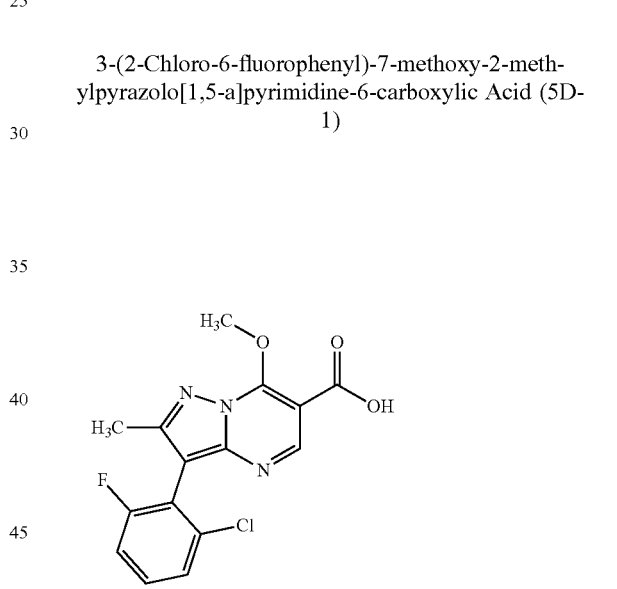

Ethyl 3-(2-chloro-6-fluorophenyl)-7-methoxy-2-methylpyrazolo[1,5-a]pyrimidine-6-carboxylate (1.9 g, 5.22 mmol) was dissolved in THF. Sodium hydroxide (313 mg, 7.83 mmol) dissolved in 8 mL water was added. The mixture was stirred at room temperature overnight and after this evaporated under reduced pressure. The residue was diluted with water and extracted with ethyl acetate. The aqueous layer was separated and acidified with 1 N HCl until pH 3. The occurring precipitate was filtered off and air-dried to afford an off-white solid (1.45 g, 82.5%) which has been used in the next step without further purification.

1H NMR (400 MHz, DMSO-d6, Method M1): δ 12.65 (brs, 1H, OH), 8.70 (s, 1H), 7.65-7.55 (m, 2H), 7.47-7.42 (dt, 1H), 3.46 (s, 3H), 2.11 (s, 3H).

3-(3,5-Dichlorophenyl)-7-methoxy-2-methylpyrazolo[1,5-a]pyrimidine-6-carboxylic acid (5D-2)

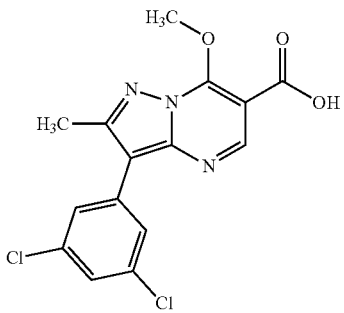 [SMILES: COc1c(C(=O)O)cnc2c(-c3cc(Cl)cc(Cl)c3)c(C)nn12]

Ethyl 3-(3,5-dichlorophenyl)-7-methoxy-2-methylpyrazolo[1,5-a]pyrimidine-6-carboxylate (85 mg, 0.22 mmol) was dissolved in THF. Sodium hydroxide (13 mg, 0.33 mmol) dissolved in 2 mL water was added. The mixture was stirred at 50° C. overnight and after this evaporated under reduced pressure. The residue was diluted with water and extracted with ethyl acetate. The aqueous layer was separated and acidified with 1 N HCl until pH 3. The occurring precipitate was filtered off and air-dried to afford an off-white solid (76 mg, 70.5%) which has been used in the next step without further purification.

1H NMR (400 MHz, DMSO-d6, Method M1): δ 12.65 (brs, 1H, OH), 8.71 (s, 1H), 7.71 (s, 1H), 7.58 (s, 2H), 3.51 (s, 3H), 2.17 (s, 3H).

3-(3,4-Difluorophenyl)-7-methoxy-2-methylpyrazolo{1,5-a}pyrimidine-6-carboxylic acid (5D-3)

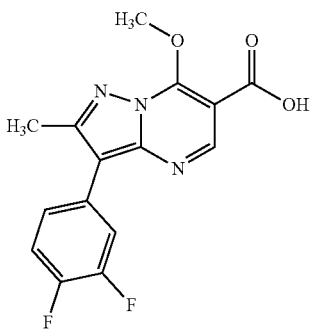 [SMILES: COc1c(C(=O)O)cnc2c(-c3ccc(F)c(F)c3)c(C)nn12]

Ethyl 3-(3,4-difluorophenyl)-7-methoxy-2-methylpyrazolo[1,5-a]pyrimidine-6-carboxylate (115 mg, 0.33 mmol) was dissolved in 35 mL THF. Sodium hydroxide (20 mg, 0.5 mmol) dissolved in 22 mL water was added. The mixture was stirred at room temperature overnight and after this evaporated under reduced pressure. The residue was diluted with water and extracted with ethyl acetate. The aqueous layer was separated and acidified with 1 N HCl until pH 3. The occurring precipitate was filtered off and air-dried to afford an off-white solid (62 mg, 55.7%) which has been used in the next step without further purification.

1H NMR (400 MHz, DMSO-d6, Method M1): δ 12.65 (bs, 1H, OH), 8.71 (s, 1H), 7.62-7.50 (m, 2H), 7.30 (m, 1H), 3.48 (s, 3H), 2.16 (s, 3H).

Intermediates 6B

Ethyl 3-bromo-7-hydroxy-2-methylpyrazolo[1,5-a]pyrimidine-6-carboxylate (6B-1)

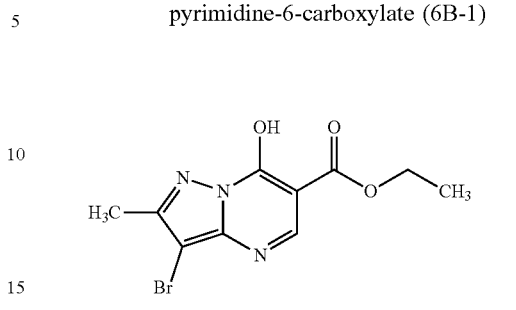

4-Bromo-3-methyl-1H-pyrazol-5-amine (14 g, 79.5 mmol) was suspended in 150 mL glacial acetic acid. Then diethyl (ethoxymethylene)malonate (18.9 g, 87.4 mmol) was added slowly at room temperature. The mixture was refluxed for 6 hours. After cooling, the precipitate was filtered off and washed with ethanol and diethyl ether to afford an off-white solid (16.2 g, 67.4%) which has been used in the next step without further purification.

1H NMR (400 MHz, DMSO-d6, Method M1): δ 13.3 (brs, 1H), 8.36 (s, 1H), 4.26-4.21 (q, 2H), 2.29 (s, 3H), 1.28 (t, 3H).

Intermediates 6C

Ethyl 3-bromo-7-methoxy-2-methylpyrazolo[1,5-a]pyrimidine-6-carboxylate (6C-1)

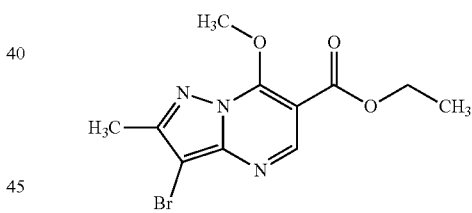

Ethyl 3-bromo-7-hydroxy-2-methylpyrazolo[1,5-a]pyrimidine-6-carboxylate (6 g, 19.9 mmol) and potassium carbonate (5.53 g, 39.9 mmol) were dissolved in 250 mL THF. The reaction mixture was cooled to 0° C. and methyl iodide (8.51 g, 59.9 mmol) was added drop wise. The reaction mixture was stirred at room temperature overnight, followed by addition of further equivalents of methyl iodide (8.51 g, 59.9 mmol) and heating to 60° C. for 8 hours. The reaction was not completed. After addition of water and extraction with ethyl acetate, the insoluble starting material has been removed, and the organic layer was separated, dried over sodium sulfate and the solvents were evaporated under reduced pressure. The remaining off-white solid (1.85 g, 23.6%) has been used in the further steps without purification 1H NMR (400 MHz, DMSO-d6, Method M1): δ 8.60 (s, 1H), 4.26-4.12 (q, 2H), 4.07 (s, 3H), 2.30 (s, 3H), 1.26 (t, 3H).

Intermediates 6D

3-Bromo-7-methoxy-2-methylpyrazolo[1,5-a]pyrimidine-6-carboxylic Acid (6D-1)

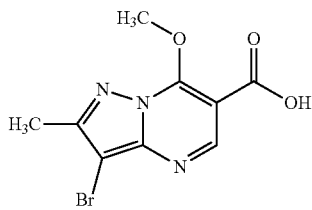 [SMILES: COc1c(C(=O)O)cnc2c(Br)c(C)nn12]

Ethyl 3-bromo-7-methoxy-2-methylpyrazolo[1,5-a]pyrimidine-6-carboxylate (210 mg, 0.48 mmol) was dissolved in THF. Sodium hydroxide (28.9 mg, 0.72 mmol) dissolved in 1.2 mL water was added. The mixture was stirred at room temperature overnight and after this evaporated under reduced pressure. The residue was diluted with water and extracted with ethyl acetate. The aqueous layer was separated and acidified with 1 N HCl until pH 3. The occurring precipitate was filtered off and air-dried to afford an off-white solid (126 mg) which has been used in the next step without further purification.

1H NMR (400 MHz, DMSO-d6, Method M1): δ 12.6 (bs, 1H, OH), 8.71 (s, 1H), 4.11 (s, 3H), 2.33 (s, 3H).

Intermediates 6E

(S)-3-Bromo-N-(chroman-4-yl)-7-methoxy-2-methylpyrazolo[1,5-a]pyrimidine-6-carboxamide

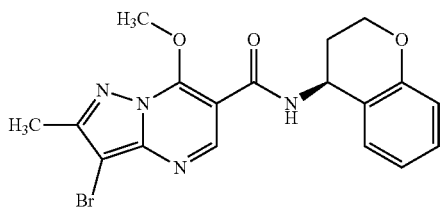 [SMILES: COc1c(C(=O)N[C@H]2CCOc3ccccc32)cnc2c(Br)c(C)nn12]

To a stirred mixture of 3-bromo-7-methoxy-2-methylpyrazolo[1,5-a]pyrimidine-6-carboxylic acid (crude material 75% purity 126 mg, 0.33 mmol), (S)-chroman-4-amine hydrochloride (54.2 mg, 0.36 mmol) and N,N-diisopropylethylamine (64 mg, 0.49 mmol) in dichloromethane (15 mL) were added T3P® (Propylphosphonic anhydride solution 50% in DMF, 210 mg, 0.33 mmol) at room temperature. The resulting mixture was stirred for 48 h. The reaction mixture was diluted with more dichloromethane and mixed with 1 N sodium hydroxide. The dichloromethane phase was separated via a Whatman cartridge. The aqueous phase was extracted again with dichloromethane. The combined extracts were dried via a sodium sulfate/silica gel cartridge and concentrated in vacuo. Purification by flash chromatography with an ethyl acetate/cyclohexane gradient afforded 100 mg (67.6%) of the title compound.

1H NMR (400 MHz, DMSO-d6, Method M1): δ 9.12 (d, 1H, NH), 8.73 (s, 1H), 7.24-7.17 (m, 2H), 6.89 (t, 1H), 6.83 (d, 1H), 5.25-5.20 (m, 1H), 4.32-4.27 (m, 1H), 4.19-4.16 (m, 1H), 4.15 (s, 1H), 2.32 (s, 3H), 2.22-2.18 (m, 1H), 2.07-2.03 (m, 1H).

Intermediates 7A

Ethyl 7-hydroxy-2-methylpyrazolo[1,5-a]pyrimidine-6-carboxylate (7A-1)

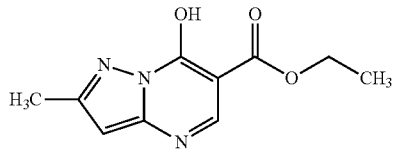 [SMILES: CCOC(=O)c1cnc2cc(C)nn2c1O]

Diethylethoxymethylenemalonate (20.98 mL, 103.82 mmol) was added to a solution of 3-methyl-1H-pyrazol-5-amine (10 g, 103.3 mmol) in acetic acid (90 mL) under nitrogen atmosphere at room temperature. The reaction mixture was refluxed at 105° C. for 2.5 h. The reaction completion was confirmed by TLC. The reaction mixture was cooled to 0-5° C. and stirred for 20 minutes. The precipitated solids were filtered, washed with ethanol (10 mL) and dried to get ethyl 7-hydroxy-2-methylpyrazolo[1,5-a] pyrimi-dine-6-carboxylate (13.5 g, 59.3%) as an off-white solid.

1H NMR (400 MHz, CDCl3, Method M2): δ 12.98 (brs, 1H), 8.52 (s, 1H), 6.13 (s, 1H), 4.22 (q, 2H, J=7.00 Hz), 2.30 (s, 3H), 1.28 (t, 3H, J=7.0 Hz).

Intermediates 7B

Ethyl 7-chloro-2-methylpyrazolo[1,5-a]pyrimidine-6-carboxylate (7B-1)

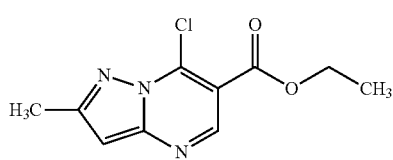 [SMILES: CCOC(=O)c1cnc2cc(C)nn2c1Cl]

Ethyl 7-hydroxy-2-methylpyrazolo[1,5-a]pyrimidine-6-carboxylate (50 g, 226 mmol) was added to phosphorus oxychloride (500 mL) under nitrogen atmosphere at room temperature. The reaction mixture was cooled to 0-5° C. and N,N-diethylaniline (50 mL, 311.6 mmol) was added slowly over 0.5 h at the same temperature (exothermic observed during the addition). The reaction mixture was stirred at 120° C. for 4 h and the reaction completion was confirmed by TLC. The reaction mixture was cooled and concentrated to get a brown residue. The residue was quenched with ice cold water (1.0 L). The resulting cold aqueous solution was extracted with diethylether (3×150 mL), combined organic layers were washed with saturated sodium bicarbonate solution (200 mL) and brine (200 mL), dried over MgSO4 and concentrated to get a brown liquid. The crude product was purified by flash column chromatography using 0-15% of ethyl acetate in petrol ether as eluent to get ethyl 7-chloro-2-methylpyrazolo[1,5-a]pyrimidine-6-carboxylate (25.3 g, 46.8%) as light green solid.

1H NMR (400 MHz, CDCl3, Method M2): δ 8.91 (s, 1H), 6.67 (s, 1H), 4.49 (q, 2H, J=7.0 Hz), 2.62 (s, 3H), 1.47 (t, 3H, J=7.20 Hz).

Intermediates 7C

Ethyl 3-bromo-7-chloro-2-methylpyrazolo[1,5-a]pyrimidine-6-carboxylate (7C-1)

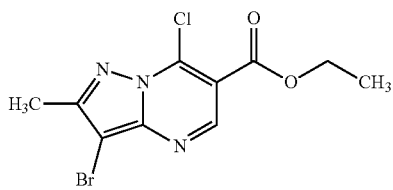 [SMILES: CCOC(=O)c1cnc2c(Br)c(C)nn2c1Cl]

Ethyl 7-chloro-2-methylpyrazolo[1,5-a]pyrimidine-6-carboxylate (20 g, 83 mmol) and sodium acetate (20.7 g, 62 mmol) were dissolved in acetic acid (200 mL) under nitrogen atmosphere. Bromine (13.3 g, 83 mmol) in acetic acid (10 mL) was added drop wise over 20 minutes at room temperature. The reaction mixture was stirred at room temperature for an additional hour and the reaction completion was confirmed by TLC. The reaction mixture was cooled to 0° C. and 500 mL of water were added. The precipitated solids were filtered off and dried to get ethyl 3-bromo-7-chloro-2-methylpyrazolo[1,5-a]pyrimidine-6-carboxylate (10.9 g, 41%) as light yellow solid.

1H NMR (400 MHz, CDCl3, Method M2): δ 8.97 (s, 1H), 4.49 (q, J=7.20 Hz, 2H), 2.61 (s, 3H), 1.46 (t, 3H, J=7.20 Hz).

Intermediates 7D

Ethyl 3-bromo-7-(dimethylamino)-2-methylpyrazolo[1,5-a]pyrimidine-6-carboxylate (7D-1)

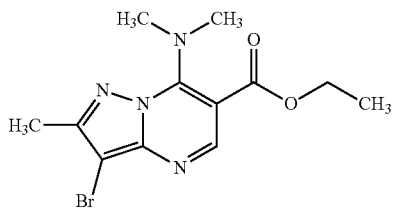 [SMILES: CCOC(=O)c1cnc2c(Br)c(C)nn2c1N(C)C]

A 250 mL pressure tube was charged with ethyl 3-bromo-7-chloro-2-methylpyrazolo[1,5-a]pyrimidine-6-carboxylate (20 g, 62 mmol) in ethanol (100 mL) under nitrogen atmosphere at room temperature. N,N-dimethylamine (2M in THF, 39.4 mL, 78.8 mmol) was added drop wise over 20 minutes. The tube was sealed and the mixture was stirred at room temperature for 2.5 h. Then the mixture was concentrated and the crude product was purified by flash column chromatography using 0-19% of ethyl acetate in petrol ether to get ethyl 3-bromo-7-(dimethylamino)-2-methylpyrazolo[1,5-a]pyrimidine-6-carboxylate (10.3 g, 50%) as an off-white solid.

1H NMR (400 MHz, CDCl3, Method M2): δ 8.68 (s, 1H), 4.39 (q, 2H, J=7.12 Hz), 3.31 (s, 6H), 2.47 (s, 3H), 1.39 (t, 3H, J=7.12 Hz).

Ethyl 3-bromo-2-methyl-7-(morpholin-4-yl)pyrazolo[1,5-a]pyrimidine-6-carboxylate (7D-2)

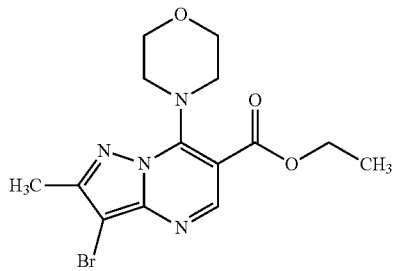 [SMILES: CCOC(=O)c1cnc2c(Br)c(C)nn2c1N1CCOCC1]

A microwave tube was charged with ethyl 3-bromo-7-chloro-2-methylpyrazolo[1,5-a]pyrimidine-6-carboxylate (2 g, 6.27 mmol) in ethanol (10 mL) under nitrogen atmosphere at room temperature. Morpholine (0.82 g, 9.4 mmol) was added and the reaction mixture was treated in a microwave device (Biotage) for 30 min at 100° C. Then the mixture was concentrated and the crude product was purified by flash column chromatography using a n-hexane/ethyl acetate gradient to get ethyl 3-bromo-2-methyl-7-(morpholin-4-yl)pyrazolo[1,5-a]pyrimidine-6-carboxylate (1.66 g, 71.6%) as an off-white solid.

1H NMR (400 MHz, DMSO-d6, Method M1): δ 8.60 (s, 1H), 4.36-4.30 (q, 2H), 3.83-3.81 (m, 4H), 3.63-3.60 (m, 4H), 2.40 (s, 3H), 1.40 (t, 3H).

Intermediates 7E

3-Bromo-2-methyl-7-(morpholin-4-yl)pyrazolo[1,5-a]pyrimidine-6-carboxylic Acid (7E-2)

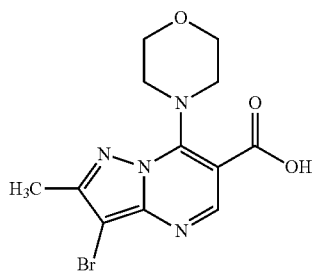 [SMILES: Cc1nn2c(N3CCOCC3)c(C(=O)O)cnc2c1Br]

Ethyl 3-bromo-2-methyl-7-(morpholin-4-yl)pyrazolo[1,5-a]pyrimidine-6-carboxylate (500 mg, 1.35 mmol) was dissolved in 25 mL dichloromethane and cooled to −10° C. BBr3 (10.8 mL 1 M in dichloromethane, 10.8 mmol) was added slowly at the same temperature. The reaction mixture was kept at −10° C. for 1 hour and the allowed to warm to room temperature overnight. The reaction mixture was quenched with 35 mL water under cooling. The organic phase was separated, dried over sodium sulfate and evaporated. Some solid material appears in the aqueous phase, which has been filtered-off and dried. The combined raw material of both phases has been used without purification in the next step.

1H NMR (400 MHz, DMSO-d6, Method M1): δ 13.10 (bs, COOH), 8.62 (s, 1H), 3.82 (m, 4H), 3.63 (m, 4H), 2.40 (s, 3H).

Intermediates 7F

3-Bromo-N-[(4S)-3,4-dihydro-2H-chromen-4-yl]-2-methyl-7-(morpholin-4-yl)pyrazolo[1,5-a]pyrimidine-6-carboxamide (7F-2)

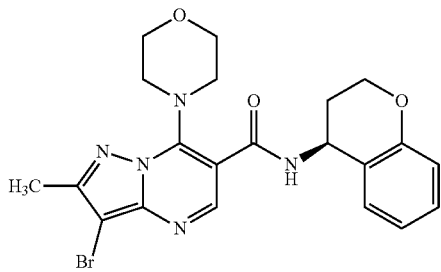 [SMILES: Cc1nn2c(N3CCOCC3)c(C(=O)N[C@H]3CCOc4ccccc43)cnc2c1Br]

To a stirred mixture of 3-bromo-2-methyl-7-(morpholin-4-yl)pyrazolo[1,5-a]pyrimidine-6-carboxylic acid (crude material 60% purity 430 mg, 0.75 mmol), (S)-chroman-4-amine hydrochloride (168 mg, 0.9 mmol) and N,N-diisopropylethylamine (195 mg, 1.51 mmol) in dichloromethane (15 mL) were added N-(3-dimethylaminopropyl)-N-ethylcarbodiimide hydrochloride (145 mg, 0.75 mmol), 1-hydroxy-1H-benzotriazole (51 mg, 0.37 mmol) and 4-N,N-dimethylamino pyridine (46.2 mg, 0.37 mmol) at room temperature. The resulting mixture was stirred overnight. The reaction mixture was mixed with water (50 mL) and the dichloromethane phase was separated via a Whatman cartridge. The aqueous phase was extracted again with dichloromethane. The combined extracts were dried via a sodium sulfate/silica gel cartridge and concentrated in vacuo. Purification by flash chromatography with an ethyl acetate/cyclohexane gradient afforded 310 mg (86.8%) of the title compound.

1H NMR (400 MHz, DMSO-d6, Method M1): b 9.05 (d, 1H, NH), 8.35 (s, 1H), 7.34 (d, 1H), 7.19 (t, 1H), 6.92 (t, 1H), 6.81 (d, 1H), 5.22-5.18 (m, 1H), 4.30-4.20 (m, 2H), 3.82-3.79 (m, 4H), 3.59-3.58 (m, 4H), 2.40 (s, 3H), 2.23-2.17 (m, 1H), 2.08-2.03 (m, 1H).

Intermediates 8A

Ethyl 3-(2,3-dichlorophenyl)-7-(dimethylamino)-2-methylpyrazolo[1,5-a]pyrimidine-6-carboxylate (8A-1)

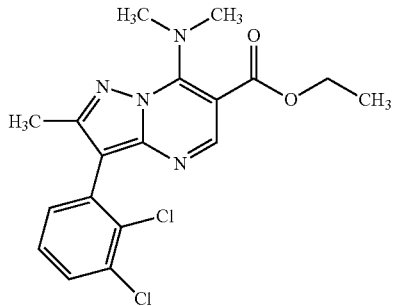 [SMILES: CCOC(=O)c1cnc2c(-c3cccc(Cl)c3Cl)c(C)nn2c1N(C)C]

A microwave tube was charged with 25 mL dioxane, ethyl 3-bromo-7-(dimethylamino)-2-methylpyrazolo[1,5-a]pyrimi-dine-6-carboxylate (500 mg, 1.52 mmol), 2,3-dichlorophenyl boronic acid (292 mg, 1.52 mmol), aqueous cesium carbonate solution (996 mg, 3.05 mmol in 2.98 mL water) and (1,1'-bis(diphenylphosphino)-ferrocene-palladium-dichloromethane complex (112 mg, 0.15 mmol). The reaction mixture was degassed with argon for 5 min and was treated in a microwave device (Biotage) for 30 min at 100° C. The crude mixture was filtered and washed through a silica gel/sodium sulfate cartridge. The solvents of the filtrate were evaporated under reduced pressure, the remaining raw material was purified by flash column chromatography using a n-hexane/ethyl acetate gradient to get ethyl 3-(2,3-dichlorophenyl)-7-(dimethylamino)-2-methylpyrazolo[1,5-a]pyrimidine-6-carboxylate (354 mg, 29.5%) as an off-white solid.

1H NMR (400 MHz, DMSO-d6, Method M1): δ 8.74 (s, 1H), 7.70-7.68 (dd, 1H), 7.47-7.39 (m, 2H), 4.35-4.29 (q, 2H), 3.28 (s, 6H), 2.32 (s, 3H), 1.33 (t, 3H).

Ethyl 3-(2,3-dichlorophenyl)-2-methyl-7-(morpholin-4-yl)pyrazolo[1,5-a]pyrimidine-6-carboxylate (8A-2)

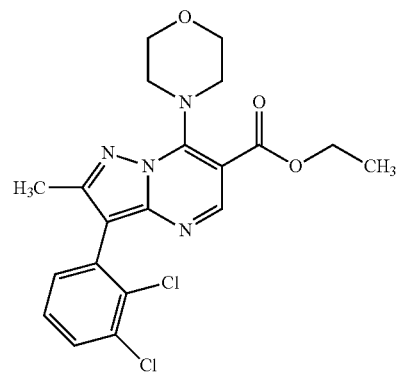 [SMILES: CCOC(=O)c1cnc2c(-c3cccc(Cl)c3Cl)c(C)nn2c1N1CCOCC1]

A microwave tube was charged with 25 mL dioxane, ethyl 3-bromo-2-methyl-7-(morpholin-4-yl)pyrazolo[1,5-a]pyrimidine-6-carboxylate (700 mg, 1.89 mmol), 2,3-dichlorophenyl boronic acid (452 mg, 2.37 mmol), aqueous sodium bicarbonate solution (1.67 g, 15.7 mmol in 7.9 mL water) and (1,1'-bis(diphenylphosphino)-ferrocene-palladium-chloride (115 mg, 0.15 mmol). The reaction mixture was degassed with argon for 5 min and was treated in a microwave device (Biotage) for 30 min at 100° C. The crude mixture was filtered and washed through a silica gel/sodium sulfate cartridge. The solvents of the filtrate were evaporated under reduced pressure, the remaining raw material was purified by suspension into DMF and filtration to get ethyl 3-(2,3-dichlorophenyl)-2-methyl-7-(morpholin-4-yl)pyrazolo[1,5-a]pyrimidine-6-carboxylate (150 mg, 17.5%) as off-white solid.

1H NMR (400 MHz, DMSO-d6, Method M1): δ (broad signals) 8.53 (s, 1H), 7.70 (d, 1H), 7.45-7.42 (m, 2H), 4.34 (q, 2H), 3.86 (m, 4H), 3.67 (m, 4H), 2.33 (s, 3H), 1.33 (t, 3H).

143

Intermediates 8B

3-(2,3-Dichlorophenyl)-7-(dimethylamino)-2-methylpyrazolo[1,5-a]pyrimidine-6-carboxylic Acid (8B-1)

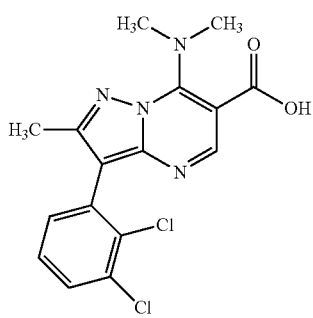 [SMILES: Cc1nn2c(N(C)C)c(C(=O)O)cnc2c1-c1cccc(Cl)c1Cl]

Ethyl 3-(2,3-dichlorophenyl)-7-(dimethylamino)-2-methylpyrazolo[1,5-a]pyrimidine-6-carboxylate (165 mg, 0.41 mmol) was dissolved in 6.85 mL dichloromethane and cooled to −10° C. BBr$_3$ (0.63 mL 1 M in dichloromethane, 0.63 mmol) was added slowly at the same temperature. The reaction mixture was kept at −10° C. for 1 hour and the allowed to warm to room temperature overnight. The reaction mixture was quenched with 10 mL water under cooling. The organic phase was separated, dried over sodium sulfate and evaporated. The remaining oil was purified by reverse phase flash chromatography with an acetonitrile/water gradient to afford a yellow oil (38 mg, 24.8%).

1H NMR (400 MHz, DMSO-d6, Method M1): δ 13.1 (bs, OH), 8.48 (s, 1H), 7.69-7.67 (dd, 1H), 7.46-7.39 (m, 2H), 3.28 (s, 6H), 2.30 (s, 3H).

144

3-(2,3-Dichlorophenyl)-2-methyl-7-(morpholin-4-yl)pyrazolo[1,5-a]pyrimidine-6-carboxylic Acid (8B-2)

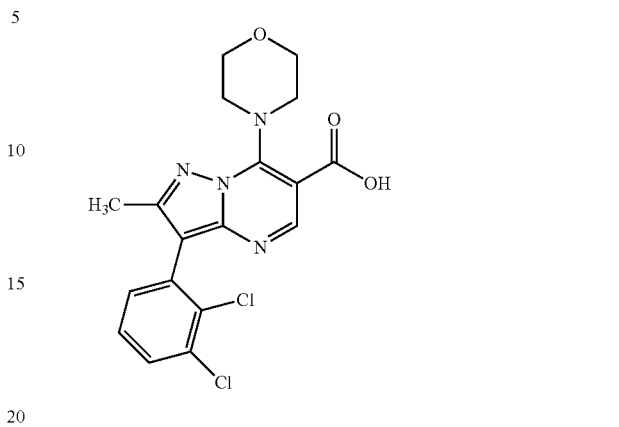

Ethyl 3-(2,3-dichlorophenyl)-2-methyl-7-(morpholin-4-yl)pyrazolo[1,5-a]pyrimidine-6-carboxylate (181.5 mg, 0.41 mmol) was dissolved in 12 mL dichloromethane and cooled to −10° C. BBr$_3$ (3.34 mL 1 M in dichloromethane, 3.33 mmol) was added slowly at the same temperature. The reaction mixture was kept at −10° C. for 1 hour and the allowed to warm to room temperature overnight. The reaction mixture was quenched with 35 mL water under cooling. The organic phase was separated, dried over sodium sulfate and evaporated. Some solid material appears in the aqueous phase, which has been filtered-off and dried. The combined raw material of the organic phase and the filtration step was purified by reverse phase flash chromatography with an acetonitrile/water gradient to afford an off-white solid (40 mg, 23.1%).

1H NMR (400 MHz, DMSO-d6, Method M1): δ 8.47 (s, 1H), 7.69-7.66 (dd, 1H), 7.46-7.34 (m, 2H), 3.83 (m, broad signal, 4H), 3.67 (m, broad signal, 4H), 2.31 (s, 3H).

TABLE 1

Examples

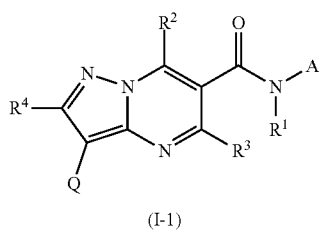

(I-1)

| Number | R1 | R2 | R3 | R4 | Q | Chiral Descriptor A | A | logP (Method L0) [a] |
|---|---|---|---|---|---|---|---|---|
| 1 | H | Isopropyl | H | Methyl | 3-(Trifluoromethyl)phenyl | rac | 2,3-Dihydro-1H-inden-1-yl | 5.29 |
| 2 | H | Isopropyl | H | Methyl | 3-(Trifluoromethyl)phenyl | rac | 1,2,3,4-Tetrahydronaphthalin-1-yl | 5.59 |
| 3 | H | Isopropyl | H | Methyl | 3-(Trifluoromethyl)phenyl | (S) | 1,2,3,4-Tetrahydronaphthalin-1-yl | 5.59 |
| 4 | H | Isopropyl | H | Methyl | 3-(Trifluoromethyl)phenyl | (S) | 2,3-Dihydro-1H-inden-1-yl | 5.3 |
| 5 | H | Isopropyl | H | Methyl | 3-(Trifluoromethyl)phenyl | (S) | 7-Methyl-1,2,3,4-tetrahydronaphthalin-1-yl | 5.99 |
| 6 | H | Isopropyl | H | Methyl | 3-(Trifluoromethyl)phenyl | (S) | 3,4-Dihydro-2H-chromen-4-yl | 5.03 |
| 7 | H | Isopropyl | H | Methyl | 3,5-Dichlorochloroophenyl | (S) | 1,2,3,4-Tetrahydronaphthalin-1-yl | 6.39 |
| 8 | H | Isopropyl | H | Methyl | 3,5-Dichlorophenyl | (S) | 2,3-Dihydro-1H-inden-1-yl | |
| 9 | H | Methyl | H | Methyl | 2-Chlorophenyl | (S) | 1,2,3,4-Tetrahydronaphthalin-1-yl | |
| 10 | H | Isopropyl | H | H | 3,5-Dichlorophenyl | (S) | 2,3-Dihydro-1H-inden-1-yl | |
| 11 | H | Isopropyl | H | H | 3,5-Dichlorophenyl | (S) | 1,2,3,4-Tetrahydronaphthalin-1-yl | |
| 12 | H | H | H | H | 3-(Trifluoromethyl)phenyl | (S) | 2,3-Dihydro-1H-inden-1-yl | |
| 13 | H | H | H | H | 4-Chlorophenyl | (S) | 2,3-Dihydro-1H-inden-1-yl | |
| 14 | H | Methyl | H | Methyl | 2-Chlorophenyl | (S) | 2,3-Dihydro-1H-inden-1-yl | |

TABLE 1-continued

Examples $$\text{(I-1)}$$

Structure: pyrazolo[1,5-a]pyrimidine-6-carboxamide with substituents R1 (on amide N), R2 (at 7-position), R3 (at 5-position), R4 (at 2-position), Q (at 3-position), A (on amide N).

| Number | R1 | R2 | R3 | R4 | Q | Chiral Descriptor A | A | logP (Method L0) [a] |
|---|---|---|---|---|---|---|---|---|
| 15 | H | Methyl | H | Methyl | 3-(Trifluoromethyl)phenyl | (S) | 1,2,3,4-Tetrahydronaphthalin-1-yl | |
| 16 | H | Methyl | H | Methyl | 3-(Trifluoromethyl)phenyl | (S) | 2,3-Dihydro-1H-inden-1-yl | |
| 17 | H | H | H | Methyl | 3,5-Dichlorophenyl | (S) | 2,3-Dihydro-1H-inden-1-yl | |
| 18 | H | H | H | Methyl | 3-(Trifluoromethyl)phenyl | (S) | 2,3-Dihydro-1H-inden-1-yl | |
| 19 | H | Isopropyl | H | Methyl | 2-Chlorophenyl | (S) | 1,2,3,4-Tetrahydronaphthalin-1-yl | |
| 20 | H | Isopropyl | H | Methyl | 2-Chlorophenyl | (S) | 2,3-Dihydro-1H-inden-1-yl | |
| 21 | H | Isopropyl | H | H | 2-Chlorophenyl | (S) | 1,2,3,4-Tetrahydronaphthalin-1-yl | |
| 22 | H | H | H | H | 2-Chlorophenyl | (S) | 2,3-Dihydro-1H-inden-1-yl | |
| 23 | H | Isopropyl | H | H | 4-Chlorophenyl | (S) | 2,3-Dihydro-1H-inden-1-yl | |
| 24 | H | Isopropyl | H | H | 2-Chlorophenyl | (S) | 2,3-Dihydro-1H-inden-1-yl | |
| 25 | H | Isopropyl | H | H | 4-Chlorophenyl | (S) | 1,2,3,4-Tetrahydronaphthalin-1-yl | |
| 26 | H | Methyl | H | H | 3,5-Dichlorophenyl | (S) | 1,2,3,4-Tetrahydronaphthalin-1-yl | |
| 27 | H | Methyl | H | Methyl | 4-Chlorophenyl | (S) | 2,3-Dihydro-1H-inden-1-yl | |
| 28 | H | Methyl | H | Methyl | 4-Chlorophenyl | (S) | 1,2,3,4-Tetrahydronaphthalin-1-yl | |
| 29 | H | Isopropyl | H | Methyl | 4-Chlorophenyl | (S) | 1,2,3,4-Tetrahydronaphthalin-1-yl | |
| 30 | H | H | H | Methyl | 3-Chlorophenyl | (S) | 2,3-Dihydro-1H-inden-1-yl | |
| 31 | H | Methyl | H | H | 4-Chlorophenyl | (S) | 2,3-Dihydro-1H-inden-1-yl | |
| 32 | H | Isopropyl | H | Methyl | 4-Chlorophenyl | (S) | 2,3-Dihydro-1H-inden-1-yl | |
| 33 | H | H | H | Methyl | 4-Chlorophenyl | (S) | 2,3-Dihydro-1H-inden-1-yl | |
| 34 | H | H | H | H | 3-Chlorophenyl | (S) | 2,3-Dihydro-1H-inden-1-yl | |
| 35 | H | Methyl | H | H | 3-(Trifluoromethyl)phenyl | (S) | 2,3-Dihydro-1H-inden-1-yl | |
| 36 | H | Isopropyl | H | H | 3-Chlorophenyl | (S) | 1,2,3,4-Tetrahydronaphthalin-1-yl | |
| 37 | H | Isopropyl | H | H | 3-(Trifluoromethyl)phenyl | (S) | 2,3-Dihydro-1H-inden-1-yl | |
| 38 | H | Methyl | H | H | 3-(Trifluoromethyl)phenyl | (S) | 1,2,3,4-Tetrahydronaphthalin-1-yl | |
| 39 | H | Isopropyl | H | H | 3-(Trifluoromethyl)phenyl | (S) | 1,2,3,4-Tetrahydronaphthalin-1-yl | |
| 40 | H | Isopropyl | H | H | 3-Chlorophenyl | (S) | 2,3-Dihydro-1H-inden-1-yl | |
| 41 | H | Methyl | H | H | 4-Chlorophenyl | (S) | 1,2,3,4-Tetrahydronaphthalin-1-yl | |
| 42 | H | Methyl | H | H | 2-Chlorophenyl | (S) | 1,2,3,4-Tetrahydronaphthalin-1-yl | |
| 43 | H | Methyl | H | H | 2-Chlorophenyl | (S) | 2,3-Dihydro-1H-inden-1-yl | |
| 44 | H | Methyl | H | H | 3-Chlorophenyl | (S) | 1,2,3,4-Tetrahydronaphthalin-1-yl | 4.33 |
| 45 | H | Isopropyl | H | Methyl | 3-Chlorophenyl | (S) | 1,2,3,4-Tetrahydronaphthalin-1-yl | 5.51 |
| 46 | H | Methyl | H | Methyl | 3-Chlorophenyl | (S) | 1,2,3,4-Tetrahydronaphthalin-1-yl | 4.42 |
| 47 | H | H | H | H | 3,5-Dichlorophenyl | (S) | 2,3-Dihydro-1H-inden-1-yl | 4.74 |
| 48 | H | Isopropyl | H | Trifluoromethyl | 3-Chlorophenyl | (S) | 2,3-Dihydro-1H-inden-1-yl | 5.46 |
| 49 | H | Isopropyl | H | Trifluoromethyl | 4-Chlorophenyl | (S) | 2,3-Dihydro-1H-inden-1-yl | 5.48 |
| 50 | H | H | H | Trifluoromethyl | 3-Chlorophenyl | (S) | 2,3-Dihydro-1H-inden-1-yl | 4.57 |
| 51 | H | Isopropyl | H | Trifluoromethyl | 3-Chlorophenyl | (S) | 1,2,3,4-Tetrahydronaphthalin-1-yl | 5.74 |
| 52 | H | Methyl | H | H | 3-Chlorophenyl | (S) | 2,3-Dihydro-1H-inden-1-yl | 4.04 |
| 53 | H | Methyl | H | Trifluoromethyl | 4-Chlorophenyl | (S) | 1,2,3,4-Tetrahydronaphthalin-1-yl | 4.97 |
| 54 | H | Isopropyl | H | Trifluoromethyl | 4-Chlorophenyl | (S) | 1,2,3,4-Tetrahydronaphthalin-1-yl | 5.76 |
| 55 | H | Methyl | H | Trifluoromethyl | 3-Chlorophenyl | (S) | 2,3-Dihydro-1H-inden-1-yl | 4.68 |
| 56 | H | Isopropyl | H | Trifluoromethyl | 3-(Trifluoromethyl)phenyl | (S) | 1,2,3,4-Tetrahydronaphthalin-1-yl | 5.8 |
| 57 | H | Methyl | H | Trifluoromethyl | 4-Chlorophenyl | (S) | 2,3-Dihydro-1H-inden-1-yl | 4.7 |
| 58 | H | Methyl | H | Chloro | 3-Chlorophenyl | (S) | 1,2,3,4-Tetrahydronaphthalin-1-yl | 4.9 |
| 59 | H | Methyl | H | Methyl | 3-Chlorophenyl | (S) | 2,3-Dihydro-1H-inden-1-yl | 4.12 |
| 60 | H | Methyl | H | Methyl | 3,5-Dichlorophenyl | (S) | 2,3-Dihydro-1H-inden-1-yl | 4.96 |
| 61 | H | Methyl | H | Methyl | 3,5-Dichlorophenyl | (S) | 1,2,3,4-Tetrahydronaphthalin-1-yl | 5.29 |
| 62 | H | H | H | Methyl | 2-Chlorophenyl | (S) | 2,3-Dihydro-1H-inden-1-yl | 3.52 |
| 63 | H | H | H | Chloro | 4-Chlorophenyl | (S) | 2,3-Dihydro-1H-inden-1-yl | |
| 64 | H | Isopropyl | H | Chloro | 3,5-Dichlorophenyl | (S) | 1,2,3,4-Tetrahydronaphthalin-1-yl | 6.69 |
| 65 | H | Methyl | H | H | 3,5-Dichlorophenyl | (S) | 2,3-Dihydro-1H-inden-1-yl | 4.84 |
| 66 | H | Methyl | H | Chloro | 3,5-Dichlorophenyl | (S) | 2,3-Dihydro-1H-inden-1-yl | 5.47 |
| 67 | H | H | H | Chloro | 3,5-Dichlorophenyl | (S) | 2,3-Dihydro-1H-inden-1-yl | 5.39 |
| 68 | H | Methyl | H | Chloro | 3,5-Dichlorophenyl | (S) | 1,2,3,4-Tetrahydronaphthalin-1-yl | 5.78 |
| 69 | H | Methyl | H | Chloro | 3-(Trifluoromethyl)phenyl | (S) | 1,2,3,4-Tetrahydronaphthalin-1-yl | 5.03 |

TABLE 1-continued

Examples $$\text{(I-1)}$$

| Number | R1 | R2 | R3 | R4 | Q | Chiral Descriptor A | A | logP (Method L0) [a] |
|---|---|---|---|---|---|---|---|---|
| 70 | H | Isopropyl | H | Chloro | 3-(Trifluoromethyl)phenyl | (S) | 2,3-Dihydro-1H-inden-1-yl | 5.55 |
| 71 | H | Methyl | H | Chloro | 3-(Trifluoromethyl)phenyl | (S) | 2,3-Dihydro-1H-inden-1-yl | 4.73 |
| 72 | H | Isopropyl | H | Chloro | 3-(Trifluoromethyl)phenyl | (S) | 1,2,3,4-Tetrahydronaphthalin-1-yl | 5.85 |
| 73 | H | Isopropyl | H | Chloro | 4-Chlorophenyl | (S) | 2,3-Dihydro-1H-inden-1-yl | 5.47 |
| 74 | H | Methyl | H | Chloro | 2-Chlorophenyl | (S) | 2,3-Dihydro-1H-inden-1-yl | 3.99 |
| 75 | H | Methyl | H | Chloro | 3-Chlorophenyl | (S) | 2,3-Dihydro-1H-inden-1-yl | 4.6 |
| 76 | H | Isopropyl | H | Chloro | 4-Chlorophenyl | (S) | 1,2,3,4-Tetrahydronaphthalin-1-yl | 5.79 |
| 77 | H | Methyl | H | Chloro | 2-Chlorophenyl | (S) | 1,2,3,4-Tetrahydronaphthalin-1-yl | 4.26 |
| 78 | H | Isopropyl | H | Chloro | 2-Chlorophenyl | (S) | 1,2,3,4-Tetrahydronaphthalin-1-yl | 5.07 |
| 79 | H | Isopropyl | H | Chloro | 2-Chlorophenyl | (S) | 2,3-Dihydro-1H-inden-1-yl | 4.79 |
| 80 | H | H | H | Trifluoromethyl | 4-Chlorophenyl | (S) | 2,3-Dihydro-1H-inden-1-yl | 4.61 |
| 81 | H | Methyl | H | Trifluoromethyl | 2-Chlorophenyl | (S) | 2,3-Dihydro-1H-inden-1-yl | 4.24 |
| 82 | H | Methyl | H | Trifluoromethyl | 3,5-Dichlorophenyl | (S) | 1,2,3,4-Tetrahydronaphthalin-1-yl | 5.66 |
| 83 | H | Methyl | H | Trifluoromethyl | 3-(Trifluoromethyl)phenyl | (S) | 1,2,3,4-Tetrahydronaphthalin-1-yl | 5.03 |
| 84 | H | H | H | Trifluoromethyl | 2-Chlorophenyl | (S) | 2,3-Dihydro-1H-inden-1-yl | 4.15 |
| 85 | H | Methyl | H | Trifluoromethyl | 3-(Trifluoromethyl)phenyl | (S) | 2,3-Dihydro-1H-inden-1-yl | 4.77 |
| 86 | H | Methyl | H | Trifluoromethyl | 3-Chlorophenyl | (S) | 1,2,3,4-Tetrahydronaphthalin-1-yl | 4.94 |
| 87 | H | H | H | Trifluoromethyl | 3-(Trifluoromethyl)phenyl | (S) | 2,3-Dihydro-1H-inden-1-yl | 4.66 |
| 88 | H | Isopropyl | H | Trifluoromethyl | 2-Chlorophenyl | (S) | 2,3-Dihydro-1H-inden-1-yl | 4.96 |
| 89 | H | Isopropyl | H | Trifluoromethyl | 2-Chlorophenyl | (S) | 1,2,3,4-Tetrahydronaphthalin-1-yl | 5.24 |
| 90 | H | Methyl | H | Trifluoromethyl | 2-Chlorophenyl | (S) | 1,2,3,4-Tetrahydronaphthalin-1-yl | 4.5 |
| 91 | H | Isopropyl | H | Trifluoromethyl | 3-(Trifluoromethyl)phenyl | (S) | 2,3-Dihydro-1H-inden-1-yl | 5.51 |
| 92 | H | Isopropyl | H | Methyl | 2-Fluorophenyl | (S) | 3,4-Dihydro-2H-chromen-4-yl | 4.18 |
| 93 | H | Isopropyl | H | Methyl | 2-Fluorophenyl | (S) | 6-Chloro-3,4-dihydro-2H-chromen-4-yl | 4.67 |
| 94 | H | Isopropyl | H | Methyl | 2-Fluorophenyl | (S) | 1,2,3,4-Tetrahydronaphthalin-1-yl | 4.72 |
| 95 | H | Isopropyl | H | Methyl | 2-Fluorophenyl | (S) | 2,3-Dihydro-1H-inden-1-yl | 4.41 |
| 96 | H | Isopropyl | H | Methyl | 2,6-Difluorophenyl | (S) | 3,4-Dihydro-2H-chromen-4-yl | 4.13 |
| 97 | H | Isopropyl | H | Methyl | 2,6-Difluorophenyl | (S) | 6-Chloro-3,4-dihydro-2H-chromen-4-yl | 4.61 |
| 98 | H | Isopropyl | H | Methyl | 2,6-Difluorophenyl | (S) | 1,2,3,4-Tetrahydronaphthalin-1-yl | 4.67 |
| 99 | H | Isopropyl | H | Methyl | 2,6-Difluorophenyl | (S) | 2,3-Dihydro-1H-inden-1-yl | 4.37 |
| 100 | H | Isopropyl | H | Methyl | 3,4-Difluorophenyl | (S) | 3,4-Dihydro-2H-chromen-4-yl | 4.56 |
| 101 | H | Isopropyl | H | Methyl | 3,4-Difluorophenyl | (S) | 6-Chloro-3,4-dihydro-2H-chromen-4-yl | 5.03 |
| 102 | H | Isopropyl | H | Methyl | 3,4-Difluorophenyl | (S) | 1,2,3,4-Tetrahydronaphthalin-1-yl | 5.14 |
| 103 | H | Isopropyl | H | Methyl | 3,4-Difluorophenyl | (S) | 2,3-Dihydro-1H-inden-1-yl | 4.82 |
| 104 | H | Isopropyl | H | Methyl | 2-Chlorophenyl | (S) | 6-Chloro-3,4-dihydro-2H-chromen-4-yl | 4.87 |
| 105 | H | Isopropyl | H | Methyl | 3-Chlorophenyl | (S) | 6-Chloro-3,4-dihydro-2H-chromen-4-yl | 5.36 |
| 106 | H | Isopropyl | H | Methyl | 4-Chlorophenyl | (S) | 6-Chloro-3,4-dihydro-2H-chromen-4-yl | 5.36 |
| 107 | H | Isopropyl | H | Methyl | 2-Chlorophenyl | (S) | 3,4-Dihydro-2H-chromen-4-yl | 4.37 |
| 108 | H | Isopropyl | H | Methyl | 2,6-Difluorophenyl | (S) | 7-Methyl-1,2,3,4-tetrahydronaphthalin-1-yl | 5.09 |
| 109 | H | Isopropyl | H | Methyl | 3-Chlorophenyl | (S) | 7-Methyl-1,2,3,4-tetrahydronaphthalin-1-yl | 5.9 |
| 110 | H | Isopropyl | H | Methyl | 2-Fluorophenyl | (S) | 7-Methyl-1,2,3,4-tetrahydronaphthalin-1-yl | 5.16 |
| 111 | H | Isopropyl | H | Methyl | 2-Chlorophenyl | (S) | 7-Methyl-1,2,3,4-tetrahydronaphthalin-1-yl | 5.37 |
| 112 | H | Isopropyl | H | Methyl | 3,4-Difluorophenyl | (S) | 7-Methyl-1,2,3,4-tetrahydronaphthalin-1-yl | 5.55 |

TABLE 1-continued

Examples $$\text{(I-1)}$$

| Number | R1 | R2 | R3 | R4 | Q | Chiral Descriptor A | A | logP (Method L0) [a] |
|---|---|---|---|---|---|---|---|---|
| 113 | H | Isopropyl | H | Methyl | 4-Chlorophenyl | (S) | 7-Methyl-1,2,3,4-tetrahydro-naphthalin-1-yl | 5.88 |
| 114 | H | Isopropyl | H | Methyl | 2,5-Difluorophenyl | (S) | 6-Chloro-3,4-dihydro-2H-chromen-4-yl | 4.82 |
| 115 | H | Isopropyl | H | Methyl | 2,5-Difluorophenyl | (S) | 1,2,3,4-Tetrahydronaphthalin-1-yl | 4.89 |
| 116 | H | Isopropyl | H | Methyl | 2,5-Difluorophenyl | (S) | 2,3-Dihydro-1H-inden-1-yl | 4.59 |
| 117 | H | Isopropyl | H | Methyl | 3-Chlorophenyl | (S) | 3,4-Dihydro-2H-chromen-4-yl | 4.87 |
| 118 | H | Isopropyl | H | Methyl | 4-Chlorophenyl | (S) | 3,4-Dihydro-2H-chromen-4-yl | 4.88 |
| 119 | H | Isopropyl | H | Methyl | 4-Chloro-3-(cyclopropylcarbamoyl)phenyl | (S) | 1,2,3,4-Tetrahydronaphthalin-1-yl | 4.07 |
| 120 | H | Isopropyl | H | Methyl | 4-Chloro-3-(cyclopropylcarbamoyl)phenyl | (S) | 2,3-Dihydro-1H-inden-1-yl | 3.78 |
| 121 | H | Isopropyl | H | Methyl | 2,5-Difluorophenyl | (S) | 3,4-Dihydro-2H-chromen-4-yl | 4.41 |
| 122 | H | Isopropyl | H | Methyl | 3,4,5-Trichlorophenyl | (S) | 2,3-Dihydro-1H-inden-1-yl | 6.58 |
| 123 | H | Isopropyl | H | Methyl | 2,2-Difluoro-1,3-benzodioxol-5-yl | (S) | 2,3-Dihydro-1H-inden-1-yl | 5.25 |
| 124 | H | Isopropyl | H | Methyl | 3-Chloro-5-(trifluoromethyl)phenyl | (S) | 1,2,3,4-Tetrahydronaphthalin-1-yl | 6.36 |
| 125 | H | Isopropyl | H | Methyl | 3,4,5-Trichlorophenyl | (S) | 1,2,3,4-Tetrahydronaphthalin-1-yl | 6.86 |
| 126 | H | Isopropyl | H | Methyl | 4-Isopropylphenyl | (S) | 1,2,3,4-Tetrahydronaphthalin-1-yl | 6.01 |
| 127 | H | Isopropyl | H | Methyl | 3,5-Dichloro-4-fluorophenyl | (S) | 2,3-Dihydro-1H-inden-1-yl | 5.91 |
| 128 | H | Isopropyl | H | Methyl | 3,5-Dichloro-4-fluorophenyl | (S) | 1,2,3,4-Tetrahydronaphthalin-1-yl | 6.26 |
| 129 | H | Isopropyl | H | Trifluoromethyl | 1-(2,2,2-Trifluoroethyl)-1H-pyrazol-4-yl | (S) | 3,4-Dihydro-2H-chromen-4-yl | 4.21 |
| 130 | H | Isopropyl | H | Methyl | 2-Chloro-6-fluorophenyl | (S) | 3,4-Dihydro-2H-chromen-4-yl | 4.44 |
| 131 | H | Isopropyl | H | Methyl | 2-Chloro-6-fluorophenyl | (S) | 1,2,3,4-Tetrahydronaphthalin-1-yl | 5.02 |
| 132 | H | Isopropyl | H | Methyl | 2-Chloro-6-fluorophenyl | (S) | 2,3-Dihydro-1H-inden-1-yl | 4.71 |
| 133 | H | Isopropyl | H | Trifluoromethyl | 2,4,6-Trifluorophenyl | (S) | 2,3-Dihydro-1H-inden-1-yl | 5.01 |
| 134 | H | Isopropyl | H | Methyl | 2,3-Difluorophenyl | (S) | 1,2,3,4-Tetrahydronaphthalin-1-yl | 4.9 |
| 135 | H | Isopropyl | H | Trifluoromethyl | 2,6-Difluorophenyl | (S) | 2,3-Dihydro-1H-inden-1-yl | 4.81 |
| 136 | H | Isopropyl | H | Methyl | 2,3-Difluorophenyl | (S) | 3,4-Dihydro-2H-chromen-4-yl | 4.34 |
| 137 | H | Isopropyl | H | Trifluoromethyl | 3-(Trifluoromethoxy)phenyl | (S) | 3,4-Dihydro-2H-chromen-4-yl | 5.31 |
| 138 | H | Isopropyl | H | Trifluoromethyl | 2,6-Difluorophenyl | (S) | 1,2,3,4-Tetrahydronaphthalin-1-yl | 5.06 |
| 139 | H | Isopropyl | H | Trifluoromethyl | 2,6-Difluorophenyl | (S) | 3,4-Dihydro-2H-chromen-4-yl | 4.56 |
| 140 | H | Isopropyl | H | Trifluoromethyl | 2,4,6-Trifluorophenyl | (S) | 3,4-Dihydro-2H-chromen-4-yl | 4.77 |
| 141 | H | Isopropyl | H | Methyl | 2,3-Difluorophenyl | (S) | 2,3-Dihydro-1H-inden-1-yl | 4.6 |
| 142 | H | Isopropyl | H | Trifluoromethyl | 3-(Methoxymethyl)phenyl | (S) | 3,4-Dihydro-2H-chromen-4-yl | 4.6 |
| 143 | H | Isopropyl | H | Trifluoromethyl | 3-Chloro-5-(trifluoromethyl)phenyl | (S) | 3,4-Dihydro-2H-chromen-4-yl | 5.78 |
| 144 | H | Isopropyl | H | Trifluoromethyl | 3-(Methoxymethyl)phenyl | (S) | 2,3-Dihydro-1H-inden-1-yl | 4.87 |
| 145 | H | Isopropyl | H | Methyl | 3-(Difluoromethyl)phenyl | (S) | 1,2,3,4-Tetrahydronaphthalin-1-yl | 4.93 |
| 146 | H | Isopropyl | H | Methyl | 2,2-Difluoro-1,3-benzodioxol-4-yl | (S) | 1,2,3,4-Tetrahydronaphthalin-1-yl | 5.47 |
| 147 | H | Isopropyl | H | Methyl | 2,2-Difluoro-1,3-benzodioxol-4-yl | (S) | 2,3-Dihydro-1H-inden-1-yl | 5.17 |
| 148 | H | Isopropyl | H | Methyl | 2,2-Difluoro-1,3-benzodioxol-5-yl | (S) | 1,2,3,4-Tetrahydronaphthalin-1-yl | 5.59 |
| 149 | H | Isopropyl | H | Trifluoromethyl | 3-(Trifluoromethoxy)phenyl | (S) | 2,3-Dihydro-1H-inden-1-yl | 5.55 |
| 150 | H | Isopropyl | H | Trifluoromethyl | 3-Chloro-5-(trifluoromethyl)phenyl | (S) | 2,3-Dihydro-1H-inden-1-yl | 6.22 |
| 151 | H | Isopropyl | H | Methyl | 3-(Difluoromethyl)phenyl | (S) | 2,3-Dihydro-1H-inden-1-yl | 4.67 |
| 152 | H | Isopropyl | H | Methyl | 3,5-Dichlorophenyl | (S) | 3,4-Dihydro-2H-chromen-4-yl | 5.84 |
| 153 | H | Isopropyl | H | Methyl | 3-(Difluoromethyl)phenyl | (S) | 3,4-Dihydro-2H-chromen-4-yl | 4.41 |
| 154 | H | Isopropyl | H | Methyl | 2,6-Dichlorophenyl | (S) | 3,4-Dihydro-2H-chromen-4-yl | 4.56 |
| 155 | H | Isopropyl | H | Trifluoromethyl | 5-Fluoropyridin-3-yl | (S) | 2,3-Dihydro-1H-inden-1-yl | 4.25 |
| 156 | H | Isopropyl | H | Trifluoromethyl | 5-Chloropyridin-3-yl | (S) | 2,3-Dihydro-1H-inden-1-yl | 4.7 |
| 157 | H | Isopropyl | H | Trifluoromethyl | 3-Fluorophenyl | (S) | 2,3-Dihydro-1H-inden-1-yl | 5.02 |

TABLE 1-continued

Examples (I-1)

| Number | R1 | R2 | R3 | R4 | Q | Chiral Descriptor A | A | logP (Method L0) [a] |
|---|---|---|---|---|---|---|---|---|
| 158 | H | Isopropyl | H | Trifluoromethyl | 2-Fluorophenyl | (S) | 2,3-Dihydro-1H-inden-1-yl | 4.76 |
| 159 | H | Isopropyl | H | Trifluoromethyl | 3,4,5-Trifluorophenyl | (S) | 2,3-Dihydro-1H-inden-1-yl | 5.4 |
| 160 | H | Isopropyl | H | Trifluoromethyl | 4-Fluoro-3-methoxyphenyl | (S) | 2,3-Dihydro-1H-inden-1-yl | 4.89 |
| 161 | H | Isopropyl | H | Trifluoromethyl | 6-Fluoropyridin-3-yl | (S) | 2,3-Dihydro-1H-inden-1-yl | 4.35 |
| 162 | H | Isopropyl | H | Trifluoromethyl | 4-Fluorophenyl | (S) | 2,3-Dihydro-1H-inden-1-yl | 4.95 |
| 163 | H | Isopropyl | H | Trifluoromethyl | 5,6-Difluoropyridin-3-yl | (S) | 2,3-Dihydro-1H-inden-1-yl | 4.76 |
| 164 | H | Isopropyl | H | Trifluoromethyl | 6-Chloropyridin-3-yl | (S) | 2,3-Dihydro-1H-inden-1-yl | 4.7 |
| 165 | H | Isopropyl | H | Methyl | 2-Chloro-3-fluorophenyl | (S) | 2,3-Dihydro-1H-inden-1-yl | 4.74 |
| 166 | H | Isopropyl | H | Methyl | 2,3,4-Trifluorophenyl | (S) | 3,4-Dihydro-2H-chromen-4-yl | 4.54 |
| 167 | H | Isopropyl | H | Trifluoromethyl | 3,5-Dichlorophenyl | (S) | 2,3-Dihydro-1H-inden-1-yl | 6.06 |
| 168 | H | Isopropyl | H | Methyl | 2,3-Dichlorophenyl | (S) | 2,3-Dihydro-1H-inden-1-yl | 5.13 |
| 169 | H | Isopropyl | H | Methyl | 2,3-Dichlorophenyl | (S) | 1,2,3,4-Tetrahydronaphthalin-1-yl | 5.46 |
| 170 | H | Isopropyl | H | Methyl | 2,3-Dichlorophenyl | (S) | 3,4-Dihydro-2H-chromen-4-yl | 4.85 |
| 171 | H | Isopropyl | H | Methyl | 2,5-Dichlorophenyl | (S) | 2,3-Dihydro-1H-inden-1-yl | 5.31 |
| 172 | H | Isopropyl | H | Methyl | 2,5-Dichlorophenyl | (S) | 1,2,3,4-Tetrahydronaphthalin-1-yl | 5.64 |
| 173 | H | Isopropyl | H | Methyl | 2,5-Dichlorophenyl | (S) | 3,4-Dihydro-2H-chromen-4-yl | 5 |
| 174 | H | Isopropyl | H | Methyl | Phenyl | (S) | 2,3-Dihydro-1H-inden-1-yl | 4.59 |
| 175 | H | Isopropyl | H | Methyl | Phenyl | (S) | 1,2,3,4-Tetrahydronaphthalin-1-yl | 4.94 |
| 176 | H | Isopropyl | H | Methyl | Phenyl | (S) | 3,4-Dihydro-2H-chromen-4-yl | 4.28 |
| 177 | H | Isopropyl | H | Methyl | 6-Methoxypyridin-2-yl | (S) | 2,3-Dihydro-1H-inden-1-yl | 4.89 |
| 178 | H | Isopropyl | H | Methyl | 6-Fluoropyridin-2-yl | (S) | 2,3-Dihydro-1H-inden-1-yl | 4.6 |
| 179 | H | Isopropyl | H | Methyl | 6-(Trifluoromethyl)pyridin-2-yl | (S) | 2,3-Dihydro-1H-inden-1-yl | 5.39 |
| 180 | H | Isopropyl | H | Methyl | 2,4-Dichlorophenyl | (S) | 3,4-Dihydro-2H-chromen-4-yl | 5.02 |
| 181 | H | Isopropyl | H | Methyl | 2,4-Dichlorophenyl | (S) | 2,3-Dihydro-1H-inden-1-yl | 5.31 |
| 182 | H | Isopropyl | H | Methyl | 2,4-Dichlorophenyl | (S) | 1,2,3,4-Tetrahydronaphthalin-1-yl | 5.59 |
| 183 | H | Isopropyl | H | Methyl | 6-Chloropyridin-2-yl | (S) | 2,3-Dihydro-1H-inden-1-yl | 5.1 |
| 184 | H | Isopropyl | H | Methyl | 2-Fluoro-3-methoxyphenyl | (S) | 3,4-Dihydro-2H-chromen-4-yl | 2.84 |
| 185 | H | Isopropyl | H | Methyl | 3,4,5-Trifluorophenyl | (S) | 3,4-Dihydro-2H-chromen-4-yl | 4.97 |
| 186 | H | Isopropyl | H | Methyl | 3-Chloro-4-fluorophenyl | (S) | 3,4-Dihydro-2H-chromen-4-yl | 5.01 |
| 187 | H | Isopropyl | H | Methyl | 3-Fluoro-4-(trifluoromethyl)phenyl | (S) | 3,4-Dihydro-2H-chromen-4-yl | 4.85 |
| 188 | H | Isopropyl | H | Methyl | 2-Fluoro-3-isopropoxyphenyl | (S) | 3,4-Dihydro-2H-chromen-4-yl | 4.79 |
| 189 | H | Isopropyl | H | Methyl | 3-Chloro-2-fluorophenyl | (S) | 3,4-Dihydro-2H-chromen-4-yl | 4.72 |
| 190 | H | Isopropyl | H | Methyl | 4-Chloro-3,5-difluorophenyl | (S) | 3,4-Dihydro-2H-chromen-4-yl | 5.39 |
| 191 | H | Isopropyl | H | Methyl | 2-Chloro-3-fluorophenyl | (S) | 3,4-Dihydro-2H-chromen-4-yl | 4.46 |
| 192 | H | Isopropyl | H | Methyl | 2,4-Difluoro-3-methoxyphenyl | (S) | 3,4-Dihydro-2H-chromen-4-yl | 4.32 |
| 193 | H | Isopropyl | H | Methyl | 2-Methylphenyl | (S) | 3,4-Dihydro-2H-chromen-4-yl | 4.44 |
| 194 | H | Isopropyl | H | Methyl | 3,5-Dichloro-4-fluorophenyl | (S) | 3,4-Dihydro-2H-chromen-4-yl | 5.65 |
| 195 | H | Isopropyl | H | Methyl | 6-Chloropyridin-2-yl | (S) | 3,4-Dihydro-2H-chromen-4-yl | 4.85 |
| 196 | H | Isopropyl | H | Trifluoromethyl | 3,5-Dichlorophenyl | (S) | 3,4-Dihydro-2H-chromen-4-yl | 5.84 |
| 197 | H | Isopropyl | H | Trifluoromethyl | 3,5-Dichloro-4-fluorophenyl | (S) | 3,4-Dihydro-2H-chromen-4-yl | 5.48 |
| 198 | H | Isopropyl | H | i-Propyl-thio | 3,5-Dichlorophenyl | (S) | 3,4-Dihydro-2H-chromen-4-yl | 7 |
| 199 | H | Isopropyl | H | i-Propyl-thio | 3,5-Dichlorophenyl | (S) | 2,3-Dihydro-1H-inden-1-yl | 7.34 |
| 200 | H | Isopropyl | H | Ethylthio | 3,5-Dichlorophenyl | (S) | 3,4-Dihydro-2H-chromen-4-yl | 6.71 |
| 201 | H | Isopropyl | H | Ethylthio | 3,5-Dichlorophenyl | (S) | 2,3-Dihydro-1H-inden-1-yl | 6.93 |
| 202 | H | Isopropyl | H | Methylthio | 3,5-Dichlorophenyl | (S) | 3,4-Dihydro-2H-chromen-4-yl | 6.35 |
| 203 | H | Isopropyl | H | Methylthio | 3,5-Dichlorophenyl | (S) | 2,3-Dihydro-1H-inden-1-yl | 6.67 |
| 204 | H | Isopropyl | H | Methyl | 3-Bromophenyl | (S) | 3,4-Dihydro-2H-chromen-4-yl | 5.02 |
| 205 | H | Isopropyl | H | Methyl | 3-Bromophenyl | (S) | 2,3-Dihydro-1H-inden-1-yl | 5.31 |
| 206 | H | Isopropyl | H | Methyl | 4-Bromophenyl | (S) | 3,4-Dihydro-2H-chromen-4-yl | 5.02 |
| 207 | H | Isopropyl | H | Methyl | 4-Bromophenyl | (S) | 2,3-Dihydro-1H-inden-1-yl | 5.31 |
| 208 | H | Isopropyl | H | Methyl | 3,5-Dichloropyridin-2-yl | (S) | 3,4-Dihydro-2H-chromen-4-yl | 4.27 |
| 209 | H | Isopropyl | H | Methyl | 3,5-Dichloropyridin-2-yl | (S) | 2,3-Dihydro-1H-inden-1-yl | 4.51 |
| 210 | H | Isopropyl | H | Methyl | 2,6-Difluorophenyl | rac | 2,3-Dihydro-1-benzofuran-3-yl | 3.99 |
| 211 | H | Isopropyl | H | Ethylsulfonyl | 3,5-Dichlorophenyl | (S) | 2,3-Dihydro-1H-inden-1-yl | 4.62 |

TABLE 1-continued

Examples (I-1)

| Number | R1 | R2 | R3 | R4 | Q | Chiral Descriptor A | A | logP (Method L0) [a] |
|---|---|---|---|---|---|---|---|---|
| 212 | H | Isopropyl | H | Ethylsulfonyl | 3,5-Dichlorophenyl | (S) | 3,4-Dihydro-2H-chromen-4-yl | 4.37 |
| 213 | H | Isopropyl | H | Methyl | 3-Chloro-2,4-difluorophenyl | (S) | 3,4-Dihydro-2H-chromen-4-yl | 4.8 |
| 214 | H | Isopropyl | H | i-Propyl-sulfonyl | 3,5-Dichlorophenyl | (S) | 2,3-Dihydro-1H-inden-1-yl | 4.85 |
| 215 | H | Isopropyl | H | Methyl | 2-Fluoro-3-(trifluoromethoxy)phenyl | (S) | 3,4-Dihydro-2H-chromen-4-yl | 5.02 |
| 216 | H | Isopropyl | H | Methyl | 4-Chloro-2-fluoro-3-methoxyphenyl | (S) | 3,4-Dihydro-2H-chromen-4-yl | 4.74 |
| 217 | H | Isopropyl | H | i-Propyl-sulfonyl | 3,5-Dichlorophenyl | (S) | 3,4-Dihydro-2H-chromen-4-yl | 4.57 |
| 218 | H | Isopropyl | H | Methyl | 2-Chloro-4-fluorophenyl | (S) | 3,4-Dihydro-2H-chromen-4-yl | 4.51 |
| 219 | H | Isopropyl | H | Methyl-sulfonyl | 3,5-Dichlorophenyl | (S) | 3,4-Dihydro-2H-chromen-4-yl | 4.16 |
| 220 | H | Isopropyl | H | Methyl | 4-Chloro-3-fluorophenyl | (S) | 3,4-Dihydro-2H-chromen-4-yl | 5.08 |
| 221 | H | Isopropyl | H | Methyl | 5,6-Difluoropyridin-3-yl | (S) | 3,4-Dihydro-2H-chromen-4-yl | 4.13 |
| 222 | H | sec-Butyl | H | Methyl | 2-Chloro-6-fluorophenyl | (S) | 2,3-Dihydro-1H-inden-1-yl | 4.98 |
| 223 | H | Isopropyl | H | Methyl | 2,6-Dichlorophenyl | (S) | 2,3-Dihydro-1H-inden-1-yl | 4.87 |
| 224 | H | Isobutyl | H | Methyl | 2-Chloro-6-fluorophenyl | (S) | 2,3-Dihydro-1H-inden-1-yl | 4.82 |
| 225 | H | Isobutyl | H | Methyl | 2-Chloro-6-fluorophenyl | (S) | 3,4-Dihydro-2H-chromen-4-yl | 4.56 |
| 226 | H | sec-Butyl | H | Methyl | 2-Chloro-6-fluorophenyl | (S) | 3,4-Dihydro-2H-chromen-4-yl | 4.72 |
| 227 | H | 4-Fluorobenzyl | H | Methyl | 2-Chloro-6-fluorophenyl | (S) | 2,3-Dihydro-1H-inden-1-yl | 4.92 |
| 228 | H | 4-Fluorobenzyl | H | Methyl | 2-Chloro-6-fluorophenyl | (S) | 3,4-Dihydro-2H-chromen-4-yl | 4.72 |
| 229 | H | Isopropyl | H | Methyl-sulfonyl | 3,5-Dichlorophenyl | (S) | 2,3-Dihydro-1H-inden-1-yl | 4.35 |
| 230 | H | Isopropyl | H | Methyl | 3,4-Dichlorophenyl | (S) | 3,4-Dihydro-2H-chromen-4-yl | 5.48 |
| 231 | H | Isopropyl | H | Methyl | 4-Chloropyridin-3-yl | (S) | 3,4-Dihydro-2H-chromen-4-yl | 3.9 |
| 232 | H | Isopropyl | H | Methyl | 2,6-Difluoro-3-methoxyphenyl | (S) | 3,4-Dihydro-2H-chromen-4-yl | 4.04 |
| 233 | H | Isopropyl | H | Methyl | 2-Chloro-6-fluoro-3-methoxyphenyl | (S) | 3,4-Dihydro-2H-chromen-4-yl | 4.23 |
| 234 | H | Isopropyl | H | Methyl | 2,3,5-Trichlorophenyl | (S) | 3,4-Dihydro-2H-chromen-4-yl | 5.48 |
| 235 | H | Isopropyl | H | Methyl | 2,4,6-Trifluoro-3-methoxyphenyl | (S) | 3,4-Dihydro-2H-chromen-4-yl | 4.38 |
| 236 | H | Isopropyl | H | Methyl | 2,4,6-Trifluorophenyl | (S) | 3,4-Dihydro-2H-chromen-4-yl | 4.3 |
| 237 | H | Isopropyl | H | Methyl | 2-Chloro-6-fluorophenyl | rac | 6-Methyl-3,4-dihydro-2H-chromen-4-yl | 4.67 |
| 238 | H | Isopropyl | H | Methyl | 1-Methyl-2,3-dihydro-1H-indol-6-yl | (S) | 3,4-Dihydro-2H-chromen-4-yl | 4.13 |
| 239 | H | Isopropyl | H | Methyl | 1,3-Benzodioxol-5-yl | (S) | 3,4-Dihydro-2H-chromen-4-yl | 4.08 |
| 240 | H | Isopropyl | H | Methyl | 3-Chloro-5-(trifluoromethyl)phenyl | (S) | 3,4-Dihydro-2H-chromen-4-yl | 5.65 |
| 241 | H | Isopropyl | H | Methyl | 3,4-Difluoro-5-methoxyphenyl | (S) | 3,4-Dihydro-2H-chromen-4-yl | 4.6 |
| 242 | H | Isopropyl | H | Methyl | 3,4-Dimethoxyphenyl | (S) | 3,4-Dihydro-2H-chromen-4-yl | 3.9 |
| 243 | H | Isopropyl | H | Methyl | 1H-Indol-6-yl | (S) | 3,4-Dihydro-2H-chromen-4-yl | 3.76 |
| 244 | H | Isopropyl | H | Methyl | 4-Fluoro-3-methoxyphenyl | (S) | 3,4-Dihydro-2H-chromen-4-yl | 4.32 |
| 245 | H | Isopropyl | H | Methyl | 4-Fluoro-1,3-benzodioxol-5-yl | (S) | 3,4-Dihydro-2H-chromen-4-yl | 4.18 |
| 246 | H | Isopropyl | H | Methyl | 4-Chloro-2,6-difluorophenyl | (S) | 3,4-Dihydro-2H-chromen-4-yl | 4.82 |
| 247 | H | Isopropyl | H | Methyl | 2-Chloro-3-methoxyphenyl | (S) | 3,4-Dihydro-2H-chromen-4-yl | 4.19 |
| 248 | H | Isopropyl | H | Methyl | 2,3-Dihydro-1H-indol-6-yl | (S) | 3,4-Dihydro-2H-chromen-4-yl | 2.2 |
| 249 | H | Isopropyl | H | Methyl | 3,4,5-Trimethoxyphenyl | (S) | 3,4-Dihydro-2H-chromen-4-yl | 3.94 |
| 250 | H | Isopropyl | H | Methyl | 1-Oxo-2,3-dihydro-1H-inden-5-yl | (S) | 3,4-Dihydro-2H-chromen-4-yl | 3.75 |
| 251 | H | Isopropyl | H | Methyl | 2,2-Difluoro-1,3-benzodioxol-5-yl | (S) | 3,4-Dihydro-2H-chromen-4-yl | 5.03 |
| 252 | H | Isopropyl | H | Methyl | 2-Oxo-2,3-dihydro-1H-indol-5-yl | (S) | 3,4-Dihydro-2H-chromen-4-yl | 2.87 |
| 253 | H | Isopropyl | H | Methyl | 2,3,6-Trifluorophenyl | (S) | 3,4-Dihydro-2H-chromen-4-yl | 4.32 |
| 254 | H | Isopropyl | H | Methyl | 2-Chloro-6-fluorophenyl | rac | 6-Fluoro-3,4-dihydro-2H-chromen-4-yl | 4.45 |
| 255 | H | Isopropyl | H | Methyl | 3-Chloro-2,6-difluorophenyl | (S) | 3,4-Dihydro-2H-chromen-4-yl | 4.72 |
| 256 | H | Isopropyl | H | Methyl | 5-Chloro-2-fluorophenyl | (S) | 3,4-Dihydro-2H-chromen-4-yl | 4.87 |
| 257 | H | Isopropyl | H | Methyl | 2,2-Difluoro-1,3-benzodioxol-4-yl | (S) | 3,4-Dihydro-2H-chromen-4-yl | 4.87 |
| 258 | H | Isopropyl | H | Methyl | 6-Chloro-2,3-difluorophenyl | (S) | 3,4-Dihydro-2H-chromen-4-yl | 4.46 |
| 259 | H | Isopropyl | H | Methyl | 3,4-Difluoro-5-hydroxyphenyl | (S) | 3,4-Dihydro-2H-chromen-4-yl | 3.61 |
| 260 | H | Isopropyl | H | Methyl | 3-(Dimethylamino)-2-fluorophenyl | (S) | 3,4-Dihydro-2H-chromen-4-yl | 4.18 |
| 261 | H | Isopropyl | H | Methyl | 3,5-Dichloro-2-fluorophenyl | (S) | 2,3-Dihydro-1H-inden-1-yl | 5.65 |
| 262 | H | Isopropyl | H | Methyl | 3,5-Dichloro-2-fluorophenyl | (S) | 3,4-Dihydro-2H-chromen-4-yl | 5.36 |
| 263 | H | Isopropyl | H | Methyl | 7-Fluoro-1,3-benzodioxol-4-yl | (S) | 3,4-Dihydro-2H-chromen-4-yl | 4.13 |
| 264 | H | Isopropyl | H | Methyl | 2-Cyanphenyl | (S) | 3,4-Dihydro-2H-chromen-4-yl | 3.68 |
| 265 | H | Isopropyl | H | Methyl | 3,5-Dichloro-2-fluorophenyl | (S) | 1,2,3,4-Tetrahydronaphthalin-1-yl | 6.01 |
| 266 | H | Isopropyl | H | Methyl | 1,3-Benzodioxol-4-yl | (S) | 3,4-Dihydro-2H-chromen-4-yl | 4.02 |

TABLE 1-continued

Examples (I-1)

| Number | R1 | R2 | R3 | R4 | Q | Chiral Descriptor A | A | logP (Method L0) [a] |
|---|---|---|---|---|---|---|---|---|
| 267 | H | Methyl | Methyl | Methyl | 2,3-Dichlorophenyl | (S) | 3,4-Dihydro-2H-chromen-4-yl | 3.86 |
| 268 | H | Methyl | Methyl | Methyl | 3,5-Dichlorophenyl | (S) | 3,4-Dihydro-2H-chromen-4-yl | 4.76 |
| 269 | H | Cyclopropyl | H | Difluoromethyl | 2,4-Difluoro-3-methoxyphenyl | (S) | 3,4-Dihydro-2H-chromen-4-yl | |
| 270 | H | Cyclopropyl | H | Difluoromethyl | 2,3-Difluorophenyl | (S) | 3,4-Dihydro-2H-chromen-4-yl | |
| 271 | H | Cyclopropyl | H | Difluoromethyl | 2,6-Dichlorophenyl | (S) | 3,4-Dihydro-2H-chromen-4-yl | |
| 272 | H | Cyclopropyl | H | Difluoromethyl | 3,5-Dichloro-4-fluorophenyl | (S) | 3,4-Dihydro-2H-chromen-4-yl | |
| 273 | H | Cyclopropyl | H | Difluoromethyl | 3-Chlorophenyl | (S) | 3,4-Dihydro-2H-chromen-4-yl | |
| 274 | H | Cyclopropyl | H | Difluoromethyl | 3,4-Difluorophenyl | (S) | 3,4-Dihydro-2H-chromen-4-yl | |
| 275 | H | Isopropyl | H | Chloro | 3-Chlorophenyl | (S) | 3,4-Dihydro-2H-chromen-4-yl | |
| 276 | H | Isopropyl | H | Difluoromethyl | 3-Chlorophenyl | (S) | 3,4-Dihydro-2H-chromen-4-yl | |
| 277 | H | Isopropyl | H | Difluoromethyl | 3-Chloro-2,6-difluorophenyl | (S) | 3,4-Dihydro-2H-chromen-4-yl | |
| 278 | H | Isopropyl | H | Difluoromethyl | 3,4-Difluorophenyl | (S) | 3,4-Dihydro-2H-chromen-4-yl | |
| 279 | H | Isopropyl | H | Difluoromethyl | 2,3-Difluorophenyl | (S) | 3,4-Dihydro-2H-chromen-4-yl | |
| 280 | H | Cyclopropyl | H | Difluoromethyl | 3-Chloro-2,6-difluorophenyl | (S) | 3,4-Dihydro-2H-chromen-4-yl | |
| 281 | H | Isopropyl | H | Chloro | 2,3-Difluorophenyl | (S) | 3,4-Dihydro-2H-chromen-4-yl | |
| 282 | H | Isopropyl | H | Difluoromethyl | 3,5-Dichloro-4-fluorophenyl | (S) | 3,4-Dihydro-2H-chromen-4-yl | |
| 283 | H | Isopropyl | H | Methyl | 3-(Dimethylamino)-2,4-difluorophenyl | (S) | 3,4-Dihydro-2H-chromen-4-yl | |
| 284 | H | Cyclopropyl | H | Methyl | 2,4-Difluoro-3-methoxyphenyl | (S) | 3,4-Dihydro-2H-chromen-4-yl | |
| 285 | H | Isopropyl | H | Chloro | 2,3-Difluorophenyl | (S) | 2,3-Dihydro-1H-inden-1-yl | |
| 286 | H | Isopropyl | H | Chloro | 2,3-Difluorophenyl | (S) | 1,2,3,4-Tetrahydronaphthalin-1-yl | |
| 287 | H | Isopropyl | H | Methyl | 3-Chlorophenyl | (S) | 2,3-Dihydro-1H-inden-1-yl | 5.19 |
| 288 | H | Isopropyl | H | Methyl | 3-(Methylsulfonyl)phenyl | (S) | 2,3-Dihydro-1H-inden-1-yl | 3.57 |
| 289 | H | Isopropyl | H | Methyl | 3-Methoxyphenyl | (S) | 2,3-Dihydro-1H-inden-1-yl | 4.51 |
| 290 | H | Isopropyl | H | Methyl | 3-Fluorophenyl | (S) | 2,3-Dihydro-1H-inden-1-yl | 4.73 |
| 291 | H | Isopropyl | H | Methyl | 3-Cyanphenyl | (S) | 2,3-Dihydro-1H-inden-1-yl | 4.31 |
| 292 | H | Isopropyl | H | Methyl | 3-Fluoro-5-(trifluoromethyl)phenyl | (S) | 2,3-Dihydro-1H-inden-1-yl | 5.6 |
| 293 | H | Isopropyl | H | Methyl | 4-Cyan-3-(trifluoromethyl)phenyl | (S) | 2,3-Dihydro-1H-inden-1-yl | 4.97 |
| 294 | H | Isopropyl | H | Methyl | 4-Fluoro-3-(trifluoromethyl)phenyl | (S) | 2,3-Dihydro-1H-inden-1-yl | 5.36 |
| 295 | H | Isopropyl | H | Methyl | 6-Chloropyridin-3-yl | (S) | 2,3-Dihydro-1H-inden-1-yl | 4.21 |
| 296 | H | Isopropyl | H | Methyl | Pyrimidin-5-yl | (S) | 2,3-Dihydro-1H-inden-1-yl | 2.99 |
| 297 | H | Isopropyl | H | Methyl | Pyridin-3-yl | (S) | 2,3-Dihydro-1H-inden-1-yl | 2.19 |
| 298 | H | Isopropyl | H | Methyl | 3-Acetamidophenyl | (S) | 2,3-Dihydro-1H-inden-1-yl | 3.3 |
| 299 | H | Isopropyl | H | Methyl | 3-(Dimethylamino)phenyl | (S) | 2,3-Dihydro-1H-inden-1-yl | 3.9 |
| 300 | H | Isopropyl | H | Methyl | 3-(Methoxymethyl)phenyl | (S) | 2,3-Dihydro-1H-inden-1-yl | 4.43 |
| 301 | H | Isopropyl | H | Methyl | 4-Cyanphenyl | (S) | 2,3-Dihydro-1H-inden-1-yl | 4.28 |
| 302 | H | Isopropyl | H | Methyl | 4-Fluorophenyl | (S) | 2,3-Dihydro-1H-inden-1-yl | 4.63 |
| 303 | H | Isopropyl | H | Methyl | 1-Methyl-1H-pyrazol-4-yl | (S) | 2,3-Dihydro-1H-inden-1-yl | 3.13 |
| 304 | H | Cyclopropyl | H | Methyl | 3-(Trifluoromethyl)phenyl | (S) | 2,3-Dihydro-1H-inden-1-yl | 4.55 |
| 305 | H | Methoxymethyl | H | Methyl | 3-(Trifluoromethyl)phenyl | (S) | 2,3-Dihydro-1H-inden-1-yl | 4.52 |
| 306 | H | Ethyl | H | Methyl | 3-(Trifluoromethyl)phenyl | (S) | 2,3-Dihydro-1H-inden-1-yl | 4.86 |
| 307 | H | Isopropyl | H | Methyl | 1H-Pyrazol-4-yl | (S) | 2,3-Dihydro-1H-inden-1-yl | 2.75 |
| 308 | H | Isopropyl | H | Methyl | 3-[(Methylsulfonyl)amino]phenyl | (S) | 2,3-Dihydro-1H-inden-1-yl | 3.44 |
| 309 | H | Isopropyl | H | Methyl | 3-(Trifluoromethoxy)phenyl | (S) | 2,3-Dihydro-1H-inden-1-yl | 5.48 |
| 310 | H | Isopropyl | H | Methyl | 1-(2,2,2-Trifluoroethyl)-1H-pyrazol-4-yl | (S) | 2,3-Dihydro-1H-inden-1-yl | 3.81 |
| 311 | H | Difluoromethyl | H | Methyl | 3-(Trifluoromethyl)phenyl | (S) | 2,3-Dihydro-1H-inden-1-yl | 4.36 |
| 312 | H | Isopropyl | H | Methyl | 3-Methoxy-5-(trifluoromethyl)phenyl | (S) | 2,3-Dihydro-1H-inden-1-yl | 5.41 |
| 313 | H | Isopropyl | H | Methyl | 2-Chloropyridin-4-yl | (S) | 2,3-Dihydro-1H-inden-1-yl | 4.23 |
| 314 | H | Isopropyl | H | Methyl | 5-Chloropyridin-3-yl | (S) | 2,3-Dihydro-1H-inden-1-yl | 4.19 |
| 315 | H | Isopropyl | H | Methyl | 3-[(Trifluoroacetyl)amino]phenyl | (S) | 2,3-Dihydro-1H-inden-1-yl | 4.28 |
| 316 | H | Isopropyl | H | Methyl | 3-(Morpholin-4-yl)phenyl | (S) | 2,3-Dihydro-1H-inden-1-yl | 4.26 |

TABLE 1-continued

Examples (I-1)

| Number | R1 | R2 | R3 | R4 | Q | Chiral Descriptor A | A | logP (Method L0) [a] |
|---|---|---|---|---|---|---|---|---|
| 317 | H | Isopropyl | H | Methyl | 3-Chloro-5-(trifluoromethyl)phenyl | (S) | 2,3-Dihydro-1H-inden-1-yl | 6.07 |
| 318 | H | Isopropyl | H | Methyl | Pyridin-4-yl | (S) | 2,3-Dihydro-1H-inden-1-yl | 1.84 |
| 319 | H | Isopropyl | H | Methyl | 3-(Cyclopropylmethoxy)phenyl | (S) | 2,3-Dihydro-1H-inden-1-yl | 5.28 |
| 320 | H | Isopropyl | H | Methyl | 3-(Cyanmethoxy)phenyl | (S) | 2,3-Dihydro-1H-inden-1-yl | 4.09 |
| 321 | H | Isopropyl | H | Methyl | 3-Isopropoxyphenyl | (S) | 2,3-Dihydro-1H-inden-1-yl | 5.28 |
| 322 | H | Isopropyl | H | Methyl | 3-Ethoxyphenyl | (S) | 2,3-Dihydro-1H-inden-1-yl | 4.94 |
| 323 | H | Isopropyl | H | Methyl | 3,5-Difluorophenyl | (S) | 2,3-Dihydro-1H-inden-1-yl | 5.02 |
| 324 | H | Isopropyl | H | Methyl | 3-Chloro-5-fluorophenyl | (S) | 2,3-Dihydro-1H-inden-1-yl | 5.49 |
| 325 | H | Isopropyl | H | Methyl | 3-Fluoro-5-methoxyphenyl | (S) | 2,3-Dihydro-1H-inden-1-yl | 4.8 |
| 326 | H | Isopropyl | H | Methyl | 4-(Morpholin-4-yl)phenyl | (S) | 2,3-Dihydro-1H-inden-1-yl | 4.2 |
| 327 | H | Isopropyl | H | Methyl | 4-Acetamidophenyl | (S) | 2,3-Dihydro-1H-inden-1-yl | 3.24 |
| 328 | H | Isopropyl | H | Methyl | 3-(1H-Pyrazol-1-yl)phenyl | (S) | 2,3-Dihydro-1H-inden-1-yl | 4.4 |
| 329 | H | Isopropyl | H | Methyl | 3-(Pyrrolidin-1-yl)phenyl | (S) | 2,3-Dihydro-1H-inden-1-yl | 5.44 |
| 330 | H | Isopropyl | H | Methyl | 4-[(Methylsulfonyl)amino]phenyl | (S) | 2,3-Dihydro-1H-inden-1-yl | 3.38 |
| 331 | H | Isopropyl | H | Methyl | 4-(Trifluoromethoxy)phenyl | (S) | 2,3-Dihydro-1H-inden-1-yl | 5.41 |
| 332 | H | Isopropyl | H | Methyl | 4-(Trifluoromethyl)phenyl | (S) | 2,3-Dihydro-1H-inden-1-yl | 5.32 |
| 333 | H | Isopropyl | H | Methyl | 4-Methoxyphenyl | (S) | 2,3-Dihydro-1H-inden-1-yl | 4.43 |
| 334 | H | Isopropyl | H | Methyl | 4-(Difluoromethyl)phenyl | (S) | 2,3-Dihydro-1H-inden-1-yl | 4.63 |
| 335 | H | Isopropyl | H | Methyl | 4-(Difluoromethoxy)phenyl | (S) | 2,3-Dihydro-1H-inden-1-yl | 4.66 |
| 336 | H | Isopropyl | H | Methyl | 4-(2,2,2-Trifluoroethoxy)phenyl | (S) | 2,3-Dihydro-1H-inden-1-yl | 4.91 |
| 337 | H | Isopropyl | H | Methyl | 3-(Difluoromethoxy)phenyl | (S) | 2,3-Dihydro-1H-inden-1-yl | 4.7 |
| 338 | H | Isopropyl | H | Methyl | 3-(2,2,2-Trifluoroethoxy)phenyl | (S) | 2,3-Dihydro-1H-inden-1-yl | 4.97 |
| 339 | H | Isopropyl | H | Methyl | 4-Ethoxyphenyl | (S) | 2,3-Dihydro-1H-inden-1-yl | 4.87 |
| 340 | H | Isopropyl | H | Methyl | 4-(Methoxymethyl)phenyl | (S) | 2,3-Dihydro-1H-inden-1-yl | 4.41 |
| 341 | H | Isopropyl | H | Methyl | 4-(Methylamino)phenyl | (S) | 2,3-Dihydro-1H-inden-1-yl | 3.32 |
| 342 | H | Isopropyl | H | Methyl | 4-(Dimethylamino)phenyl | (S) | 2,3-Dihydro-1H-inden-1-yl | 3.91 |
| 343 | H | Isopropyl | H | Methyl | 4-Fluorophenyl | (S) | 1,2,3,4-Tetrahydronaphthalin-1-yl | 4.95 |
| 344 | H | Isopropyl | H | Methyl | 3-(Methoxymethyl)phenyl | (S) | 1,2,3,4-Tetrahydronaphthalin-1-yl | 4.74 |
| 345 | H | Isopropyl | H | Methyl | 3-(Trifluoromethoxy)phenyl | (S) | 1,2,3,4-Tetrahydronaphthalin-1-yl | 5.82 |
| 346 | H | Isopropyl | H | Methyl | 3-Methoxyphenyl | (S) | 1,2,3,4-Tetrahydronaphthalin-1-yl | 4.82 |
| 347 | H | Isopropyl | H | Methyl | 3-Fluorophenyl | (S) | 1,2,3,4-Tetrahydronaphthalin-1-yl | 5.04 |
| 348 | H | Cyclopropyl | H | Methyl | 3-(Dimethylamino)phenyl | (S) | 2,3-Dihydro-1H-inden-1-yl | 2.98 |
| 349 | H | Cyclopropyl | H | Methyl | 2-Chlorophenyl | (S) | 2,3-Dihydro-1H-inden-1-yl | 3.88 |
| 350 | H | Cyclopropyl | H | Methyl | 3-(Methoxymethyl)phenyl | (S) | 2,3-Dihydro-1H-inden-1-yl | 3.65 |
| 351 | H | Cyclopropyl | H | Methyl | 3-Methoxyphenyl | (S) | 2,3-Dihydro-1H-inden-1-yl | 3.74 |
| 352 | H | Cyclopropyl | H | Methyl | 3-Chlorophenyl | (S) | 2,3-Dihydro-1H-inden-1-yl | 4.38 |
| 353 | H | Cyclopropyl | H | Methyl | 3-Fluorophenyl | (S) | 2,3-Dihydro-1H-inden-1-yl | 3.95 |
| 354 | H | Isopropyl | H | Methyl | 3-(Morpholin-4-ylmethyl)phenyl | (S) | 2,3-Dihydro-1H-inden-1-yl | 2.01 |
| 355 | H | Isopropyl | H | Methyl | 3-[(Diethylamino)methyl]phenyl | (S) | 2,3-Dihydro-1H-inden-1-yl | 2.12 |
| 356 | H | Isopropyl | H | Methyl | 3-(Piperidin-1-yl)phenyl | (S) | 2,3-Dihydro-1H-inden-1-yl | 3.25 |
| 357 | H | Cyclopropyl | H | Methyl | 2-Fluorophenyl | (S) | 2,3-Dihydro-1H-inden-1-yl | 3.67 |
| 358 | H | Cyclopropyl | H | Methyl | 3,4-Difluorophenyl | (S) | 2,3-Dihydro-1H-inden-1-yl | 4.1 |
| 359 | H | Isopropyl | H | Methyl | 1-(2,2,2-Trifluoroethyl)-1H-pyrazol-4-yl | (S) | 1,2,3,4-Tetrahydronaphthalin-1-yl | 4.11 |
| 360 | H | Cyclopropyl | H | Methyl | 3-(Trifluoromethoxy)phenyl | (S) | 2,3-Dihydro-1H-inden-1-yl | 4.72 |
| 361 | H | Isopropyl | H | Methyl | 3-(Dimethylamino)phenyl | (S) | 1,2,3,4-Tetrahydronaphthalin-1-yl | 4.32 |
| 362 | H | Isopropyl | H | Methyl | 5-Chloropyridin-3-yl | (S) | 1,2,3,4-Tetrahydronaphthalin-1-yl | 4.52 |
| 363 | H | Isopropyl | H | Methyl | 3-Methoxy-5-(trifluoromethyl)phenyl | (S) | 1,2,3,4-Tetrahydronaphthalin-1-yl | 5.7 |
| 364 | H | Isopropyl | H | Methyl | 3-(3,3-Difluoroazetidin-1-yl)phenyl | (S) | 2,3-Dihydro-1H-inden-1-yl | 4.89 |
| 365 | H | Isopropyl | H | Methyl | 3-(Pyrrolidin-1-ylmethyl)phenyl | (S) | 2,3-Dihydro-1H-inden-1-yl | 2.08 |
| 366 | H | Isopropyl | H | Methyl | 3-[(Dimethylamino)methyl]phenyl | (S) | 2,3-Dihydro-1H-inden-1-yl | 1.95 |
| 367 | H | Isopropyl | H | Methyl | 3-[(2,2,2-Trifluoroethoxy)methyl]phenyl | (S) | 2,3-Dihydro-1H-inden-1-yl | 4.99 |
| 368 | H | Isopropyl | H | Methyl | 3-{[Ethyl(methyl)amino]methyl}phenyl | (S) | 2,3-Dihydro-1H-inden-1-yl | 2.05 |
| 369 | H | Isopropyl | H | Methyl | 3-(Isopropoxymethyl)phenyl | (S) | 2,3-Dihydro-1H-inden-1-yl | 5.25 |
| 370 | H | Isopropyl | H | Methyl | 3-(Ethoxymethyl)phenyl | (S) | 2,3-Dihydro-1H-inden-1-yl | 4.86 |
| 371 | H | Trifluoromethyl | H | Methyl | 3-(Methoxymethyl)phenyl | (S) | 2,3-Dihydro-1H-inden-1-yl | 4.32 |
| 372 | H | Isopropyl | H | Methyl | 3-(Azetidin-1-yl)phenyl | (S) | 2,3-Dihydro-1H-inden-1-yl | 4.67 |
| 373 | H | Isopropyl | H | Methyl | 3-[Ethyl(methyl)amino]phenyl | (S) | 2,3-Dihydro-1H-inden-1-yl | 3.48 |
| 374 | H | Isopropyl | H | Methyl | 1-Ethyl-1H-pyrazol-4-yl | (S) | 2,3-Dihydro-1H-inden-1-yl | 3.44 |

TABLE 1-continued

Examples (I-1)

| Number | R1 | R2 | R3 | R4 | Q | Chiral Descriptor | A | logP (Method L0) [a] |
|---|---|---|---|---|---|---|---|---|
| 375 | H | Isopropyl | H | Methyl | 1-(2-Methoxyethyl)-1H-pyrazol-4-yl | (S) | 2,3-Dihydro-1H-inden-1-yl | 3.26 |
| 376 | H | Isopropyl | H | Methyl | 1-(Cyclopropylmethyl)-1H-pyrazol-4-yl | (S) | 2,3-Dihydro-1H-inden-1-yl | 3.83 |
| 377 | H | Isopropyl | H | Methyl | 1-(2,2-Difluoroethyl)-1H-pyrazol-4-yl | (S) | 2,3-Dihydro-1H-inden-1-yl | 3.49 |
| 378 | H | Isopropyl | H | Methyl | 3-Chloro-5-methoxyphenyl | (S) | 1,2,3,4-Tetrahydronaphthalin-1-yl | 5.55 |
| 379 | H | Isopropyl | H | Methyl | 3-(Diethylamino)phenyl | (S) | 2,3-Dihydro-1H-inden-1-yl | 2.81 |
| 380 | H | Isopropyl | H | Methyl | 3-[(Methylsulfinyl)methyl]phenyl | (S) | 2,3-Dihydro-1H-inden-1-yl | 3.05 |
| 381 | H | Isopropyl | H | Methyl | 4-Fluorophenyl | (S) | 3,4-Dihydro-2H-chromen-4-yl | 4.36 |
| 382 | H | Trifluoromethyl | H | Methyl | 3-Chlorophenyl | (S) | 2,3-Dihydro-1H-inden-1-yl | 4.97 |
| 383 | H | Trifluoromethyl | H | Methyl | 3-(Trifluoromethoxy)phenyl | (S) | 2,3-Dihydro-1H-inden-1-yl | 5.21 |
| 384 | H | Trifluoromethyl | H | Methyl | 3-(Trifluoromethyl)phenyl | (S) | 2,3-Dihydro-1H-inden-1-yl | 5.04 |
| 385 | H | Trifluoromethyl | H | Methyl | 3-(Dimethylamino)phenyl | (S) | 2,3-Dihydro-1H-inden-1-yl | 4.1 |
| 386 | H | Trifluoromethyl | H | Methyl | 3-Methoxyphenyl | (S) | 2,3-Dihydro-1H-inden-1-yl | 4.34 |
| 387 | H | Trifluoromethyl | H | Methyl | 3-Fluorophenyl | (S) | 2,3-Dihydro-1H-inden-1-yl | 4.53 |
| 388 | H | Isopropyl | H | Methyl | 3-[(Methylsulfanyl)methyl]phenyl | (S) | 2,3-Dihydro-1H-inden-1-yl | 5 |
| 389 | H | Isopropyl | H | Methyl | 3-[(Cyclopropylmethoxy)methyl]phenyl | (S) | 2,3-Dihydro-1H-inden-1-yl | 5.24 |
| 390 | H | Isopropyl | H | Methyl | 3-(Propoxymethyl)phenyl | (S) | 2,3-Dihydro-1H-inden-1-yl | 5.4 |
| 391 | H | Isopropyl | H | Methyl | 3-Methoxy-5-(trifluoromethyl)phenyl | (S) | 3,4-Dihydro-2H-chromen-4-yl | 5.13 |
| 392 | H | Isopropyl | H | Methyl | 3-(Methoxymethyl)phenyl | (S) | 3,4-Dihydro-2H-chromen-4-yl | 4.16 |
| 393 | H | Isopropyl | H | Methyl | 3-(Dimethylamino)phenyl | (S) | 3,4-Dihydro-2H-chromen-4-yl | 3.64 |
| 394 | H | Isopropyl | H | Methyl | 3-(Trifluoromethoxy)phenyl | (S) | 3,4-Dihydro-2H-chromen-4-yl | 5.19 |
| 395 | H | Isopropyl | H | Methyl | 3-Methoxyphenyl | (S) | 3,4-Dihydro-2H-chromen-4-yl | 4.24 |
| 396 | H | Isopropyl | H | Methyl | 3-Fluorophenyl | (S) | 3,4-Dihydro-2H-chromen-4-yl | 4.45 |
| 397 | H | Isopropyl | H | Methyl | 1[2-(Morpholin-4-yl)ethyl]-1H-pyrazol-4-yl | (S) | 2,3-Dihydro-1H-inden-1-yl | 1.81 |
| 398 | H | Isopropyl | H | Methyl | 1-Isopropyl-1H-pyrazol-4-yl | (S) | 2,3-Dihydro-1H-inden-1-yl | 3.77 |
| 399 | H | Isopropyl | H | Methyl | 3-[(4-Methylpiperazin-1-yl)methyl]phenyl | (S) | 2,3-Dihydro-1H-inden-1-yl | 1.98 |
| 400 | H | Isopropyl | H | Methyl | 3-[(Methylsulfonyl)methyl]phenyl | (S) | 2,3-Dihydro-1H-inden-1-yl | 3.39 |
| 401 | H | Isopropyl | H | Methyl | 1-(2,2,2-Trifluoroethyl)-1H-pyrazol-4-yl | (S) | 3,4-Dihydro-2H-chromen-4-yl | 3.57 |
| 402 | H | Isopropyl | H | Methyl | 5-Chloropyridin-3-yl | (S) | 3,4-Dihydro-2H-chromen-4-yl | 3.91 |
| 403 | H | Isopropyl | H | Methyl | 3-Chloro-5-methoxyphenyl | (S) | 3,4-Dihydro-2H-chromen-4-yl | 4.96 |
| 404 | H | Isopropyl | H | Methyl | 1-[2-(Dimethylamino)ethyl]-1H-pyrazol-4-yl | (S) | 2,3-Dihydro-1H-inden-1-yl | 1.75 |
| 405 | H | Cyclopropyl | H | Methyl | 2,6-Difluorophenyl | (S) | 2,3-Dihydro-1H-inden-1-yl | 3.66 |
| 406 | H | Isopropyl | H | Cyclopropyl | 3-(Trifluoromethoxy)phenyl | (S) | 2,3-Dihydro-1H-inden-1-yl | 6.11 |
| 407 | H | Isopropyl | H | Cyclopropyl | 3-(Dimethylamino)phenyl | (S) | 2,3-Dihydro-1H-inden-1-yl | 4.81 |
| 408 | H | Isopropyl | H | Cyclopropyl | 3-Methoxyphenyl | (S) | 2,3-Dihydro-1H-inden-1-yl | 5.19 |
| 409 | H | Isopropyl | H | Cyclopropyl | 3-(Methoxymethyl)phenyl | (S) | 2,3-Dihydro-1H-inden-1-yl | 5.13 |
| 410 | H | Trifluoromethyl | H | Methyl | 2,6-Difluorophenyl | (S) | 2,3-Dihydro-1H-inden-1-yl | 4.16 |
| 411 | H | Isopropyl | H | Cyclopropyl | 3-Chlorophenyl | (S) | 2,3-Dihydro-1H-inden-1-yl | 5.87 |
| 412 | H | Trifluoromethyl | H | Methyl | 2-Chlorophenyl | (S) | 2,3-Dihydro-1H-inden-1-yl | 4.43 |
| 413 | H | Isopropyl | H | Cyclopropyl | 2,6-Difluorophenyl | (S) | 2,3-Dihydro-1H-inden-1-yl | 4.96 |
| 414 | H | Isopropyl | H | Cyclopropyl | 2-Chlorophenyl | (S) | 2,3-Dihydro-1H-inden-1-yl | 5.87 |
| 415 | H | Isopropyl | H | Cyclopropyl | 3-(Trifluoromethyl)phenyl | (S) | 2,3-Dihydro-1H-inden-1-yl | 5.94 |
| 416 | H | Isopropyl | H | Cyclopropyl | 3-Fluorophenyl | (S) | 2,3-Dihydro-1H-inden-1-yl | 5.41 |
| 417 | H | Cyclopropyl | H | Methyl | 3-(Difluoromethoxy)phenyl | (S) | 2,3-Dihydro-1H-inden-1-yl | 4.01 |
| 418 | H | Cyclopropyl | H | Methyl | 3-(Cyclopropyloxy)phenyl | (S) | 2,3-Dihydro-1H-inden-1-yl | 4.29 |
| 419 | H | Isopropyl | H | Methyl | 1-(Cyclopropylmethyl)-1H-pyrazol-4-yl | (S) | 3,4-Dihydro-2H-chromen-4-yl | 3.59 |
| 420 | H | Isopropyl | H | Methyl | 1-(Cyclopropylmethyl)-1H-pyrazol-4-yl | (S) | 1,2,3,4-Tetrahydronaphthalin-1-yl | 4.13 |
| 421 | H | Cyclopropyl | H | Methyl | 1-(2,2,2-Trifluoroethyl)-1H-pyrazol-4-yl | (S) | 2,3-Dihydro-1H-inden-1-yl | 3.17 |
| 422 | H | Cyclopropyl | H | Methyl | 2,5-Difluorophenyl | (S) | 2,3-Dihydro-1H-inden-1-yl | 3.84 |
| 423 | H | Cyclopropyl | H | Methyl | 3-Methoxy-5-(trifluoromethyl)phenyl | (S) | 2,3-Dihydro-1H-inden-1-yl | 4.7 |
| 424 | H | Cyclopropyl | H | Methyl | 2,3-Difluorophenyl | (S) | 2,3-Dihydro-1H-inden-1-yl | 3.84 |

TABLE 1-continued

Examples (I-1)

| Number | R1 | R2 | R3 | R4 | Q | Chiral Descriptor A | A | logP (Method L0) [a] |
|---|---|---|---|---|---|---|---|---|
| 425 | H | Cyclopropyl | H | Methyl | 3-Chloro-5-(trifluoromethyl)phenyl | (S) | 2,3-Dihydro-1H-inden-1-yl | 5.34 |
| 426 | H | Isopropyl | H | Methyl | 1H-Pyrazol-1-yl | (S) | 2,3-Dihydro-1H-inden-1-yl | 3.29 |
| 427 | H | Isopropyl | H | Difluoromethyl | 3-(Dimethylamino)phenyl | (S) | 2,3-Dihydro-1H-inden-1-yl | 4.3 |
| 428 | H | Isopropyl | H | Difluoromethyl | 3-Methoxyphenyl | (S) | 2,3-Dihydro-1H-inden-1-yl | 4.42 |
| 429 | H | Isopropyl | H | Difluoromethyl | 3-Fluorophenyl | (S) | 2,3-Dihydro-1H-inden-1-yl | 4.57 |
| 430 | H | Isopropyl | H | Difluoromethyl | 3-(Methoxymethyl)phenyl | (S) | 2,3-Dihydro-1H-inden-1-yl | 4.36 |
| 431 | H | Isopropyl | H | Difluoromethyl | 3-(Trifluoromethoxy)phenyl | (S) | 2,3-Dihydro-1H-inden-1-yl | 5.18 |
| 432 | H | Isopropyl | H | Difluoromethyl | 3-Chlorophenyl | (S) | 2,3-Dihydro-1H-inden-1-yl | 4.92 |
| 433 | H | Isopropyl | H | Difluoromethyl | 3-(Trifluoromethyl)phenyl | (S) | 2,3-Dihydro-1H-inden-1-yl | 5.03 |
| 434 | H | Isopropyl | H | Difluoromethyl | 2,6-Difluorophenyl | (S) | 2,3-Dihydro-1H-inden-1-yl | 4.23 |
| 435 | H | Isopropyl | H | Difluoromethyl | 2-Chlorophenyl | (S) | 2,3-Dihydro-1H-inden-1-yl | 4.43 |
| 436 | H | Cyclopropyl | H | Methyl | 3-Chloro-2,6-difluorophenyl | (S) | 2,3-Dihydro-1H-inden-1-yl | 4.18 |
| 437 | H | Cyclopropyl | H | Methyl | 2,3,6-Trifluorophenyl | (S) | 2,3-Dihydro-1H-inden-1-yl | 3.83 |
| 438 | H | Cyclopropyl | H | Methyl | 2,4,6-Trifluorophenyl | (S) | 2,3-Dihydro-1H-inden-1-yl | 3.87 |
| 439 | H | Cyclopropyl | H | Methyl | 3-Methoxyphenyl | (S) | 1,2,3,4-Tetrahydronaphthalin-1-yl | 4.03 |
| 440 | H | Isopropyl | H | Methyl | 3-(3,3-Difluoroazetidin-1-yl)phenyl | (S) | 3,4-Dihydro-2H-chromen-4-yl | 4.64 |
| 441 | H | Cyclopropyl | H | Methyl | 3-(3,3-Difluoroazetidin-1-yl)phenyl | (S) | 2,3-Dihydro-1H-inden-1-yl | 4.16 |
| 442 | H | Cyclopropyl | H | Methyl | 2-Chloro-6-fluorophenyl | (S) | 2,3-Dihydro-1H-inden-1-yl | 3.89 |
| 443 | H | Isopropyl | H | Methyl | 3-(Cyclopropylsulfonyl)phenyl | (S) | 2,3-Dihydro-1H-inden-1-yl | 3.99 |
| 444 | H | Isopropyl | H | Methyl | 3-(3-Cyanazetidin-1-yl)phenyl | (S) | 3,4-Dihydro-2H-chromen-4-yl | 3.91 |
| 445 | H | Cyclopropyl | H | Methyl | 2,6-Difluorophenyl | (S) | 3,4-Dihydro-2H-chromen-4-yl | 3.43 |
| 446 | H | Cyclopropyl | H | Methyl | 1-(Cyclopropylmethyl)-1H-pyrazol-4-yl | (S) | 2,3-Dihydro-1H-inden-1-yl | 3.15 |
| 447 | H | Isopropyl | H | Methyl | 4-Chloro-1H-pyrazol-1-yl | (S) | 2,3-Dihydro-1H-inden-1-yl | 4.13 |
| 448 | H | Cyclopropyl | H | Methyl | 2,5-Difluorophenyl | (S) | 3,4-Dihydro-2H-chromen-4-yl | 3.61 |
| 449 | H | Cyclopropyl | H | Methyl | 3-(Trifluoromethyl)phenyl | (S) | 3,4-Dihydro-2H-chromen-4-yl | 4.31 |
| 450 | H | Cyclopropyl | H | Methyl | 2-Fluorophenyl | (S) | 3,4-Dihydro-2H-chromen-4-yl | 3.45 |
| 451 | H | Cyclopropyl | H | Methyl | 3-(Methoxymethyl)phenyl | (S) | 3,4-Dihydro-2H-chromen-4-yl | 3.43 |
| 452 | H | Cyclopropyl | H | Methyl | 2-Chlorophenyl | (S) | 3,4-Dihydro-2H-chromen-4-yl | 3.64 |
| 453 | H | Cyclopropyl | H | Methyl | 3-(Dimethylamino)phenyl | (S) | 3,4-Dihydro-2H-chromen-4-yl | 2.72 |
| 454 | H | Cyclopropyl | H | Methyl | 3-Methoxyphenyl | (S) | 3,4-Dihydro-2H-chromen-4-yl | 3.5 |
| 455 | H | Cyclopropyl | H | Methyl | 3-Chlorophenyl | (S) | 3,4-Dihydro-2H-chromen-4-yl | 4.13 |
| 456 | H | Cyclopropyl | H | Methyl | 3-Fluorophenyl | (S) | 3,4-Dihydro-2H-chromen-4-yl | 3.71 |
| 457 | H | Cyclopropyl | H | Methyl | 2,3-Difluorophenyl | (S) | 3,4-Dihydro-2H-chromen-4-yl | 3.61 |
| 458 | H | Cyclopropyl | H | Methyl | 2-Chloro-6-fluorophenyl | (S) | 3,4-Dihydro-2H-chromen-4-yl | 3.65 |
| 459 | H | Isopropyl | H | Methyl | 3-(3-Fluoroazetidin-1-yl)phenyl | (S) | 3,4-Dihydro-2H-chromen-4-yl | 4.36 |
| 460 | H | Cyclopropyl | H | Methyl | 3-(3-Cyanazetidin-1-yl)phenyl | (S) | 2,3-Dihydro-1H-inden-1-yl | 3.44 |
| 461 | H | Isopropyl | H | Methyl | 1-Methyl-2,3-dihydro-1H-indol-4-yl | (S) | 3,4-Dihydro-2H-chromen-4-yl | 4.11 |
| 462 | H | Cyclopropyl | H | Methyl | 3-(Trifluoromethoxy)phenyl | (S) | 3,4-Dihydro-2H-chromen-4-yl | 4.47 |
| 463 | H | Cyclopropyl | H | Methyl | 4-Fluorophenyl | (S) | 3,4-Dihydro-2H-chromen-4-yl | 3.62 |
| 464 | H | Cyclopropyl | H | Methyl | 3-(3,3-Difluoroazetidin-1-yl)phenyl | (S) | 3,4-Dihydro-2H-chromen-4-yl | 3.92 |
| 465 | H | Cyclopropyl | H | Methyl | 3-Chloro-5-(trifluoromethyl)phenyl | (S) | 3,4-Dihydro-2H-chromen-4-yl | 5.11 |
| 466 | H | Cyclopropyl | H | Methyl | 3-(3-Fluoroazetidin-1-yl)phenyl | (S) | 2,3-Dihydro-1H-inden-1-yl | 3.85 |
| 467 | H | Cyclopropyl | H | Methyl | 2,6-Dichlorophenyl | (S) | 3,4-Dihydro-2H-chromen-4-yl | 3.88 |
| 468 | H | Cyclopropyl | H | Methyl | 1-(2,2,2-Trifluoroethyl)-1H-pyrazol-4-yl | (S) | 3,4-Dihydro-2H-chromen-4-yl | 2.95 |
| 469 | H | Cyclopropyl | H | Methyl | 3,5-Dichlorophenyl | (S) | 3,4-Dihydro-2H-chromen-4-yl | 4.96 |
| 470 | H | Cyclopropyl | H | Methyl | 1-(Cyclopropylmethyl)-1H-pyrazol-4-yl | (S) | 3,4-Dihydro-2H-chromen-4-yl | 2.92 |
| 471 | H | Cyclopropyl | H | Methyl | 3,4-Difluorophenyl | (S) | 3,4-Dihydro-2H-chromen-4-yl | 3.86 |
| 472 | H | Cyclopropyl | H | Methyl | 2-Chloro-3-fluorophenyl | (S) | 3,4-Dihydro-2H-chromen-4-yl | 3.72 |
| 473 | H | Cyclopropyl | H | Methyl | 2,3-Dichlorophenyl | (S) | 3,4-Dihydro-2H-chromen-4-yl | 4.07 |
| 474 | H | Cyclopropyl | H | Methyl | 1-Methyl-2,3-dihydro-1H-indol-4-yl | (S) | 3,4-Dihydro-2H-chromen-4-yl | 3.25 |
| 475 | H | Cyclopropyl | H | Methyl | 2-Chloro-4-fluorophenyl | (S) | 3,4-Dihydro-2H-chromen-4-yl | 3.79 |
| 476 | H | Cyclopropyl | H | Methyl | 3,5-Dichloro-4-fluorophenyl | (S) | 3,4-Dihydro-2H-chromen-4-yl | 4.95 |

TABLE 1-continued

Examples $$\text{(I-1)}$$

Structure: pyrazolo[1,5-a]pyrimidine with R2 at position 7, R3 at position 5, R4 at position 2, Q at position 3, and C(=O)N(R1)(A) at position 6.

| Number | R1 | R2 | R3 | R4 | Q | Chiral Descriptor A | A | logP (Method L0) [a] |
|---|---|---|---|---|---|---|---|---|
| 477 | H | Ethyl | H | Methyl | 2,3-Difluorophenyl | (S) | 3,4-Dihydro-2H-chromen-4-yl | |
| 478 | H | Ethyl | H | Methyl | 2,6-Difluorophenyl | (S) | 3,4-Dihydro-2H-chromen-4-yl | |
| 479 | H | Ethyl | H | Methyl | 2-Chloro-6-fluorophenyl | (S) | 3,4-Dihydro-2H-chromen-4-yl | |
| 480 | H | Cyclopropyl | H | Methyl | 3-Chloro-2-fluorophenyl | (S) | 3,4-Dihydro-2H-chromen-4-yl | |
| 481 | H | Isopropyl | H | Methyl | 1H-Indol-4-yl | (S) | 3,4-Dihydro-2H-chromen-4-yl | |
| 482 | H | Cyclopropyl | H | Methyl | 2,4,6-Trifluoro-3-methoxyphenyl | (S) | 3,4-Dihydro-2H-chromen-4-yl | |
| 483 | H | Isopropyl | H | Methyl | 1-Methyl-1H-indol-4-yl | (S) | 3,4-Dihydro-2H-chromen-4-yl | |
| 484 | H | Ethyl | H | Methyl | 2,3-Dichlorophenyl | (S) | 3,4-Dihydro-2H-chromen-4-yl | |
| 485 | H | Ethyl | H | Methyl | 2,4-Dichlorophenyl | (S) | 3,4-Dihydro-2H-chromen-4-yl | |
| 486 | H | Ethyl | H | Methyl | 2,5-Dichlorophenyl | (S) | 3,4-Dihydro-2H-chromen-4-yl | |
| 487 | H | Ethyl | H | Methyl | 3,4-Difluorophenyl | (S) | 3,4-Dihydro-2H-chromen-4-yl | |
| 488 | H | Ethyl | H | Methyl | 3-Chlorophenyl | (S) | 3,4-Dihydro-2H-chromen-4-yl | |
| 489 | H | Ethyl | H | Methyl | 3-Chloro-2,6-difluorophenyl | (S) | 3,4-Dihydro-2H-chromen-4-yl | |
| 490 | H | Ethyl | H | Methyl | 2,3,4-Trifluorophenyl | (S) | 3,4-Dihydro-2H-chromen-4-yl | |
| 491 | H | Ethyl | H | Methyl | 2,6-Dichlorophenyl | (S) | 3,4-Dihydro-2H-chromen-4-yl | |
| 492 | H | Cyclopropyl | H | Difluoromethyl | 2,5-Dichlorophenyl | (S) | 3,4-Dihydro-2H-chromen-4-yl | |
| 493 | H | Cyclopropyl | H | Difluoromethyl | 2,6-Difluorophenyl | (S) | 3,4-Dihydro-2H-chromen-4-yl | |
| 494 | H | Isopropyl | H | Difluoromethyl | 2,5-Dichlorophenyl | (S) | 3,4-Dihydro-2H-chromen-4-yl | |
| 495 | H | Isopropyl | H | Difluoromethyl | 2,6-Difluorophenyl | (S) | 3,4-Dihydro-2H-chromen-4-yl | |
| 496 | H | Ethyl | H | Methyl | 2,4-Difluoro-3-methoxyphenyl | (S) | 3,4-Dihydro-2H-chromen-4-yl | |
| 497 | H | Ethyl | H | Methyl | 3,5-Dichloro-4-fluorophenyl | (S) | 3,4-Dihydro-2H-chromen-4-yl | |
| 498 | H | Cyclopropyl | H | Difluoromethyl | 2,3,4-Trifluorophenyl | (S) | 3,4-Dihydro-2H-chromen-4-yl | |
| 499 | H | Cyclopropyl | H | Difluoromethyl | 2-Chloro-6-fluorophenyl | (S) | 3,4-Dihydro-2H-chromen-4-yl | |
| 500 | H | Isopropyl | H | Chloro | 3,4-Difluorophenyl | (S) | 3,4-Dihydro-2H-chromen-4-yl | |
| 501 | H | Cyclopropyl | H | Methyl | 3-Hydroxyphenyl | (S) | 3,4-Dihydro-2H-chromen-4-yl | |
| 502 | H | Isopropyl | H | Difluoromethyl | 2,4-Difluoro-3-methoxyphenyl | (S) | 3,4-Dihydro-2H-chromen-4-yl | |
| 503 | H | Isopropyl | H | Difluoromethyl | 2,6-Dichlorophenyl | (S) | 3,4-Dihydro-2H-chromen-4-yl | |
| 504 | H | Cyclopropyl | H | Methyl | 2-Fluoro-5-(trifluoromethyl)phenyl | (S) | 3,4-Dihydro-2H-chromen-4-yl | |
| 505 | H | Isopropyl | H | Difluoromethyl | 2,3-Dichlorophenyl | (S) | 3,4-Dihydro-2H-chromen-4-yl | |
| 506 | H | Isopropyl | H | Difluoromethyl | 2-Chloro-6-fluorophenyl | (S) | 3,4-Dihydro-2H-chromen-4-yl | |
| 507 | H | Isopropyl | H | Difluoromethyl | 2,4-Dichlorophenyl | (S) | 3,4-Dihydro-2H-chromen-4-yl | |
| 508 | H | Isopropyl | H | Difluoromethyl | 2,3,4-Trifluorophenyl | (S) | 3,4-Dihydro-2H-chromen-4-yl | |
| 509 | H | Cyclopropyl | H | Methyl | 2-Chloro-5-(trifluoromethyl)phenyl | (S) | 3,4-Dihydro-2H-chromen-4-yl | |
| 510 | H | Cyclopropyl | H | Methyl | 2,3-Dihydro-1-benzofuran-4-yl | (S) | 3,4-Dihydro-2H-chromen-4-yl | |
| 511 | H | Cyclopropyl | H | Difluoromethyl | 2,4-Dichlorophenyl | (S) | 3,4-Dihydro-2H-chromen-4-yl | |
| 512 | H | Cyclopropyl | H | Difluoromethyl | 2,3-Dichlorophenyl | (S) | 3,4-Dihydro-2H-chromen-4-yl | |
| 513 | H | Methoxy | H | Methyl | 2-Chloro-6-fluorophenyl | (S) | 2,3-Dihydro-1H-inden-1-yl | 2.96 |
| 514 | H | Methoxy | H | Methyl | 2-Chloro-6-fluorophenyl | (S) | 3,4-Dihydro-2H-chromen-4-yl | 4.93 |
| 515 | H | Methoxy | H | Methyl | 3,5-Dichloro-2-fluorophenyl | (S) | 3,4-Dihydro-2H-chromen-4-yl | 3.17 |
| 516 | H | Morpholin-4-yl | H | Methyl | 3,5-Dichlorophenyl | (S) | 3,4-Dihydro-2H-chromen-4-yl | 3.99 |
| 517 | H | Morpholin-4-yl | H | Methyl | 2,3-Dichlorophenyl | (S) | 3,4-Dihydro-2H-chromen-4-yl | 3.51 |
| 518 | H | Dimethylamino | H | Methyl | 2,3-Dichlorophenyl | (S) | 3,4-Dihydro-2H-chromen-4-yl | 3.94 |
| 519 | H | Methoxy | H | Methyl | 3,4-Difluorophenyl | (S) | 3,4-Dihydro-2H-chromen-4-yl | 2.88 |
| 520 | H | Dimethylamino | H | Methyl | 3,5-Dichlorophenyl | (S) | 3,4-Dihydro-2H-chromen-4-yl | 4.92 |
| 521 | H | Methoxy | H | Methyl | 3,5-Dichlorophenyl | (S) | 3,4-Dihydro-2H-chromen-4-yl | 3.56 |
| 522 | H | (Dimethylamino)methyl | H | Methyl | 2,3-Dichlorophenyl | (S) | 2,3-Dihydro-1H-inden-1-yl | 2.08 |
| 523 | H | (Dimethylamino)methyl | H | Methyl | 2,3-Dichlorophenyl | (S) | 3,4-Dihydro-2H-chromen-4-yl | 2.17 |
| 524 | H | Morpholino | H | Methyl | 2-Fluoro-3-chlorophenyl | (S) | 3,4-Dihydro-2H-chromen-4-yl | 4.69 |
| 525 | H | Cyclopropyl | H | Methyl | 2-Chloro-5-pyridyl | (S) | 3,4-Dihydro-2H-chromen-4-yl | 2.96 |

TABLE 1-continued

Examples (I-1)

| Number | R1 | R2 | R3 | R4 | Q | Chiral Descriptor A | A | logP (Method L0) [a] |
|---|---|---|---|---|---|---|---|---|
| 526 | H | Cyclopropyl | H | Methyl | 2-Morpholino-4-pyridyl | (S) | 3,4-Dihydro-2H-chromen-4-yl | 1.53 |
| 527 | H | Cyclopropyl | H | Methyl | 2-Morpholino-3-fluoro-4-pyridyl | (S) | 3,4-Dihydro-2H-chromen-4-yl | 2.96 |
| 528 | H | Cyclopropyl | H | Methyl | 2-Acetamido-4-pyridyl | (S) | 3,4-Dihydro-2H-chromen-4-yl | 1.69 |
| 529 | H | N-Methyl-(2-methylsulfanyl-ethyl)amino | H | Methyl | 2,3-Dichlorophenyl | (S) | 3,4-Dihydro-2H-chromen-4-yl | 4.69 |
| 530 | H | Morpholino | H | Methyl | 2-Fluoro-3-(trifluoromethyl)phenyl | (S) | 3,4-Dihydro-2H-chromen-4-yl | 3.99 |
| 531 | H | Morpholino | H | Methyl | 2,4,6-Trifluoro-3-methoxyphenyl | (S) | 3,4-Dihydro-2H-chromen-4-yl | 2.88 |
| 532 | H | Morpholino | H | Methyl | 2-Chloro-3-(trifluoromethyl)phenyl | (S) | 3,4-Dihydro-2H-chromen-4-yl | 5.59 |
| 533 | H | Morpholino | H | Methyl | 2,4-Difluoro-3-methoxyphenyl | (S) | 3,4-Dihydro-2H-chromen-4-yl | 4.46 |
| 534 | H | Morpholino | H | Methyl | 2,3-Difluorophenyl | (S) | 3,4-Dihydro-2H-chromen-4-yl | 4.32 |
| 535 | H | Morpholino | H | Methyl | 2,3,6-Trifluorophenyl | (S) | 3,4-Dihydro-2H-chromen-4-yl | 3.29 |
| 536 | H | Morpholino | H | Methyl | 2-Methylphenyl | (S) | 3,4-Dihydro-2H-chromen-4-yl | 4.18 |
| 537 | H | Cyclopropyl | H | Methyl | 3,5-Difluorophenyl | (S) | 3,4-Dihydro-2H-chromen-4-yl | 3.99 |
| 538 | H | Cyclopropyl | H | Methyl | 2,3,5-Trichlorophenyl | (S) | 3,4-Dihydro-2H-chromen-4-yl | 4.8 |
| 539 | H | Cyclopropyl-amino | H | Methyl | 3,5-Difluorophenyl | (S) | 3,4-Dihydro-2H-chromen-4-yl | 4.46 |
| 540 | H | N-Methyl-([rac]2-methyl-sulfinylethyl)amino | H | Methyl | 3,5-Dichlorophenyl | (S) | 3,4-Dihydro-2H-chromen-4-yl | 2.88 |
| 541 | H | N-Methyl-(2-methylsulfonyl-ethyl)amino | H | Methyl | 3,5-Dichlorophenyl | (S) | 3,4-Dihydro-2H-chromen-4-yl | 3.29 |
| 542 | H | Cyclopropyl-amino | H | Methyl | 3,5-Dichlorophenyl | (S) | 3,4-Dihydro-2H-chromen-4-yl | 5.59 |
| 543 | H | Morpholino | H | Methyl | 2,4-Difluoro-3-(dimethylamino)-phenyl | (S) | 3,4-Dihydro-2H-chromen-4-yl | |
| 544 | H | Morpholino | H | Methyl | 2,6-Dichlorophenyl | (S) | 3,4-Dihydro-2H-chromen-4-yl | |
| 545 | H | Morpholino | H | Methyl | 2,6-Difluoro-3-chlorophenyl | (S) | 3,4-Dihydro-2H-chromen-4-yl | |
| 546 | H | Cyclopropyl-amino | H | Methyl | 2,3-Dichlorophenyl | (S) | 3,4-Dihydro-2H-chromen-4-yl | 4.32 |
| 547 | H | Dimethylamino | H | Methyl | 2-Fluoro-5-(trifluoromethyl)-phenyl | (S) | 3,4-Dihydro-2H-chromen-4-yl | |
| 548 | H | Methylamino | H | Methyl | 2,3-Dichlorophenyl | (S) | 3,4-Dihydro-2H-chromen-4-yl | 4.18 |
| 549 | H | Dimethylamino | H | Methyl | 2,3-Difluorophenyl | (S) | 3,4-Dihydro-2H-chromen-4-yl | |
| 550 | H | Dimethylamino | H | Methyl | 2,4-Difluoro-3-(dimethylamino)-phenyl | (S) | 3,4-Dihydro-2H-chromen-4-yl | |
| 551 | H | Dimethylamino | H | Methyl | 2,4-Difluoro-3-methoxy-phenyl | (S) | 3,4-Dihydro-2H-chromen-4-yl | |
| 552 | H | Dimethylamino | H | Methyl | 2-Fluoro-3-chlorophenyl | (S) | 3,4-Dihydro-2H-chromen-4-yl | |
| 553 | H | Dimethylamino | H | Methyl | 2-Methylphenyl | (S) | 3,4-Dihydro-2H-chromen-4-yl | |
| 554 | H | Dimethylamino | H | Methyl | 2,3,6-Trifluorophenyl | (S) | 3,4-Dihydro-2H-chromen-4-yl | |
| 555 | H | N-Methyl-cyclo-propylamino | H | Methyl | 3,5-Dichlorophenyl | (S) | 3,4-Dihydro-2H-chromen-4-yl | |
| 556 | H | N-Methyl-2-(dimethylamino)ethyl-amino | H | Methyl | 3,5-Dichlorophenyl | (S) | 3,4-Dihydro-2H-chromen-4-yl | |
| 557 | H | Cyclopropyl | H | Methyl | 2,3,5-Trifluorophenyl | (S) | 3,4-Dihydro-2H-chromen-4-yl | 3.72 |
| 558 | H | N-Methyl-(1-methyl-piperidin-4-yl)-amino | H | Methyl | 3,5-Dichlorophenyl | (S) | 3,4-Dihydro-2H-chromen-4-yl | |
| 559 | H | N-Methyl-2,2-difluoroethyl-amino | H | Methyl | 3,5-Dichlorophenyl | (S) | 3,4-Dihydro-2H-chromen-4-yl | |
| 560 | H | N-methyl-2-(2-oxopyrrolidin-1-yl)ethyl]amino | H | Methyl | 3,5-Dichlorophenyl | (S) | 3,4-Dihydro-2H-chromen-4-yl | |
| 561 | H | 2-[2-(2-Methoxyethoxy)ethoxy]ethyl-N-methyl-amino | H | Methyl | 3,5-Dichlorophenyl | (S) | 3,4-Dihydro-2H-chromen-4-yl | |

TABLE 2

LC-MS and NMR data
NMR peak forms are stated as they appear in the spectra, possible higher order effects have not been considered.

| Example No | LC-MS (Method L2-L4) | NMR |
|---|---|---|
| 177 | (Method L2): $R_t$ = 4.14 min; m/z = 442 (M + H)$^+$ | $^1$H NMR (300 MHz, DMSO-d6, Method M2) δ 9.10 (d, J = 8.2 Hz, 1H), 8.60 (s, 1H), 8.07 (d, J = 7.5 Hz, 1H), 7.77 (t, J = 7.9 Hz, 1H), 7.45-7.35 (m, 1H), 7.34-7.19 (m, 3H), 6.66 (d, J = 8.1 Hz, 1H), 5.53 (q, J = 7.9 Hz, 1H), 4.06-3.88 (m, 4H), 3.08-2.79 (m, 5H), 2.62-2.44 (m, 1H), 2.04-1.83 (m, 1H), 1.57 (dd, J = 6.9, 5.3 Hz, 6H). |
| 178 | (Method L2): $R_t$ = 4.30 min; m/z = 430 (M + H)$^+$ | $^1$H NMR (300 MHz, DMSO-d6, Method M2) δ 9.11 (d, J = 8.1 Hz, 1H), 8.65 (s, 1H), 8.39 (dd, J = 7.6, 2.6 Hz, 1H), 8.06 (q, J = 8.1 Hz, 1H), 7.45-7.35 (m, 1H), 7.33-7.18 (m, 3H), 7.00 (dd, J = 8.0, 2.7 Hz, 1H), 5.54 (q, J = 7.8 Hz, 1H), 4.10-3.84 (m, 1H), 3.06-2.75 (m, 5H), 2.62-2.53 (m, 1H), 2.02-1.83 (m, 1H), 1.56 (dd, J = 6.9, 5.3 Hz, 6H). |
| 179 | (Method L2): $R_t$ = 4.30 min; m/z = 480 (M + H)$^+$ | $^1$H NMR (300 MHz, DMSO-d6, MEthod M2) δ 9.12 (d, J = 8.2 Hz, 1H), 8.72 (d, J = 8.1 Hz, 1H), 8.67 (s, 1H), 8.16 (t, J = 7.9 Hz, 1H), 7.72 (d, J = 7.5 Hz, 1H), 7.46-7.35 (m, 1H), 7.34-7.20 (m, 3H), 5.54 (q, J = 7.8 Hz, 1H), 4.07-3.88 (m, 1H), 3.08-2.77 (m, 5H), 2.62-2.53 (m, 1H), 2.02-1.85 (m, 1H), 1.57 (dd, J = 7.0, 5.2 Hz, 6H). |
| 183 | (Method L2): $R_t$ = 4.22 min; m/z = 446 (M + 1)$^+$ | $^1$H NMR (300 MHz, DMSO-d6, Method M2) δ 9.11 (d, J = 8.2 Hz, 1H), 8.64 (s, 1H), 8.43 (d, J = 7.8 Hz, 1H), 7.94 (t, J = 7.9 Hz, 1H), 7.45-7.18 (m, 5H), 5.53 (q, J = 7.8 Hz, 1H), 4.07-3.87 (m, 1H), 3.08-2.75 (m, 5H), 2.63-2.54 (m, 1H), 2.03-1.84 (m, 1H), 1.56 (dd, J = 6.9, 5.3 Hz, 6H). |
| 269 | (Method L2): $R_t$ = 3.86 min; m/z = 527 (M + 1)$^+$ | $^1$H NMR (400 MHz, DMSO-d6, Method M2) δ 9.19 (d, J = 8.0 Hz, 1H), 8.61 (s, 1H), 7.45-7.15 (m, 5H), 6.97-6.89 (m, 1H), 6.84-6.78 (m, 1H), 5.29-5.20 (m, 1H), 4.35-4.17 (m, 2H), 3.97 (s, 3H), 2.66-2.57 (m, 1H), 2.29-2.18 (m, 1H), 2.13-2.02 (m, 1H), 1.45-1.38 (m, 2H), 1.29-1.24 (m, 2H). |
| 270 | (Method L2): $R_t$ = 3.91 min; m/z = 497 (M + 1)$^+$ | $^1$H NMR (400 MHz, DMSO-d6, Method M2) δ 9.19 (d, J = 8.0 Hz, 1H), 8.63 (s, 1H), 7.57-7.48 (m, 1H), 7.48-7.15 (m, 5H), 6.93 (td, J = 7.5, 1.2 Hz, 1H), 6.81 (dd, J = 8.2, 1.1 Hz, 1H), 5.30-5.16 (m, 1H), 4.36-4.16 (m, 2H), 2.66-2.56 (m, 1H), 2.30-2.14 (m, 1H), 2.14-2.00 (m, 1H), 1.46-1.37 (m, 2H), 1.31-1.21 (m, 2H). |
| 271 | (Method L2): $R_t$ = 3.87 min; m/z = 529/531 (M + 1)$^+$ | $^1$H NMR (400 MHz, DMSO-d6, Method M2) δ 9.22 (d, J = 8.0 Hz, 1H), 8.56 (s, 1H), 7.66-7.60 (m, 2H), 7.55-7.49 (m, 1H), 7.38-7.08 (m, 3H), 6.95-6.89 (m, 1H), 6.82-6.77 (m, 1H), 5.27-5.19 (m, 1H), 4.34-4.26 (m, 1H), 4.25-4.16 (m, 1H), 2.67-2.58 (m, 1H), 2.28-2.17 (m, 1H), 2.12-2.01 (m, 1H), 1.47-1.41 (m, 2H), 1.30-1.24 (m, 2H). |
| 272 | (Method L2): $R_t$ = 4.25 min; m/z = 547/549 (M + 1)$^+$ | $^1$H NMR (400 MHz, DMSO-d6, Method M2) δ 9.21 (d, J = 8.0 Hz, 1H), 8.71 (s, 1H), 7.87 (d, J = 6.5 Hz, 2H), 7.68-7.11 (m, 3H), 6.93 (td, J = 7.5, 1.2 Hz, 1H), 6.81 (dd, J = 8.2, 1.0 Hz, 1H), 5.28-5.20 (m, 1H), 4.34-4.18 (m, 2H), 2.66-2.57 (m, 1H), 2.28-2.18 (m, 1H), 2.12-2.02 (m, 1H), 1.45-1.38 (m, 2H), 1.30-1.21 (m, 2H). |
| 273 | (Method L2): $R_t$ = 3.99 min; m/z = 495 (M + 1)$^+$ | $^1$H NMR (400 MHz, DMSO-d6, Method M2) δ 9.20 (d, J = 8.0 Hz, 1H), 8.68 (s, 1H), 7.78 (t, J = 1.8 Hz, 1H), 7.70-7.64 (m, 1H), 7.60-7.13 (m, 5H), 6.94 (td, J = 7.5, 1.2 Hz, 1H), 6.82 (dd, J = 8.2, 1.1 Hz, 1H), 5.29-5.21 (m, 1H), 4.36-4.19 (m, 2H), 2.67-2.57 (m, 1H), 2.29-2.18 (m, 1H), 2.13-2.03 (m, 1H), 1.45-1.35 (m, 2H), 1.30-1.22 (m, 2H). |
| 274 | (Method L3): $R_t$ = 3.98 min; m/z = 497 (M + 1)$^+$ | $^1$H NMR (400 MHz, DMSO-d6, Method M2) δ 9.20 (d, J = 8.0 Hz, 1H), 8.66 (s, 1H), 7.80-7.67 (m, 1H), 7.65-7.28 (m, 4H), 7.25-7.10 (m, 1H), 6.99-6.87 (m, 1H), 6.86-6.77 (m, 1H), 5.31-5.19 (m, 1H), 4.36-4.17 (m, 2H), 2.66-2.55 (m, 1H), 2.30-2.17 (m, 1H), 2.15-2.01 (m, 1H), 1.45-1.35 (m, 2H), 1.30-1.20 (m, 2H). |
| 275 | (Method L2): $R_t$ = 4.47 min; m/z = 481/483 (M + 1)$^+$ | $^1$H NMR (400 MHz, DMSO-d6, Method M2) δ 9.26 (d, J = 8.0 Hz, 1H), 8.69 (s, 1H), 7.91 (t, J = 1.8 Hz, 1H), 7.87-7.78 (m, 1H), 7.55 (t, J = 7.9 Hz, 1H), 7.49-7.42 (m, 1H), 7.39-7.31 (m, 1H), 7.24-7.13 (m, 1H), 6.98-6.89 (m, 1H), 6.86-6.76 (m, 1H), 5.29-5.19 (m, 1H), 4.34-4.17 (m, 2H), 3.91 (m, 1H), 2.29-2.15 (m, 1H), 2.13-2.00 (m, 1H), 1.54 (m, 6H). |
| 276 | (Method L2): $R_t$ = 4.50 min; m/z = 497 (M + 1)$^+$ | $^1$H NMR (400 MHz, DMSO-d6, Method M2) δ 9.27 (d, J = 8.0 Hz, 1H), 8.71 (s, 1H), 7.78 (t, J = 1.8 Hz, 1H), 7.67 (dt, J = 7.8, 1.2 Hz, 1H), 7.62-7.28 (m, 4H), 7.24-7.13 (m, 1H), 6.94 (td, J = 7.5, 1.2 Hz, 1H), 6.81 (dd, J = 8.2, 1.1 Hz, 1H), 5.30-5.20 (m, 1H), 4.35-4.18 (m, 2H), 3.95 (hept, J = 7.0 Hz, 1H), 2.30-2.16 (m, 1H), 2.14-2.00 (m, 1H), 1.56 (dd, J = 9.5, 7.0 Hz, 6H). |
| 277 | (Method L1): $R_t$ = 4.31 min; m/z = 533 (M + 1)$^+$ | $^1$H NMR (400 MHz, DMSO-d6, Method M2) δ 9.26 (d, J = 8.0 Hz, 1H), 8.68 (s, 1H), 7.85-7.76 (m, 1H), 7.50-7.14 (m, 4H), 6.97-6.89 (m, 1H), 6.81 (dd, J = 8.2, 1.1 Hz, 1H), 5.28-5.19 (m, 1H), 4.34-4.15 (m, 2H), 3.94 (p, J = 7.0 Hz, 1H), 2.29-2.16 (m, 1H), 2.12-2.01 (m, 1H), 1.57 (dd, J = 9.9, 7.1 Hz, 6H). |
| 278 | (Method L2): $R_t$ = 4.18 min; m/z = 499 (M + 1)$^+$ | $^1$H NMR (400 MHz, DMSO-d6, Method M2) δ 9.27 (d, J = 8.0 Hz, 1H), 8.70 (s, 1H), 7.81-7.67 (m, 1H), 7.67-7.13 (m, 5H), 7.00-6.88 (m, 1H), 6.87-6.75 (m, 1H), 5.25 (q, J = 5.7 Hz, 1H), 4.36-4.16 (m, 2H), 4.02-3.87 (m, 1H), 2.30-2.16 (m, 1H), 2.14-2.01 (m, 1H), 1.56 (dd, J = 9.6, 7.1 Hz, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 279 | (Method L2): $R_t$ = 4.19 min; m/z = 499 (M + 1)$^+$ | $^1$H NMR (400 MHz, DMSO-d6, Method M2) δ 9.27 (d, J = 8.0 Hz, 1H), 8.66 (s, 1H), 7.57-7.49 (m, 1H), 7.49-7.21 (m, 4H), 7.21-7.15 (m, 1H), 6.98-6.90 (m, 1H), 6.84-6.78 (m, 1H), 5.28-5.20 (m, 1H), 4.35-4.17 (m, 2H), 3.94 (h, J = 7.1 Hz, 1H), 2.29-2.16 (m, 1H), 2.12-2.01 (m, 1H), 1.57 (dd, J = 9.8, 7.1 Hz, 6H). |
| 280 | (Method L2): $R_t$ = 4.10 min; m/z = 531 (M + 1)$^+$ | $^1$H NMR (400 MHz, DMSO-d6, Method M2) δ 9.18 (d, J = 7.9 Hz, 1H), 8.64 (d, J = 0.9 Hz, 1H), 7.86-7.74 (m, 1H), 7.49-7.14 (m, 4H), 6.97-6.88 (m, 1H), 6.81 (dd, J = 8.2, 0.9 Hz, 1H), 5.29-5.18 (m, 1H), 4.36-4.16 (m, 2H), 2.66-2.57 (m, 1H), 2.30-2.17 (m, 1H), 2.14-2.00 (m, 1H), 1.49-1.36 (m, 2H), 1.33-1.19 (m, 2H). |
| 281 | (Method L2): $R_t$ = 4.30 min; m/z = 483 (M + 1)$^+$ | $^1$H NMR (400 MHz, DMSO-d6, Method M2) δ 9.26 (d, J = 8.0 Hz, 1H), 8.63 (s, 1H), 7.61-7.48 (m, 1H), 7.47-7.31 (m, 3H), 7.24-7.12 (m, 1H), 6.99-6.88 (m, 1H), 6.81 (d, J = 8.2 Hz, 1H), 5.23 (q, J = 5.6 Hz, 1H), 4.36-4.14 (m, 2H), 3.97-3.84 (m, 1H), 2.28-2.15 (m, 1H), 2.12-2.00 (m, 1H), 1.55 (m, 6H). |
| 282 | (Method L2): $R_t$ = 4.61 min; m/z = 549/551 (M + 1)$^+$ | $^1$H NMR (400 MHz, DMSO-d6, Method M2) δ 9.28 (d, J = 8.0 Hz, 1H), 8.75 (s, 1H), 7.88 (d, J = 6.4 Hz, 2H), 7.65-7.30 (m, 2H), 7.25-7.11 (m, 1H), 6.94 (td, J = 7.5, 1.2 Hz, 1H), 6.81 (dd, J = 8.2, 1.1 Hz, 1H), 5.33-5.18 (m, 1H), 4.38-4.16 (m, 2H), 3.95 (hept, J = 6.7 Hz, 1H), 2.30-2.16 (m, 1H), 2.14-1.98 (m, 1H), 1.56 (dd, J = 9.4, 7.1 Hz, 6H). |
| 283 | (Method L2): $R_t$ = 4.13 min; m/z = 506 (M + H)$^+$ | $^1$H NMR (400 MHz, Chloroform-d, Method M2) δ 8.36 (s, 1H), 7.31-7.16 (m, 2H), 7.11-7.02 (m, 1H), 6.99-6.83 (m, 3H), 6.14 (d, J = 7.4 Hz, 1H), 5.34 (q, J = 5.4 Hz, 1H), 4.34 (m, 1H), 4.24-4.04 (m, 2H), 2.99-2.88 (m, 6H), 2.49 (d, J = 1.6 Hz, 3H), 2.44-2.33 (m, 1H), 2.22 (m, 1H), 1.72-1.60 (m, 6H). |
| 284 | (Method L2): $R_t$ = 3.79 min; m/z = 491 (M + H)$^+$ | $^1$H NMR (400 MHz, Chloroform-d, Method M2) δ 8.44 (s, 1H), 7.32-7.24 (m, 1H), 7.21 (t, J = 7.7 Hz, 1H), 7.14-7.05 (m, 1H), 7.04-6.96 (m, 1H), 6.93 (t, J = 7.1 Hz, 1H), 6.86 (d, J = 8.2 Hz, 1H), 6.27 (d, J = 7.4 Hz, 1H), 5.36 (q, J = 5.3 Hz, 1H), 4.35 (m, 1H), 4.25-4.15 (m, 1H), 4.03 (s, 3H), 2.58 (m, 1H), 2.52-2.33 (m, 4H), 2.22 (m, 1H), 1.77-1.67 (m, 2H), 1.28 (m, 2H). |
| 285 | (Method L2): $R_t$ = 4.20 min; m/z = 467 (M + H)$^+$ | $^1$H NMR (400 MHz, Chloroform-d, Method M2) δ 8.48 (s, 1H), 7.38-7.15 (m, 7H), 6.10 (d, J = 8.2 Hz, 1H), 5.68 (q, J = 7.5 Hz, 1H), 4.08 (m, 1H), 3.11-2.90 (m, 2H), 2.75 (m, 1H), 2.02-1.90 (m, 1H), 1.65 (m, 6H). |
| 286 | (Method L2): $R_t$ = 4.29 min; m/z = 481 (M + H)$^+$ | $^1$H NMR (400 MHz, Chloroform-d, Method M2) δ 8.46 (s, 1H), 7.36-7.10 (m, 7H), 6.11 (d, J = 8.3 Hz, 1H), 5.43-5.34 (m, 1H), 4.07 (m, 1H), 2.83 (q, J = 7.0, 6.4 Hz, 2H), 2.24-2.13 (m, 1H), 2.07-1.77 (m, 3H), 1.65 (m, 6H). |
| 287 | (Method L2): $R_t$ = 3.94 min; m/z = 445 (M + H)$^+$ | $^1$H NMR (300 MHz, Chloroform-d, Method M2) δ 8.42 (s, 1H), 7.69 (t, J = 1.8 Hz, 1H), 7.57 (m, 1H), 7.43-7.32 (m, 2H), 7.32-7.21 (m, 4H), 6.07 (d, J = 8.3 Hz, 1H), 5.69 (q, J = 7.6 Hz, 1H), 4.11 (p, J = 7.0 Hz, 1H), 3.08-2.88 (m, 2H), 2.75 (m, 1H), 2.64 (s, 3H), 2.03-1.88 (m, 1H), 1.65 (dd, J = 7.0, 4.1 Hz, 6H). |
| 288 | (Method L2): $R_t$ = 3.39 min; m/z = 489 (M + H)$^+$ | $^1$H NMR (300 MHz, Chloroform-d, Method M2) δ 8.45 (s, 1H), 8.29 (t, J = 1.7 Hz, 1H), 8.02 (m, 1H), 7.84 (m, 1H), 7.65 (t, J = 7.8 Hz, 1H), 7.41-7.33 (m, 1H), 7.32-7.21 (m, 3H), 6.15 (d, J = 8.3 Hz, 1H), 5.70 (q, J = 7.5 Hz, 1H), 4.18-4.05 (m, 1H), 3.13-2.89 (m, 5H), 2.76 (m, 1H), 2.68 (s, 3H), 2.06-1.90 (m, 1H), 1.66 (dd, J = 7.0, 3.8 Hz, 6H). |
| 289 | (Method L2): $R_t$ = 3.71 min; m/z = 441 (M + H)$^+$ | $^1$H NMR (300 MHz, Chloroform-d, Method M2) δ 8.40 (s, 1H), 7.42-7.32 (m, 2H), 7.32-7.21 (m, 5H), 6.87 (m, 1H), 6.07 (d, J = 8.3 Hz, 1H), 5.69 (q, J = 7.6 Hz, 1H), 4.12 (p, J = 7.1 Hz, 1H), 3.85 (s, 3H), 3.12-2.88 (m, 2H), 2.76 (m, 1H), 2.65 (s, 3H), 2.03-1.88 (m, 1H), 1.65 (dd, J = 7.0, 4.2 Hz, 6H). |
| 290 | (Method L2): $R_t$ = 3.78 min; m/z = 429 (M + H)$^+$ | $^1$H NMR (300 MHz, Chloroform-d; Method M2) δ 8.42 (s, 1H), 7.51-7.20 (m, 7H), 7.00 (m, 1H), 6.09 (d, J = 8.4 Hz, 1H), 5.68 (q, J = 7.6 Hz, 1H), 4.11 (p, J = 7.0 Hz, 1H), 3.12-2.88 (m, 2H), 2.82-2.68 (m, 1H), 2.65 (s, 3H), 2.03-1.88 (m, 1H), 1.65 (dd, J = 7.0, 4.1 Hz, 6H). |
| 291 | (Method L2): $R_t$ = 3.65 min; m/z = 436 (M + H)$^+$ | $^1$H NMR (300 MHz, Chloroform-d, Method M2) δ 8.44 (s, 1H), 8.02 (s, 1H), 7.95 (m, 1H), 7.61-7.51 (m, 2H), 7.40-7.22 (m, 4H), 6.13 (d, J = 8.2 Hz, 1H), 5.69 (q, J = 7.5 Hz, 1H), 4.11 (p, J = 7.1 Hz, 1H), 3.13-2.89 (m, 2H), 2.83-2.61 (m, 4H), 2.04-1.90 (m, 1H), 1.65 (dd, J = 7.0, 3.9 Hz, 6H). |
| 292 | (Method L2): $R_t$ = 4.07 min; m/z = 497 (M + H)$^+$ | $^1$H NMR (300 MHz, Chloroform-d, Method M2) δ 8.46 (s, 1H), 7.81 (s, 1H), 7.69 (d, J = 9.9 Hz, 1H), 7.40-7.20 (m, 5H), 6.11 (d, J = 8.4 Hz, 1H), 5.69 (q, J = 7.6 Hz, 1H), 4.11 (p, J = 7.1 Hz, 1H), 3.13-2.87 (m, 2H), 2.76 (m, 1H), 2.67 (s, 3H), 2.04-1.89 (m, 1H), 1.65 (dd, J = 7.0, 3.8 Hz, 6H). |
| 293 | (Method L2): $R_t$ = 3.90 min; m/z = 504 (M + H)$^+$ | $^1$H NMR (300 MHz, Chloroform-d, Method M2) δ 8.50 (s, 1H), 8.29 (s, 1H), 8.10 (dd, J = 8.1, 1.4 Hz, 1H), 7.87 (d, J = 8.1 Hz, 1H), 7.41-7.21 (m, 4H), 6.16 (d, J = 8.3 Hz, 1H), 5.69 (q, J = 7.5 Hz, 1H), 4.11 (p, J = 7.0 Hz, 1H), 3.14-2.89 (m, 2H), 2.77 (m, 1H), 2.71 (s, 3H), 1.97 (m, 1H), 1.65 (dd, J = 7.0, 3.6 Hz, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 294 | (Method L2): $R_t$ = 3.99 min; m/z = 497 (M + H)$^+$ | $^1$H NMR (300 MHz, Chloroform-d, Method M2) δ 8.43 (s, 1H), 7.93 (dd, J = 6.8, 2.0 Hz, 1H), 7.86 (m, 1H), 7.40-7.21 (m, 5H), 6.09 (d, J = 8.3 Hz, 1H), 5.69 (q, J = 7.6 Hz, 1H), 4.11 (p, J = 7.1 Hz, 1H), 3.13-2.89 (m, 2H), 2.76 (m, 1H), 2.63 (s, 3H), 2.04-1.89 (m, 1H), 1.65 (dd, J = 7.0, 3.8 Hz, 6H). |
| 295 | (Method L2): $R_t$ = 3.59 min; m/z = 446 (M + H)$^+$ | $^1$H NMR (300 MHz, Chloroform-d, Method M2) δ 8.67 (d, J = 2.2 Hz, 1H), 8.42 (s, 1H), 8.06 (dd, J = 8.3, 2.5 Hz, 1H), 7.45-7.33 (m, 2H), 7.32-7.21 (m, 3H), 6.16 (d, J = 8.3 Hz, 1H), 5.69 (q, J = 7.5 Hz, 1H), 4.10 (p, J = 7.1 Hz, 1H), 3.13-2.89 (m, 2H), 2.76 (m, 1H), 2.64 (s, 3H), 1.97 (m, 1H), 1.65 (dd, J = 7.0, 3.7 Hz, 6H). |
| 296 | (Method L2): $R_t$ = 3.11 min; m/z = 413 (M + H)$^+$ | $^1$H NMR (300 MHz, Chloroform-d, Method M2) δ 8.99 (s, 2H), 8.86 (s, 1H), 8.46 (s, 1H), 7.41-7.33 (m, 1H), 7.27 (m, 2H), 6.79 (d, J = 8.3 Hz, 1H), 5.70 (q, J = 7.5 Hz, 1H), 4.06 (p, J = 7.0 Hz, 1H), 3.14-2.89 (m, 2H), 2.82-2.59 (m, 4H), 2.00 (m, 1H), 1.62 (t, J = 7.1 Hz, 6H). |
| 297 | (Method L2): $R_t$ = 2.61 min; m/z = 412 (M + H)$^+$ | $^1$H NMR (300 MHz, Chloroform-d, Method M2) δ 8.65 (d, J = 1.8 Hz, 1H), 8.41 (s, 1H), 8.29 (dd, J = 4.8, 1.3 Hz, 1H), 7.97 (m, 1H), 7.41-7.21 (m, 5H), 6.80 (d, J = 8.2 Hz, 1H), 5.70 (q, J = 7.5 Hz, 1H), 4.16-3.98 (m, 1H), 3.13-2.89 (m, 2H), 2.83-2.68 (m, 1H), 2.60 (s, 3H), 2.09-1.91 (m, 1H), 1.62 (t, J = 7.4 Hz, 6H). |
| 298 | (Method L2): $R_t$ = 3.27 min; m/z = 468 (M + H)$^+$ | $^1$H NMR (300 MHz, Chloroform-d, Method M2) δ 8.37 (s, 1H), 7.85 (s, 1H), 7.67 (s, 1H), 7.43 (m, 1H), 7.35 (q, J = 6.1, 4.7 Hz, 3H), 7.29-7.17 (m, 3H), 6.46 (d, J = 8.3 Hz, 1H), 5.62 (q, J = 7.5 Hz, 1H), 4.16-4.02 (m, 1H), 3.10-2.85 (m, 2H), 2.75-2.58 (m, 4H), 2.05 (s, 3H), 2.02-1.86 (m, 1H), 1.62 (dd, J = 7.0, 3.8 Hz, 6H). |
| 299 | (Method L2): $R_t$ = 3.32 min; m/z = 454 (M + H)$^+$ | $^1$H NMR (300 MHz, Chloroform-d, Method M2) δ 8.39 (s, 1H), 7.35 (dd, J = 7.9, 5.9 Hz, 2H), 7.31-7.20 (m, 3H), 7.06-6.96 (m, 2H), 6.71 (dd, J = 8.3, 2.6 Hz, 1H), 6.08 (d, J = 8.3 Hz, 1H), 5.69 (q, J = 7.6 Hz, 1H), 4.12 (p, J = 7.0 Hz, 1H), 3.10-2.89 (m, 2H), 2.98 (s, 6H), 2.75 (m, 1H), 2.65 (s, 3H), 1.95 (m, 1H), 1.65 (dd, J = 7.0, 4.3 Hz, 6H). |
| 300 | (Method L2): $R_t$ = 3.66 min; m/z = 455 (M + H)$^+$ | $^1$H NMR (300 MHz, Chloroform-d; Method M2) δ 8.40 (s, 1H), 7.65-7.56 (m, 2H), 7.45 (t, J = 7.6 Hz, 1H), 7.36 (dd, J = 5.2, 2.8 Hz, 1H), 7.26 (m, 4H), 6.09 (d, J = 8.4 Hz, 1H), 5.69 (q, J = 7.6 Hz, 1H), 4.53 (s, 2H), 4.12 (p, J = 7.0 Hz, 1H), 3.41 (s, 3H), 3.12-2.88 (m, 2H), 2.75 (m, 1H), 2.64 (s, 3H), 2.05-1.88 (m, 1H), 1.65 (dd, J = 7.0, 4.2 Hz, 6H). |
| 301 | (Method L2): $R_t$ = 3.66 min; m/z = 436 (M + H)$^+$ | $^1$H NMR (300 MHz, Chloroform-d, Method M2) δ 8.45 (s, 1H), 7.89-7.82 (m, 2H), 7.76-7.68 (m, 2H), 7.40-7.21 (m, 4H), 6.16 (d, J = 8.3 Hz, 1H), 5.69 (q, J = 7.5 Hz, 1H), 4.10 (p, J = 7.0 Hz, 1H), 3.13-2.87 (m, 2H), 2.76 (m, 1H), 2.67 (s, 3H), 2.04-1.89 (m, 1H), 1.65 (dd, J = 7.0, 3.8 Hz, 6H). |
| 302 | (Method L2): $R_t$ = 3.75 min; m/z = 429 (M + H)$^+$ | $^1$H NMR (300 MHz, Chloroform-d, Method M2) δ 8.39 (s, 1H), 7.68-7.55 (m, 2H), 7.38-7.08 (m, 6H), 6.08 (d, J = 8.3 Hz, 1H), 5.68 (q, J = 7.6 Hz, 1H), 4.10 (p, J = 7.1 Hz, 1H), 3.12-2.88 (m, 2H), 2.75 (m, 1H), 2.61 (s, 3H), 2.03-1.87 (m, 1H), 1.65 (dd, J = 7.0, 4.1 Hz, 6H). |
| 303 | (Method L2): $R_t$ = 3.18 min; m/z = 415 (M + H)$^+$ | $^1$H NMR (300 MHz, Chloroform-d; Method M2) δ 8.36 (s, 1H), 7.90 (s, 1H), 7.87-7.83 (m, 1H), 7.41-7.33 (m, 1H), 7.32-7.21 (m, 3H), 6.18 (d, J = 8.3 Hz, 1H), 5.69 (q, J = 7.5 Hz, 1H), 4.08 (m, 1H), 3.95 (s, 3H), 3.13-2.89 (m, 2H), 2.76 (m, 1H), 2.63 (s, 3H), 2.05-1.89 (m, 1H), 1.63 (dd, J = 7.0, 4.3 Hz, 6H). |
| 304 | (Method L2): $R_t$ = 3.71 min; m/z = 477 (M + H)$^+$ | $^1$H NMR (300 MHz, DMSO-d6, Method M2) δ = 9.02 (d, J = 8.2 Hz, 1H), 8.54 (s, 1H), 8.12 (s, 1H), 8.03 (d, J = 7.3 Hz, 1H), 7.77-7.62 (m, 2H), 7.45-7.37 (m, 1H), 7.32-7.18 (m, 3H), 5.52 (q, J = 7.6 Hz, 1H), 3.07-2.82 (m, 2H), 2.71-2.57 (m, 4H), 2.56-2.51 (m, 1H), 2.03-1.85 (m, 1H), 1.56-1.47 (m, 2H), 1.26-1.16 (m, 2H). |
| 305 | (Method L2): $R_t$ = 3.70 min; m/z = 481 (M + H)$^+$ | $^1$H NMR (300 MHz, DMSO-d6, Method M2) δ = 8.96 (d, J = 8.2 Hz, 1H), 8.71 (s, 1H), 8.13 (s, 1H), 8.04 (d, J = 7.5 Hz, 1H), 7.79-7.65 (m, 2H), 7.46-7.38 (m, 1H), 7.34-7.21 (m, 3H), 5.52 (q, J = 7.7 Hz, 1H), 5.16 (s, 2H), 3.36 (s, 3H), 3.06-2.81 (m, 2H), 2.65 (s, 3H), 2.58-2.52 (m, 1H), 2.02-1.89 (m, 1H). |
| 306 | (Method L2): $R_t$ = 3.83 min; m/z = 465 (M + H)$^+$ | $^1$H NMR (300 MHz, DMSO-d6, Method M2) δ = 9.05 (d, J = 8.0 Hz, 1H), 8.67 (s, 1H), 8.15 (s, 1H), 8.04 (d, J = 7.6 Hz, 1H), 7.78-7.63 (m, 2H), 7.42-7.34 (m, 1H), 7.32-7.21 (m, 3H), 5.60-5.51 (m, 1H), 3.40 (q, J = 7.4 Hz, 2H), 3.08-2.80 (m, 2H), 2.66 (s, 3H), 2.57-2.52 (m, 1H), 2.03-1.91 (m, 1H), 1.38 (t, J = 7.4 Hz, 3H). |
| 307 | (Method L2): $R_t$ = 3.05 min; m/z = 401 (M + H)$^+$ | $^1$H NMR (300 MHz, Chloroform-d, Method M2) δ 8.41 (s, 1H), 8.02 (s, 2H), 7.38 (d, J = 6.4 Hz, 1H), 7.34-7.21 (m, 3H), 6.67 (d, J = 8.2 Hz, 1H), 5.69 (q, J = 7.5 Hz, 1H), 4.17-4.04 (m, 1H), 3.13-2.88 (m, 2H), 2.81-2.64 (m, 1H), 2.61 (s, 3H), 2.06-1.91 (m, 1H), 1.62 (dd, J = 7.0, 5.1 Hz, 6H). |
| 308 | (Method L2): $R_t$ = 3.37 min; m/z = 504 (M + H)$^+$ | $^1$H NMR (300 MHz, Chloroform-d; Method M2) δ 8.40 (s, 1H), 7.54 (d, J = 1.8 Hz, 1H), 7.48-7.31 (m, 3H), 7.31-7.18 (m, 3H), 7.10 (m, 1H), 7.01 (s, 1H), 6.29 (d, J = 8.3 Hz, 1H), 5.66 (q, J = 7.6 Hz, 1H), 4.10 (p, J = 7.1 Hz, 1H), 3.11-2.87 (m, 5H), 2.79-2.58 (m, 4H), 2.03-1.88 (m, 1H), 1.64 (dd, J = 7.0, 3.8 Hz, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 309 | (Method L2): $R_t$ = 4.03 min; m/z = 495 (M + H)$^+$ | $^1$H NMR (300 MHz, Chloroform-d, Method M2) δ = 8.43 (s, 1H), 7.69-7.61 (m, 1H), 7.58 (s, 1H), 7.48 (t, J = 8.0 Hz, 1H), 7.40-7.21 (m, 4H), 7.20-7.12 (m, 1H), 6.08 (d, J = 8.2 Hz, 1H), 5.69 (q, J = 7.5 Hz, 1H), 4.11 (p, J = 7.0 Hz, 1H), 3.12-2.89 (m, 2H), 2.76 (m, 1H), 2.65 (s, 3H), 2.04-1.89 (m, 1H), 1.65 (dd, J = 7.0, 4.0 Hz, 6H). |
| 310 | (Method L2): $R_t$ = 3.46 min; m/z = 483 (M + H)$^+$ | $^1$H NMR (300 MHz, Chloroform-d, Method M2) δ = 8.39 (s, 1H), 8.05 (d, J = 12.8 Hz, 2H), 7.41-7.33 (m, 1H), 7.32-7.22 (m, 3H), 6.13 (d, J = 8.4 Hz, 1H), 5.69 (q, J = 7.6 Hz, 1H), 4.76 (q, J = 8.4 Hz, 2H), 4.09 (p, J = 7.0 Hz, 1H), 3.13-2.89 (m, 2H), 2.76 (m, 1H), 2.66 (s, 3H), 2.05-1.89 (m, 1H), 1.63 (dd, J = 7.0, 4.1 Hz, 6H). |
| 311 | (Method L2): $R_t$ = 3.67 min; m/z = 487 (M + H)$^+$ | $^1$H NMR (300 MHz, DMSO-d6, Method M2) δ = 9.15 (d, J = 8.1 Hz, 1H), 8.80 (s, 1H), 8.11 (s, 1H), 8.07-8.00 (m, 1H), 7.97-7.59 (m, 3H), 7.45-7.38 (m, 1H), 7.32-7.20 (m, 3H), 5.51 (q, J = 7.7 Hz, 1H), 3.06-2.81 (m, 2H), 2.66 (s, 3H), 2.59-2.52 (m, 1H), 2.02-1.85 (m, 1H). |
| 312 | (Method L2): $R_t$ = 4.01 min; m/z = 509 (M + H)$^+$ | $^1$H NMR (300 MHz, Chloroform-d, Method M2) δ = 8.44 (s, 1H), 7.54 (s, 1H), 7.46 (s, 1H), 7.40-7.21 (m, 4H), 7.07 (s, 1H), 6.08 (d, J = 8.3 Hz, 1H), 5.69 (q, J = 7.5 Hz, 1H), 4.11 (p, J = 7.1 Hz, 1H), 3.89 (s, 3H), 3.13-2.88 (m, 2H), 2.76 (m, 1H), 2.66 (s, 3H), 2.04-1.89 (m, 1H), 1.65 (dd, J = 7.0, 3.9 Hz, 6H). |
| 313 | (Method L2): $R_t$ = 3.62 min; m/z = 446 (M + H)$^+$ | $^1$H NMR (300 MHz, Chloroform-d, Method M2) δ 8.49 (s, 1H), 8.37 (dd, J = 5.3, 0.5 Hz, 1H), 7.85-7.80 (m, 1H), 7.68 (dd, J = 5.3, 1.5 Hz, 1H), 7.40-7.33 (m, 1H), 7.33-7.21 (m, 3H), 6.21 (d, J = 8.3 Hz, 1H), 5.69 (q, J = 7.5 Hz, 1H), 4.10 (p, J = 7.1 Hz, 1H), 3.14-2.90 (m, 2H), 2.83-2.72 (m, 1H), 2.71 (s, 3H), 2.03-1.91 (m, 1H), 1.64 (dd, J = 7.0, 3.6 Hz, 6H). |
| 314 | (Method L2): $R_t$ = 3.59 min; m/z = 446 (M + H)$^+$ | $^1$H NMR (300 MHz, Chloroform-d, Method M2) δ 8.74 (s, 1H), 8.42 (d, J = 15.3 Hz, 2H), 8.10 (t, J = 2.1 Hz, 1H), 7.45-7.34 (m, 1H), 7.34-7.23 (m, 3H), 6.32 (d, J = 8.3 Hz, 1H), 5.70 (q, J = 7.5 Hz, 1H), 4.09 (p, J = 7.0 Hz, 1H), 3.13-2.90 (m, 2H), 2.76 (m, 1H), 2.65 (s, 3H), 2.05-1.90 (m, 1H), 1.64 (dd, J = 7.0, 5.0 Hz, 6H). |
| 315 | (Method L2): $R_t$ = 3.66 min; m/z = 522 (M + H)$^+$ | $^1$H NMR (300 MHz, Chloroform-d, Method M2) δ 8.40 (s, 1H), 8.19 (s, 1H), 7.92 (d, J = 1.7 Hz, 1H), 7.56-7.41 (m, 3H), 7.38-7.31 (m, 1H), 7.25 (m, 3H), 6.20 (d, J = 8.3 Hz, 1H), 5.66 (q, J = 7.5 Hz, 1H), 4.10 (p, J = 7.0 Hz, 1H), 3.12-2.87 (m, 2H), 2.73 (m, 1H), 2.64 (s, 3H), 2.02-1.88 (m, 1H), 1.64 (dd, J = 7.1, 3.7 Hz, 6H). |
| 316 | (Method L2): $R_t$ = 3.57 min; m/z = 496 (M + H)$^+$ | $^1$H NMR (300 MHz, Chloroform-d, Method M2) δ = 8.40 (s, 1H), 7.42-7.32 (m, 2H), 7.26 (m, 4H), 7.20-7.12 (m, 1H), 6.92-6.84 (m, 1H), 6.08 (d, J = 8.4 Hz, 1H), 5.69 (q, J = 7.5 Hz, 1H), 4.12 (p, J = 7.1 Hz, 1H), 3.91-3.83 (m, 4H), 3.25-3.16 (m, 4H), 3.12-2.88 (m, 2H), 2.75 (m, 1H), 2.64 (s, 3H), 2.03-1.88 (m, 1H), 1.65 (dd, J = 7.0, 4.2 Hz, 6H). |
| 317 | (Method L2): $R_t$ = 4.22 min; m/z = 513 (M + H)$^+$ | $^1$H NMR (300 MHz, Chloroform-d, Method M2) δ 8.46 (s, 1H), 7.96-7.86 (m, 2H), 7.53 (s, 1H), 7.40-7.32 (m, 1H), 7.32-7.21 (m, 3H), 6.09 (d, J = 8.2 Hz, 1H), 5.69 (q, J = 7.5 Hz, 1H), 4.11 (p, J = 7.1 Hz, 1H), 3.08-2.89 (m, 2H), 2.83-2.69 (m, 1H), 2.67 (s, 3H), 2.04-1.89 (m, 1H), 1.65 (dd, J = 7.0, 3.8 Hz, 6H). |
| 318 | (Method L2): $R_t$ = 2.44 min; m/z = 412 (M + H)$^+$ | $^1$H NMR (300 MHz, Chloroform-d, Method M2) δ 8.62-8.54 (m, 2H), 8.46 (s, 1H), 7.73-7.67 (m, 2H), 7.65-7.48 (m, 1H), 7.47-7.21 (m, 3H), 6.41 (d, J = 8.4 Hz, 1H), 5.69 (q, J = 7.5 Hz, 1H), 4.10 (p, J = 7.1 Hz, 1H), 3.13-2.89 (m, 2H), 2.82-2.65 (m, 4H), 2.03-1.90 (m, 1H), 1.65 (dd, J = 7.0, 3.8 Hz, 6H). |
| 319 | (Method L4): $R_t$ = 4.44 min; m/z = 481 (M + H)$^+$ | $^1$H NMR (300 MHz, DMSO-d6, Method M2) δ = 9.06 (d, J = 8.2 Hz, 1H), 8.49 (s, 1H), 7.41-7.32 (m, 2H), 7.31-7.20 (m, 5H), 6.93-6.83 (m, 1H), 5.53 (q, J = 7.8 Hz, 1H), 4.03-3.90 (m, 1H), 3.85 (d, J = 7.0 Hz, 2H), 3.07-2.78 (m, 2H), 2.60 (s, 3H), 2.58-2.51 (m, 1H), 2.00-1.85 (m, 1H), 1.56 (dd, J = 6.9, 5.3 Hz, 6H), 1.31-1.19 (m, 1H), 0.62-0.52 (m, 2H), 0.38-0.29 (m, 2H). |
| 320 | (Method L4): $R_t$ = 3.59 min; m/z = 466 (M + H)$^+$ | $^1$H NMR (300 MHz, DMSO-d6, Method M2) δ = 9.07 (d, J = 8.3 Hz, 1H), 8.51 (s, 1H), 7.51-7.35 (m, 4H), 7.31-7.21 (m, 3H), 7.09-6.99 (m, 1H), 5.53 (q, J = 7.9 Hz, 1H), 5.22 (s, 2H), 4.05-3.90 (m, 1H), 3.06-2.79 (m, 2H), 2.63 (s, 3H), 2.60-2.52 (m, 1H), 2.01-1.85 (m, 1H), 1.57 (dd, J = 6.9, 5.3 Hz, 6H). |
| 321 | (Method L2): $R_t$ = 4.44 min; m/z = 469 (M + H)$^+$ | $^1$H NMR (300 MHz, DMSO-d6, Method M2) δ = 9.06 (d, J = 8.1 Hz, 1H), 8.49 (s, 1H), 7.42-7.21 (m, 8H), 6.89-6.83 (m, 1H), 5.52 (q, J = 7.9 Hz, 1H), 4.69-4.59 (m, 1H), 4.02-3.91 (m, 1H), 3.04-2.81 (m, 2H), 2.60 (s, 3H), 2.57-2.53 (m, 1H), 2.00-1.85 (m, 1H), 1.56 (dd, J = 7.0, 5.3 Hz, 6H), 1.30 (d, J = 6.0 Hz, 6H). |
| 322 | (Method L4): $R_t$ = 4.34 min; m/z = 455 (M + H)$^+$ | $^1$H NMR (300 MHz, DMSO-d6, Method M2) δ = 9.06 (d, J = 8.2 Hz, 1H), 8.49 (s, 1H), 7.43-7.31 (m, 2H), 7.31-7.21 (m, 5H), 6.92-6.84 (m, 1H), 5.53 (q, J = 7.9 Hz, 1H), 4.07 (q, J = 7.0 Hz, 2H), 4.02-3.91 (m, 1H), 3.06-2.79 (m, 2H), 2.61 (s, 3H), 2.57-2.51 (m, 1H), 2.02-1.85 (m, 1H), 1.56 (dd, J = 6.9, 5.3 Hz, 6H), 1.36 (t, J = 7.0 Hz, 3H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 323 | (Method L2): $R_t$ = 3.88 min; m/z = 447 (M + H)$^+$ | $^1$H NMR (300 MHz, DMSO-d6) δ = 9.09 (d, J = 8.2 Hz, 1H), 8.58 (s, 1H), 7.57-7.46 (m, 2H), 7.43-7.34 (m, 1H), 7.34-7.11 (m, 4H), 5.53 (q, J = 7.9 Hz, 1H), 4.03-3.88 (m, 1H), 3.06-2.81 (m, 2H), 2.66 (s, 3H), 2.61-2.52 (m, 1H), 2.01-1.85 (m, 1H), 1.56 (dd, J = 7.0, 5.2 Hz, 6H). |
| 324 | (Method L2): $R_t$ = 4.03 min; m/z = 463 (M + H)$^+$ | $^1$H NMR (300 MHz, DMSO-d6, Method M2) δ = 9.08 (d, J = 8.2 Hz, 1H), 8.59 (s, 1H), 7.73 (s, 1H), 7.65-7.56 (m, 1H), 7.44-7.32 (m, 2H), 7.32-7.19 (m, 3H), 5.53 (q, J = 7.8 Hz, 1H), 4.05-3.89 (m, 1H), 3.06-2.80 (m, 2H), 2.65 (s, 3H), 2.61-2.52 (m, 1H), 2.01-1.85 (m, 1H), 1.56 (dd, J = 6.8, 5.4 Hz, 6H). |
| 325 | (Method L4): $R_t$ = 4.31 min; m/z = 459 (M + H)$^+$ | $^1$H NMR (300 MHz, DMSO-d6, Method M2) δ = 9.07 (d, J = 8.1 Hz, 1H), 8.54 (s, 1H), 7.43-7.36 (m, 1H), 7.32-7.14 (m, 5H), 6.79 (dt, J = 11.1, 2.2 Hz, 1H), 5.53 (q, J = 7.8 Hz, 1H), 4.05-3.90 (m, 1H), 3.82 (s, 3H), 3.06-2.79 (m, 2H), 2.63 (s, 3H), 2.60-2.52 (m, 1H), 1.99-1.85 (m, 1H), 1.56 (dd, J = 6.8, 5.3 Hz, 6H). |
| 326 | (Method L4): $R_t$ = 3.99 min; m/z = 496 (M + H)$^+$ | $^1$H NMR (300 MHz, DMSO-d6, Method M2) δ = 9.04 (d, J = 8.2 Hz, 1H), 8.43 (s, 1H), 7.59 (d, J = 8.8 Hz, 2H), 7.43-7.33 (m, 1H), 7.32-7.20 (m, 3H), 7.05 (d, J = 8.9 Hz, 2H), 5.52 (q, J = 7.8 Hz, 1H), 4.05-3.89 (m, 1H), 3.84-3.69 (m, 4H), 3.22-3.08 (m, 4H), 3.06-2.79 (m, 2H), 2.57 (s, 3H), 2.56-2.51 (m, 1H), 1.97-1.84 (m, 1H), 1.56 (dd, J = 6.9, 5.3 Hz, 6H). |
| 327 | (Method L4): $R_t$ = 3.64 min; m/z = 468 (M + H)$^+$ | $^1$H NMR (300 MHz, DMSO-d6, Method M2) δ = 10.00 (s, 1H), 9.05 (d, J = 8.3 Hz, 1H), 8.46 (s, 1H), 7.71-7.60 (m, 4H), 7.42-7.33 (m, 1H), 7.33-7.20 (m, 3H), 5.52 (q, J = 7.7 Hz, 1H), 4.03-3.89 (m, 1H), 3.04-2.80 (m, 2H), 2.58 (s, 3H), 2.57-2.54 (m, 1H), 2.06 (s, 3H), 2.00-1.85 (m, 1H), 1.56 (dd, J = 6.9, 5.4 Hz, 6H). |
| 328 | (Method L4): $R_t$ = 4.13 min; m/z = 477 (M + H)$^+$ | $^1$H NMR (300 MHz, DMSO-d6, Method M2) δ = 9.08 (d, J = 8.2 Hz, 1H), 8.54 (s, 1H), 8.53-8.49 (m, 1H), 8.23 (t, J = 1.8 Hz, 1H), 7.82-7.73 (m, 2H), 7.70-7.55 (m, 2H), 7.43-7.34 (m, 1H), 7.31-7.21 (m, 3H), 6.57 (dd, J = 2.4, 1.8 Hz, 1H), 5.53 (q, J = 7.8 Hz, 1H), 4.07-3.91 (m, 1H), 3.06-2.79 (m, 2H), 2.66 (s, 3H), 2.60-2.51 (m, 1H), 2.01-1.85 (m, 1H), 1.58 (dd, J = 7.0, 5.2 Hz, 6H). |
| 329 | (Method L4): $R_t$ = 4.58 min; m/z = 480 (M + H)$^+$ | $^1$H NMR (300 MHz, DMSO-d6, Method M2) δ = 9.05 (d, J = 8.2 Hz, 1H), 8.46 (s, 1H), 7.42-7.34 (m, 1H), 7.32-7.19 (m, 4H), 6.92 (d, J = 7.8 Hz, 1H), 6.88-6.83 (m, 1H), 6.50 (dd, J = 8.2, 1.8 Hz, 1H), 5.52 (q, J = 7.9 Hz, 1H), 4.05-3.89 (m, 1H), 3.26 (t, J = 6.5 Hz, 4H), 3.06-2.79 (m, 2H), 2.59 (s, 3H), 2.58-2.51 (m, 1H), 2.09-1.82 (m, 5H), 1.56 (dd, J = 7.0, 5.2 Hz, 6H). |
| 330 | (Method L4): $R_t$ = 3.75 min; m/z = 504 (M + H)$^+$ | $^1$H NMR (300 MHz, DMSO-d6, Method M2) δ = 9.78 (s, 1H), 9.06 (d, J = 8.2 Hz, 1H), 8.47 (s, 1H), 7.73-7.64 (m, 2H), 7.40-7.20 (m, 6H), 5.52 (q, J = 7.8 Hz, 1H), 4.01-3.90 (m, 1H), 3.03 (s, 3H), 3.01-2.79 (m, 2H), 2.59 (s, 3H), 2.57-2.51 (m, 1H), 1.97-1.85 (m, 1H), 1.56 (dd, J = 7.0, 5.3 Hz, 6H). |
| 331 | (Method L4): $R_t$ = 4.42 min; m/z = 495 (M + H)$^+$ | $^1$H NMR (300 MHz, DMSO-d6, Method M2) δ = 9.08 (d, J = 8.2 Hz, 1H), 8.51 (s, 1H), 7.90-7.83 (m, 2H), 7.50-7.45 (m, 2H), 7.41-7.34 (m, 1H), 7.31-7.21 (m, 3H), 5.53 (q, J = 7.8 Hz, 1H), 4.04-3.88 (m, 1H), 3.06-2.80 (m, 2H), 2.62 (s, 3H), 2.59-2.51 (m, 1H), 2.01-1.84 (m, 1H), 1.57 (dd, J = 7.0, 5.3 Hz, 6H). |
| 332 | (Method L4): $R_t$ = 4.41 min; m/z = 479 (M + H)$^+$ | $^1$H NMR (300 MHz, DMSO-d6, Method M2) δ = 9.09 (d, J = 8.2 Hz, 1H), 8.56 (s, 1H), 8.01 (d, J = 8.1 Hz, 2H), 7.83 (d, J = 8.2 Hz, 2H), 7.43-7.35 (m, 1H), 7.31-7.21 (m, 3H), 5.53 (q, J = 7.8 Hz, 1H), 4.04-3.90 (m, 1H), 3.06-2.80 (m, 2H), 2.66 (s, 3H), 2.60-2.51 (m, 1H), 2.01-1.84 (m, 1H), 1.57 (dd, J = 7.0, 5.3 Hz, 6H). |
| 333 | (Method L4): $R_t$ = 4.10 min; m/z = 441 (M + H)$^+$ | $^1$H NMR (300 MHz, DMSO-d6, Method M2) δ = 9.05 (d, J = 8.2 Hz, 1H), 8.45 (s, 1H), 7.68-7.58 (m, 2H), 7.41-7.34 (m, 1H), 7.32-7.20 (m, 3H), 7.09-7.00 (m, 2H), 5.53 (q, J = 7.9 Hz, 1H), 4.03-3.90 (m, 1H), 3.80 (s, 3H), 3.05-2.81 (m, 2H), 2.57 (s, 3H), 2.56-2.51 (m, 1H), 2.00-1.84 (m, 1H), 1.56 (dd, J = 7.0, 5.2 Hz, 6H). |
| 334 | (Method L4): $R_t$ = 4.19 min; m/z = 461 (M + H)$^+$ | $^1$H NMR (300 MHz, DMSO-d6) δ = 9.09 (d, J = 8.2 Hz, 1H), 8.56 (s, 1H), 8.01 (d, J = 8.1 Hz, 2H), 7.83 (d, J = 8.2 Hz, 2H), 7.43-7.35 (m, 1H), 7.31-7.21 (m, 3H), 5.53 (q, J = 7.8 Hz, 1H), 4.04-3.90 (m, 1H), 3.06-2.80 (m, 2H), 2.66 (s, 3H), 2.60-2.51 (m, 1H), 2.01-1.84 (m, 1H), 1.57 (dd, J = 7.0, 5.3 Hz, 6H). |
| 335 | (Method L4): $R_t$ = 4.21 min; m/z = 477 (M + H)$^+$ | $^1$H NMR (300 MHz, DMSO-d6, Method M2) δ = 9.06 (d, J = 8.2 Hz, 1H), 8.49 (s, 1H), 7.82-7.74 (m, 2H), 7.43-7.35 (m, 1H), 7.28 (t, J = 74.2 Hz, 1H), 7.34-7.20 (m, 6H), 5.53 (q, J = 7.8 Hz, 1H), 4.06-3.86 (m, 1H), 3.06-2.77 (m, 2H), 2.60 (s, 3H), 2.58-2.51 (m, 1H), 2.00-1.85 (m, 1H), 1.56 (dd, J = 7.0, 5.3 Hz, 6H). |
| 336 | (Method L4): $R_t$ = 4.30 min; m/z = 509 (M + H)$^+$ | $^1$H NMR (300 MHz, DMSO-d6) δ = 9.06 (d, J = 8.2 Hz, 1H), 8.49 (s, 1H), 7.82-7.74 (m, 2H), 7.43-7.35 (m, 1H), 7.28 (t, J = 74.2 Hz, 1H), 7.34-7.20 (m, 6H), 5.53 (q, J = 7.8 Hz, 1H), 4.06-3.86 (m, 1H), 3.06-2.77 (m, 2H), 2.60 (s, 3H), 2.58-2.51 (m, 1H), 2.00-1.85 (m, 1H), 1.56 (dd, J = 7.0, 5.3 Hz, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 337 | (Method L4): $R_t$ = 4.21 min; m/z = 477 (M + H)$^+$ | $^1$H NMR (300 MHz, DMSO-d6, Method M2) δ = 9.07 (d, J = 8.2 Hz, 1H), 8.54 (s, 1H), 7.65-7.56 (m, 2H), 7.54-7.49 (m, 1H), 7.43-7.35 (m, 1H), 7.28 (t, J = 73.2 Hz, 1H), 7.31-7.21 (m, 4H), 7.13 (dd, J = 8.0, 2.0 Hz, 1H), 5.53 (q, J = 7.8 Hz, 1H), 4.06-3.89 (m, 1H), 3.07-2.79 (m, 2H), 2.63 (s, 3H), 2.60-2.51 (m, 1H), 2.02-1.82 (m, 1H), 1.56 (dd, J = 6.9, 5.2 Hz, 6H). |
| 338 | (Method L4): $R_t$ = 4.30 min; m/z = 409 (M + H)$^+$ | $^1$H NMR (300 MHz, DMSO-d6, Method M2) δ = 9.06 (d, J = 8.3 Hz, 1H), 8.51 (s, 1H), 7.46-7.34 (m, 4H), 7.34-7.20 (m, 3H), 7.06-6.99 (m, 1H), 5.53 (q, J = 7.8 Hz, 1H), 4.80 (q, J = 8.9 Hz, 2H), 4.03-3.90 (m, 1H), 3.06-2.80 (m, 2H), 2.62 (s, 3H), 2.59-2.51 (m, 1H), 2.00-1.84 (m, 1H), 1.56 (dd, J = 7.0, 5.2 Hz, 6H). |
| 339 | (Method L4): $R_t$ = 4.25 min; m/z = 455 (M + H)$^+$ | $^1$H NMR (300 MHz, DMSO-d6, Method M2) δ = 9.04 (d, J = 8.3 Hz, 1H), 8.44 (s, 1H), 7.67-7.58 (m, 2H), 7.41-7.33 (m, 1H), 7.32-7.20 (m, 3H), 7.07-6.98 (m, 2H), 5.52 (q, J = 7.8 Hz, 1H), 4.07 (q, J = 7.0 Hz, 2H), 4.01-3.89 (m, 1H), 3.05-2.77 (m, 2H), 2.57 (s, 3H), 2.55-2.51 (m, 1H), 2.01-1.84 (m, 1H), 1.56 (dd, J = 7.0, 5.3 Hz, 6H), 1.36 (t, J = 7.0 Hz, 3H). |
| 340 | (Method L4): $R_t$ = 4.06 min; m/z = 455 (M + H)$^+$ | $^1$H NMR (300 MHz, DMSO-d6, Method M2) δ = 9.06 (d, J = 8.2 Hz, 1H), 8.49 (s, 1H), 7.72 (d, J = 8.1 Hz, 2H), 7.47-7.33 (m, 3H), 7.33-7.19 (m, 3H), 5.53 (q, J = 7.9 Hz, 1H), 4.45 (s, 2H), 4.05-3.89 (m, 1H), 3.32 (s, 3H), 3.06-2.80 (m, 2H), 2.60 (s, 3H), 2.57-2.51 (m, 1H), 2.01-1.85 (m, 1H), 1.57 (dd, J = 6.9, 5.3 Hz, 6H). |
| 341 | (Method L4): $R_t$ = 3.98 min; m/z = 440 (M + H)$^+$ | $^1$H NMR (300 MHz, DMSO-d6, method M2) δ = 9.02 (d, J = 8.3 Hz, 1H), 8.40 (s, 1H), 7.47-7.34 (m, 3H), 7.30-7.21 (m, 3H), 6.68-6.60 (m, 2H), 5.69 (q, J = 5.0 Hz, 1H), 5.52 (q, J = 8.0 Hz, 1H), 4.02-3.88 (m, 1H), 3.06-2.79 (m, 2H), 2.71 (d, J = 5.1 Hz, 3H), 2.54 (s, 3H), 2.53-2.52 (m, 1H), 1.99-1.85 (m, 1H), 1.55 (dd, J = 7.0, 5.3 Hz, 6H). |
| 342 | (Method L4): $R_t$ = 4.23 min; m/z = 454 (M + H)$^+$ | $^1$H NMR (300 MHz, DMSO-d6, Method M2) δ = 9.03 (d, J = 8.3 Hz, 1H), 8.41 (s, 1H), 7.57-7.49 (m, 2H), 7.41-7.33 (m, 1H), 7.30-7.20 (m, 3H), 6.88-6.79 (m, 2H), 5.52 (q, J = 8.0 Hz, 1H), 3.95 (p, J = 7.1 Hz, 1H), 3.06-2.95 (m, 1H), 2.93 (s, 6H), 2.90-2.80 (m, 1H), 2.56 (s, 3H), 2.55-2.53 (m, 1H), 2.00-1.85 (m, 1H), 1.56 (dd, J = 6.9, 5.3 Hz, 6H). |
| 343 | (Method L2): $R_t$ = 3.78 min; m/z = 443 (M + H)$^+$ | $^1$H NMR (300 MHz, Chloroform-d, Method M2) δ 8.38 (s, 1H), 7.66-7.57 (m, 2H), 7.38-7.31 (m, 1H), 7.25-7.17 (m, 3H), 7.14 (dt, J = 9.6, 2.5 Hz, 3H), 6.07 (d, J = 8.3 Hz, 1H), 5.44-5.34 (m, 1H), 4.10 (p, J = 7.1 Hz, 1H), 2.83 (q, J = 6.0 Hz, 2H), 2.62 (s, 3H), 2.27-2.12 (m, 1H), 2.09-1.78 (m, 3H), 1.65 (t, J = 7.1 Hz, 6H). |
| 344 | (Method L2): $R_t$ = 3.68 min; m/z = 469 (M + H)$^+$ | $^1$H NMR (300 MHz, Chloroform-d, Method M2) δ 8.39 (s, 1H), 7.64-7.55 (m, 2H), 7.45 (t, J = 7.6 Hz, 1H), 7.38-7.26 (m, 2H), 7.24-7.17 (m, 2H), 7.17-7.10 (m, 1H), 6.08 (d, J = 8.2 Hz, 1H), 5.43-5.34 (m, 1H), 4.53 (s, 2H), 4.17-4.05 (m, 1H), 3.41 (s, 3H), 2.83 (q, J = 5.9 Hz, 2H), 2.63 (s, 3H), 2.27-2.11 (m, 1H), 2.09-1.80 (m, 3H), 1.65 (t, J = 7.1 Hz, 6H). |
| 345 | (Method L2): $R_t$ = 3.69 min; m/z = 509 (M + H)$^+$ | $^1$H NMR (300 MHz, Chloroform-d, Method M2) δ 8.42 (s, 1H), 7.65 (dt, J = 7.8, 1.2 Hz, 1H), 7.58 (s, 1H), 7.47 (t, J = 8.0 Hz, 1H), 7.35 (dd, J = 5.1, 4.0 Hz, 1H), 7.21 (dd, J = 5.1, 4.0 Hz, 2H), 7.19-7.10 (m, 2H), 6.08 (d, J = 8.3 Hz, 1H), 5.45-5.34 (m, 1H), 4.11 (p, J = 7.1 Hz, 1H), 2.83 (q, J = 6.1 Hz, 2H), 2.28-2.11 (m, 1H), 2.09-1.78 (m, 3H), 1.65 (t, J = 7.0 Hz, 6H). |
| 346 | (Method L2): $R_t$ = 3.74 min; m/z = 455 (M + H)$^+$ | $^1$H NMR (300 MHz, Chloroform-d, Method M2) δ 8.39 (s, 1H), 7.42-7.32 (m, 2H), 7.25-7.17 (m, 4H), 7.17-7.08 (m, 1H), 6.86 (m, 1H), 6.08 (d, J = 8.4 Hz, 1H), 5.44-5.33 (m, 1H), 4.10 (p, J = 7.0 Hz, 1H), 3.85 (s, 3H), 2.83 (q, J = 5.9 Hz, 2H), 2.64 (s, 3H), 2.28-2.10 (m, 1H), 2.09-1.79 (m, 3H), 1.64 (t, J = 7.1 Hz, 7H). |
| 347 | (Method L2): $R_t$ = 3.69 min; m/z = 443 (M + H)$^+$ | $^1$H NMR (300 MHz, Chloroform-d, Method M2) δ 8.41 (s, 1H), 7.44 (m, 3H), 7.39-7.31 (m, 1H), 7.21 (dd, J = 5.0, 4.0 Hz, 2H), 7.16-7.09 (m, 1H), 7.04-6.95 (m, 1H), 6.09 (d, J = 8.2 Hz, 1H), 5.44-5.34 (m, 1H), 4.16-4.04 (m, 1H), 2.83 (q, J = 6.0 Hz, 2H), 2.65 (s, 3H), 2.10-1.79 (m, 3H), 1.65 (t, J = 7.1 Hz, 6H). |
| 348 | (Method L2): $R_t$ = 2.76 min; m/z = 452 (M + H)$^+$ | $^1$H NMR (300 MHz, DMSO-d6, Method M2) δ 8.99 (d, J = 8.1 Hz, 1H), 8.44 (s, 1H), 7.46-7.34 (m, 1H), 7.25 (tq, J = 7.7, 3.8 Hz, 4H), 7.06-6.95 (m, 2H), 6.69 (dd, J = 8.2, 2.4 Hz, 1H), 5.52 (q, J = 7.8 Hz, 1H), 2.93 (s, 7H), 2.85 (dd, J = 15.9, 8.0 Hz, 1H), 2.70-2.52 (m, 5H), 1.95 (dq, J = 12.7, 8.4 Hz, 1H), 1.48 (dt, J = 6.2, 3.1 Hz, 2H), 1.24-1.15 (m, 2H). |
| 349 | (Method L2): $R_t$ = 3.38 min; m/z = 443 (M + H)$^+$ | $^1$H NMR (300 MHz, DMSO-d6, Method M2) δ 9.00 (d, J = 8.1 Hz, 1H), 8.39 (s, 1H), 7.66-7.57 (m, 1H), 7.49-7.36 (m, 4H), 7.31-7.19 (m, 3H), 5.51 (q, J = 7.7 Hz, 1H), 3.05-2.93 (m, 1H), 2.87 (q, J = 8.0 Hz, 1H), 2.67-2.56 (m, 2H), 2.35 (s, 3H), 2.01-1.86 (m, 1H), 1.49 (dd, J = 5.5, 2.3 Hz, 2H), 1.21 (dd, J = 8.8, 2.2 Hz, 2H). |
| 350 | (Method L2): $R_t$ = 3.27 min; m/z = 453 (M + H)$^+$ | $^1$H NMR (300 MHz, DMSO-d6, Method M2) δ 9.00 (d, J = 8.1 Hz, 1H), 8.47 (s, 1H), 7.70-7.59 (m, 2H), 7.49-7.37 (m, 1H), 7.31-7.20 (m, 4H), 5.52 (q, J = 7.7 Hz, 1H), 4.47 (s, 2H), 3.33 (s, 3H), 3.06-2.94 (m, 1H), 2.87 (dt, J = 16.0, 8.2 Hz, 1H), 2.68-2.52 (m, 5H), 2.02-1.87 (m, 1H), 1.48 (dt, J = 6.3, 3.2 Hz, 2H), 1.20 (dq, J = 7.3, 4.0 Hz, 2H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 351 | (Method L2): $R_t$ = 3.33 min; m/z = 439 (M + H)$^+$ | $^1$H NMR (300 MHz, DMSO-d6, Method M2) δ 9.00 (d, J = 8.1 Hz, 1H), 8.47 (s, 1H), 7.44-7.35 (m, 2H), 7.31-7.21 (m, 5H), 6.89 (dd, J = 8.0, 2.5 Hz, 1H), 5.52 (q, J = 7.7 Hz, 1H), 3.80 (s, 3H), 3.07-2.94 (m, 1H), 2.93-2.78 (m, 1H), 2.67-2.52 (m, 5H), 1.94 (dt, J = 7.9, 3.9 Hz, 1H), 1.48 (dt, J = 5.9, 3.0 Hz, 2H), 1.23-1.18 (m, 2H). |
| 352 | (Method L2): $R_t$ = 3.08 min; m/z = 443 (M + H)$^+$ | $^1$H NMR (300 MHz, DMSO-d6, Method M2) δ 9.01 (d, J = 8.2 Hz, 1H), 8.52 (s, 1H), 7.83 (s, 1H), 7.69 (d, J = 7.4 Hz, 1H), 7.50 (t, J = 7.8 Hz, 1H), 7.37 (d, J = 8.7 Hz, 2H), 7.32-7.19 (m, 3H), 5.52 (q, J = 7.4 Hz, 1H), 3.06-2.94 (m, 1H), 2.93-2.81 (m, 1H), 2.60 (s, 5H), 1.98-1.83 (m, 1H), 1.49 (d, J = 3.3 Hz, 2H), 1.27-1.19 (m, 2H). |
| 353 | (Method L2): $R_t$ = 3.42 min; m/z = 427 (M + H)$^+$ | $^1$H NMR (300 MHz, DMSO-d6, Method M2) δ 9.02 (d, J = 8.1 Hz, 1H), 8.51 (s, 1H), 7.59 (dd, J = 8.6, 1.5 Hz, 2H), 7.51 (td, J = 8.0, 6.5 Hz, 1H), 7.44-7.37 (m, 1H), 7.25 (td, J = 6.3, 5.8, 2.9 Hz, 3H), 7.18-7.09 (m, 1H), 5.52 (d, J = 7.8 Hz, 1H), 2.97 (dd, J = 8.7, 3.7 Hz, 1H), 2.88 (q, J = 7.8 Hz, 1H), 2.67-2.52 (m, 5H), 2.01-1.89 (m, 1H), 1.48 (dt, J = 6.3, 3.2 Hz, 2H), 1.24-1.15 (m, 2H). |
| 354 | (Method L2): $R_t$ = 2.46 min; m/z = 510 (M + H)$^+$ | $^1$H NMR (300 MHz, DMSO-d6, Method M2) δ 9.06 (d, J = 8.2 Hz, 1H), 8.49 (s, 1H), 7.69-7.51 (m, 2H), 7.47-7.34 (m, 2H), 7.32-7.20 (m, 4H), 5.53 (q, J = 7.9 Hz, 1H), 4.08-3.91 (m, 1H), 3.63-3.49 (m, 2H), 3.05-2.79 (m, 2H), 2.60 (m, 4H), 2.44-2.34 (m, 4H), 1.93 (dd, J = 12.5, 8.1 Hz, 1H), 1.57 (dd, J = 7.0, 5.2 Hz, 6H). |
| 355 | (Method L2): $R_t$ = 2.52 min; m/z = 496 (M + H)$^+$ | $^1$H NMR (300 MHz, DMSO-d6, Method M2) δ 9.04 (d, J = 8.2 Hz, 1H), 8.46 (s, 1H), 7.66-7.50 (m, 2H), 7.42-7.32 (m, 2H), 7.29-7.18 (m, 4H), 5.51 (q, J = 7.9 Hz, 1H), 3.96 (m, 1H), 3.57 (s, 2H), 3.03-2.77 (m, 2H), 2.54 (m, 4H), 2.45 (m, 4H), 1.90 (m, 1H), 1.54 (dd, J = 6.8, 5.3 Hz, 6H), 0.97 (t, J = 7.1 Hz, 6H). |
| 356 | (Method L2): $R_t$ = 2.83 min; m/z = 494 (M + H)$^+$ | $^1$H NMR (300 MHz, DMSO-d6, Method M2) δ 9.05 (d, J = 8.2 Hz, 1H), 8.48 (s, 1H), 7.38 (q, J = 3.7 Hz, 1H), 7.33-7.19 (m, 5H), 7.07 (d, J = 7.7 Hz, 1H), 6.89 (dd, J = 8.2, 1.9 Hz, 1H), 5.52 (q, J = 7.9 Hz, 1H), 3.98 (m, 1H), 3.21-3.12 (m, 4H), 3.05-2.80 (m, 2H), 2.59 (m, 4H), 2.00-1.85 (m, 1H), 1.69-1.47 (m, 12H). |
| 357 | (Method L2): $R_t$ = 3.31 min; m/z = 427 (M + H)$^+$ | $^1$H NMR (300 MHz, DMSO-d6, Method M2) δ 9.00 (d, J = 8.1 Hz, 1H), 8.43 (s, 1H), 7.53 (td, J = 7.5, 1.6 Hz, 1H), 7.48-7.20 (m, 7H), 5.51 (q, J = 7.7 Hz, 1H), 3.06-2.93 (m, 1H), 2.86 (dt, J = 15.8, 8.1 Hz, 1H), 2.67-2.52 (m, 2H), 2.41 (d, J = 1.4 Hz, 3H), 1.94 (dq, J = 12.7, 8.4 Hz, 1H), 1.48 (dt, J = 6.2, 3.1 Hz, 2H), 1.21 (dt, J = 8.7, 3.5 Hz, 2H). |
| 358 | (Method L2): $R_t$ = 3.48 min; m/z = 445 (M + H)$^+$ | $^1$H NMR (300 MHz, DMSO-d6, Method M2) δ 9.02 (d, J = 8.1 Hz, 1H), 8.50 (s, 1H), 7.85-7.74 (m, 1H), 7.61-7.48 (m, 2H), 7.41 (d, J = 4.8 Hz, 1H), 7.26 (tq, J = 6.5, 3.9 Hz, 3H), 5.52 (q, J = 7.8 Hz, 1H), 3.05-2.94 (m, 1H), 2.87 (dt, J = 15.9, 8.0 Hz, 1H), 2.67-2.53 (m, 5H), 2.01-1.87 (m, 1H), 1.47 (dt, J = 6.3, 3.1 Hz, 2H), 1.25-1.16 (m, 2H). |
| 359 | (Method L2): $R_t$ = 3.50 min; m/z = 497 (M + H)$^+$ | $^1$H NMR (300 MHz, Chloroform-d, Method M2) δ 8.38 (s, 1H), 8.07 (s, 1H), 8.03 (d, J = 0.5 Hz, 1H), 7.36 (dd, J = 5.2, 3.9 Hz, 1H), 7.25-7.18 (m, 2H), 7.14 (dd, J = 5.3, 3.8 Hz, 1H), 6.11 (d, J = 8.6 Hz, 1H), 5.48-5.32 (m, 1H), 4.75 (q, J = 8.4 Hz, 2H), 4.08 (p, J = 7.1 Hz, 1H), 2.83 (q, J = 5.9 Hz, 2H), 2.66 (s, 3H), 2.27-2.12 (m, 1H), 2.10-1.79 (m, 3H), 1.63 (t, J = 7.0 Hz, 6H). |
| 360 | (Method L2): $R_t$ = 3.71 min; m/z = 493 (M + H)$^+$ | $^1$H NMR (300 MHz, DMSO-d6, Method M2) δ 9.02 (d, J = 8.1 Hz, 1H), 8.52 (s, 1H), 7.83-7.76 (m, 2H), 7.61 (t, J = 8.3 Hz, 1H), 7.44-7.38 (m, 1H), 7.33-7.20 (m, 4H), 5.52 (q, J = 7.7 Hz, 1H), 3.06-2.94 (m, 1H), 2.87 (dt, J = 15.9, 8.2 Hz, 1H), 2.69-2.54 (m, 5H), 1.95 (dq, J = 12.7, 8.4 Hz, 1H), 1.50 (dt, J = 6.2, 3.1 Hz, 2H), 1.26-1.16 (m, 2H). |
| 361 | (Method L2): $R_t$ = 3.29 min; m/z = 468 (M + H)$^+$ | $^1$H NMR (300 MHz, Chloroform-d, Method M2) δ 8.37 (s, 1H), 7.39-7.28 (m, 2H), 7.21 (dd, J = 5.3, 3.8 Hz, 2H), 7.13 (dd, J = 5.3, 3.8 Hz, 1H), 7.06-6.96 (m, 2H), 6.75-6.68 (m, 1H), 6.07 (d, J = 8.3 Hz, 1H), 5.44-5.34 (m, 1H), 4.11 (p, J = 7.1 Hz, 1H), 2.98 (s, 6H), 2.83 (q, J = 5.8 Hz, 2H), 2.64 (s, 3H), 2.27-2.11 (m, 1H), 2.10-1.79 (m, 3H), 1.65 (t, J = 7.1 Hz, 6H). |
| 362 | (Method L2): $R_t$ = 3.66 min; m/z = 460 (M + H)$^+$ | $^1$H NMR (300 MHz, Chloroform-d, Method M2) δ 8.76 (d, J = 1.9 Hz, 1H), 8.42 (d, J = 5.9 Hz, 2H), 8.13-8.08 (m, 1H), 7.36 (dd, J = 5.2, 4.0 Hz, 1H), 7.25-7.18 (m, 2H), 7.14 (dd, J = 5.3, 3.9 Hz, 1H), 6.22 (d, J = 8.3 Hz, 1H), 5.45-5.35 (m, 1H), 4.09 (p, J = 7.0 Hz, 1H), 2.84 (q, J = 5.9 Hz, 2H), 2.66 (s, 3H), 2.28-2.12 (m, 1H), 2.11-1.79 (m, 3H), 1.64 (dd, J = 8.0, 7.1 Hz, 6H). |
| 363 | (Method L2): $R_t$ = 4.04 min; m/z = 523 (M + H)$^+$ | $^1$H NMR (300 MHz, Chloroform-d, Method M2) δ 8.42 (s, 1H), 7.57-7.52 (m, 1H), 7.46 (d, J = 1.8 Hz, 1H), 7.35 (dd, J = 5.3, 3.8 Hz, 1H), 7.25-7.17 (m, 2H), 7.13 (dd, J = 5.3, 3.8 Hz, 1H), 7.06 (s, 1H), 6.08 (d, J = 8.3 Hz, 1H), 5.46-5.34 (m, 1H), 4.10 (p, J = 7.1 Hz, 1H), 3.89 (s, 3H), 2.83 (q, J = 5.9 Hz, 2H), 2.65 (s, 3H), 2.28-2.12 (m, 1H), 2.10-1.80 (m, 3H), 1.65 (t, J = 7.0 Hz, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 364 | (Method L2): $R_t$ = 3.79 min; m/z = 502 (M + H)$^+$ | $^1$H NMR (300 MHz, DMSO-d6, Method M2) δ 9.06 (d, J = 8.2 Hz, 1H), 8.48 (s, 1H), 7.42-7.20 (m, 5H), 7.15 (d, J = 8.0 Hz, 1H), 6.89-6.83 (m, 1H), 6.58-6.50 (m, 1H), 5.52 (q, J = 7.9 Hz, 1H), 4.29 (t, J = 12.3 Hz, 4H), 4.08-3.90 (m, 1H), 3.05-2.80 (m, 2H), 2.59 (s, 4H), 1.98-1.84 (m, 1H), 1.56 (dd, J = 7.0, 5.2 Hz, 6H). |
| 365 | (Method L2): $R_t$ = 2.51 min; m/z = 494 (M + H)$^+$ | $^1$H NMR (300 MHz, DMSO-d6, Method M2) δ 9.05 (d, J = 8.2 Hz, 1H), 8.49 (s, 1H), 7.69-7.55 (m, 2H), 7.46-7.34 (m, 2H), 7.25 (m, 4H), 5.53 (q, J = 7.8 Hz, 1H), 3.98 (p, J = 6.9 Hz, 1H), 3.68 (s, 2H), 3.05-2.79 (m, 2H), 2.60 (m, 8H), 2.01-1.85 (m, 1H), 1.71 (s, 4H), 1.57 (dd, J = 7.0, 5.2 Hz, 6H). |
| 366 | (Method L2): $R_t$ = 2.44 min; m/z = 468 (M + H)$^+$ | $^1$H NMR (300 MHz, DMSO-d6, Method M2) δ 9.05 (d, J = 8.3 Hz, 1H), 8.49 (s, 1H), 7.66-7.56 (m, 2H), 7.47-7.34 (m, 2H), 7.25 (m, 4H), 5.53 (q, J = 7.9 Hz, 1H), 3.98 (p, J = 7.0 Hz, 1H), 3.47 (s, 2H), 3.06-2.79 (m, 2H), 2.60 (m, 4H), 2.19 (s, 6H), 2.01-1.85 (m, 1H), 1.57 (dd, J = 7.0, 5.2 Hz, 6H). |
| 367 | (Method L2): $R_t$ = 3.81 min; m/z = 523 (M + H)$^+$ | $^1$H NMR (300 MHz, Chloroform-d, MEthod M2) δ 8.40 (s, 1H), 7.64 (d, J = 7.4 Hz, 2H), 7.52-7.43 (m, 1H), 7.40-7.20 (m, 5H), 6.09 (d, J = 8.3 Hz, 1H), 5.68 (q, J = 7.6 Hz, 1H), 4.75 (s, 2H), 4.12 (p, J = 7.0 Hz, 1H), 3.86 (q, J = 8.7 Hz, 2H), 3.12-2.88 (m, 2H), 2.75 (m, 1H), 2.64 (s, 3H), 2.03-1.88 (m, 1H), 1.65 (dd, J = 7.0, 4.1 Hz, 6H). |
| 368 | (Method L2): $R_t$ = 2.54 min; m/z = 469 (M + H)$^+$ | $^1$H NMR (300 MHz, Chloroform-d, Method M2) δ 8.40 (s, 1H), 7.62-7.53 (m, 2H), 7.46-7.20 (m, 6H), 6.10 (d, J = 8.4 Hz, 1H), 5.69 (q, J = 7.6 Hz, 1H), 4.12 (p, J = 7.1 Hz, 1H), 3.59 (s, 2H), 3.12-2.88 (m, 2H), 2.75 (dd, J = 12.8, 4.6 Hz, 1H), 2.64 (s, 3H), 2.50 (q, J = 7.1 Hz, 2H), 2.25 (s, 3H), 2.04-1.89 (m, 1H), 1.65 (dd, J = 7.0, 4.2 Hz, 6H), 1.12 (t, J = 7.1 Hz, 3H). |
| 369 | (Method L2): $R_t$ = 3.85 min; m/z = 483 (M + H)$^+$ | $^1$H NMR (300 MHz, Chloroform-d, Method M2) δ 8.40 (s, 1H), 7.63 (s, 1H), 7.57 (d, J = 7.7 Hz, 1H), 7.48-7.26 (m, 6H), 6.05 (d, J = 8.4 Hz, 1H), 5.70 (q, J = 7.6 Hz, 1H), 4.59 (s, 2H), 4.12 (p, J = 7.0 Hz, 1H), 3.72 (p, J = 6.1 Hz, 1H), 3.12-2.89 (m, 2H), 2.76 (m, 1H), 2.64 (s, 3H), 1.96 (m, 1H), 1.66 (dd, J = 7.0, 4.2 Hz, 6H), 1.23 (d, J = 6.1 Hz, 6H). |
| 370 | (Method L2): $R_t$ = 3.73 min; m/z = 469 (M + H)$^+$ | $^1$H NMR (300 MHz, Chloroform-d, Method M2) δ 8.40 (s, 1H), 7.66-7.55 (m, 2H), 7.44 (t, J = 7.6 Hz, 1H), 7.40-7.26 (m, 4H), 7.25-7.21 (m, 1H), 6.07 (d, J = 8.3 Hz, 1H), 5.69 (q, J = 7.6 Hz, 1H), 4.58 (s, 2H), 4.12 (p, J = 7.1 Hz, 1H), 3.57 (q, J = 7.0 Hz, 2H), 3.12-2.88 (m, 2H), 2.75 (m, 1H), 2.64 (s, 3H), 2.05-1.88 (m, 1H), 1.65 (dd, J = 7.0, 4.2 Hz, 6H), 1.25 (t, J = 7.0 Hz, 3H). |
| 371 | (Method L2): $R_t$ = 3.55 min; m/z = 481 (M + H)$^+$ | $^1$H NMR (300 MHz, DMSO-d6, Method M2) δ 11.85 (s, 1H), 8.51 (s, 1H), 7.66-7.57 (m, 2H), 7.45 (t, J = 7.6 Hz, 1H), 7.41-7.26 (m, 5H), 5.60 (s, 1H), 4.47 (s, 2H), 3.32 (s, 3H), 3.13-3.01 (m, 1H), 2.99-2.85 (m, 1H), 2.72-2.59 (m, 1H), 2.49 (s, 3H), 2.31-2.19 (m, 1H). |
| 372 | (Method L2): $R_t$ = 3.60 min; m/z = 466 (M + H)$^+$ | $^1$H NMR (300 MHz, Chloroform-d, Method M2) δ 8.39 (s, 1H), 7.40-7.34 (m, 1H), 7.33-7.26 (m, 4H), 7.03-6.96 (m, 1H), 6.73-6.68 (m, 1H), 6.45-6.38 (m, 1H), 6.12 (d, J = 8.3 Hz, 1H), 5.69 (q, J = 7.6 Hz, 1H), 4.11 (p, J = 7.0 Hz, 1H), 3.90 (t, J = 7.2 Hz, 4H), 3.12-2.88 (m, 2H), 2.77 (m, 1H), 2.63 (s, 3H), 2.36 (p, J = 7.2 Hz, 2H), 1.97 (m, 1H), 1.64 (dd, J = 7.0, 4.8 Hz, 6H). |
| 373 | (Method L2): $R_t$ = 2.90 min; m/z = 468 (M + H)+ | $^1$H NMR (300 MHz, Chloroform-d, Method M2) δ 8.39 (s, 1H), 7.40-7.22 (m, 5H), 7.04-6.92 (m, 2H), 6.69 (dd, J = 8.3, 2.6 Hz, 1H), 6.06 (d, J = 8.4 Hz, 1H), 5.69 (q, J = 7.5 Hz, 1H), 4.12 (p, J = 7.1 Hz, 1H), 3.43 (q, J = 7.1 Hz, 2H), 3.13-2.88 (m, 5H), 2.75 (m, 1H), 2.65 (s, 3H), 1.96 (m, 1H), 1.65 (dd, J = 7.0, 4.3 Hz, 6H), 1.15 (t, J = 7.1 Hz, 3H). |
| 374 | (Method L2): $R_t$ = 3.24 min; m/z = 429 (M + H)+ | $^1$H NMR (300 MHz, Chloroform-d, Method M2) δ 8.38 (s, 1H), 7.96 (s, 1H), 7.90 (d, J = 0.6 Hz, 1H), 7.40-7.34 (m, 1H), 7.32-7.27 (m, 2H), 7.23 (d, J = 3.6 Hz, 1H), 6.08 (d, J = 8.3 Hz, 1H), 5.75-5.67 (m, 1H), 4.24 (q, J = 7.3 Hz, 2H), 4.10 (p, J = 7.1 Hz, 1H), 3.14-2.89 (m, 2H), 2.83-2.70 (m, 1H), 2.66 (s, 3H), 1.96 (ddd, J = 15.7, 13.0, 7.8 Hz, 1H), 1.64 (dd, J = 7.0, 4.1 Hz, 6H), 1.55 (t, J = 7.3 Hz, 3H). |
| 375 | (Method L2): $R_t$ = 3.16 min; m/z = 459 (M + H)$^+$ | $^1$H NMR (300 MHz, Chloroform-d, Method M2) δ 8.38 (s, 1H), 8.00 (d, J = 0.6 Hz, 1H), 7.95 (d, J = 0.6 Hz, 1H), 7.41-7.34 (m, 1H), 7.28 (d, J = 1.7 Hz, 2H), 7.26-7.22 (m, 1H), 6.11 (d, J = 8.4 Hz, 1H), 5.70 (q, J = 7.6 Hz, 1H), 4.35 (t, J = 5.4 Hz, 2H), 4.10 (p, J = 7.1 Hz, 1H), 3.80 (t, J = 5.4 Hz, 2H), 3.35 (s, 3H), 3.13-2.89 (m, 2H), 2.83-2.69 (m, 1H), 2.65 (s, 3H), 2.04-1.89 (m, 1H), 1.63 (dd, J = 7.0, 4.1 Hz, 6H). |
| 376 | (Method L2): $R_t$ = 3.39 min; m/z = 455 (M + H)$^+$ | $^1$H NMR (300 MHz, Chloroform-d, Method M2) δ 8.38 (s, 1H), 8.03 (d, J = 0.5 Hz, 1H), 7.91 (d, J = 0.7 Hz, 1H), 7.40-7.34 (m, 1H), 7.28 (d, J = 1.7 Hz, 2H), 7.24 (d, J = 1.6 Hz, 1H), 6.10 (d, J = 8.2 Hz, 1H), 5.70 (q, J = 7.7 Hz, 1H), 4.16-4.01 (m, 3H), 3.13-2.88 (m, 2H), 2.82-2.69 (m, 1H), 2.65 (s, 3H), 2.03-1.89 (m, 1H), 1.63 (dd, J = 7.1, 4.2 Hz, 6H), 1.41-1.30 (m, 1H), 0.71-0.62 (m, 2H), 0.45-0.37 (m, 2H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 377 | (Method L2): $R_t$ = 3.29 min; m/z = 465 (M + H)+ | $^1$H NMR (300 MHz, Chloroform-d, Method M2) δ 8.39 (s, 1H), 8.01 (d, J = 2.0 Hz, 2H), 7.41-7.33 (m, 1H), 7.32-7.27 (m, 2H), 7.24 (s, 1H), 6.38-5.89 (m, 2H), 5.69 (q, J = 7.6 Hz, 1H), 4.52 (td, J = 13.5, 4.3 Hz, 2H), 4.09 (p, J = 7.0 Hz, 1H), 3.14-2.89 (m, 2H), 2.83-2.69 (m, 1H), 2.65 (s, 3H), 2.04-1.89 (m, 1H), 1.63 (dd, J = 7.0, 4.0 Hz, 6H). |
| 378 | (Method L2): $R_t$ = 4.01 min; m/z = 489 (M + H)+ | $^1$H NMR (300 MHz, Chloroform-d, Method M2) δ 8.41 (s, 1H), 7.35 (dd, J = 5.2, 3.9 Hz, 1H), 7.30-7.27 (m, 1H), 7.21 (dd, J = 5.2, 3.9 Hz, 2H), 7.18-7.10 (m, 2H), 6.87-6.82 (m, 1H), 6.09 (d, J = 8.3 Hz, 1H), 5.44-5.34 (m, 1H), 4.10 (p, J = 7.1 Hz, 1H), 3.84 (s, 3H), 2.83 (q, J = 5.9 Hz, 2H), 2.64 (s, 3H), 2.26-2.13 (m, 1H), 2.09-1.81 (m, 3H), 1.64 (t, J = 7.0 Hz, 6H). |
| 379 | (Method L2): $R_t$ = 2.72 min; m/z = 482 (M + H)+ | $^1$H NMR (300 MHz, Chloroform-d, Method M2) δ 8.39 (s, 1H), 7.40-7.34 (m, 1H), 7.34-7.22 (m, 4H), 6.99-6.94 (m, 1H), 6.91 (d, J = 7.6 Hz, 1H), 6.65 (dd, J = 8.4, 2.0 Hz, 1H), 6.05 (d, J = 8.3 Hz, 1H), 5.69 (q, J = 7.6 Hz, 1H), 4.13 (p, J = 7.0 Hz, 1H), 3.39 (q, J = 7.0 Hz, 4H), 3.12-2.88 (m, 2H), 2.76 (m, 1H), 2.65 (s, 3H), 2.05-1.89 (m, 1H), 1.66 (dd, J = 7.0, 4.3 Hz, 6H), 1.19 (t, J = 7.0 Hz, 6H). |
| 380 | (Method L2): $R_t$ = 3.07 min; m/z = 487 (M + H)+ | $^1$H NMR (300 MHz, Chloroform-d, Method M2) δ 8.42 (s, 1H), 7.71-7.60 (m, 2H), 7.47 (t, J = 7.7 Hz, 1H), 7.41-7.33 (m, 1H), 7.33-7.19 (m, 4H), 6.13 (d, J = 8.3 Hz, 1H), 5.70 (q, J = 7.6 Hz, 1H), 4.19-4.06 (m, 2H), 3.97 (d, J = 12.8 Hz, 1H), 3.13-2.89 (m, 2H), 2.83-2.69 (m, 1H), 2.65 (s, 3H), 2.50 (s, 3H), 2.04-1.89 (m, 1H), 1.66 (dd, J = 7.0, 4.0 Hz, 6H). |
| 381 | (Method L2): $R_t$ = 3.60 min; m/z = 455 (M + H)+ | $^1$H NMR (300 MHz, Chloroform-d, Method M2) δ 8.37 (s, 1H), 7.66-7.57 (m, 2H), 7.30-7.10 (m, 4H), 6.98-6.83 (m, 2H), 6.15 (d, J = 7.4 Hz, 1H), 5.39-5.29 (m, 1H), 4.33 (dd, J = 6.1, 3.4 Hz, 1H), 4.25-4.04 (m, 2H), 2.62 (s, 3H), 2.46-2.32 (m, 1H), 2.27-2.15 (m, 1H), 1.64 (dd, J = 7.0, 6.1 Hz, 6H). |
| 382 | (Method L2): $R_t$ = 4.14 min; m/z = 471 (M + H)+ | $^1$H NMR (300 MHz, DMSO-d6, Method M2) δ 11.88 (s, 1H), 8.53 (s, 1H), 7.80 (t, J = 1.8 Hz, 1H), 7.65 (dt, J = 7.8, 1.2 Hz, 1H), 7.50 (t, J = 7.9 Hz, 1H), 7.41-7.27 (m, 5H), 5.62 (t, J = 6.6 Hz, 1H), 3.13-3.01 (m, 1H), 2.92 (dt, J = 15.8, 7.6 Hz, 1H), 2.73-2.59 (m, 1H), 2.50 (s, 3H), 2.32-2.20 (m, 1H). |
| 383 | (Method L4): $R_t$ = 4.42 min; m/z = 521 (M + H)+ | $^1$H NMR (300 MHz, DMSO-d6, Method M2) δ 11.89 (s, 1H), 8.53 (s, 1H), 7.81 (s, 1H), 7.72 (d, J = 7.9 Hz, 1H), 7.60 (t, J = 8.0 Hz, 1H), 7.41-7.28 (m, 5H), 5.61 (t, J = 6.4 Hz, 1H), 3.12-3.00 (m, 1H), 2.92 (dt, J = 15.9, 7.5 Hz, 1H), 2.74-2.60 (m, 1H), 2.53 (s, 3H), 2.32-2.20 (m, 1H). |
| 384 | (Method L4): $R_t$ = 4.36 min; m/z = 505 (M + H) | $^1$H NMR (300 MHz, DMSO-d6, Method M2) δ 11.89 (s, 1H), 8.54 (s, 1H), 8.15 (s, 1H), 7.98 (d, J = 7.3 Hz, 1H), 7.74-7.65 (m, 2H), 7.40-7.28 (m, 4H), 5.62 (t, J = 6.7 Hz, 1H), 3.14-3.00 (m, 1H), 2.92 (dt, J = 15.9, 7.5 Hz, 1H), 2.66 (dtd, J = 11.0, 8.0, 4.0 Hz, 1H), 2.54 (s, 3H), 2.26 (dq, J = 13.6, 6.9 Hz, 1H). |
| 385 | (Method L2): $R_t$ = 3.34 min; m/z = 480 (M + H)+ | $^1$H NMR (300 MHz, DMSO-d6, Method M2) δ 11.82 (s, 1H), 8.51 (s, 1H), 7.40-7.23 (m, 5H), 7.15 (d, J = 2.1 Hz, 1H), 6.94 (d, J = 7.7 Hz, 1H), 6.71 (dd, J = 8.1, 2.3 Hz, 1H), 5.60 (t, J = 6.6 Hz, 1H), 3.12-3.00 (m, 1H), 2.93 (s, 7H), 2.74-2.57 (m, 1H), 2.50 (s, 3H), 2.34-2.17 (m, 1H). |
| 386 | (Method L2): $R_t$ = 4.13 min; m/z = 467 (M + H)+ | $^1$H NMR (300 MHz, DMSO-d6, Method M2) δ 11.84 (s, 1H), 8.52 (s, 1H), 7.41-7.24 (m, 7H), 6.94-6.88 (m, 1H), 5.60 (t, J = 6.4 Hz, 1H), 3.79 (s, 3H), 3.12-3.01 (m, 1H), 2.92 (dt, J = 15.8, 7.5 Hz, 1H), 2.71-2.59 (m, 1H), 2.50-2.49 (m, 3H), 2.31-2.19 (m, 1H). |
| 387 | (Method L2): $R_t$ = 3.66 min; m/z = 455 (M + H)+ | $^1$H NMR (300 MHz, DMSO-d6, Method M2) δ 11.87 (s, 1H), 8.53 (s, 1H), 7.59-7.47 (m, 3H), 7.41-7.27 (m, 4H), 7.21-7.12 (m, 1H), 5.62 (t, J = 7.0 Hz, 1H), 3.13-3.00 (m, 1H), 2.92 (dt, J = 15.8, 7.6 Hz, 1H), 2.73-2.59 (m, 1H), 2.51 (s, 3H), 2.26 (dq, J = 14.6, 7.0 Hz, 1H). |
| 388 | (Method L2): $R_t$ = 3.80 min; m/z = 471 (M + H)+ | $^1$H NMR (300 MHz, Chloroform-d, Method M2) δ 8.40 (s, 1H), 7.64-7.52 (m, 2H), 7.46-7.32 (m, 2H), 7.26 (m, 4H), 6.08 (d, J = 8.3 Hz, 1H), 5.69 (q, J = 7.6 Hz, 1H), 4.12 (p, J = 7.0 Hz, 1H), 3.75 (s, 2H), 3.12-2.88 (m, 2H), 2.82-2.68 (m, 1H), 2.64 (s, 3H), 2.04 (s, 3H), 1.95 (dd, J = 13.0, 7.9 Hz, 1H), 1.65 (dd, J = 7.0, 4.1 Hz, 6H). |
| 389 | (Method L2): $R_t$ = 3.85 min; m/z = 495 (M + H)+ | $^1$H NMR (300 MHz, Chloroform-d, Method M2) δ 8.40 (s, 1H), 7.66-7.54 (m, 2H), 7.44 (t, J = 7.6 Hz, 1H), 7.40-7.20 (m, 5H), 6.09 (d, J = 8.3 Hz, 1H), 5.75-5.63 (m, 1H), 4.61 (s, 2H), 4.12 (p, J = 7.0 Hz, 1H), 3.34 (d, J = 6.9 Hz, 2H), 3.12-2.88 (m, 2H), 2.75 (dt, J = 7.7, 4.5 Hz, 1H), 2.64 (s, 3H), 1.95 (dd, J = 12.6, 7.5 Hz, 1H), 1.65 (dd, J = 7.1, 4.3 Hz, 6H), 1.19-1.03 (m, 1H), 0.58-0.47 (m, 2H), 0.26-0.17 (m, 2H). |
| 390 | (Method L2): $R_t$ = 3.90 min; m/z = 483 (M + H)+ | $^1$H NMR (300 MHz, Chloroform-d, Method M2) δ 8.40 (s, 1H), 7.66-7.55 (m, 2H), 7.44 (t, J = 7.6 Hz, 1H), 7.40-7.20 (m, 4H), 6.08 (d, J = 8.2 Hz, 1H), 5.69 (q, J = 7.5 Hz, 1H), 4.58 (s, 2H), 4.12 (p, J = 7.0 Hz, 1H), 3.47 (t, J = 6.7 Hz, 2H), 3.12-2.88 (m, 2H), 2.75 (m, 1H), 2.64 (s, 3H), 2.03-1.88 (m, 1H), 1.74-1.57 (m, 8H), 0.95 (t, J = 7.4 Hz, 3H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 391 | (Method L2): $R_t$ = 3.88 min; m/z = 525 (M + H)⁺ | ¹H NMR (300 MHz, Chloroform-d, Method M2) δ 8.41 (s, 1H), 7.57-7.51 (m, 1H), 7.45 (s, 1H), 7.31-7.17 (m, 2H), 7.07 (s, 1H), 6.99-6.83 (m, 2H), 6.16 (d, J = 7.5 Hz, 1H), 5.35 (q, J = 5.4 Hz, 1H), 4.35 (m, 1H), 4.25-4.04 (m, 2H), 3.89 (s, 3H), 2.66 (s, 3H), 2.46-2.32 (m, 1H), 2.22 (m, 1H), 1.65 (dd, J = 7.0, 6.0 Hz, 6H). |
| 392 | (Method L2): $R_t$ = 3.48 min; m/z = 471 (M + H)⁺ | ¹H NMR (300 MHz, Chloroform-d, Method M2) δ 8.38 (s, 1H), 7.64-7.54 (m, 1H), 7.44 (t, J = 7.6 Hz, 1H), 7.32-7.16 (m, 3H), 6.98-6.82 (m, 2H), 6.19 (d, J = 7.5 Hz, 1H), 5.39-5.29 (m, 1H), 4.53 (s, 2H), 4.34 (m, 1H), 4.25-4.05 (m, 2H), 3.41 (s, 3H), 2.64 (s, 3H), 2.45-2.31 (m, 1H), 2.27-2.14 (m, 1H), 1.70-1.56 (m, 6H). |
| 393 | (Method L2): $R_t$ = 3.05 min; m/z = 470 (M + H)⁺ | ¹H NMR (300 MHz, Chloroform-d, Method M2) δ 8.36 (s, 1H), 7.37-7.16 (m, 3H), 7.05-6.82 (m, 4H), 6.71 (dd, J = 8.0, 2.3 Hz, 1H), 6.17 (d, J = 7.5 Hz, 1H), 5.39-5.29 (m, 1H), 4.39-4.28 (m, 1H), 4.25-4.05 (m, 2H), 2.98 (s, 6H), 2.65 (s, 3H), 2.45-2.31 (m, 1H), 2.27-2.14 (m, 1H), 1.69-1.60 (m, 6H). |
| 394 | (Method L2): $R_t$ = 3.88 min; m/z = 511 (M + H)⁺ | ¹H NMR (300 MHz, Chloroform-d, Method M2) δ 8.41 (s, 1H), 7.64 (dt, J = 7.8, 1.2 Hz, 1H), 7.58 (s, 1H), 7.47 (t, J = 8.0 Hz, 1H), 7.30-7.12 (m, 3H), 6.99-6.82 (m, 2H), 6.17 (d, J = 7.4 Hz, 1H), 5.34 (q, J = 5.4 Hz, 1H), 4.40-4.29 (m, 1H), 4.25-4.04 (m, 2H), 2.65 (s, 3H), 2.46-2.32 (m, 1H), 2.28-2.15 (m, 1H), 1.64 (dd, J = 7.0, 5.9 Hz, 6H). |
| 395 | (Method L2): $R_t$ = 3.56 min; m/z = 457 (M + H)⁺ | ¹H NMR (300 MHz, Chloroform-d, Method M2) δ 8.38 (s, 1H), 7.38 (t, J = 8.2 Hz, 1H), 7.31-7.16 (m, 4H), 6.98-6.82 (m, 3H), 6.16 (d, J = 7.4 Hz, 1H), 5.34 (q, J = 5.4 Hz, 1H), 4.39-4.29 (m, 1H), 4.25-4.04 (m, 2H), 3.85 (s, 3H), 2.65 (s, 3H), 2.46-2.32 (m, 1H), 2.27-2.15 (m, 1H), 1.64 (dd, J = 6.9, 6.2 Hz, 6H). |
| 396 | (Method L2): $R_t$ = 3.63 min; m/z = 445 (M + H)⁺ | ¹H NMR (300 MHz, Chloroform-d, Method M2) δ 8.40 (s, 1H), 7.50-7.36 (m, 3H), 7.30-7.17 (m, 2H), 7.05-6.90 (m, 2H), 6.86 (dd, J = 8.2, 1.1 Hz, 1H), 6.15 (d, J = 7.3 Hz, 1H), 5.35 (d, J = 7.2 Hz, 1H), 4.33 (dd, J = 6.0, 3.4 Hz, 1H), 4.25-4.04 (m, 2H), 2.65 (s, 3H), 2.46-2.33 (m, 1H), 2.28-2.16 (m, 1H), 1.64 (dd, J = 7.0, 6.1 Hz, 6H). |
| 397 | (Method L2): $R_t$ = 2.40 min; m/z = 514 (M + H)⁺ | ¹H NMR (300 MHz, Chloroform-d, Method M2) δ 8.38 (s, 1H), 8.03 (d, J = 0.5 Hz, 1H), 7.92 (d, J = 0.6 Hz, 1H), 7.41-7.33 (m, 1H), 7.32-7.27 (m, 2H) 7.24 (d, J = 5.4 Hz, 1H), 6.11 (d, J = 8.3 Hz, 1H), 5.70 (q, J = 7.5 Hz, 1H), 4.31 (t, J = 6.7 Hz, 2H), 4.10 (p, J = 7.0 Hz, 1H), 3.74-3.66 (m, 4H), 3.17-2.91 (m, 2H), 2.87 (t, J = 6.7 Hz, 2H), 2.76 (m, 1H), 2.65 (s, 3H), 2.55-2.47 (m, 4H), 2.04-1.89 (m, 1H), 1.64 (dd, J = 7.0, 4.0 Hz, 6H). |
| 398 | (Method L2): $R_t$ = 3.34 min; m/z = 443 (M + H)⁺ | ¹H NMR (300 MHz, Chloroform-d, Method M2) δ 8.38 (s, 1H), 7.99 (d, J = 0.5 Hz, 1H), 7.91 (d, J = 0.6 Hz, 1H), 7.41-7.34 (m, 1H), 7.32-7.27 (m, 2H), 7.24 (d, J = 5.4 Hz, 1H), 6.09 (d, J = 8.2 Hz, 1H), 5.70 (q, J = 7.6 Hz, 1H), 4.56 (p, J = 6.7 Hz, 1H), 4.10 (p, J = 7.0 Hz, 1H), 3.14-2.89 (m, 2H), 2.83-2.69 (m, 1H), 2.66 (s, 3H), 2.04-1.89 (m, 1H), 1.64 (dd, J = 7.1, 4.1 Hz, 6H), 1.56 (m, 6H). |
| 399 | (Method L2): $R_t$ = 2.44 min; m/z = 523 (M + H)⁺ | ¹H NMR (300 MHz, Chloroform-d, Method M2) δ 8.41 (s, 1H), 7.63-7.52 (m, 1H), 7.46-7.32 (m, 2H), 7.32-7.21 (m, 5H), 6.10 (d, J = 8.3 Hz, 1H), 5.70 (q, J = 7.5 Hz, 1H), 4.13 (p, J = 7.1 Hz, 1H), 3.60 (s, 2H), 3.13-2.89 (m, 3H), 2.77 (m, 3H), 2.59 (m, J = 25.5 Hz, 11H), 2.33 (s, 3H), 2.04-1.89 (m, 1H), 1.66 (dd, J = 7.0, 4.1 Hz, 6H). |
| 400 | (Method L2): $R_t$ = 3.26 min; m/z = 503 (M + H)⁺ | ¹H NMR (300 MHz, Chloroform-d, Method M2) δ 8.41 (s, 1H), 7.82-7.68 (m, 2H), 7.51 (t, J = 7.7 Hz, 1H), 7.41-7.21 (m, 5H), 6.10 (d, J = 8.4 Hz, 1H), 5.69 (q, J = 7.6 Hz, 1H), 4.30 (s, 2H), 4.11 (p, J = 6.9 Hz, 1H), 3.13-2.89 (m, 2H), 2.85-2.71 (m, 4H), 2.66 (s, 3H), 2.03-1.89 (m, 1H), 1.65 (dd, J = 7.0, 3.9 Hz, 6H). |
| 401 | (Method L2): $R_t$ = 3.30 min; m/z = 499 (M + H)⁺ | ¹H NMR (300 MHz, Chloroform-d, Method M2) δ 8.36 (d, J = 1.9 Hz, 1H), 8.06 (s, 1H), 8.03-7.98 (m, 1H), 7.32-7.17 (m, 2H), 6.99-6.83 (m, 2H), 6.30 (d, J = 7.6 Hz, 1H), 5.34 (q, J = 5.3 Hz, 1H), 4.72 (q, J = 8.4 Hz, 2H), 4.40-4.30 (m, 1H), 4.20 (m, 1H), 4.08 (p, J = 7.0 Hz, 1H), 2.64 (d, J = 1.8 Hz, 3H), 2.46-2.32 (m, 1H), 2.23 (m, 1H), 1.68-1.56 (m, 6H). |
| 402 | (Method L2): $R_t$ = 3.42 min; m/z = 462 (M + H)⁺ | ¹H NMR (300 MHz, Chloroform-d, MEthod M2) δ 8.67 (s, 1H), 8.42 (s, 1H), 8.31 (s, 1H), 8.07 (q, J = 2.6, 2.1 Hz, 1H), 7.32-7.18 (m, 2H), 6.96 (m, 1H), 6.88 (dd, J = 8.2, 1.0 Hz, 1H), 6.55 (d, J = 7.3 Hz, 1H), 5.41-5.31 (m, 1H), 4.41-4.31 (m, 1H), 4.26-4.01 (m, 2H), 2.64 (s, 3H), 2.47-2.33 (m, 1H), 2.24 (m, 1H), 1.63 (dd, J = 8.7, 7.1 Hz, 6H). |
| 403 | (Method L2): $R_t$ = 3.81 min; m/z = 491 (M + H)⁺ | ¹H NMR (300 MHz, Chloroform-d, Method M2) δ 8.40 (s, 1H), 7.31-7.13 (m, 4H), 6.94 (m, 1H), 6.90-6.82 (m, 2H), 6.15 (d, J = 7.4 Hz, 1H), 5.35 (q, J = 5.3 Hz, 1H), 4.40-4.30 (m, 1H), 4.25-4.04 (m, 2H), 3.84 (s, 3H), 2.64 (s, 3H), 2.46-2.32 (m, 1H), 2.22 (m, 1H), 1.64 (dd, J = 7.0, 6.1 Hz, 6H). |
| 404 | (Method L2): $R_t$ = 2.35 min; m/z = 472 (M + H)⁺ | ¹H NMR (300 MHz, Chloroform-d, Method M2) δ 8.38 (s, 1H), 7.99 (d, J = 0.6 Hz, 1H), 7.92 (d, J = 0.6 Hz, 1H), 7.41-7.34 (m, 1H), 7.32-7.27 (m, 2H), 7.26-7.22 (m, 1H), 6.10 (d, J = 8.5 Hz, 1H), 5.70 (q, J = 7.6 Hz, 1H), 4.29 (t, J = 6.9 Hz, 2H), 4.10 (p, J = 7.0 Hz, 1H), 3.14-2.89 (m, 2H), 2.87-2.69 (m, 3H), 2.65 (s, 3H), 2.30 (s, 6H), 2.04-1.89 (m, 1H), 1.69-1.59 (m, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 405 | (Method L2): $R_t$ = 3.30 min; m/z = 445 (M + H)$^+$ | $^1$H NMR (300 MHz, DMSO-d6, Method M2) δ 9.01 (d, J = 8.0 Hz, 1H), 8.44 (s, 1H), 7.59-7.48 (m, 1H), 7.42-7.36 (m, 1H), 7.30-7.20 (m, 5H), 5.51 (q, J = 7.7 Hz, 1H), 3.06-2.93 (m, 1H), 2.86 (dt, J = 15.9, 8.1 Hz, 1H), 2.67-2.52 (m, 2H), 2.36 (s, 3H), 1.93 (dq, J = 12.7, 8.4 Hz, 1H), 1.49 (dt, J = 6.1, 3.1 Hz, 2H), 1.21 (dd, J = 8.8, 3.1 Hz, 2H). |
| 406 | (Method L2): $R_t$ = 4.15 min; m/z = 521 (M + H)$^+$ | $^1$H NMR (300 MHz, Chloroform-d, Method M2) δ 8.41 (s, 1H), 7.77 (m, J = 7.8, 1.2 Hz, 1H), 7.71 (s, 1H), 7.49 (t, J = 8.0 Hz, 1H), 7.40-7.32 (m, 1H), 7.32-7.21 (m, 3H), 7.16 (m, J = 8.2, 2.2, 1.0 Hz, 1H), 6.07 (d, J = 8.3 Hz, 1H), 5.68 (d, J = 7.7 Hz, 1H), 4.11-3.96 (m, 1H), 3.12-2.88 (m, 2H), 2.82-2.68 (m, 1H), 2.20 (t, J = 8.2 Hz, 1H), 1.95 (dd, J = 13.0, 7.9 Hz, 1H), 1.61 (dd, J = 7.0, 2.6 Hz, 6H), 1.28-1.17 (m, 2H), 1.17-1.05 |
| 407 | (Method L2): $R_t$ = 3.52 min; m/z = 480 (M + H)$^+$ | $^1$H NMR (300 MHz, Chloroform-d, Method M2) δ 8.38 (s, 1H), 7.39-7.22 (m, 5H), 7.18-7.08 (m, 2H), 6.72 (dd, J = 8.0, 2.3 Hz, 1H), 6.02 (d, J = 8.2 Hz, 1H), 5.68 (q, J = 7.7 Hz, 1H), 4.03 (m, J = 7.1 Hz, 1H), 2.99 (s, 8H), 2.82-2.71 (m, 1H), 2.35-2.24 (m, 1H), 2.01-1.87 (m, 1H), 1.61 (dd, J = 7.0, 2.6 Hz, 6H), 1.20 (m, J = 5.8, 2.6 Hz, 2H), 1.06 (m, J = 8.3, 3.0 Hz, 2H). |
| 408 | (Method L2): $R_t$ = 3.89 min; m/z = 467 (M + H)$^+$ | $^1$H NMR (300 MHz, Chloroform-d, Method M2) δ 8.39 (s, 1H), 7.45-7.32 (m, 4H), 7.31-7.19 (m, 3H), 6.87 (m, J = 6.7, 2.6 Hz, 1H), 6.03 (d, J = 8.1 Hz, 1H), 5.69 (t, J = 7.6 Hz, 1H), 4.08-3.96 (m, 1H), 3.86 (s, 3H), 3.13-2.87 (m, 2H), 2.82-2.68 (m, 1H), 2.32-2.21 (m, 1H), 1.94 (dd, J = 13.0, 7.9 Hz, 1H), 1.61 (dd, J = 7.0, 2.6 Hz, 6H), 1.24-1.16 (m, 2H), 1.08 (m, J = 8.3, 3.0 Hz, 2H). |
| 409 | (Method L2): $R_t$ = 3.85 min; m/z = 481 (M + H)$^+$ | $^1$H NMR (300 MHz, Chloroform-d, Method M2) δ 8.39 (s, 1H), 7.76-7.67 (m, 2H), 7.47 (t, J = 7.6 Hz, 1H), 7.39-7.22 (m, 5H), 6.03 (d, J = 8.2 Hz, 1H), 5.70 (t, J = 7.6 Hz, 1H), 4.54 (s, 2H), 4.03 (m, J = 7.0 Hz, 1H), 3.42 (s, 3H), 3.12-2.88 (m, 2H), 2.82-2.69 (m, 1H), 2.27-2.18 (m, 1H), 2.02-1.87 (m, 1H), 1.61 (dd, J = 7.0, 2.5 Hz, 6H), 1.20 (m, J = 5.6, 2.9 Hz, 2H), 1.08 (m, J = 8.3, 2.9 Hz, 2H). |
| 410 | (Method L2): $R_t$ = 3.52 min; m/z = 473 (M + H)$^+$ | $^1$H NMR (300 MHz, DMSO-d6, Method M2) δ 11.84 (s, 1H), 8.53 (s, 1H), 7.60-7.48 (m, 1H), 7.40-7.34 (m, 3H), 7.33-7.23 (m, 3H), 5.62 (t, J = 7.0 Hz, 1H), 3.12-3.00 (m, 1H), 2.92 (dt, J = 15.7, 7.5 Hz, 1H), 2.70-2.58 (m, 1H), 2.26 (s, 4H). |
| 411 | (Method L2): $R_t$ = 4.10 min; m/z = 471 (M + H)$^+$ | $^1$H NMR (300 MHz, Chloroform-d, Method M2) δ 8.41 (s, 1H), 7.80 (t, J = 1.8 Hz, 1H), 7.69 (m, J = 7.7, 1.3 Hz, 1H), 7.44-7.32 (m, 2H), 7.32-7.22 (m, 4H), 6.02 (d, J = 8.3 Hz, 1H), 5.70 (t, J = 7.6 Hz, 1H), 4.16-3.95 (m, 1H), 3.12-2.88 (m, 2H), 2.82-2.69 (m, 1H), 2.27-2.15 (m, 1H), 2.02-1.87 (m, 1H), 1.61 (dd, J = 7.0, 2.6 Hz, 6H), 1.29-1.16 (m, 2H), 1.10 (m, J = 8.3, 2.9 Hz, 2H). |
| 412 | (Method L2): $R_t$ = 3.61 min; m/z = 471 (M + H)$^+$ | $^1$H NMR (300 MHz, DMSO-d6, Method M2) δ 11.90 (s, 1H), 8.52 (s, 1H), 7.64-7.57 (m, 1H), 7.48-7.41 (m, 3H), 7.40-7.27 (m, 4H), 5.57 (s, 1H), 3.12-3.00 (m, 1H), 2.92 (dt, J = 15.8, 7.5 Hz, 1H), 2.70-2.56 (m, 1H), 2.25 (s, 4H). |
| 413 | (Method L2): $R_t$ = 4.14 min; m/z = 473 (M + H)$^+$ | $^1$H NMR (300 MHz, Chloroform-d, Method M2) δ 8.40 (s, 1H), 7.35 (m, J = 8.4, 5.6, 2.3 Hz, 2H), 7.31-7.21 (m, 3H), 7.04 (t, J = 8.1 Hz, 1H), 6.02 (d, J = 8.6 Hz, 1H), 5.69 (t, J = 7.6 Hz, 1H), 4.09-3.97 (m, 1H), 3.12-2.88 (m, 2H), 2.82-2.68 (m, 1H), 2.01-1.86 (m, 2H), 1.62 (dd, J = 7.0, 2.8 Hz, 6H), 1.15 (d, J = 7.3 Hz, 2H), 1.03 (d, J = 8.3 Hz, 2H). |
| 414 | (Method L2): $R_t$ = 4.45 min; m/z = 471 (M + H)+ | $^1$H NMR (300 MHz, Chloroform-d, Method M2) δ 8.41 (s, 1H), 7.80 (t, J = 1.8 Hz, 1H), 7.69 (m, J = 7.7, 1.3 Hz, 1H), 7.45-7.33 (m, 2H), 7.32-7.22 (m, 4H), 6.03 (d, J = 8.5 Hz, 1H), 5.74-5.63 (m, 1H), 4.09-3.97 (m, 1H), 3.12-2.89 (m, 2H), 2.83-2.69 (m, 1H), 2.27-2.15 (m, 1H), 1.95 (dd, J = 12.6, 7.5 Hz, 1H), 1.61 (dd, J = 7.0, 2.6 Hz, 6H), 1.27-1.17 (m, 2H), 1.15-1.05 (m, 2H). |
| 415 | (Method L2): $R_t$ = 4.46 min; m/z = 505 (M + H)$^+$ | $^1$H NMR (300 MHz, Chloroform-d, Method M2) δ 8.43 (s, 1H), 8.09 (s, 1H), 8.01 (d, J = 6.8 Hz, 1H), 7.58 (d, J = 7.0 Hz, 2H), 7.39-7.33 (m, 1H), 7.27 (d, J = 7.2 Hz, 3H), 6.04 (d, J = 8.2 Hz, 1H), 5.69 (q, J = 7.5 Hz, 1H), 4.04 (p, J = 7.0 Hz, 1H), 3.14-2.88 (m, 2H), 2.83-2.69 (m, 1H), 2.18 (d, J = 21.4 Hz, 1H), 2.03-1.88 (m, 1H), 1.62 (dd, J = 7.0, 2.6 Hz, 6H), 1.26-1.18 (m, 2H), 1.15-1.06 (m, 2H). |
| 416 | (Method L2): $R_t$ = 4.30 min; m/z = 455 (M + H)$^+$ | $^1$H NMR (300 MHz, Chloroform-d, Method M2) δ 8.41 (s, 1H), 7.63-7.50 (m, 2H), 7.48-7.33 (m, 2H), 7.27 (d, J = 7.0 Hz, 3H), 7.07-6.95 (m, 1H), 6.03 (d, J = 8.5 Hz, 1H), 5.69 (d, J = 7.7 Hz, 1H), 4.11-3.96 (m, 1H), 3.13-2.88 (m, 2H), 2.84-2.68 (m, 1H), 2.23 (t, J = 8.2 Hz, 1H), 1.95 (dd, J = 12.6, 7.5 Hz, 1H), 1.61 (dd, J = 7.0, 2.6 Hz, 6H), 1.25-1.17 (m, 2H), 1.14-1.05 (m, 2H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 417 | (Method L2): $R_t$ = 3.81 min; m/z = 475 (M + H)$^+$ | $^1$H NMR (300 MHz, Chloroform-d, Method M2) δ 8.48 (s, 1H), 7.54 (m, 1H), 7.50-7.34 (m, 3H), 7.32-7.20 (m, 3H), 7.09-7.02 (m, 1H), 6.57 (t, J = 74.1 Hz, 1H), 6.22 (d, J = 8.2 Hz, 1H), 5.69 (d, J = 7.5 Hz, 1H), 3.13-2.89 (m, 2H), 2.75 (m, 1H), 2.62 (m, 4H), 1.99 (m, 1H), 1.69 (m, 2H), 1.28 (m, 2H). |
| 418 | (Method L2): $R_t$ = 3.90 min; m/z = 465 (M + H)$^+$ | $^1$H NMR (300 MHz, DMSO-d6, Method M2) δ 9.00 (d, J = 8.1 Hz, 1H), 8.47 (s, 1H), 7.42-7.21 (m, 7H), 7.05-6.98 (m, 1H), 5.52 (q, J = 7.7 Hz, 1H), 3.86 (dt, J = 5.9, 3.0 Hz, 1H), 3.05-2.94 (m, 1H), 2.87 (dt, J = 15.9, 8.1 Hz, 1H), 2.67-2.52 (m, 5H), 1.95 (dq, J = 12.6, 8.4 Hz, 1H), 1.47 (dt, J = 6.2, 3.1 Hz, 2H), 1.24-1.15 (m, 2H), 0.80 (q, J = 6.9, 5.9 Hz, 2H), 0.70 (q, J = 5.9, 4.6 Hz, 2H). |
| 419 | (Method L2): $R_t$ = 3.64 min; m/z = 471 (M + H)$^+$ | NMR (300 MHz, DMSO-d6, Method M2) δ 9.15 (d, J = 8.1 Hz, 1H), 8.45 (s, 1H), 8.18 (s, 1H), 7.93 (d, J = 0.6 Hz, 1H), 7.34 (d, J = 6.7 Hz, 1H), 7.22-7.14 (m, 1H), 6.93 (td, J = 7.5, 1.1 Hz, 1H), 6.80 (dd, J = 8.2, 1.0 Hz, 1H), 5.28-5.19 (m, 1H), 4.32-4.19 (m, 2H), 4.05 (d, J = 7.1 Hz, 2H), 3.94 (p, J = 7.0 Hz, 1H), 2.60 (s, 3H), 2.26-2.14 (m, 1H), 2.11-1.98 (m, 1H), 1.54 (t, J = 7.1 Hz, 6H), 1.33-1.22 (m, 1H), 0.59-0.50 (m, 2H), 0.43-0.36 (m, 2H). |
| 420 | (Method L2): $R_t$ = 3.83 min; m/z = 469 (M + H)$^+$ | $^1$H NMR (300 MHz, DMSO-d6, Method M2) δ 9.04 (d, J = 8.5 Hz, 1H), 8.43 (s, 1H), 8.18 (s, 1H), 7.94 (s, 1H), 7.40-7.33 (m, 1H), 7.23-7.09 (m, 3H), 5.25-5.15 (m, 1H), 4.05 (d, J = 7.1 Hz, 2H), 3.93 (p, J = 7.1 Hz, 1H), 2.76 (s, 2H), 2.60 (s, 3H), 2.11-2.00 (m, 1H), 1.96-1.75 (m, 3H), 1.54 (t, J = 7.3 Hz, 6H), 1.33-1.24 (m, 1H), 0.58-0.50 (m, 2H), 0.44-0.36 (m, 2H). |
| 421 | (Method L2): $R_t$ = 3.47 min; m/z = 481 (M + H)$^+$ | $^1$H NMR (300 MHz, DMSO-d6, Method M2) δ 8.99 (d, J = 8.2 Hz, 1H), 8.46 (s, 1H), 8.33 (s, 1H), 8.10-8.07 (m, 1H), 7.43-7.36 (m, 1H), 7.25 (m, 3H), 5.52 (q, J = 7.8 Hz, 1H), 5.23 (q, J = 9.1 Hz, 2H), 3.06-2.80 (m, 2H), 2.67-2.54 (m, 4H), 2.03-1.87 (m, 1H), 1.48 (m, 2H), 1.30-1.14 (m, 3H). |
| 422 | (Method L2): $R_t$ = 3.73 min; m/z = 445 (M + H)$^+$ | $^1$H NMR (300 MHz, Chloroform-d, Method M2) δ 8.49 (s, 1H), 7.41-7.34 (m, 1H), 7.32-7.09 (m, 5H), 7.08-6.97 (m, 1H), 6.17 (d, J = 8.3 Hz, 1H), 5.75-5.64 (m, 1H), 3.13-2.89 (m, 2H), 2.75 (m, 1H), 2.59 (m, 1H), 2.49 (d, J = 1.8 Hz, 3H), 2.06-1.91 (m, 1H), 1.71 (m, 2H), 1.34-1.22 (m, 2H). |
| 423 | (Method L2): $R_t$ = 4.04 min; m/z = 507 (M + H)$^+$ | $^1$H NMR (300 MHz, DMSO-d6, Method M2) δ 9.02 (d, J = 8.1 Hz, 1H), 8.54 (s, 1H), 7.70 (s, 1H), 7.56 (s, 1H), 7.44-7.38 (m, 1H), 7.32-7.21 (m, 3H), 7.18 (s, 1H), 5.52 (q, J = 7.7 Hz, 1H), 3.89 (s, 3H), 3.06-2.80 (m, 2H), 2.71-2.53 (m, 5H), 1.95 (m, 1H), 1.51 (m, 2H), 1.22 (m, 2H). |
| 424 | (Method L2): $R_t$ = 3.73 min; m/z = 445 (M + H)$^+$ | $^1$H NMR (300 MHz, Chloroform-d, Method M2) δ 8.49 (s, 1H), 7.38 (d, J = 6.4 Hz, 1H), 7.33-7.11 (m, 6H), 6.17 (d, J = 8.0 Hz, 1H), 5.70 (d, J = 7.5 Hz, 1H), 3.13-2.89 (m, 2H), 2.82-2.68 (m, 1H), 2.66-2.45 (m, 4H), 2.06-1.91 (m, 1H), 1.72 (m, 2H), 1.30 (m, 2H). |
| 425 | (Method L2): $R_t$ = 4.25 min; m/z = 511 (M + H)$^+$ | $^1$H NMR (300 MHz, Chloroform-d, Method M2) δ 8.53 (s, 1H), 7.93 (s, 1H), 7.88 (s, 1H), 7.53 (s, 1H), 7.42-7.36 (m, 1H), 7.27 (d, J = 8.9 Hz, 3H), 6.16 (d, J = 8.1 Hz, 1H), 5.71 (q, J = 7.5 Hz, 1H), 3.14-2.90 (m, 2H), 2.80-2.71 (m, 1H), 2.69-2.56 (m, 4H), 2.07-1.92 (m, 1H), 1.75 (m, 2H), 1.35-1.22 (m, 2H). |
| 426 | (Method L2): $R_t$ = 3.53 min; m/z = 401 (M + H)$^+$ | $^1$H NMR (300 MHz, Chloroform-d, Method M2) δ 8.31 (s, 1H), 7.93 (d, J = 1.9 Hz, 1H), 7.52 (d, J = 1.8 Hz, 1H), 7.41-7.22 (m, 4H), 6.76 (d, J = 8.4 Hz, 1H), 6.44 (q, J = 2.4 Hz, 1H), 5.71 (q, J = 7.5 Hz, 1H), 4.08 (p, J = 7.1 Hz, 1H), 3.15-2.89 (m, 2H), 2.75 (m, 1H), 2.59 (s, 3H), 2.08-1.93 (m, 1H), 1.63 (t, J = 6.8 Hz, 6H). |
| 427 | (Method L2): $R_t$ = 3.79 min; m/z = 490 (M + H)$^+$ | $^1$H NMR (300 MHz, Chloroform-d, Method M2) δ 8.50 (s, 1H), 7.41-7.21 (m, 5H), 7.16-6.72 (m, 4H), 6.07 (d, J = 8.3 Hz, 1H), 5.70 (q, J = 7.5 Hz, 1H), 4.11 (p, J = 7.1 Hz, 1H), 2.99 (s, 8H), 2.76 (m, 1H), 2.03-1.89 (m, 1H), 1.66 (dd, J = 7.0, 3.9 Hz, 6H). |
| 428 | (Method L2): $R_t$ = 3.97 min; m/z = 477 (M + H)$^+$ | $^1$H NMR (300 MHz, Chloroform-d, Method M2) δ 8.51 (s, 1H), 7.43-7.21 (m, 7H), 7.15-6.72 (m, 2H), 6.10 (d, J = 8.3 Hz, 1H), 5.69 (q, J = 7.5 Hz, 1H), 4.10 (p, J = 7.0 Hz, 1H), 3.85 (s, 3H), 3.12-2.88 (m, 2H), 2.75 (m, 1H), 1.96 (m, 1H), 1.66 (dd, J = 7.0, 3.8 Hz, 6H). |
| 429 | (Method L2): $R_t$ = 4.03 min; m/z = 465 (M + H)$^+$ | $^1$H NMR (300 MHz, Chloroform-d, Method M2) δ 8.54 (s, 1H), 7.58-7.22 (m, 7H), 7.15-6.73 (m, 2H), 6.08 (d, J = 8.3 Hz, 1H), 5.70 (q, J = 7.5 Hz, 1H), 4.16-4.03 (m, 1H), 3.13-2.90 (m, 2H), 2.78 (m, 1H), 2.03-1.90 (m, 1H), 1.66 (dd, J = 7.0, 3.7 Hz, 6H). |
| 430 | (Method L2): $R_t$ = 3.94 min; m/z = 491 (M + H)$^+$ | $^1$H NMR (300 MHz, Chloroform-d, Method M2) δ 8.51 (s, 1H), 7.71-7.60 (m, 2H), 7.46 (t, J = 7.6 Hz, 1H), 7.39-7.20 (m, 5H), 6.94 (t, J = 53.7 Hz, 1H), 6.12 (d, J = 8.4 Hz, 1H), 5.69 (q, J = 7.6 Hz, 1H), 4.53 (s, 2H), 4.16-4.03 (m, 1H), 3.41 (s, 3H), 3.13-2.89 (m, 2H), 2.75 (m, 1H), 2.03-1.88 (m, 1H), 1.66 (dd, J = 7.0, 3.8 Hz, 6H). |
| 431 | (Method L2): $R_t$ = 4.21 min; m/z = 531 (M + H)$^+$ | $^1$H NMR (300 MHz, Chloroform-d, Method M2) δ 8.54 (s, 1H), 7.74-7.65 (m, 2H), 7.53-7.45 (m, 1H), 7.39-7.19 (m, 5H), 6.95 (t, J = 53.7 Hz, 1H), 6.08 (d, J = 8.3 Hz, 1H), 5.70 (q, J = 7.5 Hz, 1H), 4.10 (p, J = 7.0 Hz, 1H), 3.13-2.90 (m, 2H), 2.83-2.70 (m, 1H), 2.05-1.89 (m, 1H), 1.66 (dd, J = 7.1, 3.6 Hz, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 432 | (Method L2): $R_t$ = 4.21 min; m/z = 531 (M + H)⁺ | ¹H NMR (300 MHz, Chloroform-d, Method M2) δ 8.54 (s, 1H), 7.74-7.65 (m, 2H), 7.53-7.45 (m, 1H), 7.39-7.19 (m, 5H), 6.95 (t, J = 53.7 Hz, 1H), 6.08 (d, J = 8.3 Hz, 1H), 5.70 (q, J = 7.5 Hz, 1H), 4.10 (p, J = 7.0 Hz, 1H), 3.13-2.90 (m, 2H), 2.83-2.70 (m, 1H), 2.05-1.89 (m, 1H), 1.66 (dd, J = 7.1, 3.6 Hz, 6H). |
| 433 | (Method L2): $R_t$ = 4.17 min; m/z = 515 (M + H)⁺ | ¹H NMR (300 MHz, Chloroform-d, Method M2) δ 8.55 (s, 1H), 8.06 (s, 1H), 7.95 (d, J = 6.9 Hz, 1H), 7.60 (q, J = 7.9 Hz, 2H), 7.39-7.33 (m, 1H), 7.33-7.21 (m, 3H), 6.95 (t, J = 53.7 Hz, 1H), 6.10 (d, J = 8.3 Hz, 1H), 5.70 (q, J = 7.5 Hz, 1H), 4.10 (p, J = 7.1 Hz, 1H), 3.13-2.89 (m, 2H), 2.76 (m, 1H), 2.04-1.90 (m, 1H), 1.66 (dd, J = 7.0, 3.6 Hz, 6H). |
| 434 | (Method L2): $R_t$ = 3.91 min; m/z = 483 (M + H)⁺ | ¹H NMR (300 MHz, Chloroform-d, Method M2) δ 8.52 (s, 1H), 7.45-7.20 (m, 5H), 7.11-6.69 (m, 3H), 6.09 (d, J = 8.3 Hz, 1H), 5.69 (q, J = 7.5 Hz, 1H), 4.17-4.04 (m, 1H), 3.12-2.89 (m, 2H), 2.82-2.68 (m, 1H), 2.02-1.88 (m, 1H), 1.67 (dd, J = 7.1, 4.0 Hz, 6H). |
| 435 | (Method L2): $R_t$ = 3.97 min; m/z = 481 (M + H)⁺ | ¹H NMR (300 MHz, Chloroform-d, Method M2) δ 8.49 (s, 1H), 7.57-7.48 (m, 1H), 7.47-7.20 (m, 7H), 6.87 (t, J = 53.9 Hz, 1H), 6.09 (d, J = 8.2 Hz, 1H), 5.69 (q, J = 7.5 Hz, 1H), 4.18-4.03 (m, 1H), 3.12-2.89 (m, 2H), 2.83-2.68 (m, 1H), 2.03-1.87 (m, 1H), 1.68 (dd, J = 7.1, 4.0 Hz, 6H). |
| 436 | (Method L2): $R_t$ = 3.85 min; m/z = 479 (M + H)⁺ | ¹H NMR (300 MHz, Chloroform-d, Method M2) δ 8.49 (d, J = 0.9 Hz, 1H), 7.46-7.32 (m, 2H), 7.31-7.19 (m, 3H), 6.99 (m, 1H), 6.20 (d, J = 8.2 Hz, 1H), 5.68 (d, J = 7.5 Hz, 1H), 3.12-2.88 (m, 2H), 2.81-2.54 (m, 2H), 2.44 (s, 3H), 2.05-1.90 (m, 1H), 1.74 (m, 2H), 1.34-1.21 (m, 2H). |
| 437 | (Method L2): $R_t$ = 3.73 min; m/z = 463 (M + H)⁺ | ¹H NMR (300 MHz, Chloroform-d, Method M2) δ 8.50 (s, 1H), 7.41-7.33 (m, 1H), 7.32-7.11 (m, 4H), 6.97 (m, 1H), 6.18 (d, J = 8.2 Hz, 1H), 5.74-5.63 (m, 1H), 3.12-2.88 (m, 2H), 2.82-2.54 (m, 2H), 2.45 (s, 3H), 1.97 (m, 1H), 1.74 (m, 2H), 1.34-1.22 (m, 2H). |
| 438 | (Method L2): $R_t$ = 3.74 min; m/z = 463 (M + H)⁺ | ¹H NMR (300 MHz, Chloroform-d, Method M2) δ 8.48 (s, 1H), 7.40-7.32 (m, 1H), 7.31-7.19 (m, 3H), 6.86-6.74 (m, 2H), 6.18 (d, J = 8.2 Hz, 1H), 5.69 (q, J = 7.5 Hz, 1H), 3.12-2.88 (m, 2H), 2.81-2.67 (m, 1H), 2.66-2.53 (m, 1H), 2.42 (s, 3H), 2.05-1.90 (m, 1H), 1.72 (m, 2H), 1.34-1.23 (m, 2H). |
| 439 | (Method L2): $R_t$ = 3.79 min; m/z = 453 (M + H)⁺ | ¹H NMR (300 MHz, Chloroform-d, Method M2) δ 8.46 (s, 1H), 7.37 (m, 2H), 7.30-7.09 (m, 5H), 6.90-6.82 (m, 1H), 6.19 (d, J = 8.4 Hz, 1H), 5.47-5.36 (m, 1H), 3.85 (s, 3H), 2.83 (q, J = 5.9 Hz, 2H), 2.67-2.51 (m, 4H), 2.27-2.14 (m, 1H), 2.09-1.84 (m, 3H), 1.68 (m, 2H), 1.33-1.21 (m, 2H). |
| 440 | (Method L2): $R_t$ = 4.03 min; m/z = 518 (M + H)⁺ | ¹H NMR (300 MHz, DMSO-d6, Method M2) δ 9.18 (d, J = 8.1 Hz, 1H), 8.47 (s, 1H), 7.33 (t, J = 7.8 Hz, 2H), 7.22-7.11 (m, 2H), 6.97-6.89 (m, 1H), 6.86 (s, 1H), 6.81 (d, J = 8.2 Hz, 1H), 6.54 (dd, J = 8.0, 1.7 Hz, 1H), 5.29-5.18 (m, 1H), 4.34-4.21 (m, 6H), 3.96 (p, J = 7.0 Hz, 1H), 2.59 (s, 3H), 2.26-2.13 (m, 1H), 2.12-1.98 (m, 1H), 1.55 (t, J = 7.0 Hz, 6H). |
| 441 | (Method L2): $R_t$ = 3.84 min; m/z = 500 (M + H)⁺ | ¹H NMR (300 MHz, Chloroform-d, Method M2) δ 8.47 (s, 1H), 7.42-7.20 (m, 5H), 7.10 (t, J = 7.8 Hz, 1H), 6.84-6.78 (m, 1H), 6.51-6.43 (m, 1H), 6.18 (d, J = 8.3 Hz, 1H), 5.70 (q, J = 7.5 Hz, 1H), 4.25 (t, J = 11.8 Hz, 4H), 3.14-2.89 (m, 2H), 2.75 (m, 1H), 2.66-2.51 (m, 4H), 2.06-1.91 (m, 1H), 1.67 (m, 2H), 1.28 (m, 2H). |
| 442 | (Method L2): $R_t$ = 3.74 min; m/z = 461 (M + H)⁺ | ¹H NMR (300 MHz, Chloroform-d, Method M2) δ 8.47 (s, 1H), 7.41-7.20 (m, 6H), 7.17-7.06 (m, 1H), 6.17 (d, J = 8.2 Hz, 1H), 5.69 (d, J = 7.5 Hz, 1H), 3.12-2.88 (m, 2H), 2.74 (m, 1H), 2.61 (m, 1H), 2.41 (s, 3H), 2.05-1.90 (m, 1H), 1.79-1.70 (m, 2H), 1.34-1.22 (m, 2H). |
| 443 | (Method L2): $R_t$ = 3.82 min; m/z = 515 (M + H)⁺ | ¹H NMR (300 MHz, DMSO-d6, Method M2) δ 9.08 (d, J = 8.2 Hz, 1H), 8.58 (s, 1H), 8.29 (t, J = 1.6 Hz, 1H), 8.10 (dt, J = 7.5, 1.5 Hz, 1H), 7.86-7.72 (m, 2H), 7.43-7.35 (m, 1H), 7.31-7.21 (m, 3H), 5.53 (q, J = 7.8 Hz, 1H), 3.99 (p, J = 7.0 Hz, 1H), 3.05-2.82 (m, 3H), 2.66 (s, 3H), 2.54 (dd, J = 8.5, 4.1 Hz, 1H), 1.93 (dd, J = 12.6, 8.1 Hz, 1H), 1.57 (dd, J = 7.0, 5.2 Hz, 6H), 1.20-1.12 (m, 2H), 1.11-1.04 (m, 2H). |
| 444 | (Method L2): $R_t$ = 3.80 min; m/z = 507 (M + H)⁺ | ¹H NMR (300 MHz, DMSO-d6, Method M2) δ 9.18 (d, J = 8.0 Hz, 1H), 8.47 (s, 1H), 7.37-7.25 (m, 2H), 7.22-7.14 (m, 1H), 7.09 (d, J = 7.8 Hz, 1H), 6.93 (t, J = 6.9 Hz, 1H), 6.82-6.76 (m, 2H), 6.46 (dd, J = 8.1, 1.7 Hz, 1H), 5.28-5.19 (m, 1H), 4.31-4.19 (m, 2H), 4.17-4.09 (m, 2H), 4.02-3.93 (m, 3H), 3.90-3.82 (m, 1H), 2.58 (s, 3H), 2.25-2.14 (m, 1H), 2.09-2.00 (m, 1H), 1.55 (t, J = 7.0 Hz, 6H). |
| 445 | (Method L2): $R_t$ = 3.57 min; m/z = 461 (M + H)⁺ | ¹H NMR (300 MHz, Chloroform-d, Method M2) δ 8.47 (s, 1H), 7.40-7.16 (m, 4H), 7.02 (t, J = 8.1 Hz, 1H), 6.97-6.82 (m, 2H), 6.25 (d, J = 7.5 Hz, 1H), 5.36 (d, J = 7.4 Hz, 1H), 4.32 (m, 1H), 4.19 (m, 1H), 2.61 (m, 1H), 2.47-2.32 (m, 4H), 2.27-2.15 (m, 1H), 1.78-1.70 (m, 2H), 1.34-1.22 (m, 2H). |
| 446 | (Method L2): $R_t$ = 3.44 min; m/z = 453 (M + H)⁺ | ¹H NMR (300 MHz, Chloroform-d, Method M2) δ 8.45 (s, 1H), 8.04 (s, 1H), 7.89 (s, 1H), 7.43-7.36 (m, 1H), 7.27 (m, 3H), 6.27 (d, J = 8.3 Hz, 1H), 5.76-5.65 (m, 1H), 4.03 (d, J = 7.1 Hz, 2H), 3.14-2.89 (m, 2H), 2.75 (m, 1H), 2.63 (s, 3H), 2.55 (m, 1H), 2.07-1.92 (m, 1H), 1.65 (m, 2H), 1.43-1.21 (m, 3H), 0.71-0.62 (m, 2H), 0.41 (q, J = 4.8 Hz, 2H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 447 | (Method L2): $R_t$ = 3.87 min; m/z = 435 (M + H)+ | $^1$H NMR (300 MHz, Chloroform-d, Method M2) δ 8.42 (d, J = 7.9 Hz, 1H), 7.99 (d, J = 0.5 Hz, 1H), 7.64 (s, 1H), 7.41-7.23 (m, 4H), 6.13 (d, J = 7.9 Hz, 1H), 5.70 (q, J = 7.4 Hz, 1H), 4.09 (p, J = 7.0 Hz, 1H), 3.14-2.90 (m, 2H), 2.84-2.70 (m, 1H), 2.62 (s, 3H), 2.05-1.90 (m, 1H), 1.63 (td, J = 6.6, 6.1, 3.7 Hz, 6H). |
| 448 | (Method L2): $R_t$ = 3.65 min; m/z = 461 (M + H)+ | $^1$H NMR (300 MHz, Chloroform-d, Method M2) δ 8.46 (s, 1H), 7.33-7.08 (m, 4H), 7.08-6.98 (m, 1H), 6.98-6.82 (m, 2H), 6.25 (d, J = 6.8 Hz, 1H), 5.37 (d, J = 6.8 Hz, 1H), 4.34 (d, J = 6.0 Hz, 1H), 4.20 (t, J = 9.5 Hz, 1H), 2.67-2.32 (m, 5H), 2.28-2.15 (m, 1H)-1.73 (m, 1H = 3.9 Hz, 2H), 1.29 (d, J = 6.5 Hz, 2H). |
| 449 | (Method L2): $R_t$ = 3.91 min; m/z = 493 (M + H)+ | $^1$H NMR (300 MHz, Chloroform-d, Method M2) δ 8.48 (s, 1H), 7.94 (s, 1H), 7.91-7.84 (m, 1H), 7.57 (d, J = 5.6 Hz, 2H), 7.33-7.17 (m, 2H), 6.99-6.83 (m, 2H), 6.26 (d, J = 7.6 Hz, 1H), 5.42-5.32 (m, 1H), 4.36 (m, 1H), 4.26-4.15 (m, 1H), 2.68-2.54 (m, 4H), 2.47-2.33 (m, 1H), 2.29-2.18 (m, 1H), 1.72 (m, 2H), 1.34-1.24 (m, 2H). |
| 450 | (Method L2): $R_t$ = 3.59 min; m/z = 443 (M + H)+ | $^1$H NMR (300 MHz, Chloroform-d, Method M2) δ 8.43 (s, 1H), 7.47 (m, 1H), 7.40-7.12 (m, 5H), 6.96-6.79 (m, 2H), 6.32 (d, J = 7.5 Hz, 1H), 5.40-5.29 (m, 1H), 4.39-4.27 (m, 1H), 4.24-4.13 (m, 1H), 2.58 (m, 1H), 2.49 (d, J = 1.4 Hz, 3H), 2.36 (m, 1H), 2.26-2.13 (m, 1H), 1.70 (m, 2H), 1.26 (m, 2H). |
| 451 | (Method L2): $R_t$ = 3.56 min; m/z = 469 (M + H)+ | $^1$H NMR (300 MHz, Chloroform-d, Method M2) δ 8.45 (s, 1H), 7.63-7.54 (m, 2H), 7.44 (t, J = 7.6 Hz, 1H), 7.33-7.16 (m, 3H), 6.98-6.83 (m, 2H), 6.28 (d, J = 7.5 Hz, 1H), 5.41-5.31 (m, 1H), 4.53 (s, 2H), 4.40-4.30 (m, 1H), 4.20 (m, 1H), 3.41 (s, 3H), 2.66-2.52 (m, 4H), 2.38 (m, 1H), 2.28-2.15 (m, 1H), 1.72-1.63 (m, 2H), 1.27 (m, 2H). |
| 452 | (Method L2): $R_t$ = 3.67 min; m/z = 459 (M + H)+ | $^1$H NMR (300 MHz, Chloroform-d, Method M2) δ 8.42 (s, 1H), 7.56-7.48 (m, 1H), 7.38-7.16 (m, 5H), 6.97-6.82 (m, 2H), 6.28 (d, J = 7.5 Hz, 1H), 5.35 (d, J = 7.4 Hz, 1H), 4.32 (m, 1H), 4.18 (m, 1H), 2.60 (m, 1H), 2.43 (s, 4H), 2.22 (m, 1H), 1.77-1.67 (m, 2H), 1.28 (m, 2H). |
| 453 | (Method L2): $R_t$ = 3.01 min; m/z = 468 (M + H)+ | $^1$H NMR (300 MHz, Chloroform-d, Method M2) δ 8.42 (s, 1H), 7.36-7.16 (m, 3H), 7.04-6.82 (m, 4H), 6.71 (m, 1H), 6.31 (d, J = 7.5 Hz, 1H), 5.35 (d, J = 7.3 Hz, 1H), 4.32 (m, 1H), 4.25-4.15 (m, 1H), 2.98 (s, 6H), 2.62 (s, 4H), 2.36 (m, 1H), 2.22 (m, 1H), 1.68-1.60 (m, 2H), 1.33-1.19 (m, 2H). |
| 454 | (Method L2): $R_t$ = 3.61 min; m/z = 455 (M + H)+ | $^1$H NMR (300 MHz, Chloroform-d, Method M2) δ 8.45 (s, 1H), 7.37 (t, J = 8.1 Hz, 1H), 7.33-7.17 (m, 4H), 6.98-6.83 (m, 3H), 6.28 (d, J = 7.5 Hz, 1H), 5.41-5.32 (m, 1H), 4.40-4.30 (m, 1H), 4.26-4.15 (m, 1H), 3.85 (s, 3H), 2.65-2.51 (m, 4H), 2.38 (m, 1H), 2.24 (m, 1H), 1.72-1.63 (m, 2H), 1.34-1.22 (m, 2H). |
| 455 | (Method M2): $R_t$ = 3.85 min; m/z = 459 (M + H)+ | $^1$H NMR (300 MHz, Chloroform-d, Method M2) δ 8.46 (s, 1H), 7.67 (t, J = 1.8 Hz, 1H), 7.55 (m, 1H), 7.38 (t, J = 7.8 Hz, 1H), 7.32-7.17 (m, 3H), 6.98-6.83 (m, 2H), 6.28 (d, J = 7.5 Hz, 1H), 5.36 (d, J = 7.4 Hz, 1H), 4.33 (m, 1H), 4.26-4.15 (m, 1H), 2.61 (s, 4H), 2.46-2.33 (m, 1H), 2.28-2.16 (m, 1H), 1.74-1.66 (m, 2H), 1.29 (m, 2H). |
| 456 | (Method M2): $R_t$ = 3.70 min; m/z = 443 (M + H)+ | $^1$H NMR (300 MHz, Chloroform-d, Method M2) δ 8.45 (s, 1H), 7.49-7.35 (m, 3H), 7.24 (h, J = 7.5 Hz, 2H), 7.04-6.82 (m, 3H), 6.31 (d, J = 7.6 Hz, 1H), 5.36 (d, J = 7.2 Hz, 1H), 4.33 (m, 1H), 4.26-4.14 (m, 1H), 2.62 (s, 4H), 2.37 (m, 1H), 2.28-2.15 (m, 1H), 1.74-1.65 (m, 2H), 1.33-1.23 (m, 2H). |
| 457 | (Method M2): $R_t$ = 3.66 min; m/z = 461 (M + H)+ | $^1$H NMR (300 MHz, Chloroform-d, Method M2) δ 8.45 (s, 1H), 7.31-7.11 (m, 5H), 6.97-6.82 (m, 2H), 6.28 (d, J = 7.4 Hz, 1H), 5.36 (d, J = 7.4 Hz, 1H), 4.40-4.29 (m, 1H), 4.25-4.14 (m, 1H), 2.59 (m, 1H), 2.49 (d, J = 1.8 Hz, 3H), 2.37 (m, 1H), 2.23 (m, 1H), 1.77-1.68 (m, 2H), 1.36-1.21 (m, 2H). |
| 458 | (Method L2): $R_t$ = 3.68 min; m/z = 477 (M + H)+ | $^1$H NMR (300 MHz, Chloroform-d, Method M2) δ 8.45 (s, 1H), 7.38-7.06 (m, 5H), 6.97-6.82 (m, 2H), 6.28 (d, J = 7.4 Hz, 1H), 5.36 (d, J = 7.3 Hz, 1H), 4.39-4.28 (m, 1H), 4.18 (m, 1H), 2.61 (m, 1H), 2.41 (s, 4H), 2.27-2.14 (m, 1H), 1.75 (m, 1H), 1.36-1.21 (m, 2H). |
| 459 | (Method L2): $R_t$ = 3.93 min; m/z = 500 (M + H)+ | $^1$H NMR (300 MHz, DMSO-d6, Method M2) δ 9.17 (d, J = 8.1 Hz, 1H), 8.46 (s, 1H), 7.36-7.25 (m, 2H), 7.21-7.15 (m, 1H), 7.05 (d, J = 7.8 Hz, 1H), 6.93 (t, J = 7.5 Hz, 1H), 6.82-6.76 (m, 2H), 6.45 (dd, J = 8.0, 1.8 Hz, 1H), 5.63-5.57 (m, 0.5H), 5.44-5.37 (m, 0.5H), 5.27-5.19 (m, 1H), 4.31-4.18 (m, 3H), 4.14 (dd, J = 9.7, 6.0 Hz, 1H), 4.00-3.90 (m, 2H), 3.87-3.81 (m, 1H), 2.58 (s, 3H), 2.25-2.15 (m, 1H), 2.10-1.99 (m, 1H), 1.55 (t, J = 7.0 Hz, 6H). |
| 460 | (Method L2): $R_t$ = 3.58 min; m/z = 489 (M + H)+ | $^1$H NMR (300 MHz, DMSO-d6, Method M2) δ 9.00 (d, J = 8.1 Hz, 1H), 8.44 (s, 1H), 7.44-7.36 (m, 1H), 7.33-7.20 (m, 4H), 7.10 (d, J = 7.8 Hz, 1H), 6.78 (d, J = 1.8 Hz, 1H), 6.45 (dd, J = 8.0, 1.7 Hz, 1H), 5.52 (q, J = 7.8 Hz, 1H), 4.16-4.08 (m, 2H), 4.03-3.95 (m, 2H), 3.90-3.80 (m, 1H), 3.05-2.94 (m, 1H), 2.87 (dt, J = 16.0, 8.3 Hz, 1H), 2.67-2.52 (m, 5H), 2.02-1.87 (m, 1H), 1.48 (dt, J = 6.2, 3.1 Hz, 2H), 1.25-1.15 (m, 2H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 461 | (Method L2): R$_t$ = 3.75 min; m/z = 482 (M + H)$^+$ | $^1$H NMR (300 MHz, Chloroform-d, Method M2) δ 8.32 (s, 1H), 7.28 (s, 1H), 7.25-7.10 (m, 2H), 7.00-6.80 (m, 2H), 6.70-6.60 (m, 1H), 6.48 (d, J = 7.7 Hz, 1H), 6.16 (d, J = 7.5 Hz, 1H), 5.41-5.27 (m, 1H), 4.40-4.27 (m, 1H), 4.25-4.03 (m, 2H), 3.28 (t, J = 8.2 Hz, 2H), 2.80 (d, J = 9.1 Hz, 5H), 2.50 (s, 3H), 2.46-2.30 (m, 1H), 2.28-2.12 (m, 1H), 1.73-1.59 (m, 6H). |
| 462 | (Method L2): R$_t$ = 3.97 min; m/z = 509 (M + H)$^+$ | $^1$H NMR (300 MHz, Chloroform-d, Method M2) δ 8.46 (s, 1H), 7.63 (d, J = 7.9 Hz, 1H), 7.56 (s, 1H), 7.47 (t, J = 8.0 Hz, 1H), 7.32-7.11 (m, 3H), 6.98-6.83 (m, 2H), 6.29 (d, J = 7.4 Hz, 1H), 5.40-5.31 (m, 1H), 4.40-4.30 (m, 1H), 4.26-4.14 (m, 1H), 2.66-2.52 (m, 4H), 2.38 (m, 1H), 2.28-2.15 (m, 1H), 1.75-1.66 (m, 2H), 1.28 (m, 2H). |
| 463 | (Method L2): R$_t$ = 3.67 min; m/z = 443 (M + H)$^+$ | $^1$H NMR (300 MHz, Chloroform-d, Method M2) δ 8.44 (s, 1H), 7.65-7.55, (m, 2H), 7.33-7.10 (m, 4H), 6.98-6.83 (m, 2H), 6.26 (d, J = 7.5 Hz 1H), 5.42-5.32 (m, 1H), 4.41-4.30 (m, 1H), 4.26-4.14 (m, 1H), 2.64-2.52 (m, 4H), 2.39 (m, 1H), 2.29-2.17 (m, 1H), 1.73-1.65 (m, 2H), 1.33-1.22 (m, 2H). |
| 464 | (Method L2): R$_t$ = 3.77 min; m/z = 516 (M + H)$^+$ | $^1$H NMR (300 MHz, Chloroform-d, Method M2) δ 8.44 (s, 1H), 7.38-7.17 (m, 3H), 7.09 (d, J = 7.7 Hz, 1H), 6.98-6.77 (m, 3H), 6.47 (m, 1H), 6.27 (d, J = 7.4 Hz, 1H), 5.41-5.31 (m, 1H), 4.40-4.14 (m, 6H), 2.65-2.51 (m, 4H), 2.38 (m, 1H), 2.28-2.15 (m, 1H), 1.72-1.63 (m, 2H), 1.32-1.22 (m, 2H). |
| 465 | (Method L2): R$_t$ = 4.18 min; m/z = 527 (M + H)$^+$ | $^1$H NMR (300 MHz, Chloroform-d; Method M2) δ 8.49 (s, 1H), 7.89 (d, J = 14.7 Hz, 2H), 7.53 (s, 1H), 7.32-7.17 (m, 2H), 6.98-6.83 (m, 2H), 6.29 (d, J = 7.4 Hz, 1H), 5.36 (q, J = 5.4 Hz, 1H), 4.36 (m, 1H), 4.26-4.15 (m, 1H), 2.64 (s, 4H), 2.40 (m, 1H), 2.29-2.16 (m, 1H), 1.80-1.68 (m, 2H), 1.34-1.22 (m, 2H). |
| 466 | (Method L2): R$_t$ = 3.75 min; m/z = 482 (M + H)$^+$ | $^1$H NMR (300 MHz, Chloroform-d, Method M2) δ 8.48 (s, 1H), 7.42-7.28 (m, 5H), 7.05 (d, J = 7.7 Hz, 1H), 6.76 (s, 1H), 6.45 (m, 1H), 6.16 (d, J = 8.6 Hz, 1H), 5.76-5.68 (m, 1H), 5.60-5.29 (m, 1H), 4.30-4.15 (m, 2H), 4.00 (m, 1H), 3.16-2.92 (m, 2H), 2.85-2.68 (m, 1H), 2.61 (s, 3H), 2.59-2.51 (m, 1H), 2.07-1.92 (m, 1H), 1.66 (d, J = 3.3 Hz, 2H), 1.28 (m, 2H). |
| 467 | (Method L2): R$_t$ = 3.77 min; m/z = 493/495 (M + H)$^+$ | $^1$H NMR (300 MHz, Chloroform-d, Method M2) δ 8.43 (s, 1H), 7.47-7.40 (m, 2H), 7.32-7.16 (m, 3H), 6.97-6.82 (m, 2H), 6.25 (d, J = 7.5 Hz, 1H), 5.41-5.31 (m, 1H), 4.40-4.29 (m, 1H), 4.19 (m, 1H), 2.68-2.55 (m, 1H), 2.37 (s, 4H), 2.27-2.14 (m, 1H), 1.82-1.73 (m, 2H), 1.36-1.24 (m, 2H). |
| 468 | (Method L2): R$_t$ = 3.40 min; m/z = 497 (M + H)$^+$ | $^1$H NMR (300 MHz, Chloroform-d, Method M2) δ 8.45 (s, 1H), 8.08 (s, 1H), 8.03 (s, 1H), 7.33-7.18 (m, 2H), 6.99-6.84 (m, 2H), 6.27 (d, J = 7.5 Hz, 1H), 5.38 (q, J = 5.4 Hz, 1H), 4.76 (q, J = 8.4 Hz, 2H), 4.41-4.31 (m, 1H), 4.21 (m, 1H), 2.67-2.51 (m, 4H), 2.39 (m, 1H), 2.29-2.17 (m, 1H), 1.73-1.65 (m, 2H), 1.32-1.20 (m, 2H). |
| 469 | (Method L2): R$_t$ = 4.15 min; m/z = 493/495 (M + H)$^+$ | $^1$H NMR (300 MHz, DMSO-d6, Method M2) δ 9.16 (d, J = 8.0 Hz, 1H), 8.56 (s, 1H), 7.81 (d, J = 1.9 Hz, 2H), 7.53 (t, J = 1.9 Hz, 1H), 7.35 (d, J = 7.8 Hz, 1H), 7.22-7.14 (m, 1H), 6.93 (m, 1H), 6.80 (m, 1H), 5.29-5.19 (m, 1H), 4.26 (m, 2H), 2.68-2.56 (m, 4H), 2.21 (m, 1H), 2.13-1.99 (m, 1H), 1.47 (m, 2H), 1.22 (m, 2H). |
| 470 | (Method L2): R$_t$ = 3.39 min; m/z = 469 (M + H)$^+$ | $^1$H NMR (300 MHz, Chloroform-d, Method M2) δ 8.41 (s, 1H), 8.01 (s, 1H), 7.85 (s, 1H), 7.34-7.17 (m, 2H), 6.98-6.83 (m, 2H), 6.46 (d, J = 7.7 Hz, 1H), 5.37 (d, J = 7.4 Hz, 1H), 4.41-4.30 (m, 1H), 3.99 (d, J = 7.1 Hz, 2H), 2.61 (s, 4H), 2.46-2.33 (m, 1H), 2.29-2.16 (m, 1H), 1.67 (m, 2H), 1.41-1.17 (m, 3H), 0.70-0.61 (m, 2H), 0.40 (q, J = 4.8 Hz, 2H). |
| 471 | (Method L2): R$_t$ = 3.79 min; m/z = 461 (M + H)$^+$ | $^1$H NMR (300 MHz, Chloroform-d, Method M2) δ 8.45 (s, 1H), 7.52 (m, 1H), 7.38 (m, 1H), 7.32-7.17 (m, 3H), 6.98-6.83 (m, 2H), 6.30 (d, J = 7.4 Hz, 1H), 5.36 (d, J = 7.4 Hz, 1H), 4.41-4.30 (m, 1H), 4.26-4.15 (m, 1H), 2.64-2.51 (m, 4H), 2.38 (m, 1H), 2.28-2.14 (m, 1H), 1.70 (m, 2H), 1.28 (m, 2H). |
| 472 | (Method L2): R$_t$ = 3.72 min; m/z = 477 (M + H)$^+$ | $^1$H NMR (300 MHz, Chloroform-d, Method M2) δ 8.43 (s, 1H), 7.36-7.13 (m, 5H), 6.97-6.82 (m, 2H), 6.25 (d, J = 7.5 Hz, 1H), 5.36 (q, J = 5.3 Hz, 1H), 4.40-4.29 (m, 1H), 4.19 (m, 1H), 2.60 (m, 1H), 2.43 (m, 4H), 2.28-2.15 (m, 1H), 1.81-1.68 (m, 2H), 1.34-1.24 (m, 2H). |
| 473 | (Method L2): R$_t$ = 3.85 min' m/z = 493/495 (M + H)$^+$ | $^1$H NMR (300 MHz, Chloroform-d, Method M2) δ 8.42 (s, 1H), 7.50 (m, 1H), 7.32-7.16 (m, 4H), 6.97-6.82 (m, 2H), 6.27 (d, J = 7.5 Hz, 1H), 5.36 (q, J = 5.3 Hz, 1H), 4.40-4.29 (m, 1H), 4.19 (m, 1H), 2.66-2.53 (m, 1H), 2.42 (s, 4H), 2.22 (m, 1H), 1.80-1.67 (m, 2H), 1.29 (m, 2H). |
| 474 | (Method L2): R$_t$ = 3.39 min; m/z = 480 (M + H)$^+$ | $^1$H NMR (300 MHz, Chloroform-d, Method M2) δ 8.40 (s, 1H), 7.29 (d, J = 7.7 Hz, 1H), 7.18 (m, 2H), 6.98-6.83 (m, 2H), 6.65 (d, J = 7.6 Hz, 1H), 6.48 (d, J = 7.7 Hz, 1H), 6.23 (d, J = 7.6 Hz, 1H), 5.37 (d, J = 7.2 Hz, 1H), 4.33 (m, 1H), 4.25-4.14 (m, 1H), 3.29 (t, J = 8.2 Hz, 2H), 2.80 (d, J = 4.2 Hz, 5H), 2.64-2.51 (m, 1H), 2.48 (s, 3H), 2.38 (m, 1H), 2.28-2.17 (m, 1H), 1.74-1.63 (m, 2H), 1.32-1.23 (m, 2H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 475 | (Method L2): $R_t$ = 3.75 min; m/z = 477 (M + H)$^+$ | $^1$H NMR (300 MHz, Chloroform-d, Method M2) δ 8.42 (s, 1H), 7.36-7.16 (m, 4H), 7.07 (m, 1H), 6.97-6.82 (m, 2H), 6.25 (d, J = 7.5 Hz, 1H), 5.41-5.31 (m, 1H), 4.34 (m, 1H), 4.19 (m, 1H), 2.59 (m, 1H), 2.41 (m, 4H), 2.27-2.15 (m, 1H), 1.82-1.66 (m, 2H), 1.29 (m, 2H). |
| 476 | (Method L2): $R_t$ = 4.17 min; m/z = 511/513 (M + H)$^+$ | $^1$H NMR (300 MHz, DMSO-d6, Method M2) δ 9.15 (d, J = 8.0 Hz, 1H), 8.55 (s, 1H), 7.92 (d, J = 6.5 Hz, 2H), 7.35 (d, J = 6.8 Hz, 1H), 7.22-7.13 (m, 1H), 6.92 (m, 1H), 6.80 (d, J = 8.2 Hz, 1H), 5.28-5.17 (m, 1H), 4.36-4.16 (m, 2H), 2.68-2.55 (m, 4H), 2.32-1.97 (m, 2H), 1.47 (m, 2H), 1.22 (m, 2H). |
| 477 | (Method L2): $R_t$ = 3.80 min, m/z = 449 (M + H)$^+$ | $^1$H NMR (400 MHz, Chloroform-d, Method M2) δ 8.47 (s, 1H), 7.32-7.26 (m, 1H), 7.26-7.12 (m, 4H), 6.97-6.83 (m, 2H), 6.22 (d, J = 7.4 Hz, 1H), 5.36 (q, J = 5.5 Hz, 1H), 4.38-4.29 (m, 1H), 4.25-4.15 (m, 1H), 3.51 (q, J = 7.4 Hz, 2H), 2.53 (d, J = 1.7 Hz, 3H), 2.44-2.33 (m, 1H), 2.26-2.15 (m, 1H), 1.51 (t, J = 7.4 Hz, 3H). |
| 478 | (Method L2): $R_t$ = 3.81 min, m/z = 465 (M + H)$^+$ | $^1$H NMR (400 MHz, Chloroform-d, Method M2) δ 8.47 (s, 1H), 7.38-7.30 (m, 2H), 7.30-7.26 (m, 1H), 7.24-7.17 (m, 1H), 7.15-7.08 (m, 1H), 6.97-6.83 (m, 2H), 6.19 (d, J = 7.4 Hz, 1H), 5.36 (q, J = 5.5 Hz, 1H), 4.38-4.29 (m, 1H), 4.24-4.14 (m, 1H), 3.53 (q, J = 7.5 Hz, 2H), 2.45 (s, 3H), 2.43-2.33 (m, 1H), 2.25-2.15 (m, 1H), 1.53 (t, J = 7.4 Hz, 3H). |
| 479 | (Method L2): $R_t$ = 3.81 min, m/z = 465 (M + H)$^+$ | $^1$H NMR (400 MHz, Chloroform-d, Method M2) δ 8.47 (s, 1H), 7.38-7.30 (m, 2H), 7.30-7.26 (m, 1H), 7.24-7.17 (m, 1H), 7.15-7.08 (m, 1H), 6.97-6.83 (m, 2H), 6.19 (d, J = 7.4 Hz, 1H), 5.36 (q, J = 5.5 Hz, 1H), 4.38-4.29 (m, 1H), 4.24-4.14 (m, 1H), 3.53 (q, J = 7.5 Hz, 2H), 2.45 (s, 3H), 2.43-2.33 (m, 1H), 2.25-2.15 (m, 1H), 1.53 (t, J = 7.4 Hz, 3H). |
| 480 | (Method L2): $R_t$ = 3.82 min; m/z = 478 (M + H)$^+$ | $^1$H NMR (400 MHz, Chloroform-d, Method M2) δ 8.46 (s, 1H), 7.39 (m, 2H), 7.28 (d, J = 8.0 Hz, 1H), 7.20 (m, 1H), 6.93 (t, J = 7.2 Hz, 1H), 6.87 (d, J = 8.2 Hz, 1H), 6.24 (d, J = 7.1 Hz, 1H), 5.37 (q, J = 5.5 Hz, 1H), 4.40-4.31 (m, 1H), 4.20 (t, J = 9.1 Hz, 1H), 2.60 (m, 1H), 2.55-2.45 (m, 3H), 2.40 (m, 1H), 2.23 (m, 1H), 1.81-1.65 (m, 2H), 1.29 (m, 2H), 1.13 (d, J = 6.1 Hz, 1H). |
| 481 | (Method L2): $R_t$ = 3.71 min; m/z = 466 (M + H)$^+$ | $^1$H NMR (400 MHz, Chloroform-d, Method M2) δ 8.35 (s, 1H), 8.25 (s, 1H), 7.40 (d, J = 8.1 Hz, 1H), 7.33-7.13 (m, 5H), 6.93 (m, 1H), 6.85 (m, 1H), 6.33 (m, 1H), 6.17 (d, J = 7.5 Hz, 1H), 5.39-5.30 (m, 1H), 4.38-4.28 (m, 1H), 4.23-4.07 (m, 2H), 2.55 (s, 3H), 2.37 (m, 1H), 2.26-2.13 (m, 1H), 1.74-1.62 (m, 6H). |
| 482 | (Method L2): $R_t$ = 3.70 min; m/z = 509 (M + H)$^+$ | $^1$H NMR (400 MHz, Chloroform-d, Method M2) δ 8.46 (s, 1H), 7.27 (d, J = 10.4 Hz, 1H), 7.25-7.17 (m, 1H), 6.93 (m, 1H), 6.90-6.77 (m, 2H), 6.25 (d, J = 7.5 Hz, 1H), 5.36 (q, J = 5.3 Hz, 1H), 4.35 (m, 1H), 4.19 (m, 1H), 3.99 (s, 3H), 2.60 (m, 1H), 2.47-2.33 (m, 4H), 2.22 (m, 1H), 1.80-1.71 (m, 2H), 1.34-1.24 (m, 2H). |
| 483 | (Method L2): $R_t$ = 3.92 min; m/z = 480 (M + H)$^+$ | $^1$H NMR (400 MHz, Chloroform-d, Method M2) δ 8.34 (s, 1H), 7.37-7.24 (m, 3H), 7.23-7.17 (m, 1H), 7.15 (m, 1H), 7.05 (d, J = 3.1 Hz, 1H), 6.92 (m, 1H), 6.85 (m, 1H), 6.27-6.23 (m, 1H), 6.19 (d, J = 7.5 Hz, 1H), 5.34 (d, J = 7.2 Hz, 1H), 4.38-4.28 (m, 1H), 4.23-4.07 (m, 2H), 3.82 (s, 3H), 2.55 (s, 3H), 2.43-2.32 (m, 1H), 2.26-2.15 (m, 1H), 1.68 (t, J = 7.3 Hz, 6H). |
| 484 | (Method L2): $R_t$ = 3.97 min, m/z = 481/483 | $^1$H NMR (400 MHz, DMSO-d6, Method M2) δ 9.17 (d, J = 8.1 Hz, 1H), 8.53 (s, 1H), 7.75-7.68 (m, 1H), 7.51-7.44 (m, 2H), 7.32 (d, J = 7.5 Hz, 1H), 7.22-7.15 (m, 1H), 6.96-6.89 (m, 1H), 6.84-6.78 (m, 1H), 5.26 (q, J = 6.0 Hz, 1H), 4.31-4.22 (m, 2H), 3.43-3.35 (m, 2H), 2.39 (s, 3H), 2.27-2.15 (m, 1H), 2.11-2.02 (m, 1H), 1.39 (t, J = 7.4 Hz, 3H). |
| 485 | (Method L2): $R_t$ = 4.07 min, m/z = 481/483 (M + H)$^+$ | $^1$H NMR (400 MHz, DMSO-d6, Method M2) δ 9.16 (d, J = 8.1 Hz, 1H), 8.53 (s, 1H), 7.79 (d, J = 2.0 Hz, 1H), 7.57-7.48 (m, 2H), 7.32 (d, J = 7.5 Hz, 1H), 7.22-7.14 (m, 1H), 6.96-6.89 (m, 1H), 6.84-6.78 (m, 1H), 5.26 (q, J = 5.9 Hz, 1H), 4.32-4.20 (m, 2H), 3.38 (q, J = 7.5 Hz, 2H), 2.39 (s, 3H), 2.26-2.15 (m, 1H), 2.11-2.01 (m, 1H), 1.39 (t, J = 7.4 Hz, 3H). |
| 486 | (Method L2): $R_t$ = 4.03 min, m/z = 481/483 (M + H)$^+$ | $^1$H NMR (400 MHz, DMSO-d6, Method M2) δ 9.20-9.14 (m, 1H), 8.55 (s, 1H), 7.66 (d, J = 8.5 Hz, 1H), 7.59-7.50 (m, 2H), 7.32 (d, J = 7.5 Hz, 1H), 7.22-7.15 (m, 1H), 6.96-6.89 (m, 1H), 6.84-6.78 (m, 1H), 5.26 (q, J = 5.9 Hz, 1H), 4.31-4.20 (m, 2H), 3.43-3.35 (m, 2H), 2.40 (s, 3H), 2.26-2.15 (m, 1H), 2.11-2.03 (m, 1H), 1.39 (t, J = 7.4 Hz, 3H). |
| 487 | (Method L2): $R_t$ = 3.92 min, m/z = 449 (M + H)$^+$ | $^1$H NMR (400 MHz, DMSO-d6), Method M2 δ 9.18 (d, J = 8.1 Hz, 1H), 8.63 (s, 1H), 7.86-7.77 (m, 1H), 7.64-7.50 (m, 2H), 7.33 (d, J = 7.5 Hz, 1H), 7.23-7.15 (m, 1H), 6.93 (t, J = 7.4 Hz, 1H), 6.82 (d, J = 8.2 Hz, 1H), 5.27 (q, J = 6.0 Hz, 1H), 4.32-4.21 (m, 2H), 3.42-3.35 (m, 2H), 2.64 (s, 3H), 2.26-2.14 (m, 1H), 2.12-2.03 (m, 1H), 1.37 (t, J = 7.4 Hz, 3H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 488 | (Method L2): $R_t$ = 4.02 min, m/z = 447 (M + H)$^+$ | $^1$H NMR (400 MHz, DMSO-d6, Method M2) δ 9.17 (d, J = 8.0 Hz, 1H), 8.63 (s, 1H), 7.85 (s, 1H), 7.70 (d, J = 7.8 Hz, 1H), 7.51 (t, J = 7.9 Hz, 1H), 7.41-7.30 (m, 2H), 7.18 (t, J = 7.3 Hz, 1H), 6.93 (t, J = 7.4 Hz, 1H), 6.81 (d, J = 8.1 Hz, 1H), 5.27 (q, J = 6.2 Hz, 1H), 4.30-4.21 (m, 2H), 3.43-3.35 (m, 2H), 2.63 (s, 3H), 2.26-2.15 (m, 1H), 2.11-1.99 (m, 1H), 1.37 (t, J = 7.4 Hz, 3H). |
| 489 | (Method L2): $R_t$ = 3.92 min, m/z = 483 (M + H)$^+$ | $^1$H NMR (400 MHz, Chloroform-d, Method M2) δ 8.50 (s, 1H), 7.46-7.37 (m, 1H), 7.28 (s, 1H), 7.25-7.18 (m, 1H), 7.04-6.97 (m, 1H), 6.94 (t, J = 7.5 Hz, 1H), 6.87 (d, J = 8.3 Hz, 1H), 6.17 (d, J = 7.6 Hz, 1H), 5.37 (q, J = 5.4 Hz, 1H), 4.39-4.30 (m, 1H), 4.24-4.15 (m, 1H), 3.53 (q, J = 7.5 Hz, 2H), 2.48 (s, 3H), 2.44-2.33 (m, 1H), 2.26-2.16 (m, 1H), 1.52 (t, J = 7.4 Hz, 3H). |
| 490 | (Method L2): $R_t$ = 3.87 min, m/z = 467 (M + H)$^+$ | $^1$H NMR (400 MHz, Chloroform-d, Method M2) δ 8.47 (s, 1H), 7.29 (s, 1H), 7.25-7.15 (m, 2H), 7.12-7.02 (m, 1H), 6.98-6.91 (m, 1H), 6.87 (d, J = 8.2 Hz, 1H), 6.19 (d, J = 7.4 Hz, 1H), 5.37 (q, J = 5.4 Hz, 1H), 4.34 (ddd, J = 9.6, 6.2, 3.2 Hz, 1H), 4.20 (ddd, J = 11.6, 9.2, 2.7 Hz, 1H), 3.51 (q, J = 7.4 Hz, 2H), 2.52 (d, J = 1.6 Hz, 3H), 2.44-2.34 (m, 1H), 2.22 (ddt, J = 10.8, 5.8, 2.6 Hz, 1H), 1.50 (t, J = 7.4 Hz, 3H). |
| 491 | (Method L2): $R_t$ = 3.91 min, m/z = 481/483 (M + H)$^+$ | $^1$H NMR (400 MHz, Chloroform-d, Method M2) δ 8.46 (s, 1H), 7.45 (d, J = 8.2 Hz, 2H), 7.32-7.27 (m, 2H), 7.23-7.17 (m, 1H), 6.93 (t, J = 7.5 Hz, 1H), 6.86 (d, J = 8.3 Hz, 1H), 6.19 (d, J = 7.4 Hz, 1H), 5.37 (q, J = 5.5 Hz, 1H), 4.34 (ddd, J = 9.8, 6.2, 3.3 Hz, 1H), 4.19 (td, J = 11.6, 10.4, 2.6 Hz, 1H), 3.53 (q, J = 7.4 Hz, 2H), 2.41 (s, 3H), 2.40-2.34 (m, 1H), 2.26-2.15 (m, 1H), 1.53 (d, J = 7.5 Hz, 3H). |
| 492 | (Method L2): $R_t$ = 3.97 min; m/z = 529/531 (M + H)$^+$ | $^1$H NMR (400 MHz, Chloroform-d, Method M2) δ 8.55 (s, 1H), 7.49-6.64 (m, 8H), 6.31-6.22 (m, 1H), 5.42-5.32 (m, 1H), 4.40-4.28 (m, 1H), 4.19 (s, 1H), 2.72-2.57 (m, 1H), 2.46-2.32 (m, 1H), 2.28-2.12 (m, 1H), 1.86-1.75 (m, 2H), 1.39-1.28 (m, 2H). |
| 493 | (Method M2): $R_t$ = 3.74 min, m/z = 497 (M + H)$^+$ | $^1$H NMR (400 MHz, Chloroform-d, Method M2) δ 8.56 (s, 1H), 7.45-6.69 (m, 8H), 6.31-6.22 (m, 1H), 5.42-5.32 (m, 1H), 4.40-4.29 (m, 1H), 4.24-4.11 (m, 1H), 2.68-2.58 (m, 1H), 2.47-2.31 (m, 1H), 2.29-2.13 (m, 1H), 1.86-1.76 (m, 2H), 1.33 (m, 2H). |
| 494 | (Method L2): $R_t$ = 4.09 min, m/z = 531/533 (M + H)$^+$ | $^1$H NMR (400 MHz, Chloroform-d, Method M2) δ 8.49 (s, 1H), 7.43 (s, 2H), 7.34 (s, 1H), 7.16 (s, 2H), 7.01-6.72 (m, 3H), 6.16 (s, 1H), 5.35 (s, 1H), 4.34 (s, 1H), 4.14 (d, J = 35.2 Hz, 2H), 2.39 (s, 1H), 2.23 (s, 1H), 1.67 (s, 6H). |
| 495 | (Method L2): $R_t$ = 3.88 min, m/z = 499 (M + H)$^+$ | $^1$H NMR (400 MHz, Chloroform-d, Method M2) δ 8.50 (s, 1H), 7.39 (s, 1H), 7.25-6.73 (m, 7H), 6.17 (s, 1H), 5.35 (s, 1H), 4.34 (s, 1H), 4.14 (d, J = 31.9 Hz, 2H), 2.39 (s, 1H), 2.23 (s, 1H), 1.67 (s, 6H). |
| 496 | (Method L2): $R_t$ = 3.80 min, m/z = 479 (M + H)$^+$ | $^1$H NMR (400 MHz, DMSO-d6, Method M2) δ 9.16 (d, J = 8.0 Hz, 1H), 8.55 (s, 1H), 7.37-7.13 (m, 4H), 6.92 (t, J = 7.4 Hz, 1H), 6.81 (d, J = 8.1 Hz, 1H), 5.31-5.21 (m, 1H), 4.24 (d, J = 17.7 Hz, 2H), 3.97 (s, 3H), 3.42-3.34 (m, 2H), 2.44 (s, 3H), 2.26-2.14 (m, 1H), 2.05 (m, 1H), 1.38 (t, J = 7.3 Hz, 3H). |
| 497 | (Method L2): $R_t$ = 4.29 min, m/z = 499/501 (M + H)$^+$ | $^1$H NMR (400 MHz, DMSO-d6, Method M2) δ 9.22-9.13 (m, 1H), 8.71-8.63 (m, 1H), 7.98-7.89 (m, 2H), 7.37-7.29 (m, 1H), 7.23-7.12 (m, 1H), 6.98-6.86 (m, 1H), 6.81 (s, 1H), 5.31-5.21 (m, 1H), 4.31-4.21 (m, 2H), 2.70-2.60 (m, 3H), 2.27-2.00 (m, 3H), 1.42-1.30 (m, 3H). |
| 498 | (Method L2): $R_t$ = 3.84 min; m/z = 515 (M + H)$^+$ | $^1$H NMR (400 MHz, Chloroform-d, Method M2) δ 8.56 (s, 1H), 7.31-7.19 (m, 3H), 7.13-7.04 (m, 1H), 7.03-6.73 (m, 3H), 6.28 (d, J = 7.5 Hz, 1H), 5.37 (q, J = 5.3 Hz, 1H), 4.40-4.31 (m, 1H), 4.25-4.15 (m, 1H), 2.67-2.58 (m, 1H), 2.46-2.35 (m, 1H), 2.28-2.18 (m, 1H), 1.86-1.73 (m, 2H), 1.38-1.30 (m, 2H). |
| 499 | (Method L2): $R_t$ = 3.78 min; m/z = 513 (M + H)$^+$ | $^1$H NMR (400 MHz, Chloroform-d, Method M2) δ 8.54 (s, 1H), 7.40-7.32 (m, 1H), 7.29-7.25 (m, 2H), 7.24-7.18 (m, 1H), 7.17-7.09 (m, 1H), 6.99-6.69 (m, 3H), 6.30 (d, J = 7.3 Hz, 1H), 5.37 (q, J = 5.3 Hz, 1H), 4.41-4.28 (m, 1H), 4.25-4.13 (m, 1H), 2.69-2.58 (m, 1H), 2.45-2.36 (m, 1H), 2.28-2.17 (m, 1H), 1.90-1.76 (m, 2H), 1.38-1.30 (m, 2H). |
| 500 | (Method L2): $R_t$ = 4.20 min; m/z = 483 (M + H)$^+$ | $^1$H NMR (400 MHz, Chloroform-d, Method M2) δ 8.47 (s, 1H), 7.76 (m, 1H), 7.64 (m, 1H), 7.31-7.19 (m, 3H), 6.95 (m, 1H), 6.91-6.85 (m, 1H), 6.16 (d, J = 7.4 Hz, 1H), 5.40-5.32 (m, 1H), 4.40-4.32 (m, 1H), 4.24-4.01 (m, 2H), 2.39 (m, 1H), 2.28-2.17 (m, 1H), 1.71-1.59 (m, 6H). |
| 501 | (Method L2): $R_t$ = 3.28 min; m/z = 441 (M + H)$^+$ | $^1$H NMR (400 MHz, DMSO-d6, Method M2) δ 9.45 (s, 1H), 9.11 (d, J = 8.0 Hz, 1H), 8.40 (s, 1H), 7.49 (d, J = 8.5 Hz, 2H), 7.34 (d, J = 7.5 Hz, 1H), 7.18 (t, J = 7.2 Hz, 1H), 6.97-6.76 (m, 4H), 5.24 (q, J = 5.4 Hz, 1H), 4.34-4.18 (m, 2H), 2.64-2.52 (m, 4H), 2.21 (m, 1H), 2.12-2.01 (m, 1H), 1.50-1.39 (m, 2H) 1.18 (m, 2H). |
| 502 | (Method L2): $R_t$ = 3.96 min, m/z = 529 (M + H)$^+$ | $^1$H NMR (400 MHz, Chloroform-d, Method M2) δ 8.48 (s, 1H), 7.25-7.11 (m, 3H), 7.07-6.76 (m, 4H), 6.21 (d, J = 7.5 Hz, 1H), 5.35 (q, J = 5.4 Hz, 1H), 4.39-4.30 (m, 1H), 4.23-4.05 (m, 2H), 4.03 (s, 3H), 2.45-2.34 (m, 1H), 2.27-2.16 (m, 1H), 1.66 (t, J = 7.4 Hz, 6H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 503 | (Method L2): $R_t$ = 4.01 min, m/z = 531/533 (M + H)⁺ | ¹H NMR (400 MHz, Chloroform-d, Method M2) δ 8.47 (s, 1H), 7.48-7.43 (m, 2H), 7.36-7.29 (m, 1H), 7.26-7.19 (m, 2H), 6.99-6.70 (m, 3H), 6.20 (d, J = 7.4 Hz, 1H), 5.40-5.33 (m, 1H), 4.21-4.05 (m, 2H), 2.46-2.34 (m, 1H), 2.28-2.17 (m, 1H), 1.68 (t, J = 7.5 Hz, 6H). |
| 504 | (Method L2): $R_t$ = 3.93 min, m/z = 511 (M + H)⁺ | ¹H NMR (400 MHz, Chloroform-d, Method M2) δ 8.47 (s, 1H), 7.78 (d, J = 4.8 Hz, 1H), 7.66-7.57 (m, 1H), 7.35-7.17 (m, 3H), 6.98-6.83 (m, 2H), 6.26 (d, J = 7.4 Hz, 1H), 5.36 (q, J = 5.2 Hz, 1H), 4.35 (m, 1H), 4.25-4.15 (m, 1H), 2.61 (m, 1H), 2.54-2.33 (m, 4H), 2.28-2.16 (m, 1H), 1.74 (q, J = 6.0 Hz, 2H), 1.29 (m, 2H). |
| 505 | (Method L2): $R_t$ = 4.08 min, m/z = 531/533 (M + H)⁺ | ¹H NMR (400 MHz, Chloroform-d, Method M2) δ 8.48 (d, J = 3.7 Hz, 1H), 7.54 (dd, J = 7.8, 1.7 Hz, 1H), 7.41-7.27 (m, 2H), 7.25-7.18 (m, 2H), 7.02-6.69 (m, 3H), 6.18 (d, J = 7.0 Hz, 1H), 5.36 (q, J = 5.4 Hz, 1H), 4.40-4.31 (m, 1H), 4.18 (t, J = 9.4 Hz, 1H), 4.10 (p, J = 7.1 Hz, 1H), 2.46-2.35 (m, 1H), 2.28-2.17 (m, 1H), 1.73-1.64 (m, 6H). |
| 506 | (Method L2): $R_t$ = 3.94 min, m/z = 515 (M + H)⁺ | ¹H NMR (400 MHz, Chloroform-d, Method M2) δ 8.49 (s, 1H), 7.41-7.32 (m, 2H), 7.26-7.18 (m, 2H), 7.17-7.08 (m, 1H), 7.01-6.73 (m, 3H), 6.19 (d, J = 7.4 Hz, 1H), 5.36 (q, J = 5.4 Hz, 1H), 4.40-4.31 (m, 1H), 4.23-4.06 (m, 1H), 2.46-2.34 (m, 1H), 2.27-2.17 (m, 1H), 1.73-1.64 (m, 6H). |
| 507 | (Method L2): $R_t$ = 4.26 min, m/z = 531/533 (M + H)⁺ | ¹H NMR (400 MHz, DMSO-d6, Method M2) δ 9.27 (d, J = 8.0 Hz, 1H), 8.61 (s, 1H), 7.80 (d, J = 2.0 Hz, 1H), 7.61-7.13 (m, 5H), 6.93 (t, J = 7.5 Hz, 1H), 6.80 (d, J = 7.5 Hz, 1H), 5.27-5.19 (m, 1H), 4.34-4.25 (m, 1H), 4.21 (t, J = 8.6 Hz, 1H), 3.94 (p, J = 6.8 Hz, 1H), 2.28-2.15 (m, 1H), 2.12-1.99 (m, 1H), 1.64-1.49 (m, 6H). |
| 508 | (Method L2): $R_t$ = 4.13 min, m/z = 517 (M + H)⁺ | ¹H NMR (400 MHz, DMSO-d6, Method M2) δ 9.27 (d, J = 8.0 Hz, 1H), 8.67 (s, 1H), 7.57-6.67 (m, 7H), 5.24 (q, J = 5.6 Hz, 1H), 4.39-4.12 (m, 2H), 3.94 (p, J = 7.0 Hz, 1H), 2.29-2.16 (m, 1H), 2.12-2.00 (m, 1H), 1.68-1.45 (m, 6H). |
| 509 | (Method L2): $R_t$ = 4.03 min; m/z = 527 (M + H)⁺ | ¹H NMR (400 MHz, Chloroform-d, Method M2) δ 8.45 (s, 1H), 7.67-7.61 (m, 2H), 7.58 (m, 1H), 7.28 (d, J = 7.7 Hz, 1H), 7.25-7.18 (m, 1H), 6.94 (m, 1H), 6.87 (m, 1H), 6.23 (d, J = 7.5 Hz, 1H), 5.37 (d, J = 7.3 Hz, 1H), 4.35 (m, 1H), 4.20 (m, 1H), 2.66-2.57 (m, 1H), 2.43 (s, 4H), 2.22 (m, 1H), 1.79-1.72 (m, 2H), 1.31 (m, 2H). |
| 510 | (Method L2): $R_t$ = 3.73 min; m/z = 467 (M + H)⁺ | ¹H NMR (400 MHz, Chloroform-d, Method M2) δ 8.42 (s, 1H), 7.34-7.27 (m, 1H), 7.25-7.14 (m, 2H), 6.94 (m, 1H), 6.89-6.76 (m, 3H), 6.28 (d, J = 7.5 Hz, 1H), 5.41-5.32 (m, 1H), 4.56 (t, J = 8.7 Hz, 2H), 4.35 (m, 1H), 4.20 (m, 1H), 3.10 (t, J = 8.7 Hz, 2H), 2.50 (s, 4H), 2.45-2.32 (m, 1H), 2.27-2.16 (m, 1H), 1.69 (m, 2H), 1.35-1.22 (m, 2H). |
| 511 | (Method L2): $R_t$ = 4.01 min; m/z = 529/531 (M + 1)⁺ | ¹H NMR (400 MHz, DMSO-d6, Method M2) δ 9.20 (d, J = 8.0 Hz, 1H), 8.58 (s, 1H), 7.79 (d, J = 2.1 Hz, 1H), 7.59-7.46 (m, 2H), 7.41-7.11 (m, 3H), 6.96-6.88 (m, 1H), 6.84-6.77 (m, 1H), 5.29-5.18 (m, 1H), 4.35-4.16 (m, 2H), 2.66-2.57 (m, 1H), 2.28-2.17 (m, 1H), 2.12-2.02 (m, 1H), 1.48-1.34 (m, 2H), 1.32-1.20 (m, 2H). |
| 512 | (Method L2): $R_t$ = 3.95 min; m/z = 529/531 (M + 1)⁺ | ¹H NMR (400 MHz, DMSO-d6, Method M2) δ 9.27-9.13 (m, 1H), 8.58 (d, J = 3.5 Hz, 1H), 7.81-7.69 (m, 1H), 7.52-7.10 (m, 5H), 6.98-6.88 (m, 1H), 6.86-6.75 (m, 1H), 5.24 (q, J = 5.5 Hz, 1H), 4.37-4.14 (m, 2H), 2.67-2.57 (m, 1H), 2.29-2.15 (m, 1H), 2.13-2.01 (m, 1H), 1.49-1.35 (m, 2H), 1.33-1.19 (m, 2H). |
| 524 | LC-MS (Method L2): $R_t$ = 3.86 min; m/z = 522 (M + H)⁺ | ¹H NMR (400 MHz, DMSO-d6, Method M2) δ 9.04 (d, J = 8.1 Hz, 1H), 8.33 (s, 1H), 7.64-7.56 (m, 1H), 7.53-7.46 (m, 1H), 7.32 (t, J = 7.6 Hz, 2H), 7.22-7.14 (m, 1H), 6.96-6.88 (m, 1H), 6.80 (d, J = 8.2 Hz, 1H), 5.21 (q, J = 5.6 Hz, 1H), 4.33-4.19 (m, 2H), 3.83 (t, J = 4.3 Hz, 4H), 3.65 (t, J = 8.0 Hz, 4H), 2.43-2.35 (m, 3H), 2.20 (m, 1H), 2.11-1.97 (m, 1H) |
| 530 | LC-MS (Method L2): $R_t$ = 3.95 min; m/z = 556 (M + H)⁺ | ¹H NMR (400 MHz, DMSO-d6, Method M2) δ 9.06 (d, J = 8.1 Hz, 1H), 8.37 (s, 1H), 7.91 (m, 1H), 7.86-7.78 (m, 1H), 7.59 (t, J = 9.2 Hz, 1H), 7.34 (d, J = 6.9 Hz, 1H), 7.22-7.14 (m, 1H), 6.92 (m, 1H), 6.80 (m, 1H), 5.25-5.16 (m, 1H), 4.33-4.19 (m, 2H), 3.90-3.79 (m, 4H), 3.70-3.57 (m, 4H), 2.41 (d, J = 1.8 Hz, 3H), 2.21 (m, 1H), 2.11-2.00 (m, 1H). |
| 531 | LC-MS (Method L2): $R_t$ = 3.74 min; m/z = 554 (M + H)⁺ | ¹H NMR (400 MHz, DMSO-d6, Method M2) δ 9.03 (d, J = 8.1 Hz, 1H), 8.32 (s, 1H), 7.46-7.37 (m, 1H), 7.33 (d, J = 7.3 Hz, 1H), 7.21-7.13 (m, 1H), 6.92 (m, 1H), 6.80 (m, 1H), 5.25-5.17 (m, 1H), 4.33-4.18 (m, 2H), 3.93 (d, J = 2.3 Hz, 3H), 3.83 (t, J = 4.4 Hz, 4H), 3.71-3.56 (m, 4H), 2.33 (s, 3H), 2.20 (m, 1H), 2.10-2.00 (m, 1H). |
| 532 | LC-MS (Method L2): $R_t$ = 4.00 min; m/z = 572 (M + H)⁺ | ¹H NMR (400 MHz, DMSO-d6, Method M2) δ 9.05 (d, J = 8.0 Hz, 1H), 8.31 (s, 1H), 7.90-7.74 (m, 3H), 7.33 (d, J = 7.6 Hz, 1H), 7.17 (t, J = 7.6 Hz, 1H), 6.92 (t, J = 7.4 Hz, 1H), 6.80 (d, J = 8.2 Hz, 1H), 5.21 (q, J = 5.6 Hz, 1H), 4.34-4.18 (m, 2H), 3.84 (d, J = 4.0 Hz, 4H), 3.65 (s, 4H), 2.35 (s, 3H), 2.20 (m, 1H), 2.04 (m, 1H). |

TABLE 2-continued

LC-MS and NMR data
NMR peak forms are stated as they appear in the spectra, possible higher order effects have not been considered.

| Example No | LC-MS (Method L2-L4) | NMR |
|---|---|---|
| 533 | LC-MS (Method L2): R$_t$ = 3.73 min; m/z = 536 (M + H)$^+$ | $^1$H NMR (400 MHz, DMSO-d6, Method M2) δ 9.04 (d, J = 7.8 Hz, 1H), 8.31 (s, 1H), 7.33 (d, J = 7.4 Hz, 1H), 7.20 (m, 3H), 6.92 (t, J = 7.1 Hz, 1H), 6.80 (d, J = 8.1 Hz, 1H), 5.26-5.16 (m, 1H), 4.25 (d, J = 10.3 Hz, 2H), 3.96 (s, 3H), 3.83 (s, 4H), 3.63 (s, 4H), 2.38 (s, 3H), 2.20 (s, 1H), 2.06 (s, 1H). |
| 534 | LC-MS (Method L2): R$_t$ = 3.73 min; m/z = 506 (M + H)$^+$ | $^1$H NMR (400 MHz, DMSO-d6, Method M2) δ 9.05 (d, J = 8.1 Hz, 1H), 8.33 (s, 1H), 7.48-7.38 (m, 1H), 7.38-7.26 (m, 3H), 7.21-7.13 (m, 1H), 6.92 (t, J = 7.1 Hz, 1H), 6.80 (d, J = 8.0 Hz, 1H), 5.21 (q, J = 5.7 Hz, 1H), 4.33-4.19 (m, 2H), 3.83 (t, J = 4.2 Hz, 4H), 3.65 (t, J = 7.8 Hz, 4H), 2.40 (s, 3H), 2.21 (m, 1H), 2.11-2.01 (m, 1H). |
| 535 | LC-MS (Method L2): R$_t$ = 3.72 min; m/z = 524 (M + H)$^+$ | $^1$H NMR (400 MHz, DMSO-d6, Method M2) δ 9.04 (d, J = 8.1 Hz, 1H), 8.33 (s, 1H), 7.58 (m, 1H), 7.33 (d, J = 6.8 Hz, 1H), 7.31-7.23 (m, 1H), 7.22-7.13 (m, 1H), 6.92 (m, 1H), 6.80 (m, 1H), 5.25-5.17 (m, 1H), 4.33-4.18 (m, 2H), 3.84 (t, J = 4.4 Hz, 4H), 3.66 (t, J = 8.9 Hz, 4H), 2.35 (s, 3H), 2.20 (m, 1H), 2.10-2.00 (m, 1H). |
| 536 | LC-MS (Method L2): R$_t$ = 3.75 min; m/z = 484 (M + H)$^+$ | $^1$H NMR (400 MHz, DMSO-d6, Method M2) δ 9.03 (d, J = 8.1 Hz, 1H), 8.25 (s, 1H), 7.36-7.13 (m, 6H), 6.91 (m, 1H), 6.83-6.76 (m, 1H), 5.21 (q, J = 5.5 Hz, 1H), 4.26 (m, 2H), 3.83 (s, 4H), 3.63 (s, 4H), 2.29 (s, 3H), 2.20 (m, 1H), 2.12 (s, 3H), 2.09-1.98 (m, 1H). |
| 539 | LC-MS (Method L0): m/z = 476 (M + 1)$^+$ | $^1$H NMR (400 MHz, DMSO-d6, Method M1) δ (only characteristical signals in the aromatic field observed): 9.1 (d, 1H, NH), 8.43 (s, 1H), 7.55 (d, 2H), 7.32 (d, 1H), 7.16 (t, 1H), 7.07 (t, 1H), 6.92 (t, 1H), 6.81 (d, 1H). |
| 543 | LC-MS (Method L2): R$_t$ = 3.80 min; m/z = 549 (M + H)$^+$ | $^1$H NMR (400 MHz, DMSO-d6, Method M2) δ 9.04 (d, J = 8.1 Hz, 1H), 8.30 (s, 1H), 7.33 (d, J = 7.4 Hz, 1H), 7.21-7.05 (m, 3H), 6.92 (t, J = 7.4 Hz, 1H), 6.80 (d, J = 8.2 Hz, 1H), 5.21 (q, J = 5.7 Hz, 1H), 4.25 (m, 2H), 3.83 (t, J = 4.2 Hz, 4H), 3.70-3.56 (m, 4H), 2.84 (s, 6H), 2.36 (s, 3H), 2.21 (m, 1H), 2.11-1.99 (m, 1H). |
| 544 | LC-MS (Method L2): R$_t$ = 3.83 min; m/z = 538 (M + H)$^+$ | $^1$H NMR (400 MHz, Chloroform-d, Method M2) δ 8.65 (s, 1H), 7.51 (d, J = 7.3 Hz, 1H), 7.44 (d, J = 8.1 Hz, 2H), 7.33-7.18 (m, 3H), 6.98-6.85 (m, 2H), 5.37-5.28 (m, 1H), 4.35 (ddd, J = 10.8, 5.4, 3.4 Hz, 1H), 4.18 (td, J = 11.7, 10.8, 2.6 Hz, 1H), 3.89-3.67 (m, 8H), 2.35 (s, 4H), 2.26-2.15 (m, 1H). |
| 545 | LC-MS (Method L2): R$_t$ = 3.85 min; m/z = 540 (M + H)$^+$ | $^1$H NMR (400 MHz, Chloroform-d, Method M2) δ 8.71 (s, 1H), 7.63-7.55 (m, 1H), 7.41 (m, 1H), 7.29-7.19 (m, 2H), 7.03-6.86 (m, 3H), 5.32 (q, J = 5.2 Hz, 1H), 4.40-4.31 (m, 1H), 4.19 (m, 1H), 3.86-3.63 (m, 8H), 2.49-2.31 (m, 4H), 2.26-2.15 (m, 1H). |
| 547 | LC-MS (Method L2): R$_t$ = 3.94 min; m/z = 514 (M + H)$^+$ | $^1$H NMR (400 MHz, DMSO-d6, Method M2) δ 9.03 (d, J = 8.1 Hz, 1H), 8.31 (s, 1H), 7.91 (m, 1H), 7.81 (m, 1H), 7.58 (t, J = 9.2 Hz, 1H), 7.33 (d, J = 7.3 Hz, 1H), 7.22-7.13 (m, 1H), 6.92 (t, J = 7.4 Hz, 1H), 6.80 (d, J = 8.1 Hz, 1H), 5.20 (q, J = 5.7 Hz, 1H), 4.26 (m, 2H), 3.26 (s, 6H), 2.40 (d, J = 1.6 Hz, 3H), 2.18 (m, 1H), 2.04 (m, 1H). |
| 548 | LC-MS (Method L0): m/z = 482/484 (M + 1)$^+$ | $^1$H NMR (400 MHz, DMSO-d6, Method M1) δ 8.45 (d, 1H, NH), 8.30 (s, 1H), 7.65 (d, 1H), 7.47-7.38 (m, 2H), 7.25 (d, 1H), 7.15 (t, 1H), 6.91 (t, 1H), 6.78 (d, 1H), 5.26-5.20 (m, 1H), 4.28-4.23 (m, 2H), 2.17-2.10 (m, 1H), 2.30 (s, 3H), 2.07-1.99 (m, 1H); NHMe under solvents. |
| 549 | LC-MS (Method L2): R$_t$ = 3.73 min; m/z = 464 (M + H)$^+$ | $^1$H NMR (400 MHz, DMSO-d6, Method M2) δ 9.02 (d, J = 8.1 Hz, 1H), 8.27 (s, 1H), 7.47-7.38 (m, 1H), 7.37-7.26 (m, 3H), 7.20-7.14 (m, 1H), 6.91 (t, J = 7.4 Hz, 1H), 6.80 (d, J = 8.1 Hz, 1H), 5.24-5.15 (m, 1H), 4.31-4.19 (m, 2H), 3.25 (s, 6H), 2.40 (s, 3H), 2.25-2.14 (m, 1H), 2.08-1.99 (m, 1H). |
| 550 | LC-MS (Method L2): R$_t$ = 3.78 min; m/z = 507 (M + H)$^+$ | $^1$H NMR (400 MHz, DMSO-d6, Method M2) δ 9.01 (d, J = 8.1 Hz, 1H), 8.24 (s, 1H), 7.31 (d, J = 7.5 Hz, 1H), 7.21-7.05 (m, 3H), 6.91 (t, J = 7.4 Hz, 1H), 6.80 (d, J = 7.8 Hz, 1H), 5.24-5.16 (m, 1H), 4.32-4.19 (m, 2H), 3.24 (s, 6H), 2.84 (s, 6H), 2.39-2.31 (m, 3H), 2.24-2.13 (m, 1H), 2.08-1.98 (m, 1H). |
| 551 | LC-MS (Method L2): R$_t$ = 3.73 min; m/z = 494 (M + H)$^+$ | $^1$H NMR (400 MHz, DMSO-d6, Method M2) δ 9.01 (d, J = 8.1 Hz, 1H), 8.25 (s, 1H), 7.31 (d, J = 7.1 Hz, 1H), 7.27-7.12 (m, 3H), 6.91 (t, J = 7.0 Hz, 1H), 6.80 (d, J = 8.1 Hz, 1H), 5.26-5.15 (m, 1H), 4.32-4.17 (m, 2H), 3.96 (s, 3H), 3.25 (s, 6H), 2.37 (s, 3H), 2.24-2.13 (m, 1H), 2.09-1.98 (m, 1H). |
| 552 | LC-MS (Method L2): R$_t$ = 3.86 min; m/z = 480/482 (M + H)$^+$ | $^1$H NMR (400 MHz, DMSO-d6, Method M2) δ 9.02 (d, J = 8.1 Hz, 1H), 8.27 (s, 1H), 7.63-7.54 (m, 1H), 7.53-7.46 (m, 1H), 7.35-7.28 (m, 2H), 7.21-7.14 (m, 1H), 6.95-6.88 (m, 1H), 6.84-6.76 (m, 1H), 5.25-5.15 (m, 1H), 4.34-4.17 (m, 2H), 3.26 (s, 6H), 2.42-2.37 (m, 3H), 2.24-2.12 (m, 1H), 2.09-1.97 (m, 1H). |
| 553 | LC-MS (Method L2): R$_t$ = 3.72 min; m/z = 442 (M + H)$^+$ | $^1$H NMR (400 MHz, Chloroform-d, Method M2) δ 8.48 (s, 1H), 7.34-7.26 (m, 3H), 7.25-7.17 (m, 3H), 6.93 (t, J = 6.9 Hz, 2H), 6.87 (d, J = 8.3 Hz, 2H), 5.34 (q, J = 5.6 Hz, 1H), 4.34 (m, 1H), 4.24-4.14 (m, 1H), 3.30 (s, 6H), 2.39 (s, 4H), 2.17 (s, 4H). |
| 554 | LC-MS (Method L2): R$_t$ = 3.73 min; m/z = 482 (M + H)$^+$ | $^1$H NMR (400 MHz, Chloroform-d) δ 8.52 (s, 1H), 7.28 (s, 1H), 7.24-7.11 (m, 2H), 7.01-6.85 (m, 3H), 6.77 (d, J = 7.5 Hz, 1H), 5.34 (q, J = 5.6 Hz, 1H), 4.34 (m, 1H), 4.23-4.14 (m, 1H), 3.32 (s, 6H), 2.46-2.32 (m, 4H), 2.22-2.12 (m, 1H). |

TABLE 2-continued

LC-MS and NMR data
NMR peak forms are stated as they appear in the spectra,
possible higher order effects have not been considered.

| Example No | LC-MS (Method L2-L4) | NMR |
|---|---|---|
| 555 | LC-MS (Method L2): $R_t$ = 4.430 min; m/z = 522/524 (M + H)$^+$ | $^1$H NMR (400 MHz, DMSO-d6, Method M2) δ 9.05 (d, J = 8.0 Hz, 1H), 8.45 (s, 1H), 7.82 (d, J = 1.8 Hz, 2H), 7.48 (t, J = 1.8 Hz, 1H), 7.34 (d, J = 7.4 Hz, 1H), 7.17 (t, 1H), 6.91 (t, 1H), 6.81 (d, J = 8.2 Hz, 1H), 5.19 (q, J = 5.6 Hz, 1H), 4.31-4.23 (m, 2H), 3.39 (s, 3H), 3.13-3.05 (m, 1H), 2.58 (s, 3H), 2.24-2.11 (m, 1H), 2.09-1.95 (m, 1H), 0.73 (d, J = 5.3 Hz, 2H), 0.54-0.46 (m, 2H). |
| 556 | LC-MS (Method L2): $R_t$ = 4.530 min; m/z = 553/555 (M + H)$^+$ | $^1$H NMR (400 MHz, DMSO-d6, Method M2) δ 9.18 (d, J = 8.1 Hz, 1H), 8.46 (s, 1H), 7.82 (d, J = 1.9 Hz, 2H), 7.51 (t, J = 1.9 Hz, 1H), 7.35 (d, J = 7.3 Hz, 1H), 7.19 (t, J = 7.7 Hz, 1H), 6.92 (t, J = 7.5 Hz, 1H), 6.81 (d, J = 8.1 Hz, 1H), 5.25-5.17 (m, 1H), 4.32-4.23 (m, 2H), 4.21-4.09 (m, 4H), 3.21-3.10 (m, 9H), 2.64 (s, 3H), 2.26-2.15 (m, 1H), 2.11-1.99 (m, 1H). |
| 558 | LC-MS (Method L2): $R_t$ = 3.087 min; m/z = 579/581 (M + H)$^+$ | $^1$H NMR (400 MHz, DMSO-d6, Method M2) δ 9.03 (d, J = 8.1 Hz, 1H), 8.40 (s, 1H), 7.84 (d, J = 1.8 Hz, 2H), 7.49 (t, J = 1.8 Hz, 1H), 7.34 (d, J = 7.4 Hz, 1H), 7.19 (t, 1H), 6.92 (t, J = 7.1 Hz, 1H), 6.80 (d, J = 8.1 Hz, 1H), 5.19 (q, J = 5.8 Hz, 1H), 4.34-4.18 (m, 3H), 2.97 (s, 3H), 2.92-2.81 (m, 2H), 2.60 (s, 3H), 2.23-2.11 (m, 4H), 2.07-1.97 (m, 2H), 1.97-1.84 (m, 5H). |
| 559 | LC-MS (Method L2): $R_t$ = 4.334 min; m/z = 546/548 (M + H)$^+$ | $^1$H NMR (400 MHz, DMSO-d6, Method M2) δ 9.14 (d, J = 8.1 Hz, 1H), 8.50 (s, 1H), 7.83 (d, J = 1.9 Hz, 2H), 7.51 (t, J = 1.8 Hz, 1H), 7.34 (d, J = 7.2 Hz, 1H), 7.22-7.14 (m, 1H), 6.93 (t, J = 7.1 Hz, 1H), 6.81 (d, J = 8.1 Hz, 1H), 6.65-6.29 (m, 1H), 5.22 (q, J = 5.7 Hz, 1H), 4.35-4.19 (m, 4H), 3.21 (s, 3H), 2.63 (s, 3H), 2.23-2.14 (m, 1H), 2.10-1.98 (m, 1H). |
| 560 | LC-MS (Method L2): $R_t$ = 3.982 min; m/z = 593/595 (M + H)$^+$ | $^1$H NMR (400 MHz, DMSO-d6, Method M2) δ 9.09 (d, J = 8.1 Hz, 1H), 8.40 (s, 1H), 7.84 (d, J = 1.9 Hz, 2H), 7.49 (t, J = 1.8 Hz, 1H), 7.35 (d, J = 7.2 Hz, 1H), 7.18 (t, 1H), 6.92 (t, J = 7.1 Hz, 1H), 6.80 (d, J = 8.1 Hz, 1H), 5.20 (q, J = 5.6 Hz, 1H), 4.33-4.18 (m, 2H), 3.95-3.79 (m, 2H), 3.62-3.50 (m, 2H), 3.38-3.27 (m, 2H), 3.18 (s, 3H), 2.62 (s, 3H), 2.27-2.13 (m, 1H), 2.12-1.98 (m, 3H), 1.80-1.69 (m, 2H). |
| 561 | LC-MS (Method L2): $R_t$ = 4.201 min; m/z = 628/630 (M + H)$^+$ | $^1$H NMR (400 MHz, DMSO-d6, Method M2) δ 8.91 (d, J = 8.1 Hz, 1H), 8.42 (s, 1H), 7.83 (d, J = 1.9 Hz, 2H), 7.49 (t, J = 1.8 Hz, 1H), 7.34 (d, J = 7.3 Hz, 1H), 7.18 (t, 1H), 6.92 (t, J = 7.1 Hz, 1H), 6.81 (d, J = 8.1 Hz, 1H), 5.22 (q, J = 5.8 Hz, 1H), 4.33-4.19 (m, 2H), 4.13-3.94 (m, 2H), 3.77-3.63 (m, 2H), 3.43-3.35 (m, 2H), 3.31-3.24 (m, 6H), 3.18 (s, 3H), 3.15 (s, 3H), 2.61 (s, 3H), 2.26-2.13 (m, 1H), 2.11-1.97 (m, 1H). |

Table 3: NMR Peaklist

1H-NMR data of selected examples are written in form of 1H-NMR-peak lists. To each signal peak are listed the δ-value in ppm and the signal intensity in round brackets. Between the δ-value-signal intensity pairs are semicolons as delimiters.

The peak list of an example has therefore the form:

$\delta_1$ (intensity$_1$); $\delta_2$ (intensity$_2$); ... ; $\delta_i$ (intensity$_1$); ... ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

Example 1: $^1$H-NMR(400.0 MHz, d$_6$-DMSO): δ = 9.092(1.5);9.07(1.5);8.577(7.6);8.316(0.5);8.128(2.5);8.040(1.3);8.021(1.5);7.746(0.8);7.726(1.9);7.707(1.3);7.677(1.8);7.657(0.9);7.404(0.9);7.392(1.2);7.383(1.2);7.298(0.5);7.286(1.0);7.276(1.7);7.266(1.1);7.255(3.9);7.248(2.3);7.241(2.0);7.233(2.1);5.556(0.4);5.536(1.3);5.516(1.3);5.496(0.4);4.019(0.4);4.001(0.9);3.984(1.3);3.966(1.0);3.948(0.4);3.325(128.4);3.026(0.3);3.017(0.4);3.004(0.4);2.995(0.4);2.986(0.7);2.977(0.7);2.964(0.7);2.955(0.7);2.891(1.1);2.871(0.8);2.852(0.6);2.831(0.3);2.675(0.9);2.671(1.1);2.666(0.9);2.662(0.7);2.657(1.0);2.646(16.0);2.575(0.4);2.566(0.5);2.555(0.8);2.544(1.0);2.535(1.3);2.524(3.8);2.511(61.4);2.506 (124.4);2.502 (163.6);2.497(116.4);2.493(55.2);2.328(1.1);2.324(0.8);2.333(0.8);2.333(0.8);2.328(1.1);2.324(0.8);1.989(0.4);1.970 (0.9);1.949 (0.9);1.938(0.4);1.928(0.9);1.917(0.8);1.907(0.4);1.897(0.8);1.586(7.2);1.568(13.9);1.551(7.1);0.146(0.6);0.008(5.1);0.000 (142.0);−0.009(5.1);−0.150(0.6)

Example 2: $^1$H-NMR(400.0 MHz, d$_6$-DMSO): δ = 9.097(1.5);9.076(1.6);8.541(7.3);8.524(0.3);8.127(2.6);8.037(1.4);8.018(1.6);7.742(0.8);7.723(2.0);7.703(1.4);7.673(1.9);7.653(0.9);7.387(1.1);7.380(1.2);7.364(1.5);7.225(0.5);7.212(1.5);7.206(2.5);7.197(2.5);7.189(2.8);7.183(1.8);7.170(0.6);7.165(0.4);7.133(1.7);7.117(1.0);7.111(0.9);5.232(0.4);5.216(0.8);5.200(0.8);5.182(0.4);4.038(0.5);4.020(0.5);3.997(0.3);3.979(0.9);3.962(1.3);3.944(1.0);3.926(0.4);3.325 (79.0);2.789(0.7);2.773(1.7);2.759(1.7);2.744(0.7);2.675(0.4);2.671(0.6);2.667(0.5);2.654(1.2);2.643(16.0);2.524(1.5);2.511(30.8);2.507(61.8);2.502(81.1);2.498(58.5);2.493(28.4);2.333(0.4);2.329(0.5);2.324(0.4);2.067(0.4);2.059(0.5);2.047(0.7);2.038(0.7);2.024(0.5);1.989(2.2);1.949 (0.5);1.938(0.5);1.922(0.6);1.903(0.5);1.882(0.5);1.862(0.7);1.831 (1.0);1.815(1.2);1.796(0.5);1.586 (7.3);1.568(7.7);1.561(7.8);1.543(7.1);1.398(4.3);1.193(0.6);1.175(1.2);1.157(0.6);0.008(2.5);0.000(65.7);−0.009(2.5)

Example 3: $^1$H-NMR(400.0 MHz, d$_6$-DMSO): δ = 9.097(2.1);9.076(2.2);8.582(0.8);8.541(5.9);8.316(0.4);8.172(0.8);8.127(2.3);8.067(0.7);8.036(2.2);8.018(2.4);7.742(1.4);7.723(3.1);7.703(2.4);7.673(2.9);7.655(1.8);7.413(0.6);7.381(1.9);7.365(2.3);7.226(1.5);7.207(3.5);7.198(3.7);7.189(4.3);7.172(2.6);7.189(4.3);7.172(2.6);7.118(2.0);5.215(1.5);5.198(1.6);3.995(0.8);3.979(1.4);3.961(1.8);3.944(1.4);3.926(0.7);3.373(19.6);3.366(18.7);3.351(9.6);3.326(144.7);3.244(2.6);2.788(1.8);2.771(3.1);2.760(3.3);2.690(2.9);2.672(2.8);2.644(16.0);2.547(44.0);2.502(189.5);2.328(1.6);2.080(0.9);2.057(1.2);2.038(1.4);1.963(0.8);1.947(1.3);1.920(1.6);1.902(1.5);1.882(1.0);1.830 (2.3);1.814(2.5);1.586 (10.6);1.561(11.3);1.543(9.8);1.568(10.6);1.561(11.3);1.543(9.8);1.447(0.7);1.398(2.6);0.147(0.3);0.045(6.5);0.025(3.1);0.000 (53.4);−0.148(0.4)

Example 4: $^1$H-NMR(400.0 MHz, d$_6$-DMSO): δ = 9.096(1.7);9.075(1.7);8.575(6.8);8.127(2.8);8.040(1.5);8.020(1.8);7.747(0.9);7.727(2.1);7.708(1.5);7.678(2.1);7.658(1.1);7.403(1.0);7.392(1.4);7.383(1.3);7.297(0.6);7.287(1.1);7.276(1.2);7.266(1.2);7.260(1.2);7.248(2.6);7.242(2.3);7.234(2.3);7.224(0.3);5.554(0.5);5.535 (1.4);5.516(1.4);5.495(0.5);4.016(0.4);3.999(0.9);3.982(1.3);3.964(1.0);3.946(0.4);3.429(0.7);3.355(406.0);3.349(378.6);3.346(449.4);3.294(1.1);3.288(0.9);3.025(0.4);3.017(0.4);3.003(0.4);2.994(0.5);2.986(0.8);2.977(0.8);2.964(0.8);2.912(0.6);2.891(1.3);2.871(0.4);2.677(1.0);2.672(1.3);2.668(1.1);2.646(16.0);2.575(0.5);2.567(0.5);2.555(0.9);2.546(1.1);2.535(1.4);2.508(145.7);2.503(197.4);2.499(154.0);2.330(1.2);2.326(1.0);1.970(0.4);1.949(0.9);1.939(0.4);1.928(0.9);1.918(0.9);1.907(0.5);1.897(0.8);1.585(7.3);1.568(14.2);1.551(7.2);1.146(0.5);0.016(0.3);0.000(113.0);−0.150(0.5)

Example 5: $^1$H-NMR(400.0 MHz, d$_6$-DMSO): δ = 9.074(1.5);9.052(1.5);8.550(7.6);8.317(0.4);8.125(2.5);8.042(1.3);8.022(1.6);7.744(0.8);7.724(1.9);7.705(1.3);7.675(1.8);7.656(0.9);7.168(3.0);7.005(7.6);6.574(0.7);5.194(0.3);5.179(0.7);5.162(0.8);5.143(0.4);3.981(0.9);3.964(1.2);3.946(0.9);3.928(0.3);3.324(112.2);2.713(1.5);2.701(1.6);2.680(0.7);2.675(1.2);2.671 (1.5);2.666(1.2);2.661(0.8);2.656(1.1);2.645(16.0);2.524(3.3);2.519(5.1);2.506(151.7);2.502(203.6);2.497(150.8);2.493(75.4);2.337(0.5);2.333(1.4);2.324(1.0);2.277(12.0);2.054(0.4);2.046(0.3);2.034(0.6);2.024(0.7);2.011(0.5);1.923(0.5);1.912(0.9);1.898(0.6);1.878(0.5);1.852(0.4);1.830(0.6);1.825(0.6);1.799(0.9);1.783(1.1);1.577(1.1);1.568(7.3);1.547(7.3);1.550(6.8);1.398(5.7);0.146(0.9);0.008(6.6);0.000(200.9);−0.009(8.0);−0.150(0.9)

Example 6: $^1$H-NMR(400.0 MHz, d$_6$-DMSO): δ = 9.217(1.6);9.197(1.7);8.573(7.5);8.132(2.7);8.036(1.4);8.017 (1.7);7.743(0.8);7.723(2.0);7.704(1.4);7.675(1.9);7.655(1.0);7.356(1.6);7.337(1.7);7.204(0.7);7.200(0.8);7.183(1.6);7.165(1.0);7.162(1.0);6.954(1.1);6.951(1.2);6.933(2.0);6.916(0.9);6.914(1.0);6.815(2.3);6.797(1.0);6.795(2.0);6.758(1.2);5.262(0.4);5.247(1.0);5.228(1.0);5.213(0.4);4.308(0.4);4.301(0.3);4.289(0.9);4.280(0.8);4.272(1.0);4.262(1.1);4.253(1.0);4.240(0.8);4.232(1.1);4.212(0.4);4.021(0.4);4.014(0.4);3.996(0.9);3.978(1.3);3.961(1.0);3.943(0.4);3.325(16.7);2.676(0.3);2.671(0.5);2.666(0.8);2.654(1.1);2.645(16.0);2.525(0.8);2.511(18.0);2.507(37.3);2.503(50.1);2.498(38.9);2.493(18.1);2.494(18.9);2.228(0.4);2.215(0.6);2.206(0.6);2.194(0.7);2.182(0.5);2.083(0.5);2.074(0.6);2.067(0.7);2.056(0.5);2.051(0.5);2.040(0.5);2.032(0.5);1.989(1.5);1.583(7.3);1.568(14.2);1.551(7.2);1.568(8.1);1.542(7.1);1.397(2.8);1.193(0.4);1.175(0.8);1.158(0.4);0.008(1.7);0.000(49.3);−0.008(1.9)

Example 7: $^1$H-NMR(400.0 MHz, d$_6$-DMSO): δ = 9.095(1.7);9.073(1.7);8.567(7.3);8.317(0.4);8.128(2.4);8.041(1.2);8.021(1.5);7.812(8.3);7.536(3.6);7.527(1.9);7.383(1.1);7.376(1.1);7.360(1.5);7.223(0.4);7.210(1.6);7.205(2.6);7.196(2.6);7.187(3.0);7.183(2.0);7.170(0.6);7.165(0.4);7.132(1.7);7.117(1.1);7.110(0.9);5.229(0.4);5.214(0.8);5.198(0.9);5.180(0.4);3.978(0.4);3.960(1.0);3.942(1.3);3.925(1.0);3.907(0.4);3.314(54.7);3.288(0.7);3.278(1.8);2.759(1.8);2.744(0.7);2.711(0.4);2.675(0.6);2.670(0.9);2.666(0.8);2.644(16.0);2.541(55.2);2.523(2.4);2.506(86.4);2.501(115.3);2.497(88.1);2.497(38.1);2.332(0.6);2.328(0.8);2.323(0.6);2.328(0.8);2.073(0.4);2.059(0.5);2.046(0.7);2.038(0.7);2.023(0.5);2.023(0.5);1.936 (0.5);1.920 (0.6);1.901 (0.5);1.881 (0.5);1.861(0.7);1.856(0.6);1.829(1.0);1.813(1.2);1.577 (0.5);1.549(7.7);1.532 (7.0);0.146(0.4);0.008(3.4);0.000(87.8);−0.008(4.2);−0.150(0.4)

Example 8: $^1$H-NMR(400.0 MHz, d$_6$-DMSO): δ = 9.096(1.5);9.076(1.5);8.599(6.5);7.818(7.9);7.813(8.3);7.542(2.3);7.538(4.3);7.533(2.2);7.400(1.0);7.388(1.3);7.378(1.3);7.298(0.6);7.288(1.0);7.276(1.8);7.267(1.1);7.256(4.0);7.248(2.2);7.242(2.0);7.234(2.2);7.248(2.0);7.234(2.2);7.234(2.2);5.554(0.5);5.534 (1.3);5.514 (1.3);5.493(0.4);3.997(0.3);3.980(0.9);3.962(1.3);3.945(0.9);3.927(0.4);3.901(15.2);3.347(214.4);3.339(203.2);3.025(0.4);3.017(0.4);3.004(0.4);2.995(0.4);2.986(0.7);2.977(0.7);2.964(0.7);2.956(0.7);2.912(0.6);2.892(1.2);2.871(0.8);2.853(0.6);2.832(0.3);2.676(0.8);2.672(1.2);2.667(0.9);2.646(16.0);2.577(0.4);2.568(0.5);2.557(0.8);2.547(1.0);2.536(1.3);2.525(3.7);2.512(62.6);2.508(128.8);2.503(171.2);2.498(123.5);2.494(59.3);2.334(0.7);2.330(0.9);2.325(0.7);1.946(0.8);1.945(0.8);1.905(0.4);1.895(0.7);1.574(7.0);1.556(13.5);1.539(6.9);0.000(0.8)

Example 9: $^1$H-NMR(400.0 MHz, d$_6$-DMSO): δ = 8.999(1.1);8.978(1.2);8.504(6.0);7.619(1.0);7.606(1.2);7.596(0.4);7.454(6.2);7.446(7.4);7.432(0.5);7.351(0.9);7.341(1.1);7.329(1.2);7.198(2.3);7.192(1.5);7.187(1.8);7.182(1.7);7.175(2.9);7.164(0.5);7.134(1.5);7.122(1.0);7.111(0.7);5.259(0.3);5.242(0.7);5.227(0.7);5.209(0.4);5.214(0.8);5.198(0.9);5.229(0.4);5.180(0.4);3.978(0.4);3.925 (1.0);3.907(0.4);3.942(1.3);3.925(1.0);3.343(142.1);3.358(132.5);3.314(54.7);3.907(0.4);3.343(142.1);3.176(0.3);2.895(15.1);2.795(0.6);2.777(1.4);2.763(1.5);2.747(0.6);2.677(0.6);2.672(0.8);2.668(0.6);2.542(0.4);2.525(2.1);2.512(47.8);2.508(97.6);2.503(128.8);2.499(92.3);2.494(44.0);2.375 (16.0);2.334(0.6);2.330(0.7);2.325(0.5);2.056(0.4);2.047(0.6);2.037(0.5);2.022(0.4);1.956(0.4);1.944(0.4);1.929(0.6);1.869(0.4);1.863(0.5);1.845(0.6);1.829(1.0);1.819(1.0);0.000(0.8)

Example 10: $^1$H-NMR(400.0 MHz, d$_6$-DMSO): δ = 9.123(1.4);9.103(1.4);9.028(6.0);8.722(6.6);8.274(8.3);8.269(8.9);7.465(2.6);7.461(4.8);7.456(2.7);7.414(1.2);7.402(1.4);7.393(1.5);7.302(0.7);7.291(1.2);7.280(2.1);7.271(1.6);7.262(4.8);7.254(3.0);7.248(2.7);7.240(2.5);7.230(0.3);5.563(0.5);5.544(1.6);5.523(1.6);5.503(0.5);3.981(0.4);3.964 (1.0);3.946(1.5);3.929(1.1);3.911(0.5);3.901(13.8);3.361(183.1);3.350(185.0);3.346(187.4);3.342(188.0);3.176(0.3);3.164(0.5);3.029(0.5);3.021(0.5);3.008(0.5);2.999(0.6);2.982(0.9);2.968(0.8);2.919(0.7);2.898(1.4);2.878(1.0);2.859(0.7);2.838(0.4);2.677(0.7);2.673(1.0);2.668(0.7);2.590(0.4);2.581(0.4);2.570(0.8);2.561(0.9);2.550(0.9);2.539(1.3);2.526(2.9);2.512(64.8);2.508(133.6);2.504(177.5);2.499(128.8);2.495(63.8);2.330(1.0);2.326(0.8);1.970(0.4);1.948(1.0);1.938(0.5);1.928(1.0);1.917(1.0);1.906(0.5);1.897(0.9);1.875(0.3);1.575(8.3);1.558(16.0);1.540(8.2);0.000(1.2)

Example 11: $^1$H-NMR(601.6 MHz, d$_6$-DMSO): δ = 9.129(1.2);9.108(1.3);9.026(5.2);8.695(5.9);8.277(6.7);8.272(7.0);7.468(2.0);7.463(3.8);7.458(2.0);7.404(0.9);7.397(1.3);7.381(1.3);7.237(0.4);7.224(1.2);7.218(1.9);7.209(2.2);7.200(2.7);7.195(4.8);7.187(1.8);7.182(0.5);7.177(0.4);7.142(1.4);7.127(0.9);7.120(0.7);5.227(0.7);5.211(0.7);5.195(0.8);5.177(0.4);3.947(0.8);3.930(1.1);3.907(16.0);3.895(0.4);3.366(210.8);3.355(207.0);2.799(0.6);2.781(1.4);2.768(1.4);2.753(0.6);2.683(0.6);2.679(0.8);2.674(0.6);2.532(2.0);2.518(48.6);2.514(101.1);2.510(135.2);2.505(97.8);2.501(47.2);2.336(0.7);2.332(1.0);2.328(0.8);2.323(0.4);2.077(0.4);2.063(0.5);2.055(0.5);2.043(0.4);1.952(0.6);1.941(0.4);1.923(0.5);1.903(0.4);1.894(0.4);1.875(0.6);1.869(0.5);1.843(0.9);1.827(1.0);1.581(6.1);1.564(6.4);1.556(6.5);1.538(6.0)

Example 12: $^1$H-NMR(601.6 MHz, d$_6$-DMSO): δ = 9.677(7.2);9.674(7.3);9.140(7.2);9.136(7.1);9.088(3.0);9.073(16.0);8.547(4.8);8.476(2.6);8.463(2.7);7.727(1.6);7.714(3.6);7.701(2.2);7.636(3.0);7.623(2.2);7.360(2.8);7.348(3.5);7.314(2.4);7.302(3.8);7.270 (1.6);7.259(3.3);7.247(2.0);7.234(2.4);7.222(3.0);7.211(1.1);5.609(0.8);5.596(2.4);5.582(2.5);5.569(0.8);3.332(2742.4);3.059(0.7);3.054(0.8);3.045(0.9);3.039(0.9);3.033(1.2);3.028(1.2);3.019(1.2);3.013(1.1);2.977(0.3);2.922(0.9);2.908(1.9);2.895(1.5);2.882(1.3);2.868(0.7);2.617(3.1);2.61444.2(1.5);2.611(3.1);2.555(0.7);2.549(0.8);2.542 (1.5);2.536(1.5);2.528(2.4);2.523(8.5);2.520(10.6);2.517(10.7);

-continued 2.508(230.8);2.505(477.2);2.502(643.7);2.499(481.5);2.496(234.2);2.383(3.0);2.389(1.7);2.386(4.1);2.383(3.0);2.095(3.1);2.034(0.6);2.020(1.6);2.013(0.7);2.006(1.7);1.999(1.6);1.992(0.8);1.985(1.5);1.971(0.5);1.236(0.5);0.978(0.4);0.967(0.8);0.955(0.4);0.005(0.7);0.000(19.5)

Example 13: $^1$H-NMR(400.0 MHz, $d_6$-DMSO): δ = 9.653(4.5);9.648(4.7);9.088(5.4);9.082(6.8);9.061(2.0);8.937(8.9);8.209(6.1);8.205(2.3);8.192(2.1);8.188(6.8);7.549(0.9);7.543(7.1);7.538(2.4);7.526(2.1);7.521(6.8);7.357(1.8);7.340(2.4);7.314(1.4);7.296(2.8);7.273(1.2);7.257(2.3);7.237(2.7);7.218(1.8);7.201(0.6);5.616(0.6);5.596(1.8);5.577(1.7);5.557(0.6);3.901(16.0);3.349(305.2);3.341(296.8);3.164(0.3);3.070(0.5);3.062(0.6);3.049(0.6);3.040(0.6);3.030(0.9);3.022(1.0);3.009(0.9);3.000(0.9);2.931(0.6);2.911(1.4);2.891(1.1);2.871(0.9);2.850(0.5);2.677(0.9);2.672(1.2);2.668(0.9);2.564(0.6);2.555(0.7);2.544(1.2);2.532(1.8);2.525(4.7);2.512(80.5);2.508(166.1);2.503(223.7);2.499(162.8);2.494(79.8);2.334(0.9);2.330(1.3);2.325(1.0);2.086(1.3);2.048(0.4);2.027(1.1);2.016(0.5);2.006 (1.2);1.995(1.1);1.985(0.5);1.975(1.0);1.953(0.4);1.046(0.3);1.031(0.4);0.000(1.2)

Example 14: $^1$H-NMR(400.0 MHz, $d_6$-DMSO): δ = 8.996(1.2);8.976(1.3);8.534(5.9);7.628(1.0);7.619(1.1);7.614(0.9);7.609(1.3);7.603(1.2);7.462(1.8);7.457(6.4);7.449(6.8);7.434(0.6);7.383(1.0);7.371(1.3);7.363(1.2);7.296(0.6);7.287(1.0);7.274(1.7);7.267(0.6);7.260(0.7);7.248(2.8);7.236(2.2);7.230(1.4);7.226(1.8);7.213(0.3);5.572(0.4);5.552(1.3);5.532(1.3);5.513(0.4);3.901(12.2);3.345(148.9);3.338(147.0);3.176(0.9);3.163(0.9);3.026(0.4);3.018(0.4);3.004(0.4);2.996(0.5);2.987(0.7);2.979(0.8);2.965(0.8);2.957(0.7);2.916(15.8);2.890(1.2);2.870(0.8);2.850(0.4);2.676(0.6);2.672(0.8);2.667(0.6);2.563(0.5);2.554(0.5);2.543(1.0);2.511(53.3);2.507(105.5);2.503(138.6);2.498(100.1);2.494(49.2);2.378(16.0);2.334(0.6);2.329(0.8);2.325(0.6);1.974(0.8);1.964(0.4);1.953(0.8);1.325(0.6);2.334(0.6);1.942(0.8);1.932(0.4);1.921(0.7);0.000(1.1)

Example 15: $^1$H-NMR(400.0 MHz, $d_6$-DMSO): δ = 9.031(0.7);9.009(0.7);8.650(3.1);8.149(1.3);8.054(0.7);8.035(0.7);7.750(0.4);7.731(1.0);7.712(1.0);7.712(1.0);7.680(0.9);7.660(0.5);7.358(0.6);7.369(0.5);7.358(0.6);7.346(0.7);7.205(1.2);7.199(0.8);7.194(1.1);7.188(0.7);7.182(1.5);7.140(0.8);7.128(0.6);7.118(0.4);5.245(0.4);3.901(16.0);3.346(99.6);3.340(86.5);2.906(8.4);2.803(0.3);2.784(0.7);2.768(0.8);2.753(0.4);2.677(0.4);2.672(0.6);2.667(0.5);2.653(8.7);2.525(1.828(0.5);0.000(0.8)

Example 16: $^1$H-NMR(400.0 MHz, $d_6$-DMSO): δ = 9.030(0.7);9.010(0.7);8.681(2.8);8.152(1.4);8.057(0.7);8.038(0.8);7.754(0.5);7.734(1.1);7.715(0.8);7.664(0.5);7.391(0.8);7.382(0.7);7.302(0.4);7.293(0.6);7.280(1.7);7.273(0.4);7.267(0.4);7.254(1.5);7.242(1.3);7.232(1.0);5.558(0.7);5.538(0.7);3.901(16.0);3.368(126.0);3.346(116.8);2.989(0.5);2.975(0.4);2.967(0.4);2.926(8.2);2.897(0.7);2.876(0.5);2.857(0.4);2.677(0.5);2.673(0.7);2.668(0.5);2.657(8.8);2.552(0.5);2.543(0.7);2.512(42.2);2.508(84.8);2.504(113.0);2.499(83.3);2.335(0.5);2.330 (0.7);2.326(0.5);1.986 (0.5);1.966 (0.5);1.955 (0.5);1.934 (0.4);0.000(0.9)

Example 17: $^1$H-NMR(400.0 MHz, $d_6$-DMSO): δ = 9.558(2.6);9.553(3.0);9.054(3.8);9.048(3.5);9.037(1.6);7.830(6.7);7.825(7.3);7.568(2.1);7.563(4.0);7.559(2.2);7.347(1.2);7.330(1.7);7.313(1.0);7.295(2.0);7.272(0.8);7.256(1.7);7.236(2.0);7.218(1.4);7.200(0.5);5.609(0.4);5.590(1.2);5.570(1.2);5.550(0.4);3.901(16.0);3.365(282.0);3.347(273.1);3.176(0.6);3.164(0.5);3.058(0.5);3.044(0.5);3.058(0.5);3.036(0.6);3.027(0.8);3.019(0.8);3.004(0.8);2.997(0.7);2.930(0.6);2.908(1.1);2.888(0.9);2.869(0.7);2.849(0.4);2.677(1.5);2.673(1.3);2.668(1.6);2.634(15.7);2.542(1.3);2.512(79.8);2.508(161.6);2.504(215.8);2.499(158.0);2.330(1.2);2.020(0.8);2.010(0.4);2.000(0.8);1.989(0.8);1.978(0.4);1.969(0.7);0.000(1.6)

Example 18: $^1$H-NMR(400.0 MHz, $d_6$-DMSO): δ = 9.552(2.7);9.547(3.0);9.050(1.5);9.034(3.7);9.0294(6.8);8.128(2.5);8.068(1.3);8.049(1.5);7.762(0.7);7.743(1.4);7.700(2.0);7.681(0.9);7.350(1.3);7.332(1.7);7.312(1.1);7.295(2.0);7.271(0.9);7.257(1.7);7.236(2.0);7.219(1.3);7.199(0.6);5.593(1.2);5.574(0.4);5.554(0.4);3.901(8.9);3.369(193.8);3.357(161.5);3.350(168.3);3.177(0.3);3.164(0.3);3.068(0.4);3.060(0.5);3.045(0.5);3.037(0.5);3.028(0.7);3.020(0.8);3.006(0.7);2.999(0.7);2.929(0.5);2.909(1.1);2.888(0.8);2.869(0.6);2.673(0.8);2.669(0.6);2.635(16.0);2.561(0.4);2.553(0.5);2.542(0.9);2.526(2.5);2.513(51.8);2.509(106.8);2.504(142.7);2.500(103.3);2.495(49.8);2.335(0.6);2.326(0.6);2.024(0.9);1.993(0.8);1.982(0.4);1.972(0.8);0.000(0.9)

Example 19: $^1$H-NMR(400.0 MHz, $d_6$-DMSO): δ = 9.084(1.6);9.063(1.6);8.378(5.5);7.618(1.0);7.608(1.7);7.600(1.7);7.594(1.3);7.456(2.1);7.448(6.9);7.439(5.6);7.425(1.2);7.358(1.0);7.351(1.2);7.337(1.5);7.213(0.5);7.196(2.5);7.188(2.6);7.178(2.9);7.162(0.7);7.127(1.8);7.112(1.2);7.105(1.0);5.206(0.9);5.189(1.0);5.172(0.5);3.968(3.3);3.951(0.9);3.933(1.2);3.916(1.0);3.901(15.9);3.385(270.1);3.377(251.2);3.364(235.8);3.354(256.6);3.177(0.7);3.164(0.7);2.805(0.4);2.780(0.9);2.763(2.0);2.750(2.0);2.708(0.4);2.673(1.4);2.543(1.3);2.509(179.2);2.504(233.9);2.500(172.3);2.370(16.0);2.331(1.4);2.311(1.4);2.070(0.4);2.033(0.8);2.024(0.8);2.011(0.6);1.940(0.6);1.914(0.7);1.894(0.6);1.874(0.6);1.855(0.8);1.822(1.1);1.806(1.4);1.593(7.0);1.576(7.2);1.566(7.3);1.548(6.8);1.237(0.4);0.000(1.6)

Example 20: $^1$H-NMR(400.0 MHz, $d_6$-DMSO): δ = 9.084(1.4);9.063(1.4);8.416(5.5);7.623(1.1);7.616(1.8);7.607(1.8);7.602(1.3);7.465(2.1);7.456(7.1);7.447(5.9);7.433(1.3);7.383(1.0);7.372(1.5);7.362(1.4);7.296(0.7);7.285(1.3);7.274(2.1);7.263(1.3);7.252(4.2);7.245(2.7);7.239(2.5);7.230(2.4);7.224(1.7);5.525(1.0);5.506(1.5);5.486(0.5);3.995(0.4);3.977(0.9);3.960(1.2);3.942(0.9);3.925(0.5);3.906(11.3);3.411(202.6);3.402(196.6);3.385(161.9);3.377(169.7);3.361(216.8);3.182(0.5);3.169(0.5);3.015(0.6);3.000(0.6);2.983(0.9);2.974(0.9);2.961(1.0);2.953(0.9);2.907(0.7);2.886(1.4);2.866(1.1);2.846(0.8);2.827(0.5);2.678(1.1);2.547(1.5);2.514(141.1);2.509(180.3);2.505(133.3);2.378(16.0);2.336(1.1);1.967(0.3);1.945(0.9);1.934(0.5);1.924(0.9);1.914(0.9);1.904(0.4);1.894(0.8);1.597(7.0);1.579(13.0);1.561(6.8)

Example 21: $^1$H-NMR(400.0 MHz, $d_6$-DMSO): δ = 3.555(16.0);3.551(15.7);3.541(14.1);3.529(13.3);3.525(13.6);3.519(13.2);3.513(13.4);3.505(14.6);3.499(15.5);3.494(15.2);2.523(2.0);2.519(4.2);2.514(5.7);2.510(4.2);2.505(2.0)

Example 22: $^1$H-NMR(400.0 MHz, $d_6$-DMSO): δ = 9.668(2.2);9.663(4.0);9.090(2.2);9.070(2.3);9.038(4.7);8.704(5.9);8.702(5.9);7.842(2.2);7.822(2.5);7.617(2.9);7.597(3.5);7.485(1.3);7.467(3.0);7.448(1.9);7.419(1.9);7.414(2.1);7.399(2.5);7.395(2.6);7.380(1.0);7.376(1.0);7.357(2.0);7.339(2.7);7.314(1.7);7.296(3.3);7.273(1.4);7.256(2.8);7.236(3.4);7.218(2.3);7.201(0.8);5.616(0.6);5.596(1.8);5.576(1.8);5.557(0.6);3.902(16.0);3.899(14.9);3.417(254.2);3.414(264.0);3.395(194.4);3.387(191.1);3.376(177.0);3.371(172.9);3.364(210.1);3.358(219.0);3.177(0.6);3.164(0.6);3.061(0.8);3.047(0.8);3.038(0.8);3.029(1.1);3.021(1.2);3.007(1.2);3.000(1.1);2.930(0.8);2.910(1.7);2.889(1.3);2.871(1.0);2.850(0.6);2.678(1.0);2.674(1.3);2.669(1.0);2.564(0.7);2.557(0.7);2.545(1.3);2.513(81.5);2.509(167.9);2.504(226.0);2.500(165.7);2.496(82.2);2.336(0.9);2.331(1.3);2.327(1.0);2.048(0.5);2.027(1.3);2.017(0.6);2.007(1.3);1.996(1.2);1.985(0.5);1.975(1.1);1.955(0.4);0.000(1.0)

Example 23: $^1$H-NMR(400.0 MHz, $d_6$-DMSO): δ = 9.121(1.3);9.101(1.2);8.880(4.3);8.628(4.9);8.173(4.8);7.528(5.9);7.507(5.9);7.403(1.3);7.393(1.7);7.384(1.7);7.303(0.9);7.290(1.6);7.280(2.6);7.271(2.0);7.262(5.8);7.254(3.9);7.248(3.3);7.240(3.0);5.562(0.6);5.541(1.7);5.522(1.7);5.504(0.6);3.972(0.5);3.955(1.0);3.938(1.4);3.920(1.1);3.901(9.5);3.689(0.4);3.680(0.4);3.625(0.5);3.620(0.4);3.561(0.8);3.442(221.8);3.436(215.7);3.428(220.3);3.417(185.1);3.407(182.6);3.392(167.2);3.386(166.8);3.379(199.3);3.370(175.5);3.198(0.3);3.177(0.5);3.165(0.4);3.029(0.5);3.022(0.6);3.008(0.6);2.998(0.6);2.989(1.0);2.981(1.1);2.967(1.0);2.960(1.0);2.917(0.7);2.897(1.6);2.877(1.3);2.857(0.9);2.836(0.5);2.579(0.6);2.568(0.9);2.558(1.2);2.548(1.1);2.537(1.8);2.528(3.8);2.510(146.3);2.506(194.4);2.501(142.4);2.332(0.8);2.332(1.1);0.5);1.975(1.952(1.2);1.941(0.5);1.932(1.2);1.921(1.2);1.911(0.5);1.901(1.1);1.879(0.4);1.579(8.3);1.561(16.0);1.544(8.3);1.234(0.3);0.000(1.1)

Example 24: $^1$H-NMR(400.0 MHz, $d_6$-DMSO): δ = 9.120(1.3);9.100(1.4);8.644(6.9);8.569(4.5);7.798(2.1);7.779(2.3);7.608(2.3);7.605(2.5);7.588(2.8);7.585(3.0);7.466(1.2);7.451(2.7);7.448(2.7);7.432(1.8);7.429(1.7);7.404(2.2);7.400(3.2);7.385(3.6);7.380(3.7);7.366(3.7);7.362(1.0);7.300(0.8);7.288(1.5);7.278(2.5);7.268(1.9);7.258(5.7);7.250(3.6);7.244(3.2);7.236(3.0);7.227(0.5);5.559(0.6);5.539(1.7);5.519(1.7);5.499(0.6);3.985(0.5);3.967(1.0);3.951(1.3);3.934(1.1);3.914(0.6);3.901(9.6);3.632(0.4);3.619(0.4);3.431(258.5);3.407(182.4);3.397(189.0);3.388(179.8);3.382(179.9);3.375(209.5);3.369(203.2);3.238(0.5);3.228(0.4);3.217(0.4);3.178(0.4);3.165(0.3);3.027(0.5);3.019(0.6);3.005(0.6);2.996(0.6);2.988(1.0);2.978(1.1);2.957(1.0);2.914(0.8);2.893(1.6);2.873(1.3);2.854(0.8);2.833(0.5);2.674(1.1);2.582(0.6);2.573(0.6);2.563(1.1);2.552(1.4);2.542(1.6);2.510(143.7);2.506(186.6);2.501(137.6);2.332(1.0);1.973(0.4);1.952(1.2);1.941(0.5);1.932(1.2);1.921(1.2);1.910(0.5);1.900(1.0);1.879(0.4);1.601(8.5);1.583(16.0);1.565(8.4);0.000(1.2)

Example 25: $^1$H-NMR(400.0 MHz, $d_6$-DMSO): δ = 18.355(0.4);16.141(0.3);9.120(3.5);9.100(3.5);8.871(7.3);8.595(8.3);8.188(7.1);8.169(8.1);7.978(0.3);7.523(9.4);7.503(9.4);7.384(3.3);7.367(3.8);7.233(1.4);7.212(5.0);7.203(6.0);7.194(5.7);7.175(1.6);7.136(4.7);7.120(2.5);5.192(1.1);5.222(2.2);5.207(2.5);5.192(1.1);4.106(0.4);4.058(0.3);4.044(0.3);3.946(0.8);3.931(1.1);3.912(2.7);3.901(15.8);3.899(16.0);3.836(0.4);3.801(0.5);3.788(0.4);3.752(0.4);3.727(0.6);3.710(0.6);3.702(0.6);3.690(0.6);3.663(0.7);3.594(1.0);3.584(1.1);3.550(1.7);3.431(531.7);3.415(436.6);3.399(413.8);3.392(401.1);3.386(395.8);3.379(469.9);3.373(428.5);3.289(2.3);3.213(0.9);

-continued 3.192(0.8);3.165(1.0);3.178(0.6);3.154(0.6);3.102(0.4);3.080(0.4);3.060(0.4);3.102(0.4);2.953(0.3);2.832(0.5);2.818(0.6);2.791(2.0);2.773(4.6);2.760(4.7);2.721(0.6);2.704(0.4);2.697(0.4);2.679(1.8);2.674(2.5);2.670(1.8); 2.528(6.7);2.514(159.6);2.510(333.6);2.505(446.7);2.501(322.6);2.496(155.0);2.461(1.0);2.447(0.8);2.443(0.7);2.427(0.5);2.421(0.5);2.402(0.5);2.337(1.9);2.332(2.5);2.328(1.8);2.058(1.9);2.010(0.4);1.947(1.4);1.922(1.8); 1.898(1.6);1.890(1.6);1.869(1.9);1.835(2.9);1.819(3.3);1.623(0.4);1.604(0.5);1.579(14.3);1.561(15.5);1.553(16.0);1.535(14.2);1.506(0.4);1.248(0.5);0.659(0.3);0.000(1.6);−0.232(0.3).
Example 26: $^{1}$H-NMR(400.0 MHz, d$_6$-DMSO): δ = 9.064(0.9);9.055(4.2);9.043(1.1);8.288(4.7);8.283(5.3);7.468(1.3);7.463(2.6);7.459(1.5);7.382(0.8);7.372(0.8);7.359(0.9);7.210(1.5);7.205(1.1);7.199(1.4); 7.193(1.2);7.187(1.9);7.144(1.0);7.131(0.8);7.121(0.5);5.256(0.5);5.237(0.6);3.901(16.0);3.356(376.4);3.348(333.4);3.344(341.1);3.176(0.8);3.163(0.8);2.915(10.2);2.805(0.6);2.786(1.1);2.772(1.2);2.731(0.3);2.672(1.4); 2.508(175.0);2.503(228.3);2.499(165.7);2.330(1.3);2.086(0.4);2.064(0.4);1.935(0.4);1.834(0.7);0.000(0.9).
Example 27: $^{1}$H-NMR(400.0 MHz, d$_6$-DMSO): δ = 9.029(1.6);9.009(1.6);8.627(4.9);7.812(4.0);7.791(5.2);7.759(6.2);7.538(5.5);7.398(1.3);7.386(1.8);7.377(1.6);7.307(0.8);7.297(1.5);7.284(2.4);7.271(1.1);7.258(4.1); 7.247(3.0);7.242(2.0);7.237(2.6);7.223(0.4);5.584(0.5);5.564(1.5);5.544(1.6);5.524(0.4);3.402(216.6);3.375(152.8);3.363(193.8);3.183(0.4);3.170(0.5);3.039(0.5);3.031(0.6);3.017(0.6);3.009(0.6); 3.000(1.0);2.992(1.0);2.977(1.0);2.969(1.0);2.911(14.4);2.880(1.2);2.862(0.8);2.841(0.8);2.679(1.1);2.674(0.8);2.624(16.0);2.575(0.5);2.568(0.6);2.557(1.0);2.546(1.5);2.532(3.8);2.518(70.6);2.514(145.6); 2.510(194.1);2.505(140.6);2.500(68.2);2.463(0.3);2.345(0.4);2.341(0.8);2.336(1.1);2.332(0.8);2.010(0.4);1.989(1.1);1.979(0.5);1.968(1.1);1.958(1.1);1.947(0.5);1.936(1.0);1.915(0.3);0.005(0.5).
Example 28: $^{1}$H-NMR(400.0 MHz, d$_6$-DMSO): δ = 3.564(16.0);3.558(15.0);3.548(13.4);3.538(12.6);3.532(13.1);3.523(12.7);3.519(14.3);3.511(14.3);3.505(15.2);3.495(13.6);2.875(0.4);2.608(0.4);2.519(1.8);2.514(3.9); 2.510(5.3);2.505(3.9);2.501(1.9).
Example 29: $^{1}$H-NMR(400.0 MHz, d$_6$-DMSO): δ = 9.091(1.5);9.070(1.5);8.472(5.0);7.782(3.8);7.761(5.1);7.542(5.6);7.521(5.0);7.367(1.4);7.350(1.6);7.224(2.7);7.206(2.7);7.197(2.7);7.188(3.0);7.183(2.4);7.169(0.7); 7.133(1.8);7.117(1.2);7.112(1.1);5.196(1.0);3.950(0.9);3.933(1.2);3.915(1.0);3.901(16.0);3.415(367.8);3.408(340.9);3.392(297.9);3.380(263.8);3.362(298.9);3.177(1.5);3.164(1.5);2.771(2.0);2.757(2.1);2.714(0.4); 2.674(1.0);2.605(15.2);2.509(207.9);2.505(276.4);2.500(209.8);2.331(1.5);2.036(0.9);1.920(0.7);1.878(0.6);1.852(0.8);1.826(1.2);1.811(1.4);1.578(6.8);1.560(7.3);1.552(8.0);1.534(6.9);0.000(1.9).
Example 30: $^{1}$H-NMR(400.0 MHz, d$_6$-DMSO): δ = 9.537(2.3);9.532(3.6);9.051(1.9);9.031(1.8);9.012(3.8);7.848(3.2);7.729(1.7);7.709(2.1);7.525(3.6);7.505(2.0);7.463(2.2);7.403(2.2);7.383(1.6);7.345(1.6); 7.327(2.3);7.312(1.5);7.294(2.8);7.271(1.2);7.254(2.3);7.235(2.9);7.216(1.9);7.198(0.6);5.611(0.5);5.592(1.5);5.572(1.5);5.552(0.5);3.901(16.0);3.428(254.9);3.406(161.1);3.401(158.0);3.396(159.6);3.392(159.6); 3.387(157.4);3.382(152.9);3.374(170.3);3.367(177.4);3.177(0.6);3.164(0.6);3.058(0.7);3.044(0.7);3.035(0.7);3.026(1.0);3.018(1.1);3.004(1.0);2.996(1.0);2.928(0.7);2.908(1.4);2.887(1.1);2.868(0.9);2.847(0.5); 2.674(1.0);2.615(16.0);2.552(0.7);2.541(1.2);2.509(127.2);2.505(171.2);2.501(129.2);2.332(1.0);2.044(0.4);2.023(1.1);2.013(0.5);2.002(1.1);1.991(1.1);1.980(0.5);1.970(1.0);1.949(0.4);−0.001(0.9).
Example 31: $^{1}$H-NMR(400.0 MHz, d$_6$-DMSO): δ = 9.063(1.7);9.044(1.8);8.910(3.5);8.726(3.3);8.721(4.3);8.215(4.0);8.210(4.1);8.193(5.1);7.531(3.3);7.520(5.9);7.510(5.7);7.406(1.5);7.395(2.1);7.387(1.9);7.296(1.7); 7.283(2.8);7.270(1.2);7.257(4.8);7.247(3.4);7.236(3.1);5.585(0.6);5.566(1.8);5.546(1.8);5.526(0.6);3.901(10.7);3.898(7.8);3.420(314.2);3.405(296.7);3.391(245.3);3.384(241.3);3.371(296.6);3.367(299.0);3.176(0.7); 3.030(0.8);3.016(0.8);2.999(1.2);2.991(1.4);2.976(1.3);2.968(1.3);2.927(16.0);2.901(2.0);2.881(1.4);2.861(1.1);2.842(0.6);2.673(1.6);2.582(0.7);2.573(0.8);2.562(1.2);2.553(1.6);2.541(1.8);2.509(198.1);2.504(261.5); 2.500(192.9);2.331(1.5);2.009(0.5);1.988(1.3);1.978(0.6);1.967(1.3);1.946(0.6);1.936(1.1);1.914(0.4);0.000(1.3).
Example 32: $^{1}$H-NMR(400.0 MHz, d$_6$-DMSO): δ = 9.092(1.9);9.071(1.9);8.504(4.5);8.493(2.0);7.763(5.4);7.545(6.2);7.524(5.8);7.377(1.9);7.369(2.0);7.295(0.9);7.285(1.8);7.274(2.8);7.265(1.9);7.255(5.2); 7.247(3.8);7.242(3.6);7.233(2.9);5.551(0.6);5.531(1.7);5.510(1.7);5.492(0.6);3.971(1.9);3.901(7.8);3.894(3.2);3.714(0.3);3.703(0.4);3.433(315.9);3.422(263.8);3.410(238.8);3.402(253.1);3.391(241.1); 3.379(264.5);3.198(0.5);3.166(0.6);3.016(0.7);2.983(1.1);2.976(1.2);2.962(1.2);2.954(1.1);2.908(0.8);2.889(1.7);2.868(1.3);2.848(0.9);2.828(0.6);2.674(1.4);2.607(16.0);2.565(0.7);2.542(1.6);2.509(169.0); 2.505(226.5);2.501(173.4);2.331(1.3);1.969(0.4);1.947(1.1);1.937(0.6);1.926(1.2);1.896(1.0);1.874(0.4);1.577(7.9);1.559(15.2);1.541(7.9);0.000(1.1).
Example 33: $^{1}$H-NMR(400.0 MHz, d$_6$-DMSO): δ = 9.527(2.1);9.522(3.2);9.049(1.6);9.028(1.7);8.990(4.8);7.562(6.4);7.541(5.7);7.342(1.6);7.324(2.3);7.311(1.5);7.294(2.8);7.269(1.1); 7.255(2.3);7.235(2.7);7.216(1.8);7.198(0.6);5.610(0.6);5.590(1.4);5.570(1.5);5.553(0.5);3.901(7.6);3.575(0.5);3.548(0.6);3.438(214.1);3.435(210.7);3.415(174.0);3.403(166.4);3.394(159.0);3.389(156.5); 3.382(190.0);3.375(177.9);3.283(0.8);3.277(0.7);3.185(0.5);3.177(0.5);3.064(0.5);3.057(0.6);3.043(0.6);3.033(0.7);3.025(1.0);3.017(1.1);3.003(1.0);2.995(0.9);2.925(0.7);2.906(1.4);2.886(1.1);2.865(0.8);2.845(0.5); 2.680(0.8);2.675(1.1);2.671(0.8);2.602(16.0);2.557(0.6);2.550(0.7);2.537(1.2);2.528(3.4);2.515(62.5);2.510(132.5);2.506(179.0);2.501(129.1);2.497(61.9);2.337(0.7);2.332(1.1);2.328(0.8);2.043(0.5);2.022(1.2);1); 2.011(0.5);2.001(1.1);1.991(1.2);1.980(0.5);1.970(1.0);0.000(1.0).
Example 34: $^{1}$H-NMR(400.0 MHz, d$_6$-DMSO): δ = 9.657(5.3);9.1154(4.9);9.112(5.9);9.088(2.7);9.068(2.8);8.988(7.5);8.508(0.4);8.266(5.5);8.145(2.6);8.126(2.8);7.518(2.8);7.498(5.8);7.478(3.3);7.359(2.6);7.341(6.6); 7.319(4.0);7.298(4.2);7.274(2.0);7.257(3.7);7.239(4.1);7.220(2.9);7.203(1.2);5.616(0.8);5.596(2.4);5.577(2.5);5.557(0.9);3.901(16.0);3.398(383.0);3.392(330.7);3.385(304.5);3.368(260.8);3.353(381.7);3.177(1.0);3.164(1.0); 3.064(1.1);3.050(1.2);3.023(1.6);3.023(1.7);3.010(1.7);3.003(1.7);2.932(1.1);2.912(2.2);2.892(1.8);2.873(1.4);2.853(0.8);2.731(0.4);2.678(1.5);2.674(2.1);2.566(1.0);2.557(1.7);2.547(1.9);2.527(6.9);2.513(125.4);2.509(257.3); 2.505(343.4);2.500(252.5);2.336(1.4);2.331(1.9);2.327(1.5);2.049(0.7);2.028(1.8);2.018(0.8);2.007(1.7);1.996(1.7);1.987(0.8);1.976(1.5);1.954(0.6);1.235(0.5);1.005(0.4);0.988(0.7);0.970(0.4);0.067(0.4); 0.000(1.5).
Example 35: $^{1}$H-NMR(400.0 MHz, d$_6$-DMSO): δ = 9.063(1.3);9.046(6.1);8.792(5.4);8.583(3.1);8.467(1.5);8.447(1.7);7.720(0.9);7.700(2.2);7.680(1.5);7.619(2.1);7.600(1.5);7.418(1.2);7.407(1.7);7.398(1.6);7.297(1.3); 7.285(2.1);7.272(1.0);7.258(3.5);7.248(2.8);7.238(2.5);5.588(0.5);5.568(1.5);5.548(1.6);5.528(0.6);3.901(9.7);3.418(193.1);3.405(226.7);3.385(168.3);3.366(155.7);3.354(158.9);3.177(0.6);3.164(0.7);3.034(0.6);3.020(0.6); 3.002(1.0);2.994(1.0);2.980(1.0);2.972(1.0);2.948(16.0);2.925(1.0);2.904(1.5);2.883(1.1);2.864(0.8);2.844(0.5);2.673(1.0);2.585(0.5);2.565(1.0);2.556(1.1);2.544(1.3);2.509(127.0);2.505(159.4);2.500(121.3); 2.331(0.9);2.012(0.4);1.991(1.0);1.981(0.5);1.970(1.0);1.959(1.0);1.939(0.9);0.000(1.1).
Example 36: $^{1}$H-NMR(400.0 MHz, d$_6$-DMSO): δ = 9.121(2.4);9.100(2.5);8.928(6.8);8.925(5.7);8.637(7.2);8.273(5.8);8.115(2.7);8.095(3.0);7.499(3.0);7.479(6.4);7.459(6.4);7.390(2.5);7.373(3.1);7.320(3.5);7.315(3.6); 7.301(2.8);7.296(2.9);7.232(1.0);7.213(4.1);7.204(5.7);7.189(4.0);7.176(1.4);7.137(3.8);7.121(2.4);7.115(2.1);5.208(1.9);5.208(1.9);3.956(0.6);3.939(1.4);3.922(2.0);3.901(16.0);3.427(359.7);3.422(359.6); 3.411(318.8);3.404(296.4);3.393(285.4);3.383(267.0);3.377(258.4);3.370(316.9);3.363(325.4);3.165(0.8);2.817(0.6);2.792(1.6);2.776(3.7);2.762(3.8);2.719(0.6);2.674(2.1);2.669(1.6);2.527(5.4);2.514(124.2); 2.509(261.2);2.505(350.7);2.500(251.9);2.496(119.9);2.336(1.4);2.332(2.0);2.327(1.5);2.095(0.7);2.072(1.1);2.059(1.5);1.947(1.0);1.921(1.4);1.899(1.2);1.889(1.1);1.869(1.5);1.837(2.1);1.822(2.6);1.581(12.3);1.563(13.1); 1.556(13.6);1.538(12.0);1.235(0.4);0.000(1.7).
Example 37: $^{1}$H-NMR(400.0 MHz, d$_6$-DMSO): δ = 3.548(16.0);3.519(15.0);3.508(12.0);3.501(13.4);3.495(14.3);3.491(14.3);2.514(3.8);2.510(5.0);2.505(3.8);1.565(0.4).
Example 38: $^{1}$H-NMR(400.0 MHz, d$_6$-DMSO): δ = 9.065(1.5);9.039(5.7);9.034(3.7);8.762(5.0);8.579(3.5);8.461(1.6);8.442(1.7);7.717(1.2);7.698(2.7);7.678(1.7);7.617(2.4);7.598(1.6);7.384(1.3);7.375(1.6);7.363(1.8); 7.224(0.5);7.211(3.0);7.200(3.1);7.189(3.7);7.176(0.7);7.144(2.2);7.132(1.5);7.122(1.1);5.273(0.5);5.256(1.1);5.239(1.2);5.223(0.5);3.990(1.9);3.588(0.4);3.422(262.7);3.419(263.8);3.411(246.7);3.391(217.6);3.387(215.6); 3.379(197.7);3.368(242.8);3.177(0.6);3.165(0.5);2.928(16.0);2.833(0.4);2.805(1.0);2.788(2.2);2.772(2.3);2.758(1.1);2.731(0.4);2.675(1.2);2.509(162.7);2.505(205.7);2.502(151.4);2.332(1.2);2.100(0.4);2.066(1.0); 2.043(0.7);1.967(0.6);1.954(0.7);1.937(0.9);1.916(0.8);1.908(0.7);1.888(1.0);1.862(0.9);1.854(0.9);1.837(1.3);1.807(0.7);0.000(1.3).
Example 39: $^{1}$H-NMR(400.0 MHz, d$_6$-DMSO): δ = 9.124(2.6);9.102(2.5);9.000(7.6);8.666(8.1);8.562(6.0);8.433(2.7);8.413(3.0);7.714(2.2);7.694(4.9);7.674(3.2);7.614(4.3);7.594(2.9);7.398(2.8);7.381(3.3);7.235(1.1); 7.221(3.4);7.213(4.1);7.206(6.0);7.195(4.7);7.190(4.2);7.177(1.5);7.171(3.5);7.138(4.1);7.121(2.6);7.115(2.3);5.227(1.7);5.209(2.0);4.078(0.4);4.014(0.3);3.996(0.4);3.980(0.8);3.962(1.8);3.944(2.3);3.927(1.8);3.901(1.5);

| |
|---|
| 3.843(0.4);3.818(0.4);3.736(0.4);3.701(0.6);3.689(0.6);3.662(0.7);3.652(0.8);3.641(0.8);3.619(0.8);3.533(1.7);3.434(451.5);3.431(473.2);3.423(411.2);3.412(381.4);3.400(353.0);3.391(346.4);3.385(340.2);3.378(402.0);3.372(389.2);3.292(1.8);3.213(0.7);3.178(0.7);3.165(0.7);3.136(0.3);3.096(0.3);3.084(0.3);2.832(0.3);2.815(0.5);2.792(1.6);2.775(3.8);2.762(4.0);2.719(0.6);2.706(0.4);2.679(1.6);2.675(2.2);2.670(1.6);2.572(0.4);2.566(0.5);2.528(6.4);2.515(137.7);2.510(289.3);2.506(390.5);2.501(282.1);2.497(135.2);2.336(1.6);2.333(2.3);2.328(1.7);2.100(0.6);2.095(0.7);2.073(1.3);2.059(1.7);2.038(1.2);1.963(0.5);1.950(1.2);1.937(1.2);1.922(1.5);1.903(1.3);1.892(1.2);1.884(1.0);1.872(1.6);1.840(2.3);1.824(2.9);1.803(1.2);1.778(0.7);1.762(0.4);1.587(13.9);1.570(15.3);1.563(16.0);1.545(13.9);1.255(0.6);0.852(0.5);0.833(0.5);0.809(0.4);0.000(2.1)−3.342(0.3) |
| Example 40: ¹H-NMR(400.0 MHz, d₆-DMSO): δ = 9.130(1.4);9.110(1.3);8.938(4.2);8.672(4.5);8.277(3.9);8.273(3.0);8.123(1.7);8.104(1.7);8.487(4.0);7.467(2.3);7.415(1.2);7.403(1.7);7.393(1.8);7.327(2.1);7.323(2.1);7.305(2.4);7.284(2.6);7.276(1.7);7.266(5.4);7.258(3.7);7.252(3.3);7.244(2.9);5.568(0.5);5.547(1.6);5.527(1.6);5.508(0.6);3.984(0.5);3.965(0.9);3.949(1.3);3.931(1.1);3.904(11.4);3.633(0.3);3.599(0.4);3.567(0.6);3.540(0.9);3.440(275.7);3.419(204.1);3.412(205.5);3.399(173.3);3.393(172.7);3.387(209.7);3.180(0.5);3.035(0.6);3.026(0.7);3.012(0.7);3.003(0.7);2.986(1.1);2.972(1.1);2.964(1.0);2.922(0.8);2.902(1.6);2.881(1.2);2.862 (0.9);2.842(0.6);2.679 (1.1);2.674(0.8);2.594(0.5);2.584(0.5);2.574(0.8);2.564(1.1);2.554(1.1);2.543(1.5);2.533(3.3);2.514(133.8);2.509(179.2);2.505(133.8);2.336(1.0);1.978(0.4);1.957 (1.1);1.947(0.6);1.936(1.2);1.926(1.2);1.915(0.6);1.905(1.0);1.883(0.4);1.884(8.2);1.567(16.0);1.549(8.4);0.003(0.5) |
| Example 41: ¹H-NMR(400.0 MHz, d₆-DMSO): δ = 9.055(1.3);9.034(1.4);8.903(5.8);8.698(6.2);8.211(4.4);8.195(1.7);8.190(4.9);7.535(0.7);7.528(5.3);7.524(1.9);7.511(1.7);7.507(5.2);7.376(1.0);7.367(1.2);7.354(1.4);7.223(0.8);7.209(2.1);7.205(1.7);7.198(2.4);7.192(1.9);7.186(2.6);7.174(0.6);7.143(1.6);7.130(1.1);7.120(0.8);5.257(0.8);5.241(0.8);5.224(0.4);3.901(11.1);3.350(18.4);3.338(127.8);3.176(0.5);3.163(0.5);3.145(0.8);2.908(16.0);2.804(0.7);2.787(1.5);2.771(1.9);7.186(2.6);7.174(0.6);7.143(1.6);7.130(1.1);7.120(0.8);2.667(0.6);2.672(0.8);2.667(0.6);2.525(2.2);2.512(50.6);2.507(106.5);2.503(143.5);2.494(50.3);2.334(0.6);2.330(0.8);2.325(0.6);2.083(0.5);2.065(0.7) (0.5);1.964(0.4);1.949(0.5);1.936(0.6);1.914(0.5);1.887(0.7);1.862(0.6);1.853(0.6);1.819(0.5);1.806(0.5);0.000(1.2) |
| Example 42: ¹H-NMR(400.0 MHz, d₆-DMSO): δ = 9.049(1.1);9.028(1.2);8.661(7.7);8.646(6.2);7.820(1.5);7.815(1.6);7.801(1.7);7.796(1.8);7.610(1.7);7.607(1.7);7.590(2.0);7.587(2.1);7.474(0.7);7.471(0.8);7.456(1.8);7.452(1.8);7.437(1.2);7.433(1.1);7.405(1.0);7.401(1.4);7.386(1.5);7.381(1.7);7.372(1.2);7.359(1.4);7.362(1.7);7.349(1.3);7.207(2.0);7.202(1.5);7.196(2.1);7.189(1.7);7.184(2.5);7.171(0.5);7.141(1.4);7.129(1.0);7.118(0.7);5.273(0.5);7.257(0.5);5.240(0.7);5.223(0.3);3.901 (1.9);3.346(134.0);3.339(128.5);3.176(0.5);3.163(0.5);2.928(1.6);2.785(1.3);2.770(1.5);2.755(0.6);2.676(0.5);2.672(0.7);2.667(0.5);2.525(2.0);2.512(44.5);2.507(92.0);2.503(122.5);2.498(87.9);2.494(41.8);2.334(0.5);2.329(0.7);2.325(0.5);2.081 (0.4);2.062(0.6);2.052(0.5);2.038(0.5);1.962 (0.4);1.948(0.4);1.934(0.6);1.911(0.5);1.886(0.6);1.879(0.5);1.866 (0.5);1.860(0.5);1.853(0.5);1.835(0.8);1.817(0.5);1.805(0.4);0.000(1.1) |
| Example 43: ¹H-NMR(400.0 MHz, d₆-DMSO): δ = 9.051(0.8);9.031(0.8);8.674(4.6);8.670(6.1);7.823(1.1);7.819(1.2);7.804(1.2);7.800(1.3);7.612(1.2);7.609(1.3);7.593(1.5);7.589(1.5);7.477(0.7);7.474(0.6);7.459(1.4);7.455(1.3);7.440(0.9);7.436(0.9);7.408 (1.3);7.403(1.6);7.389(1.6);7.384(2.0);7.370(0.6);7.365(0.5);7.304(0.4);7.294(0.7);7.283(1.2);7.275(1.4);7.268(0.5);7.256(2.1);7.251(1.4);7.244(1.4);7.239(1.0);7.234(1.3);5.568(0.9);5.548(0.9);3.901 (6.0);3.357(96.6);3.353(94.1);3.344(88.5);2.997(0.5);2.988(0.5);2.975(0.5);2.967(0.5);2.949(11.6);2.921(0.4);2.900(0.8);2.880(0.6);2.861(0.4);2.676(0.4);2.672(0.5);2.668(0.4);2.560(0.5);2.551(0.5);2.540(0.7);2.525(1.5);2.512(31.6);2.507(66.0);2.503(88.6);2.498(64.6);2.494(31.6);2.330(0.4);2.325(0.4);1.986(0.6);1.965(0.6);1.954(0.6);1.934(0.5);0.000(0.7) |
| Example 44: ¹H-NMR(400.0 MHz, d₆-DMSO): δ = 9.188(0.6);9.055(1.5);9.034(1.5);8.962(6.8);8.865(0.7);8.734(6.3);8.283(2.0);8.247(0.3);8.144(1.6);8.124(1.7);8.502(1.4);7.482(3.0);7.474(0.5);7.462(0.5);7.433(1.1);7.382(1.1);7.372(1.2);7.359(1.4);7.323(1.6);7.320(1.5);7.303(1.4);7.300(1.4);7.223(0.4);7.209(2.4);7.187(2.9);7.174(0.6);7.143(1.7);7.130(1.2);7.121(0.9);5.275(0.4);5.258(0.8);5.241(0.8);5.224(0.4);3.901(9.9);3.322(254.3);3.278(0.3);3.176(0.4);3.163(0.4);2.914(16.0);2.805(0.7);2.788(1.6);2.773(1.8);2.750(0.8);2.731(2.0);2.675(0.8);2.671(1.0);2.666(0.8);2.541(1.0);2.506(130.3);2.497(125.7);2.333(0.8);2.329(1.0);57(0.6);2.048(0.6);2.043(0.6);1.966(0.5);1.953(0.6);1.938(0.7);1.916(0.6);1.908(0.6);1.887(0.7);1.881(0.7);1.868(0.6);1.864(0.7);1.854(0.7);1.837(1.0);1.807(0.5);1.784(0.3);1.235(0.6);0.008(0.5);0.000(12.6);−0.008(0.5) |
| Example 45: ¹H-NMR(400.0 MHz, d₆-DMSO): δ = 9.089(1.5);9.068(1.6);8.513(6.3);7.838(3.4);7.702(1.7);7.683(2.1);7.525(0.7);7.505(2.9);7.485(1.7);7.378(3.2);7.358(3.2);7.224(0.4);7.206(2.6);7.197(2.6);7.188(3.0);7.170(0.7);7.133(1.8);7.117(1.2);5.214(1.0);5.197(1.1);3.976(0.4);3.959(1.0);3.941(1.3);3.924(1.0);3.901(11.4);3.341(302.9);3.163(0.5);2.813(0.3);2.772(2.1);2.759(2.1);2.716(0.4);2.672(1.2);2.623(16.0);2.503(194.7);2.499(153.3);2.329(1.1);2.037(0.9);1.921(0.8);1.881(0.6);1.859(0.8);1.829(1.2);1.814(1.4);1.579(7.3);1.561(7.8);1.553(8.1);1.536(7.2);0.000(1.3) |
| Example 46: ¹H-NMR(400.0 MHz, d₆-DMSO): δ = 9.026(1.5);9.005(1.5);8.627(5.9);7.856(3.3);7.211(1.7);7.701(2.0);7.534(1.5);7.514(3.0);7.494(1.6);7.389(1.8);7.366(2.4);7.355(1.4);7.343(1.5);7.218(0.4);7.206(2.5);7.194(2.4);7.183(3.1);7.171(0.6);7.141(1.8);7.128(1.3);7.118(1.3);7.098(0.4);5.265(0.4);5.249(0.9);5.233(1.0);5.214(0.5);3.901 (10.8);3.364(203.4);3.350(213.9);3.177(0.5);3.164(0.5);2.891(15.7);2.803(0.8);2.785(1.9);2.770(1.9);2.755(0.8);2.725(0.4);2.672 (0.9);2.632 (16.0);2.508(127.1);2.504(153.7);2.499(111.3);2.330(0.9);2.090(0.3);2.057 (0.8);2.046(0.7);2.032 (0.6);1.964(0.5);1.952(0.6);1.936(0.8);1.914(0.6);1.898(0.6);1.877(0.8);1.852(0.7);1.843(0.9);1.826(1.2);1.801 (0.6);0.000(1.0) |
| Example 47: ¹H-NMR(400.0 MHz, d₆-DMSO): δ = 9.682(4.8);9.677(6.1);9.153(5.8);9.148(6.4);9.096(2.7);9.076(3.0);9.068(8.9);8.270(11.6);8.266(14.4);7.487(3.8);7.482(7.3);7.478(4.5);7.360(2.5);7.343(3.3);7.316(2.0);7.298(3.9);7.275(1.0);7.259(3.2);7.239(3.9);7.220(2.6);7.203(0.8);5.614(0.8);5.594(2.4);5.555(0.8);3.901(16.0);3.506(0.4);3.502(0.4);3.375(249.9);3.360(225.0);3.352(261.0);3.256(0.5);3.176(0.5);3.164(0.4);3.071(0.7);3.063(0.8);3.049(0.8);3.041(0.9);3.032(1.3);3.024(1.4);3.011(1.3);3.002(1.2);2.921(1.2);2.913(2.0);2.851 (0.6);2.673(1.2);2.669(0.9);2.567(0.7);2.559(0.8);2.548(1.4);2.537(1.8);2.508(165.2);2.504(212.2);2.500(158.1);2.331(1.2);2.047(0.6);2.026(1.6);1.984(0.7);1.974(1.3);1.953(0.5);1.233(0.5);0.067(0.5);0.000(1.6) |
| Example 48: ¹H-NMR(400.0 MHz, d₆-DMSO): δ = 9.179(1.2);9.159(1.3);8.750(5.8);7.643(2.7);7.585(0.5);7.567(1.5);7.548(3.8);7.543(2.7);7.523(1.1);7.509(1.1);7.515(0.6);7.509(1.1);7.504(0.6);7.411(0.9);7.389(1.2);7.389(1.1);7.304(0.6);7.294(1.0);7.282(1.7);7.272(1.0);7.261(3.6);7.255(2.0);7.248(1.7);7.239(2.0);7.220(0.8);5.560(0.4);5.545(1.1);5.525(1.2);5.505(0.4);3.970(0.8);3.952(1.2);3.935(0.8);3.917(0.4);3.901(16.0);3.344(243.0);3.337(234.2);3.176(0.5);3.163(0.5);3.022(0.4);3.009(0.4);2.991 (0.7);2.982(0.7);2.969(0.7);2.961(0.6);2.920(0.5);2.899(1.1);2.879(0.8);2.860(0.6);2.676(0.8);2.672(1.2);2.667(0.8);2.663(0.4);2.592(0.3);2.583(0.4);2.573(0.6);2.563(0.7);2.552(0.8);2.541(1.1);2.525(3.2);2.512(73.2);2.507(153.3);2.503(205.5);2.498(147.1);2.494(69.4);2.334(0.9);2.329(1.2);2.325(0.9);1.954(0.8);1.943(0.4);1.934(0.7);1.923(0.7);1.913(0.4);1.903(0.7);1.582(6.5);1.564(12.6);1.546(6.4);0.000(1.8) |
| Example 49: ¹H-NMR(400.0 MHz, d₆-DMSO): δ = 9.174(0.7);9.154(0.8);8.720(4.3);7.599(16.0);7.407(0.7);7.396(0.8);7.386(1.1);7.292(0.7);7.281(1.1);7.272(0.7);7.261(2.4);7.254(1.3);7.247(1.2);7.239(1.3);5.543(0.8);5.524(0.8);3.964(0.6);3.946(0.8);3.928(0.6);3.349(116.0);3.339(104.5);3.901(8.5);3.349(116.0);3.339(104.5);3.901(0.5);3.905(0.5);2.967(0.4);2.959(0.4);2.981(0.5);2.967(0.4);2.959(0.4);2.919(0.3);2.899(0.7);2.879(0.5);2.860(0.4);2.677(0.4);2.672(0.6);2.668(0.4);2.571(0.4);2.562(0.5);2.551 (0.5);2.540(0.7);2.525(1.8);2.512 (36.4);2.507(73.6);2.503(97.0);2.498(69.7);2.494(33.6);2.334(0.4);2.330(0.5);2.325(0.4);1.953(0.5);1.933(0.5);1.921(0.5);1.901(0.4);1.580(4.3);1.563(8.4);1.545(4.3);0.000(0.7) |
| Example 50: ¹H-NMR(400.0 MHz, d₆-DMSO): δ = 9.764(2.0);9.758(2.1);9.174(0.9);9.166(2.4);9.154(0.9);7.658(0.7);7.581(0.9);7.563(3.2);7.547(1.4);7.541(1.3);7.536(0.6);7.530(0.4);7.524(0.6);7.518(0.4);7.362(0.8);7.344(1.1);7.319(0.7);7.302(1.0);7.279(0.6);7.264(1.0);7.243(1.2);7.225(0.8);5.594(0.8);5.574(0.8);3.347(119.4);3.339(119.9);3.176(0.6);3.163(0.6);3.053(0.3);3.035(0.3);3.026(0.5);3.012(0.4);3.004(0.5);2.917(0.6);2.897(0.5);2.878(0.4);2.677(0.4);2.672(0.6);2.668(0.4);2.556(0.4);2.547(0.5);2.536(0.6);2.525(1.8);2.512(37.8);2.494(38.1);2.499(78.0);2.494(38.1);2.503(107.1);2.499(78.0);2.494(38.1);2.508(79.4);2.503(107.1);2.499(78.0);2.494(38.1);2.330(0.4);2.028(0.6);2.008(0.5);1.997(0.5);1.976(0.5);1.988(0.5);0.000(0.9) |
| Example 51: ¹H-NMR(400.0 MHz, d₆-DMSO): δ = 9.170(1.7);9.149(1.7);8.717(7.2);8.312(0.4);7.640(3.1);7.595(0.5);7.581(0.9);7.563(1.7);7.545(4.4);7.540(4.3);7.529(2.5);7.523(3.2);7.511(0.7);7.505(1.1);7.501(0.6);7.391(1.1);7.383(1.2);7.369(1.6);7.226(0.4);7.210(2.5);7.201(2.6);7.192(2.8);7.176(0.6);7.138(1.8);7.124(1.7);7.116(0.9);5.243(0.5);5.227(0.9);5.209(0.9);5.193(0.4);3.964(0.4);3.946(1.0);3.929(1.4);3.911(1.2); |

-continued 3.901(16.0);3.372(0.6);3.323(312.1);3.163(0.3);2.791(0.7);2.776(1.8);2.761(1.9);2.746(0.8);2.675(0.8);2.671(1.1);2.666(0.8);2.506(10.5);2.502(168.9);2.497(128.7);2.333(0.8);2.329(1.0);2.324(0.8);2.076(0.5);
2.068(0.6);2.058(0.8);2.040(0.7);1.935(0.5);1.923(0.5);1.897(0.8);1.880(1.1);1.872(0.9);1.862(0.7);1.857(0.7);1.847(0.8);1.830(1.2);1.812(0.7);1.800(0.5);1.792(0.5);1.583(7.3);1.565(7.7);1.557(7.8);1.539(7.2);0.000(6.0)
Example 52: ¹H-NMR(400.0 MHz, d₆-DMSO): δ = 9.059(1.5);9.039(1.6);8.969(5.7);8.763(5.8);8.291(3.4);8.147(1.8);8.127(2.0);7.506(1.4);7.486(3.0);7.466(1.7);7.413(1.3);7.401(1.7);7.393(1.5);7.323(1.9);7.307(2.2);
7.288(2.2);7.272(1.1);7.259(3.7);7.247(2.7);7.237(2.4);5.588(0.5);5.569(1.5);5.549(1.6);5.530(0.6);3.352(194.4);3.342(184.4);3.177(0.6);3.164(0.6);3.032(0.6);3.018(0.6);3.009(0.7);3.000(1.0);2.992(1.0);
2.979(1.0);2.971(1.0);2.933(16.0);2.904(1.5);2.884(1.1);2.864(0.8);2.844(0.5);2.672(0.8);2.585(0.6);2.576(0.8);2.565(1.0);2.556(1.3);2.545(1.6);2.507(104.1);2.503(132.7);2.499(101.7);2.330(0.8);2.010(0.4);1.988(1.0);
1.978(0.5);1.967(1.0);1.957(1.0);1.946(0.5);1.936(0.9);0.000(0.8)
Example 53: ¹H-NMR(400.0 MHz, d₆-DMSO): δ = 9.132(0.8);9.111(0.8);8.774(2.8);7.604(16.0);7.371(0.6);7.359(0.7);7.348(0.8);7.209(1.7);7.200(1.2);7.194(1.3);7.186(2.2);7.176(0.3);7.145(1.0);7.134(0.7);7.123(0.5);
5.257(0.5);5.240 (0.5);3.901(7.3);3.377 (121.5);3.370(107.0);3.357(99.7);3.350(111.3);2.924(8.4);2.807(0.4);2.786(0.9);2.772(1.0);2.756(0.5);2.677(0.4);2.673(0.6);2.669 (0.4);2.526(1.5);2.512(36.6);2.508(75.7);
2.504(101.2);2.499(73.6);2.495(35.9);2.335(0.4);2.326(0.4);2.330(0.6);2.670(0.4);2.049(0.4);1.909(0.4);1.891 (0.5);1.866(0.4);1.859(0.4);1.842(0.5);1.818(0.4);0.000(0.7)
Example 54: ¹H-NMR(400.0 MHz, d₆-DMSO): δ = 9.169(1.1);9.148(1.1);8.685(3.9);8.680(2.0);7.596(16.0);7.380(0.9);7.371(187.9);3.356(203.2);3.348(186.6);2.773(1.4);2.759(1.5);2.744(0.6);2.672(0.8);2.503(136.4);2.499(105.2);2.330(0.7);
5.223(0.7);5.207(0.7);3.936(0.7);3.919(0.9);3.901(8.4);3.897(4.8);3.884(0.3);3.381(195.3);3.371(187.9);3.356(203.2);3.348(186.6);2.773(1.4);2.759(1.5);2.744(0.6);2.672(0.8);2.503(136.4);2.499(105.2);2.330(0.7);
2.056(0.6);2.040(0.5);1.933(0.5);1.921(0.4);1.895(0.6);1.877(0.8);1.856(0.6);1.842(0.6);1.826(1.0);1.809(0.5);1.792(0.4);1.580(4.8);1.565(5.0);1.554(5.4);1.536(4.7);0.000(0.7)
Example 55: ¹H-NMR(400.0 MHz, d₆-DMSO): δ = 9.141(1.2);9.121(1.2);8.831(5.8);7.649(2.9);7.593(0.5);7.574(1.7);7.557(4.3);7.552(3.0);7.528(1.1);7.521(0.7);7.515(1.2);7.510(0.6);7.409(1.0);
7.396(1.4);7.388(1.2);7.308(0.6);7.300(1.0);7.287(1.8);7.279(0.6);7.273(0.8);7.261(2.6);7.257(2.8);7.248(2.5);7.239(1.8);5.588(0.5);5.568(1.4);5.548(1.3);5.529(0.5);3.901(12.7);3.347(178.0);3.339(186.5);3.041(0.4);
3.033(0.4);3.020(0.4);3.011(0.5);3.002(0.7);2.993(0.8);2.980(0.8);2.971(0.8);2.951(16.0);2.906(1.2);2.886(0.9);2.867(0.6);2.847(0.3);2.677(0.7);2.672(0.9);2.668(0.6);2.588(0.3);2.579(0.4);2.569(0.7);2.559(0.8);
2.548(0.9);2.537(1.1);2.525(2.8);2.512(59.9);2.508(123.5);2.503(163.3);2.498(115.8);2.494(54.1);2.334(0.7);2.330(0.9);2.325(0.7);2.013(0.3);1.992(0.9);1.981(0.4);1.971(0.9);1.960(0.8);1.950(0.4);1.940 (0.8);
0.000(1.5)
Example 56: ¹H-NMR(400.0 MHz, d₆-DMSO): δ = 9.181(1.5);9.160(1.6);8.735(6.2);7.920(2.9);7.898(1.3);7.880(1.9);7.831(1.0);7.811(2.6);7.797(2.3);7.777(2.0);7.758(0.7);7.395(1.1);7.387(1.3);7.373(1.6);7.227(0.4);
7.211(2.5);7.202(3.0);7.193(2.9);7.189(2.6);7.176(0.7);7.139(1.9);7.125(1.2);7.116(1.1);5.242(0.4);5.228(1.0);5.209(0.9);3.979(0.3);3.962(1.0);3.944(1.3);3.927(1.0);3.902(16.0);3.351(231.7);3.339(222.6);3.176(0.7);
3.163(0.7);2.776(1.9);2.762(2.0);2.525(1.9);2.512(38.5);2.507 (80.9);2.503(108.3);2.498(72.1);2.494(36.5);2.334(0.4);2.330(0.6);2.325(0.5);1.990 (0.5);1.970(0.5);1.959(0.5);1.939(0.5);1.932(0.9);0.000(0.9)
2.558(0.5);2.547(0.5);2.535(0.7);2.525(1.9);2.512(38.5);2.507 (80.9);2.503(108.3);2.498(72.1);2.494(36.5);2.334(0.4);2.330(0.6);2.325(0.5);1.990 (0.5);1.970(0.5);1.959(0.5);1.939(0.5);1.932(0.9);0.000(0.9)
1.937(0.5);1.899 (0.9);1.882(1.1)
Example 57: ¹H-NMR(400.0 MHz, d₆-DMSO): δ = 9.136(0.8);9.116(0.8);8.804(3.4);7.607(16.0);7.406(0.6);7.393(0.8);7.385(1.0);7.308(0.4);7.299(0.6);7.286(1.0);7.278(0.4);7.272(0.5);7.260(1.5);7.256(1.6);7.247(1.5);
7.238(1.0);5.567(0.8);5.548(0.8);3.901(7.7);3.348(140.6);3.339 (133.3);3.000(0.4);2.978(0.4);2.970(0.4);2.946 (9.0);2.926(0.4);2.904(0.7);2.884(0.5);2.866(0.4);2.677(0.4);2.672(0.6);2.667(0.4);2.567(0.4);
7.442(1.2);7.369(1.0);7.358(1.2);7.346(1.4);7.219(0.3);7.208(2.6);7.201(1.9);7.197(2.0);7.185(3.1);7.174(0.5);7.143(1.6);7.132(1.2);7.121(0.8);5.267(0.4);5.249(0.8);5.234(0.8);5.218(0.4);3.901(7.8);
Example 58: ¹H-NMR(400.0 MHz, d₆-DMSO): δ = 9.092(1.5);9.070(1.6);8.749(6.3);7.935(3.1);7.931(1.8);7.935(1.8);7.931(1.8);7.935(3.1);7.845(2.0);7.580(3.2);7.541(2.0);7.465(1.7);7.462(1.7);7.445(1.2);
7.442(1.2);7.369(1.0);7.358(1.2);7.346(1.4);7.219(0.3);7.208(2.6);7.201(1.9);7.197(2.0);7.185(3.1);7.174(0.5);7.143(1.6);7.132(1.2);7.121(0.8);5.267(0.4);5.249(0.8);5.234(0.8);5.218(0.4);3.901(7.8);
3.327(153.9);3.262(0.6);3.169(1.3);3.105(0.4);2.884(16.0);2.804(0.7);2.787(1.5);2.771(1.6);2.755(0.8);2.675(0.7);2.671(0.9);2.667(0.7);2.506(118.4);2.502(154.3);2.497(117.5);2.329(1.6);2.098(0.4);2.078(0.5);2.069(0.5);
2.059(0.7);2.037(0.6);1.959(0.5);1.947(0.5);1.931(0.7);1.908(0.6);1.884(0.8);1.879(0.6);1.866(0.8);1.860 (0.7);1.852(0.7);1.835(1.0);1.817(0.6);1.804(0.5);1.341(0.5);1.332(0.5);1.324(0.8);1.306(0.4);1.045(0.5);1.030(0.5);
0.000(6.7)
Example 59: ¹H-NMR(400.0 MHz, d₆-DMSO): δ = 9.019(1.8);8.998(1.8);8.657(5.8);7.724(1.9);7.705(2.3);7.535(1.4);7.515(2.9);7.496(1.6);7.387(3.5);7.377(2.1);7.373(1.7);7.292(1.4);7.281(2.1);7.266(0.9);
7.252(3.7);7.242(2.7);7.236(2.2);7.232(2.7);7.218(0.5);7.218(0.5);5.561(1.6);5.522(0.5);5.522(0.5);3.901(9.3);3.323(260.8);3.028(0.5);3.013(0.5);2.996(0.9);2.988(0.9);2.974(1.0);2.912(16.0);2.899(1.8);2.877(1.1);
7.182(3.1);7.171 (0.5);7.140(1.5);7.128(1.1);7.118(0.8);5.262(0.3);5.247(0.7);5.230(0.8);5.212 (0.4);3.901(12.6);3.353(194.7);3.343(185.7);3.176 (0.5);3.163(0.5);2.893(15.2);2.802(0.6);2.784(1.4);2.769(1.5);2.753(0.7);
2.858(0.8);2.836(0.5);2.671(1.2);2.636(15.7);2.572(0.7);2.564(0.7);2.562(0.6);2.542(0.6);2.524(0.2);2.329(1.0);2.005(0.3);1.984(1.0);1.974(0.5);1.963(1.0);1.953(0.9);1.942(0.5);1.932(0.9);0.000(5.9)
Example 60: ¹H-NMR(601.6 MHz, d₆-DMSO): δ = 9.029(1.6);9.015(1.6);8.704(6.1);7.835(7.8);7.832(7.8);7.553(2.8);7.550(3.5);7.546(1.8);7.396(1.1);7.387(1.3);7.383(1.2);7.297(0.8);7.293(1.0);7.284(1.6);7.264(0.4);
7.261(0.6);7.252(1.9);7.249(2.6);7.243(2.7);7.237(2.1);5.567(0.4);5.554(1.3);5.528(0.4);3.322(157.3);3.058(0.5);3.021(0.4);3.015(0.4);3.001(0.5);2.994(0.6);2.989(0.7);2.980(0.7);2.975(0.6);
2.914(15.6);2.892(1.1);2.879(0.8);2.866(0.7);2.852(0.4);2.496(42.4);2.388(0.6);2.385(0.6);2.382(0.6);1.972(0.8);1.965(0.4);1.958(0.9);1.951(0.8);1.944(0.4);1.937(0.8);0.000(2.7)
2.504(89.1);2.501(118.8);2.498(87.2);2.496(42.4);2.388(0.6);2.385(0.6);2.382(0.6);1.972(0.8);1.965(0.4);1.958(0.9);1.951(0.8);1.944(0.4);1.937(0.8);0.000(2.7)
Example 61: ¹H-NMR(400.0 MHz, d₆-DMSO): δ = 9.525(1.9);9.520(2.2);9.038(1.0);9.018(1.0);8.924(2.1);8.918(2.4);7.633(1.8);7.629(3.4);7.624(2.1);7.547(2.2);7.542(2.1);7.537(2.2);7.365(0.9);7.355(1.1);7.343(1.3);7.205(2.5);7.199(1.6);7.194(1.8);7.189(1.8);
7.182(3.1);7.171 (0.5);7.140(1.5);7.128(1.1);7.118(0.8);5.262(0.3);5.247(0.7);5.230(0.8);5.212 (0.4);3.901(12.6);3.353(194.7);3.343(185.7);3.176 (0.5);3.163(0.5);2.893(15.2);2.802(0.6);2.784(1.4);2.769(1.5);2.753(0.7);
2.727(0.3);2.677(0.7);2.672(1.0);2.668(0.8);2.651(16.0);2.525(2.2);2.512(53.8);2.508(114.6);2.503(154.9);2.499(110.8);2.494(52.1);2.334(0.6);2.330(0.9);2.325(0.6);2.074(0.4);2.055(0.6);2.045(0.6);2.031(0.5);1.962(0.5);
1.951(0.4);1.936(0.6);1.911(0.6);1.870(0.5);1.870(0.5);1.852(0.6);1.870(0.5);1.852(0.6);1.843(0.7);1.826 (1.0);0.000(1.2)
Example 62: ¹H-NMR(400.0 MHz, d₆-DMSO): δ = 9.525(1.9);9.520(2.2);9.038(1.0);9.018(1.0);8.924(2.1);8.918(2.4);7.633(1.8);7.629(3.4);7.624(2.1);7.547(2.2);7.542(2.1);7.537(2.2);7.365(0.9);7.355(1.1);7.343(1.3);7.205(2.5);7.199(1.6);7.194(1.8);7.189(1.8);
7.340(0.9);7.322(1.2);7.308(0.8);7.291(1.4);7.268(0.6);7.250(1.2);7.232(1.4);7.222(1.4);7.214(0.9);7.196(0.3);7.118(0.8);5.262(0.3);5.247(0.7);5.230(0.8);5.212 (0.4);3.901(12.6);3.353(194.7);3.343(185.7);3.176 (0.5);3.163(0.5);2.893(15.2);2.802(0.6);2.784(1.4);2.769(1.5);2.753(0.7);
3.052(0.3);3.037(0.4);3.028(0.4);3.019(0.5);3.012(0.5);2.998(0.5);2.990(0.5);2.980(0.5);2.330(0.7);2.017(0.6);1.997(0.6);1.986(0.5);1.965(0.5);0.000(0.5)
2.503(120.8);2.499(89.2);2.495(44.4);2.368(11.5);2.335(0.7);2.330(0.7);2.326(0.5);1.965(0.5);0.000(0.5)
Example 64: ¹H-NMR(400.0 MHz, d₆-DMSO): δ = 9.170(1.3);9.150(1.4);8.697(4.0);7.926(7.1);7.922(7.8);7.633(1.8);7.629(3.4);7.624(2.1);7.547(2.2);7.542(2.1);7.537(2.2);7.365(1.4);7.228(0.4);7.211(2.3);7.203(2.6);7.194(2.7);
7.190(2.1);7.176(0.6);7.139(1.7);7.125(1.1);7.116(1.0);5.227(0.4);5.213(0.8);5.194(0.8);5.890(1.4);3.872(0.9);3.855(0.3);3.681(0.3);3.669(0.3);3.609(0.3);3.446(514.0);3.439(415.0);
3.435(379.4);3.429(395.7);3.424(381.2);3.417(467.6);3.413(445.5);3.231(0.6);3.179(0.5);3.166(0.5);3.141(0.4);3.072(0.3);2.818(0.4);2.791(0.7);2.775(1.7);2.761(1.7);2.746(0.8);2.682(0.8);2.678(1.1);2.673(0.9);
2.547(0.3);2.531(2.3);2.517(65.0);2.513(137.3);2.508(183.6);2.504(132.1);2.499(62.7);2.335(1.1);2.330(0.8);2.087(0.4);2.064(0.5);2.052(0.7);2.036 (0.6);1.939(0.5);1.913(0.7);1.891(0.8);1.869(0.9);1.864(0.8);
1.837(0.9);1.820(1.1);1.794(0.5);1.556(6.8);1.538(7.2);1.530(7.5);1.516(6.7);1.236(0.8);0.000 (1.0)
Example 65: ¹H-NMR(400.0 MHz, d₆-DMSO): δ = 9.064(2.9);9.043(0.6);8.808(2.5);8.292(3.1);8.288(3.2);7.471(0.9);7.467(1.7);7.462(0.9);7.413(0.4);7.402(0.6);7.393(0.5);7.298(0.5);7.285(0.7);7.272(0.3);7.259(1.2);
7.247(0.9);7.237(0.6);7.176(0.6);7.139(1.7);7.125(1.1);7.116(1.0);5.227(0.4);5.213(0.8);5.194(0.8);5.890(1.4);3.872(0.9);3.855(0.3);3.681(0.3);3.669(0.3);3.609(0.3);3.346(286.0);3.337(311.9);3.176(0.4);3.163(0.4);2.935(6.6);2.903(0.5);2.883(0.4);2.676(0.9);2.672(1.2);2.667(0.9);2.566(0.9);2.555(0.5);2.546(0.6);
2.525(3.8);2.512(78.7);2.507(161.4);2.503(214.0);2.498(154.1);2.494(74.6);2.334(0.9);2.329(1.2);2.325(1.0);1.985(0.4);1.964(0.3);0.000(1.8)

-continued

| |
|---|
| Example 66: ¹H-NMR(400.0 MHz, d₆-DMSO): δ = 9.107(1.1);8.822(4.8);7.951(7.2);7.946(7.9);7.646(2.0);7.641(3.8);7.636(2.1);7.405(0.9);7.393(1.2);7.385(1.1);7.306(0.5);7.298(0.9);7.285(1.6);7.271(0.7);7.258(2.2);7.254(2.7);7.246(2.3);7.237(1.8);7.220(0.4);5.577(0.4);5.558(1.2);5.539(1.2);5.519(193.6);3.359(193.6);3.344(188.8);3.176(0.5);3.163(0.5);3.040(0.4);3.032(0.4);3.017(0.5);3.009(0.5);3.000(0.7);2.992(0.8);2.728(0.3);2.673(1.0);2.508(139.2);2.503(177.2);2.499(127.0);2.335(0.8);2.330(1.0);2.059(0.8);1.959(0.5);1.945(0.5);1.929(0.7);1.908(0.7);1.885(0.8);1.859(0.7);1.851(0.7);1.834(1.0);0.000(1.4) 2.503(177.2);2.499(127.3);2.495(60.8);2.335(0.7);2.330(1.0);1.985(0.8);1.975(0.3);1.965(0.8);1.934(0.7);1.944(0.4);1.934(0.7);1.234(0.3);0.000(1.7) |
| Example 67: ¹H-NMR(400.0 MHz, d₆-DMSO): δ = 9.645(2.5);9.640(2.7);9.159(3.0);9.154(2.9);9.127(1.4);9.107(1.4);7.938(7.1);7.934(7.4);7.660(1.9);7.656(3.4);7.651(1.8);7.352(1.2);7.334(1.7);7.317(1.0);7.299(1.9);7.279(0.8);7.276(0.8);7.261(1.6);7.240(1.9);7.222(1.3);7.203(0.5);5.609(0.4);5.589(1.2);5.570(1.2);5.550(0.4);3.901(16.0);3.431(0.8);3.354(291.9);3.343(300.0);3.176(0.5);3.163(0.5);3.071(0.4);3.063(0.4);3.049(0.4);3.040(0.4);3.031(0.6);3.023(0.7);3.009(0.6);2.933(0.5);2.913(1.0);2.893(0.8);2.874(0.6);2.677(1.0);2.672(1.4);2.668(1.0);2.663(0.5);2.559(0.4);2.548(0.8);2.536(1.2);2.525(4.2);2.512(88.7);2.508(184.4);2.503(245.0);2.498(175.0);2.494(82.8);2.334(1.1);2.330(1.4);2.325(1.0);1.4);2.325(1.0);1.4);2.021(0.8);2.011(0.4);2.001(0.8);1.990(0.8);1.980(0.4);1.969(0.7);0.000(1.9) |
| Example 68: ¹H-NMR(400.0 MHz, d₆-DMSO): δ = 9.105(1.4);9.085(1.5);8.792(5.9);7.948(7.9);7.943(8.5);7.643(2.2);7.638(4.1);7.369(2.3);7.369(1.1);7.358(1.3);7.347(1.5);7.208(2.9);7.200(2.2);7.193(2.4);7.186(3.6);7.144(1.7);7.133(1.3);7.122(0.9);5.264(0.9);5.247(0.9);5.231(0.9);3.901(11.6);3.367(193.1);3.362(205.8);3.354(210.0);3.347(238.1);3.176(0.4);3.164(0.4);2.885(16.0);2.829(0.3);2.804(0.8);2.786(1.7);2.771(1.8);2.755(0.8);2.728(0.3);2.673(1.0);2.508(139.2);2.503(177.2);2.499(127.0);2.335(0.8);2.330(1.0);2.059(0.8);1.959(0.5);1.945(0.5);1.929(0.7);1.908(0.7);1.885(0.8);1.859(0.7);1.851(0.7);1.834(1.0);0.000(1.4) |
| Example 69: ¹H-NMR(400.0 MHz, d₆-DMSO): δ = 9.104(1.7);9.083(1.7);8.770(5.5);8.226(3.0);8.201(1.7);8.183(1.8);7.803(0.7);7.783(2.1);7.764(3.2);7.759(3.0);7.739(0.8);7.372(1.1);7.361(1.4);7.350(1.6);7.209(3.2);7.198(2.3);7.193(2.6);7.186(4.1);7.175(0.8);7.144(1.5);7.133(1.5);7.121(1.1);5.264(0.4);5.247(0.9);5.232(0.9);5.221(0.9);3.901(15.1);3.361(314.7);3.346(277.4);3.212(0.4);3.176(0.8);3.164(0.8);3.005(0.3);2.897(16.0);2.829(0.4);2.804(0.9);2.786(1.8);2.771(2.1);2.754(1.3);2.729(0.6);2.681(1.2);2.673(1.4);2.668(1.1);2.526(3.1);2.513(79.6);2.508(169.7);2.504(230.1);2.499(168.2);2.495(82.3);2.335(0.9);2.330(1.3);2.326(1.0);2.078(0.6);2.059(0.8);1.961(0.6);1.946(0.6);1.932(0.8);1.909(0.8);1.861(0.9);1.854(0.8);1.835(1.1);1.235(0.6);0.988(0.5);0.000(1.3) |
| Example 70: ¹H-NMR(400.0 MHz, d₆-DMSO): δ = 9.162(1.7);9.142(1.7);8.716(5.1);8.204(3.4);8.181(1.8);8.163(1.9);7.805(0.7);7.786(2.2);7.767(4.1);7.744(0.9);7.417(1.2);7.405(1.7);7.396(1.6);7.308(0.7);7.298(1.3);7.286(2.4);7.277(1.5);7.265(4.8);7.259(3.1);7.253(2.9);7.243(3.1);7.209(0.6);7.187(0.6);7.185(1.6);5.561(0.6);5.542(1.6);5.522(1.7);5.502(0.6);3.975(0.4);3.958(1.0);3.940(1.4);3.923(1.1);3.907(15.2);3.382(344.4);3.360(325.8);3.183(0.8);3.170(0.7);3.036(0.6);3.027(0.6);3.014(0.7);2.996(1.0);2.988(1.1);2.975(1.1);2.966(1.0);2.923(0.8);2.902(1.2);2.882(1.2);2.862(0.9);2.843(0.5);2.679(1.3);2.590(0.6);2.581(0.7);2.571(1.1);2.561(1.4);2.550(1.6);2.514(167.6);2.510(219.2);2.506(162.4);2.337(1.2);1.980 (0.4);1.959(1.1);1.948(0.5);1.938(1.1);1.927(0.1);1.907 (0.9);1.885(0.4);1.573(8.5);1.555(16.0);1.538(8.2);1.241(0.3);0.000(0.4) |
| Example 71: ¹H-NMR(400.0 MHz, d₆-DMSO): δ = 9.104(1.3);8.801(5.5);8.230(2.9);8.204(1.6);8.185(1.6);7.804(0.7);7.786(2.2);7.767(4.1);7.742(0.7);7.409(1.2);7.396(1.5);7.389(1.4);7.306(0.7);7.297(1.1);7.284(2.0);7.277(0.8);7.271(1.0);7.254(3.3);7.245(2.7);7.236(2.2);7.221(0.4);5.579(0.5);5.560(1.4);5.540(1.5);5.520(0.5);3.901(11.9);3.362(215.4);3.347(191.8);3.342(190.8);3.177(0.5);3.163(0.5);3.041(0.5);3.032(0.5);3.019(0.5);3.010(0.6);3.001(0.9);2.993(0.9);2.979(0.9);2.971(0.8);2.917(16.0);2.902(1.6);2.881(1.2);2.861(0.7);2.841(0.4);2.677(0.8);2.673(1.0);2.669(0.8);2.579(0.4);2.571(0.5);2.559(0.8);2.549(1.0); 2.539(1.1);2.526(3.1);2.508(133.6);2.504(177.1);2.499(130.3);2.334(0.7);2.330(1.0);2.326(0.8);2.011(0.4); |
| Example 72: ¹H-NMR(400.0 MHz, d₆-DMSO): δ = 9.150(1.3);9.129(1.3);9.002(0.3);8.676(6.2);8.668(0.5);8.198(2.5);8.174(1.3);8.156(1.3);7.795(0.5);7.776(1.6);7.758(2.9);7.755(2.8);7.392(1.0);7.384(1.1);7.369(1.3);7.227(0.4);7.214(1.5);7.210(2.2);7.201(2.4);7.192(2.6);7.187(1.8);7.175(0.5);7.169(0.3);7.137(1.5);7.122(1.0);7.114(0.8);5.232(0.4);5.217(0.7);5.199(0.7);3.947(0.4);3.929(0.9);3.911(1.3);3.894(1.0);3.877(0.4);3.348(188.3);3.338(179.6);3.163(0.3);2.790(0.6);2.775(1.5);2.760(1.5);2.745(0.7);2.672(0.9);2.668(0.7);2.542(0.7);2.525(2.7);2.512(57.7);2.508(118.5);2.503(157.4);2.499(113.2);2.494(54.1);2.334(0.6);2.330 (0.8);2.325(0.6);2.073(0.4);2.064(0.5);2.052(0.6);2.042(0.5);2.034(0.5);1.940 (0.4);1.930(0.4);1.914(0.6);1.892(0.7);1.872(0.8);1.823(1.0);1.797(0.4);1.588(0.4);1.567(6.7);1.550(7.0);1.543 (7.2);1.525(6.4);0.000(1.4) |
| Example 73: ¹H-NMR(400.0 MHz, d₆-DMSO): δ = 9.143(1.9);9.122(2.0);8.651(7.8);8.312(0.4);7.889(5.2);7.867(6.2);7.600(6.1);7.579(5.4);7.400(1.2);7.388(1.6);7.379(1.3);7.300(0.7);7.289(1.3);7.278(2.3);7.269(1.4);7.258(4.5);7.251(2.8);7.244(2.5);7.236(2.4);7.226(0.4);5.554(0.6);5.534(1.7);5.514(1.7);5.494(0.6);3.947(0.4);3.930(1.2);3.912(1.7);3.901(7.4);3.877(0.5);3.403(0.4);3.389(0.4);3.325(356.4);3.273(0.4);3.027(0.4);3.019(0.5);3.005(0.5);2.997(0.6);2.988(0.9);2.979(1.0);2.966(0.9);2.957(0.8);1.0);2.966(0.9);2.957(0.9);1.938(0.5);1.928(1.0);1.917(1.0);1.907(0.5);1.897(0.9);1.559(8.3);1.542(16.0);1.528(8.2);0.000(7.1) 2.506(127.6);2.502(165.7);2.498(128.6);2.329(1.0);2.325(0.8);1.970(0.4);1.948(1.0);1.938(0.5);1.928(1.0);1.917(1.0);1.907(0.5);1.897(0.9);1.559(8.3);1.542(16.0);1.528(8.2);0.000(7.1) |
| Example 74: ¹H-NMR(400.0 MHz, d₆-DMSO): δ = 9.067(1.5);8.904(7.5);8.664(5.8);8.312(0.4);7.652(1.5);7.640(1.0);7.635(2.1);7.632(1.5);7.534(0.7);7.525(0.8);7.520(0.9);7.511(1.8);7.505(1.0);7.494(7.2);7.483(1.6);7.380(1.4);7.372(1.3);7.299(0.6);7.291(1.0);7.278(1.4);7.264(0.8);7.248(2.9);7.239(2.4);7.230(1.9);7.214(0.3);5.572(0.4);5.552(1.3);5.532(1.3);5.513(0.4);3.901(9.8);3.378(0.3);3.368(0.5);3.324(260.5);3.031(0.3);3.022(0.4);3.009(0.4);3.000(0.5);2.991(0.7);2.983(0.8);2.969(0.8);2.961(0.7);2.913 (16.0);2.895(1.4);2.874(0.9);2.855(0.6);2.834(0.4);2.675(0.7);2.671(0.9);2.666(0.7);2.570(0.4); 2.562(0.5);2.551(0.8);2.541(1.2);2.506(109.9);2.502(141.1);2.497(107.5);2.333(0.7);2.328(0.9);2.324(0.7);1.965(0.4);1.955(0.8);1.944(0.8);1.934(0.4);1.924(0.7);0.000(6.6) |
| Example 75: ¹H-NMR(400.0 MHz, d₆-DMSO): δ = 9.093(1.4);9.073(1.4);8.970(0.4);8.779(5.7);8.764(0.5);8.312(0.4);7.764(2.9);7.742(1.7);7.738(2.8);7.733(1.9);7.867(1.6);7.848(1.8);7.583(1.4);7.563(2.8);7.543(1.7);7.467(1.6);7.464(1.7);7.447(1.1);7.444(1.1);7.404(1.1);7.392(1.4);7.383(1.3);7.305(0.7);7.297(1.1);7.284(1.9);7.270(0.9);7.254(2.9);7.245(2.5);7.236(2.0);7.221(0.4);5.581(0.4);5.561(1.3);5.541(1.3);5.522(0.5);3.901(7.1);3.373(0.6);3.323(291.7);3.267(0.4);3.039(0.4);3.030(0.4);3.017(0.5);3.009(0.5);3.000(0.8);2.991(0.8);2.978(0.8);2.970(0.7);2.935(1.1);2.922(0.8);2.904(16.0);2.882(1.0);2.863(0.7);2.842(0.4);2.675(0.9);2.671(1.1);2.666(0.9);2.580(0.5);2.571(0.5);2.560(0.9);2.551(1.2);2.540(1.5);2.506(136.5);2.502(174.9);2.497(133.1);2.328(1.0);2.324(0.8);2.009(0.3);1.987(0.9);1.976(0.4);1.967(0.9);1.956(0.8);1.945(0.4);1.935(0.8);0.000(7.8) |
| Example 76: ¹H-NMR(400.0 MHz, d₆-DMSO): δ = 9.142(1.7);9.120(1.7);8.616(8.0);7.886(5.3);7.8822(0.7);7.870(1.9);7.865(6.5);7.859(0.9);7.604(0.8);7.597(6.6);7.593(2.1);7.581(1.8);7.576(5.7);7.569(0.7);7.381(1.2);7.374(1.3);7.359(1.6);7.393(1.1);7.380(1.4);7.372(1.3);7.299(0.6);7.291(1.0);7.278(1.4);7.264(0.8);7.248(2.9);7.186(2.3);7.173(0.6);7.168(0.4);7.135(1.1);7.121(1.1);7.113(1.0);5.230(0.5);5.215(0.9);5.197(0.9);5.181(0.4);3.921(0.5);3.901(16.0);3.886(1.5);3.868(1.1);3.851(0.4);3.346(298.0);3.342(302.1);3.176(0.8);3.163(0.8);2.789(0.7);2.773(1.8);2.758(1.9);2.744(0.8);2.676(0.8);2.672(1.1);2.667(0.8);2.525(2.8);2.512(68.5);2.507(144.1);2.503(193.9);2.498(140.5);2.494(68.3);2.334(0.8);2.329(1.1);2.325(0.8);2.071(0.5);2.061(0.6);2.050(0.7);2.033(0.6);1.938(0.5);1.927(0.7);1.912(0.7);1.888(0.8);1.867(0.9);1.844(0.7);1.835(1.0);1.818(1.2);1.796(0.5);1.559(8.1);1.542(8.4);1.533(8.7);1.516(8.0);0.000(1.8) |
| Example 77: ¹H-NMR(400.0 MHz, d₆-DMSO): δ = 9.077(1.6);9.055(1.7);8.632(6.0);7.651(1.7);7.634(2.2);7.534(0.5);7.524(1.0);7.521(1.0);7.511(1.9);7.493(8.2);7.357(1.1);7.346(1.5);7.335(1.6);7.203(2.8);7.195(2.4);7.188(2.6);7.180(3.5);7.139(1.4);7.129(1.4);7.117(1.0);5.225(1.0);5.243(1.0);5.225(1.0);3.900(12.0);3.544(0.5);3.408(585.6);3.392(526.3);3.177(0.5);3.166(0.5);2.890(16.0);2.822(0.4);2.798(0.9);2.780(1.9);2.764(2.0);2.748(0.9);2.721(0.4);2.675(1.0);2.510(132.2);2.506(167.3);2.502 (124.0);2.333(0.9);2.083(0.4);2.050(0.9);1.936 (0.6);1.921(0.8);1.900(0.9);1.878(0.9);1.842(0.8);1.828(1.1);0.000(0.8) |
| Example 78: ¹H-NMR(400.0 MHz, d₆-DMSO): δ = 9.137(2.0);9.116(2.0);8.529(5.8);7.648(1.9);7.628(2.4);7.625(1.9);7.526(0.9);7.519(1.2);7.510(1.6);7.504(3.5);7.498(2.9);7.488(7.8);7.473(1.5);7.453(0.4);7.354(1.5);7.216(0.6);7.202(3.2);7.191(3.6);7.180(3.8);7.166(0.9);7.130(2.4);7.117(1.7);7.108(1.3);5.222(0.6);5.206(1.2);5.189(1.3);5.173(0.6);3.901(16.0);3.870(0.8);3.355(314.7);3.346(309.8);3.341(291.7);3.176(0.6);3.163(0.6);2.807(0.3);2.781(1.0);2.766(2.5);2.752(2.6);2.736(1.1);2.710(0.4);2.676(1.0);2.672(1.4);2.525(3.7);2.507(175.9);2.503(237.1);2.499(179.4);2.503(237.1);2.499(179.4);2.334(0.9);2.329(1.3);2.326(1.0);2.073(0.4);2.050(0.8); 2.494(68.3);2.329(1.1);2.325(0.8);2.071(0.5);2.061(0.6);2.050(0.7);1.818(1.2);1.796(0.5);1.559(8.1);1.542(8.4);1.533(8.7);1.516(8.0);0.000(1.8) 2.038(1.0);2.022 (0.9);1.904(1.0);1.883(1.1);1.865(1.2);1.843(0.9);1.817(1.5);1.801(1.0);1.790 (0.7);1.782 (0.7);1.577(9.7);1.560(10.1);1.550(10.8);1.532(9.9);0.000(1.6) |

-continued

| |
|---|
| Example 79: ¹H-NMR(400.0 MHz, d₆-DMSO): δ = 9.139(2.2);9.118(2.2);8.565(5.2);7.651(2.2);7.632(2.4);7.627(1.9);7.529(0.7);7.507(3.0);7.499(3.5);7.491(7.6);7.487(4.2);7.475(1.4);7.471(1.2);7.456(0.5); 7.375(1.4);7.295(0.8);7.285(1.5);7.273(2.6);7.263(1.5);7.251(5.1);7.246(3.0);7.240(2.9);7.229(3.0);5.540(0.6);5.520(1.9);5.480(0.7);3.946(0.5);3.929(1.1);3.911(1.6);3.901(13.8);3.877(0.5);3.357(242.8); 3.339(252.0);3.176(0.6);3.163(0.5);3.011(0.6);2.999(0.6);2.981(1.0);2.972(1.0);2.959(1.0);2.907(0.8);2.886(1.7);2.867(1.3);2.847(0.9);2.826(0.6);2.672(1.3);2.668(1.0);2.572(0.6);2.563(0.7);2.552(1.3); 2.542(1.8);2.512(81.5);2.507(163.1);2.503(216.7);2.499(158.5);2.494(78.3);2.334(0.9);2.325(0.9);1.955(0.7);1.916(0.8);1.576(8.2);1.558(16.0);1.540(8.4);1.237(0.3);0.000(1.4) |
| Example 80: ¹H-NMR(400.0 MHz, d₆-DMSO): δ = 9.755(3.1);9.750(3.3);9.166(1.7);9.146(4.6);9.141(3.9);7.639(0.6);7.617(16.0);7.594(0.8);7.359(1.4);7.341(2.0);7.318(1.2);7.300(2.2);7.278(1.0);7.261(1.9);7.241(2.3); 7.222(1.6);7.204(0.6);5.614(0.5);5.594(1.3);5.575(1.4);5.555(0.5);3.901(5.3);3.325(273.1);3.176(0.4);3.163(0.4);3.072(0.4);3.064(0.5);3.051(0.5);3.042(0.5);3.033(0.8);3.026(0.8);3.011(0.8);3.003(0.7);2.936(0.5); 2.916(1.2);2.896(0.9);2.876(0.7);2.856(0.4);2.671(0.9);2.574(0.5);2.565(0.7);2.554(1.1);2.542(1.6);2.502(138.7);2.329(0.8);2.206(0.8);2.016(0.5);2.006(0.9);1.995(0.9);1.985(0.5);1.974(0.8);0.000(4.8) |
| Example 81: ¹H-NMR(400.0 MHz, d₆-DMSO): δ = 9.124(1.2);8.748(3.9);7.652(1.8);7.633(2.5);7.550(0.6);7.539(1.4);7.527(1.3);7.519(1.1);7.508(1.2);7.499(0.3);7.483(5.0);7.473(3.1);7.402(0.9);7.390(1.2); 7.382(1.1);7.303(0.5);7.295(0.9);7.282(1.7);7.269(0.8);7.252(2.7);7.243(2.7);7.234(1.9);7.218(0.3);5.558(0.9);5.537(1.0);5.517(0.3);3.901(16.0);3.357(187.9);3.344(190.1);3.175(0.4);3.165(0.4);3.034(0.3);3.025(0.4); 3.012(0.4);3.002(0.4);2.994(0.7);2.985(0.8);2.959(11.6);2.921(0.8);2.900(1.1);2.879(0.8);2.860(0.3);2.840(0.3);2.673(0.8);2.577(0.4);2.565(0.5);2.557(0.7);2.554(0.2);2.545(0.9);2.525(2.9);2.508(107.1);2.503(140.8);2.499(102.8); 2.334(0.6);2.330(0.8);2.326(0.6);1.977(0.5);1.956(0.6);1.931(0.4);1.925(0.4);0.000(1.0) |
| Example 82: ¹H-NMR(400.0 MHz, d₆-DMSO): δ = 9.148(1.9);9.127(2.0);8.842(6.3);7.738(2.1);7.729(3.0);7.625(7.4);7.622(7.9);7.373(1.3);7.361(1.7);7.351(1.7);7.210(2.9);7.203(3.1);7.196(3.3);7.188(3.8); 7.147(1.9);7.136(1.6);7.125(1.1);5.273(0.5);5.256(1.2);5.239(1.2);3.903(2.3);3.394(0.3);3.382(0.5);3.324(317.1);3.279(0.5);2.934(16.0);2.832(0.3);2.805(0.9);2.788(2.1);2.772(2.4);2.757(1.1);2.729(0.4);2.671(1.4); 2.502(217.7);2.328(1.3);2.099(0.4);2.085(0.7);2.066(1.0);2.049(0.8);1.955(0.6);1.940(0.7);1.911(1.1);1.892 (1.2);1.867(0.9);1.841(1.2);1.820(0.8);1.807(0.7);1.250(0.4);1.235(0.4);0.000(7.8) |
| Example 83: ¹H-NMR(400.0 MHz, d₆-DMSO): δ = 9.148(1.4);9.127(1.5);8.820(6.1);7.926(2.9);7.908(1.3);7.889(1.8);7.838(0.9);7.818(2.5);7.806(2.1);7.787(0.6);7.377(1.1);7.366(1.3);7.354(1.5);7.211(2.7); 7.202(2.3);7.196(2.5);7.188(3.4);7.147(1.7);7.136(1.5);7.125(0.9);5.274(0.4);5.257(1.0);5.240(0.9);3.358(222.5);3.347(227.0);3.177(0.4);3.164(0.3);2.945(0.6);2.806(1.0);2.788(1.7);2.774(1.9); 2.757(0.9);2.673(0.9);2.504(146.9);2.331(0.8);2.087(0.6);2.067(0.8);2.050(0.7);1.959(0.5);1.944(0.6);1.929(0.7);1.912(0.8);1.896(1.0);1.871(0.7);1.864(0.7);1.845(1.0);1.819(0.6);0.000(1.0) |
| Example 84: ¹H-NMR(400.0 MHz, d₆-DMSO): δ = 9.763(5.0);9.166(2.0);9.146(2.0);9.099(5.2);7.660(2.9);7.640(3.9);7.557(1.1);7.549(1.4);7.542(1.7);7.534(2.4);7.522(1.4);7.515(2.2);7.497(8.5);7.482(2.6); 7.462(0.5);7.363(2.1);7.346(2.8);7.317(1.9);7.298(3.7);7.278(1.6);7.260(3.1);7.239(3.6);7.221(2.4);7.203(0.8);5.611(0.7);5.591(2.0);5.572(2.1);5.552(0.7);3.901(16.0);3.509(0.4);3.455(0.8);3.365(288.5);3.360(332.2); 3.347(453.9);3.175(0.5);3.164(0.5);3.066(0.7);3.058(0.7);3.044(0.8);3.027(1.2);3.020(1.3);3.005(1.3);2.989(1.6);2.928(1.3);2.914(1.8);2.894(1.4);2.876(1.1);2.853(0.6);2.672(1.3);2.571(0.6);2.563(0.7);2.552(1.4); 2.543(2.0);2.507(205.7);2.503(243.7);2.499(185.1);2.330(1.4);2.045(0.4);2.023(1.1);2.001(1.3);1.991(1.2);1.971(1.1);1.949(0.4);1.237(0.5);-0.001(1.5) |
| Example 85: ¹H-NMR(400.0 MHz, d₆-DMSO): δ = 9.150(2.0);9.129(2.0);8.852(5.8);7.931(3.6);7.921(1.7);7.893(2.3);7.841(1.1);7.822(3.0);7.808(2.5);7.790(2.1);7.770(0.7);7.413(1.5);7.400(1.9);7.394(1.7);7.301(1.4); 7.288(2.4);7.258(3.9);7.248(3.9);7.240(2.7);7.223(0.5);5.588(0.6);5.569(1.7);5.549(1.7);5.530(0.6);3.903(2.1);3.398(0.5);3.330(379.4);3.267(0.5);3.243(0.3);3.035(0.6);3.020(0.6);3.002(1.1);2.995(1.1);2.966(16.0); 2.927(0.6);2.906(1.6);2.886(1.2);2.866(0.8);2.846(0.5);2.671(1.1);2.578(0.6);2.566(1.1);2.557(1.5);2.503(177.6);2.329 |
| Example 86: ¹H-NMR(400.0 MHz, d₆-DMSO): δ = 9.136(1.1);9.115(1.1);8.802(5.4);7.645(2.4);7.572(1.4);7.554(3.4);7.549(2.4);7.536(2.0);7.531(2.5);7.526(1.1);7.518(0.6);7.513(1.0);7.508(0.5);7.373(0.8); 7.361(1.0);7.350(1.1);7.210(2.1);7.201(1.6);7.195(1.8);7.177(0.5);7.146(1.3);7.135(0.9);7.123(0.7);5.275(0.3);5.257(0.7);5.241(0.6);3.901(16.0);3.352(218.1);3.344(208.0);3.176(0.6);3.163(0.6);3.053(0.4); 3.036(0.4);3.021(0.4);3.004(0.3);2.990(0.3);2.930(13.4);2.806(0.5);2.788(1.2);2.773(1.4);2.757(0.7);2.730(0.8);2.677(0.6);2.673(0.8);2.668(0.8);2.525(2.1);2.508(105.8);2.503(140.6);2.499(103.2);2.334(0.6);2.330(0.8); 2.086(0.4);2.067(0.6);2.050(0.5);1.936(0.3);1.942(0.4);1.927(0.6);1.893(0.7);1.869(0.5);1.843(0.5);1.820(0.5);1.806(0.4);1.005(0.5);0.987(1.1);0.969(0.5);0.000(1.2) |
| Example 87: ¹H-NMR(400.0 MHz, d₆-DMSO): δ = 9.778(4.1);9.773(4.4);9.178(6.3);9.173(5.2);9.158(1.9);7.907(2.1);7.849(1.0);7.829(2.8);7.814(2.3);7.795(2.1);7.777(0.7);7.364(1.8);7.347(2.4);7.320(1.4); 7.303(2.7);7.280(1.2);7.264(2.3);7.244(2.7);7.225(1.8);7.207(0.6);5.615(0.6);5.595(1.7);5.575(1.7);5.555(0.6);3.901(16.0);3.357(273.0);3.346(272.0);3.177(0.4);3.164(0.4);3.076(0.5);3.067(0.5);3.054(0.6); 3.045(0.6);3.036(0.9);3.028(0.9);3.014(0.9);3.006(0.9);2.938(0.6);2.918(1.4);2.897(1.1);2.326(0.8);2.051(0.4);2.030(1.1);2.326(0.8);2.331(1.1);2.326(0.8);2.331(1.1);1.988(0.5);1.978(0.1);1.957(0.4);0.000(1.5) |
| Example 88: ¹H-NMR(400.0 MHz, d₆-DMSO): δ = 9.188(1.9);9.168(1.9);8.669(4.2);8.660(4.2);7.647(2.1);7.628(2.9);7.545(0.9);7.538(1.1);7.529(1.3);7.522(1.9);7.509(1.0);7.502(2.5);7.486(4.6);7.483(4.6);7.467(1.6); 7.448(0.4);7.413(0.7);7.401(0.9);7.392(1.4);7.380(1.0);7.371(0.8);7.299(0.7);7.289(1.3);7.277(2.3);7.268(1.3);7.255(4.5);7.250(2.6);7.244(2.4);7.233(2.5);7.222(0.4);5.550(0.6);5.530(1.7);5.511(1.7);5.492(0.6);5.368(0.7); 3.963(0.8);3.951(1.0);3.946(1.0);3.932(0.8);3.928(0.8);3.901(16.0);3.354(308.4);3.344(290.7);3.176(0.5);3.164(0.5);3.020(0.5);3.007(0.4);2.989(0.8);2.981(0.9);2.968(0.7);2.959(0.9);2.951(0.6);2.913(0.7); 2.892(1.5);2.872(1.1);2.853(0.8);2.832(0.4);2.677(0.8);2.672(1.1);2.668(0.8);2.583(0.4);2.563(0.8);2.553(1.1);2.543(1.5);2.512(73.7);2.508(149.9);2.503(200.0);2.499(146.8);2.334(0.9);2.330(1.2);2.326(0.9); 1.955(0.6);1.936 (0.9);1.924(0.7);1.916(0.7);1.904(0.6);1.597(5.0);1.591(5.3);1.578(9.6);1.574(10.4);1.560(5.7);1.557 (5.6);1.237(0.3);0.000(1.2) |
| Example 89: ¹H-NMR(400.0 MHz, d₆-DMSO): δ = 9.185(1.0);8.634(3.7);8.623(3.7);7.644(1.3);7.624(1.9);7.542(0.9);7.535(1.4);7.526(1.1);7.519(1.9);7.515(0.9);7.507(0.9);7.500(2.3);7.488(2.4);7.481(4.2); 7.463(1.2);7.446(0.3);7.390(0.6);7.380(0.7);7.368(1.4);7.359(0.8);7.368(1.4);7.359(0.8);7.346(0.8);7.205(2.5);7.195(2.3);7.183(2.9);7.170(0.6);7.134(1.9);7.121(1.3);7.111(1.0);5.217(0.9);5.199(0.9);3.948(0.6);3.931(1.1);3.913(1.2);3.901(16.0); 3.379(207.4);3.371(199.8);3.358(191.3);3.349(218.3);3.177(0.5);3.164(0.5);2.785(0.8);2.769(1.9);2.754(2.0);2.737(1.0);2.712(0.4);2.678(0.8);2.673(1.1);2.669(0.9);2.526(2.7);2.513(67.2);2.508(139.1);2.504(185.5); 2.500(133.9);2.495(64.5);2.335(0.8);2.331(1.0);2.326(0.8);2.080(0.3);2.057(0.6);2.046(0.8);2.030 (0.7);2.016(0.5);1.876(0.8);1.823(1.1);1.807(0.7);1.595(6.6);1.578(6.8);1.567(6.4);1.550(6.0);0.987(0.4); 0.000(1.8) |
| Example 90: ¹H-NMR(400.0 MHz, d₆-DMSO): δ = 9.118(1.4);9.097(1.5);8.722(3.9);8.194(1.7);7.629(2.5);7.548(0.8);7.536(1.5);7.525(1.1);7.517(1.5);7.505(1.4);7.497(0.4);7.480(5.2);7.469(3.5);7.368(1.0); 7.356(1.2);7.345(1.3);7.214(0.4);7.204(2.9);7.195(2.4);7.189(2.6);7.181(3.6);7.172(0.6);7.149(0.4);7.140(1.7);7.130(1.2);7.117(0.9);5.249(0.7);3.901(16.0);3.354(267.3);3.346(295.2);3.176(0.4);3.163(0.4);2.938(10.2); 2.936(10.8);2.798(0.7);2.781(1.6);2.765(1.8);2.750(1.1);2.676(0.7);2.672(1.1);2.668(0.8);2.525(2.5);2.512(62.0);2.508(129.1);2.503(173.1);2.499(125.2);2.494(60.8);2.334(0.7);2.330(1.0);2.325(0.7);2.059(0.7);2.041(0.6); 1.906(0.8);1.888(0.9);1.863(0.6);1.856(0.6);1.837(0.9);1.813(0.6);0.988(0.5);0.000(1.2) |
| Example 91: ¹H-NMR(400.0 MHz, d₆-DMSO): δ = 9.185(2.0);9.165(2.0);8.772(7.1);7.925(3.5);7.902(1.7);7.884(2.2);7.815(2.9);7.800(2.4);7.781(2.2);7.762(0.7);7.416(1.4);7.405(1.8);7.395(1.6);7.304(0.8); 7.294(1.5);7.282(2.4);7.273(1.5);7.261(4.6);7.255(3.0);7.249(2.7);7.239(2.5);7.235(3.5);7.229(2.4);7.225(1.8);7.207(0.6);5.615(0.6);5.595(1.8);5.575(1.7);5.566(0.6);5.546(1.8);5.527(1.7);5.507(0.6);4.006(0.3);3.988(1.2);3.953(1.2);3.970(1.0);3.902(0.5);3.902(2.7);3.452(0.3);3.434(0.4);3.424(0.4); 3.412(0.6);3.331(459.7);3.269(0.4);3.031(0.4);3.022(0.5);3.009(0.6);3.000(0.7);2.992(1.0);2.982(1.0);2.969(1.0);2.921(0.7);2.900(1.5);2.880(1.2);2.860(0.8);2.840(0.4);2.671(1.1);2.591(0.6);2.582(0.7); 2.572(1.1);2.561(1.4);2.540(2.2);2.506(152.3);2.502(184.7);2.329(1.1);1.977(0.4);1.956(1.0);1.946(0.6);1.936(1.1);1.925(1.0);1.915(0.5);1.905(0.9);1.588(8.4);1.571(16.0);1.553(8.3);0.000(6.1) |
| Example 92: ¹H-NMR(400.0 MHz, d₆-DMSO): δ = 9.210(2.6);9.189(2.7);8.448(12.5);8.317(0.7);7.561(1.2);7.557(1.3);7.542(2.3);7.538(2.9);7.519(1.5);7.470(0.5);7.475(0.5);7.457(1.4);7.436(1.8);7.432(1.1); 7.423(1.1);7.418(0.9);7.357(2.1);7.339(4.0);7.333(5.5);7.319(3.0);7.313(4.9);7.296(1.5);7.294(1.4);7.199(1.2);7.178(2.5);7.160(1.6);7.157(1.5);6.947(1.8);6.945(1.9);6.928(3.1);6.910(1.5);6.908(1.5); 6.812(3.4);6.810(3.5);6.792(3.1);5.255(0.7);5.241(1.0);5.221(1.6);5.207(0.7);4.310(0.6);4.294(0.8);4.283(1.4);4.274(1.3);4.267(1.5);4.258(1.2);4.250(1.2);4.242(1.5);4.229(1.3);4.222(1.7);4.201(0.6); 0.000(1.8) |

-continued

| |
|---|
| 4.194(0.5);3.982(0.6);3.965(1.5);3.947(2.1);3.929(1.6);3.912(0.6);3.368(0.3);3.329(342.4);2.675(2.0);2.667(1.5);2.524(4.9);2.511(111.5);2.507(227.3);2.502(301.1);2.498(219.6);2.493(107.4);2.434(15.8); 2.432(16.0);2.333(1.4);2.329(2.0);2.324(1.4);2.244(0.3);2.233(0.5);2.222(0.8);2.209(1.0);2.200(1.0);2.187(1.1);2.175(0.8);2.166(0.5);2.064(1.0);2.047(0.8);2.042(0.8);2.029(0.8);2.023(0.7);2.014(0.5); 2.007(0.4);1 1.568(12.2);1.561(2.2);1.543(11.6);1.398(3.5);0.951(0.6);0.934(0.7);0.008(2.3);0.000(73.1);−0.008(2.6) |
| Example 93: $^1$H-NMR(400.0 MHz, d$_6$-DMSO): δ = 9.231(2.3);9.211(2.4);8.483(11.2);7.566(1.0);7.562(1.2);7.547(2.0);7.543(2.6);7.527(1.0);7.523(1.4);7.479(0.5);7.474(0.5);7.465(0.6);7.460(1.2);7.457(1.1);7.440(1.6); 7.435(1.0);7.426(0.9);7.422(0.8);7.361(5.2);7.355(4.2);7.335(4.6);7.316(4.1);7.299(1.2);7.238(2.3);7.232(2.1);7.217(2.5);7.210(2.4);6.854(5.5);6.832(4.9);5.251(0.6);5.235(1.4);5.217(1.3);5.202(0.6);4.329(0.4); 4.321(0.6);4.312(0.5);4.302(1.3);4.293(1.0);4.284(1.2);4.275(0.9);4.259(1.0);4.251(1.2);4.239(1.0);4.231(1.1);4.223(0.6);4.211(0.6);4.203(0.5);3.984(0.5);3.967(1.3);3.949(1.8);3.931(1.4);3.914(0.5);3.330(166.4); 2.976(0.6);2.960(0.8);2.943(0.6);2.676(0.6);2.671(0.8);2.667(0.6);2.525(2.1);2.520(3.1);2.511(46.2);2.507(95.1);2.502(126.3);2.498(91.8);2.493(44.8);2.459(0.4);2.439(13.8);2.436(13.9);2.425(1.0);2.407(1.2);2.389(0.4); 2.333(0.6);2.325(0.9);2.239(0.4);2.235(0.4);2.227(0.6);2.213(0.8);2.205(0.8);2.200(0.7);2.192(0.9);2.185(0.6);2.179(0.6);2.172(0.4);2.079(0.4);2.072(0.6);2.068(0.7);2.063(0.9);2.055(1.0);2.045(0.8);2.038(0.8); 2.028(0.7);2.020(0.6);2.011(0.4);1.592(0.2);1.574(11.2);1.569(11.5);1.551(10.0);1.398(16.0);0.951(8.9);0.93449.1);0.008(1.0);0.000(32.3);−0.008(1.2) |
| Example 94: $^1$H-NMR(400.0 MHz, d$_6$-DMSO): δ = 9.091(2.5);8.420(11.7);8.317(0.5);7.561(1.2);7.557(1.4);7.542(2.3);7.538(2.9);7.519(1.6);7.473(0.5);7.469(0.6);7.460(0.7);7.455(1.4);7.435(1.8);7.430(1.1); 7.421(1.0);7.417(0.9);7.367(1.8);7.359(3.4);7.345(2.6);7.332(5.2);7.3124.7);7.295(1.5);7.283(1.2);7.272(0.7);7.261(1.3);7.251(1.4);7.243(2.7);7.237(2.4);7.229(2.5);7.205(2.4);7.200(4.0);7.191(3.9);7.183(4.5);7.178(3.2);7.165(0.9);7.160(0.6);7.129(2.6);7.114(1.6); 7.107(1.4);5.226(0.6);5.211(1.2);5.194(1.3);5.176(0.6);3.969(0.6);3.952(1.5);3.934(2.1);3.916(1.5);3.889(0.6);3.328(145.8);2.810(0.3);2.784(1.1);2.768(2.7);2.754(2.7);2.740(1.1);2.711(0.4);2.676(1.1);2.671(1.5); 2.667(1.1);2.524(4.1);2.511(83.2);2.506(168.0);2.502(222.2);2.498(165.1);2.493(83.6);2.433(15.7);2.431(16.0);2.407(0.4);2.333(1.1);2.329(1.5);2.324(1.5);2.324(1.2);2.075(0.5);2.060(0.7);2.052(0.8);2.039(1.0);2.030(1.1);2.016(0.8); 1.942(0.8);1.931(0.7);1.916(1.0);1.897(0.8);1.876(0.8);1.855(1.1);1.850(1.1);1.824(1.6);1.808(1.9);1.763(0.5);1.590(11.4);1.572(11.7);1.563(12.0);1.545(11.3);0.008(2.6) |
| Example 95: $^1$H-NMR(400.0 MHz, d$_6$-DMSO): δ = 9.086(1.8);9.065(1.8);8.455(8.4);8.317(1.3);7.565(0.9);7.561(1.4);7.546(1.6);7.542(2.1);7.523(1.1);7.477(0.4);7.472(0.4);7.463(0.5);7.459(1.0);7.438(1.3);7.434(0.8); 7.424(0.7);7.420(0.7);7.384(1.2);7.372(1.5);7.362(2.7);7.335(3.7);7.315(3.4);7.299(1.2);7.296(1.5);7.283(1.2);7.272(0.7);7.261(1.3);7.251(1.4);7.243(2.7);7.237(2.4);7.229(2.5);7.548(0.5);5.529(1.5);5.508(1.6);5.489(0.5); 3.992(0.4);3.974(1.1);3.956(1.5);3.939(1.1);3.921(0.4);3.367(0.5);3.328(431.6);3.019(0.4);3.010(0.5);2.997(0.5);2.989(0.5);2.979(0.9);2.971(0.9);2.958(1.0);2.949(0.9);2.906(0.6);2.886(1.4);2.865(1.0);2.846(0.8); 2.850(0.4);2.675(2.6);2.671(3.5);2.667(2.6);2.618(0.4);2.592(0.4);2.569(0.9);2.548(1.6);2.524(9.7);2.511(191.9);2.506(386.5);2.502(510.2);2.497(377.1);2.493(189.1);2.437(11.3);2.434(11.5);2.407(0.5); 2.333(2.4);2.329(3.3);2.324(2.5);1.962(0.4);1.941(1.0);1.931(0.4);1.920(1.0);1.899(0.5);1.889(0.9);1.590(8.4);1.572(16.6);1.554(8.3);1.398(3.4);0.951(3.4);0.934(3.5);0.920(0.4);0.146(0.7);0.008(4.7); 0.000(147.1);−0.008(6.0);−0.150(0.7) |
| Example 96: $^1$H-NMR(400.0 MHz, d$_6$-DMSO): δ = 9.221(2.1);9.201(2.2);8.462(8.6);8.377(0.9);8.317(0.4);8.257(1.5);8.180(0.9);7.575(0.5);7.559(1.1);7.555(1.0);7.538(1.9);7.521(1.1);7.517(1.2);7.501(0.5);7.340(2.2); 7.322(2.4);7.275(2.3);7.254(4.2);7.233(2.1);7.198(1.1);7.194(1.1);7.177(2.2);7.159(1.4);7.156(1.3);6.945(1.5);6.926(2.7);6.907(1.2);6.811(2.9);6.790(2.7);5.251(0.6);5.236(1.4);5.217(1.4);5.203(0.6);4.310(0.4); 4.302(0.6);4.294(0.5);4.283(1.2);4.274(1.1);4.266(1.0);4.258(1.0);4.243(1.0);4.236(1.2);4.222(1.1);4.215(1.3);4.194(0.6);4.187(0.5);3.980(0.5);3.962(1.2);3.944(1.7);3.927(1.5);3.909(0.5);3.329(175.6);2.675(1.1); 2.671(1.4);2.507(162.4);2.502(205.1);2.498(152.4);2.493(74.2);2.434(1.1);2.329(1.4);2.325(10.1);1.545(9.2);1.398(1.4);1.235(0.4);0.951(1.2);0.935(1.3);0.000(53.1) |
| Example 97: $^1$H-NMR(400.0 MHz, d$_6$-DMSO): δ = 9.243(2.2);9.223(2.3);8.500(8.9);7.579(0.5);7.562(1.1);7.558(1.0);7.541(2.0);7.525(1.2);7.521(1.2);7.504(0.5);7.443(0.4);7.365(4.1);7.359(4.2);7.345(1.0);7.328(0.4); 7.287(0.5);7.276(2.6);7.257(4.2);7.237(4.1);7.231(2.5);7.215(2.4);7.209(2.2);7.191(0.4);7.172(0.7);7.147(0.3);7.129(0.6);7.113(0.4);7.093(0.6);7.086(0.5);7.069(0.8);7.051(0.5);7.048(0.5);7.029(0.4);6.853(5.1);6.831(5.0); 6.813(0.5);6.709(0.9);6.707(0.9);6.689(0.8);5.758(4.8);5.247(0.6);5.232(1.4);5.214(1.4);5.198(0.6);4.321(0.6);4.311(0.6);4.301(1.3);4.293(1.2);4.284(1.2);4.276(1.2);4.267(1.2);4.252(1.2);4.245(1.3); 4.232(1.6);4.224(1.9);4.204(1.0);4.197(0.6);4.141(0.4);4.133(0.4);4.124(0.5);4.116(0.5);4.038(0.6);4.020(0.6);3.982(0.5);3.965(1.3);3.947(1.8);3.930(1.4);3.912(0.6);3.331(10.7);2.715(0.3);2.695(0.3);2.676(0.5);2.672(0.6); 2.667(0.5);2.507(44.1);2.503(58.1);2.498(43.7);2.490(21.4);2.440(0.4);2.386(16.0);2.333(0.5);2.330(0.6);2.248(0.3);2.240(0.5);2.227(0.8);2.213(0.9);2.206(0.9);2.192(1.0);2.185(0.7);2.180(0.7);2.172(0.5);2.078(0.5);2.070(0.7); 2.061(1.0);2.054(1.1);2.043(0.9);2.037(0.9);2.026(0.9);2.019(0.9);2.004(0.7);1.990(0.3);1.967(0.5);1.956(0.5);1.909(0.4);1.885(0.6);1.865(0.5);1.711(0.3);1.595(9.5);1.577(10.7);1.572(11.2); 1.554(9.5);1.532(0.5);1.397(0.5);1.233(0.4);1.193(0.8);1.184(0.4);1.175(1.5);1.168(0.3);1.158(0.7);1.091(0.5);0.934(0.9);0.951(0.9);0.000(15.6);−0.008(0.8) |
| Example 98: $^1$H-NMR(400.0 MHz, d$_6$-DMSO): δ = 9.102(2.1);9.080(2.2);8.433(9.9);8.317(1.1);7.574(0.5);7.558(1.1);7.553(1.0);7.537(1.9);7.520(1.1);7.516(1.2);7.499(0.5);7.437(0.3);7.366(1.5);7.358(1.6);7.343(1.9); 7.275(1.8);7.271(3.3);7.251(3.3);7.234(1.7);7.231(1.7);7.215(0.7);7.199(3.2);7.190(3.2);7.181(3.6);7.177(2.8);7.164(0.7);7.158(0.6);7.177(2.8);7.153(1.0);7.537(1.9);7.520(1.1);7.516(2.2);7.119(1.1);7.113(1.4);7.105(1.1);5.223(0.5);5.206(1.0);5.191(1.1);5.174(0.5); 3.965(0.5);3.947(1.3);3.929(1.7);3.911(1.5);3.894(0.5);3.370(0.4);3.328(392.1);2.781(1.0);2.765(2.3);2.751(2.3);2.736(1.0);2.707(0.4);2.676(2.4);2.671(3.4);2.667(2.5);2.584(0.3);2.524(8.5);2.511(181.4);2.506(369.8); 2.502(490.7);2.498(364.2);2.493(183.3);2.434(0.7);2.329(1.5);2.325(1.0);2.333(1.1);2.333(2.3);2.329(3.2);2.324(2.4);2.072(0.4);2.057(0.7);2.048(0.7);2.036(0.9);2.027(0.9);2.013(0.7);1.936(0.6);1.926(0.6);1.912(0.8);1.889(0.7); 1.874(0.7);1.863(1.4);1.855(1.0);1.832(0.9);1.824(1.3);1.807(1.6);1.787(0.7);1.592(9.5);1.575(9.8);1.564(10.0);1.547(9.5);1.398(3.8);1.234(0.4);0.146(0.7);0.008(5.2);0.000(163.5);−0.008(6.8);−0.150(0.8) |
| Example 99: $^1$H-NMR(400.0 MHz, d$_6$-DMSO): δ = 9.096(2.0);9.076(1.9);8.468(7.6);8.317(0.6);7.561(1.2);7.578(0.6);7.561(1.2);7.540(1.9);7.524(1.2);7.502(0.4);7.384(1.2);7.372(1.9);7.363(1.7);7.275(4.6);7.256(6.3); 7.250(6.3);7.242(4.6);7.236(4.8);7.227(2.7);5.542(0.7);5.524(1.7);5.485(0.6);3.987(0.6);3.970(1.3);3.952(1.7);3.935(1.4);3.916(0.5);3.502(0.3);3.490(0.4);3.460(0.4);3.450(0.4);3.412(0.6);3.335(225.6); 3.327(658.0);3.016(0.7);3.010(0.7);2.994(0.9);2.977(1.4);2.969(1.1);2.956(1.3);2.905(0.9);2.884(1.3);2.864(1.3);2.846(0.9);2.823(0.6);2.675(7.2);2.671(8.1);2.667(5.6);2.632(0.7);2.506(1048.5);2.502(1152.5);2.498(772.5); 2.383(14.2);2.333(6.5);2.329(7.4);2.325(4.9);1.956(0.5);1.936(1.1);1.915(1.1);1.904(1.1);1.884(0.9);1.862(0.3);1.574(16.0);1.556(8.3);1.398(9.4);0.951(1.9);0.935(1.8);0.146(1.3);0.007(74.7);0.000(288.0); −0.009(9.9);−0.149(1.2) |
| Example 100: $^1$H-NMR(400.0 MHz, d$_6$-DMSO): δ = 9.221(1.6);9.201(1.6);8.529(7.4);8.317(0.8);7.826(0.7);7.810(0.8);7.806(0.8);7.802(0.8);7.795(0.8);7.790(0.8);7.775(0.8);7.770(0.8);7.603(0.4);7.598(0.4);7.590(0.5);7.581(1.4); 7.576(1.7);7.571(1.7);7.564(1.1);7.552(1.7);7.547(1.2);7.530(0.5);7.525(1.3);7.504(0.5);7.346(1.5);7.328(1.6);7.203(0.7);7.200(0.9);7.182(1.6);7.165(1.0);7.161(1.0);6.953(1.1);6.950(1.2);6.932(2.0);6.916(0.9);6.913(0.9); 6.817(2.1);6.796(1.9);6.794(1.9);5.260(0.4);5.245(1.0);5.226(1.0);5.211(0.4);4.307(0.4);4.299(0.3);4.287(0.9);4.279(0.8);4.271(0.9);4.262(0.8);4.256(0.8);4.248(0.9);4.235(0.8);4.227(1.1);4.207(0.4); 3.980(0.3);3.962(0.9);3.944(1.3);3.927(1.0);3.909(0.4);3.349(0.4);3.329(125.0);2.676(0.7);2.671(0.9);2.667(0.7);2.619(16.0);2.524(2.2);2.511(50.2);2.507(102.1);2.502(135.0);2.498(100.1);2.493(50.6);2.333(0.6);2.329(0.9); 2.324(0.7);2.320(0.3);2.226(0.4);2.213(0.6);2.205(0.6);2.192(0.7);2.180(0.5);2.078(0.4);2.069(0.6);2.062(0.7);2.051(0.5);2.046(0.5);2.035(0.5);2.027(0.5);1.572(7.0);1.554(7.6);1.548(7.7);1.530(6.9);1.398(3.8);0.008(1.3); 0.000(40.6);−0.008(1.6) |
| Example 101: $^1$H-NMR(400.0 MHz, d$_6$-DMSO): δ = 9.242(1.7);9.222(1.7);8.565(7.0);8.317(0.5);7.830(0.8);7.826(0.9);7.799(0.9);7.794(0.9);7.780(0.8);7.775(0.8);7.607(0.4);7.602(0.4);7.585(1.4); 7.580(1.6);7.573(2.1);7.554(1.2);7.548(1.2);7.527(1.3);7.506(0.5);7.368(2.6);7.362(2.9);7.242(1.6);7.236(1.4);7.220(1.7);7.214(1.6);6.858(3.6);6.836(3.2);5.254(0.5);5.238(1.1);5.220(1.1);5.205(0.5);4.332(0.3);4.325(0.4); 4.316(0.4);4.305(1.0);4.297(0.8);4.287(0.9);4.280(0.7);4.263(0.7);4.255(0.9);4.244(0.8);4.235(1.1);4.228(0.5);4.215(0.4);3.982(0.4);3.964(1.0);3.946(1.3);3.929(1.0);3.911(0.4);3.328(122.3);2.676(1.0);2.671(1.4); 2.667(1.1);2.623(16.0);2.507(160.0);2.502(209.2);2.498(157.8);2.333(1.0);2.329(1.4);2.325(1.0);2.231(0.4);2.218(0.6);2.209(0.7);2.196(0.7);2.183(0.5);2.082(0.3);2.076(0.5);2.066(0.7);2.060(0.7);2.049(0.6);2.042(0.6); 2.032(0.5);2.024(0.5);2.015(0.3);1.577(7.1);1.559(8.5);1.555(8.8);1.537(7.1);1.398(9.1);0.951(0.8);0.934(0.9);0.008(2.3);0.000(62.1);−0.008(3.2) |

-continued

Example 102: ¹H-NMR(400.0 MHz, d₆-DMSO): δ = 9.104(1.5);9.083(1.6);8.502(7.1);7.827(0.8);7.823(0.9);7.807(0.8);7.802(0.9);7.796(0.8);7.791(0.8);7.776(0.8);7.771(0.8);7.603(0.4);7.598(0.4);7.590(0.5);7.581(1.3);7.576(1.5);7.570(2.1);7.550(1.2);7.544(1.2);7.523(1.4);7.502(0.6);7.377(1.1);7.370(1.2);7.354(1.5);7.224(0.5);7.211(1.5);7.206(2.5);7.197(2.5);7.188(2.8);7.183(1.9);7.170(0.6);7.165(0.4);7.133(1.7);7.117(1.0);7.110(0.9);6.575(1.0);5.230(0.4);5.216(0.8);5.198(0.9);5.181(0.4);3.967(0.4);3.950(1.0);3.932(1.3);3.915(1.0);3.897(0.4);3.330(33.1);2.787(0.7);2.772(1.7);2.758(1.7);2.743(0.7);2.671(0.4);2.619(16.0);2.511(19.0);2.507(38.2);2.502(50.4);2.498(37.6);2.057(0.5);2.045(0.3);2.036(0.7);2.022(0.5);1.946(0.5);1.920(0.6);1.909(0.5);1.900(0.5);1.880(0.5);1.860(0.7);1.853(0.6);1.828(1.0);1.812(1.2);1.576(7.1);1.559(7.4);1.550(7.5);1.533(7.0);1.397(2.5);0.008(0.5);0.000(14.5);−0.008(0.6)

Example 103: ¹H-NMR(400.0 MHz, d₆-DMSO): δ = 9.100(1.6);9.079(1.6);8.536(7.0);7.828(0.8);7.825(0.9);7.809(0.8);7.804(0.9);7.798(0.8);7.793(0.8);7.778(0.8);7.773(0.8);7.606(0.4);7.602(0.4);7.593(0.5);7.585(1.4);7.580(1.6);7.574(2.0);7.568(1.2);7.554(1.2);7.549(1.2);7.528(1.3);7.506(0.5);7.392(1.0);7.380(1.3);7.371(1.3);7.298(0.6);7.286(1.1);7.276(1.8);7.266(1.2);7.255(4.0);7.248(2.5);7.242(2.2);7.233(2.2);6.575(0.7);5.554(0.5);5.535(1.4);5.515(1.4);5.495(0.5);3.989(0.4);3.971(0.9);3.954(1.3);3.936(1.0);3.918(0.4);3.024(0.3);3.016(0.4);3.001(0.4);2.993(0.6);2.984(0.7);2.975(0.8);2.962(0.8);2.954(0.7);2.911(0.6);2.890(1.2);2.870(0.9);2.851(0.6);2.830(0.4);2.676(0.6);2.671(0.8);2.621(16.0);2.574(0.5);2.566(0.5);2.555(0.8);2.546(1.2);2.535(1.2);2.524(2.9);2.511(43.1);2.507(85.8);2.502(112.5);2.498(83.6);2.333(0.5);2.329(0.7);2.324(0.6);1.967(0.3);1.946(0.9);1.936(0.5);1.925(0.9);1.914(0.6);1.904(0.4);1.894(0.8);1.576(7.2);1.558(13.8);1.541(7.1);1.398(2.7);0.008(1.2);0.000(33.7);−0.008(1.4)

Example 104: ¹H-NMR(400.0 MHz, d₆-DMSO): δ = 9.227(0.9);9.207(0.9);8.445(3.2);7.623(0.5);7.621(0.5);7.613(0.8);7.604(0.8);7.599(0.6);7.462(1.1);7.454(3.3);7.442(2.6);7.429(0.7);7.357(1.1);7.352(1.2);7.235(0.8);7.228(0.7);7.213(0.9);7.207(0.9);8.445(3.2);6.850(1.9);6.828(1.7);5.229(0.5);5.211(0.5);4.298(0.5);4.289(0.4);4.281(0.5);7.623(0.5);7.623(0.5);4.272(0.4);4.253(0.3);4.246(0.5);4.233(0.4);4.226(0.6);3.965(0.4);3.947(0.6);3.930(0.4);3.329(63.3);7.671(0.4);2.666(0.3);2.524(1.1);2.507(49.6);2.502(65.2);2.498(49.1);2.375(8.2);2.329(0.4);2.209(0.3);2.188(0.4);2.060(0.3);2.052(0.4);1.595(3.7);1.578(4.1);1.572(3.8);1.554(3.3);1.398(3.3);1.398(16.0);0.008(0.3);0.000(10.1);−0.008(0.4)

Example 105: ¹H-NMR(400.0 MHz, d₆-DMSO): δ = 9.238(1.1);9.218(1.1);8.580(5.1);7.847(1.2);7.842(2.0);7.838(1.4);7.710(0.8);7.708(1.0);7.704(0.9);7.691(1.0);7.687(1.2);7.684(1.0);7.528(1.1);7.508(2.1);7.488(1.2);7.389(1.1);7.387(1.2);7.384(1.1);7.381(1.2);7.371(1.9);7.366(2.4);7.364(2.5);7.242(1.0);7.220(1.0);7.213(1.1);6.858(2.5);6.836(2.2);5.255(0.3);5.239(0.7);5.222(1.0);5.221(0.7);5.206(0.3);4.317(0.3);4.306(0.6);4.298(0.6);4.288(0.7);4.280(0.6);4.266(0.5);4.258(0.7);4.245(0.6);4.238(0.8);4.230(0.4);4.217(0.3);3.976(0.6);3.958(0.9);3.941(0.7);3.355(1.1);3.330(55.3);2.672(0.4);2.667(0.4);2.628(10.6);2.525(3.5);2.520(3.8);2.511(17.9);2.507(35.1);2.502(47.2);2.498(36.5);2.493(20.5);2.424(0.5);2.407(0.4);2.329(0.3);2.231(0.3);2.218(0.4);2.210(0.5);2.197(0.5);2.190(0.3);2.184(0.4);2.078(0.3);2.068(0.4);2.061(0.5);2.051(0.4);2.044(0.5);2.034(0.4);2.026(0.4);1.581(4.7);1.564(5.5);1.559(5.7);1.541(4.8);1.397(16.0);0.950(2.8);0.934(2.9);0.919(0.5);0.008(0.4);0.000(10.5);−0.009(0.7)

Example 106: ¹H-NMR(400.0 MHz, d₆-DMSO): δ = 9.233(1.3);9.213(1.4);8.539(4.2);7.770(0.8);7.524(3.1);7.360(2.2);7.347(1.2);7.331(0.5);7.366(3.6);7.546(3.8);7.524(3.1);7.366(2.2);7.241(1.2);7.235(1.1);7.219(1.4);7.213(1.2);6.857(2.7);6.835(2.0);5.253(0.4);5.238(0.9);5.221(0.9);5.205(0.4);4.324(0.4);4.304(0.8);4.296(0.8);4.286(0.9);4.280(0.7);4.256(0.8);4.243(0.7);4.237(0.9);4.216(0.4);3.966(0.7);3.949(1.0);3.931(0.7);3.329(133.9);2.671(1.0);2.611(10.5);2.502(140.6);2.425(0.5);2.407(0.5);2.329(1.0);2.231(0.4);2.217(0.6);2.208(0.6);2.196(0.6);2.075(0.5);2.059(0.7);2.048(0.6);2.041(0.6);2.031(0.5);1.990(0.4);1.579(5.1);1.560(7.0);1.539(5.1);1.398(16.0);0.951(2.6);0.934(2.8);0.920(0.8);0.000(14.6)

Example 107: ¹H-NMR(400.0 MHz, d₆-DMSO): δ = 9.206(1.8);9.186(1.8);8.410(6.7);7.620(1.2);7.617(1.2);7.610(1.8);7.601(1.4);7.596(1.4);7.590(0.6);7.472(0.5);7.459(2.6);7.450(7.0);7.439(5.3);7.426(1.5);7.335(1.6);7.316(1.8);7.195(0.9);7.192(0.9);7.174(1.9);7.157(1.1);7.154(1.1);6.940(1.3);6.922(2.2);6.903(1.0);6.858(2.5);6.836(2.2);5.255(0.3);5.239(0.7);5.236(1.2);5.217(1.2);5.203(0.6);4.305(0.4);4.299(0.5);4.291(0.5);4.279(1.1);4.270(1.1);4.263(1.2);4.254(1.0);4.238(1.1);4.224(1.0);4.217(1.3);4.196(0.5);4.189(0.4);3.983(0.4);3.965(1.0);3.947(1.3);3.930(1.0);3.912(0.6);3.331(123.2);2.976(0.4);2.960(0.5);2.943(0.4);2.671(0.6);2.506(76.2);4.263(1.2);2.498(76.7);2.443(0.5);2.425(0.8);2.407(0.8);2.372(1.6);0.2329(0.6);2.333(0.6);2.329(0.7);2.227(0.5);2.218(0.6);2.205(0.8);2.197(0.8);2.184(0.9);2.171(0.6);2.163(0.4);2.184(0.4);2.061(0.9);2.054(0.9);2.042(0.7);2.027(0.6);2.020(0.6);1.989(1.2);1.590(7.4);1.570(8.3);1.564(8.3);1.546(7.2);1.398(15.9);1.193(0.3);1.175(0.6);1.157(0.3);1.175(0.6);0.951(5.4);0.934(5.7);0.920(0.8);0.000(14.6)

Example 108: ¹H-NMR(400.0 MHz, d₆-DMSO): δ = 9.078(2.1);9.056(2.2);8.443(9.7);7.575(0.4);7.559(1.4);7.521(1.1);7.517(1.2);7.500(0.5);7.283(0.5);7.272(1.9);7.252(3.0);7.233(1.5);7.223(0.4);7.152(4.1);6.999(0.5);5.757(5.3);5.187(0.5);5.171(1.0);5.154(1.1);5.136(0.5);3.974(0.4);3.957(1.7);3.921(1.3);3.904(0.5);3.328(67.5);3.272(0.8);2.707(2.1);2.694(2.2);2.680(1.0);2.672(0.8);2.667(0.6);2.524(1.1);2.511(27.5);2.507(56.3);2.502(75.7);2.498(57.4);2.493(29.5);2.434(0.4);2.382(15.6);2.333(0.5);2.329(0.4);2.266(16.0);2.063(0.4);2.049(0.6);2.039(0.7);2.028(0.8);2.018(1.0);2.004(0.6);1.989(1.5);1.914(0.6);1.899(0.6);1.887(0.8);1.869(0.7);1.849(0.3);1.840(0.5);1.819(0.8);1.814(0.8);1.795(1.3);1.787(1.4);1.777(1.4);1.772(1.3);1.733(0.4);1.602(9.2);1.585(9.3);1.573(9.5);1.555(9.2);1.397(1.7);1.290(0.4);1.234(0.4);1.193(0.5);1.175(0.8);1.157(0.4);0.000(0.4)

Example 109: ¹H-NMR(400.0 MHz, d₆-DMSO): δ = 9.074(1.8);9.053(1.8);8.525(7.0);8.317(0.4);7.846(2.0);7.842(3.3);7.838(2.3);7.707(1.8);7.687(2.1);7.526(1.6);7.506(3.2);7.486(1.8);7.383(1.8);7.380(1.7);7.363(1.3);7.360(1.3);7.164(3.5);7.004(8.7);5.178(0.9);5.162(1.1);5.144(0.5);3.981(0.4);3.964(1.0);3.946(1.4);3.928(1.0);3.911(0.4);3.328(186.6);2.713(1.9);2.701(2.0);2.681(0.9);2.675(1.1);2.671(1.4);2.667(1.1);2.626(16.0);2.506(127.0);2.502(166.4);2.498(132.9);2.436(0.4);2.329(1.2);2.324(0.9);2.277(13.0);2.070(0.4);2.045(0.6);2.025(0.9);2.011(0.5);1.989(0.5);1.923(0.6);1.896(0.7);1.879(0.6);1.847(0.4);1.819(0.8);1.800(1.2);1.794(1.3);1.781(1.3);1.588(7.3);1.570(7.7);1.561(7.8);1.543(7.2);1.398(6.9);0.000(1.4)

Example 110: ¹H-NMR(400.0 MHz, d₆-DMSO): δ = 9.066(2.1);9.045(2.2);8.428(10.1);8.316(0.9);7.565(1.1);7.546(1.8);7.542(2.4);7.523(1.3);7.475(0.4);7.470(0.5);7.461(0.5);7.456(1.2);7.454(1.0);7.436(1.5);7.431(0.9);7.422(0.9);7.418(0.8);7.357(1.7);7.333(4.7);7.313(3.9);7.297(1.2);7.294(1.1);7.152(4.1);7.001(10.3);6.574(0.4);5.189(0.5);5.174(1.0);5.157(1.1);5.139(0.5);5.157(1.1);5.139(0.5);3.977(0.4);3.959(1.2);3.941(1.7);3.924(1.3);3.906(0.5);3.327(430.2);2.725(0.9);2.709(2.0);2.697(2.2);2.680(1.5);2.676(2.0);2.671(2.6);2.667(2.0);2.541(1.0);2.524(5.7);2.520(8.8);2.511(120.7);2.506(251.2);2.502(340.8);2.497(258.7);2.493(132.0);2.436(12.7);2.433(3.2);2.333(1.7);2.329(2.3);2.324(1.8);2.268(16.0);2.065(0.4);2.051(0.6);2.042(0.7);2.030(0.8);2.021(1.0);2.007(0.5);1.919(0.6);1.904(0.7);1.893(0.8);1.875(0.6);1.840(0.4);1.818(0.8);1.795(1.3);1.787(1.4);1.770(1.3);1.599(9.3);1.582(9.4);1.571(9.6);1.553(9.2);1.398(5.1);0.0000(4.1)

Example 111: ¹H-NMR(400.0 MHz, d₆-DMSO): δ = 9.064(1.6);9.043(1.7);8.390(7.0);7.620(1.0);7.618(1.1);7.610(1.6);7.601(1.4);7.596(1.3);7.589(0.4);7.459(2.1);7.450(6.4);7.449(6.1);7.439(4.4);7.426(1.5);7.414(3.0);6.998(8.1);5.185(0.4);5.171(0.8);5.153(0.9);5.135(0.4);3.979(0.3);3.961(0.9);3.943(1.3);3.926(0.9);3.908(0.4);3.328(87.6);2.721(0.7);2.705(1.7);2.693(1.8);2.676(1.0);2.671(0.8);2.666(0.6);2.506(66.1);2.502(86.2);2.497(64.7);2.374(16.0);2.333(0.5);2.329(0.6);2.324(0.5);2.263(12.2);2.045(0.5);2.036(0.5);2.024(0.7);2.015(0.8);2.002(0.4);1.916(0.5);1.902(0.5);1.891(0.6);1.871(0.5);1.838(0.4);1.817(0.7);1.812(0.7);1.793(1.0);1.786(1.1);1.769(1.1);1.732(0.3);1.604(7.0);1.586(7.2);1.574(6.8);1.556(6.6);1.398(7.2);0.000(0.9)

Example 112: ¹H-NMR(400.0 MHz, d₆-DMSO): δ = 9.080(1.5);9.058(1.6);8.510(8.2);7.831(0.7);7.826(0.8);7.811(0.8);7.806(0.7);7.795(0.8);7.780(0.7);7.775(0.8);7.607(0.4);7.602(0.4);7.594(0.5);7.584(1.1);7.580(1.3);7.571(2.0);7.551(1.2);7.545(1.2);7.529(0.5);7.524(1.3);7.503(0.5);7.160(2.9);7.005(7.4);7.003(7.2);5.179(0.7);5.161(0.8);5.142(0.4);3.955(0.9);3.938(1.2);3.920(0.9);3.903(0.3);3.328(91.1);3.327(91.1);2.728(0.6);2.713(1.4);2.701(1.5);2.676(0.6);2.671(0.7);2.667(0.5);2.662(0.3);2.525(1.4);2.525(1.4);2.521(16.0);2.525(1.4);2.521(16.0);2.511(27.5);2.507(57.3);2.502(57.1);2.498(28.3);2.333(28.3);2.493(28.3);2.333(0.3);2.329(0.3);2.324(0.4);2.275(11.4);2.055(0.4);2.047(0.4);2.034(0.5);2.025(0.7);2.011(0.4);1.922(0.4);1.907(0.4);1.896(0.5);1.877(0.4);1.824(0.6);1.818(0.6);1.799(0.8);1.792(0.9);1.788(0.8);1.776(0.9);1.762(0.4);1.585(6.7);1.567(6.8);1.558(7.0);1.540(6.6);1.398(2.0);0.951(0.4);0.934(0.4);0.000(0.7)

Example 113: ¹H-NMR(400.0 MHz, d₆-DMSO): δ = 9.071(1.6);9.049(1.7);8.485(7.6);8.355(0.4);8.316(1.3);7.795(0.5);7.789(0.4);7.772(1.6);7.767(5.6);7.761(0.7);7.550(0.6);7.544(5.6);7.539(1.7);7.527(1.5);7.522(4.8);7.515(0.5);7.160(3.0);7.004(7.5);5.191(0.4);5.178(0.7);5.159(0.8);5.142(0.4);3.975(0.3);3.957(0.9);3.939(1.2);3.922(0.9);3.904(0.4);3.364(0.4);3.327(579.0);2.952(1.2);2.729(0.7);2.712(1.5);2.700(1.6);

Example 114: ¹H-NMR(400 MHz, d₆-DMSO): δ = 9.243(1.2);9.223(1.2);8.525(5.5);7.431(1.8);7.423(0.7);7.417(1.0);7.408(1.8);7.401(0.8);7.395(1.5);7.385(1.1);7.372(0.7);7.365(1.9);7.359(2.1);7.321(0.4);7.312(0.6);7.302(0.6);7.291(0.8);7.283(0.5);7.280(0.4);7.269(0.4);7.239(1.2);7.233(1.1);7.217(1.3);7.211(1.2);6.855(2.8);6.833(2.5);5.235(0.7);5.218(0.7);4.303(0.7);4.295(0.5);4.285(0.6);4.277(0.5);4.29(0.5);4.251(0.6);4.239(0.5);4.231(0.8);4.223(0.3);3.964(0.7);3.947(1.0);3.929(0.7);3.332(25.2);2.525(0.4);2.512(8.6);2.503(23.3);2.498(17.2);2.494(8.6);2.460(6.8);2.457(6.9);2.229(0.3);2.215(0.4);2.207(0.4);2.202(0.3);2.194(0.5);2.181(0.3);2.065(0.4);2.058(0.5);2.048(0.4);2.031(0.3);1.588(5.2);1.570(5.8);1.565(5.9);1.547(5.1);1.397(16.0);0.000(1.0)

Example 115: ¹H-NMR(400 MHz, d₆-DMSO): δ = 9.102(2.6);9.081(2.7);8.460(1.2.9);8.317(0.6);7.426(2.0);7.418(1.5);7.412(1.9);7.403(4.6);7.391(3.0);7.380(2.8);7.368(2.9);7.362(2.0);7.347(2.4);7.316(0.9);7.306(1.4);7.297(1.4);7.286(1.7);7.278(1.0);7.275(1.0);7.264(0.8);7.256(0.5);7.224(0.4);7.219(0.7);7.206(2.5);7.201(4.0);7.193(4.1);7.184(4.5);7.179(3.3);7.167(0.9);7.161(0.5);7.130(2.6);7.116(1.6);7.108(1.4);5.226(0.6);5.211(1.2);5.193(1.3);5.176(0.6);3.946(1.5);3.929(2.1);3.911(1.6);3.893(0.6);3.328(211.7);2.812(0.3);2.785(1.1);2.768(2.7);2.754(2.7);2.740(1.1);2.711(0.4);2.676(1.2);2.671(1.7);2.667(1.2);2.524(4.0);2.520(6.1);2.511(87.9);2.507(182.0);2.502(243.4);2.497(181.9);2.493(91.8);2.453(15.4);2.335(1.2);2.329(1.7);2.324(1.2);2.075(0.5);2.060(0.7);2.052(0.8);2.039(1.0);2.031(1.1);2.017(0.8);1.989(0.3);1.941(0.8);1.930(0.7);1.915(1.0);1.896(0.8);1.877(0.8);1.856(1.1);1.851(1.0);1.825(1.6);1.809(1.9);1.789(0.8);1.765(0.5);1.584(11.6);1.567(11.9);1.558(12.2);1.540(11.5);1.398(2.6);0.000(6.8)

Example 116: ¹H-NMR(400 MHz, d₆-DMSO): δ = 9.098(1.9);9.077(1.9);8.495(8.7);8.317(0.4);7.430(1.3);7.422(1.2);7.416(1.5);7.407(2.9);7.399(1.3);7.394(2.6);7.384(2.5);7.372(2.0);7.365(1.6);7.320(0.6);7.310(1.0);7.300(1.1);7.296(1.2);7.287(1.8);7.283(1.7);7.273(2.2);7.263(1.4);7.252(4.6);7.245(2.6);7.238(2.3);7.230(2.5);6.574(0.3);5.548(0.5);5.529(1.6);5.490(0.5);3.987(0.4);3.969(1.1);3.952(1.5);3.934(1.1);3.916(0.4);3.329(197.2);3.020(0.4);3.012(0.5);2.998(0.5);2.990(0.5);2.980(0.8);2.972(0.9);2.959(0.9);2.950(0.8);2.907(0.6);2.887(1.4);2.867(1.0);2.847(0.7);2.827(0.4);2.676(0.8);2.671(1.1);2.667(0.8);2.570(0.5);2.561(0.5);2.550(0.6);2.541(1.1);2.530(1.5);2.524(3.1);2.511(60.7);2.507(122.5);2.502(162.1);2.497(119.6);2.493(59.5);2.457(10.9);2.454(11.2);2.338(0.4);2.333(0.8);2.329(1.1);2.324(0.8);1.963(0.4);1.942(1.0);1.931(0.4);1.921(1.0);1.910(1.0);1.900(0.4);1.890(0.9);1.584(8.3);1.567(16.0);1.549(8.2);1.398(6.6);0.951(1.1);0.934(1.1);0.000(4.4)

Example 117: ¹H-NMR(400 MHz, d₆-DMSO): δ = 9.216(1.4);9.196(1.4);8.545(6.3);8.317(0.4);7.844(1.7);7.839(2.8);7.834(1.6);7.755(0.8);7.526(1.5);7.506(2.9);7.486(1.6);7.384(1.4);7.381(1.4);7.364(1.1);7.360(1.1);7.359(1.0);7.350(1.4);7.332(1.5);7.204(0.7);7.200(0.7);7.182(1.5);7.165(1.0);7.161(0.9);6.953(1.0);6.951(1.1);6.932(1.8);6.916(0.8);6.914(0.8);6.816(1.9);6.814(1.9);6.796(1.8);5.260(0.4);5.246(0.9);5.226(0.9);5.212(0.4);4.307(0.3);4.288(0.8);4.279(0.7);4.272(0.9);4.262(0.8);4.258(0.8);4.250(0.9);4.237(0.7);4.229(1.0);4.209(0.4);3.972(0.8);3.955(1.2);3.937(0.9);3.330(259.5);2.675(1.0);2.671(1.3);2.667(1.0);2.625(14.4);2.524(3.3);2.511(73.7);2.506(147.8);2.502(194.6);2.498(143.0);2.493(70.9);2.333(1.0);2.329(1.3);2.324(1.0);2.228(0.4);2.205(0.6);2.193(0.6);2.180(0.4);2.069(0.6);2.062(0.7);2.051(0.5);2.046(0.5);2.035(0.6);0.4);1.575(6.4);1.557(7.0);1.533(6.3);1.398(16.0);0.000(0.6)

Example 118: ¹H-NMR(400 MHz, d₆-DMSO): δ = 9.214(1.5);9.194(1.6);8.505(7.7);7.789(0.6);7.783(4.6);7.778(1.7);7.766(1.7);7.761(5.6);7.755(0.7);7.550(1.0);7.544(5.8);7.539(1.9);7.527(1.7);7.522(4.8);7.515(0.6);7.346(1.5);7.327(1.6);7.202(0.7);7.199(0.7);7.181(1.5);7.164(1.0);7.160(1.2);6.950(1.2);6.934(1.8);6.931(1.9);6.916(0.9);6.913(0.9);6.816(2.0);6.814(2.1);6.796(1.8);5.261(0.5);5.247(0.9);5.227(0.9);5.213(0.4);4.306(0.4);4.299(0.3);4.287(0.9);4.279(0.8);4.271(0.9);4.257(0.9);4.249(0.8);4.236(0.8);4.229(1.1);4.208(0.4);3.983(0.3);3.966(0.9);3.948(1.3);3.931(0.9);3.331(45.4);2.607(16.0);2.525(0.6);2.520(0.9);2.511(13.9);2.507(28.5);2.502(37.9);2.498(28.1);2.493(14.0);2.227(0.4);2.205(0.6);2.192(0.6);2.184(0.4);2.180(0.4);2.076(0.7);2.051(0.5);2.046(0.5);2.035(0.5);2.028(0.5);1.989(0.4);1.575(6.8);1.557(7.3);1.551(7.4);1.533(6.7);1.397(8.0)

Example 119: ¹H-NMR(400 MHz, d₆-DMSO): δ = 9.093(1.7);9.072(2.0);8.528(2.2);8.510(7.6);7.790(1.7);7.784(1.9);7.769(1.7);7.763(2.6);7.749(4.2);7.744(3.0);7.563(3.1);7.584(3.6);7.376(1.3);7.369(1.3);7.354(1.7);7.224(0.5);7.210(1.7);7.205(2.8);7.196(2.7);7.188(3.2);7.183(2.1);7.170(0.6);7.164(0.4);7.132(1.7);7.117(1.2);7.111(1.0);5.227(0.4);5.212(0.9);5.195(1.0);5.177(0.4);3.978(0.4);3.961(1.0);3.943(1.4);3.926(1.1);3.908(0.4);3.330(16.9);2.868(0.6);2.858(0.8);2.849(1.2);2.839(1.2);2.831(0.9);2.821(0.7);2.811(0.4);2.787(0.8);2.771(2.0);2.758(1.9);2.671(0.8);2.667(0.6);2.630(0.7);2.612(16.0);2.506(101.2);2.502(128.5);2.498(94.8);2.333(0.7);2.329(0.8);2.325(0.6);2.079(0.4);2.064(0.5);2.056(0.6);2.042(0.9);2.034(0.9);2.021(0.5);1.944(0.6);1.917(0.7);1.899(0.6);1.878(0.5);1.854(0.8);1.824(1.2);1.810(1.3);1.576(7.3);1.558(7.9);1.550(7.9);1.533(0.7);2.329(0.8);2.325(0.6);1.397(0.6);0.719(0.7);0.706(2.4);0.701(3.1);0.689(3.0);0.683(2.5);0.672(0.9);0.537(1.0);0.526(3.1);0.520(3.0);0.511(2.7);0.499(0.8);0.146(0.9);0.008(10.0);0.000(179.9);–0.008(8.8);–0.150(0.9)

Example 120: ¹H-NMR(400 MHz, d₆-DMSO): δ = 9.088(1.8);9.068(1.8);8.544(9.0);8.531(2.1);7.793(1.6);7.787(1.9);7.772(1.6);7.766(2.6);7.750(4.2);7.745(3.0);7.587(3.7);7.566(3.1);7.393(1.0);7.381(1.3);7.371(1.4);7.296(0.6);7.285(1.7);7.274(1.9);7.265(1.2);7.244(1.9);7.247(2.4);7.240(2.2);7.232(2.3);5.552(0.5);5.533(1.5);5.513(1.4);5.493(0.5);4.037(0.6);4.020(0.7);4.001(0.5);3.983(1.0);3.965(1.4);3.947(1.0);3.930(0.4);3.330(71.8);3.022(0.4);3.014(0.4);3.001(0.4);2.992(0.5);2.983(0.8);2.974(0.8);2.961(0.8);2.953(0.7);2.910(0.6);2.889(1.4);2.860(0.8);2.851(1.7);2.841(1.2);2.831(1.0);2.822(0.6);2.676(0.3);2.671(0.5);2.666(0.4);2.634(0.6);2.615(16.0);2.573(0.4);2.564(0.4);2.553(0.7);2.544(0.9);2.533(1.0);2.519(2.3);2.511(26.1);2.506(52.8);2.502(70.1);2.497(51.5);2.493(25.9);2.329(0.5);2.324(0.3);1.989(2.7);1.964(0.3);1.942(0.9);1.932(0.4);1.922(0.9);1.911(0.9);1.900(0.4);1.891(0.8);1.576(7.3);1.559(13.8);1.541(7.1);1.397(2.8);1.193(0.7);1.175(1.4);1.157(0.7);1.720(0.8);0.707(2.2);0.702(3.0);0.690(2.8);0.684(2.4);0.673(1.0);0.539(1.0);0.528(2.9);0.522(2.7);0.518(2.5);0.513(2.5);0.500(0.8);0.146(0.7);0.008(5.1);0.000(137.6);–0.009(6.0);–0.150(0.7)

Example 121: ¹H-NMR(400 MHz, d₆-DMSO): δ = 9.222(1.5);9.201(1.6);8.489(5.9);7.427(1.1);7.414(1.1);7.404(2.5);7.392(1.7);7.382(1.5);7.370(0.8);7.342(1.5);7.322(1.7);7.309(0.8);7.299(0.8);7.288(1.0);7.280(0.6);7.266(0.5);7.197(0.8);7.179(1.6);7.162(0.9);7.158(0.9);6.946(1.1);6.928(2.1);6.792(1.9);5.255(0.6);5.241(1.0);5.221(1.0);5.207(0.4);4.303(0.4);4.296(0.3);4.284(0.9);4.276(0.8);4.268(0.9);4.260(0.7);4.250(0.7);4.243(0.9);4.228(0.8);4.221(1.0);4.201(0.4);4.194(0.3);3.976(0.3);3.961(0.9);3.908(0.4);3.331(78.6);2.676(0.4);2.671(0.5);2.507(57.1);2.502(75.5);2.498(59.0);2.4520.5);2.333(0.4);2.329(0.5);2.223(0.4);2.210(0.6);2.201(0.8);2.189(0.7);2.176(0.5);2.074(0.4);2.066(0.6);2.059(0.7);2.048(0.5);2.044(0.5);2.031(0.5);2.025(0.4);1.989(0.4);1.581(6.4);1.563(6.9);1.556(7.2);1.538(6.4);1.398(16.0);0.146(0.5);0.008(4.0);0.000(100.9);–0.150(0.5)

Example 122: ¹H-NMR(400 MHz, d₆-DMSO): δ = 9.108(1.6);9.088(1.7);8.624(7.2);8.034(15.3);7.863(0.6);7.402(1.0);7.390(1.3);7.380(1.3);7.298(0.6);7.288(1.1);7.276(1.8);7.267(1.1);7.256(3.9);7.249(2.3);7.242(2.0);7.234(2.1);7.202(3.4);5.535(1.4);5.515(1.4);5.495(0.5);3.998(0.4);3.980(0.9);3.963(1.3);3.945(1.3);3.927(0.4);3.329(44.3);3.025(0.3);3.016(0.4);3.002(0.4);2.994(0.4);2.985(0.7);2.976(0.8);2.963(0.8);2.954(0.7);2.913(0.5);2.892(1.2);2.872(0.9);2.852(0.6);2.832(0.4);2.671(0.8);2.659(16.0);2.577(0.4);2.568(0.4);2.557(0.7);2.548(0.8);2.537(0.9);2.525(1.9);2.511(28.0);2.507(57.1);2.502(75.6);2.498(56.2);2.334(0.4);2.329(0.5);2.325(0.4);1.966(0.3);1.944(0.9);1.934(0.4);1.924(0.9);1.913(0.8);1.902(0.4);1.893(0.8);1.573(7.2);1.555(13.6);1.538(7.0);1.397(8.9);0.000(7.5)

Example 123: ¹H-NMR(400 MHz, d₆-DMSO): δ = 9.099(1.6);9.078(1.6);8.521(0.7);8.515(7.3);7.734(3.3);7.731(3.5);7.556(0.7);7.553(6.8);7.535(3.3);7.532(3.6);7.525(5.1);7.504(0.9);7.390(0.9);7.378(1.2);7.369(1.3);7.298(0.5);7.286(1.1);7.276(1.8);7.264(1.2);7.254(2.5);7.248(2.5);7.241(2.3);7.233(2.2);5.554(0.5);5.535(1.3);5.514(1.3);5.495(0.4);3.989(0.3);3.971(0.9);3.954(1.3);3.936(0.9);3.918(0.4);3.328(96.1);3.015(0.4);3.002(0.4);2.993(0.5);2.984(0.7);2.975(0.8);2.962(0.7);2.953(0.7);2.910(0.5);2.890(1.2);2.870(0.9);2.850(0.6);2.829(0.3);2.676(0.8);2.671(1.0);2.667(0.8);2.609(16.0);2.574(0.5);2.565(0.5);2.554(0.8);2.545(1.0);2.534(1.3);2.524(3.3);2.520(4.5);2.511(56.7);2.507(115.4);2.502(152.5);2.498(110.7);2.493(54.1);2.459(1.2);2.334(0.7);2.329(1.0);2.324(0.7);1.946(0.8);1.936(0.4);1.926(0.9);1.915(0.9);1.905(0.4);1.895(0.8);1.578(6.9);1.561(13.4);1.543(6.8);1.533(0.8);1.515(0.9);1.498(0.5);1.398(6.7);0.008(0.5);0.000(14.9);–0.008(0.5)

-continued

Example 124: ¹H-NMR(400.0 MHz, d₆-DMSO): δ = 9.112(0.6);9.091(0.6);8.596(2.8);8.129(1.0);8.097(1.0);7.784(0.9);7.390(0.4);7.382(0.4);7.367(0.5);7.212(0.5);7.207(0.9);7.198(0.9);7.189(1.0);7.184(0.7);7.134(0.6);7.119(0.4);3.975(0.3);3.958(0.5);3.940(0.3);3.329(28.1);2.772(0.6);2.759(0.6);2.667(5.9);2.525(0.7);2.511(14.9);2.507(30.5);2.502(40.2);2.498(29.5);2.493(14.5);1.830(0.4);1.814(0.4);1.580(2.5);1.563(2.6);1.556(2.7);1.538(2.4);1.398(16.0);0.000(4.1)

Example 125: ¹H-NMR(400.0 MHz, d₆-DMSO): δ = 9.112(0.9);9.091(0.9);8.590(4.3);8.034(0.1);7.384(0.6);7.377(0.7);7.362(0.8);7.212(0.9);7.207(1.5);7.198(1.5);7.189(1.7);7.185(1.1);7.134(1.0);7.119(0.6);7.112(0.5);5.214(0.5);5.196(0.5);3.957(0.5);3.939(0.7);3.922(0.6);3.328(61.8);2.788(0.4);2.772(1.0);2.759(1.0);2.745(0.4);2.675(0.6);2.671(0.9);2.657(9.3);2.524(1.9);2.511(41.7);2.507(83.9);2.502(110.1);2.498(81.6);2.493(41.1);2.333(0.5);2.329(0.7);2.324(0.5);2.046(0.4);2.037(0.4);1.916(0.4);1.853(0.4);1.826(0.6);1.813(0.7);1.572(4.0);1.547(4.4);1.529(4.0);1.398(16.0);0.008(0.4);0.000(10.6);−0.009(0.4)

Example 126: ¹H-NMR(400.0 MHz, d₆-DMSO): δ = 9.083(1.5);9.0621(1.5);8.427(6.4);7.638(3.7);7.618(4.5);7.374(1.0);7.368(1.2);7.349(5.0);7.374(1.0);7.329(3.6);7.223(0.4);7.209(1.3);7.2042(1.7);7.195(2.2);7.186(2.3);7.181(1.7);7.167(0.5);7.163(0.4);7.130(1.5);7.114(0.9);7.108(0.8);5.758(3.8);5.233(0.3);5.217(0.7);5.200(0.8);5.182(0.4);3.954(0.8);3.937(1.1);3.919(0.9);3.902(0.3);3.330(1.1);2.964(0.4);2.946(0.9);2.929(1.3);2.912(1.0);2.890(1.0);2.786(0.6);2.770(1.6);2.756(1.6);2.731(1.8);2.506(18.6);2.502(24.3);2.497(18.1);2.063(0.4);2.055(0.5);2.042(0.6);2.034(0.7);2.019(0.5);1.949(0.5);1.938(0.4);1.922(0.6);1.903(0.5);1.880(0.4);1.858(0.6);1.853(0.6);1.835(0.7);1.827(0.9);1.811(1.1);1.791(0.5);1.581(6.1);1.564(6.4);1.555(6.5);1.537(6.0);1.240(15.7);1.149(0.5);1.132(0.4);0.008(1.4);0.000(33.9);−0.008(1.6)

Example 127: ¹H-NMR(400.0 MHz, d₆-DMSO): δ = 9.104(0.9);9.084(0.9);8.595(4.2);7.942(4.0);7.9264(0.5);7.386(0.8);7.376(0.7);7.298(0.3);7.288(0.6);7.276(1.1);7.266(0.7);7.255(2.3);7.248(1.3);7.242(1.2);7.233(1.2);5.534(0.8);5.514(0.8);3.976(0.5);3.959(0.8);3.941(0.6);3.568(1.0);3.329(30.2);2.985(0.4);2.977(0.5);2.963(0.4);2.955(0.4);2.891(0.7);2.871(0.5);2.852(0.4);2.676(0.4);2.672(0.5);2.667(0.4);2.640(9.1);2.556(0.5);2.547(0.6);2.536(0.7);2.525(1.9);2.511(30.1);2.507(60.4);2.502(79.1);2.498(58.3);2.494(29.3);2.334(0.4);2.329(0.5);2.325(0.4);1.944(0.5);1.924(0.5);1.913(0.5);1.892(0.5);1.573(4.1);1.556(7.9);1.538(4.0);1.398(16.0);0.008(0.5);0.000(14.1);−0.008(0.6)

Example 128: ¹H-NMR(400.0 MHz, d₆-DMSO): δ = 9.109(1.7);9.088(1.8);8.561(7.4);8.529(0.3);7.940(6.9);7.381(1.1);7.374(1.3);7.359(1.6);7.224(0.5);7.206(2.7);7.197(2.6);7.188(3.0);7.184(2.2);7.171(0.6);7.166(0.9);7.133(1.8);7.118(1.1);7.111(1.5);5.758(7.9);5.228(0.4);5.213(0.9);5.191(0.5);3.971(0.4);3.954(1.0);3.936(1.4);3.918(1.0);3.901(0.4);3.331(68.4);2.788(0.8);2.772(1.9);2.758(1.9);2.745(0.8);2.733(0.4);2.676(0.5);2.671(0.6);2.667(0.5);2.655(0.9);2.637(16.0);2.525(1.5);2.507(64.3);2.503(84.0);2.498(62.2);2.334(0.4);2.329(0.6);2.325(0.4);2.080(0.3);2.065(0.5);2.058(0.6);2.044(0.7);2.036(0.8);2.022(0.6);1.944(0.5);1.932(0.5);1.917(0.7);1.898(0.6);1.878(0.6);1.858(0.7);1.852(0.7);1.827(1.1);1.812(1.3);1.768(0.3);1.573(7.2);1.555(7.9);1.547(7.8);1.530(7.1);0.008(0.5);0.000(14.1);−0.008(0.6)

Example 129: ¹H-NMR(400.0 MHz, d₆-DMSO): δ = 9.295(3.4);9.275(3.5);8.735(16.0);8.310(9.2);8.003(9.1);7.370(3.0);7.351(3.2);7.212(1.5);7.208(1.6);7.191(3.1);7.173(2.0);7.170(2.0);6.961(2.2);6.958(2.4);6.942(3.7);6.940(4.0);6.924(1.9);6.921(2.0);6.8244(2.3);6.8224(3.9);6.8014(3.8);5.757(11.6);5.319(1.7);5.296(5.6);5.2374(1.0);5.250(3.4);5.237(2.1);5.223(0.9);4.327(0.6);4.318(0.8);4.311(0.8);4.299(1.6);4.291(1.4);4.283(1.7);4.274(1.2);4.247(1.2);4.240(1.6);4.226(1.5);4.219(2.2);4.213(1.0);4.198(0.9);4.191(0.7);3.962(0.3);3.944(1.9);3.926(2.8);3.909(2.0);3.892(0.7);3.332(224.2);3.314(0.9);2.677(0.6);2.672(0.9);2.668(0.6);2.526(2.0);2.521(3.2);2.512(46.7);2.508(97.8);2.503(131.1);2.499(98.0);2.494(49.4);2.334(0.6);2.330(0.9);2.325(0.6);2.267(0.4);2.259(0.6);2.254(0.6);2.246(0.9);2.232(1.3);2.224(1.3);2.211(1.3);2.198(0.9);2.190(0.6);2.105(0.6);2.097(0.9);2.089(1.2);2.082(1.4);2.067(1.1);2.055(0.9);2.048(0.9);2.039(0.6);2.032(0.4);1.990(0.4);1.563(14.1);1.545(15.3);1.539(16.0);1.521(14.0);1.413(0.7);1.396(0.7);1.234(0.6);0.008(2.2);0.000(72.0);−0.009(2.9)

Example 130: ¹H-NMR(400.0 MHz, d₆-DMSO): δ = 9.225(0.9);9.205(0.9);8.4364(0.7);7.540(0.7);7.526(0.8);7.521(0.9);7.515(1.1);7.509(2.1);7.495(0.3);7.492(0.3);7.388(0.2);7.375(0.7);7.371(0.7);7.355(0.3);7.338(0.8);7.319(0.9);7.195(0.4);7.192(0.6);7.174(0.9);7.157(0.6);7.153(0.5);6.940(0.6);6.922(1.1);6.807(1.1);6.788(1.1);5.234(0.5);5.215(0.6);4.280(0.5);4.272(0.4);4.264(0.5);4.256(0.4);4.241(0.4);4.234(0.5);4.219(0.4);4.213(0.6);3.962(0.5);3.944(0.7);3.927(0.5);3.329(29.8);2.524(0.5);2.502(32.1);2.498(23.8);2.344(7.9);2.329(0.3);2.207(0.3);2.198(0.3);2.185(0.4);2.062(0.4);2.054(0.4);1.593(2.9);1.574(3.0);1.567(3.3);1.549(3.0);1.398(16.0);0.008(0.5);0.000(15.7);−0.008(0.7)

Example 131: ¹H-NMR(400.0 MHz, d₆-DMSO): δ = 9.106(1.3);9.0851(3);9.085(1.2);8.4075(5);7.559(0.3);7.539(1.2);7.525(1.2);7.519(1.5);7.515(3.1);7.509(0.5);7.498(0.5);7.495(0.5);7.490(0.5);7.398(0.5);7.393(0.7);7.388(0.5);7.374(1.0);7.369(1.2);7.362(1.3);7.353(1.5);7.341(1.3);7.212(0.3);7.196(1.9);7.187(2.0);7.177(2.1);7.161(0.5);7.125(1.4);7.111(1.9);7.102(0.7);5.221(0.3);5.206(0.7);5.188(0.7);5.172(0.4);3.947(0.7);3.930(1.1);3.912(0.8);3.329(67.5);2.779(0.6);2.762(1.5);2.748(1.5);2.733(0.6);2.675(0.4);2.671(0.5);2.667(0.4);2.498(53.1);2.343(11.7);2.502(69.1);2.498(53.7);2.502(50.7);2.044(0.5);2.032(0.6);2.023(0.6);2.015(0.4);2.010(0.4);1.989(0.3);1.936(0.4);1.926(0.4);1.910(0.6);1.888(0.5);1.875(0.5);1.856(0.5);1.832(0.6);1.824(0.9);1.807(1.1);1.785(0.5);1.596(4.4);1.578(4.6);1.568(5.3);1.550(4.9);1.398(16.0);0.000(27.1)

Example 132: ¹H-NMR(400.0 MHz, d₆-DMSO): δ = 9.101(1.0);9.080(1.0);8.443(5.5);7.563(0.3);7.543(0.9);7.528(1.0);7.523(1.1);7.516(1.5);7.511(2.8);7.496(0.5);7.399(0.5);7.395(0.6);7.396(0.7);7.383(0.7);7.379(0.8);7.374(1.3);7.370(1.2);7.360(0.9);7.353(0.6);7.351(0.5);7.290(0.3);7.280(0.6);7.268(1.1);7.258(0.7);7.247(2.4);7.240(1.4);7.234(1.2);7.225(1.5);5.521(0.8);5.501(0.8);3.970(0.6);3.953(0.8);3.935(0.6);3.330(32.6);3.305(0.4);3.302(0.4);2.976(0.4);4.213(0.8);3.962(0.5);2.946(0.4);2.902(0.3);2.881(0.7);2.861(0.5);2.842(0.4);2.544(0.5);2.534(0.6);2.524(0.9);2.511(9.4);2.507(19.1);2.502(25.8);2.498(19.0);2.493(9.8);2.477(1.1);2.347(9.5);2.329(0.4);1.935(0.5);1.915(0.5);1.904(0.5);1.883(0.5);1.598(2.8);1.594(2.9);1.576(6.3);1.559(5.7);1.397(16.0);0.000(16.8);−0.009(0.7)

Example 133: ¹H-NMR(400.0 MHz, d₆-DMSO): δ = 9.475(0.7);9.0962(3);9.169(1.9);9.149(2.0);8.749(8.6);8.317(0.6);7.462(2.3);7.441(3.6);7.418(2.4);7.406(1.5);7.395(1.7);7.385(1.6);7.301(0.8);7.292(1.5);7.280(2.6);7.271(1.5);7.258(4.8);7.252(2.8);7.247(2.7);7.236(2.4);7.225(0.4);7.155(0.4);5.551(0.6);5.532(1.7);5.512(1.7);5.121(7.4);5.106(3.5);5.532(1.7);5.532(1.7);5.532(1.7);3.961(1.2);3.943(1.7);3.926(1.2);3.908(0.5);3.868(0.3);3.331(128.6);2.765(3.2);2.676(1.3);2.507(201.9);2.464(16.0);2.460(15.7);2.333(1.5);2.040(1.5);3.002(0.6);2.993(0.6);2.984(1.0);2.975(1.4);2.963(1.1);2.953(0.9);2.916(0.8);2.896(1.7);2.876(1.3);2.856(0.9);2.836(0.5);2.825(2.7);2.525(1.5);2.345(2.7);2.667(1.5);2.667(1.2);2.589(0.6);2.580(0.7);2.569(1.1);2.559(1.3);2.549(1.5);2.538(1.9);2.525(4.7);2.507(168.3);2.503(216.6);2.498(158.1);2.329(1.1);1.929(0.5);1.920(1.1);1.908(1.0);1.898(1.0);1.888(0.5);1.867(0.3);1.587(8.8);1.569(16.0);1.551(8.5);1.398(0.7);1.220(1.1);1.203(1.8);1.186(0.9);0.952(0.4);0.008(0.9);0.000(26.3);−0.008(1.2)

Example 134: ¹H-NMR(400.0 MHz, d₆-DMSO): δ = 9.106(2.0);9.0962(3);8.4644.8);8.4575.2);7.498(0.9);7.4864.5);7.473(1.5);7.458(1.5);7.453(1.6);7.434(0.8);7.395(1.7);7.385(1.6);7.395(1.7);7.370(4.0);7.361(4.1);7.333(2.1);7.325(1.8);7.314(1.5);7.202(3.9);7.192(4.6);7.186(3.9);7.131(2.6);7.117(2.0);5.201(1.8);3.949(1.1);3.939(1.5);3.932(1.5);3.921(1.2);3.338(113.8);3.331(128.6);2.765(3.2);2.676(1.3);2.507(201.9);2.464(16.0);2.460(15.7);2.333(1.5);2.040(1.5);1.919(1.3);1.858(1.4);1.812(1.3);1.595(6.4);1.589(7.4);1.571(12.0);1.562(8.8);1.551(7.8);1.545(7.5);1.405(5.1);1.398(5.8);0.007(10.4);0.005(8.6);0.000(13.0)

Example 135: ¹H-NMR(400.0 MHz, d₆-DMSO): δ = 9.170(2.0);9.150(2.1);8.808(0.5);8.736(7.8);7.670(0.4);7.653(0.9);7.649(0.9);7.632(1.7);7.615(1.0);7.6111.1);7.594(0.5);7.406(1.4);7.395(1.9);7.386(1.8);7.326(2.6);7.305(5.2);7.291(2.2);7.284(3.7);7.270(1.5);7.258(4.7);7.252(2.9);7.246(2.7);7.236(2.7);7.2251(0.3);5.552(0.5);5.5331(1.7);5.515(1.7);5.494(0.6);3.983(0.4);3.965(1.2);3.948(1.7);3.930(1.2);3.913(0.5);3.330(164.8);3.023(0.4);3.014(0.5);3.002(0.6);2.993(0.7);2.984(1.0);2.975(1.1);2.964(2.3);2.954(1.0);2.915(0.7);2.895(1.6);2.875(1.2);2.856(0.8);2.835(0.5);2.675(0.9);2.672(1.1);2.667(0.9);2.589(0.5);2.580(0.6);2.570(1.0);2.559(1.2);2.549(1.2);2.538(1.6);2.507(128.1);2.502(166.5);2.498(127.0);2.329(1.1);2.325(0.8);1.961(0.4);1.940(1.1);1.908(1.0);1.899(0.9);1.888(1.0);1.867(0.3);1.592(8.6);1.574(16.0);1.556(8.6);1.398(7.9);0.951(1.4);0.934(1.5);0.008(0.7);0.000(17.5)

Example 136: ¹H-NMR(400.0 MHz, d₆-DMSO): δ = 9.223(2.4);9.202(2.5);8.485(7.7);7.493(0.6);7.473(1.5);7.452(1.4);7.432(0.7);7.391(0.9);7.373(2.2);7.358(2.0);7.344(3.9);7.324(4.3);7.313(1.9);7.291(0.6);7.197(1.2);7.179(2.5);7.161(1.6);6.946(1.7);6.927(2.9);6.908(1.5);6.812(3.1);6.791(2.8);5.757(1.0);5.254(0.7);5.240(1.6);5.222(1.7);5.207(0.8);4.303(0.7);4.295(0.7);4.284(1.5);4.275(1.4);4.268(1.6);4.260(1.3);4.248(1.3);4.241(1.5);4.221(1.7);4.200(0.8);4.194(0.7);3.981(0.5);3.963(1.3);3.946(1.8);3.928(1.4);3.911(0.6);3.330(73.1);2.671(0.7);2.502(108.5);2.458(16.0);2.397(0.6);2.329(0.8);2.286(0.3);2.223(0.8);2.211(1.1);2.202(1.2);2.189(1.2);2.065(1.4);2.060(1.3);2.048(1.1);2.031(0.9);1.585(9.2);1.567(10.7);1.560(11.0);1.542(9.3);1.397(0.4);1.234(0.4);1.094(0.4);1.025(0.4);1.011(0.4);0.950(0.8);0.937(0.8);0.000(9.2)

-continued

Example 137: ¹H-NMR(400.0 MHz, d₆-DMSO): δ = 9.317(3.3);9.297(3.5);8.759(3.1);8.759(3.1);7.692(1.7);7.673(5.2);7.653(5.1);7.644(5.1);7.621(1.9);7.565(4.7);7.468(2.7);7.448(2.3);7.367(3.3);7.349(3.6);7.211(1.5);7.208(1.6);7.191(3.4);7.173(2.1);7.170(2.1);6.956(2.4);6.938(4.1);6.919(2.0);6.823(4.5);6.803(4.1);5.759(0.5);5.270(0.9);5.256(2.1);5.237(2.2);5.223(1.0);4.326(0.7);4.318(0.9);4.310(0.9);4.298(1.8);4.290(1.6);4.282(1.9);4.274(1.4);4.247(1.4);4.241(1.7);4.226(1.6);4.219(2.3);4.198(1.0);4.191(0.8);3.990(0.7);3.972(1.9);3.955(2.7);3.937(2.0);3.920(0.8);3.332(48.4);2.673(0.5);2.508(56.5);2.504(72.3);2.500(54.7);2.330(0.5);2.265(0.4);2.255(0.6);2.244(1.0);2.230(1.3);2.222(1.4);2.209(1.4);2.196(1.0);2.187(0.7);2.100(0.9);2.091(1.4);2.084(1.5);2.070(1.2);2.056(1.0);2.050(1.0);2.041(0.7);1.583(13.8);1.565(15.8);1.559(16.0);1.542(13.7);1.512(0.3);0.000(8.2)

Example 138: ¹H-NMR(400.0 MHz, d₆-DMSO): δ = 9.161(1.9);9.140(1.9);8.778(0.5);8.699(7.6);8.318(0.4);7.666(0.4);7.649(0.9);7.645(0.9);7.628(1.7);7.611(1.0);7.608(1.0);7.591(0.5);7.386(1.4);7.376(1.7);7.363(2.0);7.348(0.4);7.324(1.8);7.320(1.8);7.303(3.3);7.282(1.6);7.220(0.5);7.208(3.1);7.203(2.3);7.197(3.1);7.191(2.7);7.185(3.7);7.173(0.7);7.135(2.7);7.122(1.5);7.112(1.1);5.234(0.6);5.220(1.2);5.201(1.2);5.186(0.5);3.955(0.4);3.938(1.2);3.920(1.6);3.885(0.5);3.330(199.2);2.941(1.2);2.812(0.3);2.785(0.9);2.770(2.3);2.754(2.2);2.739(1.0);2.713(0.3);2.671(1.5);2.667(1.1);2.507(166.2);2.502(218.3);2.498(168.0);2.333(1.1);2.329(1.4);2.325(1.1);2.083(0.4);2.060(0.8);2.049(1.0);2.034(0.8);2.020(0.6);1.921(0.5);1.895(1.2);1.880(1.5);1.872(1.4);1.857(1.1);1.848(1.0);1.826(1.4);1.808(0.8);1.799(0.7);1.593(8.4);1.575(8.7);1.565(9.0);1.547(8.5);1.398(16.0);0.000(22.6)

Example 139: ¹H-NMR(400.0 MHz, d₆-DMSO): δ = 9.293(3.0);9.273(3.0);8.796(1.5);8.744(2.6);8.729(12.0);8.696(0.5);8.317(0.7);7.667(0.7);7.650(1.5);7.646(1.4);7.629(2.6);7.612(1.5);7.608(1.6);7.592(0.7);7.358(3.3);7.339(3.6);7.324(3.7);7.302(6.6);7.281(3.2);7.207(1.5);7.204(1.6);7.186(3.3);7.168(2.0);7.165(1.9);6.948(2.2);6.929(3.8);6.913(1.7);6.911(1.8);6.817(4.1);6.798(3.7);5.256(1.0);5.243(2.0);5.223(1.9);5.210(0.8);4.323(0.7);4.315(1.0);4.307(0.9);4.296(1.7);4.287(1.5);4.279(1.7);4.272(1.3);4.225(1.3);4.219(1.6);4.204(1.5);4.198(2.1);4.176(0.9);4.169(0.8);3.974(0.7);3.957(1.8);3.939(2.5);3.921(1.9);3.904(0.7);3.568(0.5);3.377(0.4);3.332(400.5);2.955(2.6);2.676(1.4);2.672(2.0);2.667(1.5);2.507(230.5);2.503(301.3);2.498(225.6);2.397(0.6);2.334(1.5);2.329(2.0);2.325(1.5);2.263(0.5);2.251(0.7);2.241(1.0);2.228(1.3);2.219(1.3);2.207(1.4);2.194(1.0);2.186(0.7);2.096(0.7);2.089(0.9);2.080(1.3);2.074(1.5);2.065(1.0);2.060(1.2);2.046(1.0);2.040(1.1);2.031(0.7);2.024(0.5);1.989(0.3);1.590(12.9);1.572(13.9);1.565(14.6);1.548(13.0);1.512(0.4);1.398(16.0);1.294(0.3);1.276(0.3);1.235(0.9);1.093(0.6);1.077(0.4);1.028(0.5);1.024(0.7);1.010(0.5);1.007(0.7);0.008(1.2);0.000(36.3);−0.008(1.7)

Example 140: ¹H-NMR(400.0 MHz, d₆-DMSO): δ = 9.294(3.4);9.274(3.5);8.744(15.5);8.707(0.3);8.459(0.5);7.460(3.0);7.438(5.2);7.417(3.1);7.358(3.3);7.339(3.4);7.208(1.7);7.205(1.7);7.187(3.4);7.170(2.2);7.166(2.1);7.104(0.3);6.951(2.3);6.949(2.5);6.930(4.2);6.914(2.0);6.911(2.0);6.820(4.4);6.818(4.4);6.800(4.1);5.257(0.9);5.243(2.0);7.224(2.1);5.210(1.0);4.324(0.7);4.316(1.0);4.309(0.9);4.297(1.6);4.288(1.5);4.281(1.7);4.272(1.2);4.226(1.3);4.220(1.6);4.204(1.5);4.198(2.2);4.176(1.0);4.169(0.8);3.971(0.7);3.954(2.0);3.936(2.8);3.919(2.1);3.901(0.8);3.332(86.3);2.677(0.6);2.672(0.8);2.668(0.7);2.526(1.5);2.512(43.1);2.508(88.8);2.503(117.9);2.499(86.5);2.495(43.2);2.460(1.0);2.334(0.6);2.330(0.8);2.326(0.6);2.264(0.5);2.255(0.7);2.251(0.7);2.242(1.0);2.229(1.4);2.207(1.4);2.201(1.4);2.194(1.0);2.187(0.7);2.096(0.7);2.090(0.9);2.081(1.3);2.075(1.5);2.060(1.2);2.046(1.1);2.040(1.0);2.032(0.7);2.025(0.6);1.585(14.4);1.568(15.5);1.561(16.0);1.543(14.4);1.398(0.4);1.208(0.4);1.191(0.4);0.969(0.3);0.952(1.4);0.936(1.2);0.008(0.5);0.000(16.5);−0.009(0.7)

Example 141: ¹H-NMR(400.0 MHz, d₆-DMSO): δ = 9.100(2.0);9.079(2.1);8.492(8.1);7.500(0.4);7.496(0.5);7.480(0.9);7.475(1.2);7.461(0.7);7.455(1.1);7.450(1.0);7.435(0.6);7.430(0.6);7.395(0.9);7.376(3.3);7.365(2.6);7.347(1.2);7.335(1.1);7.327(1.3);7.314(1.2);7.295(1.1);7.284(1.4);7.273(2.2);7.263(1.4);7.252(4.6);7.244(2.9);7.238(2.6);7.230(2.5);7.220(0.4);5.528(1.7);5.509(1.7);5.489(0.6);3.990(0.4);3.972(1.1);3.955(1.6);2.551(0.8);2.540(1.1);2.506(90.7);2.502(116.3);2.498(88.1);2.461(13.0);2.426(0.5);2.407(0.4);2.329(0.8);1.962(0.4);1.941(1.0);1.931(0.5);1.920(1.1);1.910(1.0);1.899(0.5);1.889(1.0);1.868(0.4);1.858(0.3);1.588(8.4);1.571(16.0);1.553(8.3);1.397(7.4);0.951(2.8);0.935(3.0);0.920(0.4);0.000(16.5)

Example 142: ¹H-NMR(400.0 MHz, d₆-DMSO): δ = 9.292(2.7);9.272(2.8);8.709(10.9);8.696(1.3);7.521(4.8);7.521(4.8);7.499(3.6);7.493(3.0);7.485(1.9);7.375(2.2);7.362(5.0);7.395(0.4);7.383(1.9);7.344(3.4);7.209(1.3);7.206(1.5);7.188(3.0);7.171(1.9);7.167(1.9);6.954(2.2);6.935(3.7);6.911(1.9);6.821(4.0);6.800(3.5);5.758(2.2);5.254(1.7);5.235(1.8);5.221(0.8);4.482(16.0);4.323(0.6);4.316(0.8);4.308(0.8);4.297(1.5);4.288(1.4);4.280(1.6);4.273(1.2);4.245(1.1);4.238(1.5);4.223(1.5);4.217(2.0);4.195(0.9);4.189(0.7);3.985(0.6);3.968(1.6);3.950(2.2);3.932(1.7);3.914(0.8);3.330(31.7);3.321(37.2);2.676(0.5);2.672(0.6);2.668(0.5);2.507(67.6);2.503(90.1);2.498(69.0);2.334(0.5);2.330(0.7);2.325(0.5);2.264(0.4);2.251(0.6);2.242(0.9);2.229(1.1);2.220(1.2);2.207(1.3);2.198(0.9);2.195(0.9);2.186(0.6);2.093(0.8);2.085(1.1);2.079(1.3);2.063(1.0);2.051(0.9);2.044(0.9);2.036(0.6);1.989(0.5);1.584(11.2);1.566(12.5);1.560 (13.1);1.542 (12.4);1.525(1.8);1.520(1.7);1.502(1.4);1.234(0.5);0.008(0.4);0.000(10.8)

Example 143: ¹H-NMR(400.0 MHz, d₆-DMSO): δ = 9.340(3.1);9.320(3.4);8.817(13.8);8.318(0.4);7.980(5.6);7.976(6.1);7.895(6.7);7.368(3.1);7.350(3.4);7.212(1.4);7.209(1.6);7.191(3.2);7.174(2.0);7.170(2.0);6.955(2.4);6.937(4.0);6.918(1.9);6.823(4.4);6.802(3.9);5.758(9.5);5.269(0.9);5.255(2.0);5.236(2.0);5.222(0.9);4.325(0.6);4.317(0.8);4.309(0.8);4.298(1.7);4.289(1.7);4.281(1.7);4.273(1.3);4.249(1.2);4.242(1.7);4.228(1.5);4.221(2.2);4.200(0.9);4.193(0.7);3.984(0.7);3.966(2.7);3.949(1.9);3.931(0.7);3.569(1.2);3.330(66.2);2.892(0.7);2.732(0.6);2.672(0.7);2.668(0.6);2.526(1.7);2.508(82.1);2.503(111.2);2.499(84.6);2.334(0.6);2.330(0.8);2.326(0.4);2.252(0.6);2.242(0.9);2.229(1.3);2.220(1.3);2.208(1.4);2.195(0.9);2.187(0.6);2.105(0.6);2.098(0.9);2.089(1.2);2.083(1.4);2.067(1.1);2.055(1.0);2.048(0.9);2.040(0.6);2.033(0.5);1.990(0.4);1.582(13.4);1.564(15.0);1.559(16.0);1.541(13.2);1.397(1.1);0.008(0.4);0.000(13.7)

Example 144: ¹H-NMR(400.0 MHz, d₆-DMSO): δ = 9.167(2.0);9.147(2.1);8.714(8.8);8.701(0.7);7.522(3.6);7.501(2.7);7.497(2.2);7.488(5.5);7.411(1.4);7.399(2.0);7.389(2.8);7.378(1.8);7.364(1.5);7.304(0.7);7.293(1.4);7.281(2.4);7.272(2.5);7.261(4.9);7.254(2.9);7.247(2.7);7.239(2.6);7.229(0.4);5.565(0.6);5.545(1.7);5.525(1.7);5.506(0.6);4.484(11.6);3.993(0.4);3.975(1.1);3.958(1.6);3.940(1.2);3.921(0.6);3.331(177.5);3.323(29.1);3.029(0.4);3.020(0.5);3.007(0.5);2.997(0.6);2.989(0.9);2.980(1.0);2.967(1.0);2.958(0.9);2.919(0.7);2.899(1.2);2.878(1.1);2.859(0.8);2.839(0.5);2.676(0.7);2.672(1.0);2.591(0.4);2.581(0.5);2.571(0.9);2.561(1.1);2.551(1.1);2.540(1.4);2.507 (113.3);2.503(146.5);2.498(109.2);2.498(21.7);2.494(10.6);2.068(0.4);2.059(0.5);2.047(0.6);2.038(0.7);2.024(0.5);1.949(0.5);1.937(0.4);1.922(0.6);1.903(0.5);1.861(0.6);1.830(1.0);1.814(1.1);1.588(7.1);1.570(7.3);1.562(7.4);1.544(6.9);0.000(1.5)

Example 145: ¹H-NMR(400.0 MHz, d₆-DMSO): δ = 9.127(3.2);9.106(3.2);8.488(16.0);8.318(1.0);7.427(3.2);7.424(3.9);7.411(3.2);7.408(7.4);7.404(7.1);7.391(7.0);7.387(4.4);7.380(2.2);7.373(2.3);7.357(2.9);7.344(5.9);7.324(6.2);7.304(2.4);7.228(0.6);7.222(0.9);7.209(2.8);7.204(5.1);7.195(5.1);7.187(5.7);7.181(3.8);7.168(1.1);7.163(0.8);7.132(3.2);7.116(2.0);7.109(1.5);7.227(0.7);5.212(1.5);5.195(1.6);5.178(0.8);3.972(0.7);3.955(1.8);3.937(2.6);3.919(1.9);3.902(0.7);3.330(357.2);3.197(2.8);2.811(0.4);2.786(1.3);2.769(3.1);2.756(3.2);2.740(1.4);2.713(0.4);2.680(0.9);2.676(1.8);2.671(2.5);2.667(1.2);2.520(9.6);2.511(137.0);2.507(291.2);2.502(414.7);2.498(286.5);2.493(140.3);2.456(0.6);2.338(0.9);2.334(1.8);2.329(2.5);2.325(1.9);2.076(0.6);2.061(0.8);2.053(0.9);2.040(1.3);2.031(1.2);2.017(1.0);1.957(0.4);1.942(0.9);1.932(0.9);1.916(1.2);1.892(1.0);1.881(1.0);1.862(1.3);1.857(1.1);1.840(1.2);1.830(1.7);1.813(2.3);1.790(0.9);1.766(0.6);1.587(14.0);1.570(14.7);1.562(15.1);1.544(14.0);0.008(0.4);0.000(15.3);−0.008(0.6)

Example 146: ¹H-NMR(400.0 MHz, d₆-DMSO): δ = 9.124(1.8);9.103(1.8);8.525(8.7);8.318(0.4);7.430(1.8);7.427(2.2);7.415(1.9);7.411(3.9);7.408(4.1);7.395(4.6);7.392(3.2);7.377(1.5);7.347(3.2);7.328(3.5);7.308(1.4);7.230(0.3);7.225(0.5);7.212(1.4);7.206(2.3);7.197(2.5);7.188(2.6);7.183(1.8);7.170(0.6);7.132(1.6);7.116(1.1);7.106(3.1);6.966(1.4);5.233(0.1);5.218(0.7);5.201(0.8);5.183(0.4);3.991(0.3);3.973(0.9);3.956(1.3);3.938(0.9);3.921(0.4);3.332(17.0);2.788(0.7);2.772(1.6);2.758(1.6);2.744(0.7);2.628(16.0);2.602(0.5);2.525(0.5);2.520(0.8);2.511(10.9);2.507(22.6);2.503(30.0);2.498(21.7);2.494(10.6);2.068(0.4);2.059(0.5);2.047(0.6);2.038(0.7);2.024(0.5);1.949(0.5);1.937(0.4);1.922(0.6);1.903(0.5);1.861(0.6);1.830(1.0);1.814(1.1);1.588(7.1);1.570(7.3);1.562(7.4);1.544(6.9);0.000(1.5)

Example 147: ¹H-NMR(400.0 MHz, d₆-DMSO): δ = 9.124(1.8);9.103(1.8);8.525(8.7);8.318(0.4);7.430(1.8);7.427(2.2);7.415(1.9);7.411(3.9);7.408(4.1);7.395(4.6);7.392(3.2);7.377(1.5);7.347(3.2);7.328(3.5);7.308(1.4);7.296(0.7);7.285(1.2);7.274(2.0);7.264(1.3);7.254(4.6);7.246(2.7);7.240(2.4);7.232(2.5);7.076(0.9);2.961(0.9);2.953(0.8);2.909(0.6);2.888(1.4);2.868(1.0);2.849(0.7);2.828(0.4);2.676(0.7);2.672(1.0);2.667(0.8);2.571(0.5);2.562(0.5);2.552(0.9);2.543(1.1);2.531(1.4);3.014(0.4);3.001(0.5);2.992(0.5);2.992(0.5);2.984(0.8);2.975(0.9);

-continued 2.520(5.0);2.511(55.0);2.507(123.4);2.503(148.4);2.498(107.4);2.494(53.5);2.334(0.7);2.329(0.9);2.325(0.7);1.968(0.4);1.947(1.0);1.937(0.5);1.927(1.0);1.916 (1.0);1.905(0.4);1.895(0.9);1.588(8.3);1.570(16.0);1.553(8.2); 0.000(5.6)

Example 148: $^1$H-NMR(400.0 MHz, d$_6$-DMSO): δ = 9.105(1.6);9.083(1.6);8.481(7.3);7.731(3.3);7.728(3.6);7.553(0.7);7.550(0.6);7.532(3.3);7.528(3.6);7.521(5.1);7.500(1.0);7.374(1.0);7.367(1.2);7.352(1.5);7.223(0.4); 7.210(1.4);7.205(2.5);7.197(2.4);7.188(2.8);7.183(1.9);7.170(0.6);7.165(0.4);7.133(1.6);7.118(1.0);7.111(0.9);5.231(0.4);5.215(0.8);5.199(0.8);5.181(0.4);3.966(0.3);3.949(0.9);3.931(1.3);3.914(0.9);3.896(0.4); 3.334(133.7);2.996(0.5);2.788(0.7);2.771(1.7);2.758(1.7);2.744(0.7);2.712(1.6);2.676(0.4);2.672(0.5);2.667(0.4);2.606(16.0);2.574(0.6);2.542(302.9);2.526(2.6);2.520(2.6);2.511(28.5);2.507(59.0);2.503(79.0);2.498(59.1); 2.494(30.6);2.368(1.4);2.334(0.4);2.329(0.5);2.325(0.4);2.075(1.1);2.065(0.4);2.056(0.5);2.044(0.7);2.035(0.7);2.021(0.5);1.946(0.5);1.934(0.5);1.919(0.6);1.901(0.5);1.879(0.5);1.858(0.7);1.853(0.6);1.828(1.0);1.811(1.2); 1.579(6.8);1.561(7.1);1.552(7.3);1.535(6.8);1.298(0.8);1.258(1.0);0.000(3.5)

Example 149: $^1$H-NMR(400.0 MHz, d$_6$-DMSO): δ = 9.191(1.8);9.171(1.9);8.785(0.4);8.763(9.2);8.318(0.4);7.695(1.0);7.675(3.2);7.656(3.1);7.644(2.9);7.625(1.0);7.565(2.4);7.467(1.3);7.470(1.5);7.467(1.3);7.450(1.2);7.448(1.1); 7.416(1.1);7.404(1.5);7.394(1.5);7.305(0.7);7.294(1.2);7.282(2.2);7.274(1.3);7.264(4.6);7.256(2.6);7.249(2.3);7.240(2.6);7.230(0.3);5.567(0.5);5.548(1.6);5.528(1.6);5.508(0.5);4.038(0.5);4.020(0.5);3.997(0.4);3.979(1.1); 3.961(1.6);3.944(1.2);3.926(0.4);3.569(0.8);3.331(101.7);3.031(0.4);3.022(0.5);3.009(0.5);2.991(0.8);2.983(0.9);2.969(0.4);2.961(0.8);2.921(0.6);2.900(1.4);2.880(1.0);2.861(0.7);2.840(0.4);2.676(0.5); 2.672(0.7);2.667(0.5);2.593(0.4);2.584(0.4);2.573(0.8);2.563(0.9);2.552(0.9);2.541(1.1);2.532(1.1);2.525(1.9);2.521(2.9);2.512(40.0);2.508(83.3);2.503(111.1);2.498(81.9);2.494(41.0);2.334(0.5);2.330(0.7);2.325(0.6); 1.990(2.2);1.977(0.4);1.956(1.0);1.945(0.5);1.936(1.0);1.924(1.0);1.915(0.5);1.904(0.9);1.883(0.3);1.567(16.0);1.550(8.2);1.530(0.5);1.513(0.8);1.496(0.4);1.398(6.3);1.176(1.2);1.158(0.6);0.008(1.2); 0.000(40.8);−0.008(1.8)

Example 150: $^1$H-NMR(400.0 MHz, d$_6$-DMSO): δ = 9.214(1.5);9.193(1.6);8.822(6.9);8.318(0.7);7.985(2.7);7.980(3.0);7.975(2.9);7.896(2.7);7.420(1.0);7.408(1.2);7.399(1.2);7.306(0.5);7.296(1.0);7.283(1.7);7.274(1.0); 7.263(3.4);7.256(2.0);7.250(1.8);7.240(2.0);7.228(0.7);5.549(1.3);5.529(1.3);5.509(0.4);4.007(0.3);3.990(0.9);3.972(1.3);3.954(1.0);3.937(0.4);3.568(2.2);3.331(232.5);3.023(0.4);3.010(0.4);3.001(0.4);2.992(0.7); 2.983(0.7);2.970(0.7);2.962(0.7);2.922(0.5);2.901(1.2);2.881(0.9);2.861(0.6);2.841(0.3);2.676(1.1);2.671(1.5);2.667(1.2);2.593(0.4);2.584(0.4);2.573(0.7);2.563(0.9);2.542(1.2);2.525(4.1);2.507(177.3); 2.502(232.9);2.498(172.2);2.334(1.1);2.329(1.5);2.325(1.1);1.989(0.6);1.956(0.8);1.946(0.4);1.936(0.6);1.925(0.8);1.915(0.4);1.905(0.7);1.584(6.7);1.566(12.6);1.549(6.5);1.398(16.0);0.146 (0.4);0.008(2.6);0.000(81.2); −0.008(3.6);−0.150(0.4)

Example 151: $^1$H-NMR(400.0 MHz, d$_6$-DMSO): δ = 9.094(1.0);9.074(1.1);8.543(5.2);7.954(1.6);7.911(1.0);7.650(4.1);7.631(1.4);7.611(0.8);7.523(1.1);7.504(0.8);7.401(0.6);7.391(0.8);7.389(0.8);7.380(0.8); 7.297(0.7);7.285(0.7);7.275(1.2);7.265(0.9);7.255(2.8);7.248(2.5);7.241(1.6);7.233(1.5);7.108(1.8);6.968(0.9);5.519(0.9);3.996(0.6);3.979(0.9);3.961(0.6);3.332(9.0);2.985(0.5);2.977(0.9);2.963(0.5);2.955(0.4); 2.912(0.4);2.891(0.8);2.871(0.6);2.851(0.4);2.630(10.9);2.557(0.4);2.548(0.5);2.537(0.5);2.525(0.8);2.512(7.5);2.507(15.5);2.503(20.2);2.498(14.7);2.494(7.1);1.989(0.9);1.949(0.6);1.929(0.6);1.918(0.6);1.897(0.5); 1.588(4.7);1.571(9.0);1.553(4.6);1.397(16.0);1.175(0.5);0.008(1.3);0.000(35.2);−0.009(1.2)

Example 152: $^1$H-NMR(400.0 MHz, d$_6$-DMSO): δ = 9.228(1.1);9.208(1.0);8.599(4.4);7.817(4.8);7.812(5.1);7.542(1.2);7.538(2.3);7.533(1.2);7.353(0.9);7.334(1.0);7.204(0.5);7.201(0.5);7.183(0.9);7.166(0.6);7.162(0.6); 6.953(0.7);6.951(0.7);6.932(1.2);6.916(0.6);6.913(0.6);6.817(1.3);6.815(1.3);6.797(1.2);6.795(1.2);5.244(0.6);5.225(0.8);4.289(0.5);4.280(0.5);4.272(0.6);4.264(0.5);4.257(0.5);4.250(0.6);4.236(0.5);4.229(0.6);3.974(0.6); 3.956(0.8);3.938(0.6);3.331(44.5);2.679(0.5);2.672(0.4);2.646(9.3);2.525(0.9);2.511(18.0);2.507(36.8);2.503(48.4);2.498(35.3);2.494(17.5);2.329(0.3);2.215(0.4);2.206(0.4);2.193(0.4);2.069(0.4);2.063(0.4);1.571(4.2); 1.553(4.5);1.547(4.7);1.530(4.0);1.397(16.0);0.008(2.5);0.000(69.7);−0.009(2.8)

Example 153: $^1$H-NMR(400.0 MHz, d$_6$-DMSO): δ = 9.218(0.7);9.198(0.7);8.538(3.0);7.955(1.1);7.906(0.5);7.887(0.6);7.647(0.4);7.628(0.9);7.609(0.5);7.521(0.7);7.502(0.5);7.355(0.6);7.336(0.7);7.245(0.5);7.200(0.3); 7.182(0.7);7.161(0.4);7.105(1.1);6.965(0.6);6.954(0.5);6.951(0.5);6.935(0.8);6.917(0.9);6.914(0.4);6.817(0.9);6.815(0.9);6.797(0.8);6.795(0.8);5.249(0.4);5.230(0.4);4.289(0.4);4.280(0.3);4.273(0.4); 4.262(0.5);4.253(0.4);4.240(0.3);4.233(0.5);3.989(0.4);3.971(0.5);3.954(0.4);3.333(8.3);2.629 (6.4);2.511(4.9);2.507(12.8);2.498(9.4);1.989(0.8);1.584(2.9);1.567 (3.2);1.560(3.2);1.543(2.8);1.397(16.0); 1.175(0.4);0.008(0.8);0.000(20.7);−0.008(1.0)

Example 154: $^1$H-NMR(400.0 MHz, d$_6$-DMSO): δ = 9.231(1.1);9.211(1.1);8.410(5.1);7.643(1.1);7.640(2.9);7.621(3.1);7.619(3.4);7.516(1.8);7.495(1.7);7.475(1.0);7.334(1.0);7.315(1.1);7.192(0.5);7.188(0.5);7.171(1.0); 7.153(1.0);7.149(0.7);6.938(0.7);6.935(0.8);6.919(1.2);6.917(1.3);6.900(0.6);6.898(0.6);6.805(1.4);6.785(1.3);5.232(0.7);5.213(0.7);4.277(0.6);4.268(0.5);4.261(0.6);4.252(0.5);4.241(0.5);4.234(0.6); 4.220(0.5);4.213(0.7);3.962(0.6);3.945(0.9);3.927(0.6);3.315(32.7);2.510(16.9);2.506(33.5);2.501(45.2);2.497(34.5);2.492(17.7);2.328(0.3);2.304(0.6);2.196(0.4);2.183(0.5);2.061(0.4);2.054(0.5);2.039(0.3); 1.593(4.6);1.575(4.8);1.567(4.9);1.549(4.6);1.398(16.0);0.951(1.3);0.935(1.3);0.008(2.5);0.000(52.9);−0.008(2.3)

Example 155: $^1$H-NMR(400.0 MHz, d$_6$-DMSO): δ = 9.206(1.8);9.186(1.9);8.789(8.6);8.781(1.2);8.686(3.3);8.679(3.5);8.652(3.1);7.958(1.0);7.952(1.4);7.947(1.0);7.933(1.0);7.928(1.2);7.922(1.0);7.414(1.2);7.403(1.6); 7.393(1.7);7.305(0.7);7.295(1.3);7.283(2.3);7.274(1.4);7.263(2.3);7.256(2.9);7.249(2.6);7.241(2.8);7.230(0.4);5.568(0.5);5.549(1.6);5.529(1.5);5.509(0.6);3.993(0.5);3.975(1.2);3.958(1.6);3.940(1.3);3.922(0.5); 3.340(179.5);3.032(0.5);3.023(0.5);3.010(0.5);2.994(3.4);2.984(1.0);2.971(1.0);2.961(0.9);2.922(0.7);2.901(1.1);2.861(0.8);2.841(1.1);2.710(0.7);2.675(1.7);2.670(2.3);2.666(1.8);2.594(0.7);2.586(0.8);2.575(1.2); 2.565(1.7);2.540(141.4);2.523(7.2);2.510(133.4);2.506(265.8);2.501(355.6);2.497(269.8);2.492(138.7);2.366(0.6);2.332(1.6);2.328(2.2);2.323(1.6);1.979(0.4);1.958(1.0);1.947(0.5);1.938(1.0);1.926(1.0);1.917(0.5); 1.906(0.9);1.885(0.3);1.587(8.3);1.569(16.0);1.552(8.2);1.511(2.1);1.494(1.1);1.235(0.6);0.008(1.0);0.000(27.7);−0.008(1.0)

Example 156: $^1$H-NMR(400.0 MHz, d$_6$-DMSO): δ = 9.206(1.8);9.185(1.9);8.797(8.1);8.726(6.7);8.720(7.6);8.139(1.9);8.134(3.4);8.129(2.0);7.414(1.2);7.403(1.5);7.393(1.5);7.306(0.7);7.295(1.3);7.283(2.2);7.274(1.3); 7.263(4.5);7.256(2.7);7.249(2.3);7.241(2.6);7.230(0.4);5.568(0.5);5.548(1.6);5.528(1.6);5.509(0.6);3.994(0.4);3.977(1.2);3.959(1.6);3.941(1.2);3.924(0.5);3.333(249.0);3.333(0.3);3.022(0.5);3.010(0.5);3.000(0.6); 2.994(1.8);2.983(1.0);2.970(0.9);2.962(0.9);2.921(0.7);2.901(1.4);2.881(1.1);2.861(0.8);2.840(0.5);2.675(1.8);2.670(2.5);2.666(1.9);2.594(0.6);2.585(0.7);2.574(1.2);2.564(1.5);2.554(1.9);2.540(60.0);2.523(9.6); 2.510(137.7);2.506(272.9);2.501(366.4);2.497(281.3);2.492(149.0);2.332(1.7);1.978(0.4);1.957(1.0);1.937(1.0);1.925(1.0);1.916(0.5);1.905(0.9);1.585(8.3);1.568(16.0);1.550(8.2); 1.236(0.6);0.008(0.7);0.000(18.3);−0.008(0.9)

Example 157: $^1$H-NMR(400.0 MHz, d$_6$-DMSO): δ = 9.176(1.9);9.155(1.9);8.742(8.0);7.601(0.7);7.585(1.0);7.581(1.8);7.565(1.6);7.561(1.3);7.545(1.1);7.429(3.5);7.410(3.1);7.397(3.0);7.389(1.8);7.320(0.8);7.315(0.8); 7.293(2.6);7.281(2.6);7.272(2.0);7.261(4.6);7.254(2.8);7.248(2.5);7.240(2.6);7.229(0.4);5.564(0.6);5.545(1.6);5.525(1.6);5.506(0.6);3.985(0.4);3.967(1.2);3.949(1.6);3.932(1.2);3.914(0.5);3.324(291.6);3.050(0.4); 3.021(0.5);3.008(0.5);2.994(1.0);2.981(0.9);2.968(0.9);2.920(0.7);2.899(1.5);2.879(1.1);2.860(0.8);2.839(0.5);2.675(1.6);2.670(2.2);2.666(1.8);2.592(0.6);2.583(0.6);2.572(1.0);2.561(1.4);2.552(1.7);2.540(25.2); 2.531(3.0);2.506 (245.9);2.501(333.1);2.497(260.7);2.332(1.6);2.328(2.2);2.324(1.7);1.975(0.4);1.954(1.0);1.943(0.5);1.934(1.0);1.922(1.0);1.912(0.5);1.902(0.9);1.881(0.3);1.582(8.2);1.564(16.0);1.547(8.3);1.235(0.5); 0.008(0.4);0.000(10.7);−0.008(0.6)

Example 158: $^1$H-NMR(400.0 MHz, d$_6$-DMSO): δ = 9.161(1.9);9.140(2.0);8.781(0.5);8.699(9.3);7.564(0.6);7.550(1.0);7.544(2.4);7.526(3.2);7.508(1.7);7.393(3.3);7.383(1.7);7.369(3.3);7.350(4.1);7.332(1.2);7.329(1.1); 7.301(0.7);7.291(1.2);7.279(2.2);7.270(1.2);7.258(4.5);7.252(2.6);7.245(2.3);7.236(2.7);7.198(0.5);7.070(0.4);6.943(0.4);5.557(0.5);5.537(1.6);5.517(1.6);5.497(0.5);3.983(0.4);3.965(1.2);3.948(1.6);3.930(1.2);3.912(0.5);

-continued 3.492(0.3);3.332(583.0);3.158(0.4);3.025(0.5);3.017(0.6);3.004(0.6);2.986(1.0);2.978(1.0);2.964(1.0);2.955(1.0);2.916(0.8);2.896(1.5);2.876(1.2);2.856(0.8);2.836(0.5);2.675(2.8);2.670(3.9);2.666(3.0); 2.588(0.7);2.579(1.0);2.569 (1.4);2.559 (1.7);2.540 (11.0);2.524(17.4);2.510 (211.5);2.506(435.1);2.501(590.8);2.497(447.4);2.492(227.1);2.501(1.5);2.506(0.5);2.497(1.3);2.328(3.8);2.323(2.9);2.289(0.5);1.966 (0.4);1.945(1.0);1.935(0.5); 1.926(1.0);1.914(1.0);1.905(0.5);1.894(0.9);1.873(0.3);1.590(8.5);1.572(16.0);1.554(8.3);1.529(0.6);1.511(0.9);1.494(0.5);1.236(0.5);0.008(0.8);0.000(24.3);−0.008(0.8)

Example 159: ¹H-NMR(400.0 MHz, d₆-DMSO): δ = 9.199(1.8);9.179(1.9);8.777(9.3);7.538(2.1);7.521(2.3);7.516(2.4);7.499(2.2);7.410(1.2);7.397(1.5);7.388(1.5);7.305(0.6);7.295(1.2);7.283(2.1);7.274(1.3);7.262(4.5); 7.256(2.5);7.249(2.2);7.240(2.7);7.230(0.4);5.565(0.5);5.546(1.5);5.526(1.6);5.507(0.6);3.979(0.4);3.961(1.1);3.944(1.6);3.926(1.2);3.908(0.5);3.336(321.7);3.030(0.5);3.022(0.5);3.009(0.5);2.994(3.4);2.983(1.0); 2.969 (1.0);2.960 (0.9);2.920 (0.7);2.900 (1.5);2.880 (1.1);2.861 (0.8);2.840 (0.5);2.711 (0.8);2.675 (1.9);2.670 (2.6);2.666 (1.0);2.592 (0.7);2.583 (0.8);2.573 (1.3);2.562 (1.5);2.541 (137.4);2.524 (7.2);2.519 (10.8); 2.510 (142.3);2.506(291.7);2.501(394.9);2.497(296.4);2.492(148.2);2.367(0.5);2.333(1.8);2.328(2.5);2.323(1.9);2.290(0.4);1.976(0.4);1.955(1.0);1.944(0.5);1.935(1.0);1.923(0.9);1.913(0.5);1.903(0.9);1.882(0.3);1.575(8.3); 1.558(16.0);1.540(8.2);1.511(0.7);1.494(0.4);1.235(0.8);0.008(0.9);0.000(25.4);−0.009(0.8)

Example 160: ¹H-NMR(400.0 MHz, d₆-DMSO): δ = 9.172(1.5);9.152(1.6);8.722(6.3);7.409(1.0);7.397(1.3);7.386(2.1);7.365(1.6);7.357(1.4);7.347(1.3);7.343(1.5);7.336(1.7);7.327(1.3);7.322(1.4);7.304(0.6);7.293(1.0); 7.281(1.8);7.272 (1.1);7.261 (3.6);7.254 (2.1);7.247 (1.9);7.239 (2.0);7.132 (0.7);7.128 (0.8);7.122 (0.9);7.117 (0.8);7.112 (0.7);7.101 (0.7);7.096 (0.6);5.564 (0.4);5.544 (1.3);5.525 (1.3);5.505 (0.4);3.988 (0.3); 3.971(0.9);3.953(1.3);3.935(1.0);3.918(0.4);3.848(16.0);3.343(67.2);3.021(0.4);3.008(0.4);2.999(0.4);2.990(0.7);2.981(0.8);2.968(0.7);2.959(0.7);2.930(0.6);3.007(0.8);2.994(3.7);2.981(0.8);2.918(0.5);2.898(1.2);2.878(0.8);2.859(0.6);2.839(0.4);2.674(0.9);2.670(1.2); 2.666(0.9);2.589(0.4);2.580(0.5);2.570(0.8);2.559(0.9);2.540(4.7);2.505(135.2);2.501(182.0);2.496(141.8);2.332(0.9);2.328(1.2);2.323(0.9);1.954(0.8);1.944(0.4);1.934(0.8);1.922(0.7);1.913(0.4);1.902(0.7); 1.581(6.2);1.564 (12.0);1.546 (6.2);1.528 (0.4);1.511 (0.5);0.008 (0.5);0.000 (13.7);−0.008 (0.6)

Example 161: ¹H-NMR(400.0 MHz, d₆-DMSO): δ = 9.194(1.5);9.173(1.6);9.159(1.6);9.139(1.6);8.781(8.5);8.757(7.2);8.426(1.9);8.420(2.0);8.195(0.6);8.189(0.6);8.175(1.2);8.169(1.2);8.154(0.7);8.148(0.6);7.407(3.0); 7.399(3.5);7.386(3.3);7.379(1.7);7.304(1.1);7.282(3.7);7.273(2.3);7.272(2.8);7.262(7.8);7.255(4.4);7.248(4.0);7.240(2.8);7.229(0.6);7.198(0.5);7.070(0.8);6.943(0.5);5.565(0.5);5.546(1.4);5.535(1.7);5.526(1.5);5.516(1.6); 5.496(0.5);3.990(0.4);3.972(1.0);3.955(1.1);3.937(2.1);3.919(2.0);3.902(1.3);3.884(0.5);3.342(320.1);3.139(0.7);3.029(1.3);3.020(0.9);3.007(0.8);2.994(3.7);2.981(1.5);2.968(1.3);2.959(1.4);2.919(1.1);2.898(2.4); 2.879(1.8);2.858(1.2);2.837(0.7);2.711(0.6);2.675(3.1);2.670(4.2);2.666(3.1);2.589(0.8);2.568(1.6);2.559(2.4);2.540(128.0);2.523(11.6);2.510(235.5);2.506(479.6);2.501(646.0);2.496(487.3);2.492(245.0);2.419(0.5); 2.366(0494(8.4);1.298(0.4);1.259(0.5);1.235(1.2);0.008(1.1);0.000(37.2);−0.009(1.2)

Example 162: ¹H-NMR(400.0 MHz, d₆-DMSO): δ = 20.010(0.8);9.164(1.7);9.144(1.7);8.706(8.8);7.623(2.0);7.609(2.4);7.601(2.9);7.587(2.6);7.387(4.0);7.365(5.8);7.343(2.8);7.280(2.1);7.271(1.3);7.260(4.6);7.253(2.7); 7.247(2.5);7.238 (2.8);7.198 (0.7);7.070 (0.8);6.942 (0.8);5.543 (1.6);5.523 (1.6);5.514 (1.3);5.362 (1.3);5.342 (1.1);5.258 (2.7);7.248 (2.8);7.240 (2.8);7.197 (1.0);7.069 (1.0);6.941 (0.9);5.566 (0.6);5.546 (1.5);5.526 (1.5);5.507 (0.5);3.992 (0.4);3.973 (1.1);3.955 (1.7); 2.670(9.5);2.665(7.1);2.571(2.0);2.561(2.1);2.540(19.5);2.523(24.3);2.519(36.7);2.510(494.7);2.505(1026.6);2.501(1397.6);2.492(538.1);2.332(6.5);2.328(9.1);2.323(6.7);1.951(1.0);1.931(1.0);1.919(1.0); 1.900(0.9);1.581(8.3);1.564(16.0);1.546(8.2);1.512(0.7);1.298(0.7);1.259(0.9);1.235(0.6);0.008(2.7);0.000(76.2);−0.009(2.4)

Example 163: ¹H-NMR(400.0 MHz, d₆-DMSO): δ = 9.215(1.9);9.194(2.0);8.790(8.8);8.782(0.5);8.275(0.8);8.271(1.0);8.238(3.9);8.226(1.1);7.413(1.3);7.401(1.7);7.392(1.6);7.305(0.7);7.295(1.4);7.283(2.4);7.274(1.4); 7.263(4.6);7.256 (2.7);7.250 (2.5);7.241 (2.5);7.230 (0.4);5.568 (0.6);5.548 (1.7);5.529 (1.7);5.510 (0.6);5.489 (0.4);3.997 (1.3);3.954 (1.6);3.937 (1.3);3.920 (0.5);3.348 (141.9);3.032 (0.4);3.023 (0.5);3.010 (0.5);2.994 (3.1); 2.984(1.0);2.970(1.0);2.962(0.9);2.921(0.7);2.901(1.5);2.881(1.1);2.862(0.8);2.841(0.4);2.711(0.8);2.671(1.2);2.595(0.5);2.585(0.7);2.575(1.2);2.564(1.6);2.541(164.1);2.506(139.8);2.501(184.3);2.497(144.0);2.367(0.8); 2.328(1.2);2.324(0.9);1.979(0.4);1.958(1.0);1.948(0.5);1.918(1.0);1.926(1.0);1.917(0.5);1.906(0.9);1.885(0.3);1.584(8.3);1.567(16.0);1.549(8.2);1.529(0.6);1.512(0.7);1.494(0.4);1.235(0.4);0.000(5.3)

Example 164: ¹H-NMR(400.0 MHz, d₆-DMSO): δ = 9.195(1.8);9.175(1.9);9.161(0.3);8.781(1.2);8.773(9.7);8.063(1.7);8.048(1.9);8.042(1.9);7.732(3.5);7.712(3.1);7.412(1.2); 7.400(1.6);7.391(1.5);7.304(0.7);7.294(1.3);7.282(2.3);7.273(1.5);7.262(5.0);7.255(2.8);7.248(2.8);7.248(2.8);7.197(1.0);7.069(1.0);6.941(0.9);5.566(0.6);5.546(1.5);5.526(1.5);5.507(0.5);5.526(1.5);3.992(0.4);3.973(1.1);3.955(1.7); 3.938(1.3);3.921 (0.6);3.565 (0.4);3.562 (0.4);3.534 (0.4);3.461 (1.1);3.422 (1.9);3.333 (641.3);3.193 (0.7);3.184 (0.6);3.141 (0.5);3.117 (0.4);3.108 (0.4);3.098 (0.4);3.032 (0.6);3.023 (0.6);3.009 (0.6);2.994 (2.8); 2.981(1.0);2.968(1.0);2.960(1.0);2.921(0.7);2.899(1.6);2.879(1.1);2.859(0.8);2.839(0.5);2.779(0.4);2.711(0.4);2.679(3.3);3.184(0.6);3.149(0.5);3.117(0.4);2.665(7.4);2.661(3.5);2.631(0.5);2.616(0.5);2.592(0.8);2.584(0.8);2.572(1.1); 2.561(1.5);2.540 (102.2);2.523 (25.5);2.518 (38.5);2.510 (531.1);2.505 (1097.2);2.501 (1491.8);2.492 (1112.8);2.492 (550.4);2.454 (2.1);2.444 (1.9);2.424 (1.3);2.408 (0.8);2.379 (0.4);2.366 (0.5);2.337 (3.2);2.332 (6.9); 2.328(9.6);2.323 (7.0);2.319 (3.3);2.288 (1.2);1.977 (0.4);1.924 (1.0);1.915 (0.5);1.905 (0.9);1.883 (0.3);1.604 (0.4);1.599 (0.5);1.582 (8.5);1.565 (16.0);1.547 (8.1);1.528 (1.2);1.511 (1.9); 1.494(1.0);1.298(0.6);1.259(0.7);1.236(1.5);0.146(1.1);0.008(7.3);0.000(241.8);−0.009(8.4);−0.150(1.0)

Example 165: ¹H-NMR(400.0 MHz, d₆-DMSO): δ = 9.082(1.2);9.062(1.3);8.443(5.0);7.493(1.7);7.482(2.5);7.471(1.3);7.463(2.5);7.381(0.8);7.370(1.0);7.360(1.0);7.342(1.1);7.335(0.8);7.328(1.6);7.319(0.8);7.290(0.5); 7.280(0.9);7.269 (1.4);7.258 (0.9);7.247 (2.9);7.240 (1.7);7.234 (1.6);7.225 (1.4);7.221 (1.6);5.542 (0.4);5.522 (1.1);5.502 (1.1);5.502 (1.1);5.483 (0.4);3.973 (0.7);3.955 (1.0);3.938 (0.7);3.316 (64.0);2.996 (0.3);2.987 (0.4);2.979 (0.6);2.970 (0.6); 2.956(0.6);2.948 (0.6);2.903 (0.4);2.882 (0.9);2.862 (0.7);2.842 (0.5);2.710 (0.6);2.675 (1.6);2.670 (2.6);2.666 (0.5);2.563 (0.4);2.554 (0.4);2.543 (0.7);2.532 (1.1);2.505 (75.5);2.501 (97.6);2.497 (74.6);2.388 (11.5);2.328 (0.7);2.323 (0.5); 1.940(0.6);1.919(0.6);1.908(0.6);1.888(0.5);1.592(5.2);1.574(9.7);1.556(5.2);1.398(16.0);0.000(1.2)

Example 166: ¹H-NMR(400.0 MHz, d₆-DMSO): δ = 9.213(2.4);9.193(2.5);8.511(0.3);8.485(10.5);8.314(0.5);7.479(0.4);7.456(1.3);7.440(1.0);7.433(2.3);7.417(4.1);7.403(1.0);7.400(1.0);7.377(0.4);7.339(2.4);7.320(2.6); 7.199(1.2);7.196 (1.5);7.178 (2.5);7.160 (1.5);7.157 (1.5);6.944 (1.8);6.925 (3.0);6.909 (1.4);6.810 (3.3);6.792 (3.0);5.253 (0.7);5.238 (1.5);5.219 (1.6);5.205 (0.7);4.310 (0.5);4.302 (0.6);4.294 (0.6);4.283 (1.4);4.274 (1.3); 4.267(1.5);4.258(1.1);4.248(1.1);4.240(1.4);4.227(1.2);4.204(1.7);4.199(0.6);4.191(0.5);3.977(0.5);3.959(1.4);3.942(2.0);3.924(1.5);3.906(0.6);3.318(117.5);2.675(0.9);2.671(1.2);2.666(0.9);2.524(3.2);2.506(145.7); 2.501(193.9);2.497(146.5);2.451(16.0);2.333(0.7);2.328(1.3);2.323(1.9);2.210(1.0);2.188(1.1);2.176(0.8);1.556 (0.5);1.488(0.4);1.398(3.3);0.008(0.9);0.000(28.6);−0.008(1.5) 2.031(0.8);2.024(0.7);2.015(0.5);2.008(0.4);1.581(10.5);1.563(10.5);1.539(10.5);1.512(0.5);1.506 (0.5);1.488(0.4);1.398(3.3);0.008(0.9);0.000(28.6);−0.008(1.5)

Example 167: ¹H-NMR(400.0 MHz, d₆-DMSO): δ = 20.006(0.7);9.191(1.4);9.171(1.5);8.793(6.3);8.312(0.9);7.727(3.1);7.722(1.9);7.625(5.5);7.621(5.4);7.402(1.2);7.390(1.2);7.283(1.6);7.262(3.3);7.240(2.0);7.200(1.6); 7.073(1.7);6.945 (1.5);5.544 (1.1);5.524 (1.1);3.970 (0.9);3.954 (1.4);3.937 (1.1);3.648 (0.8);3.602 (0.9);3.548 (1.7);3.493 (1.9);3.454 (3.1);3.414 (5.1);3.317 (18.3);2.978 (0.4);3.951 (0.5);3.317 (18.3);2.978 (0.4);3.951 (0.5);3.317 (18.3);3.224 (5.5);3.332 (6735.5);3.332 (6735.5);3.180 (2.6);3.147 (1.9);3.085 (1.5);3.022 (1.2); 2.992(1.0);2.960 (1.5);2.920 (1.2);2.880 (1.5);2.860 (1.0);2.779 (0.9);2.707 (1.1);2.675 (1.6);2.666 (12.2);2.541 (15.6);2.524 (44.4);2.510 (867.5);2.506 (1743.4);2.502 (2357.2);2.497 (1795.0);2.493 (921.1); 2.391(1.2);2.333(11.0);2.324(15.2);2.328(15.2);2.291 (1.1);1.953(0.8);1.932(0.7);1.922(0.9);1.902(0.8);1.576(6.1);1.559(11.8);1.541(6.0);1.298(1.0);1.259(1.3);1.236(3.3);0.146 (1.4);0.008(11.2);0.000(309.3); −0.008(10.8);−0.150(1.3)

Example 168: ¹H-NMR(400.0 MHz, d₆-DMSO): δ = 9.085(0.9);9.064(0.9);8.436(3.1);7.710(0.8);7.703(0.9);7.719(0.8);7.710(0.8);7.703(0.9);7.695(1.0);7.466(1.7);7.458(1.6);7.450(3.2);7.439(0.3);7.378(0.5);7.368(0.6);7.359(0.6);7.279(0.6); 7.268(0.9);7.258 (0.9);7.247 (2.0);7.240 (1.7);7.233 (1.1);7.225 (1.1);5.521 (0.8);5.520 (0.8);3.969 (0.5);3.951 (0.5);3.951 (0.5);3.940 (0.5);3.317 (18.3);2.978 (0.4);2.956 (0.4);2.947 (0.4);2.882 (0.7);2.862 (0.5);2.842 (0.4); 2.543(0.4);2.533(0.6);2.523(1.2);2.506(35.7);2.501(46.8);2.497(35.1);2.377(8.3);1.940(0.3);1.919(0.4);1.908(0.4);1.592(3.3);1.573(6.3);1.555(3.4);1.398(1.0);0.008(1.9);0.000(47.7)

-continued

Example 169: ¹H-NMR(400 MHz, d₆-DMSO): δ = 9.090(0.8);9.068(0.8);8.401(3.2);7.715(0.9);7.707(0.8);7.699(0.9);7.691(1.1);7.463(1.6);7.455(1.2);7.447(2.5);7.360(0.5);7.352(0.5);7.339(0.6);7.196(1.2);7.187(1.3);7.177(1.4);7.126(0.9);7.112(0.6);7.103(0.5);5.206(0.5);5.189(0.5);3.947(0.6);3.929(0.5);3.912(0.4);3.316(23.0);2.780(0.4);2.764(0.9);2.750(0.9);2.735(0.4);2.675(0.3);2.670(0.4);2.523(1.2);2.506(49.2);2.501(64.9);2.497(48.6);2.374(8.7);2.328(0.4);2.034(0.4);2.025(0.4);1.914(0.4);1.824(0.5);1.807(0.7);1.592(3.6);1.575(3.7);1.565(3.8);1.547(3.5);1.398(16.0);0.951(0.6);0.935(0.6);0.146(0.3);0.008(2.9);0.000(70.4);−0.150(0.3)

Example 170: ¹H-NMR(400 MHz, d₆-DMSO): δ = 9.209(0.8);9.189(0.8);8.430(3.2);7.716(0.9);7.707(0.8);7.700(1.0);7.691(1.1);7.463(1.6);7.455(1.5);7.447(2.9);7.336(0.6);7.317(0.6);7.195(0.4);7.191(0.4);7.174(0.8);7.156(0.5);7.153(0.5);6.941(0.6);6.939(0.6);6.921(1.0);6.904(0.5);6.809 (1.1);6.788(1.0);5.236(0.5);5.218(0.5);4.280(0.5);4.271(0.4);4.263(0.5);4.255(0.4);4.263(0.5);4.271(0.4);4.246(0.4);4.239(0.4);4.225(0.4);4.217(0.5);3.961(0.3);3.944(0.5);3.926(0.4);3.318(9.9);2.506 (17.8);2.502 (23.2);2.497(16.9);2.375(8.1);2.207(0.3);2.198(0.3);2.185(0.4);2.062(0.4);2.057(0.4);1.988(0.3);1.589 (3.5);1.572(3.7);1.563(3.4);1.546 (3.1);1.398(16.0);0.951 (1.6);0.935(1.7);0.008(1.0);0.000(24.8);−0.008(1.0)

Example 171: ¹H-NMR(400 MHz, d₆-DMSO): δ = 9.080(1.6);9.059(1.6);8.456(7.0);7.662(2.8);7.640(3.9);7.557(2.6);7.551(4.1);7.536(2.9);7.529(1.8);7.514(2.0);7.508(1.5);7.382(1.0);7.370(1.3);7.360(1.3);7.291(0.6);7.280(1.1);7.269(1.8);7.259(1.1);7.247(3.9);7.241(2.2);7.234(2.0);7.225(2.1);5.543(0.5);5.523(1.4);5.483(0.5);3.992(0.4);3.974(1.0);3.956(1.3);3.939(1.0);3.921(0.4);3.317(27.7);3.019(0.3);3.010(0.4);2.996(0.4);2.987(0.5);2.979(0.7);2.970(0.8);2.957(0.7);2.948(0.7);2.904(0.6);2.883(1.2);2.863(0.9);2.843(0.6);2.823(0.3);2.675(0.4);2.670(0.5);2.666(0.4);2.564(0.4);2.555(0.5);2.545(0.8);2.535(1.1);2.524(2.1);2.506(55.2);2.501(71.6);2.497(52.7);2.392(16.0);2.333(0.3);2.328(0.5);2.324(0.4);1.961(0.3);1.940(0.9);1.929(0.4);1.920(0.9);1.908(0.4);1.898(0.4);1.888(0.8);1.588(7.1);1.570(13.4);1.552(7.0);1.398(2.7);0.146(0.4);0.008(2.9);0.000(78.9);−0.008(3.3);−0.150(0.4)

Example 172: ¹H-NMR(400 MHz, d₆-DMSO): δ = 9.085(1.6);9.064(1.6);8.421(7.0);8.314(0.4);7.659(2.4);7.637(3.9);7.546(3.7);7.532(3.0);7.526(1.7);7.511(1.9);7.504(1.5);7.362(1.1);7.354(1.2);7.340(1.5);7.213(0.4);7.197(2.3);7.188(2.5);7.178(2.5);7.175(2.3);7.162(0.6);7.157(0.3);7.127(1.7);7.113(1.1);7.104(0.9);5.222(0.4);5.206(0.8);5.190(0.9);5.172(0.4);3.970(0.4);3.952(0.9);3.935 (1.3);3.917 (1.0);3.900(0.4);3.316(59.4);2.781(0.8);2.766(1.7);2.751(1.7);2.736(0.8);2.675(0.7);2.623(0.5);2.524(2.2);2.506 (101.7);2.501 (36.0);2.497 (101.7);2.389(16.0);2.371(0.4);2.332(0.6);2.328(0.9);2.324(0.7);2.069(0.3);2.063(0.6);2.056(0.5);2.047(0.5);2.034(0.7);2.025(0.7);2.011(0.5);1.988(0.5);1.940(0.5);1.927 (0.5);1.914 (0.7) (0.5);1.893 (0.5);1.876 (0.5);1.856(0.7);1.834(0.7);1.824(1.0);1.808(1.3);1.786(0.5);1.589(7.2);1.571(17.3);1.561(7.5);1.543(7.1);1.398(3.6);0.146(0.6);0.008(4.9);0.000(136.3);−0.008(5.8);−0.021(0.4);−0.150(0.6)

Example 173: ¹H-NMR(400 MHz, d₆-DMSO): δ = 9.204(0.9);9.184(0.9);8.450(3.6);7.659 (1.5);7.638(2.0);7.554(1.3);7.548(2.0);7.534 (1.3);7.527 (0.9);7.512 (1.0);7.506 (0.7);7.336(0.8);7.317(0.9);7.196(0.4);7.192(0.4);7.175(0.7);7.157(0.6);7.154(0.5);6.940(0.6);6.922(1.1);6.903(0.5);6.808(1.2);6.788(1.0);5.228(0.5);5.217(0.5);5.204(0.4);4.280(0.5);4.271(0.4);4.263(0.5);4.255(0.4);4.246(0.4);4.238(0.5);4.225(0.4);4.217(0.6);3.966(0.5);3.948(0.7);3.930(0.5);3.317(15.5);2.506 (30.9);2.501 (40.8);2.497 (30.5);2.390 (8.2);2.206(0.3);2.198 (0.3);2.185 (0.4);2.063 (0.4);2.056 (0.4);1.585(3.7);1.567(3.9);1.559 (4.0);1.541 (3.6);1.398(16.0);0.951 (0.8);0.935 (0.8);0.008 (1.4);0.000(36.5);−0.008(1.5)

Example 174: ¹H-NMR(400 MHz, d₆-DMSO): δ = 9.076(1.5);8.483(6.9);7.733(2.7);7.730(3.3);7.713(3.8);7.493(2.2);7.474(4.1);7.454(2.4);7.391 (1.0);7.379 (1.2);7.369(1.3);7.334(1.3);7.315 (2.0);7.296(1.4);7.284(1.1);7.273(1.8);7.264(1.4);7.253(4.0);7.246(2.7);7.240(2.3);7.231(2.1);7.222(0.3);7.220(0.3);7.213(0.4);5.516 (1.3);5.497(0.9);5.536(0.5);5.536(1.4);5.497 (0.5);3.999 (0.3);3.982 (1.0);3.964 (1.3);3.946(1.3);3.928 (0.4);3.319 (26.2);3.025(0.3);3.016(0.4);3.002(0.4);2.994(0.5);2.985(0.7);2.976(0.8);2.963(0.8);2.955(0.7);2.910 (0.5);2.889 (1.2);2.869 (0.9);2.850(0.6);2.830 (0.3);2.670(0.3);2.604 (16.0);2.573 (0.4);2.565 (0.4);2.554 (0.7);2.544 (0.9);2.534 (1.0);2.510 (20.0);2.506 (38.8);2.501(50.4);2.497(37.5);2.493 (19.4);1.972 (0.3);1.950 (0.9);1.940 (0.4);1.930 (0.9);1.919(0.8);1.908 (0.4);1.898 (0.8);1.585(7.1);1.567 (13.7);1.550(7.0);1.398(0.5);0.008 (2.0);0.000(43.2);−0.008(2.1)

Example 175: ¹H-NMR(400 MHz, d₆-DMSO): δ = 9.081(1.5);9.060 (1.6);8.450 (7.0);7.731 (2.8);7.728(3.4);7.710 (4.0);7.489 (2.2);7.470 (4.3);7.451 (2.4);7.376 (1.1);7.370 (1.2);7.354 (1.5);7.330 (1.3);7.311 (2.1);7.293 (0.9);7.223(0.8);7.209(1.0);7.204(2.3);7.195(2.5);7.186(2.6);7.181(1.8);7.167(0.6);7.163(0.4);7.130(1.7);7.115(1.1);7.108(0.9);5.233(0.4);5.219(0.8);5.201(0.9);5.183(0.4);3.979(0.3);3.961(1.0);3.943 (1.3);3.926(1.0);3.908 (0.4);3.318(7.4);2.788 (0.7);2.772 (1.7);2.758 (1.8);2.743 (0.7);2.601 (16.0);2.523 (0.6);2.506 (23.7);2.501 (30.7);2.497 (22.5);2.066(0.4);2.058 (0.5);2.046 (0.7);2.037 (0.7);2.022 (0.5);1.950 (0.5);1.939 (0.5);1.924 (0.6);1.905 (0.5);1.882(0.5);1.861(0.7);1.855 (0.6);1.838(0.7);1.830 (1.0);1.814 (1.2);1.586(7.2);1.568(7.5);1.560(7.5);1.542 (7.0);1.397(1.3);0.008(0.9);0.000(22.0);−0.009(0.8)

Example 176: ¹H-NMR(400 MHz, d₆-DMSO): δ = 9.198 (1.5);9.178 (1.5);8.476 (7.0);7.730(2.7);7.727(3.4);7.709 (3.8);7.490 (2.2);7.471(4.1);7.452 (2.4);7.346 (1.5);7.331 (2.3);7.329 (2.4);7.313 (2.1);7.295 (0.8);7.201 (0.7);7.197(0.8);7.180 (1.6);7.162 (1.0);7.159 (0.9);6.952 (1.1);6.949 (1.2);6.931 (1.9);6.920 (0.9);6.815 (2.1);6.794 (1.9);5.262 (0.4);5.248 (1.0);5.229 (1.0);5.214 (0.4);4.306 (0.4);4.287 (0.8);4.270 (1.0);4.260(1.2);4.252(1.0);4.239(0.8);4.231(1.1);4.211(0.4);3.990 (0.3);3.972 (0.9);3.955 (1.3);3.937 (1.0);3.920 (0.4);3.317 (19.7);2.675 (0.3);2.670 (0.5);2.666 (0.3);2.601 (16.0);2.523 (0.6);2.510 (26.1);2.506 (52.2);2.501 (68.6);2.497 (51.0);2.328(0.4);2.226(0.4);2.214 (0.6);2.205 (0.6);2.192 (0.7);2.180 (0.5);2.080 (0.5);2.072 (0.6);2.065(0.8);2.057 (0.5);2.048 (0.5);2.037(0.5);2.029 (0.5);1.581(7.0);1.563(7.5);1.557 (7.7);1.539(6.9);1.398 (2.0);0.008(1.9);0.000(48.4);−0.009(2.0)

Example 180: ¹H-NMR(400 MHz, d₆-DMSO): δ = 9.190 (0.7);9.170 (0.7);8.428 (3.3);7.775 (1.5);7.770 (1.6);7.542 (0.5);7.537(0.5);7.522 (1.3);7.516 (1.3);7.477(0.8);7.333(0.6);7.314(0.7);7.190 (0.3);7.172 (0.7);7.197 (0.8);7.180 (1.6);7.162 (1.0);7.151(0.9);6.941(0.5);6.938(0.5);6.919(0.9);6.903(0.4);6.807 (0.9);6.785 (0.8);5.234(0.4);5.216(0.4);4.278 (0.4);4.261 (0.4);4.253 (0.3);4.244 (0.3);4.237(0.4);4.224(0.3);4.217(0.5);3.962(0.4);3.944(0.5);3.927(0.4);3.307 (12.3);2.523 (0.5);2.509 (12.3);2.501 (34.5);2.496 (25.5);2.492 (12.8);2.373 (7.1);1.584 (3.1);1.566 (3.2);1.559(3.3);1.541(3.0);1.398 (16.0);0.008(0.5);0.000(18.0);−0.008(0.8)

Example 181: ¹H-NMR(400 MHz, d₆-DMSO): δ = 9.066 (1.5);9.045 (1.5);8.433 (7.3);7.777(3.3);7.772 (3.4);7.544 (1.1);7.539 (1.0);7.523 (3.0);7.518 (3.1);7.500 (4.7);7.479 (1.7);7.379 (0.9);7.367 (1.2);7.358 (1.2);7.289 (0.5);7.278 (0.4);7.267 (1.7);7.257 (0.9);7.245 (3.5);7.239 (2.0);7.232 (1.8);7.223 (2.1);5.540(0.4);5.521 (1.3);5.501 (1.3);5.481 (0.5);3.989 (0.3);3.971 (0.9);3.953 (1.3);3.936 (1.0);3.918 (0.4);3.307 (22.0);3.009 (0.4);2.996 (0.4);2.987 (0.4);2.978 (0.7);2.969(0.7);2.956 (0.7);2.947(0.5);2.881 (1.1);2.861 (0.8);2.842 (0.6);2.821 (0.3);2.670 (0.5);2.665 (0.4);2.562 (0.3);2.553 (0.4);2.542 (0.7);2.533 (0.9);2.523 (1.7);2.518 (1.9);2.509 (26.9);2.505(55.8);2.501(75.5);2.496(55.7);2.492(28.2);2.375(16.0);2.332(0.4);2.323 (0.4);1.987 (0.8);1.939 (0.8);1.929 (0.4);1.919 (0.8);1.898 (0.3);1.888 (0.7);1.587(6.8);1.569(12.8);1.551(6.7);1.398(7.3);1.175(0.4);0.008(1.2);0.000(41.1);−0.008(1.7)

Example 182: ¹H-NMR(400 MHz, d₆-DMSO): δ = 9.072 (1.5);9.051 (1.5);8.399 (7.3);7.774 (3.2);7.769(3.3);7.541 (1.1);7.536 (1.0);7.520 (2.9);7.515 (3.0);7.496 (4.3);7.475 (1.6);7.360 (0.9);7.352 (1.0);7.338 (1.3);7.211(0.4);7.194 (2.1);7.185 (2.4);7.176 (2.4);7.172 (2.1);7.160 (0.6);7.124 (1.5);7.110 (1.0);7.102 (0.8);5.222 (0.3);5.207 (0.7);5.190 (0.8);5.173 (0.4);3.967 (0.3);3.950 (0.9);3.932 (1.2);3.915 (0.9);3.897 (0.4);3.308 (11.3);2.780 (0.6);2.763(1.6);2.749(1.6);2.734(0.7);2.523(0.8);2.509(0.9);2.518(0.9);2.505 (33.8);2.500 (45.5);2.496 (33.6);2.491 (17.0);2.372 (16.0);2.054 (0.4);2.045 (0.5);2.033 (0.6);2.025 (0.6);2.010 (0.5);1.988 (0.5);1.939 (0.5);1.928 (0.4);1.913 (0.6);1.893 (0.5);1.875 (0.5);1.856 (0.6);1.849 (0.6);1.833 (0.6);1.823 (0.9);1.807 (1.2);1.784 (0.5);1.588 (6.8);1.571 (7.0);1.561 (7.2);1.543 (6.8);1.398 (1.8);0.008 (0.7);0.000 (24.9);−0.009 (1.1)

Example 184: ¹H-NMR(400 MHz, d₆-DMSO): δ = 9.198 (1.1);9.178 (1.1);8.437 (4.3);7.337 (1.1);7.318 (1.2);7.242 (0.4);7.222 (1.3);7.204 (2.4);7.189 (1.0);7.185 (1.0);7.176 (1.2);7.158 (0.7);7.155 (0.7);7.072 (0.5);7.065 (0.5);7.056 (1.0);7.038 (0.5);7.033 (0.5);6.943 (0.8);6.924 (1.4);6.906 (0.7);6.809 (1.5);6.788 (1.3);5.238 (0.7);5.220 (0.7);4.281 (0.6);4.273 (0.6);4.265 (0.7);4.256 (0.5);4.249 (0.6);4.241 (0.6);4.228 (0.6);4.221 (0.7);3.960 (0.6);3.942 (0.8);3.924 (0.7);3.883 (0.5);3.318 (49.8);2.670 (0.5);2.666 (0.4);2.506 (53.5);2.501 (72.2);2.497 (56.5);2.457 (0.5);2.419 (0.6);2.328 (0.5);2.324 (0.4);2.208 (0.4);2.199 (0.4);2.186 (0.5);2.174 (0.3);2.064 (0.4);2.058 (0.5);2.047 (0.4);2.041 (0.4);2.030 (0.3);2.023 (0.3);1.582 (4.4);1.564 (4.7);1.557 (4.9);1.539 (4.5);1.398 (16.0);0.000 (1.9)

-continued

Example 185: $^1$H-NMR(400.0 MHz, d$_6$-DMSO): δ = 9.225(1.7);9.205(1.7);8.572(7.1);7.723(0.4);7.713(2.1);7.696(2.1);7.689(2.1);7.672(2.0);7.662(0.3);7.348(1.6);7.329(1.8);7.203(0.8);7.200(0.8);7.182(1.7);7.165(1.0);7.161(1.0);6.950(1.2);6.931(2.1);6.915(0.9);6.912(1.0);6.815(2.3);6.796(2.0);5.259(0.5);5.245(1.1);5.226(1.1);5.211(0.5);4.307(0.4);4.299(0.4);4.288(0.9);4.279(0.9);4.271(1.0);4.263(0.8);4.255(0.8);4.247(1.0);4.234(0.8);4.227(1.1);4.206(0.4);4.199(0.3);3.979(0.4);3.961(1.0);3.943(1.3);3.926(1.0);3.909(0.4);3.317(66.7);2.891(1.0);2.732(0.9);2.675(0.7);2.670(0.9);2.666(0.8);2.645(16.0);2.523(2.2);2.506(105.4);2.501(139.0);2.497(104.8);2.333(0.7);2.328(0.9);2.324(0.7);2.237(0.3);2.229(0.5);2.215(0.7);2.206(0.7);2.193(0.7);2.181(0.5);2.087(0.3);2.079(0.5);2.071(0.7);2.064(0.8);2.054(0.6);2.047(0.6);2.036(0.5);2.029(0.6);1.568(7.2);1.550(7.9);1.544(8.2);1.527(7.1);1.398(3.6);0.008(0.6);0.000(17.2)

Example 186: $^1$H-NMR(400.0 MHz, d$_6$-DMSO): δ = 9.207(1.6);9.187(1.7);8.539(7.0);7.959(1.7);7.954(1.8);7.941(1.7);7.935(1.8);7.744(0.8);7.738(0.8);7.732(0.9);7.726(1.0);7.722(1.2);7.717(1.1);7.710(1.1);7.705(1.0);7.548(1.8);7.526(2.6);7.503(1.5);7.347(1.6);7.329(1.8);7.202(0.8);7.199(0.8);7.181(1.1);7.163(1.1);7.160(1.0);6.949(1.3);6.931(2.1);6.914(1.0);6.912(1.0);6.814(2.3);6.795(2.1);6.793(2.1);5.260(0.5);5.245(1.1);5.226(1.1);5.211(0.5);4.306(0.4);4.299(0.4);4.287(0.9);4.279(0.9);4.270(1.0);4.259(1.1);4.250(1.0);4.237(0.9);4.229(1.1);4.209(0.4);4.201(0.3);3.986(0.4);3.969(1.0);3.951(1.4);3.934(1.0);3.916(0.4);3.317(19.6);2.675(0.3);2.670(0.5);2.666(0.4);2.614(16.0);2.524(1.0);2.506(53.7);2.456(0.6);2.332(0.3);2.328(0.5);2.324(0.4);2.235(0.3);2.227(0.5);2.214(0.7);2.205(0.7);2.193(0.7);2.180(0.5);2.171(0.3);2.079(0.5);2.070(0.6);2.063(0.8);2.052(0.6);2.047(0.6);2.036(0.5);2.028(0.5);1.988(0.4);1.573(7.1);1.555(7.8);1.549(8.1);1.532(7.2);1.512(0.4);1.398(4.3);0.000(8.8)

Example 187: $^1$H-NMR(400.0 MHz, d$_6$-DMSO): δ = 9.219(2.4);9.199(2.6);8.510(10.1);7.920(1.2);7.902(2.3);7.885(1.3);7.833(1.1);7.815(2.3);7.798(1.5);7.554(1.8);7.535(3.1);7.515(1.5);7.346(2.5);7.327(2.7);7.199(1.2);7.196(1.2);7.179(2.7);7.161(1.6);7.158(1.6);7.160(1.9);6.947(1.8);6.945(1.8);6.926(3.1);6.910(1.6);6.907(1.5);6.814(3.4);6.793(3.2);5.755(5.6);5.257(0.7);5.243(1.6);5.224(1.7);5.210(0.8);4.313(0.5);4.304(0.6);4.297(0.6);4.285(1.5);4.276(1.4);4.269(1.6);4.260(1.3);4.253(1.4);4.245(1.5);4.232(1.3);4.225(1.8);4.204(0.7);4.197(0.6);3.997(0.5);3.979(1.4);3.962(2.0);3.944(1.5);3.927(0.6);3.321(27.3);2.892(1.7);2.733(1.6);2.672(0.3);2.507(42.0);2.503(54.0);2.498(41.2);2.463(16.0);2.406(0.5);2.329(0.3);2.247(0.4);2.234(0.5);2.226(0.8);2.213(1.0);2.204(1.1);2.191(1.1);2.179(0.8);2.171(0.5);2.085(0.5);2.078(0.8);2.069(1.1);2.063(1.2);2.051(0.9);2.047(0.9);2.035(0.8);2.028(0.8);2.012(0.4);1.590(10.5);1.573(11.6);1.566(12.0);1.548(10.5);1.513(0.4);1.508(0.4);1.398(0.4);1.266(0.4);1.249(0.4);0.000(6.3)

Example 188: $^1$H-NMR(400.0 MHz, d$_6$-DMSO): δ = 9.196(0.9);9.176(0.9);8.437(3.7);7.319(0.9);7.194(0.8);7.187(1.1);7.175(2.5);7.159(0.7);7.050(0.4);7.051(0.4);7.043(0.7);7.035(0.7);7.028(0.4);7.020(0.3);6.943(0.6);6.925(1.1);6.906(0.5);6.810(1.2);6.790(1.1);5.241(0.5);5.221(0.5);4.680(0.7);4.664(0.9);4.649(0.7);4.282(0.5);4.274(0.4);4.266(0.5);4.257(0.4);4.251(0.4);4.243(0.5);4.230(0.4);4.222(0.6);3.961(0.5);3.943(0.7);3.926(0.5);3.318(38.0);2.506(38.0);2.501(50.0);2.497(38.0);2.421(5.3);2.328(0.3);2.209(0.3);2.201(0.3);2.187(0.4);2.065(0.3);2.059(0.4);1.583(3.6);1.565(3.8);1.557(3.9);1.540(3.6);1.398(16.0);1.330(9.9);1.315(9.8);0.000(8.3)

Example 189: 1H-NMR(400.0 MHz, d$_6$-DMSO): δ = 9.212(0.8);9.192(0.9);8.481(3.2);7.639(0.4);7.635(0.4);7.618(0.8);7.601(0.4);7.598(0.5);7.547(0.5);7.543(0.4);7.527(0.8);7.511(0.5);7.507(0.5);7.361(0.7);7.341(1.9);7.322(1.3);7.199(0.4);7.195(0.4);7.178(0.8);7.160(0.5);6.944(0.6);6.925(1.0);6.907(0.5);6.811(1.1);6.791(1.0);5.240(0.5);5.221(0.5);4.283(0.4);4.274(0.4);4.267(0.5);4.258(0.4);4.249(0.4);4.242(0.5);4.228(0.4);4.221(0.5);3.965(0.5);3.947(0.6);3.929(0.5);3.322(56.5);2.506(37.7);2.502(49.8);2.497(37.4);2.449(5.0);2.189(0.3);2.059(0.4);1.585(3.3);1.567(3.5);1.560(3.6);1.542(3.3);1.398(16.0);0.000(5.7)

Example 190: $^1$H-NMR(400.0 MHz, d$_6$-DMSO): δ = 9.233(1.7);9.213(1.7);8.606(1.4);8.598(7.6);7.753(2.4);7.749(4.5);7.727(4.6);7.352(1.6);7.335(1.7);7.205(0.9);7.201(0.9);7.183(1.6);7.166(1.1);7.162(0.9);6.951(1.3);6.935(2.0);6.932(2.0);6.925(0.4);6.916(1.0);6.913(0.9);6.818(2.3);6.815(2.1);6.797(2.0);5.261(0.6);5.247(1.2);5.228(1.0);5.213(0.4);4.317(0.4);4.309(0.5);4.301(0.6);4.290(1.1);4.281(1.1);4.273(1.2);4.264(1.0);4.257(1.0);4.249(1.1);4.236(1.1);4.228(1.2);4.208(0.5);4.200(0.3);3.984(0.4);3.967(1.0);3.949(1.4);3.932(1.0);3.914(0.4);3.327(2.4);3.318(11.8);2.676(4.3);2.668(16.0);2.511(26.2);2.507(39.6);2.502(45.7);2.497(31.3);2.493(14.7);2.239(0.7);2.231(0.6);2.217(0.8);2.209(0.8);2.196(0.8);2.183(0.5);2.090(0.5);2.080(0.6);2.074(0.8);2.067(0.9);2.058(0.7);2.051(0.6);2.040(0.6);2.020(0.5);2.024(0.3);1.570(7.7);1.552(9.1);1.546(8.2);1.537(2.6);1.528(7.0);1.406(3.0);1.398(13.0);0.008(1.0);0.000(5.3)

Example 191: $^1$H-NMR(400.0 MHz, d$_6$-DMSO): δ = 9.209(1.7);7.189(1.7);8.439(6.8);7.953(0.5);7.491(2.1);7.479(3.5);7.469(1.7);7.461(3.4);7.448(0.4);7.338(3.0);7.326(2.6);7.317(2.7);7.196(0.8);7.175(1.8);7.157(1.1);7.154(1.1);6.940(1.3);6.922(2.2);6.903(1.0);6.808(2.4);6.789(2.1);5.754(1.1);5.252(0.5);5.238(1.1);5.219(1.1);5.205(0.5);4.300(0.4);4.292(0.4);4.280(1.0);4.272(0.9);4.264(1.1);4.256(0.9);4.247(0.9);4.240(1.0);4.226(0.9);4.219(1.2);4.198(0.5);4.191(0.4);3.984(0.4);3.967(0.9);3.949(1.3);3.932(1.0);3.914(0.4);3.321(17.9);2.891(3.1);2.732(2.7);2.506(23.4);2.502(30.7);2.497(23.4);2.457(0.4);2.405(0.6);2.387(16.0);2.221(0.5);2.208(0.7);2.199(0.7);2.186(0.8);2.174(0.6);2.165(0.4);2.074(0.5);2.065(0.7);2.059(0.8);2.042(0.6);2.031(0.6);2.016(0.4);1.591(7.3);1.573(7.7);1.565(7.8);1.548(7.1);1.265(0.4);1.249(0.3);0.000(1.1)

Example 192: $^1$H-NMR(400.0 MHz, d$_6$-DMSO): δ = 9.202(1.9);9.189.8.512(0.8);8.460(6.9);7.339(2.0);7.320(2.2);7.283(0.3);7.261(4.1);7.247(1.5);7.240(3.0);7.231(1.7);7.198(1.0);7.177(2.0);7.162(1.3);6.944(1.4);6.925(2.4);6.908(1.1);6.811(2.7);6.791(2.4);5.754(2.1);5.253(0.5);5.239(1.2);5.220(1.3);5.206(0.6);4.309(0.4);4.302(0.5);4.282(1.1);4.274(1.1);4.266(1.2);4.257(1.0);4.250(1.0);4.242(1.1);4.228(1.0);4.222(1.3);4.201(0.5);4.194(0.4);3.978(0.5);3.965(16.0);3.944(1.6);3.927(1.1);3.909(0.4);3.568(0.5);3.319(51.5);2.891(1.2);2.732(1.1);2.671(0.5);2.506(61.1);2.502(78.7);2.497(60.5);2.456(1.6);2.430(12.0);2.405(0.4);2.328(0.5);4.201(0.5);2.230(0.4);2.222(0.6);2.209(0.8);2.200(0.8);2.188(0.9);2.176(0.6);2.166(0.4);2.074(0.6);2.065(0.8);2.058(0.9);2.042(0.7);2.031(0.7);2.023(0.6);2.015(0.4);1.989(0.5);1.581(7.6);1.563(8.3);1.556(8.5);1.538(7.6);1.512(0.9);1.489(0.8);1.398(1.0);1.235(0.3);0.000(1.6)

Example 193: $^1$H-NMR(400.0 MHz, d$_6$-DMSO): δ = 9.182(1.7);9.162(1.7);8.511(0.3);8.379(6.8);8.314(0.5);7.346(1.1);7.329(3.6);7.312(2.5);7.303(1.5);7.297(1.7);7.285(0.7);7.278(1.4);7.257(2.2);7.250(3.0);7.245(3.3);7.233(0.5);7.194(0.8);7.190(0.8);7.173(1.7);7.155(1.1);6.939(1.2);6.921(2.1);6.904(1.0);6.807(2.3);6.787(2.1);5.2500(5.1);5.235(1.1);5.216(1.1);5.202(0.5);4.297(0.4);4.290(0.4);4.277(1.0);4.269(1.0);4.262(1.1);4.250(1.1);4.241(1.0);4.227(0.8);4.220(1.1);4.199(0.4);4.193(0.4);3.997(0.8);3.962(1.2);3.945(0.9);3.927(0.4);3.316(113.5);2.670(1.7);2.666(1.3);2.523(4.0);2.505(207.9);2.501(269.4);2.497(203.2);2.456(1.2);2.348(16.0);2.332(1.5);2.328(1.8);2.215(0.5);2.203(0.7);2.193(0.7);2.181(0.8);2.169(0.6);2.111(14.5);2.070(0.5);2.062(0.7);2.055(0.8);2.043(0.6);2.028(0.5);2.021(0.5);1.591(7.2);1.574(7.7);1.566(7.4);1.549(6.7);1.529(0.5);1.511(0.5);1.506(0.5);1.488(4.9);1.146(1.5);0.008(10.9);0.000(302.8);-0.031(0.4);-0.150(1.5)

Example 194: $^1$H-NMR(400.0 MHz, 0D013): 8 = 8.559(7.0);7.523(6.2);7.401(2.7);7.396(4.7);7.392(60.9);7.347(1.5);7.329(1.3);7.262(60.4);7.210(1.0);7.199(0.5);7.182(1.0);7.164(0.6);7.161(0.6);6.949(0.8);6.931(1.3);6.914(0.6);6.912(0.6);6.815(1.4);6.796(1.3);5.245(0.7);5.226(0.7);4.288(0.6);4.280(0.5);4.272(0.6);4.260(0.7);4.251(0.6);4.238(0.5);4.231(0.7);3.973(0.6);3.955(0.8);3.937(0.6);3.319(5.9);2.635(0.9);2.525(0.3);2.507(13.9);2.503(18.4);2.498(13.8);2.215(0.4);2.207(0.4);2.194(0.4);2.072(0.4);2.065(0.5);2.054(0.4);2.049(0.4);1.571(4.4);1.554(4.9);1.548(5.0);1.530(4.3);1.397(16.0);0.008(0.5);0.000(13.7)

Example 195: $^1$H-NMR(400.0 MHz, d$_6$-DMSO): δ = 9.242(0.8);9.222(0.8);8.635(3.3);8.430(1.2);8.410(1.3);7.953(0.9);7.933(1.7);7.913(0.9);7.360(0.8);7.347(1.5);7.329(1.3);7.206(0.4);7.202(0.4);7.185(0.8);7.168(0.5);7.164(0.5);6.957(0.5);6.955(0.6);6.937(0.9);6.920(0.4);6.918(0.4);6.817(1.0);6.799(0.9);5.254(0.5);5.235(0.5);4.295(0.4);4.286(0.4);4.278(0.5);4.270(0.4);4.259(0.4);4.251(0.4);4.238(0.4);4.231(0.5);3.988(0.4);3.970(0.6);3.952(0.5);3.320(17.5);2.796(7.3);2.507(16.3);2.503(21.6);2.498(16.2);2.204(0.3);2.075(0.4);1.578(3.3);1.556(3.3);1.536(3.8);1.398(16.0);0.008(0.6);0.000(15.6);−0.008(0.8)

Example 196: $^1$H-NMR(400.0 MHz, 0D013): 8 = 9.323(3.2);9.303(3.2);8.785(12.5);8.314(0.7);7.773(10.0);7.757(9.8);7.361(3.3);7.343(3.4);7.207(1.6);7.210(1.2);7.214(1.8);7.262(60.9);7.523(6.2);7.392(2.1);7.278(2.1);7.233(0.4);7.169(2.0);6.954(2.5);6.935(4.0);6.916(2.0);6.821(4.4);6.891(2.3);6.870(2.0);6.367(0.8);5.398(0.5);5.384(1.2);5.366(1.2);5.352(0.5);4.391(0.5);4.383(0.6);4.376(0.6);4.363(0.8);4.354(0.9);4.348(0.9);4.339(0.7);4.230(0.8);4.223(0.9);4.206(1.0);4.201(1.3);4.178(0.7);4.171(0.6);4.119(0.4);4.101(1.1);4.084(1.5);4.066(1.1);4.049(0.5);2.441(0.4);2.430(0.5);2.417(0.8);2.409(0.8);2.395(0.7);2.382(0.6);2.373(0.4);2.265(0.4);2.259(0.5);2.251(0.8);2.245(0.8);2.238(0.5);2.231(0.7);2.223(0.4);2.216(0.6);2.210(0.6);2.202(0.4);1.662(16.0);1.644(8.6);1.580(11.8);1.255(0.5);0.000(1.8)

Example 197: $^1$H-NMR(400.0 MHz, d$_6$-DMSO): δ = 9.266(1.0);5.253(2.1);5.234(2.1);5.220(0.9);4.324(0.7);4.315(1.0);4.308(1.0);4.296(1.8);4.287(1.6);4.279(1.7);4.272(1.3);4.239(1.8);4.218(2.1);4.196(0.9);4.189(0.8);3.980(0.7);3.963(1.9);3.945(2.6);6.801(3.9);6.870(2.0);6.367(0.8);5.398(0.5);5.384(1.2);5.366(1.2);5.352(0.5);

-continued 3.928(1.9);3.317(79.4);2.671(1.6);2.666(1.3);2.571(0.4);2.506(182.4);2.502(243.0);2.497(193.8);2.328(1.5);2.242(1.0);2.229(1.3);2.219(1.4);2.208(1.4);2.195(1.0);2.095(1.0);2.079(1.5);2.065(1.2);2.051(1.0); 2.045(1.0);1.574(13.2);1.557 (14.9);1.551(16.0);1.533(12.8);1.398(1.4);0.146(0.8);0.033(0.5);0.008(10.3);0.000(198.2);−0.028(0.4);−0.031 (0.4);−0.150(0.9)

Example 198: $^1$H-NMR(400.0 MHz, d$_6$-DMSO): δ = 9.220(1.3);9.199(1.3);8.634(4.0);8.314(0.7);7.889(5.2);7.886(4.5);7.545(2.3);7.353(1.3);7.334(1.4);7.204(0.6);7.185(1.3);7.166(0.8);6.953(0.9);6.935(1.6);6.917(0.7); 6.818(1.7);6.798(1.5);5.247(0.9);5.230(0.9);5.216(0.4);4.310(0.4);4.291(0.4);4.274(0.9);4.262(0.8);4.258(0.8);4.250(0.8);4.230(0.9);4.209(0.3);4.073(0.4);4.057(0.8);4.040(1.1);4.023(0.9);4.006(0.3);3.909(0.7);3.891(0.9); 3.874(0.7);3.317(186.5);2.671(2.6);2.505(364.0);2.501(406.7);2.394(0.3);2.328(2.6);2.220(0.5);2.212(0.6);2.199(0.7);2.067(0.7);2.057(0.7);2.038(0.5);1.590(4.7);1.572(5.9);1.566(5.7);1.548(4.6); 1.480(10.9);1.463(10.8);1.398(16.0);0.000(52.2)

Example 199: $^1$H-NMR(400.0 MHz, d$_6$-DMSO): δ = 9.099(1.8);9.078(1.8);8.646(5.8);8.314(0.6);7.892(7.0);7.887(7.0);7.552(2.4);7.547(3.4);7.399(1.2);7.388(1.6);7.378(1.4);7.278(2.1);7.257(3.9);7.250(2.9);7.235(2.1); 5.556(0.5);5.535(1.5);5.516(1.5);5.496(0.5);4.075(0.5);4.059(1.2);4.042(1.6);4.025(1.2);4.009(0.5);3.940(0.4);3.922(1.0);3.904(1.4);3.887(1.0);3.870(0.4);3.317(179.3);3.019(0.5);2.988(0.9);2.980(0.9);2.965(0.9); 2.916(0.6);2.895(1.3);2.874(1.0);2.855(0.7);2.835(0.4);2.670(2.6);2.505(351.4);2.501(401.1);2.497(299.4);2.328(2.6);1.949(0.9);1.929(0.9);1.918(0.9);1.897(0.8);1.594(6.8);1.576(12.4);1.558(6.6);1.482(16.0);1.465(15.6); 1.398(0.8);0.000(58.8)

Example 200: $^1$H-NMR(400.0 MHz, d$_6$-DMSO): δ = 9.221(1.6);9.201(1.7);8.639(4.9);8.314(0.4);7.912(6.2);7.909(5.8);7.543(2.8);7.354(1.8);7.334(1.8);7.204(0.8);7.185(1.7);7.166(1.0);6.953(1.2);6.934(2.0);6.916(0.9); 6.818(2.2);6.797(2.0);5.263(0.5);5.247(1.1);5.229(1.1);5.215(0.5);4.309(0.4);4.291(1.0);4.281(0.9);4.274(1.0);4.260(1.0);4.252(1.0);4.231(1.1);4.211(0.4);3.931(0.3);3.914(0.9);3.896(1.2);3.879(0.9);3.862(0.4);3.357(1.2); 3.339(3.9);3.317(82.9);2.671(1.4);2.501(218.9);2.328(1.4);2.233(0.5);2.219(0.7);2.210(0.7);2.198(0.8);2.187(0.6);2.066(0.8);2.052(0.6);2.039(0.5);2.032(0.5);1.589(6.0);1.570(7.4);1.566(7.4);1.547(5.9);1.456(3.6); 1.438(7.3);1.420(3.7);1.398(16.0);0.000(28.8)

Example 201: $^1$H-NMR(400.0 MHz, d$_6$-DMSO): δ = 9.098(2.1);9.078(2.1);8.644(8.0);8.313(1.3);7.915(8.8);7.911(9.3);7.550(2.4);7.545(4.3);7.541(2.4);7.399(1.3);7.388(1.8);7.378(1.7);7.299(0.8);7.288(1.5);7.277(2.5); 7.267(1.6);7.257(3.1);7.250(3.1);7.244(2.8);7.235(2.6);7.185(1.8);5.515(1.8);5.495(0.6);3.944(0.5);3.926(1.3);3.909(1.7);3.892(1.3);3.874(0.5);3.359(1.9);3.341(6.5);3.317(219.8);3.028(0.5);3.019(0.5); 3.006(0.6);2.997(0.7);2.988(1.0);2.980(1.0);2.966(1.0);2.958(1.0);2.915(0.6);2.895(1.6);2.874(1.2);2.855(0.8);2.835(0.8);2.670(3.5);2.580(0.5);2.572(0.9);2.561(1.6);2.506(408.2);2.501(529.4);2.497(407.1);2.328(3.2); 1.971(0.4);1.950(1.1);1.939(0.5);1.928(1.1);1.918(1.1);1.909(0.5);1.898(0.9);1.876(0.4);1.592(8.5);1.575(16.0);1.557(8.5);1.440(11.5);1.422(5.4);1.398(1.5);0.147(0.3);0.007(4.1);0.000(68.4);−0.150(0.3)

Example 202: $^1$H-NMR(400.0 MHz, d$_6$-DMSO): δ = 9.226(0.8);9.206(0.8);8.641(2.9);7.931(3.1);7.926(3.4);7.549(1.0);7.544(1.7);7.540(1.0);7.352(0.8);7.335(0.9);7.202(0.4);7.185(0.8);7.167(0.5);7.164(0.5);6.953(0.6); 6.934(1.0);6.915(0.5);6.817(1.1);6.797(0.9);5.248(0.5);5.229(0.5);4.290(0.5);4.281(0.5);4.272(0.6);4.253(0.5);4.232(0.6);4.231(0.6);4.271(0.9);4.289(0.5);4.910(0.6);3.892(0.5);3.317(28.3);2.735(7.3);2.671(0.5);2.505(64.1); 2.501(81.3);2.498(65.2);2.328(0.5);2.219 (0.3);2.210(0.4);2.197(0.4);2.073(0.3);2.067(0.4);1.590(3.2);1.572(3.8);1.567 (3.9);1.549(3.2);1.464(0.3);1.398(16.0);0.000(4.7)

Example 203: $^1$H-NMR(400.0 MHz, d$_6$-DMSO): δ = 9.104(1.5);9.084(1.6);8.647(6.5);8.314(0.7);7.933(6.8);7.928(7.0);7.551(2.0);7.546(3.5);7.542(1.9);7.400(1.0);7.389(1.3);7.379(1.3);7.299(0.6);7.289(1.1);7.278(1.8); 7.268(1.2);7.257(3.7);7.250(2.3);7.244(2.1);7.235(2.0);5.556(0.5);5.536(1.5);5.516(1.3);5.497(0.4);3.939(0.9);3.922(1.3);3.904(1.0);3.887(0.4);3.316(78.8);3.027(0.4);3.020(0.4);3.007(0.4);2.998(0.5); 2.988(0.7);2.980(0.8);2.967(0.8);2.959(0.7);2.915(0.6);2.895(1.2);2.874(0.9);2.855(0.6);2.834(0.4);2.737(16.0);2.675(1.5);2.671(1.7);2.666(1.3);2.671(0.5);2.561(1.9);2.552(1.1);2.540(1.4);2.506(197.4); 2.501(255.4);2.497(191.3);2.328(1.2);2.324(1.2);1.951(0.8);1.940(0.4);1.930(0.8);1.919(0.8);1.908(0.4);1.898(0.7);1.594(6.6);1.576(12.4);1.558(6.5);1.482(0.6);1.465(0.6);1.398(6.5);0.000(18.7)

Example 204: $^1$H-NMR(400.0 MHz, d$_6$-DMSO): δ = 9.201(1.4);9.181(1.5);8.544(5.3);7.979(2.8);7.717(1.7);7.516(1.0);7.496(1.8);7.459(1.8);7.440(2.3);7.420(0.9);7.351(1.4);7.332(1.6);7.202(0.7);7.181(1.5); 7.163(1.0);6.952(1.1);6.933(1.9);6.914(0.9);6.815(2.0);6.795(1.8);5.260(0.9);5.227(0.9);5.246(0.9);5.227(0.9);5.213(0.4);4.307(0.3);4.287(0.8);4.279(0.8);4.261(1.1);4.252(0.9);4.239(1.0);4.210(0.3);3.977(0.8); 3.959(1.1);3.942(0.8);3.313(28.9);2.670(0.6);2.619(12.2);2.505(67.7);2.501(84.9);2.497(65.2);2.328(0.6);2.228(0.4);2.215(0.6);2.205(0.6);2.193(0.6);2.181(0.4);2.080(0.4);2.072(0.6);2.064(0.7);2.054(0.5);2.047(0.5); 2.037(0.4);2.029(0.4);1.575(5.7);1.557(6.6);1.534(5.6);1.398(16.0);0.971(0.4);0.954(0.5);0.000(25.9)

Example 205: $^1$H-NMR(400.0 MHz, d$_6$-DMSO): δ = 9.082(1.2);9.062(1.2);8.551(3.6);7.980(2.4);7.741(1.3);7.722(1.5);7.518(0.9);7.499(1.7);7.462(1.3);7.443(1.8);7.423(0.7);7.387(1.2);7.377(1.1);7.285(1.0); 7.275(1.5);7.265(1.0);7.255(2.7);7.247(2.0);7.234(1.4);5.554(0.4);5.535(1.1);5.516(1.1);5.496(0.5);4.232(0.9);3.949(0.7);3.967(0.9);3.949(0.7);3.317(23.2);3.018(0.3);3.004(0.3);2.995(0.4);2.987(0.6);2.978(0.6);2.964(0.6);2.956(0.6); 2.912(0.4);2.891(0.9);2.871(0.7);2.852(0.5);2.672(0.6);2.629(9.7);2.567(0.4);2.556(0.6);2.546(0.8);2.502(81.6);2.329(0.5);1.948(0.8);1.937(0.3);1.928(0.7);1.917(0.6);1.896(0.6);1.579(4.8);1.562(9.3);1.544(4.8); 1.398(16.0);0.001(41.6);0.000(42.2)

Example 206: $^1$H-NMR(400.0 MHz, d$_6$-DMSO): δ = 9.201(1.9);9.181(2.0);8.504(7.2);7.702(7.4);7.670(7.3);7.649(3.2);7.347(1.9);7.328(2.1);7.200(0.9);7.197(0.9);7.180(2.0);7.162(1.2);7.159(1.1);6.951(1.4); 6.932(2.4);6.914(1.5);6.815(2.6);6.794(2.3);5.263(0.5);5.248(1.5);5.230(1.5);5.215(0.5);4.314(0.3);4.306(0.4);4.298(0.4);4.287(1.1);4.278(1.0);4.270(1.2);4.260(1.4);4.251(1.2);4.238(1.0);4.231(1.3);4.210(0.5);4.203(0.4); 3.987(0.4);3.970(1.1);3.952(1.5);3.935(1.1);3.917(0.4);3.316(17.1);2.605(16.0);2.502(20.6);2.497(16.1);2.236(0.4);2.228(0.5);2.215(0.7);2.206(0.8);2.194(0.8);2.181(0.6);2.173(0.4);2.088(0.4);2.081(0.5); 2.073(0.8);2.066(0.9);2.056(0.6);2.049(0.7);2.039(0.6);2.031(0.5);2.023(0.4);1.576(7.5);1.558(8.5);1.552(8.7);1.534(8.7);1.397(2.1);0.000(13.3)

Example 207: $^1$H-NMR(400.0 MHz, d$_6$-DMSO): δ = 9.076(1.8);9.055(1.9);8.509(7.0);7.727(3.1);7.706(7.2);7.674(7.2);7.652(3.2);7.390(1.1);7.378(1.5);7.368(1.5);7.295(0.7);7.284(1.2);7.273(2.0);7.263(1.5);7.253(4.3); 7.245(2.9);7.239(2.6);7.231(2.3);7.221(0.4);5.553(0.5);5.533(1.5);5.513(1.5);5.493(0.5);3.992(0.4);3.975(1.4);3.940(1.1);3.922(0.4);3.312(35.7);3.023(0.4);3.015(0.4);3.002(0.5);2.993(0.5);2.984(0.8); 2.975(0.8);2.962(0.8);2.953(0.8);2.909(0.6);2.889(1.3);2.869(1.0);2.850(0.7);2.829(0.4);2.670(0.7);2.607(16.0);2.573(0.4);2.565(0.4);2.554(0.9);2.544(1.2);2.533(1.3);2.505(75.7);2.501(100.8);2.497(79.3);2.332(0.5); 2.328(0.7);1.968(0.3);1.947(0.9);1.937(0.4);1.926(0.9);1.915(0.9);1.905(0.4);1.895(0.8);1.577(7.4);1.559(14.2);1.542(7.3);1.398(2.5);0.007(2.0);0.000(32.6)

Example 208: $^1$H-NMR(400.0 MHz, d$_6$-DMSO): δ = 9.227(1.0);9.207(1.1);8.737(1.8);8.732(1.9);8.484(3.7);8.369(1.8);8.363(1.8);7.342(1.0);7.323(1.1);7.194(0.5);7.176(1.0);7.159(0.6);6.944(0.7);6.925(1.3);6.907(0.6); 6.810(1.4);6.790(1.2);5.238(0.6);5.219(0.7);4.282(0.6);4.273(0.5);4.266(0.6);4.257(0.5);4.248(0.5);4.241(0.6);4.227(0.5);4.220(0.7);3.971(0.6);3.954(0.8);3.936(0.6);3.313(14.8);2.501(31.6);2.497(25.2);2.432(8.5); 2.209(0.4);2.200(0.4);2.187(0.4);2.069(0.4);2.063(0.5);2.049(0.3);1.587(3.9);1.569(4.3);1.562(4.5);1.545(3.9);1.398(16.0);0.952(0.7);0.936(0.8);0.007(0.7);0.000(9.7)

Example 209: $^1$H-NMR(400.0 MHz, d$_6$-DMSO): δ = 9.104(1.2);9.084(1.2);8.738(2.1);8.734(2.0);8.488(3.8);8.370(2.1);8.366(1.9);7.389(0.8);7.377(1.1);7.368(1.0);7.282(0.9);7.377(1.1);7.368(1.0);7.282(0.9);7.389(0.8);7.377(1.1);7.368(1.0);7.260(0.8);7.249(2.6);7.242(1.8); 7.227(1.4);5.547(0.5);5.528(1.0);5.508(1.0);5.488(0.4);3.979(0.7);3.961(0.9);3.943(0.7);3.313(9.2);3.000(0.3);2.982(0.6);2.974(0.6);2.960(0.7);2.952(0.6);2.906(0.4);2.886(0.9);2.865(0.7);2.846(0.5);2.537(0.7); 2.501(36.6);2.434(9.4);1.946(0.6);1.926(0.6);1.915(0.6);1.895(0.5);1.590(4.6);1.572(8.8);1.555(4.6);1.398(16.0);0.952(1.0);0.936(1.1);0.000(9.8)

Example 210: $^1$H-NMR(400.0 MHz, d$_6$-DMSO): δ = 9.370(2.9);8.352(2.9);8.312(0.5);7.572(0.9);7.555(0.9);7.551(0.9);7.534(1.7);7.517(0.9);7.514(1.1);7.497(0.5);7.443(2.2);7.424(2.4);7.268(2.5);7.259(2.1); 7.247(4.6);7.241(3.4);7.227(2.4);6.961(1.6);6.943(2.9);6.924(1.3);6.879(2.9);6.859(2.6);5.766(0.6);5.746(1.1);5.733(1.1);5.713(0.6);4.821(1.4);4.797(2.4);4.775(1.6);4.412(1.7);4.400(1.7);4.387(1.6);4.375(1.5);3.974(0.4); 3.957(1.1);3.939(1.6);3.921(1.2);3.904(0.5);3.312(30.0);2.675(0.5);2.670(0.7);2.666(0.5);2.505(81.3);2.501(108.2);2.497(84.6);2.376(14.1);2.332(0.6);2.328(0.8);1.988(0.4);1.565(8.3);1.547(16.0);1.530(8.2);1.398(3.8); 0.000(37.2)

Example 211: $^1$H-NMR(400.0 MHz, d$_6$-DMSO): δ = 9.183(2.0);9.163(2.0);8.812(7.5);7.902(0.7);7.896(0.6);7.892(0.7);7.885(0.4);7.800(7.9);7.795(8.4);7.680(2.3);7.671(2.0);7.676(3.9);7.612(1.2); 7.400(1.6);7.391(1.5);7.304(0.7);7.294(1.3);7.282(2.2);7.273(1.3);7.261(4.2);7.255(2.6);7.249(2.3);7.239(2.3);5.565(0.6);5.546(1.6);5.526(1.6);5.506(0.5);3.911(1.1);3.928(1.5);3.946(1.1);3.893(0.4);3.672(1.4);

-continued 3.654(4.4);3.636(4.4);3.617(1.4);3.315(30.3);3.031(0.4);3.023(0.4);3.010(0.5);3.000(0.5);2.992(0.8);2.983(0.9);2.970(0.9);2.962(0.3);2.922(0.6);2.901(1.4);2.881(1.0);2.861(0.7);2.841(0.4);2.675(0.4);2.670(0.5); 2.666(0.4);2.593(0.4);2.584(0.7);2.574(0.7);2.564(0.9);2.553(0.9);2.543(1.1);2.533(1.0);2.506(52.0);2.501(68.1);2.497(52.7);2.333(0.3);2.328(0.4);2.324(0.3);1.977(0.4);1.955(0.9);1.945(0.5);1.935(1.0);1.924(0.9);1.914(0.4); 1.904(0.8);1.584(7.6);1.566(4.5);1.548(7.4);1.398(16.0);1.324(4.8);1.306(10.1);1.288(4.6);0.000 (18.0)
Example 212: $^1$H-NMR(400.0 MHz, d$_6$-DMSO): δ = 9.306(1.2);9.286(1.3);8.807(4.4);7.902(0.4);7.897(0.4);7.798(0.3);7.794(5.3);7.678(1.4);7.674(2.3);7.669(1.3);7.362(1.2);7.343(1.3);7.207(0.6);7.189(1.2);7.171(0.7); 7.169(0.8);6.954(0.9);6.935(1.5);6.917(0.7);6.821(1.7);6.800(1.5);5.266(0.4);5.252(0.8);5.234(0.8);5.220(0.3);4.316(0.3);4.308(0.3);4.297(0.7);4.287(0.6);4.279(0.7);4.272(0.5);4.246(0.5);4.239(0.6);4.218(0.8);4.196(0.3); 3.935(0.7);3.918(1.0);3.900(0.7);3.672(0.8);3.654(2.7);3.635(2.7);3.617(0.9);3.315(34.8);2.670(0.4);2.501(69.7);2.497(56.8);2.328(0.5);2.244(0.4);2.229(0.5);2.221(0.5);2.209(0.5);2.195(0.4);2.095(0.4);2.086(0.5); 2.080(0.6);2.064(0.4);2.052(0.4);2.046(0.4);1.580(4.7);1.562(5.4);1.556(5.6);1.394(7.1);1.398(16.0);1.322(2.9);1.304(6.2);1.286(2.9);0.000(16.7)
Example 213: $^1$H-NMR(400.0 MHz, d$_6$-DMSO): δ = 9.209(2.5);9.189(2.6);8.482(9.7);8.313(0.5);7.623(0.9);7.602(1.8);7.587(1.9);7.582(1.9);7.566(1.2);7.471(1.5);7.475(1.5);7.453(2.6);7.431(1.2);7.427(1.1); 7.339(2.4);7.320(2.6);7.195(1.2);7.177(2.5);7.160(1.5);7.157(1.4);6.945(1.8);6.926(3.0);6.907(1.4);6.811(3.3);6.791(3.0);5.253(0.7);5.239(1.6);5.220(1.6);5.205(0.7);4.310(0.5);4.302(0.6);4.294(0.6);4.283(1.4);4.274(1.3); 4.267(1.5);4.258(1.2);4.248(1.2);4.241(1.4);4.227(1.1);4.220(1.7);4.199(0.6);4.192(0.5);3.979(0.5);3.961(1.4);3.944(2.0);3.926(1.5);3.314(84.3);2.675(0.8);2.670(1.1);2.666(0.8);2.505(128.9);2.501(164.8); 2.497(126.1);2.445(16.0);2.328(1.1);2.245(0.4);2.232(0.5);2.224(0.8);2.210(1.0);2.189(1.1);2.176(0.8);2.168(0.5);2.073(1.1);2.065(1.0);2.058(1.1);2.049(0.9);2.031(0.8);2.023(0.7);1.582(10.2);1.564(11.2); 1.557(11.5);1.540(10.1);1.234(0.4);0.000(21.2)
Example 214: $^1$H-NMR(400.0 MHz, d$_6$-DMSO): δ = 9.175(1.2);9.155(1.2);8.798(4.3);7.901(0.5);7.896(0.5);7.892(0.3);7.885(0.3);7.731(5.0);7.680(1.5);7.676(2.2);7.671(1.1);7.543(0.4);7.407(0.8);7.396(1.0); 7.386(0.9);7.303(0.4);7.293(0.8);7.281(1.4);7.272(0.8);7.260(2.5);7.254(1.6);7.248(1.4);7.238(1.4);7.564(0.3);5.544(1.4);5.505(0.3);5.524(1.0);5.505(0.3);3.937(0.8);3.920(0.9);3.903(0.7);3.771(0.8);3.754(1.1);3.737(0.8);3.314(35.4); 2.999(0.3);2.990(0.5);2.982(0.6);2.968(0.5);2.960(0.5);2.670(0.8);2.860(0.4);2.670(0.6);2.571(0.5);2.561(0.6);2.551(0.6);2.540(0.9);2.505(66.0);2.501(86.4);2.497(68.4);2.328(0.6);1.952(0.6);1. 933(0.6);1.921(0.6);1.580(4.5);1.562(8.6);1.545(4.5);1.398(16.0);1.297(10.3);1.280(10.2);0.000(21.7)
Example 215: $^1$H-NMR(400.0 MHz, d$_6$-DMSO): δ = 9.212(2.7);9.192(2.7);8.498(9.8);7.630(1.5);7.614(3.6);7.595(3.8);7.575(1.3);7.449(2.0);7.429(3.1);7.409(1.4);7.344(2.6);7.325(2.8);7.199(1.3);7.196(1.3);7.178(2.7); 7.160(1.6);6.945(1.9);6.927(3.2);6.909(1.5);6.812(3.5);6.792(3.2);5.255(0.7);5.241(1.7);5.222(1.7);5.208(0.8);4.311(0.5);4.303(0.7);4.295(0.6);4.284(1.5);4.275(1.4);4.268(1.6);4.259(1.3);4.250(1.3);4.243(1.5);4.229(1.4); 4.222(1.8);4.202(0.7);4.195(0.5);3.990(0.6);3.973(1.5);3.955(2.0);3.938(1.5);3.920(0.6);3.797(0.4);3.342(27.5);2.670(0.6);2.506(75.6);2.501(95.6);2.497(74.0);2.454(16.0);2.422(0.3);2.328(0.6);2.246(0.4); 2.235(0.5);2.225(0.8);2.212(1.1);2.203(1.1);2.190(1.1);2.178(0.8);2.170(0.5);2.073(1.4);2.062(1.2);2.045(0.9);2.034(0.8);2.027(0.8);2.013(0.4);1.586(10.6);1.568(11.8);1.562(12.1);1.544(10.4);0.000(11.2)
Example 216: $^1$H-NMR(400.0 MHz, d$_6$-DMSO): δ = 9.203(1.9);9.183(1.9);8.479(6.7);7.435(1.8);7.414(2.5);7.341(1.9);7.322(2.3);7.315(2.1);7.295(2.3);7.275(1.3);7.196(0.9);7.177(2.0);7.159(1.2);6.945(1.3);6.926(2.3); 6.908(1.1);6.811(2.5);6.790(2.1);5.255(0.6);5.239(1.2);5.221(1.3);5.206(0.6);4.308(0.4);4.301(0.5);4.294(0.5);4.282(1.1);4.273(1.0);4.266(1.2);4.257(1.0);4.251(1.0);4.243(1.1);4.228(1.0);4.222(1.3);4.201(0.5);3.984(0.4); 3.967(1.1);3.949(1.5);3.925(16.0);3.315(45.5);2.670(0.5);2.501(84.3);2.447(11.8);2.328(0.6);2.223(0.8);2.209(0.8);2.188(0.8);2.177(0.6);2.073(4.3);2.060(1.0);2.048(0.7);2.032(0.6);2.024(0.6);1.581(7.3);1. 563(8.3);1.557(8.6);1.539(7.2);1.236(0.5);0.000(9.5)
Example 217: $^1$H-NMR(400.0 MHz, d$_6$-DMSO): δ = 9.298(1.3);9.278(1.3);8.793(4.9);7.897(0.4);7.735(4.6);7.678(1.5);7.673(2.4);7.545(0.4);7.359(1.2);7.340(1.3);7.206(0.6);7.188(1.3);7.170(0.8); 7.168(0.7);6.952(0.9);6.934(1.5);6.916(0.7);6.821(1.7);6.800(1.5);5.267(0.3);5.253(0.8);5.234(0.8);5.220(0.4);4.315(0.3);4.296(0.7);4.287(0.6);4.279(0.7);4.272(0.5);4.243(0.5);4.237(0.6);4.222(0.6);4.216(0.8);4.194(0.3); 3.928(0.7);3.911(1.0);3.893(0.7);3.789(0.3);3.755(1.2);3.738(0.9);3.721(0.3);3.314(38.2);2.670(0.5);2.505(62.3);2.501(82.5);2.497(65.0);2.328(0.4);2.243(0.4);2.230(0.3);2.221(0.5);2.208(0.5);2.196(0.4); 2.094(0.3);2.085(0.5);2.079(0.6);2.063(0.4);2.051(0.4);1.578(4.8);1.554(5.6);1.536(4.8);1.398(16.0);1.296(11.4);1.279(11.3);0.000(20.4)
Example 218: $^1$H-NMR(400.0 MHz, d$_6$-DMSO): δ = 9.196(1.9);9.176(2.0);8.416(6.9);7.615(1.7);7.609(1.8);7.593(1.8);7.586(1.7);7.575(1.4);7.506(2.0);7.490(1.8);7.554(1.1);7.347(1.1);7.333(3.6);7.326(2.3); 7.312(2.5);7.305(1.1);7.191(0.9);7.173(2.0);7.155(1.2);6.939(1.4);6.921(2.4);6.902(1.1);6.807(2.6);6.787(2.3);5.250(0.6);5.236(1.3);5.217(1.3);5.202(0.6);4.306(0.3);4.297(0.5);4.290(0.5);4.278(1.1);4.270(1.0);4.262(1.2); 4.253(1.0);4.246(1.0);4.238(1.1);4.224(1.1);4.217(1.3);4.197(0.6);4.190(0.4);3.979(0.4);3.962(1.1);3.944(1.4);3.927(1.0);3.909(0.4);3.350(7.6);2.501(38.6);2.497(31.0);2.364(16.0);2.328(0.3);2.228(0.4);2.218(0.6); 2.205(0.8);2.184(0.8);2.172(0.6);2.163(0.4);2.073(3.9);2.060(0.8);2.055(0.9);2.040(0.7);2.027(0.6);2.019(0.6);1.586(7.5);1.568(8.2);1.560(8.3);1.543(7.4);0.000(5.1)
Example 219: $^1$H-NMR(400.0 MHz, d$_6$-DMSO): δ = 9.319(1.8);9.299(1.8);8.816(6.6);7.833(6.3);7.829(6.6);7.677(1.9);7.672(3.2);7.366(1.7);7.347(1.9);7.209(0.8);7.191(1.7);7.171(1.1);6.957(1.3);6.938(2.2);6.920(1.0); 6.823(2.4);6.803(2.1);5.753(1.7);5.269(0.5);5.255(1.1);5.237(1.1);5.222(0.5);4.325(0.4);4.317(0.5);4.310(0.5);4.299(0.9);4.290(0.8);4.282(0.9);4.274(0.7);4.249(0.7);4.243(0.9);4.227(0.8);4.221(1.1);4.200(0.5);4.194(0.4); 3.964(0.4);3.947(1.5);3.930(1.3);3.912(1.0);3.894(0.4);3.555(16.0);3.317(14.4);2.891(0.4);2.732(0.3);2.501(30.0);2.254(0.4);2.245(0.5);2.232(0.7);2.223(0.7);2.210(0.7);2.198(0.5);2.089(0.7);2.083(0.8); 2.068(0.6);2.055(0.5);2.048(0.5);1.589(6.5);1.571(7.7);1.566(7.8);1.548(6.4);0.000(9.5)
Example 220: $^1$H-NMR(400.0 MHz, d$_6$-DMSO): δ = 9.235(1.9);9.215(1.9);8.572(6.6);8.408(3.4);8.371(1.8);8.348(1.0);8.313(0.8);7.350(1.9);7.331(2.1);7.201(1.0);7.182(2.0);7.163(1.2);6.951(1.4);6.933(2.4);6.914(1.2); 6.816(2.6);6.796(2.3);5.261(0.6);5.246(1.3);5.228(1.3);5.213(0.6);4.316(0.4);4.308(0.5);4.299(0.5);4.288(1.2);4.279(1.1);4.272(1.3);4.263(1.1);4.255(1.1);4.248(1.2);4.227(1.3);4.207(0.5);3.984(0.4);3.967(1.1);3.949(1.5); 3.932(1.1);3.915(0.5);3.314(97.1);2.670(2.6);2.648(16.0);2.621(0.4);2.601(0.7);2.501(351.4);2.328(2.3);2.249(0.4);2.231(0.6);2.216(0.9);2.208(0.9);2.195(0.9);2.182(0.7);2.073(2.0);2.056(0.8);2.053(0.8);2.040(0.7); 2.033(0.6);1.576(7.7);1.558(9.1);1.553(9.2);1.535(7.6);1.234(0.3);0.000(7.8)
Example 221: $^1$H-NMR(400.0 MHz, d$_6$-DMSO): δ = 9.100(0.7);9.081(0.9);9.066(0.6);8.442(4.3);7.539(0.9);7.525(1.0);7.519(1.2);7.507(3.2);7.492(0.6);7.388(1.1);7.371(2.1);7.354(0.7);7.348(0.5);7.277(0.9);7.266(1.4); 7.248(1.8);7.241(2.3);7.226(1.4);7.220(0.9);5.515(0.7);5.500(0.7);3.696(0.4);3.677(0.5);3.661(0.4);3.316(371.);2.992(0.3);2.974(0.6);2.961(0.6);2.951(0.6);2.945(0.5);2.899(0.4);2.879(0.9);2.859(0.7);2.839(0.5);2.670(0.4); 2.545(0.4);2.536(0.7);2.501(53.6);2.497(43.2);2.336(9.6);2.269(0.5);2.252(0.6);2.234(0.5);1.971(0.4);1.951(0.8);1.938(0.7);1.929(0.9);1.919(0.9);1.907(0.7);1.898(0.7);1.877(0.4);1.583(1.9);1.561(2.9); 1.543(2.4);1.398(16.0);0.951(2.1);0.935(2.2);0.847(1.3);0.828(2.7);0.816(1.3);0.810(1.6);0.798(2.0);0.780(0.9);0.000(49.8)
Example 222: $^1$H-NMR(400.0 MHz, d$_6$-DMSO): δ = 9.108(1.3);9.088(1.4);8.416(5.9);7.642(4.0);7.621(5.1);7.518(2.1);7.499(1.8);7.497(1.2);7.381(0.8);7.369(1.1);7.360(1.1);7.287(0.9);7.163(1.2);7.381(0.5);7.277(0.9);7.265(1.5); 7.255(0.9);7.243(3.0);7.237(1.7);7.231(1.6);7.221(1.7);5.335(0.4);5.516(1.1);5.496(1.1);5.477(0.4);3.970(0.4);3.952(1.1);3.935(0.8);3.315(21.3);3.007(0.3);2.993(0.3);2.984(0.4);2.976(0.6);2.967(0.6);2.954(0.6);2.945(0.5); 2.898(0.4);2.878(1.0);2.858(0.7);2.838(0.5);2.558(0.3);2.549(0.4);2.538(0.6);2.510(19.2);2.506(36.5);2.501(48.3);2.497(37.2);2.492(19.0);2.328(0.4);2.307(12.6);1.937(0.7);1.927(0.3);1.917(0.7);1.906(0.7); 1.896(0.3);1.886(0.6);1.577(10.3);1.559(5.6);1.398(16.0);0.008(2.8);0.000(54.8);-0.008(2.5)
Example 223: $^1$H-NMR(400.0 MHz, d$_6$-DMSO): δ

-continued

Example 224: ¹H-NMR(400.0 MHz, d₆-DMSO): δ = 9.084(0.3);9.064(0.3);8.522(1.4);7.523(0.3);7.514(0.6);7.509(0.9);7.395(0.4);7.392(0.4);7.373(0.5);7.271(0.4);7.246(0.5);7.242(0.6);7.234(0.5);7.225(0.4);3.352(0.3);3.336(0.4);3.318(2.3);2.511(1.5);2.506(2.8);2.502(3.7);2.497(2.9);2.339(2.6);1.398(16.0);0.956(1.5);0.939(1.9);0.929(1.0);0.927(1.0);0.000(5.1)

Example 225: ¹H-NMR(400.0 MHz, d₆-DMSO): δ = 9.204(0.7);9.185(0.7);8.509(3.1);7.541(0.7);7.527(0.7);7.521(0.8);7.513(1.3);7.509(2.1);7.493(0.4);7.396(0.5);7.373(0.8);7.367(0.4);7.356(0.4);7.350(0.4);7.333(0.7);7.314(0.8);7.199(0.4);7.196(0.4);7.178(0.8);7.161(0.5);7.157(0.4);6.934(0.6);6.916(0.9);6.897(0.4);6.813(1.0);6.794(0.9);5.251(0.5);5.232(0.5);4.278(0.4);4.269(0.4);4.263(0.5);4.251(0.5);4.243(0.5);4.229(0.4);4.223(0.5);3.346(1.0);3.316(34.5);2.510(17.4);2.506(33.6);2.501(44.9);2.497(34.4);2.493(17.8);2.405(0.4);2.388(0.5);2.371(0.4);2.336(6.8);2.174(0.4);2.046(0.3);1.398(16.0);0.963(1.9);0.954(3.5);0.947(2.6);0.938(4.0);0.925(1.8);0.008(2.4);0.000(48.6);-0.008(2.3)

Example 226: ¹H-NMR(400.0 MHz, d₆-DMSO): δ = 9.227(0.8);9.221(0.9);9.201(0.8);8.436(3.4);7.537(0.9);7.517(1.3);7.506(3.1);7.490(0.5);7.390(0.8);7.369(1.1);7.345(1.1);7.332(0.9);7.325(0.9);7.316(0.8);7.192(0.6);7.173(1.2);7.153(0.7);6.943(0.5);6.925(1.0);6.913(0.9);6.895(0.4);6.806(1.7);6.786(1.5);5.244(0.6);5.228(0.8);5.212(0.6);4.293(0.3);4.274(0.8);4.266(0.8);4.258(0.8);4.251(0.7);4.230(0.8);4.216(0.6);4.209(0.5);3.679(0.5);3.662(0.5);3.316(41.0);2.670(0.5);2.501(69.1);2.334(9.7);2.291(0.4);2.256(0.5);2.230(0.6);2.219(0.6);2.207(0.6);2.195(0.6);2.184(0.6);2.173(0.5);2.052(0.6);2.045(0.6);2.018(0.4);1.969(0.3);1.950(0.6);1.932(0.6);1.916(0.5);1.584(2.1);1.567(2.2);1.555(2.5);1.538(2.3);1.398(16.0);0.953(1.0);0.938(1.0);0.846(1.3);0.828(2.7);0.802(2.3);0.783(1.0);0.000(33.4)

Example 227: ¹H-NMR(400.0 MHz, d₆-DMSO): δ = 9.159(0.8);9.139(0.8);8.608(2.7);7.543(0.6);7.528(0.8);7.521(1.3);7.508(2.6);7.499(1.3);7.492(0.9);7.485(1.1);7.393(0.5);7.390(0.5);7.371(0.8);7.366(0.5);7.353(0.4);7.348(0.3);7.283(0.9);7.265(1.8);7.255(0.7);7.251(0.7);7.231(1.0);7.214(0.5);7.196(0.7);7.178(0.8);7.160(0.4);7.155(1.1);7.130(2.0);7.108(1.0);5.540(0.6);5.520(0.6);4.813(2.5);3.317(11.4);2.981(0.4);2.971(0.4);2.959(0.4);2.950(0.3);2.878(0.6);2.858(0.4);2.506(22.0);2.501(29.0);2.497(22.7);2.334(6.2);1.947(0.4);1.926(0.4);1.915(0.3);1.398(16.0);0.008(1.2);0.000(19.6)

Example 228: ¹H-NMR(400.0 MHz, d₆-DMSO): δ = 9.263(0.5);9.243(0.5);8.592(2.0);7.543(0.6);7.527(0.5);7.519(0.9);7.506(1.7);7.497(0.9);7.490(0.5);7.483(0.8);7.390(0.3);7.370(0.5);7.365(0.3);7.209(0.3);7.165(0.7);7.160(1.0);7.143(0.6);7.137(1.4);7.115(0.7);6.881(0.4);6.862(0.7);6.801(0.7);6.780(0.7);5.259(0.3);5.240(0.3);4.819(1.7);4.240(0.4);4.231(0.4);4.203(0.3);3.318(5.5);2.506(8.8);2.501(12.1);2.497(9.6);2.335(4.1);1.398(16.0);0.952(1.3);0.936(1.3);0.008(0.4);0.000(9.4);-0.008(0.5)

Example 229: ¹H-NMR(400.0 MHz, d₆-DMSO): δ = 9.195(1.6);9.174(1.6);8.821(6.5);7.835(6.7);7.830(7.4);7.679(2.0);7.675(3.5);7.670(1.9);7.416(1.0);7.404(1.3);7.394(1.2);7.305(0.5);7.294(1.0);7.282(1.8);7.274(1.1);7.262(3.5);7.256(2.2);7.249(1.9);7.241(2.0);5.753(3.3);5.567(0.4);5.548(1.3);5.528(1.3);5.509(0.4);3.975(0.3);3.957(0.9);3.939(1.3);3.922(0.9);3.904(0.3);3.556(16.0);3.318(13.6);3.025(0.4);3.012(0.4);3.002(0.4);2.994(0.7);2.985(0.7);2.972(0.7);2.963(0.7);2.923(0.5);2.902(1.1);2.891(0.6);2.882(0.8);2.863(0.6);2.731(0.4);2.586(0.3);2.576(0.6);2.565(0.7);2.555(0.7);2.544(0.8);2.535(0.7);2.524(0.9);2.506(19.1);2.501(25.8);2.497(20.6);1.958(0.8);1.947(0.4);1.938(0.8);1.926(0.8);1.917(0.4);1.906(0.7);1.574(11.7);1.557(6.1);1.008(0.4);0.000(9.3)

Example 230: ¹H-NMR(601.0 MHz, d₆-DMSO): δ = 9.209(1.4);9.196(1.4);8.567(7.8);8.046(2.6);8.045(2.4);8.043(2.8);8.042(2.6);7.757(0.6);7.754(0.5);7.743(3.3);7.740(3.7);7.7371(4.6);7.7365(4.5);7.723(0.8);7.722(0.6);7.347(1.1);7.335(1.2);7.334(1.2);7.196(0.6);7.194(0.6);7.183(1.1);7.182(1.2);7.170(0.8);7.168(0.7);6.947(0.9);6.945(1.5);6.934(1.5);6.932(1.5);6.922(0.9);6.920(0.9);6.813(1.7);6.811(1.7);6.799(1.6);6.798(1.6);7.252(0.4);5.242(0.7);5.229(0.8);5.219(0.4);4.299(0.3);4.286(0.7);4.281(0.6);4.275(0.7);4.269(0.5);4.244(0.7);4.235(0.6);4.230(1.0);4.226(0.4);4.216(0.4);4.212(0.3);3.965(0.7);3.953(1.0);3.942(0.7);3.319(46.5);2.633(16.0);2.616(0.3);2.613(0.4);2.522(0.5);2.519(0.9);2.516(0.9);2.507(20.2);2.504(45.1);2.501(63.8);2.498(46.4);2.495(21.6);2.385(0.4);2.221(0.4);2.120(0.5);2.206(0.5);2.203(0.4);2.198(0.5);2.189(0.3);2.064(0.4);2.059(0.5);2.052(0.4);2.048(0.4);2.041(0.4);2.036(0.4);1.568(6.2);1.557(6.2);1.545(6.3);1.533(6.2);0.000(0.9)

Example 231: ¹H-NMR(400.0 MHz, d₆-DMSO): δ = 9.223(1.8);9.203(1.8);8.778(3.0);8.7843(2.8);8.7843(2.8);8.313(1.4);8.238(1.9);8.231(1.7);8.217(2.0);8.211(1.9);7.920(0.4);7.913(0.3);7.793(0.4);7.781(0.3);7.64(3.1);7.625(3.0);7.477(0.4);7.463(0.7);7.382(0.4);7.349(1.9);7.330(2.0);7.282(0.5);7.245(0.4);7.239(0.3);7.201(0.9);7.181(2.0);7.163(1.2);6.950(1.3);6.932(2.3);6.913(1.1);6.814(2.5);6.794(2.2);5.260(0.5);5.245(1.2);5.226(1.2);5.210(0.5);4.313(0.4);4.306(0.5);4.287(1.1);4.279(1.0);4.270(1.1);4.255(1.0);4.248(1.0);4.227(1.1);4.205(0.5);3.987(0.4);3.969(1.0);3.952(1.4);3.934(1.1);3.917(0.4);3.315(211.6);2.670(3.1);2.634(16.0);2.505(377.2);2.501(464.0);2.497(348.9);2.377(0.6);2.328(2.9);2.228(0.6);2.215(0.7);2.206(0.8);2.193(0.8);2.081(0.6);2.066(0.9);2.049(0.7);2.038(0.6);2.031(0.6);1.576(7.3);1.558(8.5);1.552(8.3);1.534(7.3);1.510(0.7);1.493(0.7);1.398(6.6);0.146(0.8);0.000(163.0);-0.150(0.8)

Example 232: ¹H-NMR(400.0 MHz, d₆-DMSO): δ = 9.210(1.3);9.191(1.3);8.454(5.5);8.313(0.8);7.338(1.4);7.318(1.5);7.297(0.5);7.284(0.5);7.273(1.0);7.260(1.1);7.250(0.7);7.237(0.7);7.196(1.5);7.174(2.5);7.154(1.2);6.940(1.0);6.923(1.7);6.905(0.8);6.808(1.7);6.787(1.7);5.249(0.5);5.235(0.9);5.215(0.9);5.202(0.4);4.300(0.4);4.281(0.8);4.272(0.7);4.265(0.6);4.256(0.8);4.242(0.6);4.235(0.8);4.221(0.7);4.214(0.9);4.195(0.4);3.957(0.7);3.940(1.0);3.922(0.8);3.904(0.5);3.880(10.4);3.315(85.3);2.675(1.2);2.670(1.5);2.506(182.6);2.501(237.3);2.497(178.5);2.373(10.1);2.332(1.5);2.324(1.2);2.221(0.4);2.208(0.6);2.200(0.6);2.187(0.6);2.179(0.4);2.078(0.3);2.070(0.4);2.062(0.6);2.055(0.6);2.044(0.5);2.021(0.4);1.585(5.7);1.568(6.1);1.543(5.5);1.398(16.0);0.008(2.6);0.000(53.2)

Example 233: ¹H-NMR(400.0 MHz, d₆-DMSO): δ = 9.209(0.4);9.190(0.4);8.417(1.8);7.334(0.9);7.313(0.9);7.281(0.5);7.269(0.6);7.172(0.5);6.938(0.3);6.919(0.6);6.804(0.7);6.784(0.6);3.940(0.4);3.901(0.3);3.315(30.1);2.670(0.4);2.666(0.3);2.505(48.7);2.501(64.4);2.497(51.4);2.3244(4.3);1.588(1.8);1.571(1.9);1.5621(9.1);1.545(1.7);1.398(16.0);0.000(11.8)

Example 234: ¹H-NMR(601.6 MHz, d₆-DMSO): δ = 9.2111(2.4);9.1912(2.4);8.481(7.3);7.954(0.8);7.466(1.0);7.440(1.9);7.415(1.0);7.342(2.5);7.323(2.7);7.197(1.2);7.177(2.5);7.158(1.5);6.943(1.8);6.925(3.1);6.906(1.5);6.805(2.1);6.791(1.9);5.751(4.3);5.241(0.5);5.232(1.0);5.219(1.0);5.210(0.5);4.297(0.4);4.286(0.4);4.279(0.9);4.273(0.8);4.267(0.9);4.262(0.7);4.237(0.7);4.233(0.8);4.223(0.8);4.219(1.2);4.205(0.5);4.200(0.4);3.954(0.7);3.943(0.9);3.931(0.7);3.310(16.6);2.891(1.1);2.732(0.9);2.519(0.6);2.516(0.6);2.504(28.6);2.501(39.9);2.498(29.9);2.394(16.0);2.222(0.3);2.213(0.5);2.205(0.7);2.199(0.7);2.190(0.7);2.182(0.4);2.054(0.6);2.043(0.5);2.035(0.5);1.580(6.9);1.568(7.0);1.555(6.9);1.543(6.8);0.000(2.7)

Example 235: ¹H-NMR(400.0 MHz, d₆-DMSO): δ = 9.2112(2.7);9.1912(2.8);8.466(5.8);7.917(2.8);7.913(2.9);7.584(2.6);7.333(1.2);7.320(1.3);7.186(0.8);7.175(1.6);7.163(0.9);6.934(1.2);6.922(2.0);6.909(1.0);6.811(3.2);6.790(3.0);5.753(9.2);5.251(0.7);5.236(1.6);5.219(1.6);5.204(0.7);4.302(0.6);4.295(0.6);4.284(1.4);4.274(1.4);4.267(1.4);4.260(1.1);4.238(1.3);4.217(1.6);4.195(0.6);3.979(0.5);3.962(1.3);3.935(15.2);3.909(0.6);3.317(15.0);2.924(4.3);2.733(4.1);2.672(0.4);2.502(59.4);2.457(0.5);2.385(16.0);2.329(0.4);2.224(0.8);2.211(1.0);2.202(1.0);2.190(1.0);2.179(0.8);2.058(1.1);2.046(0.9);2.030(0.8);2.024(0.7);1.584(8.5);1.566(9.8);1.560(9.7);1.542(8.4);1.512(0.3);0.000(2.4)

Example 236: ¹H-NMR(601.6 MHz, d₆-DMSO): δ = 9.200(2.2);9.1872(2.5);8.466(8.9);7.369(1.7);7.354(3.4);7.337(2.8);7.322(2.2);7.187(2.1);7.175(2.1);7.163(1.2);6.936(1.4);6.924(2.6);6.912(1.3);6.806(2.8);6.792(2.6);5.242(0.6);5.232(1.3);5.220(1.3);5.210(0.6);4.298(0.5);4.293(0.6);4.288(0.6);4.280(1.2);4.275(1.0);4.269(1.1);4.264(0.9);4.235(0.8);4.231(1.0);4.216(1.5);4.202(0.6);4.198(0.5);3.964(0.4);3.953(1.1);3.941(1.5);3.929(1.2);3.918(0.5);3.310(26.9);2.613(0.4);2.519(0.6);2.516(0.6);2.504(48.7);2.501(66.5);2.498(49.5);2.377(16.0);2.216(0.7);2.207(0.9);2.201(0.8);2.193(0.8);2.073(2.3);2.063(0.6);2.053(0.9);2.042(0.7);2.034(0.7);2.030(0.7);1.581(8.8);1.569(8.8);1.556(8.9);1.544(8.8);0.000(1.7)

Example 237: ¹H-NMR(400.0 MHz, d₆-DMSO): δ = 9.187(1.7);9.167(1.8);8.4428(2.7);7.561(0.5);7.547(1.5);7.541(1.5);7.526(1.6);7.521(1.9);7.509(4.5);7.493(0.7);7.394(1.1);7.374(1.5);7.365(0.6);7.351(0.6);7.348(0.5);7.113(2.6);6.989(1.4);6.984(1.3);6.968(1.6);6.964(1.5);6.697(3.4);6.676(3.0);5.215(0.5);5.201(1.1);5.182(1.1);5.167(0.5);4.250(0.4);4.242(0.4);4.231(1.0);4.222(0.9);4.214(1.1);4.204(1.2);4.195(1.0);4.182(0.9);4.174(1.1);4.154(0.4);3.985(0.4);3.968(1.0);3.950(1.4);3.932(1.0);3.915(0.4);3.318(81.9);2.675(0.6);2.670(0.8);2.666(0.6);5.223(3.1);2.510(47.2);2.506(90.7);2.501(118.6);2.497(88.3);2.492(43.8);2.460(0.3);2.456(0.4);2.346(16.0);2.333(0.9);2.328(0.9);2.323(0.7);2.224(13.9);2.202(0.6);2.188(0.7);2.180(0.7);2.167(0.7);2.155(0.5);2.046(0.3);2.038(0.5);2.030(0.6);2.023(0.8);2.012(0.6);2.005(0.6);1.988(1.5);1.600(5.7);1.582(6.0);1.573(6.6);1.555(5.6);1.398(6.7);1.175(0.6);0.008(1.9);0.000(42.4);-0.008(1.6)

-continued

Example 238: $^1$H-NMR(400.0 MHz, d$_6$-DMSO): δ = 9.158(0.9);9.138(0.9);8.398(4.0);8.391(0.5);7.374(1.6);7.337(0.8);7.319(1.7);7.299(0.9);7.298(0.8);7.194(0.5);7.177(1.0);7.159(0.6);7.156(0.6);6.946(0.7);6.928(1.1);6.909(0.6);6.809(1.3);6.789(1.1);6.609(1.5);6.589(1.4);6.554(0.3);5.242(0.6);5.224(0.6);4.282(0.5);4.273(0.5);4.265(0.7);4.258(0.8);4.251(0.7);4.239(0.5);4.230(0.6);3.956(0.5);3.939(0.7);3.921(0.9);3.318(36.7);3.316(35.1);3.306(1.9);3.285(2.7);3.265(1.5);2.947(1.0);2.735(10.5);2.674(0.3);2.670(0.5);2.666(0.3);2.544(8.8);2.523(1.1);2.510(27.6);2.505(57.0);2.501(76.3);2.496(56.1);2.492(27.7);2.457(1.0);2.332(0.4);2.328(0.5);2.323(0.4);2.206(0.4);2.197(0.4);2.185(0.4);2.063(0.4);2.039(0.3);1.567(3.8);1.549(4.1);1.543(4.2);1.525(3.8);1.514(0.7);1.496(0.5);1.398(16.0);1.270(0.9);1.069(3.2);0.008(1.2);0.000(35.3);−0.009(1.4)

Example 239: $^1$H-NMR(400.0 MHz, d$_6$-DMSO): δ = 9.184(1.5);9.164(1.6);8.452(7.3);8.313(0.5);7.339(1.5);7.321(1.5);7.321(1.6);7.270(3.5);7.266(3.8);7.200(0.8);7.196(0.8);7.179(1.6);7.158(2.6);7.154(1.9);7.158(2.3);7.134(2.3);7.030(3.9);7.010(2.9);6.947(1.2);6.929(2.0);6.913(0.9);6.910(0.9);6.813(2.1);6.811(2.2);6.793(2.0);6.054(13.4);5.258(0.4);5.243(0.9);5.224(1.0);5.209(0.5);4.303(0.4);4.284(0.9);4.275(0.8);4.271(0.4);4.257(1.0);4.249(1.0);4.236(0.8);4.228(1.1);4.208(1.0);4.228(1.3);4.224(1.0);3.958(0.9);3.940(1.3);3.923(1.0);3.904(0.4);3.316(149.7);2.675(1.3);2.666(1.0);2.570(16.0);2.523(4.0);2.506(165.4);2.501(220.0);2.497(160.5);2.492(78.6);2.456(1.0);2.332(0.9);2.328(1.3);2.324(1.0);2.221(0.4);2.209(0.6);2.200(0.6);2.188(0.7);2.176(0.5);2.075(0.4);2.067(0.6);2.059(0.7);2.049(0.5);2.043(0.5);2.025(0.5);1.569(6.8);1.551(7.4);1.544(7.5);1.527(7.0);1.511(0.9);1.506(0.5);1.488(0.5);1.398(16.0);0.146(0.5);0.008(3.8);0.000(107.3);−0.008(4.2);−0.150(0.5)

Example 240: $^1$H-NMR(400.0 MHz, d$_6$-DMSO): δ = 9.221(1.6);9.201(1.6);8.624(7.0);8.126(2.9);8.099(3.0);7.780(2.7);7.357(1.0);7.339(1.7);7.204(0.8);7.201(0.8);7.183(1.6);7.166(1.0);7.162(1.0);6.950(1.2);6.932(1.9);6.915(0.9);6.913(0.9);6.817(2.2);6.796(2.0);5.259(0.4);5.245(1.0);5.226(1.0);5.211(0.4);4.308(0.4);4.300(0.3);4.289(0.9);4.288(0.8);4.272(1.0);4.262(1.0);4.252(1.0);4.239(0.8);4.232(1.1);4.211(0.4);4.012(0.4);3.994(0.9);3.977(1.3);3.959(1.0);3.941(0.4);3.318(51.9);2.699(0.4);2.667(1.5);4.2);2.524(1.6);2.511(35.5);2.506(66.6);2.502(86.8);2.498(63.0);2.493(31.3);2.333(0.4);2.329(0.5);2.325(0.4);2.229(0.4);2.216(0.6);2.207(0.6);2.195(0.7);2.182(0.5);2.082(0.4);2.075(0.5);2.067(0.7);2.057(0.5);2.051(0.5);2.040(0.5);2.032(0.5);1.578(7.0);1.560(7.8);1.555(8.0);1.537(6.8);1.497(0.5);1.398(16.0);1.382(0.4);0.008(1.6);0.000(37.5);−0.008(1.5)

Example 241: $^1$H-NMR(400.0 MHz, d$_6$-DMSO): δ = 9.214(1.4);9.194(1.4);8.540(6.3);7.363(0.9);7.352(3.2);7.333(3.1);7.322(1.0);7.202(0.7);7.199(0.7);7.181(1.4);7.164(0.9);7.161(0.8);6.949(1.0);6.931(1.8);6.914(0.8);6.912(0.8);6.816(1.6);6.796(1.8);5.260(0.4);5.246(0.9);5.227(0.9);5.212(0.4);4.305(0.3);4.286(0.8);4.278(0.7);4.270(0.9);4.251(0.9);4.237(0.7);4.230(0.9);4.219(0.6);4.209(0.3);4.056(0.8);4.039(2.4);4.021(2.4);4.003(0.8);3.993(0.3);3.976(0.8);3.958(1.2);3.941(1.0);3.926(16.0);3.322(17.7);3.319(20.0);2.638(13.6);2.506(24.7);2.502(32.3);2.497(23.5);2.226(0.4);2.213(0.6);2.204(0.6);2.192(0.6);2.179(0.4);2.081(0.4);2.072(0.5);2.066(0.6);2.049(0.5);2.038(0.4);2.030(0.4);1.989(0.3);1.573(6.1);1.555(6.9);1.550(7.0);1.532(6.0);1.397(0.9);1.193(2.7);1.175(5.3);1.158(2.6);0.000(6.0)

Example 242: $^1$H-NMR(400.0 MHz, d$_6$-DMSO): δ = 9.184(1.8);9.163(1.9);8.461(5.4);8.392(0.5);7.346(1.8);7.327(2.2);7.310(3.5);7.220(1.6);7.199(2.8);7.178(2.0);7.159(1.2);7.066(2.8);7.045(2.2);6.949(1.3);6.930(2.2);6.912(1.1);6.813(2.4);6.793(2.2);6.554(0.5);5.754(10.8);5.261(6.0);5.246(1.3);5.227(1.5);5.213(0.6);4.303(0.5);4.284(1.2);4.267(1.5);4.259(1.8);4.240(1.1);4.232(1.3);4.212(0.5);3.997(0.4);3.979(1.0);3.962(1.3);3.944(1.0);3.927(0.4);3.798(15.6);3.319(21.5);2.890(1.1);2.731(1.1);2.593(13.1);2.501(34.3);2.458(1.6);2.222(0.6);2.210(0.8);2.199(0.9);2.177(0.7);2.070(0.8);2.063(0.9);2.053(0.8);2.036(0.7);2.028(0.6)1.988(0.8);1.575(6.6);1.553(8.4);1.535(6.8);1.522(1.4);1.498(0.8);1.396(0.5);1.175(0.4);0.000(4.8)

Example 243: $^1$H-NMR(400.0 MHz, d$_6$-DMSO): δ = 11.114(1.6);9.178(1.6);9.158(1.7);8.432(7.5);7.802(3.3);7.488(1.7);7.467(3.2);7.421(2.4);7.418(2.3);7.400(1.3);7.397(1.4);7.373(1.8);7.367(2.8);7.360(1.9);7.348(1.6);7.329(1.7);7.199(0.8);7.196(0.8);7.178(1.5);7.161(1.0);7.157(1.0);6.953(1.1);6.950(1.2);6.934(2.0);6.932(1.6);6.916(1.9);6.814(2.3);6.812(2.2);6.794(2.3);6.472(1.6);6.467(2.3);6.462(1.6);5.268(0.5);5.253(1.0);5.234(1.6);5.219(0.5);4.306(0.3);4.287(1.0);4.278(0.9);4.270(1.2);4.263(1.3);4.258(1.3);4.245(0.9);4.237(1.1);4.217(0.4);4.005(0.3);3.988(0.9);3.970(1.3);3.952(1.0);3.935(0.4);3.321(33.9);2.599(16.0);2.523(0.7);2.510(16.3);2.505(33.3);2.501(44.1);2.496(32.0);2.492(15.6);2.458(0.5);2.235(0.3);2.227(0.4);2.215(0.6);2.193(0.7);2.181(0.5);2.081(0.4);2.073(0.6);2.065(0.7);2.055(0.5);2.049(0.6);2.039(0.5);2.031(0.5);1.593(7.0);1.575(7.5);1.568(7.6);1.551(6.9);1.397(3.9);0.000(8.5)

Example 244: $^1$H-NMR(400.0 MHz, d$_6$-DMSO): δ = 9.199(2.2);9.179(2.1);8.504(1.3);8.495(5.5);7.486(2.4);7.465(1.9);7.346(2.4);7.328(3.2);7.307(2.1);7.278(2.4);7.263(1.9);7.256(1.9);7.251(1.9);7.197(1.3);7.180(2.2);7.159(1.2);6.949(1.6);6.930(2.4);6.914(1.1);6.814(2.7);6.793(2.2);5.244(1.6);5.228(1.5);4.284(1.6);4.269(1.8);4.260(2.0);4.232(1.5);4.210(0.5);4.056(1.0);4.058(2.4);4.020(2.3);4.002(1.0);3.977(1.2);3.960(1.5);3.942(1.1);3.925(0.5);3.876(1.6);3.321(95.0);2.670(0.6);2.608(14.4);2.505(73.7);2.501(84.6);2.328(0.5);2.211(1.0);2.190(1.0);2.064(1.2);2.038(0.8);1.998(2.0);1.988(8.9);1.576(8.3);1.554(11.2);1.535(7.0);1.398(1.2);1.193(2.7);1.175(4.8);1.157(2.3);0.010(2.0);0.000(8.1)

Example 245: $^1$H-NMR(400.0 MHz, d$_6$-DMSO): δ = 9.190(2.2);9.171(2.2);8.429(9.4);8.313(0.8);7.336(2.1);7.317(2.3);7.197(1.0);7.194(1.0);7.176(2.2);7.158(1.4);6.978(1.3);6.957(3.0);6.942(4.6);6.929(8.0);6.909(3.3);6.809(2.9);6.790(2.7);6.181(16.0);5.252(0.6);5.238(1.3);5.218(1.4);5.203(0.6);4.299(0.5);4.293(0.5);4.280(1.2);4.272(1.1);4.264(1.3);4.255(1.0);4.249(1.1);4.241(1.2);4.228(1.0);4.220(1.4);4.200(0.5);4.191(0.4);3.973(0.5);3.955(1.2);3.938(1.7);3.920(1.5);3.903(0.5);3.316(193.2);2.674(1.7);2.670(2.3);2.666(1.8);2.506(297.3);2.501(393.6);2.497(290.0);2.456(0.7);2.421(14.7);2.332(1.7);2.328(2.3);2.323(1.8);2.232(0.4);2.220(0.6);2.207(0.9);2.197(0.8);2.185(0.9);2.173(0.6);2.165(0.4);2.056(1.0);2.042(0.7);2.028(0.7);2.020(0.7);1.577(9.0);1.559(9.6);1.552(9.9);1.534(8.9);1.398(2.8);1.236(0.7);0.008(1.1);0.000(31.8);−0.008(1.4)

Example 246: $^1$H-NMR(400.0 MHz, d$_6$-DMSO): δ = 9.199(2.2);9.179(2.2);8.479(10.7);8.313(0.5);7.541(4.4);7.521(4.4);7.337(2.1);7.319(2.2);7.197(1.4);7.176(2.1);7.159(1.4);7.155(1.3);6.944(1.5);6.941(1.7);6.925(2.6);6.922(2.7);6.906(1.3);6.904(1.3);6.810(2.9);6.808(3.0);6.790(2.7);6.787(2.6);5.248(0.6);5.234(1.3);5.215(1.3);5.200(0.6);4.308(0.4);4.300(0.5);4.294(0.9);4.293(0.5);4.281(1.2);4.272(1.0);4.265(1.2);4.256(0.9);4.242(0.9);4.234(1.2);4.220(1.0);4.213(1.5);4.192(0.6);4.185(0.5);3.974(0.5);3.957(1.2);3.939(1.8);3.921(1.3);3.904(0.5);3.328(126.2);3.321(132.3);2.675(0.8);2.671(1.1);2.666(0.8);2.541(0.4);2.524(2.6);2.519(4.3);2.511(68.7);2.506(144.1);2.502(193.1);2.497(140.0);2.493(67.4);2.382(16.0);2.338(0.4);2.333(0.9);2.329(1.2);2.324(0.9);2.230(0.4);2.221(0.7);2.209(0.9);2.200(0.9);2.187(0.9);2.179(0.6);2.174(0.6);2.165(0.4);2.073(14.8);2.062(0.9);2.055(1.0);2.039(0.7);2.028(0.7);2.021(0.6);2.013(0.4);1.582(9.5);1.564(10.1);1.556(10.2);1.539(9.4);1.030(0.3);0.000(6.2)

Example 247: $^1$H-NMR(400.0 MHz, d$_6$-DMSO): δ = 9.190(1.6);9.170(1.6);8.389(6.5);8.313(0.4);7.401(1.3);7.381(2.7);7.361(1.8);7.333(1.3);7.314(1.4);7.207(2.3);7.189(2.7);7.172(1.9);7.154(1.1);7.151(1.1);7.022(2.0);7.005(1.9);6.938(1.2);6.920(2.1);6.903(1.0);6.806(2.4);6.786(2.2);5.247(0.5);5.233(1.2);5.214(1.2);5.200(0.5);4.289(0.4);4.276(1.0);4.268(1.0);4.260(1.1);4.251(1.0);4.245(0.9);4.237(1.0);4.223(0.9);4.216(1.1);4.196(0.4);3.979(0.3);3.961(0.8);3.944(1.1);3.925(1.1);3.906(16.0);3.317(89.4);2.670(0.8);2.505(102.5);2.501(132.1);2.497(102.2);2.347(15.7);2.328(0.7);2.225(0.4);2.216(0.5);2.203(0.7);2.194(0.7);2.182(0.8);2.169(0.6);2.073(7.3);2.060(0.8);2.053(0.8);2.039(0.6);2.026(0.5);1.585(7.1);1.568(7.8);1.560(7.5);1.542(6.5);0.000(4.0)

Example 248: $^1$H-NMR(400.0 MHz, d$_6$-DMSO): δ = 9.192(0.8);9.172(0.8);8.491(3.1);7.348(0.8);7.329(0.9);7.321(3.5);7.198(1.6);7.195(1.6);7.177(3.4);7.160(2.2);7.156(2.0);7.106(2.2);7.087(4.5);6.950(2.3);6.948(2.6);6.929(4.2);6.913(2.0);6.910(2.0);6.855(7.9);6.830(4.6);6.827(3.8);6.818(8.4);6.792(4.2);6.790(4.2);5.537(4.7);5.258(0.9);5.244(2.1);5.224(2.1);5.209(0.9);4.310(0.5);4.302(0.8);4.295(0.7);4.283(1.9);4.274(1.7);4.267(2.2);4.257(2.8);4.250(2.1);4.237(1.7);4.229(2.2);4.209(0.8);4.201(1.0);6.806(2.4);6.786(2.2);4.209(0.8);3.977(0.7);3.960(1.9);3.942(2.7);3.925(2.0);3.907(0.7);3.469(2.5);3.465(2.5);3.447(5.6);3.443(5.7);3.426(3.0);3.422(3.0);3.324(88.8);3.320(84.4);2.953(3.8);2.932(7.1);2.911(3.3);2.674(0.5);2.670(0.7);2.665(0.5);2.552(34.0);2.523(1.8);2.510(45.4);2.505(94.8);2.501(127.0);2.496(92.2);2.492(44.8);2.337(0.3);2.332(0.6);2.328(0.8);2.323(0.6);2.243(0.5);2.233(0.6);2.222(0.9);2.209(1.3);2.200(1.3);2.188(1.4);2.175(1.0);2.166(0.6);2.073(12.6);2.059(1.6);2.048(1.1);2.031(1.1);2.042(1.1);2.016(0.6);2.008(0.4);1.569(14.7);1.551(15.7);1.544(16.0);1.527(14.5);0.000(2.6)

Example 249: $^1$H-NMR(400.0 MHz, d$_6$-DMSO): δ = 9.170(3.5);9.150(3.6);8.418(16.0);7.340(3.2);7.321(3.5);7.198(7.2);7.179(0.8);7.158(0.5);6.948(0.6);6.930(1.0);6.911(0.5);6.814(1.1);6.794(1.0);5.243(0.5);5.225(0.5);4.284(0.5);4.274(0.5);4.268(0.6);4.259(0.7);4.253(0.6);4.239(0.4);4.231(0.5);3.988(0.5);3.970(0.6);3.953(0.5);3.812(16.0);3.710(9.4);3.318(14.1);2.623(7.0);2.505(17.6);2.501(23.2);2.497(17.7);2.187(0.3);2.064(0.4);1.988(1.1);1.575(3.2);1.557(3.9);1.553(4.0);1.535(3.2);1.397(4.9);1.175(0.6);0.008(0.6);0.000(14.9)

-continued

Example 250: ¹H-NMR(400.0 MHz, d₆-DMSO): δ = 9.219(1.4);9.199(1.4);8.564(6.1);8.313(0.4);7.955(2.9);7.863(1.3);7.843(1.7);7.737(2.7);7.717(2.0);7.354(1.4);7.334(1.5);7.204(0.7);7.200(0.7);7.184(1.4);7.166(0.9); 7.162(0.8);6.953(1.0);6.934(1.7);6.918(0.8);6.816(1.9);6.796(1.7);5.265(0.4);5.250(0.9);5.231(0.9);5.216(0.4);4.310(0.3);4.291(0.8);4.281(0.7);4.274(0.8);4.260(0.7);4.252(0.8);4.239(0.7);4.231(0.9);4.224(0.4);4.211(0.3); 3.980(0.8);3.962(1.1);3.945(0.8);3.322(111.5);3.318(129.2);3.187(1.4);3.172(1.9);3.158(1.6);2.684(2.3);2.668(16.0);2.654(2.1);2.523(2.9);2.510(72.8);2.506(148.7);2.501(197.2);2.497(144.0);2.333(0.8);2.328(1.1); 2.324(0.9);2.233(0.4);2.220 (0.5);2.211(0.6);2.198(0.6);2.186(0.4);2.083(0.4);2.074(0.6);2.067 (0.6);2.051(0.5);2.040 (0.4);2.033(0.4);1.584(5.9);1.566 (6.5);1.542(5.8);1.045 (0.4);1.029(0.4);0.0004.0)
Example 251: ¹H-NMR(400.0 MHz, d₆-DMSO): δ = 9.210(1.6);9.190(1.6);8.505(7.4);8.313(0.4);7.728(3.5);7.726(3.7);7.552(0.7);7.548(0.6);7.530(3.3);7.527(3.6);7.519(5.1);7.498(1.0);7.345(1.5);7.326(1.6);7.202(0.7); 7.199(0.8);7.181(1.6);7.164(1.0);7.160(0.9);6.949(1.2);6.931(2.0);6.914(0.9);6.814(2.2);6.795(2.0);5.261(0.4);5.246(1.0);5.227(1.0);5.212(0.4);4.306(0.4);4.298(0.3);4.286(0.9);4.278(0.8);4.270(1.0);4.257(0.9); 4.249(0.9);4.236(0.8);4.228(1.1);4.208(0.4);3.981(0.3);3.964(0.9);3.946(1.3);3.928(1.0);3.911(0.4);3.323(58.2);3.319(60.8);2.675(0.5);2.671(0.6);2.666(0.5);2.606(16.0);2.524(1.5);2.510(39.3);2.506(80.5); 2.502(106.7);2.497(77.6);2.493(38.1);2.045(0.3);1.030(0.3);0.000(2.1)
1.557(7.5);1.551(7.6);1.533(6.9);1.045(0.3);1.030(0.3);0.000(2.1)
Example 252: ¹H-NMR(400.0 MHz, d₆-DMSO): δ = 10.422(3.4);9.178(6.5);9.157(2.0);8.439(6.5);7.550(3.8);7.488(2.0);7.468(2.1);7.342(2.2);7.197(1.0);7.179(2.1);7.161(1.3);6.949(1.5);6.928(4.7);6.907(3.2); 6.812(2.7);6.792(2.5);5.259(0.6);5.244(1.4);5.225(1.4);5.210(0.6);4.303(0.5);4.284(1.3);4.275(1.2);4.267(1.5);4.258(1.8);4.237(1.1);4.230(1.4);4.210(0.5);3.976(0.4);3.959(1.1);3.941(1.5);3.924(1.1);3.906(0.4); 3.543(8.0);3.329(338.4);2.671(0.9);2.569(16.0);2.541(1.8);2.502(139.5);2.328(0.9);2.224(0.6);2.210 (0.9);2.201(0.9);2.179(0.7);2.058(1.0);2.025(0.7);2.048(0.8);2.031(0.7);2.025(0.7);1.572(0.7);1.555(9.0);1.548(9.0); 1.530(7.5);0.000(55.4)
Example 253: ¹H-NMR(400.0 MHz, d₆-DMSO): δ = 9.223(1.9);9.203(2.0);8.499(9.6);8.314(3.1);7.646(0.4);7.633(0.5);7.623(1.1);7.610(1.1);7.598(1.1);7.585(1.1);7.575(0.5);7.562(0.4);7.344(2.0);7.325(2.7);7.303(1.1); 7.281(0.5);7.199(1.0);7.195(1.0);7.178(2.1);7.160(1.4);7.156(1.3);6.945(1.5);6.943(1.7);6.927(2.6);6.924(2.7);6.908(1.3);6.905(1.3);6.810 (3.0);6.792(2.7);6.790(2.7);5.253(0.6);5.239(1.3);5.220(1.3);5.205(0.6); 4.312(0.4);4.304(0.6);4.296(0.5);4.284(1.2);4.276(1.0);4.268(1.2);4.260(0.9);4.238(1.1);4.223(1.0);4.217(1.4);4.196(0.5);4.189(0.4);3.982(0.4);3.965(1.2);3.947(1.7);3.929(1.2);3.912(0.5);3.321(28.6);3.296(1.0); 2.525(0.7);2.520(1.1);2.511(17.0);2.507(35.5);2.502(47.6);2.498(34.3);2.493(16.4);2.405(16.0);2.226(0.6);2.213(0.9);2.204(0.8);2.191(0.9);2.179(0.6);2.170(0.4);2.083(0.4);2.075(0.4);2.068(0.8); 2.061(0.9);2.045(0.7);2.033(0.6);2.026(0.6);2.017(0.4);1.589(10.0);1.572(10.5);1.564(10.2);1.546(9.5);1.008(0.5);0.000(14.1);−0.009(0.5)
Example 254: ¹H-NMR(400.0 MHz, d₆-DMSO): δ = 9.234(1.8);9.214(1.8);8.479(6.9);7.562(0.5);7.542(1.4);7.528(1.5);7.523(1.8);7.511(4.6);7.496(0.7);7.395(1.1);7.375(1.4);7.372(1.5);7.355(0.7);7.349(0.5); 7.169(1.2);7.162(1.3);7.145(1.2);7.139(1.2);7.059(0.7);7.051(0.7);7.037(1.5);7.029(1.0);7.008(0.8);6.830(1.9);6.820(1.5);6.808(1.4);5.236(0.5);5.221(1.2);5.203(1.2);5.188(0.5);4.296(0.4);4.289(0.5); 4.280(0.5);4.269(1.0);4.261(0.9);4.252(1.0);4.244(0.8);4.223(0.8);4.217(1.0);4.202(0.9);4.196(1.2);4.175(0.5);4.168(0.4);4.038(0.3);4.021(0.3);3.981(0.4);3.964(1.4);3.929(1.0);3.911(0.4);3.318(63.9);2.671(0.6); 2.506(81.8);2.501(106.3);2.497(80.3);2.346(16.0);2.328(0.8);2.222(0.8);2.208(0.7);2.200(0.7);2.187(0.8);2.063(0.6);2.057(0.5);2.047(0.7);2.041(0.8);2.029(0.6);2.012(0.6);2.005(0.5);1.997(0.4); 1.988(1.6);1.590(6.2);1.571(8.6);1.551(6.0);1.398(2.4);1.193(0.4);1.175(0.7);1.157(0.4);0.008(0.8);0.000(19.6)
Example 255: ¹H-NMR(400.0 MHz, d₆-DMSO): δ = 9.220(2.2);8.496(7.7);7.953(0.5);7.775(0.9);7.753(1.4);7.739(1.2);7.717(1.0);7.368(1.4);7.345(3.2);7.324(2.9);7.198(1.0);7.195(1.1);7.177(2.2); 7.159(1.4);7.156(1.4);6.942(1.6);6.924(2.7);6.907(1.3);6.905(1.3);6.810 (3.0);6.791(2.7);5.754(10.6);5.251(0.6);5.237(1.1);5.218(1.4);5.203(0.6);4.311(0.4);4.303(0.6);4.295(0.5);4.284(1.2);4.275(1.1);4.267(1.1);4.259(0.9); 4.244(0.9);4.237(1.2);4.222(1.1);4.216(1.4);4.195(0.6);4.188(0.5);3.981(0.4);3.964(1.1);3.946(1.6);3.928(1.2);3.911(0.5);3.319(64.4);2.891(3.4);2.732(3.0);2.675(0.4);2.671(0.6);2.541(1.2);2.506(64.4);2.502(85.5); 2.498(63.5);2.397(16.0);2.333(0.4);2.329(0.5);2.324(0.4);2.235(0.5);2.225(0.7);2.212(0.9);2.203(0.9);2.190(0.9);2.178(0.7);2.169(0.4);2.065(0.9);2.059(1.0);2.043(0.7);2.031(0.7);2.024(0.6);2.016(0.4); 1.989(0.5);1.588(8.2);1.570(8.9);1.563(8.7);1.545(7.7);0.008(0.7);0.000(19.2);−0.008(0.8)
Example 256: ¹H-NMR(400.0 MHz, d₆-DMSO): δ = 9.207(0.9);9.187(0.9);8.499(3.4);7.622(0.8);7.615(0.9);7.599(0.8);7.511(0.5);7.500(0.6);7.493(0.7);7.483(0.5);7.431(0.9);7.408(1.3); 7.385(0.6);7.343(0.9);7.324(1.0);7.199(1.0);7.179(1.0);7.160(0.6);6.947(0.7);6.928(1.2);6.910(0.6);6.813(1.3);6.792(1.2);5.241(0.6);5.223(0.6);4.284(0.5);4.275(0.5);4.268(0.6);4.259(0.5);4.251(0.5);4.244(0.5);4.223(0.6); 3.968(0.5);3.950(0.7);3.933(0.5);3.317(18.7);2.501(41.6);2.449(5.5);2.211(0.4);2.060(0.4);2.189(0.4);2.056(0.3);1.581(3.8);1.563(4.3);1.556(4.1);1.539(3.6);1.398(16.0);0.000(11.3)
Example 257: ¹H-NMR(400.0 MHz, d₆-DMSO): δ = 9.215(0.9);8.5174.9);7.424(1.0);7.420 (1.2);7.409(0.9);7.405 (1.6);7.401(2.1);7.389(2.0);7.385 (1.1);7.350 (0.8);7.343(1.8);7.331(0.8);7.343(1.8);7.323(1.8);7.303(0.7); 7.201(0.4);7.197(0.4);7.180(0.8);7.162(0.5);7.158(0.5);6.950 (0.6);6.947(0.7);6.931(1.0);6.928(1.1);6.815(1.1);6.812(1.2);6.794(1.0);6.792(1.0);5.242(0.5);5.222(0.5);4.285(0.4);4.276(0.4);4.269(0.5); 4.260(0.4);4.254(0.4);4.246(0.5);4.233(0.4);4.225(0.4);3.974(0.5);3.957(0.7);3.939(0.5);3.315(20.5);3.257(0.5);2.520(0.7);2.511(11.0);2.506(25.1);2.502(32.9);2.497(22.6);2.493(10.9);2.191(0.3);2.068(0.4);1.585(3.8); 1.567(4.1);1.561(4.2);1.544(3.8);1.398(16.0);0.000(1.8);0.000(54.7);−0.009(2.0)
Example 258: ¹H-NMR(400.0 MHz, d₆-DMSO): δ = 9.222(1.7);9.201(1.7);8.471(7.2);7.654(0.6);7.631(1.4);7.610(1.4);7.607(1.4);7.586(0.9);7.559(1.2);7.547(1.3);7.536(0.7);7.524(0.6);7.339(1.7);7.320(1.8);7.196(0.8); 7.192(0.8);7.175(1.7);7.157(1.1);7.154(1.0);6.939(1.2);6.921(2.1);6.902(1.0);6.809(2.3);6.807(2.3);6.789(2.1);5.249(0.5);5.235(1.1);5.202(0.5);4.309(0.3);4.301(0.5);4.293(0.4);4.281(0.9);4.273(0.8); 4.265(1.0);4.257(0.7);4.241(0.7);4.234(0.9);4.219(0.8);4.212(1.2);4.191(0.4);4.184(0.4);3.979(0.4);3.962(1.0);3.944(1.3);3.926(1.0);3.909(0.4);3.320(22.1);3.317(20.0);2.524(0.8);2.510(16.5);2.506(33.5);2.502(44.7); 2.497(33.1);2.493(16.7);2.371(16.0);2.231(0.3);2.223(0.5);2.210(0.7);2.201(0.7);2.188(0.7);2.176(0.5);2.074(5.9);2.064(0.7);2.057(0.8);2.048(0.5);2.041(0.6);2.030(0.5);2.023(0.5);1.909(0.4);1.592(6.6);1.574(6.9); 1.566(7.9);1.548(7.3);0.008(1.7);0.000(45.8);−0.008(2.0)
Example 259: ¹H-NMR(400.0 MHz, d₆-DMSO): δ = 10.475(0.8);9.200(1.4);9.180(1.4);8.510(7.4);7.877(0.4);7.860(0.5);7.856(0.7);7.463(0.3);7.444(0.5);7.346(1.4);7.327(1.4);7.327(0.7);7.222(1.1);7.219(1.2);7.212(1.2); 7.203(1.8);7.199(1.8);7.183(1.7);7.179(1.7);7.164(1.3);7.161(1.2);6.952(1.0);6.949(1.1);6.933(1.7);6.930(1.7);6.915(0.8);6.912(0.9);6.816(1.9);6.813(1.9);6.795(1.8);6.793(1.7);5.260(0.4);5.246(0.8);5.226(0.8); 5.212(0.4);4.287(0.7);4.278(0.7);4.270(0.8);4.262(0.7);4.255(0.7);4.248(0.8);4.235(0.7);4.227(0.9);4.220 (0.3);4.206(0.3);4.206(0.3);3.957(0.8);3.939(1.2);3.922(0.9);3.319(66.6);2.675(0.4);2.670 (0.5);2.666(0.4);2.597(15.0);2.524(1.3); 2.519(1.9);2.511 (28.7);2.506(60.8);2.501(81.6);2.497 (59.0);2.492(28.0);2.333 (0.4);2.328(0.4);2.215(0.5);2.206(0.5);2.194(0.6);2.181(0.4);2.078(0.4);2.070(0.5);2.063(0.6);2.052(0.4);2.047(0.4); 2.036(0.4);2.028(0.4);1.988(0.6);1.566(6.4);1.549(6.7);1.546(6.7);1.526(6.3);1.398(16.0);1.175(0.4);0.008(2.4);0.000(76.1);−0.000(2.5)
Example 260: ¹H-NMR(400.0 MHz, d₆-DMSO): δ = 9.189(0.9);9.169(0.9);8.433(3.9);7.339(0.8);7.320(0.8);7.197(0.4);7.173(1.2);7.153(1.4);7.133(0.9);7.022(0.7);7.017(0.8);7.001(2.0);6.982(1.2);6.945(0.7); 6.943(0.6);6.926(1.1);6.908(0.5);6.906(0.5);6.810(1.2);6.790(1.1);5.239(0.5);5.221(0.9);5.228(0.5);4.281(0.5);4.273(0.4);4.244(0.5);4.230(0.4);4.223(0.6);3.970(0.5);3.952(0.7);3.935(0.5);3.318(50.4); 2.799(16.0);2.670(0.4);2.523(0.9);2.510(25.4);2.506(50.8);2.501(66.0);2.497(47.3);2.492(22.8);2.421(5.4);2.328(0.4);2.208(0.3);2.198(0.4);2.186(0.4);2.064(0.3);2.058(0.4);1.584(3.8);1.566(4.0);1.559(4.1); 1.541(3.8);1.398(13.1);0.008(1.6);0.000(50.7);−0.009(1.8)
Example 261: ¹H-NMR(400.0 MHz, d₆-DMSO): δ = 9.094(1.7);9.073(1.7);8.534(8.9);7.839(1.8);7.832(2.0);7.817(1.9);7.648(2.0);7.641(1.9);7.633(2.1);7.627(1.9);7.390(1.0);7.378(1.3);7.368(1.3);7.294(0.6); 7.284(1.1);7.273(1.9);7.263(1.1);7.251 (4.1);7.245(2.2);7.238(2.0);7.229(2.4);6.571 (0.4);5.548(0.5);5.528(1.4);5.508(1.4);5.489(0.5);3.991 (0.4);3.973(1.0);3.955(1.4);3.938(1.1);3.920(0.4);3.316(60.4);3.022(0.3); 3.014(0.4);3.000(0.4);2.993(0.7);2.982(0.8);2.977(1.4);2.952(0.8);2.944(1.1);2.928(0.4);2.908(0.6);2.888(1.2);2.867(0.9);2.848(0.6);2.828(0.4);2.675(0.3);2.670(0.5);2.666(0.4);2.571(0.4);2.563(0.4);2.552(0.8); 2.543(0.9);2.532(1.0);2.524(1.7);2.519(2.4);2.510(27.2);2.506(56.5);2.501 (75.9);2.497(54.3);2.492(25.9);2.469(9.7);2.444(10.7);2.426(1.7);2.408(1.8);2.399(0.4);2.391(0.6);2.333(0.3);2.328(0.5);2.324(0.3);

-continued

| |
|---|
| 1.964(0.4);1.942(0.9);1.932 (0.4);1.922(0.9);1.911(0.9);1.901(0.4);1.891(0.8);1.582(7.7);1.564(14.8);1.547 (7.6);1.398(7.5);1.219(0.3);1.033(0.5);1.016(0.5);0.969(0.4);0.955(2.9);0.951(16.0);0.935(15.8);0.920(1.9); 0.008(2.0);0.000(66.6);−0.009(2.2) |
| Example 262: $^1$H-NMR(400.0 MHz, d$_6$-DMSO): δ = 9.217(0.7);9.197(0.7);8.528(2.9);7.836(0.6);7.829(0.7);7.821(0.6);7.814(0.7);7.644(0.7);7.637(0.7);7.630(0.7);7.623(0.6);7.342(0.6);7.323(0.7);7.179(0.7);7.161(0.4); 7.158(0.4);6.944(0.5);6.926(0.9);6.910(0.4);6.811(0.9);6.791(0.8);5.240(0.4);5.221(0.4);4.268(0.4);4.243(0.4);4.229(0.3);4.222(0.4);3.966(0.4);3.948(0.5);3.930(0.4);3.316(15.1);2.506(14.8); 2.502(20.1);2.497(15.4);2.464(3.9);1.579(2.7);1.561(3.0);1.555(3.0);1.537(2.7);1.398(16.0);0.952(0.4);0.008(0.6);0.000(15.0);−0.0029.0);−0.009(0.6) |
| Example 263: $^1$H-NMR(400.0 MHz, d$_6$-DMSO): δ = 9.193(0.6);9.173(0.7);8.445(3.5);7.337(0.6);7.318(0.4);7.177(0.6);7.160(0.4);7.155(0.4);7.032(0.5);7.019(0.6);7.010(1.0);6.997(0.9);6.975(1.0);6.951(1.1);6.947(0.5); 6.944(0.5);6.928(1.3);6.910(0.4);6.907(0.4);6.812(0.9);6.809(0.9);6.789(0.8);6.138(4.7);5.239(0.4);5.220(0.4);4.281(0.3);4.265(0.4);4.252(0.3);4.244(0.4);4.223(0.4);3.954(0.4);3.936(0.5);3.918(0.4); 3.316(24.7);2.523(0.4);2.519 (0.6);2.510(10.8);2.506(22.9);2.501(30.7);2.496 (22.0);2.492(10.4);2.450(6.8);1.571 (2.8);1.554(3.0);1.547(3.0);1.529 (2.8);1.398(16.0);0.008(0.8);0.000(25.6);−0.009(0.8) |
| Example 264: $^1$H-NMR(400.0 MHz, d$_6$-DMSO): δ = 9.271(1.4);9.251(1.5);8.490(7.7);7.983(1.6);7.981(1.7);7.964(1.8);7.962(1.8);7.832(0.8);7.828(0.8);7.812(1.8);7.809(1.8);7.793(1.2);7.790(1.2);7.662(2.1);7.644(1.6); 7.618(1.2);7.615(1.2);7.599(2.0);7.596(1.9);7.580(1.0);7.577(0.9);7.348(1.3);7.329(1.4);7.197(0.7);7.193(0.7);7.176(1.4);7.159(0.9);6.947(1.0);6.944(1.1);6.928(1.7);6.926(1.8);6.910(0.9);6.907(0.9);6.811(2.0); 6.809(2.0);6.791(1.8);6.788(1.7);5.261(0.4);5.245(0.9);5.226(0.9);5.211(0.4);4.301(0.3);4.284(0.8);4.274(0.7);4.266(0.8);4.253(0.7);4.245(0.8);4.231(0.7);4.224(1.0);4.216(0.4);4.203(0.4);3.970(0.8);3.953(1.2); 3.935(0.9);3.917(0.3);3.320(25.9);3.318(24.4);2.524(0.7);2.519 (1.1);2.510(18.7);2.506(39.9);2.501(53.7);2.497(38.2);2.492(18.0);2.477(16.0);2.328(0.3);2.224(0.4);2.211(0.5);2.203(0.6);2.190(0.6);2.181(0.4);2.177(0.4); 2.081(0.4);2.073(3.4);2.065(0.6);2.049(0.4);2.038(0.4);2.030(0.4);1.598(6.6);1.580(6.8);1.572(6.9);1.554(6.5);0.008(1.4);0.000(53.4);−0.009(1.8) |
| Example 265: $^1$H-NMR(400.0 MHz, d$_6$-DMSO): δ = 9.099(0.8);9.078(0.8);8.500(4.1);7.835(0.9);7.828(1.0);7.820(0.9);7.813(0.9);7.643(0.9);7.637(0.9);7.629 (1.0);7.623(0.9);7.371(0.5);7.363(0.5);7.349(0.7);7.201(1.1); 7.192(1.2);7.183(1.2);7.179(1.0);7.130(0.8);7.116(0.5);7.107(0.4);6.571(0.7);5.210(0.4);3.951(0.5);3.934(0.6);3.916(0.5);3.321 (18.1);3.318(21.1);2.769(0.8);2.755(0.8);2.740(0.3);2.524(0.5);2.511 (12.6); 2.506(26.8);2.502(36.1);2.497 (25.9);2.493(12.3);2.466 (4.4);2.462(4.5);1.827(0.5);1.811(0.6);1.583(3.5);1.565(3.6);1.538(3.4);1.398(16.0);0.008(0.6);0.000(18.0);−0.009 (0.6) |
| Example 266: $^1$H-NMR(400.0 MHz, d$_6$-DMSO): δ = 9.197(1.7);9.176(1.7);8.442(6.6);8.313(1.1);7.341(1.8);7.322(1.9);7.196(0.8);7.178 (1.7);7.160(1.2);7.019 (1.1);7.008(2.5);6.996(2.2);6.988(0.6);6.939(5.8);6.928(6.9); 6.910(1.3);6.812(2.4);6.791(2.2);6.018(10.4);5.256(0.7);5.239(1.2);5.227(1.1);5.206(0.6);4.273(1.0);4.266(1.2);4.254(1.1);4.246(1.2);4.225(1.2);4.205(0.7);4.199(0.5);4.193(0.5);3.960(0.9);3.943(1.3);3.926(1.1);3.904(0.7); 3.460(0.5);3.318(478.5);3.282(0.9);2.670(3.3);2.558(0.5);2.505(429.9);2.501(539.1);2.461(16.0);2.328(3.3);2.223(0.7);2.188(0.8);2.058(0.9);2.032(0.7);1.576(7.0);1.558(7.6);1.552(7.6);1.534(6.7); 0.147(2.7);0.059(0.5);0.033(0.5);0.000(573.1);−0.053(0.5);−0.067(0.5);−0.149(2.7);−2.166(0.5);−2.849(0.5);−3.471(0.4);−3.583(0.5) |
| Example 267: $^1$H-NMR(400.0 MHz, d$_6$-DMSO): δ = 9.159(1.5);9.139(1.6);7.952(0.4);7.711(1.8);7.707 (1.9);7.691(2.2);7.687(2.2);7.481(1.4);7.461(3.4);7.442(2.4);7.420(2.1);7.416(2.2);7.401(1.1);7.397(1.0);7.332(1.3); 7.313(1.5);7.202(0.7);7.198(0.7);7.181(1.5);7.163(1.0);7.160(0.9);6.956(1.1);6.953(1.1);6.937(1.8);6.935(1.7);6.918(0.9);6.916(0.9);6.818(2.1);6.798(1.9);5.754(1.1);5.288(0.4);5.274(0.9);5.254(0.9);5.241(0.4); 4.321(0.3);4.313(0.5);4.308(0.4);4.294(0.7);4.285(0.7);4.279(0.5);4.271(0.5);4.213 (0.6);4.207(0.7);4.184(1.0);4.162(0.4);4.156(0.4);3.316(42.3);2.891(2.9);2.732(2.5);2.705(15.4);2.675(0.4);2.670(0.5);2.666(0.3); 2.540(3.0);2.530(0.4);2.524(1.0);2.510(24.0);2.506(51.0);2.501(71.6);2.497(53.0);2.492(25.1);2.458(15.0);2.323(16.0);2.253(0.4);2.241(0.6);2.232(0.6);2.218(0.6);2.205(0.4);2.069(0.4);2.061(0.6);2.055(0.6);2.047(0.4); 2.040(0.6);2.026(0.4);0.008 (1.7);0.000(58.9);−0.008(2.0) |
| Example 268: $^1$H-NMR(400.0 MHz, d$_6$-DMSO): δ = 9.185(1.9);9.165(1.9);8.308(0.5);7.813 (7.9);7.810 (8.1);7.519(2.2);7.514 (3.9);7.510 (2.1);7.338 (1.7);7.319 (1.9);7.207(0.8);7.189(1.8);7.172(1.1);6.963(1.3);6.944(2.2); 6.926(1.0);6.824(2.5);6.804(2.2);5.294(0.5);5.280 (1.1);5.261 (1.1);5.247 (0.5);4.330(0.4);4.322(0.6);4.315 (0.6);4.304(0.8);4.295 (0.8);4.288 (0.9);4.279(0.7);4.211(0.8);4.188 (1.2);4.166(0.5);4.160 (0.5);3.506(0.4); 3.357(2057.4);2.704(15.8);2.674(1.4);2.669(1.1);2.605(16.0);2.558(16.2);2.543(1.3);2.508(157.9);2.504(216.1);2.500(166.9);2.331(1.3);2.327(1.0);2.276(0.4);2.262(0.5);2.250(0.7);2.240(0.8);2.228(0.7);2.214(0.5); 2.206(0.4);2.072 (14.9);2.054(0.7);2.040(0.6);2.027(0.4);0.146(0.8);0.008(7.2);0.000(164.1);−0.149(0.8) |
| Example 513: $^1$H-NMR(400.0 MHz, d$_6$-DMSO): δ = 9.156(0.7);9.135(0.8);8.729(2.7);7.622 (0.8);7.607(0.7);7.602(0.7);7.587(0.7);7.568(1.4);7.549(0.6);7.463(0.5);7.444(0.9);7.424(0.4);7.420(0.4);7.315(0.5); 7.297(1.4);7.275(1.4);7.261(0.9);7.237(1.0);7.219(0.6);5.516(0.4);5.501(0.4);4.057 (1.2);4.039 (3.7);4.022(3.8);4.004(1.3);3.493 (7.1);3.321 (7.4);2.993 (0.3);2.984(0.4);2.971(0.4);2.963 (0.3);2.900(0.5);2.879(0.4);2.560(0.3); 2.513(4.7);2.508 (0.0);2.504(14.1);2.499 (0.6);2.495(5.1);2.103(8.2);1.990(16.0);1.909 (0.4);1.888(0.4);1.878(0.4);1.857(0.4);1.194(4.2);1.176(8.3);1.158(4.1) |
| Example 514: $^1$H-NMR(400.0 MHz, d$_6$-DMSO): δ = 9.195(1.4);9.176(1.5);8.731(5.0);7.642 (0.5);7.626 (0.5);7.621 (1.3);7.606 (1.3);7.601 (1.2);7.586 (1.1);7.567 (2.5);7.547 (1.1);7.462 (1.0);7.441(1.7);7.420(0.8);7.259(1.4); 7.240(1.6);7.216(0.7);7.197 (1.5);7.178 (1.2);7.151(0.6);6.920 (0.9);6.902 (1.6);6.883 (0.8);6.840 (2.0);6.820(1.8);5.754 (6.0);5.256(0.7);5.239(0.7);4.332(0.4);4.326(0.4);4.306(0.9);4.298(0.7);4.286(0.7);4.279(0.6); 4.207(0.7);4.195 (0.8);4.183(0.9);4.163 (0.4);4.039(0.8);4.022 (0.8);3.492(12.6);3.322(10.8);3.177 (0.4);3.166(0.4);2.893 (0.5);2.734(0.4);2.635 (0.3);2.508 (22.7);2.503(30.8);2.499 (24.0);2.330 (0.5);2.233 (0.4);2.229(0.4); 2.214(0.6);2.207 (0.5);2.201(0.6);2.196(0.6);2.101 (14.1);2.081(0.7);2.074 (0.7);2.064 (0.6);2.057(0.6);2.046 (0.6);2.040 (0.4);1.989 (3.4);1.194 (0.9);1.176(1.8);1.159(0.9);0.008(1.6);0.000(41.4);−0.008(2.2) |
| Example 515: $^1$H-NMR(400.0 MHz, d$_6$-DMSO): δ = 9.199 (2.1);9.179 (2.2);8.793 (0.7);8.736 (6.5);7.956 (1.9);7.950 (2.2);7.941 (1.9);7.934 (1.8);7.684 (1.8);7.678 (1.7);7.670 (1.9);7.663(1.7);7.252(2.0);7.233(2.2);7.216(1.0); 7.196(1.9);7.177 (1.2);6.920 (1.2);6.901 (2.0);6.882(0.9);6.839 (2.0);6.819 (2.3);5.754 (2.3);5.253(1.0);5.239(1.0);4.333 (0.5);4.326 (0.6);4.315 (0.6);4.306(1.2);4.298 (0.8);4.204 (0.9);4.198 (0.7);4.191(0.6); 4.183(1.1);4.177 (1.0);4.162 (0.5);4.156 (0.5);3.547 (15.0);3.317 (37.9);2.891 (1.9);2.731 (1.7);2.675 (0.4);2.671 (0.5);2.666(0.4);2.541(0.8);2.506 (62.1);2.502(84.8);2.497 (65.5);2.333(0.4);2.328 (0.5);2.324 (0.4);2.232(0.5); 2.216(0.7);2.210 (0.7);2.203 (0.8);2.198(0.8);2.189 (0.6);2.154(16.0);2.138 (2.0);2.111 (0.4);2.089 (0.5);2.074(0.9);2.062 (0.7);2.057 (0.7);2.045(0.6);2.028(0.3);1.049(0.4);1.032(0.8);1.014(0.4);0.008(2.1);0.000 (50.7); −0.008(2.2) |
| Example 516: $^1$H-NMR(400.0 MHz, d$_6$-DMSO): δ = 9.072(1.8);9.052(1.9);8.438(7.3);8.427(0.4);8.350(0.4);8.313(8.6);7.826 (8.2);7.821(8.6);7.805(0.3);7.800 (0.4);7.489(2.2);7.354(1.8);7.335(2.1); 7.196(0.9);7.178 (2.0);7.161(1.2);6.944(1.4);6.926 (2.4);6.907(1.1);6.815(2.7);6.795(2.4);5.237(0.5);5.204 (1.2);5.189(0.6);4.302 (0.4);4.288 (1.1);4.261 (1.6);4.246(1.0);4.239(1.2);4.219(0.4);4.211(0.3); 4.056(0.4);4.038(1.1);4.020(1.1);4.003(0.4);3.845 (3.7);3.835(6.1);3.824(4.2);3.806 (0.7);3.584 (0.5);3.315 (110.7);2.670 (1.2);2.666(0.9);2.641(0.7);2.602 (16.0);2.505 (145.6); 2.501(191.9);2.497(146.9);2.402(0.8);2.328(1.1);2.239 (0.4);2.228 (0.5);2.216(0.7);2.206(0.8);2.194 (0.8);2.182 (0.6);2.068(0.8);2.053 (0.7);2.040(0.6);2.033(0.6);1.988(4.6);1.398(2.3);1.193(1.2);1.175(2.3);1.157(1.2); 0.146(0.8);0.133 (0.5);0.008 (7.1);0.000(163.7);−0.150(0.8) |
| Example 517: $^1$H-NMR(400.0 MHz, d$_6$-DMSO): δ = 9.048(1.4);9.028(1.5);8.277(0.7);7.696(1.8);7.692 (1.9);7.677(2.2);7.673(2.2);7.465(1.2);7.446(3.0);7.427(2.2);7.407(1.9);7.392(0.9);7.333(1.1);7.314(1.2);7.192(0.8); 7.188(0.8);7.171(1.6);7.153 (1.0);7.150 (1.0);7.150 (1.0);6.931 (1.2);6.913 (2.0);6.897(2.0);6.894 (1.0);6.808(2.2);6.787(2.0);5.217(0.8);5.199 (0.9);4.301 (0.4);4.283 (0.9);4.266 (1.1);4.258 (1.3);4.250 (1.0);4.235(0.8);4.229(1.0);4.209(0.4); 3.833(4.7);3.636(2.2);3.317(103.8);2.674(0.6);2.670(0.9);2.666 (0.7);2.510 (57.0);2.506(113.3);2.501(152.6);2.497(116.8);2.320(16.0);2.232(0.3);2.220(0.4);2.209 (0.6);2.187(0.6);2.199 (0.6);2.187(0.6);2.175(0.5);2.073(2.3); 2.062(0.8);2.047 (0.6);2.034(0.5);2.026(0.5);0.146 (0.6);0.008(5.9);0.000(136.4);−0.008(6.1);−0.150(0.6) |
| Example 518: $^1$H-NMR(400.0 MHz, d$_6$-DMSO): δ = 9.020 (1.4);9.000 (1.6);8.220 (7.3);7.687 (1.7);7.682 (1.9);7.667 (2.1);7.663 (2.2);7.458 (1.2);7.439 (3.0);7.419 (2.3);7.404(1.9);7.401(2.0);7.385 (0.8);7.382(0.8);7.318(1.3); 7.299 (1.4);7.189 (0.8);7.185 (0.8);7.168 (1.6);7.150 (1.0);7.146 (1.0);6.924 (1.2);6.905 (2.1);6.887(1.0);6.806(2.3);6.786(2.0);5.753(8.9);5.221(0.4);5.208(0.9);5.188(0.9);5.175(0.4);4.293(0.4);4.274(0.9);4.264(0.9);4.258(1.2); |

4.247(1.3);4.232(0.8);4.225(1.1);4.204(0.4);4.038(0.5);4.021(0.5);3.357(0.7);3.316(24.2);3.257(28.5);2.946(0.7);2.523(0.7);2.505(36.1);2.501(51.3);2.497(39.4);2.315(16.0);2.300(0.5);2.202(0.4);2.189(0.6);2.180(0.6);2.168(0.6);2.155(0.5);2.060(0.4);2.053(0.6);2.045(0.7);2.031(0.5);2.018(0.5);2.011(0.5);1.988(2.1);1.235(0.4);1.193(0.6);1.175(1.1);1.158(0.6);0.008(1.4);0.000(44.7);−0.008(1.8)

Example 519: 1H-NMR(400.0 MHz, d6-DMSO):
δ = 9.236(1.8);8.702(5.9);7.614(0.7);7.609(0.8);7.594(0.8);7.589(0.9);7.586(0.9);7.580(0.8);7.570(0.8);7.566(0.8);7.561(0.8);7.549(1.3);7.544(0.8);7.528(0.8);7.522(1.3);7.500(0.7);7.306(0.8);7.300(0.8);7.296(0.8);7.290(0.8);7.284(0.7);7.274(0.7);7.248(1.5);7.229(1.7);7.215(0.8);7.212(0.8);7.194(1.6);7.177(1.0);7.173(0.9);6.917(1.2);6.898(2.0);6.882(0.9);6.879(1.0);6.837(2.2);6.818(1.9);6.817(1.9);5.754(13.0);5.269(0.4);7.252(1.0);5.236(1.0);5.219(0.4);4.333(0.4);4.326(0.5);4.315(0.3);4.306(0.9);4.298(0.7);4.287(0.8);4.280(0.6);4.198(0.8);4.186(0.7);4.178(1.1);4.170(0.6);2.732(1.4);2.525(0.6);2.511(12.2);2.507(26.0);2.502(36.7);2.498(28.5);2.494(14.6);2.233(0.5);2.227(0.4);2.220(0.6);2.213(0.6);2.206(0.5);2.200(0.7);2.187(0.5);2.179(0.3);2.148(16.0);2.086(0.4);2.076(0.6);2.069(0.7);2.059(0.6);2.052(0.6);2.041(0.5);2.035(0.4);1.989(0.0);0.008(1.2);0.000(37.0);−0.008(1.6)

Example 520: 1H-NMR(400.0 MHz, d6-DMSO):
δ = 9.053(1.8);9.032(1.8);8.381(7.5);8.314(0.6);8.287(0.6);8.199(0.4);7.483(2.2);7.478(4.1);7.474(2.2);7.343(2.0);7.324(1.9);7.195(0.8);7.177(1.8);7.159(1.1);6.938(1.2);6.921(2.1);6.903(1.0);6.815(2.4);6.795(2.1);5.226(0.5);5.212(1.1);5.193(1.1);5.180(0.5);4.299(0.4);4.282(1.0);4.265(1.8);4.257(1.7);4.244(0.9);4.236(1.1);4.216(0.3);3.315(70.9);3.255(30.5);2.670(1.7);2.599(16.0);2.505(209.1);2.501(282.9);2.497(218.0);2.328(1.6);2.323(1.3);2.222(0.4);2.211(0.4);2.198(0.7);2.177(0.7);2.164(0.5);2.059(0.7);2.052(0.8);2.026(0.5);2.017(0.5);0.146(1.1);0.008(10.1);0.000(250.1);−0.008(10.6);−0.150(1.1)

Example 521: 1H-NMR(400.0 MHz, d6-DMSO):
δ = 9.226(1.8);9.206(1.9);8.715(5.9);7.715(2.0);7.711(3.9);7.706(2.2);7.573(8.3);7.568(7.7);7.250(1.6);7.230(1.8);7.217(0.8);7.213(0.8);7.196(1.6);7.178(1.0);7.174(0.9);6.920(1.1);6.918(1.2);6.900(2.0);6.883(1.0);6.881(1.0);6.840(2.3);6.819(2.0);5.754(7.4);5.270(0.4);5.254(1.0);5.237(1.0);5.221(0.5);4.333(0.4);4.326(0.5);4.315(0.5);4.306(1.0);4.298(0.7);4.287(0.8);4.280(0.6);4.206(0.6);4.199(0.8);4.186(0.7);4.178(1.1);4.170(0.6);4.158(0.5);4.151(0.4);3.520(14.5);3.319(26.1);3.306(0.4);2.892(0.5);2.732(0.4);2.671(1.4);2.498(35.3);2.502(47.1);2.498(35.3);2.235(0.5);2.221(0.6);2.214(0.7);2.200(0.9);2.188(0.6);2.181(0.5);2.161(16.0);2.089 (0.4);2.078(0.6);2.072(0.7);2.062(0.6);2.054(0.6);2.044(0.5);2.037(0.4);1.989(1.1);1.193(0.3);1.175(0.6);0.000(2.6)

Example 522: 1H-NMR(400.0 MHz, d6-DMSO):
δ = 9.994(1.0);9.975(1.0);8.694(4.7);7.731(1.1);7.722(1.1);7.716(1.2);7.731(1.1);7.722(1.1);7.716(1.2);7.707(1.3);7.498(0.3);7.478(2.2);7.472(2.2);7.472(2.2);7.463(4.2);7.454(0.4);7.424(0.8);7.411(0.7);7.404(0.8);7.305(0.5);7.298(0.7);7.284(1.2);7.265(0.5);7.252(1.0);7.247(2.0);7.238(1.8);7.230(1.5);5.506(0.6);5.488(0.6);4.252(1.0);4.234(0.9);3.321(69.2);2.994(0.4);2.984(0.5);2.972(0.5);2.963(0.5);2.923(0.4);2.902(0.8);2.883(0.6);2.862(0.4);2.675(0.4);2.671(0.5);2.666(0.4);2.556(0.5);2.545(0.7);2.534(0.6);2.524(1.8);2.510(27.6);2.506(57.4);2.502(80.2);2.497(61.1);2.372(10.3);2.333(0.4);2.329(0.5);2.324(0.4);2.135(16.0);1.950(0.4);1.918(0.4);1.899(0.3);1.398(10.9);0.952(0.6);0.936(0.6);0.146(0.4);0.008(3.5);0.000(93.2);−0.008(3.8);−0.150(0.4)

Example 523: 1H-NMR(400.0 MHz, d6-DMSO):
δ = 10.111(1.1);10.092(1.1);8.681(5.0);7.730(1.2);7.721(1.1);7.715(1.5);7.706(1.4);7.496(0.4);7.476(2.3);7.470(2.1);7.461(4.2);7.451(0.4);7.375(1.0);7.356(1.1);7.203(0.5);7.186(1.0);7.168(0.6);7.165(0.6);6.940(0.8);6.922(1.3);6.906(0.6);6.903(0.6);6.825(1.4);6.804(1.3);5.223(0.6);5.205(0.6);4.326(0.6);4.314(0.4);4.303(0.4);4.294(0.7);4.287(0.7);4.278(0.5);4.263(0.6);4.230(0.4);4.202(0.6);4.174(0.7);3.320(68.6);2.675(0.6);2.671(0.8);2.666(0.6);2.524(2.0);2.510(42.4);2.506(88.6);2.502(123.3);2.497(92.0);2.493(44.4);2.469(0.9);2.370(10.7);2.333(0.5);2.328(0.7);2.324(0.5);2.209(1.6);2.194(0.4);2.101(16.0);1.398(15.0);1.353(0.4);0.146(0.4);0.008(3.4);0.000(97.4);−0.008(3.6);−0.150(0.4)

Example 524: 1H-NMR(400.0 MHz, d6-DMSO):
δ = 9.589(0.5);9.396(0.6);9.197(1.7);9.177(1.8);9.159(14.1);8.587(0.3);8.569(7.0);7.361(1.6);7.344(1.8);7.204(0.8);7.182(1.7);7.165(1.0);6.947(1.2);6.929(2.0);6.911(1.0);6.816(2.3);6.796(2.1);5.263(0.5);5.249(1.1);5.229(1.1);5.216(0.5);4.315(0.4);4.295(0.9);4.286(0.9);4.279(1.0);4.272(0.7);4.254(0.7);4.248(1.6);4.227(1.2);4.205(0.4);3.318(46.5);2.709(0.7);2.670(2.2);2.650(16.0);2.624(1.6);2.610(0.9);2.602(0.9);2.587(0.5);2.505(243.0);2.501(314.7);2.497(229.0);2.332(1.3);2.328(1.8);2.242(0.3);2.236(0.5);2.222(0.7);2.213(0.7);2.199(0.7);2.190(0.5);2.089(0.7);2.083(0.8);2.069(0.7);2.055(0.5);2.048(0.5);1.501(0.7);1.492(2.2);1.486 (2.7);1.478(2.7);1.471(2.3);1.463(0.9);1.255(0.9);1.246(2.3);1.239(2.4);1.224(2.3);1.218(2.3);1.208(0.7);0.146(0.6);0.008(4.9);0.000(131.7);−0.150(0.6)

Example 525: 1H-NMR(400.0 MHz, d6-DMSO):
δ = 9.161(1.8);9.141(1.9);8.526(6.6);8.209(0.4);8.196(2.9);8.183(3.0);7.360(1.7);7.340(1.9);7.203(0.8);7.174(1.4);7.164(1.4);7.142(2.4);7.129(2.3);7.103(0.4);6.947(1.3);6.928(2.2);6.910(1.0);6.815(2.5);6.795(2.2);5.261(0.5);5.247(1.1);5.228(1.1);5.214(0.6);4.312(0.4);4.306(0.4);4.294(1.0);4.285(0.9);4.278(1.0);4.270(0.7);4.256(0.8);4.249(1.0);4.234(0.9);4.228(1.2);4.207(0.4);4.038(0.4);4.020(0.5);3.739(4.0);3.727(6.4);3.715(5.2);3.545(0.7);3.533(0.8);3.522(0.6);3.476(4.8);3.464(6.1);3.453(4.2);3.330(4.5);2.670(1.3);2.654(0.5);2.618(1.8);2.604(0.9);2.596(0.9);2.582(0.4);2.505(176.4);2.502(224.3);2.328(1.3);2.232(0.5);2.218(0.7);2.210(0.7);2.197(0.8);2.183(0.6);2.085(0.7);2.079(0.8);2.064(0.7);2.050(0.6);2.044(0.7);1.485(2.3);1.480(2.7);1.471(2.9);1.465(2.4);1.457 (0.9);1.237(0.9);1.228(2.4);1.222(2.4);1.206(2.4);1.200(2.3);1.192(1.0);1.174(1.1);1.157(0.5);0.146(0.4);0.000(88.2);−0.149(0.4)

Example 526: 1H-NMR(400.0 MHz, d6-DMSO):
δ = 9.153(3.1);9.132(3.2);8.486(13.4);8.086(5.4);8.073(5.7);7.353(2.8);7.334(3.0);7.199(1.3);7.195(1.4);7.178(2.9);7.160(1.8);7.157(1.8);7.091(2.7);7.079(4.9);7.067(2.7);6.940(2.2);6.921(3.7);6.905(1.6);6.903(1.8);6.811(4.0);6.790(3.6);5.757(2.6);5.256(0.8);5.242(1.8);5.209(0.8);4.317(0.5);4.309(0.7);4.302(0.7);4.290(1.5);4.282(1.4);4.274(1.0);4.266(1.2);4.249(1.2);4.242(1.6);4.228(1.4);4.221(2.0);4.200(0.8);4.193(0.6);3.756(6.6);3.745(9.1);3.733(7.7);3.393(7.3);3.381(9.0);3.370(6.5);3.319(25.1);2.890(0.7);2.731(0.6);2.675(0.7);2.670(1.0);2.666(0.8);2.643(0.6);2.629(1.3);2.621(1.3);2.615(0.9);2.607(2.7);2.600(0.9);2.593(1.4);2.586(1.4);2.571(0.7);2.524(2.4);2.510(63.7);2.506(132.9);2.501(177.8);2.497(129.3);2.493(63.8);2.448(15.6);2.445(16.0);2.332(0.8);2.328(1.0);2.324(0.8);2.251(0.4);2.242(0.6);2.230(0.8);2.217(1.2);2.208(1.2);2.195(1.2);2.182(0.9);2.174(0.6);2.088(0.8);2.079(1.1);2.073(1.5);2.058(1.0);2.045(0.9);2.038(0.8);2.031(0.6);2.024(0.4);1.492(1.2);1.482(3.7);1.475(4.6);1.467(4.7);1.461(4.1);1.452(1.5);1.298(0.4);1.258(0.6);1.238(1.5);1.228(4.2);1.222(4.1);1.206(4.0);1.200(4.1);1.190(1.1);1.175(1.3);0.146(0.3);0.008(2.3);0.000(75.6);−0.008(2.3);−0.150(0.3)

Example 527: 1H-NMR(400.0 MHz, d6-DMSO):
δ = 10.476(3.0);9.178(1.9);9.158(2.0);8.548(8.5);8.345(2.9);8.332(3.0);8.316(0.7);7.625(2.2);7.612(2.2);7.366(1.9);7.348(2.1);7.199(0.9);7.182(1.9);7.164(1.2);6.951(1.3);6.932(2.3);6.914(1.1);6.815(2.6);6.795(2.4);5.263(0.6);5.249(1.2);5.231(1.1);5.216(0.6);4.315(0.5);4.308(0.5);4.296(1.0);4.279(1.1);4.250(1.0);4.230(1.3);4.208(0.5);3.319(50.4);2.670(1.6);2.620(1.7);2.606(1.0);2.598(1.0);2.584(0.5);2.540(4.0);2.501(247.0);2.328(1.5);2.237(0.0);2.224(0.8);2.215(0.8);2.202(0.8);2.107(15.5);2.083(1.1);2.070(0.8);2.054(0.7);2.039(0.4);1.496(0.8);1.485(2.6);1.480(3.0);1.472(3.2);1.466(2.7);1.457(1.0);1.242(0.9);1.233(2.6);1.227(2.6);1.211(2.6);1.205(2.5);1.195(0.8);0.000(31.1)

Example 528: 1H-NMR(400.0 MHz, d6-DMSO):
δ = 9.040(1.3);9.020(1.4);8.244(6.1);7.693(1.5);7.688(1.6);7.673(1.8);7.669(1.9);7.462(0.9);7.443(2.5);7.424(2.2);7.413(1.8);7.397(0.6);7.325(1.3);7.306(1.4);7.190(0.8);7.172(1.5);7.152(0.9);6.928(1.1);6.909(1.9);6.891(0.8);6.809(2.1);6.790(1.8);5.220(0.4);5.207(0.9);5.189(0.9);5.175(0.4);4.290(0.4);4.277(0.8);4.261(1.0);4.252(1.1);4.244(0.9);4.222(1.0);4.201(0.4);3.941(0.4);3.925(0.5);3.909(0.3);3.878(0.8);3.318(102.8);

Example 529: 1H-NMR(400.0 MHz, d6-DMSO):

-continued 3.165(11.6);2.944(1.4);2.924(2.5);2.905(1.3);2.674(2.2);2.670(3.1);2.666(2.4);2.523(7.3);2.505(393.8);2.501(528.8);2.497(393.7);2.321(15.3);2.287(0.3);2.217(0.4);2.204(0.4);2.193(0.6);2.182(0.7);2.169(0.6);2.156(0.6);2.123(0.4);2.094(16.0);2.074(4.3);2.055(0.7);2.049(0.7);2.034(0.6);2.020(0.5);1.233(0.5);0.146(0.4);0.008(2.7);0.000(87.7);−0.149(0.5)

Example 537: 1H-NMR(400.0 MHz, d6-DMSO):
δ = 9.171(1.6);9.151(1.7);8.548(7.2);7.533(0.4);7.522(2.0);7.517(2.5);7.499(2.5);7.493(2.0);7.482(0.4);7.360(1.6);7.342(1.7);7.202(0.8);7.199(0.8);7.191(0.6);7.185(2.0);7.182(2.0);7.162(2.5);7.144(0.6);7.139(0.8);7.133(0.4);6.946(1.2);6.928(2.0);6.911(1.0);6.909(0.9);6.816(2.3);6.796(2.1);5.265(0.4);5.250(1.0);5.231(1.1);5.217(0.5);4.315(0.4);4.308(0.4);4.296(0.9);4.287(0.8);4.280(1.0);4.272(0.7);4.258(0.7);4.251(0.9);4.236(0.8);4.230(1.1);4.209(0.4);4.202(0.3);3.322(22.8);2.671(0.3);2.636(16.0);2.619(0.7);2.611(1.5);2.603(0.6);2.597(0.8);2.589(0.8);2.575(0.4);2.506(37.8);2.502(48.8);2.497(35.2);2.248(0.3);2.235(0.5);2.223(0.7);2.214(0.7);2.201(0.7);2.188(0.5);2.095(0.5);2.087(0.7);2.081(0.8);2.067(0.6);2.053(0.5);2.046(0.5);1.485(0.7);1.475(2.0);1.469(2.6);1.461(2.7);1.454(2.2);1.446(0.9);1.397(4.7);1.241(0.8);1.231(2.3);1.225(2.3);1.217(1.2);1.210(2.3);1.203(2.3);1.194(0.6);0.008(0.6);0.000(15.1)

Example 538: 1H-NMR(400.0 MHz, d6-DMSO):
δ = 9.158(1.7);9.138(1.8);8.440(6.6);8.004(0.4);7.999(0.4);7.925(3.9);7.919(4.0);7.860(0.4);7.854(0.5);7.811(0.4);7.673(0.5);7.646(0.4);7.640(0.4);7.567(3.1);7.561(3.0);7.348(1.8);7.330(1.9);7.197(0.9);7.193(0.8);7.176(1.8);7.158(1.1);7.154(1.0);6.936(1.2);6.919(2.1);6.901(1.0);6.810(2.4);6.789(2.2);5.756(2.8);5.254(0.5);5.240(1.2);5.221(1.2);5.207(0.5);4.306(0.6);4.300(0.5);4.288(1.1);4.279(1.0);4.272(1.4);4.265(0.8);4.248(8.6);4.241(1.0);4.226(0.9);4.219(1.2);4.198(0.5);3.320(40.5);2.890(0.4);2.731(0.4);2.670(0.9);2.667(0.6);2.642(0.4);2.628(1.0);2.624(1.1);2.614(0.7);2.607(1.6);2.599(0.7);2.593(1.0);2.585(0.9);2.571(0.5);2.506(111.5);2.501(142.6);2.497(105.0);2.371(16.0);2.332(0.7);2.328(0.8);2.324(0.6);2.236(0.4);2.227(0.5);2.215(0.8);2.206(0.8);2.193(0.8);2.180(0.6);2.077(0.8);2.070(0.8);2.055(0.7);2.042(0.6);2.035(0.5);2.028(0.4);1.471(2.2);1.231(2.3);1.225(2.1);1.210(2.1);1.204(2.0);1.145(0.5);1.130(0.4);0.000(13.7)

Example 540: 1H-NMR(400.0 MHz, d6-DMSO):
δ = 9.128(1.0);9.107(1.5);9.084(0.8);8.277(4.8);8.273(4.9);7.697(2.0);7.692(1.9);7.678(2.3);7.673(2.5);7.466(1.0);7.447(3.2);7.428(3.6);7.420(2.3);7.406(0.8);7.337(1.2);7.319(1.3);7.195(0.7);7.190(0.6);7.176(1.4);7.162(0.7);7.157(0.9);6.939(0.7);6.930(0.8);6.920(1.3);6.911(1.3);6.904(0.7);6.895(0.6);6.812(2.4);6.791(2.2);5.224(0.5);5.210(1.1);5.191(1.1);5.177(0.5);4.288(0.7);4.260(1.4);4.252(1.4);4.231(1.1);4.223(0.9);4.216(0.8);4.210(0.8);4.189(0.4);4.181(0.4);4.138(0.7);3.343(0.4);3.320(55.7);3.293(1.1);3.274(0.6);3.182(7.3);3.166(8.0);3.112(0.5);3.096(0.5);3.080(0.4);3.065(0.5);3.051(0.5);3.046(0.5);3.032(0.6);3.013(0.4);2.675(0.4);2.670(0.6);2.589(10.6);2.528(9.0);2.506(80.4);2.501(106.4);2.497(77.8);2.337(16.0);2.208(0.4);2.196(0.6);2.184(0.7);2.174(0.9);2.162(0.7);2.153(0.5);2.074(7.5);2.061(0.9);2.045(0.7);2.032(0.5);2.025(0.5);0.146(0.6);0.008(5.7);0.000(135.5);−0.008(6.6);−0.150(0.6)

Example 541: 1H-NMR(400.0 MHz, d6-DMSO):
δ = 9.104(1.6);9.084(1.6);8.293(7.5);7.701(1.8);7.697(1.9);7.682(2.2);7.678(2.3);7.469(1.1);7.450(3.0);7.431(2.5);7.418(2.0);7.403(0.8);7.330(1.5);7.311(1.7);7.192(0.8);7.175(1.7);7.158(1.1);7.154(1.0);6.931(1.2);6.912(2.1);6.894(1.0);6.812(2.3);6.794(2.1);5.228(0.5);5.214(1.0);5.197(1.0);5.180(0.5);4.296(0.4);4.290(0.4);4.277(0.9);4.262(1.1);4.252(1.3);4.245(1.1);4.229(0.8);4.224(1.1);4.202(0.4);4.195(0.3);4.074(1.1);3.750(1.6);3.318(68.8);3.138(12.9);3.082(14.6);2.674(1.3);2.670(1.8);2.666(1.3);2.540(2.4);2.523(5.2);2.510(120.4);2.505(242.1);2.501(318.3);2.496(231.8);2.492(115.6);2.341(16.0);2.328(2.3);2.324(1.7);2.210(0.5);2.197(0.7);2.188(0.7);2.174(0.7);2.074(5.3);2.035(0.5);2.028(0.5);1.235(0.6);0.146(1.7);0.008(16.9);0.000(386.3);−0.008(19.8);−0.150(1.7)

Example 542: 1H-NMR(400.0 MHz, d6-DMSO):
δ = 9.071(0.4);9.004(1.8);8.984(1.8);8.439(4.8);7.841(8.4);7.836(8.5);7.471(2.4);7.466(4.2);7.462(2.3);7.317(1.7);7.298(1.7);7.194(0.9);7.177(1.8);7.159(1.1);7.156(1.1);6.933(1.3);6.914(2.2);6.896(1.1);6.815(2.5);6.795(2.3);5.223(0.5);5.207(1.2);5.190(1.2);5.175(0.5);4.276(1.9);4.267(2.7);4.258(1.7);3.320(93.3);3.236(0.7);2.670(1.2);2.635(0.5);2.597(16.0);2.505(152.0);2.501(195.4);2.497(144.2);2.328(1.1);2.175(0.4);2.152(0.6);2.139(0.9);2.124(0.8);2.111(0.4);2.084(0.4);2.071(0.9);2.060(0.9);2.044(0.6);2.036(0.6);2.025(0.4);2.021(0.4);1.398(13.5);0.835(0.4);0.796(1.3);0.783(1.6);0.766(1.2);0.751(0.6);0.735(0.8);0.725(0.6);0.713(0.6);0.702(1.3);0.693(1.3);0.684(1.3);0.670(1.2);0.662(0.8);0.146(1.0);0.007(10.5);0.000(217.1);−0.150(1.0)

Example 546: 1H-NMR(400.0 MHz, d6-DMSO):
δ = 9.071(0.6);9.068(0.6);8.972(1.9);8.953(1.9);8.315(0.5);8.290(4.6);7.952(0.4);7.677(1.9);7.658(2.3);7.454(1.1);7.435(2.9);7.416(2.9);7.406(3.1);7.390(1.2);7.285(2.2);7.266(2.4);7.184(1.2);7.165(2.2);7.146(1.3);6.916(1.5);6.897(2.5);6.879(1.2);6.805(2.8);6.784(2.5);5.755(3.7);5.223(0.6);5.209(1.4);5.191(1.5);4.256(3.5);3.318(46.8);3.266(1.0);2.890(1.8);2.731(1.8);2.672(1.8);2.541(3.0);2.501(317.0);2.421(0.5);2.386(0.9);2.328(2.0);2.303(16.0);2.159(0.6);2.141(0.9);2.125(1.3);2.112(1.2);2.062(1.1);2.049(1.2);2.027(0.8);2.017(0.6);1.989(0.4);1.235(0.6);0.780(2.0);0.739(1.4);0.706(1.6);0.676(1.5);0.146(0.9);0.000(180.5);−0.150(0.9)

Example 557: 1H-NMR(400.0 MHz, d6-DMSO):
δ = 9.164(2.7);9.144(2.8);8.490(11.4);8.315(0.4);7.607(0.6);7.599(0.7);7.591(0.7);7.584(1.1);7.578(1.1);7.571(0.7);7.562(1.1);7.557(1.1);7.551(0.7);7.543(0.6);7.534(0.5);7.352(2.6);7.334(2.8);7.302(1.4);7.292(1.4);7.280(1.3);7.200(1.3);7.196(1.5);7.178(2.7);7.161(1.6);7.157(1.6);6.940(2.0);6.922(3.3);6.903(1.6);6.811(3.7);6.791(3.2);5.257(0.8);5.244(1.7);5.224(1.7);5.210(0.8);4.318(0.6);4.311(0.7);4.303(0.7);4.292(1.4);4.283(1.4);4.276(1.5);4.268(1.1);4.250(1.2);4.243(1.5);4.228(1.3);4.222(1.8);4.200(0.7);4.194(0.6);3.318(101.4);2.674(2.1);2.670(2.8);2.666(2.0);2.639(0.6);2.625(1.3);2.617(1.4);2.611(1.0);2.604(2.5);2.596(1.1);2.589(1.5);2.582(1.5);2.567(1.1);2.505(353.7);2.501(462.4);2.497(342.2);2.501(0.8);2.454(16.0);2.437(0.9);2.332(2.6);2.324(1.9);2.328(2.6);2.324(1.9);2.244(0.5);2.232(0.8);2.218(1.1);2.209(1.1);2.196(1.1);2.184(0.8);2.081(1.1);2.075(1.2);2.060(0.9);2.047(0.8);2.040(0.8);1.484(1.2);1.474(3.3);1.468(4.2);1.460(4.3);1.454(3.6);1.445(1.4);1.398(0.5);1.258(0.3);1.240(1.5);1.232(4.0);1.225(3.8);1.210(3.7);1.204(3.8);1.193(1.0);0.146(0.7);0.008(55.8);0.000(143.4);−0.008(6.3);−0.150(0.6)

Experimental Section—Biological Assays

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: C. elegans Slo-1a—Action at a Recombinant C. elegans Cell Line Generation of a Stable C. elegans CHO Cell Line A CHO cell line was obtained from ATCC, code ATCC CRL-9096. For transfection with plasmid DNA to express C. elegans Slo-1a (accession number AAL28102) CHO cells were passaged to 40% confluence before adding the transfection solution to the cell culture. The transfection solution included 300 µL OptiMEM (Life Technologies, Nr.: 31985), 2 µL (=6 µg) of plasmid DNA containing the C. elegans Slo 1a gene and 9 µL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the C. elegans Slo-1a.

Cell Culture Conditions

Cells were cultured at 37° C. and 5% $CO_2$ in MEMalpha with Gutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

TABLE 4

$pE_{50}$ values of examples in in vitro assay 1

| Example No | $pE_{50}$ |
|---|---|
| 1 | 7.4 |
| 2 | 7.5 |
| 3 | 7.3 |
| 4 | 7.5 |
| 5 | 7.2 |
| 6 | 7.9 |
| 7 | 7.7 |
| 8 | 7.5 |
| 9 | 7.8 |
| 14 | 7.7 |
| 15 | 6.7 |
| 16 | 6.7 |
| 19 | 8 |
| 20 | 7.9 |
| 21 | 6.5 |
| 23 | 7.2 |
| 24 | 7.2 |
| 25 | 6.6 |
| 27 | 7.2 |
| 29 | 6.7 |
| 31 | 6.7 |
| 32 | 7.5 |
| 37 | 6.7 |
| 40 | 6.5 |
| 41 | 4.8 |
| 42 | 6.2 |
| 43 | 6.8 |
| 45 | 7.3 |
| 46 | 6.6 |
| 48 | 6.6 |
| 56 | 6.4 |
| 59 | 7.1 |
| 60 | 5.1 |
| 61 | 5.2 |
| 62 | 5.7 |
| 70 | 7.5 |
| 72 | 7.1 |
| 73 | 6.8 |
| 74 | 7.4 |
| 77 | 7.2 |
| 78 | 7.5 |
| 79 | 7.7 |
| 81 | 6.4 |
| 88 | 7.1 |
| 89 | 6.2 |
| 91 | 7.2 |
| 92 | 8.2 |
| 93 | 7 |
| 94 | 7.8 |
| 95 | 8.2 |
| 96 | 8.4 |
| 97 | 7.2 |
| 98 | 7.9 |
| 99 | 8 |
| 100 | 8.1 |
| 101 | 6.6 |
| 102 | 7.2 |
| 103 | 7.7 |
| 104 | 7 |
| 105 | 6.8 |
| 107 | 8.3 |
| 108 | 7.3 |
| 110 | 6.7 |
| 111 | 7.2 |

TABLE 4-continued pE$_{50}$ values of examples in in vitro assay 1

| Example No | pE$_{50}$ |
|---|---|
| 114 | 6.9 |
| 115 | 7.8 |
| 116 | 8 |
| 117 | 8.3 |
| 118 | 7.8 |
| 119 | 5.5 |
| 121 | 8.2 |
| 122 | 7.9 |
| 123 | 8 |
| 124 | 8.1 |
| 125 | 7.6 |
| 126 | 6.7 |
| 127 | 8 |
| 128 | 7.9 |
| 130 | 8.4 |
| 131 | 8.1 |
| 132 | 8.2 |
| 133 | 7.1 |
| 134 | 7.9 |
| 135 | 6.9 |
| 136 | 8.2 |
| 137 | 7.6 |
| 138 | 6.5 |
| 139 | 6.9 |
| 140 | 7.1 |
| 141 | 8.1 |
| 142 | 7.1 |
| 143 | 7.9 |
| 144 | 6.8 |
| 145 | 7.5 |
| 146 | 7.6 |
| 147 | 7.3 |
| 148 | 7.4 |
| 149 | 7.2 |
| 150 | 7.3 |
| 151 | 7.5 |
| 152 | 7.7 |
| 153 | 6.9 |
| 154 | 8.2 |
| 155 | 5.5 |
| 156 | 6.2 |
| 157 | 7 |
| 158 | 6.8 |
| 159 | 6 |
| 160 | 7 |
| 165 | 8.7 |
| 166 | 8.8 |
| 167 | 7.4 |
| 168 | 8.5 |
| 169 | 8.2 |
| 170 | 8.7 |
| 171 | 8.3 |
| 172 | 8 |
| 173 | 8.4 |
| 174 | 7.8 |
| 175 | 7.2 |
| 176 | 7.9 |
| 177 | 6.8 |
| 178 | 6.1 |
| 179 | 6.4 |
| 180 | 8.1 |
| 181 | 7.9 |
| 182 | 7.9 |
| 183 | 6.4 |
| 184 | 8.5 |
| 185 | 7.9 |
| 186 | 7.8 |
| 187 | 7.9 |
| 188 | 7.9 |
| 189 | 8.9 |
| 190 | 7.6 |
| 191 | 8.9 |
| 192 | 9.4 |
| 193 | 9.1 |
| 194 | 7.9 |
| 195 | 6.8 |
| 196 | 7.3 |
| 197 | 6.3 |
| 202 | 7.6 |
| 203 | 6.7 |
| 204 | 7.8 |
| 205 | 7.6 |
| 206 | 7.9 |
| 207 | 7.3 |
| 208 | 8.8 |
| 209 | 8.9 |
| 210 | 6.8 |
| 211 | 5.9 |
| 212 | 6.3 |
| 213 | 8.8 |
| 215 | 9.1 |
| 216 | 9.1 |
| 217 | 6.4 |
| 218 | 8.8 |
| 219 | 7.7 |
| 220 | 7.7 |
| 221 | 8 |
| 222 | 7.4 |
| 223 | 7.9 |
| 224 | 7.5 |
| 225 | 7.9 |
| 226 | 7.7 |
| 227 | 5.7 |
| 228 | 5.5 |
| 229 | 7.2 |
| 230 | 8.1 |
| 231 | 7.8 |
| 232 | 8.3 |
| 233 | 8.1 |
| 234 | 8.9 |
| 235 | 9.2 |
| 236 | 8.7 |
| 237 | 7.5 |
| 238 | 6.8 |
| 239 | 7.5 |
| 240 | 8.3 |
| 241 | 8.2 |
| 242 | 7.1 |
| 243 | 6.2 |
| 244 | 8.2 |
| 245 | 7.7 |
| 246 | 8.2 |
| 247 | 8 |
| 248 | 7.3 |
| 249 | 6.8 |
| 251 | 8.5 |
| 252 | 5.9 |
| 253 | 8.9 |
| 254 | 8.1 |
| 255 | 8.8 |
| 256 | 8.6 |
| 257 | 8.2 |
| 258 | 8.8 |
| 259 | 7.8 |
| 260 | 8.5 |
| 261 | 8.8 |
| 262 | 9.3 |
| 263 | 8.8 |
| 264 | 7.6 |
| 265 | 8.6 |
| 266 | 8.7 |
| 267 | 6.8 |
| 269 | 9 |
| 270 | 8.4 |
| 271 | 8.5 |
| 272 | 7.6 |
| 273 | 8.3 |
| 274 | 7.7 |
| 275 | 7.9 |
| 276 | 8 |
| 277 | 8.8 |
| 278 | 7.5 |

TABLE 4-continued pE$_{50}$ values of examples in in vitro assay 1

| Example No | pE$_{50}$ |
|---|---|
| 279 | 8.2 |
| 280 | 8.9 |
| 281 | 8.3 |
| 282 | 8.3 |
| 283 | 9.3 |
| 284 | 9.1 |
| 285 | 8 |
| 286 | 7.9 |
| 287 | 7.8 |
| 288 | 6.7 |
| 289 | 7.8 |
| 290 | 7.8 |
| 291 | 7.3 |
| 292 | 7.4 |
| 293 | 6.5 |
| 294 | 7.3 |
| 295 | 7.2 |
| 296 | 5.1 |
| 297 | 5.9 |
| 298 | 5.9 |
| 299 | 7.8 |
| 300 | 8.2 |
| 302 | 7.9 |
| 303 | 6.1 |
| 304 | 7.7 |
| 305 | 7.2 |
| 306 | 7.3 |
| 308 | 5.8 |
| 309 | 7.5 |
| 310 | 8 |
| 311 | 6.7 |
| 312 | 7.6 |
| 313 | 6.8 |
| 314 | 7.8 |
| 315 | 6.6 |
| 316 | 6.8 |
| 317 | 7.8 |
| 318 | 6 |
| 319 | 7.6 |
| 320 | 7.3 |
| 321 | 8 |
| 322 | 7.9 |
| 323 | 7.4 |
| 324 | 7.5 |
| 325 | 7.7 |
| 326 | 5.9 |
| 328 | 7.4 |
| 329 | 7.6 |
| 331 | 6.6 |
| 332 | 7.8 |
| 333 | 7 |
| 334 | 7.6 |
| 335 | 6.9 |
| 337 | 7.9 |
| 338 | 7.5 |
| 339 | 5.6 |
| 340 | 7.4 |
| 341 | 6.7 |
| 342 | 6.7 |
| 343 | 7.7 |
| 344 | 8.1 |
| 345 | 7.9 |
| 346 | 7.9 |
| 347 | 7.4 |
| 348 | 8.4 |
| 349 | 8.6 |
| 350 | 8 |
| 351 | 8.4 |
| 352 | 8.2 |
| 353 | 8.1 |
| 354 | 6.4 |
| 355 | 5.6 |
| 356 | 6.8 |
| 357 | 8.2 |
| 358 | 7.9 |
| 359 | 7.9 |
| 360 | 7.9 |
| 361 | 7.8 |
| 362 | 7 |
| 363 | 7.2 |
| 364 | 8 |
| 365 | 5.5 |
| 366 | 5.8 |
| 367 | 6.8 |
| 368 | 5.6 |
| 369 | 7.7 |
| 370 | 7.8 |
| 372 | 7.8 |
| 373 | 7.4 |
| 374 | 7.3 |
| 375 | 6.7 |
| 376 | 8.1 |
| 377 | 7.8 |
| 378 | 7.3 |
| 379 | 7 |
| 380 | 6 |
| 381 | 8 |
| 388 | 8.1 |
| 389 | 6.6 |
| 390 | 7.4 |
| 391 | 7.6 |
| 392 | 8 |
| 393 | 8 |
| 394 | 7.8 |
| 395 | 8.1 |
| 396 | 7.8 |
| 398 | 7.7 |
| 399 | 5.1 |
| 400 | 6.9 |
| 401 | 7.9 |
| 402 | 7.7 |
| 403 | 6.8 |
| 405 | 8.5 |
| 407 | 6.9 |
| 408 | 6.5 |
| 413 | 6.6 |
| 417 | 8.1 |
| 418 | 8.5 |
| 419 | 8.1 |
| 420 | 8.1 |
| 421 | 8.1 |
| 422 | 8.4 |
| 423 | 7.2 |
| 424 | 8.6 |
| 425 | 7.1 |
| 427 | 7.7 |
| 428 | 7.6 |
| 429 | 7.4 |
| 430 | 7.8 |
| 431 | 8.2 |
| 432 | 7.5 |
| 433 | 8 |
| 434 | 8.1 |
| 435 | 7.6 |
| 436 | 8.8 |
| 437 | 8.8 |
| 438 | 8.9 |
| 439 | 8.2 |
| 440 | 7.9 |
| 441 | 8 |
| 442 | 8.7 |
| 443 | 7.3 |
| 444 | 7.8 |
| 445 | 8.7 |
| 446 | 7.9 |
| 447 | 6.4 |
| 448 | 8.5 |
| 449 | 8.2 |
| 450 | 8.5 |
| 451 | 8.1 |
| 452 | 8.6 |
| 453 | 8.6 |

TABLE 4-continued pE$_{50}$ values of examples in in vitro assay 1

| Example No | pE$_{50}$ |
|---|---|
| 454 | 8.4 |
| 455 | 8.2 |
| 456 | 8.2 |
| 457 | 8.9 |
| 458 | 8.8 |
| 459 | 8 |
| 460 | 7.4 |
| 461 | 8.7 |
| 462 | 8.2 |
| 463 | 8.1 |
| 464 | 8.5 |
| 465 | 8 |
| 466 | 8 |
| 467 | 9.4 |
| 468 | 7.8 |
| 469 | 7.8 |
| 470 | 8.1 |
| 471 | 8.4 |
| 472 | 8.8 |
| 473 | 9.3 |
| 474 | 8.2 |
| 475 | 8.7 |
| 476 | 8.2 |
| 477 | 8.2 |
| 478 | 8.2 |
| 479 | 8.2 |
| 480 | 8.9 |
| 481 | 7.7 |
| 482 | 9.2 |
| 483 | 7.8 |
| 484 | 8.6 |
| 485 | 8.2 |
| 486 | 8.4 |
| 487 | 7.7 |
| 488 | 8.2 |
| 489 | 8.8 |
| 490 | 8.3 |
| 491 | 8.3 |
| 492 | 8.9 |
| 493 | 8.7 |
| 494 | 8.5 |
| 495 | 8.3 |
| 496 | 8.9 |
| 497 | 8 |
| 498 | 8.3 |
| 499 | 8.5 |
| 500 | 7.7 |
| 501 | 6.3 |
| 502 | 8.6 |
| 503 | 7.9 |
| 504 | 8.9 |
| 505 | 8.5 |
| 506 | 8.1 |
| 507 | 8.1 |
| 508 | 8.2 |
| 509 | 8.9 |
| 510 | 8.6 |
| 511 | 8.4 |
| 512 | 8.9 |
| 516 | 8.3 |
| 517 | 9.2 |
| 518 | 9 |
| 520 | 8.1 |
| 522 | 7.8 |
| 523 | 8.0 |
| 524 | 8.9 |
| 525 | 7.1 |
| 527 | 7.5 |
| 528 | 5.9 |
| 529 | 8.1 |
| 530 | 9.0 |
| 531 | 9.0 |
| 532 | 9.0 |
| 533 | 8.9 |
| 534 | 8.5 |
| 535 | 8.6 |
| 536 | 8.3 |
| 537 | 8.3 |
| 538 | 9.5 |
| 539 | 6.8 |
| 540 | 7.7 |
| 541 | 8.0 |
| 542 | 6.5 |
| 543 | 8.6 |
| 544 | 8.3 |
| 545 | 8.8 |
| 546 | 8.2 |
| 547 | 8.9 |
| 548 | 8.2 |
| 549 | 8.4 |
| 550 | 8.7 |
| 551 | 8.9 |
| 552 | 8.7 |
| 553 | 8.2 |
| 554 | 8.7 |
| 555 | 7.6 |
| 557 | 8.7 |
| 560 | 8.2 |
| 561 | 8.2 |

In Vitro Assay 2: *Nippostrongylus brasiliensis* (NIPOBR)

Adult *Nippostrongylus brasiliensis* were washed with saline buffer containing 100 U/ml penicillin, 0.1 mg/ml streptomycin and 2.5 µg/ml amphotericin B. Test compounds were dissolved in DMSO and worms were incubated in medium in a final concentration of 10 µg/ml (10 ppm) respectively 1 µg/ml (1 ppm). An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChE compared to negative control) was higher than 80% at 10 µg/ml: 96, 127, 128, 130, 136, 141, 152, 166, 170, 184, 186, 188, 189, 192, 194, 206, 208, 209, 213, 215, 216, 219, 230, 232, 233, 234, 235, 236, 240, 241, 242, 244, 246, 253, 255, 257, 258, 260, 261, 262, 263, 265, 280, 282, 283, 284, 294, 310, 317, 359, 374, 376, 377, 392, 393, 401, 403, 419, 436, 440, 442, 451, 453, 459, 461, 467, 468, 470, 473, 474, 477, 478, 479, 481, 482, 483, 489, 490, 491, 496, 507, 516, 517, 518.

For the following examples, activity (reduction of AChE compared to negative control) was higher than 80% at 1 µg/ml: 136, 152, 192, 194, 208, 209, 215, 216, 230, 233, 234, 235, 236, 240, 241, 244, 246, 255, 258, 260, 261, 262, 263, 280, 283, 284, 436, 461, 472, 473, 475, 481, 482, 489, 496, 516, 517, 518, 531, 533, 538, 543, 545, 550, 551.

In Vitro Assay 3: *Dirofilaria immitis* Microfilariae (DIROIM L1)

≥250 *Dirofilaria immitis* microfilariae, which were freshly purified from blood, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as EC$_{50}$-values were calculated.

For the following examples, the EC50 was <10 ppm: 3, 42, 49, 77, 93, 102, 137, 138, 142, 143, 144, 145, 148, 149, 150, 155, 156, 157, 158, 159, 160, 161, 162, 163, 164, 175, 177, 178, 179, 183, 195, 196, 197, 198, 199, 200, 201, 202, 203, 207, 211, 212, 214, 217, 227, 238, 239, 242, 243, 248, 250, 252, 267, 268, 278, 286, 288, 294, 297, 298, 308, 309, 312, 313, 320, 329, 331, 334, 341, 342, 343, 354, 355, 356, 359, 362, 363, 365, 366, 367, 368, 369, 374, 375, 376, 377, 380, 389, 390, 399, 400, 401, 407, 408, 410, 411, 412, 414, 415, 416, 419, 420, 421, 423, 425, 426, 427, 429, 431, 433, 443, 444, 446, 447, 460, 466, 468, 470, 500, 501, 513, 514, 515, 519, 521, 525, 526, 527, 528, 539, 556.

For the following examples, the EC50 was <1 ppm: 4, 6, 8, 9, 14, 19, 24, 40, 74, 97, 111, 125, 133, 151, 182, 185, 187, 188, 190, 206, 210, 219, 220, 221, 223, 224, 228, 229, 231, 232, 233, 236, 237, 240, 241, 244, 245, 247, 249, 254, 258, 259, 260, 264, 265, 266, 269, 270, 271, 272, 274, 275, 287, 289, 290, 300, 304, 315, 317, 319, 321, 322, 332, 340, 344, 345, 347, 348, 358, 360, 361, 364, 370, 372, 373, 378, 379, 388, 391, 398, 413, 430, 440, 441, 451, 453, 459, 461, 474, 476, 477, 478, 481, 483, 487, 488, 491, 497, 498, 499, 502, 503, 504, 507, 508, 509, 510, 511, 512, 522, 523, 542, 543, 544, 546, 547, 555.

For the following examples, the EC50 was <0.1 ppm: 20, 45, 78, 79, 92, 94, 95, 96, 98, 99, 100, 103, 104, 107, 108, 115, 116, 117, 118, 121, 122, 127, 128, 130, 131, 132, 134, 135, 136, 139, 140, 141, 146, 147, 152, 153, 154, 165, 166, 168, 169, 170, 171, 172, 173, 174, 176, 180, 181, 184, 186, 189, 191, 192, 193, 194, 204, 205, 208, 209, 213, 215, 216, 218, 222, 225, 226, 230, 234, 235, 246, 251, 253, 255, 256, 257, 261, 262, 263, 273, 276, 277, 279, 280, 281, 282, 283, 284, 285, 299, 302, 314, 322, 323, 324, 325, 337, 346, 349, 350, 351, 352, 353, 357, 381, 392, 393, 394, 395, 396, 402, 403, 405, 417, 418, 422, 424, 428, 432, 434, 435, 436, 437, 438, 439, 442, 445, 448, 449, 450, 452, 454, 455, 456, 457, 458, 462, 463, 464, 465, 467, 469, 471, 472, 473, 475, 479, 480, 482, 484, 485, 486, 489, 490, 492, 493, 494, 495, 496, 505, 506, 516, 517, 518, 520, 524, 529, 530, 531, 532, 533, 534, 535, 536, 537, 538, 540, 541, 545, 548, 549, 550, 551, 552, 553, 554.

In Vitro Assay 4: *Dirofilaria immitis* (DIROIM L4)

10 *Dirofilaria immitis* third-stage larvae, which were freshly isolated from their vector (intermediate host), were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Within these 72 h of incubation the majority of larvae in negative control moult to fourth-stage larvae. Efficacy was determined as the reduction of motility in comparison to the negative control. Based on the evaluation of a wide concentration range, concentration-response curves as well as EC50-values were calculated.

For the following examples, the EC50 was <1 ppm: 4, 45, 152, 323, 337, 344, 348, 350, 353, 358, 364.

For the following examples, the EC50 was <0.1 ppm: 20, 79, 92, 95, 96, 98, 99, 100, 103, 107, 108, 116, 117, 121, 127, 128, 130, 131, 132, 134, 136, 141, 147, 153, 154, 165, 166, 168, 169, 170, 171, 172, 173, 184, 186, 189, 191, 192, 193, 194, 208, 209, 213, 215, 216, 226, 230, 232, 233, 234, 235, 236, 241, 244, 246, 253, 255, 256, 258, 261, 262, 263, 279, 280, 283, 300, 302, 317, 324, 325, 349, 351, 352, 357, 395, 396, 402, 403, 405, 422, 424, 434, 436, 437, 438, 442, 445, 448, 450, 452, 457, 458, 461, 463, 465, 467, 472, 473, 474, 475, 480, 482, 489, 496, 516, 517, 518, 524, 531, 533, 534, 535, 538, 545, 549, 552, 554.

In Vitro Assay 5: *Cooperia curticei* (COOPCU)

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 nematode larvae (*Cooperia curticei*) are transferred into a test tube containing the compound solution.

After 5 days percentage of larval mortality is recorded. 100% efficacy means all larvae are killed; 0% efficacy means no larvae are killed.

In this test for example, the following compounds from the preparation examples showed good activity of 100% at an application rate of 20 ppm: 192, 215, 235, 283, 481, 482, 489, 517, 518, 531, 532, 545.

In this test for example, the following compounds from the preparation examples showed good activity of 90% at an application rate of 20 ppm: 187, 234, 240, 244, 255, 260, 262, 401, 461, 473, 474, 477, 484, 548.

In this test for example, the following compounds from the preparation examples showed good activity of 80% at an application rate of 20 ppm: 6, 216, 232, 256, 261, 299, 436, 453, 472, 478, 479, 505, 547.

In Vitro Assay 6: *Haemonchus contortus* (HAEMCO)

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days the percentage of larval mortality is recorded. 100% efficacy means all larvae are killed, 0% efficacy means no larvae are killed.

In this test for example, the following compounds from the preparation examples showed good activity of 100% at an application rate of 20 ppm: 215, 235, 283, 481, 482, 517, 518, 531, 545.

In this test for example, the following compounds from the preparation examples showed good activity of 90% at an application rate of 20 ppm: 192, 234, 255, 489, 532, 548.

In this test for example, the following compounds from the preparation examples showed good activity of 80% at an application rate of 20 ppm: 187, 216, 256, 260, 401, 436, 461, 477, 478, 484.

In this test for example, the following compounds from the preparation examples showed good activity of 80% at an application rate of 4 ppm: 253, 472.

In Vitro Assay 7: *Litomosoides sigmodontis* L3 (LTMOSI)

10 *Litomosoides sigmodontis* third-stage larvae, which were freshly isolated from the pleural cavity of an infected rodent, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <1 ppm: 4, 6, 20, 290

For the following examples, the $EC_{50}$ was <0.1 ppm: 4, 8, 19, 45, 79, 92, 95, 96, 98, 99, 100, 103, 107, 108, 116, 117, 121, 127, 128, 130, 131, 132, 134, 136, 141, 147, 152, 153, 154, 166, 168, 169, 170, 171, 173, 184, 186, 189, 191, 192, 193, 194, 208, 213, 215, 216, 226, 230, 232, 233, 234, 235, 236, 241, 244, 246, 253, 255, 256, 258, 262, 283, 287, 289, 300, 302, 317, 323, 324, 325, 337, 349, 351, 352, 353, 357, 395, 396, 402, 403, 405, 422, 424, 436, 437, 438, 442, 452, 457, 458, 461, 465, 467, 472, 473, 474, 475, 482, 489, 517, 518, 531, 533, 534, 535, 538, 545, 549, 552.

Formulation Example

Exemplary formulations consisted of the active substance in 10% Transcutol, 10% Cremophor EL and 80% isotonic saline solution. First the active substance was dissolved in Transcutol. After solution in Transcutol, Cremophor and isotonic saline solution were added. These formulations were used as service formulations in the following in vivo assay.

An example for a formulation according to the present invention is the following Formulation Example 1. Therein, the active substance was dissolved in Transcutol to form a Stock solution A. Then 0.200 mL of this Stock solution A were taken and 0.200 mL Cremophor EL and 1.600 mL isotonic saline solution were added. The resulting liquid formulation (Formulation Example 1) had a volume of 2 mL.

Stock Solution A:

| | |
|---|---|
| 5.1 mg | compound of Example 255, |
| 0.255 mL | Transcutol. |

Formulation Example 1

| | |
|---|---|
| 0.200 mL | Stock solution A, |
| 0.200 mL | Cremophor EL, and |
| 1.600 mL | isotonic saline solution. |

In Vivo Assay

*Haemonchus contortus/Trichostrongylus colubriformis*/Gerbil

Gerbils, experimentally infected with *Haemonchus* and/or *Trichostrongylus*, were treated once during late prepatency. Test compounds were formulated as solutions or suspensions and applied orally or intraperitoneally. For both applications the same service formulation was used. The volume of the application amounted to normally 5 ml/kg and 10 ml/kg at a maximum. By way of example, a gerbil with 40 g body weight was treated with 0.200 mL of the formulation of Formulation Example 1. This corresponded to a treatment with 10 mg/kg body weight.

Efficacy was determined per group as reduction of worm count in stomach and small intestine, respectively, after necropsy compared to worm count in an infected and placebo-treated control group.

The following examples were tested and had an activity of 80% or higher at the given treatment:

| Treatment | Haemonchus | Trichostrongylus |
|---|---|---|
| ≤50 mg/kg orally | 96, 130, 152 | 96, 130, 152 |
| ≤20 mg/kg intraperitoneally | 96, 130, 136, 166, 168, 170, 189, 208, 213, 215, 232, 233, 234, 255, 260, 262, 263, 283, 457, 458, 461, 472, 473, 474, 475, 481, 538 | 232, 461, 474, 481 |

The invention claimed is:

1. A method for control or treatment of a helminthic disease in a human or animal, the method comprising administering to a human or animal in need thereof an anthelminthically effective amount of at least one compound of formula (I)

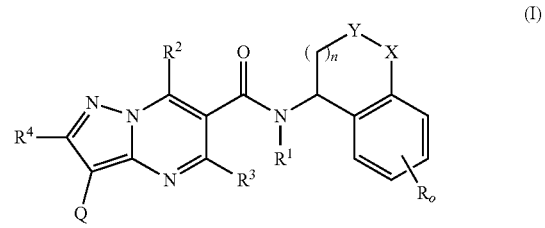

or a stereoisomer, a tautomer, an N-oxide, a hydrate, a solvate, or a salt thereof, or a mixture of any of the foregoing, wherein:

o is 0, 1, 2, 3 or 4;

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogeno alkyl, —S(O)—$C_1$-$C_4$-halogeno alkyl and —$SO_2$—$C_1$-$C_4$-halogenoalkyl having 1 to 5 halogen atoms;

n is 0 or 1;

X and Y are independently selected from the group consisting of $CR^5R^6$, O, S, and N—$R^7$, wherein at least one of X and Y is $CR^5R^6$;

$R^1$ is selected from the group consisting of hydrogen, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, amino-$C_1$-$C_4$-alkyl, $C_1$-$C_4$-alkylamino-$C_1$-$C_4$-alkyl, di-($C_1$-$C_4$-alkyl)amino-$C_1$-$C_4$-alkyl, $C_1$-$C_4$-alkylcarbonyl, $C_1$-$C_4$-halogenoalkylcarbonyl having 1 to 5 halogen atoms, $C_1$-$C_4$-alkoxycarbonyl, benzyloxycarbonyl, $C_1$-$C_4$-alkoxy-$C_1$-$C_4$-alkylcarbonyl, —$SO_2$—$C_1$-$C_4$-alkyl, and —$SO_2$—$C_1$-$C_4$-halogenoalkyl having 1 to 5 halogen atoms;

$R^2$ is hydrogen, halogen, cyano, —CHO, $C_1$-$C_4$-alkyl, $C_2$-$C_4$-alkenyl, $C_2$-$C_4$-alkynyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, benzyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH(4- to 7-membered heterocycloalkyl), —N($C_1$-$C_4$-alkyl)(4- to 7-membered heterocycloalkyl), —NH($C_1$-$C_4$-alkoxy), —N($C_1$-$C_4$-alkyl)($C_1$-$C_4$-alkoxy), —NH—$SO_2$—($C_1$-$C_4$-alkyl), —N($SO_2$—[$C_1$-$C_4$-alkyl])($C_1$-$C_4$-alkyl), ($C_1$-$C_4$-alkyl)-NH—$C_1$-$C_4$-alkyl, ($C_1$-$C_4$-alkyl)$_2$-N—$C_1$-$C_4$-alkyl, —S—$C_1$-$C_4$-alkyl, —S(O)—$C_1$-$C_4$-alkyl, —$SO_2$—$C_1$-$C_4$-alkyl, ($C_1$-$C_4$-alkoxyimino)-$C_1$-$C_4$-alkyl, or a monocyclic heterocycle selected from the group consisting of 4- to 7-membered heterocycloalkyl, 5-membered heteroaryl having at least one nitrogen atom via which the heteroaryl ring is connected to the rest of the molecule, and 6-membered heteroaryl having at least one nitrogen atom, each of which monocyclic heterocycle in $R^2$ is optionally substituted with 1, 2 or 3 substituents independently selected from the group consisting of hydrogen, halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, and wherein each $C_1$-$C_4$-alkyl, $C_3$-$C_6$-cycloalkyl and $C_1$-$C_4$-alkoxy in $R^2$ is optionally substituted with halogen, —OH, —$NH_2$, —NH($C_1$-$C_4$-alkyl), —N($C_1$-$C_4$-alkyl)$_2$, cyano, carboxy, carbamoyl, alkoxycarbonyl, —C(O)—NH($C_1$-$C_4$-alkyl), —C(O)—N($C_1$-$C_4$-alkyl)$_2$, —C(O)—NH($C_3$-$C_6$-cycloalkyl), $C_1$-$C_4$-alkoxy, —S—$C_1$-$C_4$-alkyl, —S(O)—$C_1$-$C_4$-alkyl, or —$SO_2$—$C_1$-$C_4$-alkyl, or optionally substituted by a monocyclic heterocycle selected from the group consisting of 4- to 7-membered heterocycloalkyl and a 5-membered heteroaryl having at least one nitrogen atom via which the heteroaryl ring is connected to the $C_1$-$C_4$-alkyl or $C_3$-$C_6$-cycloalkyl, each of which is optionally substituted with 1, 2 or 3 substituents independently selected from the group consisting of hydrogen, halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms;

$R^3$ is selected from the group consisting of hydrogen, halogen, $C_1$-$C_4$-alkyl, $C_1$-$C_4$-halogenoalkyl having 1 to 5 halogen atoms, and $C_3$-$C_6$-cycloalkyl;

$R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, and —$SO_2$—$C_1$-$C_4$-alkyl;

$R^5$ is selected from the group consisting of hydrogen, fluorine and $C_1$-$C_4$-alkyl;

$R^6$ is selected from the group consisting of hydrogen, fluorine and $C_1$-$C_4$-alkyl;

$R^7$ is selected from the group consisting of hydrogen and $C_1$-$C_4$-alkyl; and Q is selected from the group consisting of 6- or 10-membered aryl and 5- to 10-membered heteroaryl, each of which is optionally substituted with 1, 2, 3, 4 or 5 substituents.

2. The method of claim 1, wherein:

o is 0, 1, 2, 3, or 4;

R is selected from the group consisting of hydrogen, halogen, $C_1$-$C_4$-alkyl and $C_1$-$C_4$-halogenoalkyl having 1 to 5 halogen atoms;

n is 0 or 1;

X and Y are independently selected from the group consisting of $CR^5R^6$, O, S, and N—$R^7$, wherein at least one of X and Y is $CR^5R^6$;

$R^1$ is selected from the group consisting of hydrogen, $C_1$-$C_4$-alkyl, $C_3$-$C_6$-cycloalkyl, $C_1$-$C_4$-alkylcarbonyl, $C_1$-$C_4$-alkoxycarbonyl, $C_3$-$C_4$-alkenyl, $C_3$-$C_4$-alkynyl, and $C_1$-$C_4$-alkoxy-$C_1$-$C_4$-alkyl;

$R^2$ is hydrogen, halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, benzyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH(4- to 7-membered heterocycloalkyl), —N($C_1$-$C_4$-alkyl)(4- to 7-membered heterocycloalkyl), —NH($C_1$-$C_4$-alkoxy), —N($C_1$-$C_4$-alkyl)($C_1$-$C_4$-alkoxy), —NH—$SO_2$—($C_1$-$C_4$-alkyl), —N($SO_2$—[$C_1$-$C_4$-alkyl])($C_1$-$C_4$-alkyl), ($C_1$-$C_4$-alkyl)-NH—$C_1$-$C_4$-alkyl, ($C_1$-$C_4$-alkyl)$_2$-N—$C_1$-$C_4$-alkyl, —S—$C_1$-$C_4$-alkyl, —S(O)—$C_1$-$C_4$-alkyl, —$SO_2$—$C_1$-$C_4$-alkyl, ($C_1$-$C_4$-alkoxyimino)-$C_1$-$C_4$-alkyl, or a monocyclic heterocycle selected from the group consisting of 4- to 7-membered heterocycloalkyl, 5-membered heteroaryl having at least one nitrogen atom via which the heteroaryl ring is connected to the rest of the molecule, and 6-membered heteroaryl having at least one nitrogen atom, each of which monocyclic heterocycle in $R^2$ is optionally substituted with 1, 2 or 3 substituents independently selected from the group consisting of hydrogen, halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, and wherein each $C_1$-$C_4$-alkyl, $C_3$-$C_6$-cycloalkyl and $C_1$-$C_4$-alkoxy in $R^2$ is optionally substituted with halogen, —OH, —$NH_2$, —NH($C_1$-$C_4$-alkyl), —N($C_1$-$C_4$-alkyl)$_2$, cyano, carboxy, carbamoyl, alkoxycarbonyl, —C(O)—NH($C_1$-$C_4$-alkyl), —C(O)—N($C_1$-$C_4$-alkyl)$_2$, $C_1$-$C_4$-alkoxy, —S—$C_1$-$C_4$-alkyl, —S(O)—$C_1$-$C_4$-alkyl, or —$SO_2$—$C_1$-$C_4$-alkyl, or optionally substituted by a monocyclic heterocycle selected from the group consisting of azetidine, pyrrolidine, morpholine, piperidine, piperazine, pyrrolidinone, morpholinone, piperidinone, piperazinone, pyrazole, triazole, imidazole and pyrrole, wherein a heteroaryl ring is connected to the $C_1$-$C_4$-alkyl or $C_3$-$C_6$-cycloalkyl via one of its nitrogen atoms, each of which as a substituent of $C_1$-$C_4$-alkyl, $C_3$-$C_6$-cycloalkyl and $C_1$-$C_4$-alkoxy in $R^2$ is optionally substituted with 1, 2 or 3 substituents independently selected from the group consisting of hydrogen, halogen, cyano, oxo, $C_1$-$C_4$-alkyl, and $C_1$-$C_4$-halogenoalkyl having 1 to 5 halogen atoms;

$R^3$ is selected from the group consisting of hydrogen, halogen, $C_1$-$C_4$-alkyl, $C_1$-$C_4$-halogenoalkyl having 1 to 5 halogen atoms, and $C_3$-$C_6$-cycloalkyl;

$R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, and —SO$_2$—$C_1$-$C_4$-alkyl;

$R^5$ is selected from the group consisting of hydrogen, fluorine and $C_1$-$C_4$-alkyl;

$R^6$ is selected from the group consisting of hydrogen, fluorine and $C_1$-$C_4$-alkyl;

$R^7$ is selected from the group consisting of hydrogen and $C_1$-$C_4$-alkyl; and Q is selected from the group consisting of 6- or 10-membered aryl and 5- to 10-membered heteroaryl, each of which is optionally substituted with 1, 2, 3, 4 or 5 substituents.

3. The method of claim 1, wherein:

o is 0, 1, 2, 3 or 4;

R is selected from the group consisting of hydrogen, fluorine, chlorine, and $C_1$-$C_4$-alkyl;

n is 0 or 1;

X and Y are independently selected from the group consisting of $CR^5R^6$, O, S, and N—$R^7$, wherein at least one of X and Y is $CR^5R^6$;

$R^1$ is selected from the group consisting of hydrogen and $C_1$-$C_4$-alkyl;

$R^2$ is hydrogen, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, benzyl having 1 to 5 halogen atoms, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —N($C_1$-$C_4$-alkyl)(6-membered heterocycloalkyl), —N($C_1$-$C_4$-alkyl)($C_1$-$C_4$-alkoxy), ($C_1$-$C_4$-alkyl)$_2$-N—$C_1$-$C_4$-alkyl, or 4- to 6-membered heterocycloalkyl having at least one nitrogen atom via which the heterocycloalkyl ring is connected to the rest of the molecule, wherein a heterocycloalkyl group in $R^2$ is optionally substituted with 1 to 4 substituents selected from the group consisting of fluorine, chlorine, cyano, oxo, $C_1$-$C_4$-alkyl, $C_1$-$C_4$-alkoxy, and —N($C_1$-$C_4$-alkyl)$_2$, and wherein each $C_1$-$C_4$-alkyl, $C_3$-$C_6$-cycloalkyl and $C_1$-$C_4$-alkoxy in $R^2$ is optionally substituted with halogen, —OH, —NH$_2$, —NH($C_1$-$C_4$-alkyl), —N($C_1$-$C_4$-alkyl)$_2$, cyano, carboxy, carbamoyl, alkoxycarbonyl, —C(O)—NH($C_1$-$C_4$-alkyl), —C(O)—N($C_1$-$C_4$-alkyl)$_2$, $C_1$-$C_4$-alkoxy, —S—$C_1$-$C_4$-alkyl, —S(O)—$C_1$-$C_4$-alkyl, or —SO$_2$—$C_1$-$C_4$-alkyl, or optionally substituted by a monocyclic heterocycle selected from the group consisting of azetidine, pyrrolidine, morpholine, piperidine, and piperazine, each of which as a substituent of $C_1$-$C_4$-alkyl, $C_3$-$C_6$-cycloalkyl and $C_1$-$C_4$-alkoxy in $R^2$ is optionally substituted with 1, 2 or 3 substituents independently selected from the group consisting of hydrogen, halogen, cyano, oxo, $C_1$-$C_4$-alkyl, and $C_1$-$C_4$-halogenoalkyl having 1 to 5 halogen atoms;

$R^3$ is selected from the group consisting of hydrogen and $C_1$-$C_4$-alkyl;

$R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, and —SO$_2$—$C_1$-$C_4$-alkyl;

$R^5$ is hydrogen or methyl;

$R^6$ is hydrogen or methyl;

$R^7$ is hydrogen or methyl; and

Q is a substituted phenyl ring of formula (Q1)

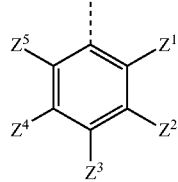

(Q1)

wherein:

$Z^1$, $Z^2$, $Z^3$, $Z^4$, and $Z^5$ are independently hydrogen, halogen, SF$_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, —O—($C_3$-$C_6$-cycloalkyl), cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl and cyano, 5-membered heteroaryl having at least one nitrogen atom via which the heteroaryl ring is connected to the rest of the molecule, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with $C_1$-$C_4$-halogenoalkoxy having 1 to 5 halogen atoms, methyl substituted with $C_3$-$C_6$-cycloalkyl-$C_1$-$C_4$-alkoxy, methyl substituted with a 4- to 6-membered heterocycloalkyl which itself is optionally substituted with 1 or 2 substituents selected from the group consisting of fluorine, methyl and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogeno-alkyl), —S(O)—($C_1$-$C_4$-halogenoalkyl), —SO$_2$—($C_1$-$C_4$-halogenoalkyl), —S—($C_1$-$C_4$-cycloalkyl), —S(O)—($C_1$-$C_4$-cycloalkyl), —SO$_2$—($C_1$-$C_4$-cycloalkyl), —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), or —NHCO($C_1$-$C_4$-halogenoalkyl) having 1 to 5 halogen atoms, or $Z^1$ and $Z^2$ are taken together with the carbon atoms to which they are attached to form a 5- or 6-membered heterocycloalkyl, a 5-membered heteroaryl, or a 6-membered heteroaryl, each of which is optionally substituted with one or two substituents selected from the group consisting of methyl, fluoro and oxo, and $Z^3$, $Z^4$, and $Z^5$ are independently hydrogen, halogen, SF$_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl and cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl and cyano, —CH$_2$—S—(C$_1$-C$_4$-alkyl), —CH$_2$—S(O)—(C$_1$-C$_4$-alkyl), —CH$_2$—SO$_2$—(C$_1$-C$_4$-alkyl), —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl), —S(O)—(C$_1$-C$_4$-halogenoalkyl), —SO$_2$—(C$_1$-C$_4$-halogenoalkyl), —CONH(C$_1$-C$_4$-alkyl), —CONH(C$_3$-C$_6$-cycloalkyl), —NHCO(C$_1$-C$_4$-alkyl), —NHCO(C$_3$-C$_6$-cycloalkyl), or —NHCO(C$_1$-C$_4$-halogenoalkyl) having 1 to 5 halogen atoms, or Z$^2$ and Z$^3$ are taken together with the carbon atoms to which they are attached to form a 5- or 6-membered cycloalkyl or heterocycloalkyl, a 5-membered heteroaryl, or a 6-membered heteroaryl, each of which is optionally substituted with one or two substituents selected from the group consisting of methyl, fluoro and oxo, and Z$^1$, Z$^4$, and Z$^5$ are independently hydrogen, halogen, SF$_5$, cyano, —CHO, nitro, C$_1$-C$_4$-alkyl, C$_1$-C$_4$-halogenoalkyl having 1 to 5 halogen atoms, hydroxy, C$_1$-C$_4$-alkoxy, C$_3$-C$_6$-cycloalkyl-C$_1$-C$_4$-alkoxy, cyano-C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, —NH—SO$_2$—(C$_1$-C$_4$-alkyl), —N(SO$_2$—[C$_1$-C$_4$-alkyl])(C$_1$-C$_4$-alkyl), (C$_1$-C$_4$-alkoxyimino)-C$_1$-C$_4$-alkyl, 4- to 6-membered heterocycloalkyl which is optionally substituted with 1 or 2 substituents selected from the group consisting of fluorine, methyl and cyano, —CH$_2$—O—(C$_1$-C$_4$-alkyl), —CH$_2$—NH(C$_1$-C$_4$-alkyl), —CH$_2$—N(C$_1$-C$_4$-alkyl)$_2$, methyl substituted with a 4- to 6-membered heterocycloalkyl which itself is optionally substituted with 1 or 2 substituents selected from the group consisting of fluorine, methyl and cyano, —CH$_2$—S—(C$_1$-C$_4$-alkyl), —CH$_2$—S(O)—(C$_1$-C$_4$-alkyl), —CH$_2$—SO$_2$—(C$_1$-C$_4$-alkyl), —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl), —S(O)—(C$_1$-C$_4$-halogenoalkyl), —SO$_2$—(C$_1$-C$_4$-halogenoalkyl), —CONH(C$_1$-C$_4$-alkyl), —CONH(C$_3$-C$_6$-cycloalkyl), —NHCO(C$_1$-C$_4$-alkyl), —NHCO(C$_3$-C$_6$-cycloalkyl), or —NHCO(C$_1$-C$_4$-halogenoalkyl) having 1 to 5 halogen atoms, or Q is a pyridine ring of formula (Q2)

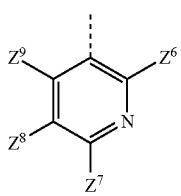

(Q2)

wherein:

Z$^6$, Z$^7$, Z$^8$ and Z$^9$ are independently selected from the group consisting of hydrogen fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), and —N(C$_1$-C$_4$-alkyl)$_2$, or Q is a pyrimidine ring of formula (Q3)

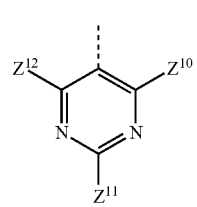

(Q3)

wherein:

Z$_{10}$, Z$^{11}$ and Z$^{12}$ are independently selected from the group consisting of hydrogen, fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH(C$_1$-C$_4$-alkyl), and —N(C$_1$-C$_4$-alkyl)$_2$, or Q is a pyridine ring of formula (Q4)

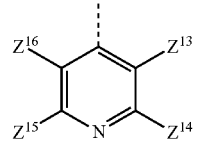

(Q4)

wherein:

Z$^{13}$, Z$^{14}$, Z$^{15}$ and Z$^{16}$ are independently hydrogen, fluorine, chlorine, bromine, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, —NH$_2$, —NH(C$_1$-C$_4$-alkyl), —N(C$_1$-C$_4$-alkyl)$_2$, —NH—CO—C$_1$-C$_4$-alkyl, or a monocyclic heterocycle selected from the group consisting of 4- to 7-membered heterocycloalkyl and 5-membered heteroaryl having at least one nitrogen atom via which the heteroaryl ring is connected to the pyridine ring, each of which monocyclic heterocycle is optionally substituted with 1, 2 or 3 substituents independently selected from the group consisting of hydrogen, halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogeno-alkyl having 1 to 5 halogen atoms, or Q is a pyridine ring of formula (Q5)

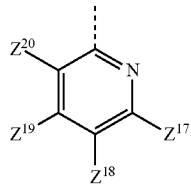

(Q5)

wherein:

$Z^{17}$, $Z^{18}$, $Z^{19}$, and $Z^{20}$ are independently selected from the group consisting of hydrogen, fluorine, chlorine, bromine, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q a pyrazole ring of formula (Q6)

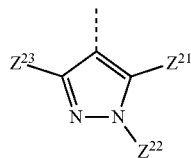

(Q6)

wherein:

$Z^{21}$ and $Z^{23}$ are independently selected from the group consisting of hydrogen, $C_1$-$C_4$-alkyl, and $C_1$-$C_4$-halogenoalkyl having 1 to 5 halogen atoms, and $Z^{22}$ is selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, ($C_1$-$C_4$-alkyl)$_2$-N—$C_1$-$C_4$-alkyl, morpholino-$C_1$-$C_4$-alkyl, and ($C_1$-$C_4$-alkyl)-NH—$C_1$-$C_4$-alkyl, or Q is a pyrazole ring of formula (Q7)

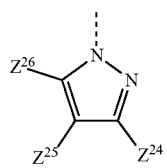

(Q7)

wherein:

$Z^{24}$, $Z^{25}$ and $Z^{26}$ are independently selected from the group consisting of hydrogen, fluorine, chlorine, bromine, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms.

4. The method of claim 1, wherein:

o is 0 or 1;

R is selected from the group consisting of hydrogen, fluorine, chlorine, and $C_1$-$C_4$-alkyl;

n is 0 or 1;

X and Y are independently selected from the group consisting of $CH_2$ and O, wherein at least one of X and Y is $CH_2$;

$R^1$ is hydrogen;

$R^2$ is hydrogen, $C_1$-$C_4$-alkyl, $C_3$-$C_6$-cycloalkyl, $C_1$-$C_4$-fluoroalkyl having 1 to 5 fluorine atoms, $C_1$-$C_4$-alkoxy-$C_1$-$C_4$-alkyl, benzyl having 1 to 5 halogen atoms, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —N($C_1$-$C_4$-alkyl)(6-membered heterocycloalkyl), —N($C_1$-$C_4$-alkyl)($C_1$-$C_4$-alkoxy), morpholino optionally substituted with 1 to 2 $C_1$-$C_4$-alkyl groups, or $C_1$-$C_4$-alkyl-N($C_1$-$C_4$-alkyl)$_2$, wherein each $C_1$-$C_4$-alkyl in $R^2$ is optionally substituted with halogen, —N($C_1$-$C_4$-alkyl)$_2$, $C_1$-$C_4$-alkoxy which itself is optionally substituted with $C_1$-$C_2$-alkoxy-substituted $C_1$-$C_2$-alkoxy, —S—$C_1$-$C_4$-alkyl, —S(O)—$C_1$-$C_4$-alkyl, —$SO_2$—$C_1$-$C_4$-alkyl, or optionally substituted by a monocyclic 4- to 7-membered heterocycloalkyl, which itself is optionally substituted with methyl or oxo;

$R^3$ is selected from the group consisting of hydrogen and $C_1$-$C_4$-alkyl;

$R^4$ is selected from the group consisting of hydrogen, halogen, $C_1$-$C_4$-alkyl, $C_1$-$C_4$-halogenoalkyl having 1 to 5 halogen atoms, $C_3$-$C_6$-cycloalkyl, —S—$C_1$-$C_4$-alkyl, —S(O)—$C_1$-$C_4$-alkyl, and —$SO_2$—$C_1$-$C_4$-alkyl; and Q is a substituted phenyl ring of formula (Q1)

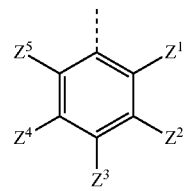

(Q1)

wherein:

$Z^1$, $Z^2$, $Z^3$, $Z^4$, and $Z^5$ are independently hydrogen, fluorine, chlorine, bromine, cyano, methyl, propyl, difluoromethyl, trifluoromethyl, hydroxy, methoxy, ethoxy, isopropoxy, —O-cyclopropyl, —$OCH_2$-cyclopropyl, —$OCH_2CN$, trifluoromethoxy, difluoromethoxy, trifluoroethoxy, methylamino, dimethylamino, methyl-ethylamino, diethylamino, acetylamino, methylsulfonamide, trifluoroacetylamino, —$SO_2Me$, —$SO_2$-cyclopropyl, —$CH_2$—O-methyl, —$CH_2$—O-ethyl, —$CH_2$—$OCH_2$-cyclopropyl, —$CH_2$—O-isopropyl, —$CH_2$—N($CH_3$)$_2$, —$CH_2$—N($CH_2CH_3$)$_2$, —$CH_2$—N($CH_3$)($CH_2CH_3$), —$CH_2$—$SCH_3$, —$CH_2$—S(O)$CH_3$, —$CH_2$—$SO_2$—$CH_3$, —C(O)NH-cyclopropyl,

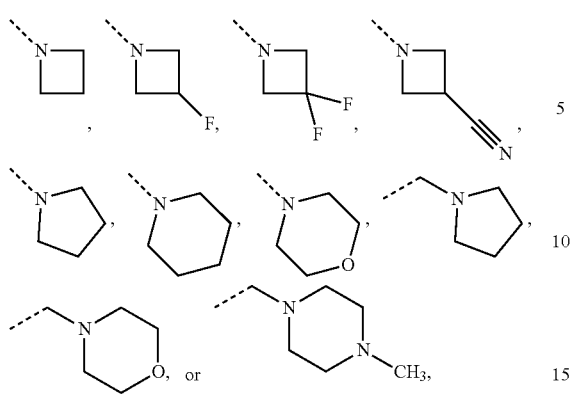

or $Z^1$ and $Z^2$ are taken together with the carbon atoms to which they are attached to form a 5-membered heterocycloalkyl or a 5-membered heteroaryl, each of which is optionally substituted with one or two substituents selected from the group consisting of methyl, fluorine and oxo, and $Z^3$, $Z^4$, and $Z^5$ are independently hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methylethylamino, diethylamino, acetylamino, methylsulfonamide, trifluoroacetylamino, —SO$_2$Me, —SO$_2$-cyclopropyl, —CH$_2$—O—methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl,

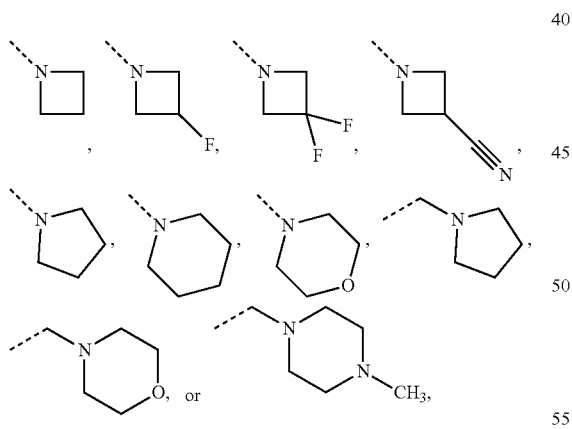

or $Z^2$ and $Z^3$ are taken together with the carbon atoms to which they are attached to form a 5-membered cycloalkyl, a 5-membered heterocycloalkyl or a 5-membered heteroaryl, each of which is optionally substituted with one or two substituents selected from the group consisting of methyl, fluorine and oxo, and $Z^1$, $Z^4$, and $Z^5$ are independently hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methylethylamino, diethylamino, acetylamino, methylsulfonamide, trifluoroacetylamino, —SO$_2$Me, —SO$_2$-cyclopropyl, —CH$_2$—O—methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl,

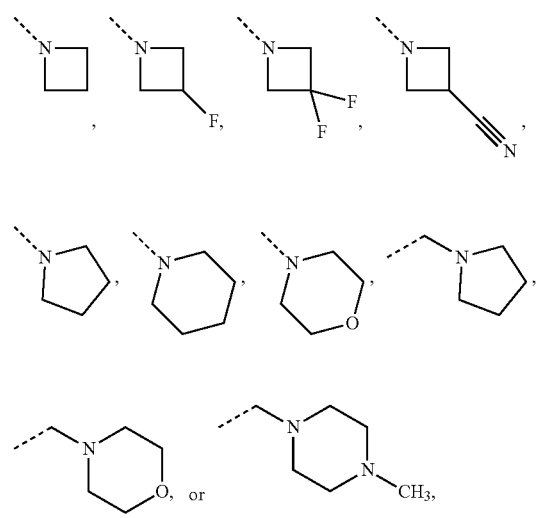

or

Q is a pyridine ring of formula (Q2)

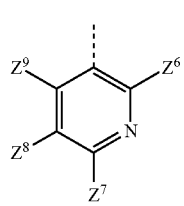

(Q2)

wherein:

$Z^6$, $Z^7$, $Z^8$ and $Z^9$ are independently selected from the group consisting of hydrogen, fluorine and chlorine, or Q is a pyrimidine ring of formula (Q3)

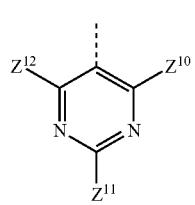

(Q3)

wherein:

$Z^{10}$, $Z^{11}$ and $Z^{12}$ are independently selected from the group consisting of hydrogen, fluorine, chlorine, and $C_1$-$C_4$-alkyl, or Q is a pyridine ring of formula (Q4)

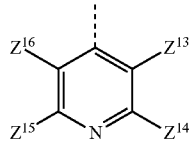

(Q4)

wherein:

$Z^{13}$, $Z^{14}$, $Z^{15}$ and $Z^{16}$ are independently hydrogen, fluorine, chlorine, $C_1$-$C_4$-alkyl, $NH_2$, —$NH(C_1$-$C_4$-alkyl), —$N(C_1$-$C_4$-alkyl)$_2$, —NH—CO—$C_1$-$C_4$-alkyl, morpholino, pyrazole, triazole, imidazole or pyrrole, wherein a heteroaryl ring is connected to the pyridine ring via one of its nitrogen atoms, each of which is optionally substituted with 1, 2 or 3 substituents independently selected from the group consisting of hydrogen, halogen, cyano, $C_1$-$C_4$-alkyl, and $C_1$-$C_4$-halogenoalkyl having 1 to 5 halogen atoms, or Q is a pyridine ring of formula (Q5)

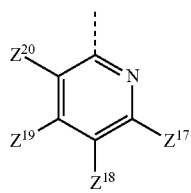

(Q5)

wherein:

$Z^{17}$, $Z^{18}$, $Z^{19}$ and $Z^{20}$ are independently selected from the group consisting of hydrogen, fluorine, chlorine, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, or Q a pyrazole ring of formula (Q6)

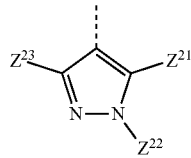

(Q6)

wherein:

$Z^{21}$ and $Z^{23}$ are each hydrogen, and $Z^{22}$ is selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, $C_1$-$C_4$-alkyl-$N(C_1$-$C_4$-alkyl)$_2$, and morpholino-$C_1$-$C_4$-alkyl, or Q is a pyrazole ring of formula (Q7)

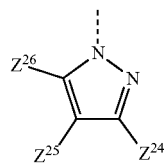

(Q7)

wherein:

$Z^{24}$, $Z^{25}$ and $Z^{26}$ are independently selected from the group consisting of hydrogen, fluorine, chlorine, cyano, methyl, and triflouromethyl.

5. The method according to claim 1, wherein:

o is 0 or 1;

R is selected from the group consisting of hydrogen, fluorine, chlorine, and methyl;

n is 0 or 1;

X is selected from the group consisting of $CH_2$ and O;

Y is $CH_2$;

$R^1$ is hydrogen;

$R^2$ is selected from the group consisting of hydrogen, methyl, ethyl, isopropyl, isobutyl, sec-butyl, cyclopropyl, methoxymethyl, difluoromethyl, trifluoromethyl, 4-fluorobenzyl, methoxy, methylamino, dimethylamino, cyclopropylamino, —$N(CH_3)$(cyclopropyl), —$N(CH_3)(CH_2$—$N(CH_3)_2)$, —$N(CH_3)(CH_2$—$CHF_2)$, —$N(CH_3)((CH_2)_2O(CH_2)_2)O(CH_2)_2)OCH_3)$, —$N(CH_3)((CH_2)_2$—S—$CH_3)$, —$N(CH_3)((CH_2)_2$—S(O)—$CH_3)$, —$N(CH_3)((CH_2)_2$—$SO_2$—$CH_3)$, —$N(CH_3)$(1-methyl-piperidin-4-yl), —$N(CH_3)((CH_2)_2$-(oxopyrrolidin-1-yl)), morpholino, and $CH_2$—N$(CH_3)_2$;

$R^3$ is selected from the group consisting of hydrogen and methyl;

$R^4$ is selected from the group consisting of hydrogen, chlorine, methyl, cyclopropyl, difluoromethyl, trifluoromethyl, —S-methyl, —S-ethyl, —S-isopropyl, —$S(O)_2$-methyl, —$S(O)_2$-ethyl, and —$S(O)_2$-isopropyl; and Q is a substituted phenyl ring of formula (Q1)

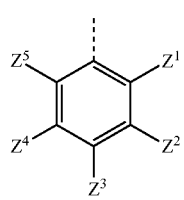

(Q1)

wherein:

$Z^1$, $Z^2$, $Z^3$, $Z^4$, and $Z^5$ are independently hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methyl-ethylamino, diethylamino, acetylamino, methylsulfonamide, trifluoroacetylamino, —SO$_2$Me, —SO$_2$-cyclopropyl, —CH$_2$—O—methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl,

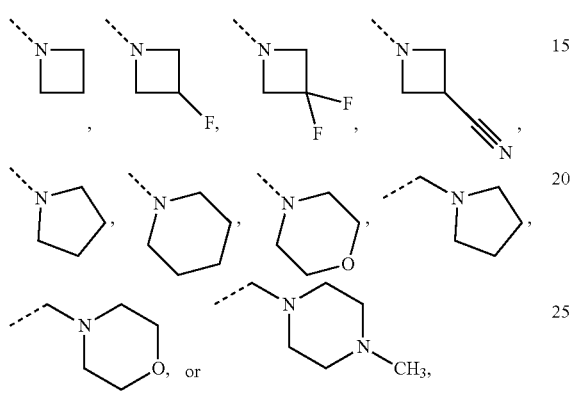

wherein at least two of $Z^1$, $Z^2$, $Z^3$, $Z^4$, and $Z^5$ are hydrogen, or

Q is a pyridine ring of formula (Q2)

(Q2)

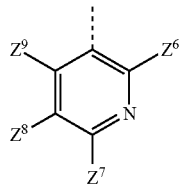

wherein:

$Z^6$ is hydrogen;

$Z^7$ and $Z^8$ are independently selected from the group consisting of hydrogen, fluorine, and chlorine, and $Z^9$ is selected from the group consisting of hydrogen and chlorine, or Q is a pyrimidine ring of formula (Q3)

(Q3)

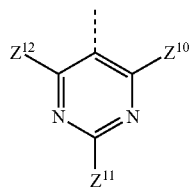

wherein:

$Z^{10}$ and $Z^{12}$ are each hydrogen, and $Z^{11}$ is selected from the group consisting of hydrogen and chlorine, or Q is a pyridine ring of formula (Q4)

(Q4)

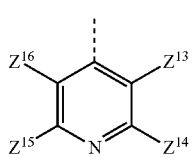

wherein:

$Z^{13}$, $Z^{15}$, and $Z^{16}$ are each hydrogen, and $Z^{14}$ is selected from the group consisting of hydrogen, chlorine, —NH$_2$, —NH—CO—C$_1$-C$_4$-alkyl, —NH(C$_1$-C$_4$-alkyl), —N(C$_1$-C$_4$-alkyl)$_2$, and morpholino, or Q is a pyridine ring of formula (Q5)

(Q5)

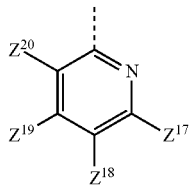

wherein:

$Z^{17}$ is selected from the group consisting of fluorine, chlorine, methoxy, and trifluoromethyl, $Z^{18}$ and $Z^{20}$ are independently selected from the group consisting of hydrogen and chlorine, and $Z^{19}$ is hydrogen, or Q a pyrazole ring of formula (Q6)

(Q6)

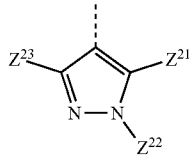

wherein:

$Z^{21}$ and $Z^{23}$ are each hydrogen, and $Z^{22}$ is selected from the group consisting of hydrogen, methyl, ethyl, isopropyl, methoxyethyl, —CH$_2$-cyclopropyl, —CH$_2$CF$_3$, —CH$_2$CHF$_2$, —CH$_2$-morpholino, —CH$_2$—CH$_2$—N(CH$_3$)$_2$, and —CH$_2$—CH$_2$-morpholino, or Q is a pyrazole ring of formula (Q7)

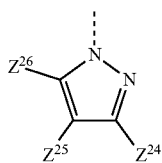

(Q7)

wherein:

$Z^{24}$ and $Z^{26}$ are each hydrogen, and $Z^{25}$ is selected from the group consisting of hydrogen and chlorine, or Q is selected from the group consisting of

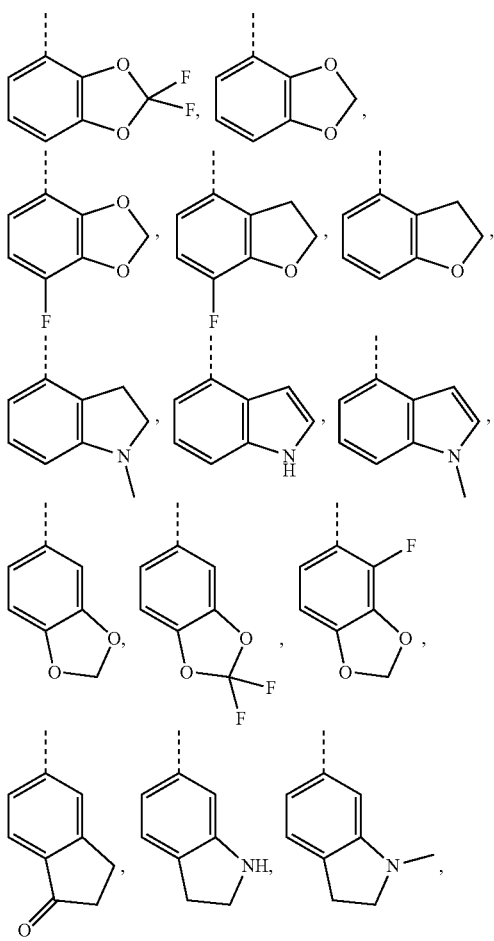

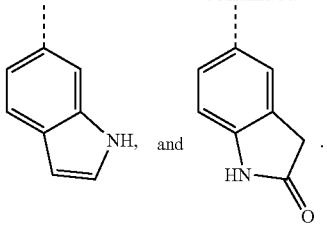

6. The method of claim 1, wherein:

o is 0 or 1;

R is selected from the group consisting of hydrogen, fluorine, chlorine, and methyl;

n is 0 or 1;

X is selected from the group consisting of CH$_2$ and O;

Y is CH$_2$;

$R^1$ is hydrogen;

$R^2$ is selected from the group consisting of hydrogen, methyl, ethyl, isopropyl, isobutyl, sec-butyl, cyclopropyl, methoxymethyl, difluoromethyl, trifluoromethyl, 4-fluorobenzyl, methoxy, methylamino, dimethylamino, cyclopropylamino, —N(CH$_3$)(cyclopropyl), —N(CH$_3$)(CH$_2$—N(CH$_3$)$_2$), —N(CH$_3$)(CH$_2$—CHF$_2$), —N(CH$_3$)((CH$_2$)$_2$O(CH$_2$)$_2$)O(CH$_2$)$_2$)OCH$_3$), —N(CH$_3$)((CH$_2$)$_2$—S—CH$_3$), —N(CH$_3$)((CH$_2$)$_2$—S(O)—CH$_3$), —N(CH$_3$)((CH$_2$)$_2$—SO$_2$—CH$_3$), —N(CH$_3$)(1-methyl-piperidin-4-yl), —N(CH$_3$)((CH$_2$)$_2$-(oxopyrrolidin-1-yl)), morpholino, and CH$_2$—N(CH$_3$)$_2$;

$R^3$ is selected from the group consisting of hydrogen and methyl;

$R^4$ is selected from the group consisting of hydrogen, chlorine, methyl, cyclopropyl, difluoromethyl, trifluoromethyl, —S-methyl, —S-ethyl, —S-isopropyl, —S(O)$_2$-methyl, —S(O)$_2$-ethyl, and —S(O)$_2$-isopropyl; and Q is a substituted phenyl ring of formula (Q1)

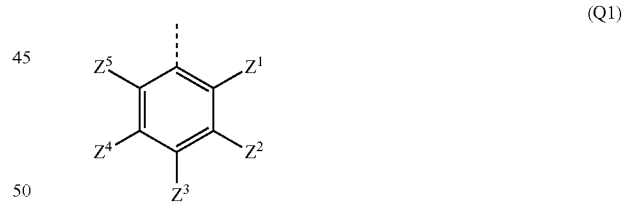

(Q1)

wherein:

$Z^1$, $Z^2$, $Z^3$, $Z^4$, and $Z^5$ are independently hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methyl-ethylamino, diethylamino, acetylamino, methylsulfonamide, trifluoroacetylamino, —SO$_2$Me, —SO$_2$-cyclopropyl, —CH$_2$—O-methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl, 283
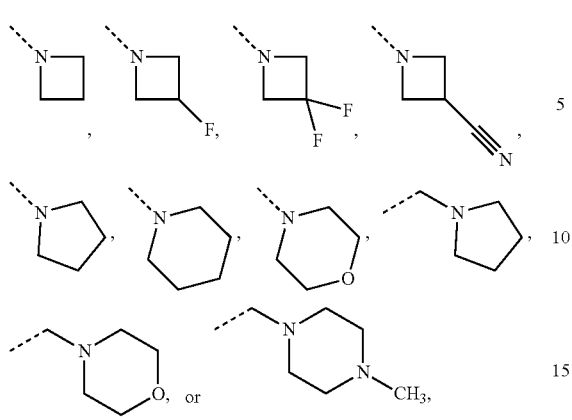
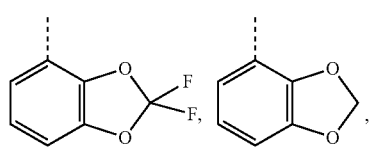
wherein at least two of $Z^1$, $Z^2$, $Z^3$, $Z^4$, and $Z^5$ are hydrogen,
or
Q is selected from the group consisting of
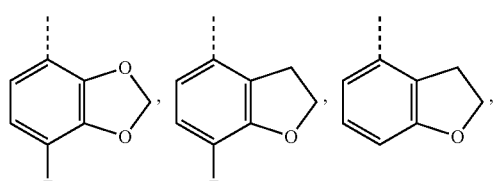
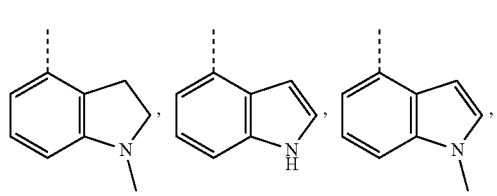
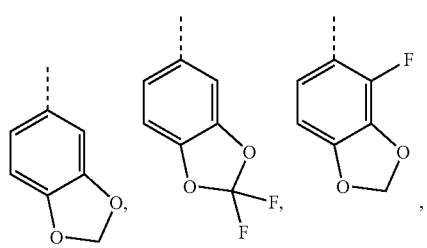
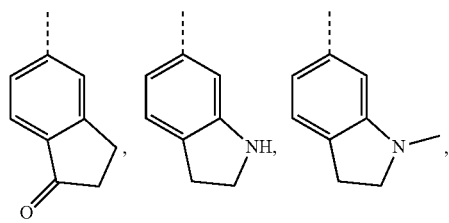
284
-continued
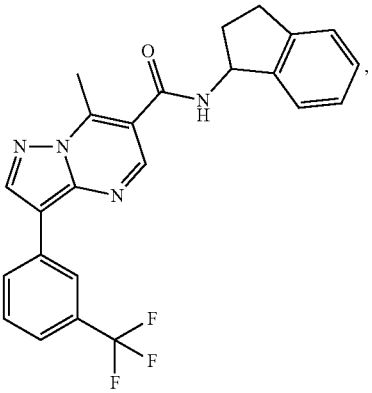
7. The method of claim 1, wherein the compound of formula (I) is not:
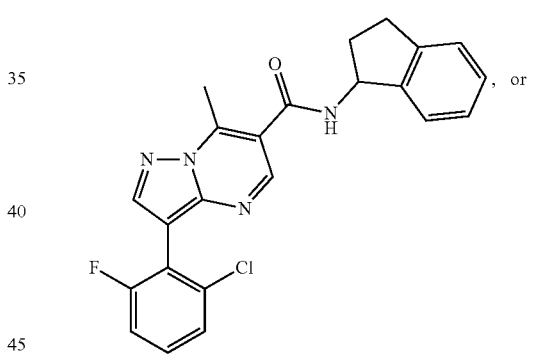
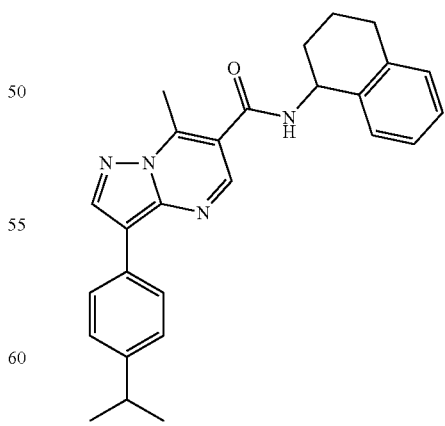
or a stereoisomer, a tautomer, an N-oxide, a hydrate, a solvate, or a salt thereof, or a mixture of any of the foregoing.

8. The method of claim 1, wherein the compound of formula (I) is selected from the group consisting of:
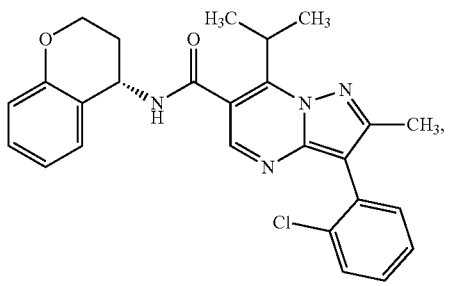
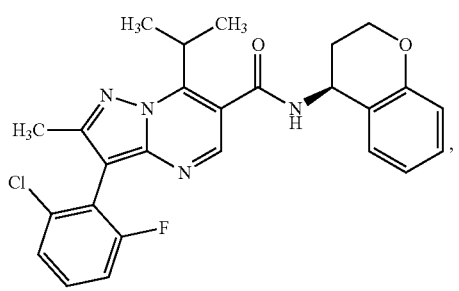
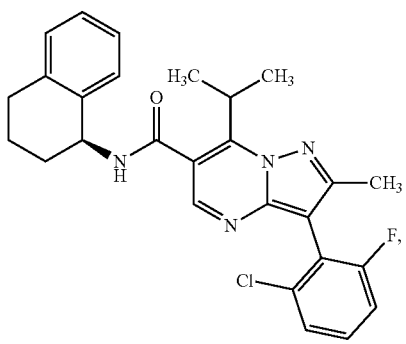
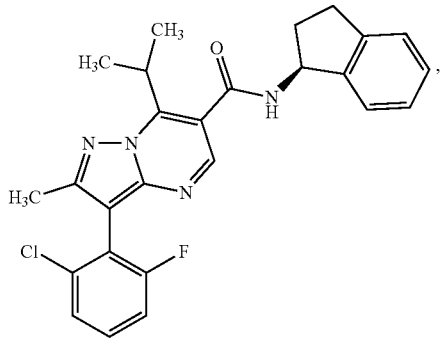
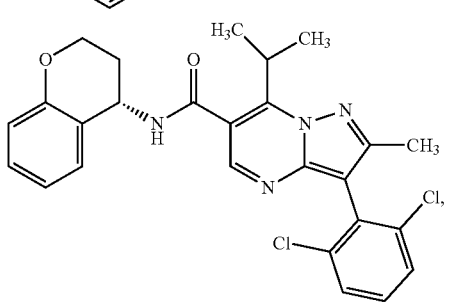
-continued
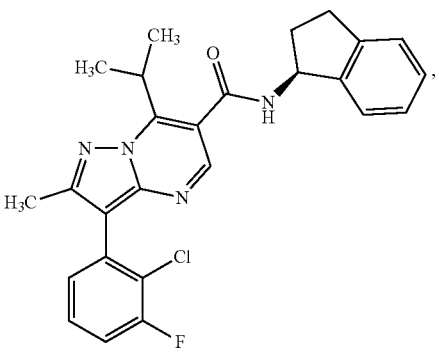
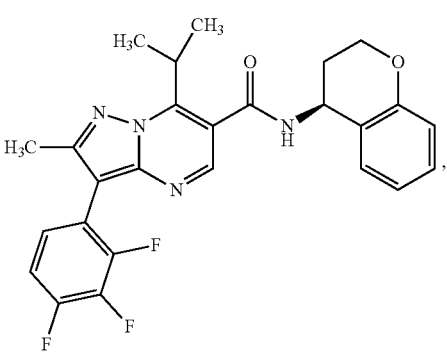
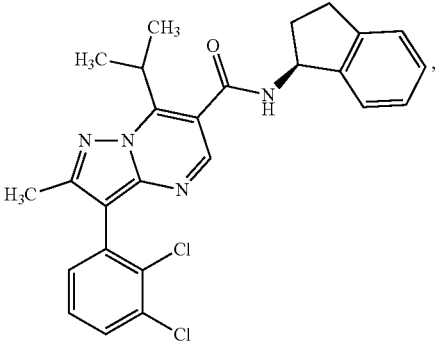
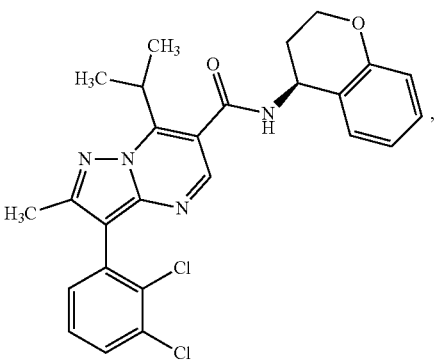

-continued
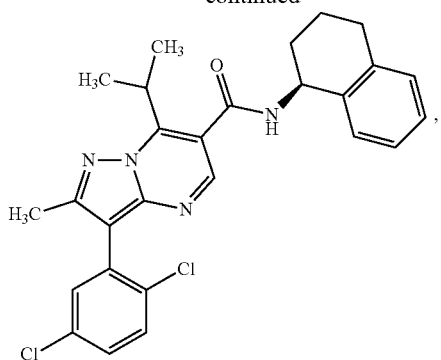
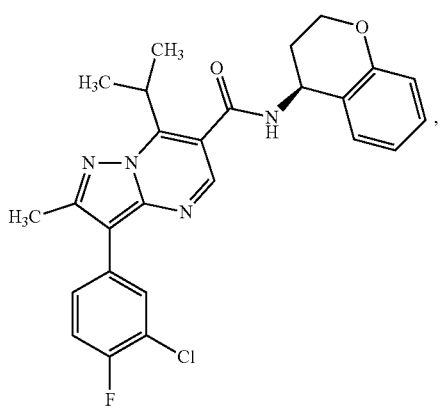
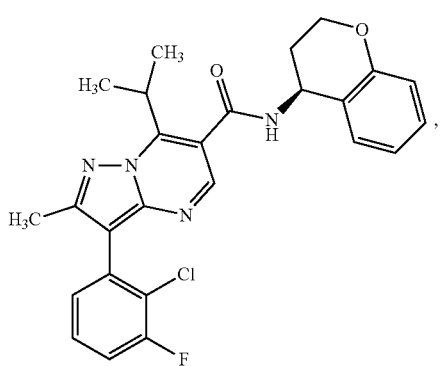
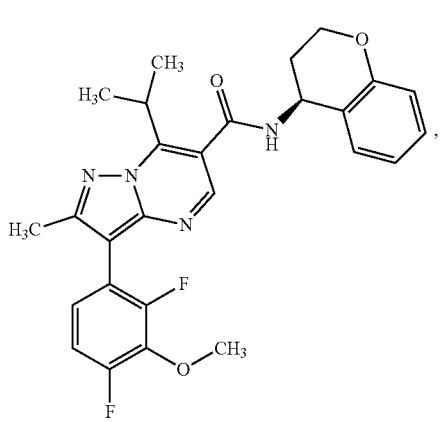
-continued
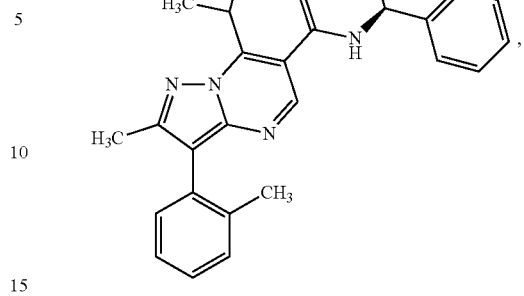
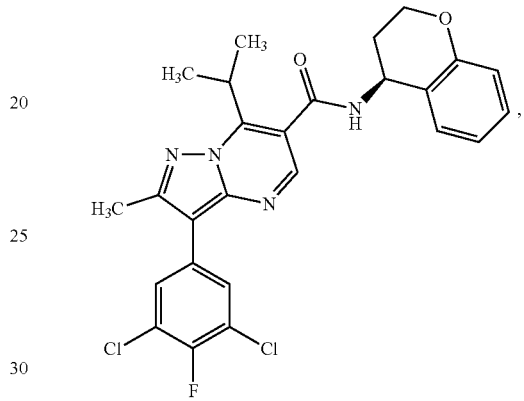
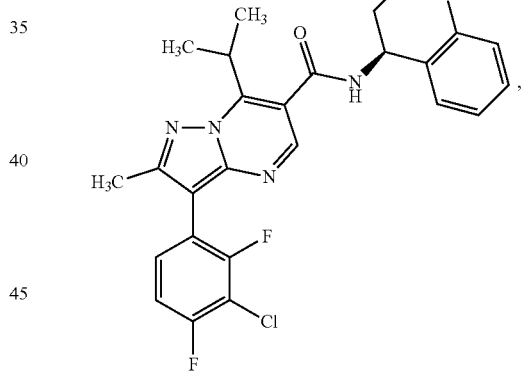
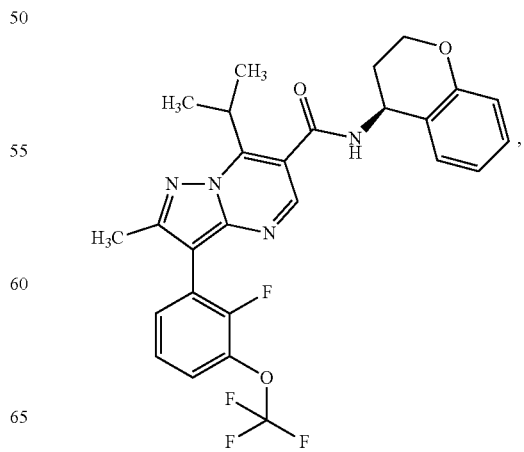

289
-continued
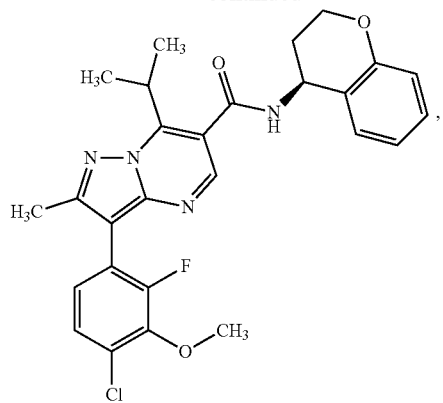
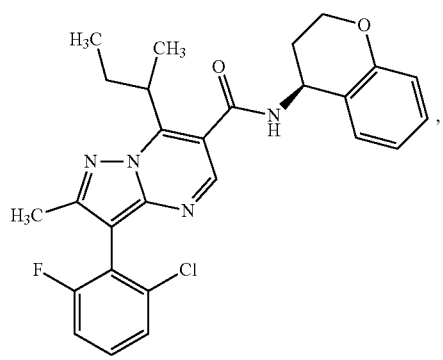
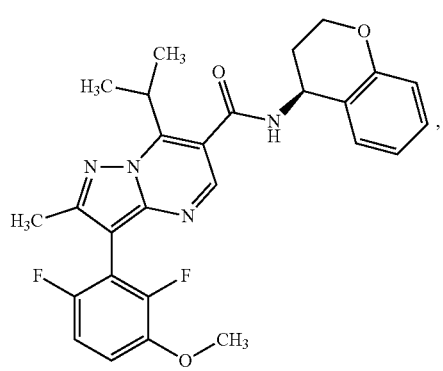
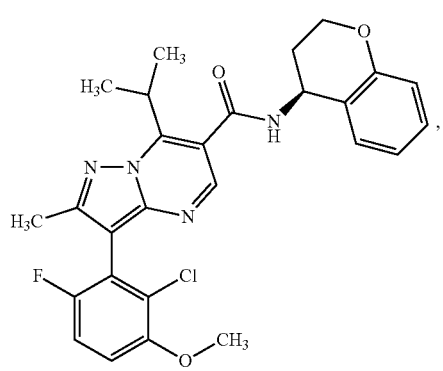
290
-continued
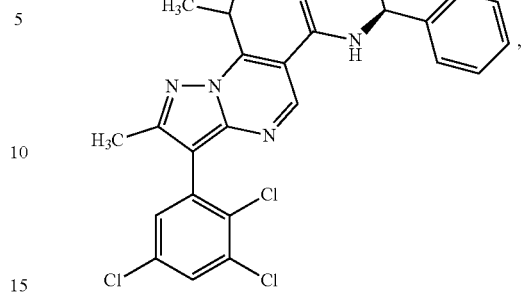
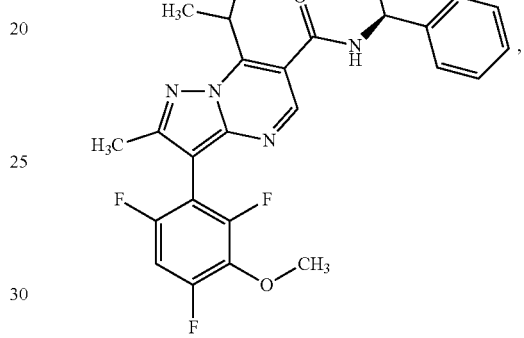
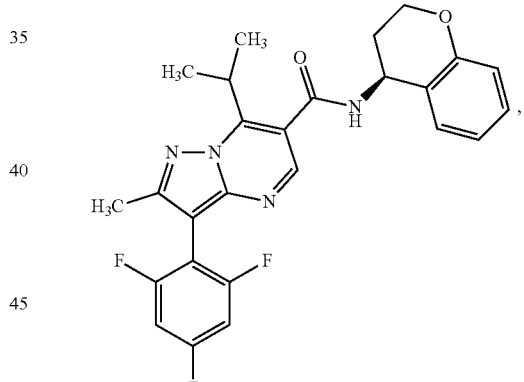
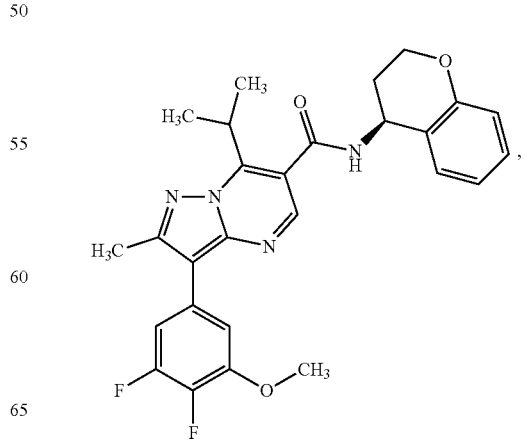

-continued
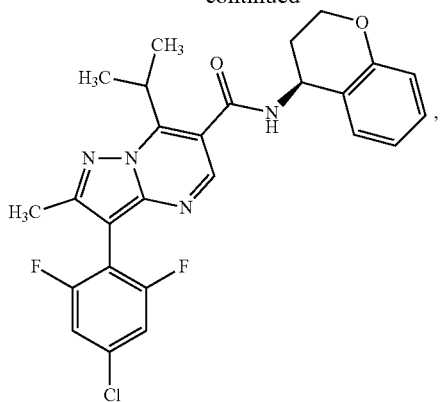
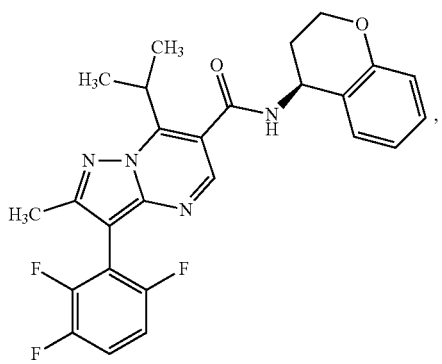
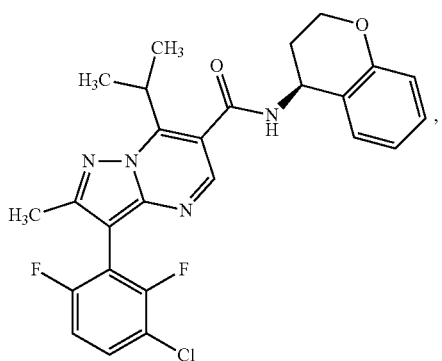
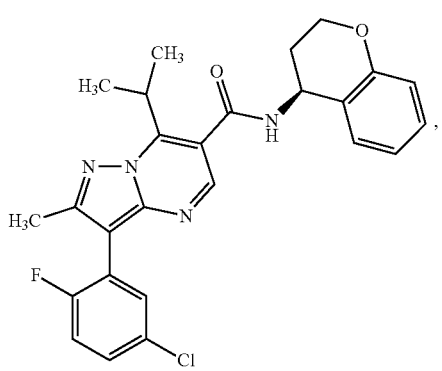
-continued
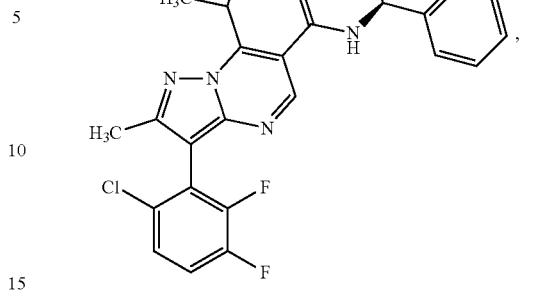
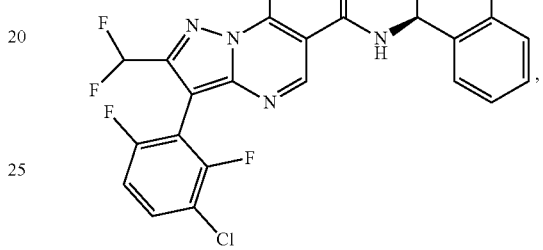
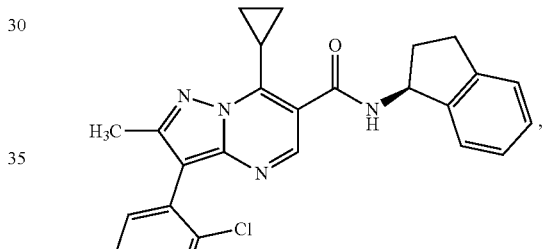
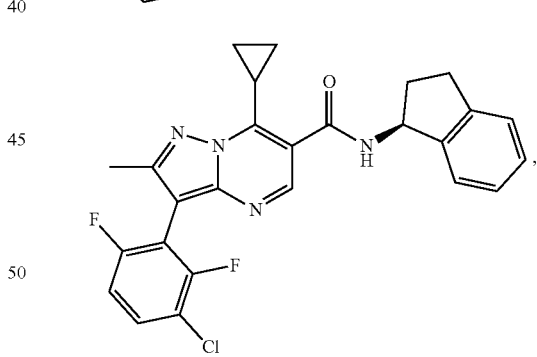
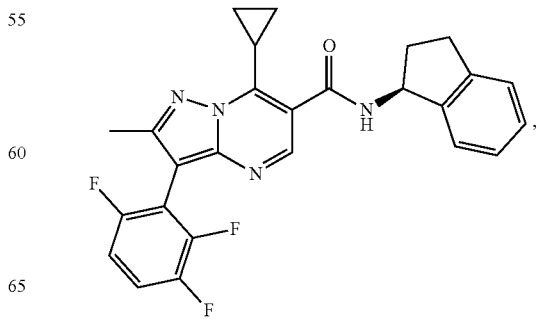

293
-continued
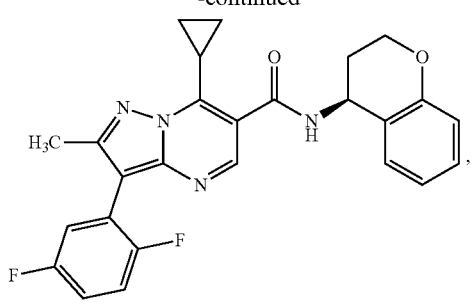,
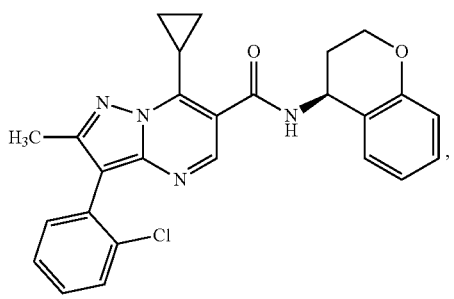,
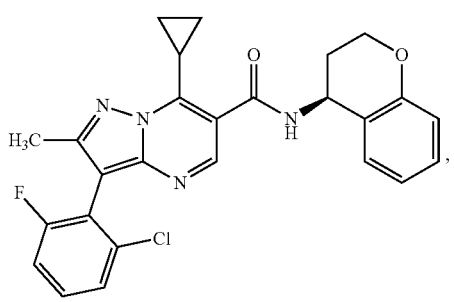,
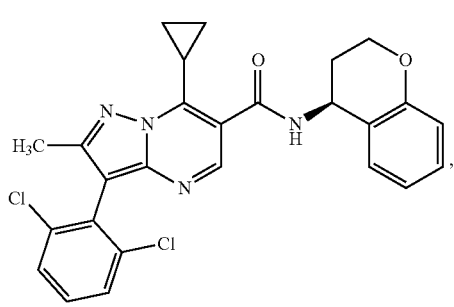,
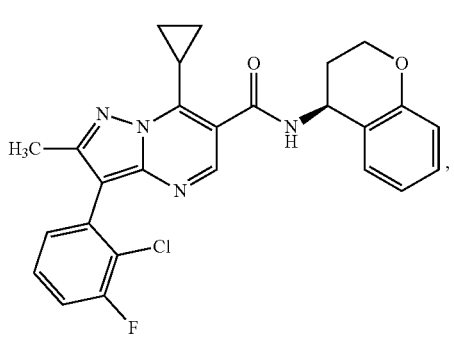,
294
-continued
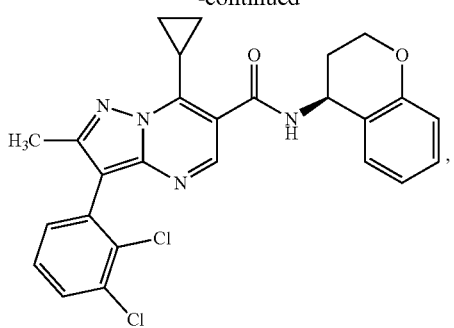,
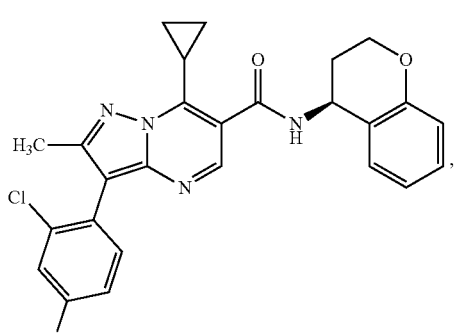,
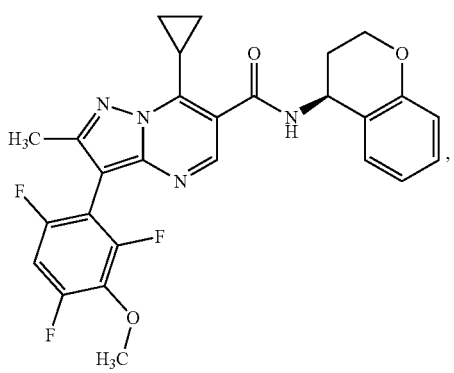,
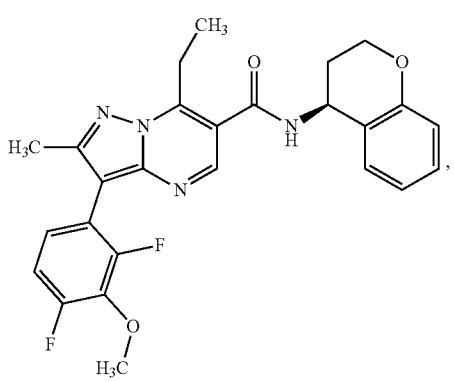, 295
-continued
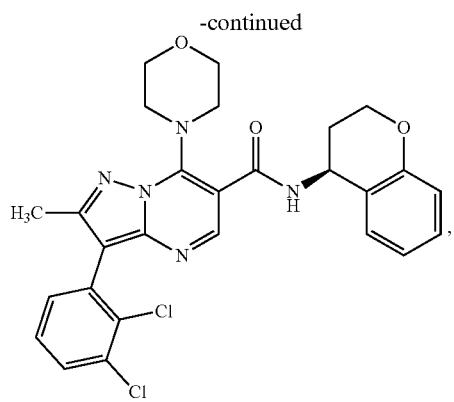
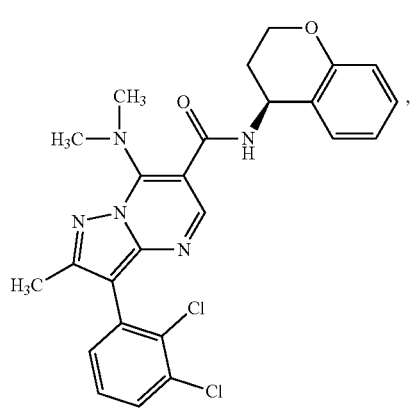
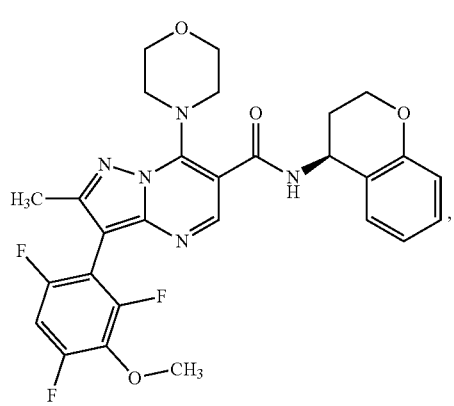
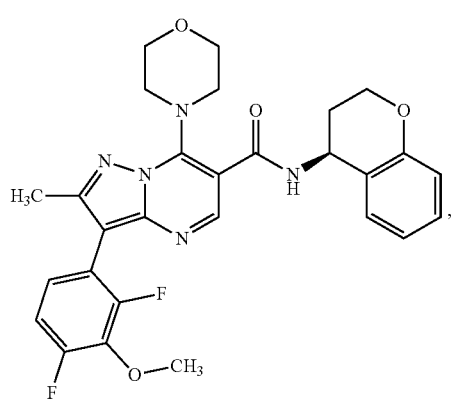
296
-continued
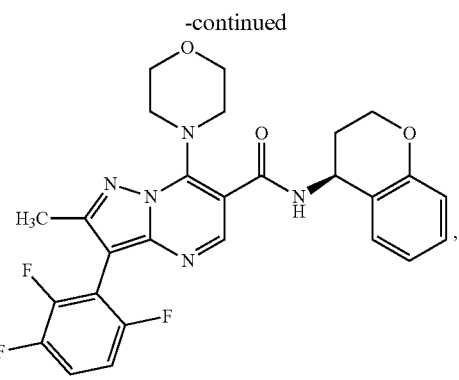
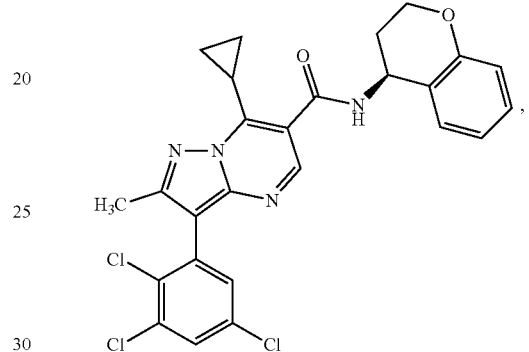
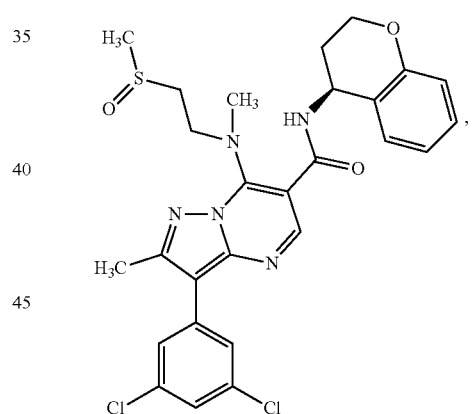
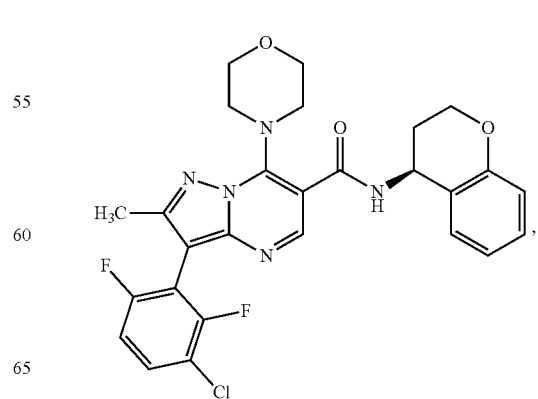

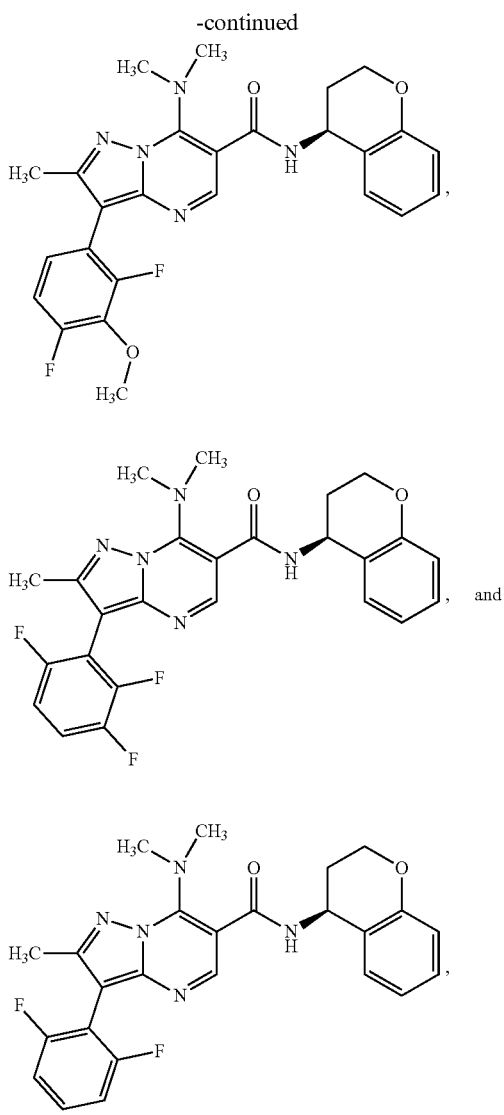

or a stereoisomer, a tautomer, an N-oxide, a hydrate, a solvate, or a salt thereof, or a mixture of any of the foregoing.

9. The method of claim 1, wherein the method is for control of a helminthic disease in the human or animal.

10. A method for control or treatment of a helminthic disease in a human or animal, the method comprising administering to a human or animal in need thereof an anthelminthically effective amount of at least one compound of formula (II)

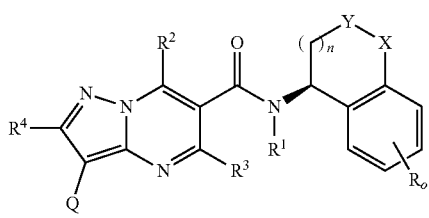

(II)

or a stereoisomer, a tautomer, an N-oxide, a hydrate, a solvate, or a salt thereof, or a mixture of any of the foregoing, wherein:
o is 0 or 1;
R is selected from the group consisting of hydrogen, fluorine, chlorine, and methyl;
n is 0 or 1;
X is selected from the group consisting of $CH_2$ and O;
Y is $CH_2$;
$R^1$ is hydrogen;
$R^2$ is selected from the group consisting of hydrogen, methyl, ethyl, isopropyl, isobutyl, sec-butyl, cyclopropyl, methoxymethyl, difluoromethyl, trifluoromethyl, 4-fluorobenzyl, methoxy, methylamino, dimethylamino, cyclopropylamino, —N(CH$_3$)(cyclopropyl), —N(CH$_3$)(CH$_2$—N(CH$_3$)$_2$), —N(CH$_3$)(CH$_2$—CHF$_2$), —N(CH$_3$)((CH$_2$)$_2$O(CH$_2$)$_2$)O(CH$_2$)$_2$)—OCH$_3$), —N(CH$_3$)((CH$_2$)$_2$—S—CH$_3$), —N(CH$_3$)((CH$_2$)$_2$—S(O)—CH$_3$), —N(CH$_3$)((CH$_2$)$_2$—SO$_2$—CH$_3$), —N(CH$_3$)(1-methyl-piperidin-4-yl), —N(CH$_3$)((CH$_2$)$_2$-(oxopyrrolidin-1-yl)), morpholino, and —CH$_2$—N(CH$_3$)$_2$;
$R^3$ is selected from the group consisting of hydrogen and methyl;
$R^4$ is selected from the group consisting of hydrogen, chlorine, methyl, cyclopropyl, difluoromethyl, trifluoromethyl, —S-methyl, —S-ethyl, —S-isopropyl, —S(O)$_2$-methyl, —S(O)$_2$-ethyl, and —S(O)$_2$-isopropyl; and
Q is a substituted phenyl ring of formula (Q1)

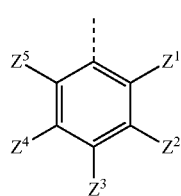

(Q1)

wherein:
$Z^1$, $Z^2$, $Z^3$, $Z^4$, and $Z^5$ are independently hydrogen, fluorine, chlorine, bromine, cyano, methyl, propyl, difluoromethyl, trifluoromethyl, hydroxy, methoxy, ethoxy, isopropoxy, —O-cyclopropyl, —OCH$_2$-cyclopropyl, —OCH$_2$CN, trifluoromethoxy, difluoromethoxy, trifluoroethoxy, methylamino, dimethylamino, methylethyl-amino, diethylamino, acetylamino, methylsulfonamide, trifluoroacetylamino, —SO$_2$Me, —SO$_2$-cyclopropyl, —CH$_2$—O-methyl, —CH$_2$—O-ethyl, —CH$_2$—O—CH$_2$-cyclopropyl, —CH$_2$—O-isopropyl, —CH$_2$—N(CH$_3$)$_2$, —CH$_2$—N(CH$_2$CH$_3$)$_2$, —CH$_2$—N(CH$_3$)(CH$_2$CH$_3$), —CH$_2$—SCH$_3$, —CH$_2$—S(O)CH$_3$, —CH$_2$—SO$_2$—CH$_3$, —C(O)NH-cyclopropyl,

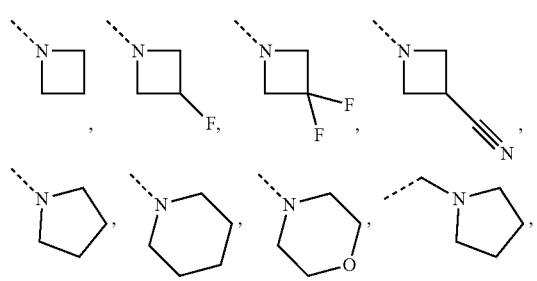

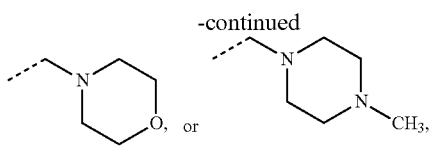

wherein at least two of $Z^1$, $Z^2$, $Z^3$, $Z^4$, and $Z^5$ are hydrogen, or

Q is a pyridine ring of formula (Q2)

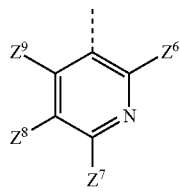

(Q2)

wherein:

$Z^6$ is hydrogen, $Z^7$ and $Z^8$ are independently selected from the group consisting of hydrogen, fluorine, and chlorine, and $Z^9$ is selected from the group consisting of hydrogen and chlorine, or Q is a pyrimidine ring of formula (Q3)

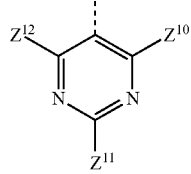

(Q3)

wherein:

$Z^{10}$ and $Z^{12}$ are each hydrogen, and $Z^{11}$ is selected from the group consisting of hydrogen and chlorine, or Q is a pyridine ring of formula (Q4)

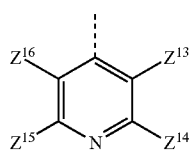

(Q4)

wherein:

$Z^{13}$, $Z^{15}$, and $Z^{16}$ are each hydrogen, and $Z^{14}$ is selected from the group consisting of hydrogen, chlorine, —NH$_2$, —NH—CO—C$_1$-C$_4$-alkyl, —NH(C$_1$-C$_4$-alkyl), —N(C$_1$-C$_4$-alkyl)$_2$, and morpholino, or Q is a pyridine ring of formula (Q5)

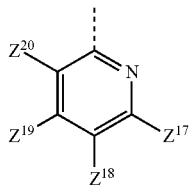

(Q5)

wherein:

$Z^{17}$ is selected from the group consisting of fluorine, chlorine, methoxy, and trifluoromethyl, $Z^{18}$ and $Z^{20}$ are independently selected from the group consisting of hydrogen and chlorine, and $Z^{19}$ is hydrogen, or Q is a pyrazole ring of formula (Q6)

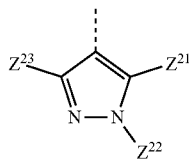

(Q6)

wherein:

$Z^{21}$ and $Z^{23}$ are each hydrogen, and $Z^{22}$ is selected from the group consisting of hydrogen, methyl, ethyl, isopropyl, methoxyethyl, —CH$_2$-cyclopropyl, —CH$_2$CF$_3$, —CH$_2$CHF$_2$, —CH$_2$-morpholino, —CH$_2$—CH$_2$—N(CH$_3$)$_2$, and —CH$_2$—CH$_2$-morpholino, or Q is a pyrazole ring of formula (Q7)

(Q7)

wherein:
Z²⁴ and Z²⁶ are each hydrogen, and
Z²⁵ is selected from the group consisting of hydrogen and chlorine,
or
Q is selected from the group consisting of

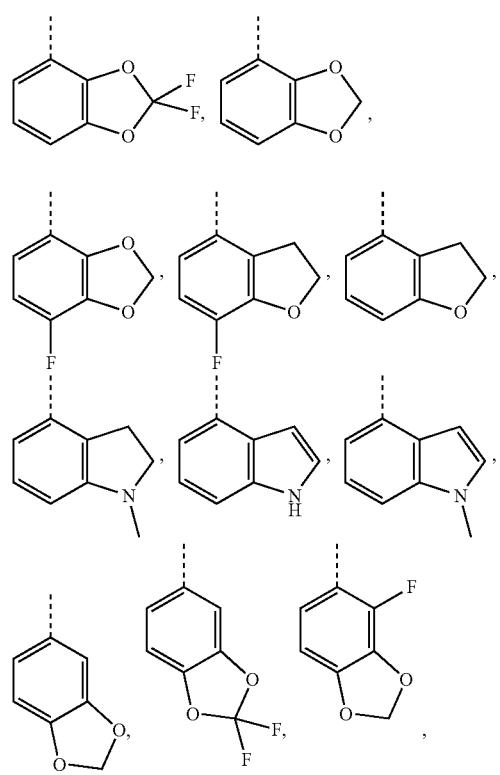

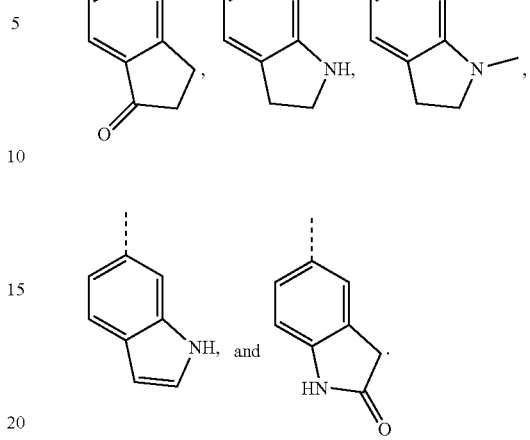

11. The method of claim 1, wherein the compound of formula (I) is administered as a pharmaceutical composition comprising the compound of formula (I), or a stereoisomer, a tautomer, an N-oxide, a hydrate, a solvate, or a salt thereof, or a mixture of any of the foregoing, and one or more pharmaceutically acceptable excipients.

12. The method of claim 10, wherein the compound of formula (II) is administered as a pharmaceutical composition comprising the compound of formula (II), or a stereoisomer, a tautomer, an N-oxide, a hydrate, a solvate, or a salt thereof, or a mixture of any of the foregoing, and one or more pharmaceutically acceptable excipients.

* * * * *